(12) United States Patent
Kataoka et al.

(10) Patent No.: US 7,528,140 B2
(45) Date of Patent: May 5, 2009

(54) SUBSTITUTED PYRROLO[3,2-D]PYRIMIDINES AS GLYCOGEN SYNTHASE KINASE (GSK) INHIBITORS

(75) Inventors: Kenichiro Kataoka, Hino (JP); Tomomi Kosugi, Hino (JP); Toshihiro Ishii, Hino (JP); Takahiro Takeuchi, Hino (JP); Takaharu Tsutsumi, Hino (JP); Akira Nakano, Hino (JP); Gen Unoki, Hino (JP); Masanori Yamamoto, Hino (JP); Yuri Sakai, Hino (JP)

(73) Assignee: Teijin Limited, Osaka (JP)

( * ) Notice: Subject to any disclaimer, the term of this patent is extended or adjusted under 35 U.S.C. 154(b) by 504 days.

(21) Appl. No.: 10/504,583

(22) PCT Filed: Feb. 24, 2003

(86) PCT No.: PCT/JP03/01977

§ 371 (c)(1),
(2), (4) Date: Aug. 16, 2004

(87) PCT Pub. No.: WO03/070729

PCT Pub. Date: Aug. 28, 2003

(65) Prior Publication Data

US 2005/0277773 A1 Dec. 15, 2005

(30) Foreign Application Priority Data

Feb. 22, 2002 (JP) ............................ 2002-046128
Dec. 17, 2002 (JP) ............................ 2002-365196
Dec. 27, 2002 (JP) ............................ 2002-379827

(51) Int. Cl.
*C07D 487/04* (2006.01)
*C07D 417/12* (2006.01)
*C07D 417/06* (2006.01)
*C07D 413/12* (2006.01)
*C07D 413/06* (2006.01)
*C07D 519/00* (2006.01)
*A61K 31/519* (2006.01)
*A61K 31/541* (2006.01)
*A61K 31/5355* (2006.01)
*A61K 31/497* (2006.01)

(52) U.S. Cl. ................ 514/265.1; 544/280; 544/262; 544/264; 544/117; 544/61; 514/263.1; 514/234.2; 514/228.5; 514/252.16; 514/262.1

(58) Field of Classification Search ................ 544/280; 514/265.1

See application file for complete search history.

(56) References Cited

U.S. PATENT DOCUMENTS

2003/0096813 A1* 5/2003 Cao et al. ................ 514/228.5
2004/0180889 A1* 9/2004 Suto et al. ................ 514/235.2

FOREIGN PATENT DOCUMENTS

WO WO 02/085909 A1 10/2002
WO WO 03/073999 A2 9/2003

OTHER PUBLICATIONS

Ryndina, S. A. et al "Torp-Ziegler Cyclization in the Synthesis of 3-Amino-4-Cyanopyrrole Derivatives", Chemistry of Heterocyclic Compounds, vol. 36, No. 12, pp. 1409-1420, 2000.*
Supplementary European Search Report.
Britikova, N.E. et al., "Pyrrolo[3,2-d]pyrimidine derivatives. II.", Khimiko-Farmatsevticheskii Zhurnal (1977), 11 (12), pp. 32-5 (abstract) CA [online, retrieval date: Apr. 7, 2003]; Chemical Abstracts 88:105260, Compounds in RN:65749-90-8, 65749-84-0.
Kadushkin, A. V. et al., "Acetals of acid lactams and amides.", Khimiko-Farmatsevticheskii Zhurnal (1994), 28 (11), pp. 15-9 (abstract) CA [online, retrieval date: Apr. 7, 2003]; Chemical Abstracts 125:48517, compounds in RN:132994-16-2, 132994-17-3.
Sizova, O.S. et al., "Pyrrolo[3,2-d]pyrimidine derivatives. IV.", Khimiko-Farmatsevticheskii Zhurnal (1982), 16 (11), pp. 1338-43 (abstract) CA [online, retrieval date: Apr. 7, 2003]; Chemical Abstracts 98: 107247, compounds in RN: 84905-65-7, 65749-85-1.

* cited by examiner

*Primary Examiner*—Brenda L Coleman
*Assistant Examiner*—Susanna Moore
(74) *Attorney, Agent, or Firm*—Sughrue Mion, PLLC

(57) ABSTRACT

The invention provides pyrrolo[3,2-d]pyrimidine derivatives represented by formula (I), and their medically acceptable salts. The compounds of the invention exhibit GSK-3 inhibiting activity and are therefore expected to be useful as therapeutic or prophylactic agents for conditions in which GSK-3 is implicated, such as diabetes, diabetes complications, Alzheimer's disease, neurodegenerative diseases, manic depression, traumatic encephalopathy, alopecia, inflammatory diseases, cancer and immune deficiency.

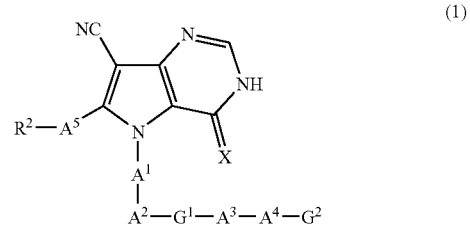

(1)

92 Claims, No Drawings

SUBSTITUTED PYRROLO[3,2-D]PYRIMIDINES AS GLYCOGEN SYNTHASE KINASE (GSK) INHIBITORS

TECHNICAL FIELD

The present invention relates to novel pyrrolopyrimidine derivatives for medical use having Glycogen Synthase Kinase 3 (GSK-3) inhibiting activity. More specifically, it relates to novel pyrrolo[3,2-d]pyrimidine derivatives which are useful as therapeutic and/or prophylactic agents for diseases in which GSK-3 activity has been implicated, particularly impaired glucose tolerance, type I diabetes, type 2 diabetes, diabetes complications (retinopathy, nephropathy, neuropathy, large artery impairment, etc.), Alzheimer's disease, neurodegenerative diseases (AIDS encephalopathy, Huntington's disease, Parkinson's disease, amyotrophic lateral sclerosis, disseminated sclerosis, etc.), bipolar affective disorder (manic depression), traumatic encephalopathy/spinal injury, epilepsy, obesity, atherosclerosis, hypertension, polycystic ovarian disease, syndrome X, alopecia, inflammatory diseases (deformant arthritis, rheumatism, atopic dermatitis, psoriasis, ulcerative colitis, Crohn's disease, sepsis, generalized inflammation, etc.), cancer, immune deficiency and the like.

BACKGROUND ART

GSK-3 is a serine/threonine kinase, for which two isoforms, α and β, have been identified and found to be coded for by separate genes (see non-patent document 1). Both of the GSK-3 isoforms adopt a monomer structure and are homeostatically activated in resting cells. GSK-3 was first identified as a kinase which inhibits activity of glycogen synthases by direct phosphorylation (see non-patent document 2). It is thought that stimulation by insulin leads to inactivation of GSK-3, thereby permitting activation of glycogen synthases and also eliciting insulin functions such as glucose transport. GSX-3 is further known to be inactivated by growth factors such as IGF-1 and FGF, via signals from receptor tyrosine kinases (see non-patent documents 3, 4, 5).

GSK-3 inhibitors are useful in the treatment of various diseases associated with GSK-3 activation. In addition, since GSK-3 inhibitors mimic activation of growth factor signaling pathways, they are also of use in treatment of diseases associated with inactivation of these signaling pathways. Several diseases for which GSK-3 inhibitors are believed to be effective are described below.

Type I diabetes is caused by autoimmune destruction of the β cells, or insulin-producing cells, of the pancreas, leading to insulin deficiency. Type I diabetes patients therefore require daily insulin injections for life support. Current insulin therapy, however, has not been successful in achieving the strict control of glucose levels accomplished by normal β cells. Type I diabetes therefore often leads to diabetes complications such as retinopathy, nephropathy, neuropathy and large artery impairment.

Type II diabetes is a multifactorial disorder wherein hyperglycemia is produced due to insulin resistance in the liver, skeletal muscle and fatty tissue, as well as insufficient secretion of insulin by the pancreas. This condition also results in numerous diabetes complications such as retinopathy, nephropathy, neuropathy and large artery impairment. Skeletal muscle is the major tissue involved in insulin-mediated glucose uptake, and the glucose taken up into the cells is either, metabolized through the glycolytic pathway/TCA cycle or stored as glycogen. Glycogen storage in the skeletal muscle is an extremely important function for glucose homeostasis, but in type II diabetes patients the glycogen storage volume in skeletal muscle is reduced. GSK-3 acts to inhibit glycogen storage in peripheral tissue by phosphorylating glycogen synthase, and to lower insulin reactivity, leading to increased blood glucose levels.

According to a recent report, accelerated expression of GSK-3 is seen in the skeletal muscle of type II diabetes patients and an inverse correlation has been found between skeletal muscle GSK-3α activity and insulin function (see non-patent document 6). Also, overexpression of GSK-3β and active GSK-3β mutants (S9A, S9E) in HEK-293 cells suppresses glycogen synthase activity (see non-patent document 7). Reduction in insulin function has been observed when GSK-3β is overexpressed in CHO cells expressing insulin receptor and insulin receptor substrate 1 (IRS-1) (see non-patent document 8). A recent study using $C_{57}BL/6J$ mice prone to obese diabetes has demonstrated a connection between accelerated GSK-3 activity and progression of insulin resistance/type II diabetes (see non-patent document 9).

Lithium salts are already known as inhibitors of GSK-3 activity (see non-patent document 10). Treatment using lithium salts is reported to lower glucose levels in both type I and type II diabetes patients and to generally improve their condition (see non-patent document 11). However, lithium salts have also been reported to exhibit various effects on molecular targets other than GSK-3.

In consideration of the above, it is expected that GSK-3 inhibitors can serve as effective drug agents for amelioration of impaired glucose tolerance, type I diabetes, type II diabetes, and their related complications.

A link has also been suggested between GSK-3 and progression of Alzheimer's disease. Alzheimer's disease is characterized by formation of senile plaques in the brain from amyloid β peptide deposits, and subsequent formation of neurofibrillary changes. These neurofibrillary changes result in the deaths of large numbers of neurons, and lead to the symptom of dementia. GSK-3 is believed to contribute to abnormal phosphorylation-of Tau protein, which is connected with neurofibrillary changes, during the course of the disease (see non-patent document 12). It has also been reported that GSK-3 inhibitors prevent neuronal death (see non-patent document 13). These findings suggest that application of GSK-3 inhibitors for Alzheimer's disease may slow progression of the condition. While treatment methods currently exist which employ agents for symptomatic therapy of Alzheimer's disease (see non-patent document 14), no agents are known that prevent neuronal death and slow progression of the condition. It is therefore expected that GSK-3 inhibitors can serve as effective drug agents for amelioration of Alzheimer's dementia.

GSK-3 inhibitors have been reported to suppress neuronal death, and especially neuronal death due to glutamate-mediated hyperexcitation (see non-patent documents 15 and 16). This suggests the possibility that GSK-3 inhibitors may be useful for treatment of bipolar affective disorder (manic depression), epilepsy and a host of neurodegenerative disorders and neural diseases. As neurodegenerative disorders there may be mentioned Alzheimer's disease described above, as well as AIDS encephalopathy, Huntington's disease, Parkinson's disease, amyotrophic lateral sclerosis, disseminated sclerosis, Pick's disease, progressive supranuclear palsy, and the like. Glutamate-mediated hyperexcitation is believed to be a cause of brain disorders in such conditions as cerebral apoplexy (cerebral infarction, encephalorrhagia, subarachnoid hemorrhage), traumatic encephalopathy/spinal injury, bacterial/viral infection and the like, and GSK-3 inhibitors are therefore expected to be useful against these conditions as well. All of these disorders are accompanied by death of neurons, and at the current time no drug exists that can effectively suppress such neuronal death. It is therefore believed that GSK-3 inhibitors can serve as effective drug agents for amelioration of various forms of neurodegenerative disorders, bipolar affective disorder (manic depression), epilepsy, cerebral apoplexy, traumatic encephalopathy/spinal injury, and the like.

In vitro research has also been reported indicating that Wint10B strongly suppresses differentiation of preadipocytes to mature adipocytes (see non-patent document 17). GSK-3 specific inhibitors mimic the Wint10B signal in adipose cells, and particularly stabilize free cytosolic β-catenin to block induction of c/EBPα and PPARγ, thereby inhibiting adipogenesis (see non-patent document 18). These findings have led to expectations for GSK-3 inhibitors as effective agents for treatment of obesity.

β-Catenin is known as a biological substrate of GSK-3. β-Catenin is phosphorylated by GSK-3 and undergoes proteosome-dependent degradation (see non-patent document 19). Since transient β-catenin stabilization is thought to play a role in hair development (see non-patent document 20), this suggests that GSK-3 inhibitors may serve as effective drug agents for alopecia.

In addition, research on fibroblasts from GSK-3β knockout mice has raised the possibility that GSK-3β upregulates activity of transcription factor NFκ-B. (see non-patent document 21). NFκ-B is responsible for cell response to a large number of inflammatory stimuli. It is therefore believed that GSK-3 inhibitors may, through downregulation of NFκ-B activity, serve as effective drug agents for treatment of inflammatory conditions such as deformant arthritis, rheumatism, atopic dermatitis, psoriasis, ulcerative colitis, Crohn's disease, sepsis, generalized inflammatory reaction syndrome, and the like.

The transcription factor NF-AT is dephosphorylated by calcineurin, resulting in a reinforced immune response (see non-patent document 22). GSK-3 instead phosphorylates NF-AT and exports it out of the nucleus, thereby working in a direction to suppress expression of early immune response genes. These findings suggest that GSK-3 inhibitors may serve as effective drug agents promoting immune activation for cancer immunotherapy and the like.

As substances previously known to have GSK-3 inhibiting activity there have been reported hymenialdisine derivatives (see non-patent document 23 and patent document 1), maleinimide derivatives (see non-patent document 24), Paullone derivatives (see non-patent document 25 and patent document 2), purine derivatives (see patent document 3), pyrimidine and pyridine derivatives (see patent document 4), hydroxyflavone derivatives (see patent document 5), pyrimidone derivatives (see patent documents 6, 7, 8, 9, 10, 11, 12 and 13), pyrrole-2,5-dione derivatives (see patent documents 14 and 15), diamino-1,2,4-triazolecarboxylic acid derivatives (see patent document 16), pyrazine derivatives (see patent document 17), bicyclic inhibitors (see patent document 18), indirubin derivatives (see patent document 19), carboxamide derivatives (see patent document 20), peptide inhibitors (see patent document 21), 2,4-diaminothiazole derivatives (see patent document 22), thiadiazolidinedione derivatives (see patent document 23) and aromatic amide derivatives (see patent document 24).

Non-patent document 1: Trends Biochem. Sci., 1991, Vol. 16, p. 177.
Non-patent document 2: Eur. J. Biochem., 1980, Vol. 107, p. 519.
Non-patent document 3: Biochem. J. (UK), 1993, Vol. 294, p. 625.
Non-patent document 4: Biochem. J. (UK), 1994, Vol. 303, p. 21.
Non-patent document 5: Biochem. J. (UK), 1994, Vol. 303, p. 27.
Non-patent document 6: Diabetes USA, 2000, Vol. 49, p. 263.
Non-patent document 7: Proc. Natl. Acad. Sci. USA, 1996, Vol. 93, p. 10228.
Non-patent document 8: Proc. Natl. Acad. Sci. USA, 1997, Vol. 94, p. 9660.
Non-patent document 9: Diabetes USA, 1999, Vol. 48, p. 1662.
Non-patent document 10: Proc. Natl. Acad. Sci. USA, 1996, Vol. 93, p. 8455.
Non-patent document 11: Biol. Trace Elements Res., 1997, Vol. 60, p. 131.
Non-patent document 12: Acta Neuropathol., 2002, Vol. 103, p. 91.
Non-patent document 13: J. Neurochem., 2001, Vol. 77, p. 94.
Non-patent document 14: Expert Opin. Pharmacother., 1999, Vol. 1, p. 121.
Non-patent document 15: Proc. Natl. Acad. Sci. USA, 1998, Vol. 95, p. 2642.
Non-patent document 16: J. Neurochem., 2001, Vol. 77, p. 94.
Non-patent document 17: Science, 2000, Vol. 289, p. 950.
Non-patent document 18: J. Biol. Chem, 2002, Vol. 277, p. 30998.
Non-patent document 19: EMBO J., 1998, Vol. 17, p. 1371.
Non-patent document 20: Cell, 1998, Vol. 95, p. 605.
Non-patent document 21: Nature, 2000, Vol. 406, p. 86.
Non-patent document 22: Science, 1997, Vol. 275, p. 1930.
Non-patent-document 23: Chemistry & Biology, 2000, Vol. 7, p. 51.
Non-patent document 24: Chemistry & Biology, 2000, Vol. 7, p. 793.
Non-patent document 25: Eur. J. Biochem., 2000, Vol. 267, p. 5983.
Patent document 1: WO01/41768 pamphlet
Patent document 2: WO01/60374 pamphlet
Patent document 3: WO98/16528 pamphlet
Patent document 4: WO99/65897 pamphlet
Patent document 5: WO00/17184 pamphlet
Patent document 6: WO00/18758 pamphlet
Patent document 7: WO01/70683 pamphlet
Patent document 8: WO01/70729 pamphlet
Patent document 9: WO01/70728 pamphlet
Patent document 10: WO01/70727 pamphlet
Patent document 11: WO01/70727 pamphlet
Patent document 12: WO01/70726 pamphlet
Patent document. 13: WO01/70725 pamphlet
Patent document 14: WO00/21927 pamphlet
Patent document 15: WO01/74771 pamphlet
Patent document 16: WO01/09106 pamphlet
Patent document 17: WO01/44206 pamphlet
Patent document 18: WO01/44246 pamphlet
Patent document 19: WO01/37819 pamphlet
Patent document 20: WO01/42224 pamphlet
Patent document 21: WO01/49709 pamphlet
Patent document 22: WO01/56567 pamphlet
Patent document 23: WO01/85685 pamphlet
Patent document 24: WO01/81345 pamphlet It is an object of the present invention to provide clinically useful novel compounds with selective and powerful inhibiting action against GSK-3.

DISCLOSURE OF THE INVENTION

As a result of much diligent research directed toward achieving the object stated above, the present inventors have completed the present invention upon discovering that the novel pyrrolo[3,2-d]pyrimidine derivatives represented by formula (I) below and their medically acceptable salts exhibit excellent GSK-3 inhibiting activity.

In other words, the present invention provides (1) A pyrrolo[3,2-d]pyrimidine derivatives represented by the following formula (I), and their medically acceptable salts.

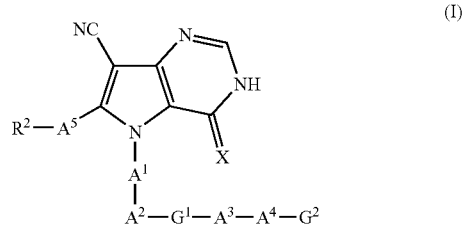

[wherein X represents an oxygen atom or sulfur atom;

$A^1$ represents a single bond, or a $C_{1-6}$ aliphatic hydrocarbon group with the bonded nitrogen atom and $A^2$ being bonded on the same or different carbon atoms of $A^1$;

$A^2$ represents a single bond or a group binding $A^1$ and $G^1$ in the form of $A^1$-C(=O)-$G^1$, $A^1$-C(=O)O-$G^1$, $A^1$-C(=O) $NR^{101}$-$G^1$, $A^1$-C(=S)$NR^{102}$-$G^1$, $A^1$-C(=$NR^{103}$)-$G^1$, $A^1$-O-$G^1$, $A^1$-OC(=O)-$G^1$, $A^1$-$NR^{104}$-$G^1$, $A^1$-$NR^{105}$C(=O)-$G^1$, $A^1$-$NR^{106}$S(=O)$_2$-$G^1$, $A^1$-$NR^{107}$C(=O)O-$G^1$, $A^1$-$NR^{108}$C (=O)$NR^{109}$-$G^1$, $A^1$-$NR^{110}$C(=S)-$G^1$, $A^1$-$NR^{111}$C(=S) $NR^{112}$-$G^1$, $A^1$-S-$G^1$, $A^1$-S(=O)-$G^1$, $A^1$-S(=O)$_2$-$G^1$ or $A^1$-S(=O)$_2NR^{113}$-$G^1$ (where $R^{101}$-$R^{113}$ each independently represent hydrogen or a $C_{1-4}$ aliphatic hydrocarbon group);

$G^1$ represents one group selected from among the following 1) to 4):

1) A single bond.

2) A substituted or unsubstituted $C_{3-8}$ alicyclic hydrocarbon group. (As substituents there may be mentioned one or more selected from the group consisting of fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, oxo, $C_{1-6}$ alkylsulfonyloxy, optionally substituted $C_{2-7}$ acyl, carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-8}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbons and optionally substituted $C_{1-6}$ aliphatic hydrocarbons.)

3) A substituted or unsubstituted $C_{6-14}$ aromatic hydrocarbon group. (As substituents there may be mentioned one or more selected from the group consisting of fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, oxo, $C_{1-6}$ alkylsulfonyloxy, optionally substituted $C_{2-7}$ acyl, carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-7}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbons and optionally substituted $C_{1-6}$ aliphatic hydrocarbons.)

4) A substituted or unsubstituted heterocyclic group having in the ring 1 to 4 atoms selected from the group consisting of oxygen, nitrogen and sulfur. (As substituents there may be mentioned one or more selected from the group consisting of fluorine, chlorine, bromine, iodine, hydroxyl, optionally substituted $C_{1-7}$ alkoxy, $C_{6-10}$ aryloxy, $C_{1-9}$ aralkoxy, $C_{2-7}$ acyloxy, oxo, $C_{1-6}$ alkylsulfonyloxy, optionally substituted $C_{2-7}$ acyl, carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-7}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbons and optionally substituted $C_{1-6}$ aliphatic hydrocarbons.);

$A^3$ represents a single bond, or a $C_{1-6}$ aliphatic hydrocarbon group having $G^1$ and $A^4$ bonded on the same or different carbon atoms;

$A^4$ represents a single bond or a group binding $A^3$ and $G^2$ in the form of $A^3$-C(=O)-$G^2$, $A^3$-C(=O)O-$G^2$, $A^3$-C(=O) $NR^{121}$-$G^2$, $A^3$-C(=S)$NR^{122}$-$G^2$, $A^3$-C(=$NR^{123}$)-$G^2$, $A^3$-O-$G^2$, $A^3$-C(=O)-$G^2$, $A^3$-$NR^{124}$-$G^2$, $A^3$-$NR^{125}$C(=O)-$G^2$, $A^3$-$NR^{126}$S(=O)$_2$-$G^2$, $A^3$-$NR^{127}$C(=O)O-$G^2$, $A^3$-$NR^{128}$C (=O)$NR^{129}$-$G^2$, $A^3$-$NR^{130}$C(=S)-$G^2$, $A^3$-$NR^{131}$C(=S) $NR^{132}$-$G^2$, $A^3$-S-$G^2$, $A^3$-S(=O)-$G^2$, $A^3$-S(=O)$_2$-$G^2$, $A^3$-S(=O)$_2NR^{133}$-$G^2$ or $A^3$-S(=O)$_2$O-$G^2$ (where $R^{121}$-$R^{133}$ each independently represent hydrogen or a $C_{1-4}$ aliphatic hydrocarbon group); and $G^2$ represents one group selected from among the following 1) to 5):

1) Hydrogen;

2) A substituted or unsubstituted $C_{1-10}$ aliphatic hydrocarbon group. (As substituents there may be mentioned one or more selected from the group consisting of fluorine, chlorine, bromine, iodine, hydroxyl, optionally substituted $C_{1-7}$ alkoxy, $C_{6-10}$ aryloxy, $C_{1-9}$ aralkoxy, $C_{2-7}$ acyloxy, oxo, $C_{1-6}$ alkylsulfonyloxy, optionally substituted $C_{2-7}$ acyl, carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-8}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbons, optionally substituted $C_{1-6}$ aliphatic hydrocarbons, optionally substituted $C_{6-14}$ aromatic hydrocarbons and optionally substituted heterocyclic groups (having in the ring 1 to 4 atoms selected from the group consisting of oxygen, nitrogen and sulfur).)

3) A substituted or unsubstituted $C_{3-8}$ alicyclic hydrocarbon group. (As substituents there may be mentioned one or more selected from the group consisting of fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, oxo, $C_{1-6}$ alkylsulfonyloxy, optionally substituted $C_{2-7}$ acyl, carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-7}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbons, optionally substituted $C_{1-6}$ aliphatic hydrocarbons, optionally substituted $C_{6-14}$ aromatic hydrocarbons and optionally substituted heterocyclic groups (having in the ring 1 to 4 atoms selected from the group consisting of oxygen, nitrogen and sulfur).)

4) A substituted or unsubstituted $C_{6-14}$ aromatic hydrocarbon group. (As substituents there may be mentioned one or more selected from the group consisting of fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, oxo, $C_{1-6}$ alkylsulfonyloxy, optionally substituted $C_{2-7}$ acyl, carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-8}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbons, optionally substituted $C_{1-6}$ aliphatic hydrocarbons, optionally substituted $C_{6-14}$ aromatic hydrocarbons and optionally substituted heterocyclic groups (having in the ring 1 to 4 atoms selected from the group consisting of oxygen, nitrogen and sulfur).)

5) A substituted or unsubstituted heterocyclic group having in the ring 1 to 4 atoms selected from the group consisting of oxygen, nitrogen and sulfur. (As substituents there may be mentioned one or more selected from the group consisting of fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, oxo, $C_{1-6}$ alkylsulfonyloxy, optionally substituted $C_{2-7}$ acyl, carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-1}$ acylamino, $C_{2-7}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbons, optionally substituted $C_{1-6}$ aliphatic hydrocarbons, optionally substituted $C_{6-14}$ aromatic hydrocarbons and optionally substituted heterocyclic groups (having in the ring 1 to 4 atoms selected from the group consisting of oxygen, nitrogen and sulfur).)

The above is with the proviso that among the combinations of $A^1, A^2, G^1, A^3, A^4$ and $G^2$, when $A^1$ is a single bond, $A^2, G^1, A^3$ and $A^4$ are all single bonds, that among the combinations of $A^1, A^2, G^1, A^3, A^4$ and $G^2$, when $A^1$ is not a single bond and $G^1$ and $A^3$ are both single bonds, the combination including $A^2$ and $A^4$ is $A^1$-C(=O)—C(=O)-$G^2$ or $A^1$-C(=O)NR$^{101}$-O-$G^2$, and that among the combinations of $G^1, A^3, A^4$ and $G^2$, when $A^3$ represents a $C_{1-6}$ aliphatic hydrocarbon group having $G^1$ and $A^4$ bonded on the same or different carbon atoms and $G^2$ represents a substituted or unsubstituted $C_{1-10}$ aliphatic hydrocarbon group, $A^4$ is not a single bond.

$A^5$ represents a single bond, or a group binding the carbon atom of the pyrrole ring to which $A^5$ is bonded and $R^2$ in the form of $R^2$—NR$^{201}$-pyrrole ring carbon (where $R^{201}$ represents hydrogen or a $C_{1-4}$ aliphatic hydrocarbon group).

$R^2$ represents one group selected from among the following 1) to 6):

1) Hydrogen.

2) Fluorine, chlorine, bromine or iodine.

3) A substituted or unsubstituted $C_{1-10}$ aliphatic hydrocarbon group. (As substituents there may be mentioned one or more selected from the group consisting of fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, oxo, $C_{1-6}$ alkylsulfonyloxy, optionally substituted $C_{2-7}$ acyl, carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-7}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbons, optionally substituted $C_{1-6}$ aliphatic hydrocarbons, optionally substituted $C_{6-14}$ aromatic hydrocarbons and optionally substituted heterocyclic groups (having in the ring 1 to 4 atoms selected from the group consisting of oxygen, nitrogen and sulfur).)

4) A substituted or unsubstituted $C_{3-8}$ alicyclic hydrocarbon group. (As substituents there may be mentioned one or more selected from the group consisting of fluorine, chlorine, bromine, iodine, hydroxyl, optionally substituted $C_{1-7}$ alkoxy, $C_{6-10}$ aryloxy, $C_{1-9}$ aralkoxy, $C_{2-7}$ acyloxy, oxo, $C_{1-6}$ alkylsulfonyloxy, optionally substituted $C_{2-7}$ acyl, carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-8}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbons, optionally substituted $C_{1-6}$ aliphatic hydrocarbons, optionally substituted $C_{6-14}$ aromatic hydrocarbons and optionally substituted heterocyclic groups (having in the ring 1 to 4 atoms selected from the group consisting of oxygen, nitrogen and sulfur).)

5) A substituted or unsubstituted $C_{6-14}$ aromatic hydrocarbon group. (As substituents there may be mentioned one or more selected from the group consisting of fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, oxo, $C_{1-6}$ alkylsulfonyloxy, optionally substituted $C_{2-7}$ acyl, carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-7}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbons, optionally substituted $C_{1-6}$ aliphatic hydrocarbons, optionally substituted $C_{6-14}$ aromatic hydrocarbons and optionally substituted heterocyclic groups (having in the ring 1 to 4 atoms selected from the group consisting of oxygen, nitrogen and sulfur).)

6) A substituted or unsubstituted heterocyclic group having in the ring 1 to 4 atoms selected from the group consisting of oxygen, nitrogen and sulfur. (As substituents there may be mentioned one or more selected from the group consisting of fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, oxo, $C_{1-6}$ alkylsulfonyloxy, optionally substituted $C_{2-7}$ acyl, carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-8}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbons, optionally substituted $C_{1-6}$ aliphatic hydrocarbons, optionally substituted $C_{6-14}$ aromatic hydrocarbons and optionally substituted heterocyclic groups (having in the ring 1 to 4 atoms selected from the group consisting of oxygen, nitrogen and sulfur).)

The above is with the proviso that among the combinations of $R^2$ and $A^5$, when $R^2$ is fluorine, chlorine, bromine or iodine, $A^5$ is a single bond.].

(2) A pyrrolo[3,2-d]pyrimidine derivative or a medically acceptable salt thereof according to (1), wherein X is an oxygen atom.

(3) A pyrrolo[3,2-d]pyrimidine derivative or a medically acceptable salt thereof according to (1), wherein X is a sulfur atom.

(4) A pyrrolo[3,2-d]pyrimidine derivative or a medically acceptable salt thereof according to any one of (1) to (3), wherein $A^1$ is —$(CH_2)_2$—.

(5) A pyrrolo[3,2-d]pyrimidine derivative or a medically acceptable salt thereof according to any one of (1) to (3), wherein $A^1$ is —$(CH_2)_3$—.

(6) A pyrrolo[3,2-d]pyrimidine derivative or a medically acceptable salt thereof according to any one of (1) to (5), wherein $A^1$-$A^2$-$G^1$ bond in the form of $A^1$-O-$G^1$.

(7) A pyrrolo[3,2-d]pyrimidine derivative or a medically acceptable salt thereof according to any one of (1) to (5), wherein $A^1$-$A^2$-$G^1$ bond in the form of $A^1$-OC(=O)-$G^1$.

(8) A pyrrolo[3,2-d]pyrimidine derivative or a medically acceptable salt thereof according to any one of (1) to (5), wherein $A^1$-$A^2$-$G^1$ bond in the form of $A^1$-$NR^{104}$-$G^1$.

(9) A pyrrolo[3,2-d]pyrimidine derivative or a medically acceptable salt thereof according to any one of (1) to (5), wherein $A^1$-$A^2$-$G^1$ bond in the form of $A^1$-$NR^{105}$C(=O)-$G^1$.

(10) A pyrrolo[3,2-d]pyrimidine derivative or a medically acceptable salt thereof according to any one of (1) to (5), wherein $A^1$-$A^2$-$G^1$ bond in the form of $A^1$-$NR^{106}$S(=O)$_2$-$G^1$.

(11) A pyrrolo[3,2-d]pyrimidine derivative or a medically acceptable salt thereof according to any one of (1) to (5), wherein $A^1$-$A^2$-$G^1$ bond in the form of $A^1$-$NR^{107}$C(=O)O-$G^1$.

(12) A pyrrolo[3,2-d]pyrimidine derivative or a medically acceptable salt thereof according to any one of (1) to (5), wherein $A^1$-$A^2$-$G^1$ bond in the form of $A^1$-$NR^{108}$C(=O)$NR^{109}$-$G^1$.

(13) A pyrrolo[3,2-d]pyrimidine derivative or a medically acceptable salt thereof according to any one of (1) to (5), wherein $A^1$-$A^2$-$G^1$ bond in the form of $A^1$-C(=O)-$G^1$.

(14) A pyrrolo[3,2-d]pyrimidine derivative or a medically acceptable salt thereof according to any one of (1) to (5), wherein $A^1$-$A^2$-$G^1$ bond in the form of $A^1$-C(=O)O-$G^1$.

(15) A pyrrolo[3,2-d]pyrimidine derivative or a medically acceptable salt thereof according to any one of (1) to (5), wherein $A^1$-$A^2$-$G^1$ bond in the form of $A^1$-C(=O)$NR^{101}$-$G^1$.

(16) A pyrrolo[3,2-d]pyrimidine derivative or a medically acceptable salt thereof according to any one of (1) to (5), wherein $A^1$-$A^2$-$G^1$ bond in the form of $A^1$-C(=S)$NR^{102}$-$G^1$.

(17) A pyrrolo[3,2-d]pyrimidine derivative or a medically acceptable salt thereof according to any one of (1) to (5), wherein $A^1$-$A^2$-$G^1$ bond in the form of $A^1$-C(=$NR^{103}$)-$G^1$.

(18) A pyrrolo[3,2-d]pyrimidine derivative or a medically acceptable salt thereof according to any one of (1) to (5), wherein $A^1$-$A^2$-$G^1$ bond in the form of $A^1$-$NR^{110}$C(=S)-$G^1$.

(19) A pyrrolo[3,2-d]pyrimidine derivative or a medically acceptable salt thereof according to any one of (1) to (5), wherein $A^1$-$A^2$-$G^1$ bond in the form of $A^1$-$NR^{111}$C(=S)$NR^{112}$-$G^1$.

(20) A pyrrolo[3,2-d]pyrimidine derivative or a medically acceptable salt thereof according to any one of (1) to (5), wherein $A^1$-$A^2$-$G^1$ bond in the form of $A^1$-S-$G^1$.

(21) A pyrrolo[3,2-d]pyrimidine derivative or a medically acceptable salt thereof according to any one of (1) to (5), wherein $A^1$-$A^2$-$G^1$ bond in the form of $A^1$-S(=O)-$G^1$.

(22) A pyrrolo[3,2-d]pyrimidine derivative or a medically acceptable salt thereof according to any one of (1) to (5), wherein $A^1$-$A^2$-$G^1$ bond in the form of $A^1$-S(=O)$_2$-$G^1$.

(23) A pyrrolo[3,2-d]pyrimidine derivative or a medically acceptable salt thereof according to any one of (1) to (5), wherein $A^1$-$A^2$-$G^1$ bond in the form of $A^1$-S(=O)$_2$$NR^{113}$-$G^1$.

(24) A pyrrolo[3,2-d]pyrimidine derivative or a medically acceptable salt thereof according to any one of (1) to (5), wherein $A^1$-$A^2$-$G^1$ bond in the form of $A^1$-NH-$G^1$

(25) A pyrrolo[3,2-d]pyrimidine derivative or a medically acceptable salt thereof according to any one of (1) to (5), wherein $A^1$-$A^2$-$G^1$ bond in the form of $A^1$-NHC(=O)-$G^1$.

(26) A pyrrolo[3,2-d]pyrimidine derivative or a medically acceptable salt thereof according to any one of (1) to (5), wherein $A^1$-$A^2$-$G^1$ bond in the form of $A^1$-NHS(=O)$_2$-$G^1$.

(27) A pyrrolo[3,2-d]pyrimidine derivative or a medically acceptable salt thereof according to any one of (1) to (5), wherein $A^3$-$A^2$-$G^1$ bond in the form of $A^1$-NHC(=O)O-$G^1$.

(28) A pyrrolo[3,2-d]pyrimidine derivative or a medically acceptable salt thereof according to any one of (1) to (5), wherein $A^1$-$A^2$-$G^1$ bond in the form of $A^1$-NHC(=O)NH-$G^1$.

(29) A pyrrolo[3,2-d]pyrimidine derivative or a medically acceptable salt thereof according to any one of (1) to (5), wherein $A^1$-$A^2$-$G^1$ bond in the form of $A^1$-C(=O)NH-$G^1$.

(30) A pyrrolo[3,2-d]pyrimidine derivative or a medically acceptable salt thereof according to any one of (1) to (5), wherein $A^1$-$A^2$-$G^1$ bond in the form of $A^1$-C(=S)NH-$G^1$.

(31) A pyrrolo[3,2-d]pyrimidine derivative or a medically acceptable salt thereof according to any one of (1) to (5), wherein $A^1$-$A^2$-$G^1$ bond in the form of $A^1$-C(=NH)-$G^1$.

(32) A pyrrolo[3,2-d]pyrimidine derivative or a medically acceptable salt thereof according to any one of (1) to (5), wherein $A^1$-$A^2$-$G^1$ bond in the form of $A^1$-NHC(=S)-$G^1$.

(33) A pyrrolo[3,2-d]pyrimidine derivative or a medically acceptable salt thereof according to any one of (1) to (5), wherein $A^1$-$A^2$-$G^1$ bond in the form of $A^1$-S(=O)$_2$NH-$G^1$.

(34) A pyrrolo[3,2-d]pyrimidine derivative or a medically acceptable salt thereof according to any one of (1) to (5), wherein $A^2$ is a single bond.

(35) A pyrrolo[3,2-d]pyrimidine derivative or a medically acceptable salt thereof according to any one of (6) to (34), wherein $G^1$ is a single bond.

(36) A pyrrolo[3,2-d]pyrimidine derivative or a medically acceptable salt thereof according to any one of (6) to (34), wherein $G^1$ is a substituted or unsubstituted $C_{6-14}$ aromatic hydrocarbon group.

(37) A pyrrolo[3,2-d]pyrimidine derivative or a medically acceptable salt thereof according to any one of (6) to (34), wherein $G^1$ is a substituted or unsubstituted $C_{3-8}$ alicyclic hydrocarbon group.

(38) A pyrrolo[3,2-d]pyrimidine derivative or a medically acceptable salt thereof according to any one of (6) to (34), wherein $G^1$ is a substituted or unsubstituted heterocyclic group having in the ring 1 to 4 atoms selected from the group consisting of oxygen, nitrogen and sulfur atoms.

(39) A pyrrolo[3,2-d]pyrimidine derivative or a medically acceptable salt thereof according to any one of (6) to (34), wherein $G^1$ is an unsubstituted $C_{6-14}$ aromatic hydrocarbon group.

(40) A pyrrolo[3,2-d]pyrimidine derivative or a medically acceptable salt thereof according to any one of (6) to (34), wherein $G^1$ is an unsubstituted $C_{3-8}$ alicyclic hydrocarbon group.

(41) A pyrrolo[3,2-d]pyrimidine derivative or a medically acceptable salt thereof according to any one of (6) to (34), wherein $G^1$ is an unsubstituted heterocyclic group having in the ring 1 to 4 atoms selected from the group consisting of oxygen, nitrogen and sulfur atoms.

(42) A pyrrolo[3,2-d]pyrimidine derivative or a medically acceptable salt thereof according to any one of (6) to (34), wherein $G^1$ is a substituted $C_{6-14}$ aromatic hydrocarbon group.

(43) A pyrrolo[3,2-d]pyrimidine derivative or a medically acceptable salt thereof according to any one of (6) to (34), wherein $G^1$ is a substituted $C_{3-8}$ alicyclic hydrocarbon group.

(44) A pyrrolo[3,2-d]pyrimidine derivative or a medically acceptable salt thereof according to any one of (6) to (34), wherein $G^1$ is a substituted heterocyclic group having in the ring 1 to 4 atoms selected from the group consisting of oxygen, nitrogen and sulfur atoms.

(45) A pyrrolo[3,2-d]pyrimidine derivative or a medically acceptable salt thereof according to any one of (6) to (34), wherein $G^1$ is an unsubstituted aromatic heterocyclic group having in the ring 1 or 2 atoms selected from the group consisting of oxygen, nitrogen and sulfur atoms.

(46) A pyrrolo[3,2-d]pyrimidine derivative or a medically acceptable salt thereof according to any one of (6) to (34), wherein $G^1$ is a substituted aromatic heterocyclic group having in the ring 1 or 2 atoms selected from the group consisting of oxygen, nitrogen and sulfur atoms.

(47) A pyrrolo[3,2-d]pyrimidine derivative or a medically acceptable salt thereof according to any one of (6) to (34), wherein $G^1$ is divalent unsubstituted furan, unsubstituted pyrrole, unsubstituted pyrrolidine, unsubstituted thiophene, unsubstituted oxazole, unsubstituted thiazole, unsubstituted isooxazole, unsubstituted isothiazole, unsubstituted pyrazole, unsubstituted imidazole, unsubstituted pyridine, unsubstituted pyrimidine, unsubstituted pyrazine, unsubstituted benzothiophene, unsubstituted benzofuran, unsubstituted benzimidazole, unsubstituted indole, unsubstituted quinoline, unsubstituted isoquinoline, unsubstituted quinazoline, unsubstituted purine, unsubstituted phthalazine, unsubstituted cinnoline, unsubstituted 1,8-naphthylidine or unsubstituted pteridine.

(48) A pyrrolo[3,2-d]pyrimidine derivative or a medically acceptable salt thereof according to any one of (6) to (34), wherein $G^1$ is divalent substituted furan, substituted pyrrole, substituted pyrrolidine, substituted thiophene, substituted oxazole, substituted thiazole, substituted isooxazole, substituted isothiazole, substituted pyrazole, substituted imidazole, substituted pyridine, substituted pyrimidine, substituted pyrazine, substituted benzothiophene, substituted benzofuran, substituted benzimidazole, substituted indole, substituted quinoline, substituted isoquinoline, substituted quinazoline, substituted purine, substituted phthalazine, substituted cinnoline, substituted 1,8-naphthylidine or substituted pteridine.

(49) A pyrrolo[3,2-d]pyrimidine derivative or a medically acceptable salt thereof according to any one of (6) to (34), wherein $G^1$ is divalent substituted benzene.

(50) A pyrrolo[3,2-d]pyrimidine derivative or a medically acceptable salt thereof according to any one of (6) to (34), wherein $G^1$ is divalent unsubstituted benzene.

(51) A pyrrolo[3,2-d]pyrimidine derivative or a medically acceptable salt thereof according to any one of (6) to (34), wherein $G^1$ is divalent substituted thiophene.

(52) A pyrrolo[3,2-d]pyrimidine derivative or a medically acceptable salt thereof according to any one of (6) to (34), wherein $G^1$ is divalent unsubstituted thiophene.

(53) A pyrrolo[3,2-d]pyrimidine derivative or a medically acceptable salt thereof according to any one of (6) to (34), wherein $G^1$ is divalent substituted pyridine.

(54) A pyrrolo[3,2-d]pyrimidine derivative or a medically acceptable salt thereof according to any one of (6) to (34), wherein $G^1$ is divalent unsubstituted pyridine.

(55) A pyrrolo[3,2-d]pyrimidine derivative or a medically acceptable salt thereof according to any one of (6) to (34), wherein $G^1$ is divalent substituted furan.

(56) A pyrrolo[3,2-d]pyrimidine derivative or a medically acceptable salt thereof according to any one of (6) to (34), wherein $G^1$ is divalent unsubstituted furan.

(57) A pyrrolo[3,2-d]pyrimidine derivative or a medically acceptable salt thereof according to any one of (6) to (34), wherein $G^1$ is divalent substituted pyrrole.

(58) A pyrrolo[3,2-d]pyrimidine derivative or a medically acceptable salt thereof according to any one of (6) to (34), wherein $G^1$ is divalent unsubstituted pyrrole.

(59) A pyrrolo[3,2-d]pyrimidine derivative or a medically acceptable salt thereof according to any one of (6) to (34), wherein $G^1$ is divalent substituted thiazole.

(60) A pyrrolo[3,2-d]pyrimidine derivative or a medically acceptable salt thereof according to any one of (6) to (34), wherein $G^1$ is divalent unsubstituted thiazole.

(61) A pyrrolo[3,2-d]pyrimidine derivative or a medically acceptable salt thereof according to any one of (6) to (34), wherein $G^1$ is divalent substituted isooxazole.

(62) A pyrrolo[3,2-d]pyrimidine derivative or a medically acceptable salt thereof according to any one of (6) to (34), wherein $G^1$ is divalent unsubstituted isooxazole.

(63) A pyrrolo[3,2-d]pyrimidine derivative or a medically acceptable salt thereof according to any one of (6) to (34), wherein $G^1$ is divalent substituted pyrazole.

(64) A pyrrolo[3,2-d]pyrimidine derivative or a medically acceptable salt thereof according to any one of (6) to (34), wherein $G^1$ is divalent unsubstituted pyrazole.

(65) A pyrrolo[3,2-d]pyrimidine derivative or a medically acceptable salt thereof according to any one of (6) to (34), wherein $G^1$ is divalent substituted pyrimidine.

(66) A pyrrolo[3,2-d]pyrimidine derivative or a medically acceptable salt thereof according to any one of (6) to (34), wherein $G^1$ is divalent unsubstituted pyrimidine.

(67) A pyrrolo[3,2-d]pyrimidine derivative or a medically acceptable salt thereof according to any one of (6) to (34), wherein $G^1$ is divalent substituted quinazoline.

(68) A pyrrolo[3,2-d]pyrimidine derivative or a medically acceptable salt thereof according to any one of (6) to (34), wherein $G^1$ is divalent unsubstituted quinazoline.

(69) A pyrrolo[3,2-d]pyrimidine derivative or a medically acceptable salt thereof according to any one of (1) to (5), wherein $A^1$-$A^2$-$G^1$ bond in the form of $A^1$-C(=O)-$G^1$, and $G^1$ is divalent unsubstituted pyrrolidine, piperidine, morpholine, thiomorpholine, homopiperidine, homopiperazine, 1,2,3,6-tetrahydropyridine or piperazine, bonded to $A^1$-C(=O) through the nitrogen atom.

(70) A pyrrolo[3,2-d]pyrimidine derivative or a medically acceptable salt thereof according to any one of (1) to (5), wherein $A^1$-$A^2$-$G^1$ bond in the form of $A^1$-C(=O)-$G^1$, and $G^1$ is divalent substituted pyrrolidine, piperidine, morpholine, thiomorpholine, homopiperidine, homopiperazine, 1,2,3,6-tetrahydropyridine or piperazine, bonded to $A^1$-C(=O) through the nitrogen atom.

(71) A pyrrolo[3,2-d]pyrimidine derivative or a medically acceptable salt thereof according to any one of (1) to (5), wherein $A^1$-$A^2$-$G^1$ bond in the form of $A^1$-C(=O)-$G^1$, and $G^1$ is divalent substituted piperidine, bonded to $A^1$-C(=O) through the nitrogen atom.

(72) A pyrrolo[3,2-d]pyrimidine derivative or a medically acceptable salt thereof according to any one of (1) to (5), wherein $A^1$-$A^2$-$G^1$ bond in-the form of $A^1$-C(=O)-$G^1$, and $G^1$ is divalent unsubstituted piperidine, bonded to $A^1$-C(=O) through the nitrogen atom.

(73) A pyrrolo[3,2-d]pyrimidine derivative or a medically acceptable salt thereof according to any one of (1) to (5), wherein $A^1$-$A^2$-$G^1$ bond in the form of $A^1$-C(=O)-$G^1$, and $G^1$ is divalent substituted piperazine, bonded to $A^1$-C(=O) through the nitrogen atom.

(74) A pyrrolo[3,2-d]pyrimidine derivative or a medically acceptable salt thereof according to any one of (1) to (5), wherein $A^1$-$A^2$-$G^1$ bond in the form of $A^1$-C(=O)-$G^1$, and $G^1$ is divalent unsubstituted piperazine, bonded to $A^1$-C(=O) through the nitrogen atom.

(75) A pyrrolo[3,2-d]pyrimidine derivative or a medically acceptable salt thereof according to any one of (35) to (74), wherein $A^3$ is a single bond.

(76) A pyrrolo[3,2-d]pyrimidine derivative or a medically acceptable salt thereof according to any one of (35) to (74), wherein $A^3$ is —$CH_2$—.

(77) A pyrrolo[3,2-d]pyrimidine derivative or a medically acceptable salt thereof according to any one of (35) to (74), wherein $A^3$ is —$(CH_2)_2$—.

(78) A pyrrolo[3,2-d]pyrimidine derivative or a medically acceptable salt thereof according to any one of (35) to (74), wherein $A^3$ is —$(CH_2)_3$—.

(79) A pyrrolo[3,2-d]pyrimidine derivative or a medically acceptable salt thereof according to any one of (75) to (78), wherein $A^4$ is a single bond.

(80) A pyrrolo[3,2-d]pyrimidine derivative or a medically acceptable salt thereof according to any one of (75) to (78), wherein $A^3$-$A^4$-$G^2$ bond in the form of $A^3$-C(=O)O-$G^2$.

(81) A pyrrolo[3,2-d]pyrimidine derivative or a medically acceptable salt thereof according to any one of (75) to (78), wherein $A^3$-$A^4$-$G^2$ bond in the form of $A^3$-C(=O)-$G^2$.

(82) A pyrrolo[3,2-d]pyrimidine derivative or a medically acceptable salt thereof according to any one of (75) to (78), wherein $A^3$-$A^4$-$G^2$ bond in the form of $A^3$-C(=O)N$R^{121}$-$G^2$.

(83) A pyrrolo[3,2-d]pyrimidine derivative or a medically acceptable salt thereof according to any one of (75) to 78, wherein $A^3$-$A^4$-$G^2$ bond in the form of $A^3$-O-$G^2$.

(84) A pyrrolo[3,2-d]pyrimidine derivative or a medically acceptable salt thereof according to any one of (75) to (78), wherein $A^3$-$A^4$-$G^2$ bond in the form of $A^3$-N$R^{124}$-$G^2$.

(85) A pyrrolo[3,2-d]pyrimidine derivative or a medically acceptable salt thereof according to any one of (75) to (78), wherein $A^3$-$A^4$-$G^2$ bond in the form of $A^3$-N$R^{125}$C(=O)-$G^2$.

(86) A pyrrolo[3,2-d]pyrimidine derivative or a medically acceptable salt thereof according to any one of (75) to (78), wherein $A^3$-$A^1$-$G^2$ bond in the form of $A^3$-N$R^{126}$S(=O)$_2$$G^2$.

(87) A pyrrolo[3,2-d]pyrimidine derivative or a medically acceptable salt thereof according to any one of (75) to (78), wherein $A^3$-$A^4$-$G^2$ bond in the form of $A^3$-N$R^{120}$C(=O)O-$G^2$.

(88) A pyrrolo[3,2-d]pyrimidine derivative or a medically acceptable salt thereof according to any one of (75) to (78), wherein $A^3$-$A^4$-$G^2$ bond in the form of $A^3$-N$R^{128}$C(=O)N$R^{129}$-$G^2$.

(89) A pyrrolo[3,2-d]pyrimidine derivative or a medically acceptable salt thereof according to any one of (79) to (88), wherein $G^2$ is a hydrogen atom.

(90) A pyrrolo[3,2-d]pyrimidine derivative or a medically acceptable salt thereof according to any one of (79) to (88), wherein $G^2$ is a substituted or unsubstituted $C_{1-10}$ aliphatic hydrocarbon group.

(91) A pyrrolo[3,2-d]pyrimidine derivative or a medically acceptable salt thereof according to any one of (79) to (88), wherein $G^2$ is a substituted or unsubstituted $C_{3-8}$ alicyclic hydrocarbon group.

(92) A pyrrolo[3,2-d]pyrimidine derivative or a medically acceptable salt thereof according to any one of (79) to (88), wherein $G^2$ is a substituted or unsubstituted $C_{6-14}$ aromatic hydrocarbon group.

(93) A pyrrolo[3,2-d]pyrimidine derivative or a medically acceptable salt thereof according to any one of (79) to (88), wherein $G^2$ is a substituted or unsubstituted heterocyclic group having in the ring 1 to 4 atoms selected from the group consisting of oxygen, nitrogen and sulfur atoms.

(94) A pyrrolo[3,2-d]pyrimidine derivative or a medically acceptable salt thereof according to any one of (36) to (74), wherein -$A^3$-$A^4$-$G^2$ collectively represent hydrogen.

(95) A pyrrolo[3,2-d]pyrimidine derivative or a medically acceptable salt thereof according to any one of (36) to (93), wherein -$A^3$-$A^4$-$G^2$ collectively represent a group other than hydrogen.

(96) A pyrrolo[3,2-d]pyrimidine derivative or a medically acceptable salt thereof according to (1) or any one of (75) to (94), wherein X is sulfur, $A^1$ is —$(CH_2)_2$—, $A^1$-$A^2$-$G^1$ bond in the form of $A^1$-NHC(=O)-$G^1$, and $G^1$ is substituted divalent benzene.

(97) A pyrrolo[3,2-d]pyrimidine derivative or a medically acceptable salt thereof according to (1) or any one of (75) to (93), wherein X is sulfur, $A^1$ is —$(CH_2)_2$—, $A^1$-$A^2$-$G^1$ bond in the form of $A^1$-NHC(=O)-$G^1$, $G^1$ is unsubstituted divalent benzene, and $A^3$-$A^4$-$G^2$ are collectively a group other than hydrogen.

(98) A pyrrolo[3,2-d]pyrimidine derivative or a medically acceptable salt thereof according to (1) or any one of (75) to (94), wherein X is sulfur, $A^1$ is —$(CH_2)_2$—, $A^1$-$A^2$-$G^1$ bond in the form of $A^1$-NHC(=O)-$G^1$, and $G^1$ is a divalent monocyclic or bicyclic $C_{2-9}$ aromatic heterocyclic group having in the ring 1 to 3 atoms selected from the group consisting of oxygen, nitrogen and sulfur atoms.

(99) A pyrrolo[3,2-d]pyrimidine derivative or a medically acceptable salt thereof according to (1) or any one of (75) to (94), wherein x is sulfur, $A^1$ is —$(CH_2)_2$—, $A^1$-$A^2$-$G^1$ bond in the form of $A^1$-NHC(=O)-$G^1$, and $G^1$ is a substituted divalent monocyclic or bicyclic $C_{2-9}$ aromatic heterocyclic group having in the ring 1 to 3 atoms selected from the group consisting of oxygen, nitrogen and sulfur atoms.

(100) A pyrrolo[3,2-d]pyrimidine derivative or a medically acceptable salt thereof according to (1) or any one of (75) to (93), wherein X is sulfur, $A^1$ is —$(CH_2)_2$—, $A^1$-$A^2$-$G^1$ bond in the form of $A^1$-NHC(=O)-$G^1$, and $G^1$ is an unsubstituted divalent monocyclic or bicyclic $C_{2-9}$ aromatic heterocyclic group having in the ring 1 to 3 atoms selected from the group consisting of oxygen, nitrogen and sulfur atoms, and $A^3$-$A^4$-$G^2$ are collectively a group other than hydrogen.

(101) A pyrrolo[3,2-d]pyrimidine derivative or a medically acceptable salt thereof according to (1) or any one of (75) to (94), wherein X is sulfur, $A^1$ is —$(CH_2)_2$—, $A^1$-$A^2$-$G^1$ bond in the form of $A^1$-NH-$G^1$, and $G^1$ is substituted divalent benzene.

(102) A pyrrolo[3,2-d]pyrimidine derivative or a medically acceptable salt thereof according to (1) or any one of (75) to (93), wherein X is sulfur, $A^1$ is —$(CH_2)_2$—, $A^1$-$A^2$-$G^1$ (103) A pyrrolo[3,2-d]pyrimidine derivative or a medically acceptable salt thereof according to (1) or any one of (75) to (94), wherein X is sulfur, $A^1$ is —$(CH_2)_2$—, $A^1$-$A^2$-$G^1$ bond in the form of $A^1$-NH-$G^1$, and $G^1$ is a substituted divalent monocyclic or bicyclic $C_{2-9}$ aromatic heterocyclic group having in the ring 1 to 3 atoms selected from the group consisting of oxygen, nitrogen and sulfur atoms.

(104) A pyrrolo[3,2-d]pyrimidine derivative or a medically acceptable salt thereof according to (1) or any one of (75) to (93), wherein X is sulfur, $A^1$ is —$(CH_2)_2$—, $A^1$-$A^2$-G bond in the form of $A^1$-NH-$G^1$, and $G^1$ is an unsubstituted divalent monocyclic or bicyclic $C_{2-9}$ aromatic heterocyclic group having in the ring 1 to 3 atoms selected from the group consisting of oxygen, nitrogen and sulfur atoms, and $A^3$-$A^4$-$G^2$ are collectively a group other than hydrogen.

(105) A pyrrolo[3,2-d]pyrimidine derivative or a medically acceptable salt thereof according to (1) or any one of (75) to (94), wherein X is sulfur, $A^1$ is —$(CH_2)_2$—, $A^1$-$A^2$-$G^1$ bond in the form of $A^1$-C(=O)-$G^1$, $G^1$ is a divalent monocyclic $C_{2-9}$ heterocyclic group having in the ring 1 or 2 atoms selected from the group consisting of oxygen, nitrogen and sulfur atoms, and $G^1$ is bonded to $A^1$-C(=O)— through a nitrogen atom.

(106) A pyrrolo[3,2-d]pyrimidine derivative or a medically acceptable salt thereof according to (1) or any one of (75) to (94), wherein X is sulfur, $A^1$ is —$(CH_2)_2$—, $A^1$-$A^2$-$G^1$ bond in the form of $A^1$-C(=O)-$G^1$, $G^1$ is a substituted divalent monocyclic $C_{2-9}$ heterocyclic group having in the ring 1 or 2 atoms selected from the group consisting of oxygen, nitrogen and sulfur atoms, and $G^1$ is bonded to $A^1$-C(=O)— through a nitrogen atom.

(107) A pyrrolo[3,2-d]pyrimidine derivative or a medically acceptable salt thereof according to (1) or any one of (75) to (93), wherein X is sulfur, $A^1$ is —$(CH_2)_2$—, $A^1$-$A^2$-$G^1$ bond in the form of $A^1$-C(=O)-$G^1$, $G^1$ is an unsubstituted divalent monocyclic $C_{2-9}$ heterocyclic group having in the ring 1 or 2 atoms selected from the group consisting of oxygen, nitrogen and sulfur, $G^1$ is bonded to $A^1$-C(=O)— through a nitrogen atom, and $A^3$-$A^4$-$G^2$ are collectively a group other than hydrogen.

(108) A pyrrolo[3,2-d]pyrimidine derivative or a medically acceptable salt thereof according to any one of (1) to (107), wherein $A^5$ is a single bond.

(109) A pyrrolo[3,2-d]pyrimidine derivative or a medically acceptable salt thereof according to any one of (1) to (107), wherein $A^5$ is a group binding the carbon atom of the pyrrole ring to which $A^5$ is bonded and $R^2$ in the form of $R^2$—$NR^{201}$-pyrrole ring carbon.

(110) A pyrrolo[3,2-d]pyrimidine derivative or a medically acceptable salt thereof according to (109), wherein $R^2$ is a hydrogen atom.

(111) A pyrrolo[3,2-d]pyrimidine derivative or a medically acceptable salt thereof according to (108), wherein $R^2$ is fluorine, chlorine, bromine or iodine.

(112) A pyrrolo[3,2-d]pyrimidine derivative or a medically acceptable salt thereof according to (108) or (109), wherein $R^2$ is a substituted or unsubstituted $C_{1-10}$ aliphatic hydrocarbon group.

(113) A pyrrolo[3,2-d]pyrimidine derivative or a medically acceptable salt thereof according to (108) or (109), wherein $R^2$ is a substituted or unsubstituted $C_{3-8}$ aliphatic hydrocarbon group.

(114) A pyrrolo[3,2-d]pyrimidine derivative or a medically acceptable salt thereof according to (108) or (109), wherein $R^2$ is a substituted or unsubstituted $C_{6-14}$ aromatic hydrocarbon group.

(115) A pyrrolo[3,2-d]pyrimidine derivative or a medically acceptable salt thereof according to (108) or (109), wherein $R^2$ is a substituted or unsubstituted heterocyclic group having in the ring 1 to 4 atoms selected from the group consisting of oxygen, nitrogen and sulfur atoms.

(116) A pyrrolo[3,2-d]pyrimidine derivative or a medically acceptable salt thereof according to any one of (1) to (107), wherein $R^2$-$A^5$- is substituted or unsubstituted isopropylamino, substituted or unsubstituted cyclopropylamino, substituted or unsubstituted cyclopentylamino, substituted or unsubstituted dimethylamino, substituted or unsubstituted N-methyl-ethylamino, substituted or unsubstituted N-methyl-2-propenylamino, substituted or unsubstituted N-methyl-2-propynylamino, substituted or unsubstituted 1-pyrrolidinyl, substituted or unsubstituted 1-piperazinyl, substituted or unsubstituted 1-piperidino, substituted or unsubstituted 1-morpholino or substituted or unsubstituted 1-homopiperidinyl.

(117) A pyrrolo[3,2-d]pyrimidine derivative or a medically acceptable salt thereof according to any one of (1) to (107), wherein $R^2$-$A^5$- is substituted or unsubstituted cyclopropyl, substituted or unsubstituted phenyl, substituted or unsubstituted furyl, substituted or unsubstituted thienyl, substituted or unsubstituted pyrrolyl, substituted or unsubstituted pyrazolyl, substituted or unsubstituted oxazolyl, substituted or unsubstituted isooxazolyl, substituted or unsubstituted thiazolyl, substituted or unsubstituted isothiazolyl, substituted or unsubstituted imidazolyl, substituted or unsubstituted pyridyl, substituted or unsubstituted pyrazinyl, substituted or unsubstituted pyrimidinyl, substituted or unsubstituted pyridazinyl, substituted or unsubstituted benzofuranyl or substituted or unsubstituted benzothiophenyl.

(118) A pyrrolo[3,2-d]pyrimidine derivative or a medically acceptable salt thereof according to any one of (1) to (107), wherein $R^2$-$A^5$- is substituted or unsubstituted 2-furyl, substituted or unsubstituted 2-thienyl, substituted or unsubstituted 2-pyrrolyl, substituted or unsubstituted 2-imidazolyl, substituted or unsubstituted 5-imidazolyl, substituted or unsubstituted 2-oxazolyl, substituted or unsubstituted 5-oxazolyl, substituted or unsubstituted 5-isooxazolyl, substituted or unsubstituted 2-thiazolyl, substituted or unsubstituted 5-thiazolyl, substituted or unsubstituted 5-isothiazolyl, substituted or unsubstituted 3-isothiazolyl, substituted or unsubstituted 2-pyridyl, substituted or unsubstituted 2-pyrimidinyl, substituted or unsubstituted 2-benzofuranyl or substituted or unsubstituted 2-benzothiophenyl.

(119) A pyrrolo[3,2-d]pyrimidine derivative or a medically acceptable salt thereof according to any one of (1) to (107), wherein $R^2$-$A^5$- is substituted or unsubstituted 2-furyl, substituted or unsubstituted 2-thienyl or substituted or unsubstituted 2-pyrrolyl.

(120) A pyrrolo[3,2-d]pyrimidine derivative or a medically acceptable salt thereof according to any one of (1) to (107), wherein $R^2$-$A^5$- is 3-methyl(2-furyl), 3-chloro(2-furyl), 3-methyl(2-thienyl), 3-chloro(2-thienyl) or 1-methylpyrrol-2-yl.

(121) A pyrrolo[3,2-d]pyrimidine derivative or a medically acceptable salt thereof according to any one of (1) to (107), wherein $A^5$ is a group binding the carbon atom of the pyrrole ring to which $A^5$ is bonded and $R^2$ in the form of $R^2$—$NR^{201}$-pyrrole ring carbon, and $R^2$ is a substituted or unsubstituted heterocyclic group having in the ring 1 to 4 atoms selected from the group consisting of oxygen, nitrogen and sulfur atoms.

(122) A pharmaceutical composition comprising a pyrrolo[3,2-d]pyrimidine derivative or a medically acceptable salt thereof according to any one of (1) to (121), and a pharmaceutically acceptable carrier.

(123) A GSK-3 inhibitor comprising a pyrrolo[3,2-d]pyrimidine derivative or a medically acceptable salt thereof according to any one of (1) to (121).

(124) A therapeutic or prophylactic agent for a GSK-3 associated disease, comprising a pyrrolo[3,2-d]pyrimidine derivative or a medically acceptable salt thereof according to any one of (1) to (121).

(125) A therapeutic or prophylactic agent according to (124), wherein said GSK-3 associated disease is selected from the group consisting of diabetes, diabetes complications, Alzheimer's disease, neurodegenerative diseases, manic depression, traumatic encephalopathy, alopecia, inflammatory diseases, cancer and immune deficiency.

(126) A pyrrolo[3,2-d]pyrimidine derivative represented by formula (II):

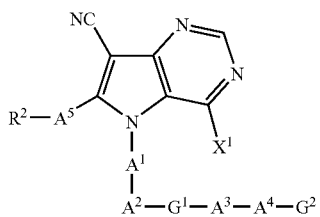

[wherein the definitions of $A^1, A^2, A^3, A^4, A^5, G^1, G^2$ and $R^2$ are the same as for formula (I) above, and $X^1$ represents chlorine, bromine, iodine, $C_{2-10}$ acylthio, $C_{2-8}$ alkoxymethylthio or $C_{1-8}$ alkyl- or arylsulfonyloxy].

(127) A pyrrolo[3,2-d]pyrimidine derivative according to (126), wherein $X^1$ is chlorine or trifluoromethanesulfonyloxy.

(128) A pyrrolo[3,2-d]pyrimidine derivative represented by formula (Ic):

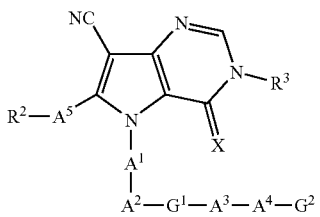

[wherein the definitions of $A^1, A^2, A^3, A^4, A^5, G^1, G^2, R^2$ and X are the same as for formula (I) above, and $R^3$ represents $C_{2-10}$ acyl, $C_{2-10}$ alkoxymethyl or substituted or unsubstituted benzyl].

BEST MODE FOR CARRYING OUT THE INVENTION

In formula (I) above, X represents an oxygen or sulfur atom. That is, the pyrrolo[3,2-d]pyrimidine derivatives of formula (I) above comprise the pyrrolo[3,2-d]pyrimidine derivatives represented by the following formula (Ia):

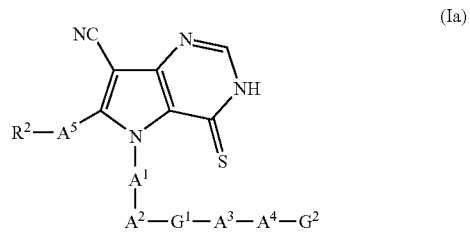

[wherein the definitions of $A^1, A^2, A^3, A^4, A^5, G^1, G^2$ and $R^2$ have the same definitions as $A^1, A^2, A^3, A^4, A^5, G^1, G^2$ and $R^2$ in formula (I) above]

and the following formula (Ib):

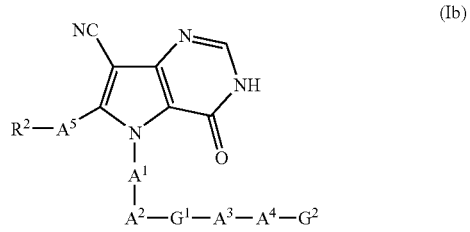

[wherein the definitions of $A^1, A^2, A^3, A^4, A^5, G^1, G^2$ and $R^2$ have the same definitions as $A^1, A^2, A^3, A^4, A^5, G^1, G^2$ and $R^2$ in formula (I) above].

X is most preferably sulfur.

In formula (I) above, $A^1$ represents a single bond or a $C_{1-6}$ aliphatic hydrocarbon group with the bonded nitrogen atom and $A^2$ being bonded on the same or different carbon atoms of $A^1$. As examples of $C_{1-6}$ aliphatic hydrocarbon groups for $A^1$ there may be mentioned methane, ethane, propane, butane, 2-methylpropane, pentane, 2-methylbutane, 2,2-dimethylpropane, hexane, 2-methylpentane, 3-methylpentane, 2,2-dimethylbutane, 2,3-dimethylbutane and 2,2,3-trimethylpropane. As examples of $C_{1-6}$ aliphatic hydrocarbon groups with the bonded nitrogen atom and $A^2$ being bonded on the same or different carbon atoms of $A^1$, there may be mentioned —CH$_2$—, —(CH$_2$)$_2$—, —(CH$_2$)$_3$—, —(CH$_2$)$_4$—, —(CH$_2$)$_5$—, —(CH$_2$)$_6$—, —CH(CH$_3$)—, —CH(CH$_3$)CH$_2$—, —CH(CH$_3$)CH(CH$_3$)—, —C(CH$_3$)$_2$CH$_2$—, —CH(CH$_3$)(CH$_2$)$_2$—, —CH$_2$CH(CH$_3$)CH$_2$—, —CH(CH$_3$)CH(CH$_3$)CH$_2$—, —CH(CH$_3$)CH$_2$CH(CH$_3$)—, —CH$_2$C(CH$_3$)$_2$CH$_2$—, —CH(CH$_3$)C(CH$_3$)$_2$CH$_2$—, —CH(CH$_2$CH$_3$) (CH$_2$)$_2$—, —CH$_2$CH(CH$_2$CH$_3$)CH$_2$—, —CH(CH$_2$CH$_3$)CH(CH$_3$)CH$_2$—, —CH(CH$_3$)CH(CH$_2$CH$_3$)CH$_2$—, —CH(CH$_2$CH$_3$)CH$_2$CH(CH$_3$)—, —CH(CH$_3$)(CH$_2$)$_3$—, —CH$_2$CH(CH$_3$)(CH$_2$)$_2$—, —CH(CH$_3$)CH(CH$_3$) (CH$_2$)$_2$—, —CH(CH$_3$)CH$_2$CH(CH$_3$)CH$_2$—, —CH$_2$CH(CH$_3$)CH(CH$_3$)CH$_2$—, —CH$_2$C(CH$_3$)$_2$(CH$_2$)$_2$—, —CH(CH$_3$)C(CH$_3$)$_2$(CH$_2$)$_2$—, —CH(CH$_2$CH$_3$) (CH$_2$)$_3$—, —CH$_2$CH(CH$_2$CH$_3$)(CH$_2$)$_2$—, —CH(CH$_3$)(CH$_2$)$_4$—, —CH$_2$CH(CH$_3$)(CH$_2$)$_3$— and —(CH$_2$)$_2$CH(CH$_3$)(CH$_2$)$_2$—. Preferred among these are —CH$_2$—, —(CH$_2$)$_2$—, —(CH$_2$)$_3$—, —(CH$_2$)$_4$—, —CH(CH$_3$)CH$_2$—, —CH(CH$_3$)CH(CH$_3$)—, —CH(CH$_3$) (CH$_2$)$_2$—, —CH$_2$CH(CH$_3$)CH$_2$— and —CH(CH$_3$)CH(CH$_3$)CH$_2$—, with —(CH$_2$)$_2$— and —(CH$_2$)$_3$— being more preferred and —(CH$_2$)$_2$— being especially preferred for $A^1$.

$A^2$ in formula (I) above represents a single bond, or a group binding $A^1$ and $G^1$ in the form of $A^1$-C(=O)-$G^1$, $A^1$-C(=O)

O-$G^1$, $A^1$-C(=O)$NR^{11}$-$G^1$, $A^1$-C(=S)$NR^{102}$-$G^1$, $A^1$-C(=$NR^{103}$)-G, $A^1$-O-$G^1$, $A^1$-OC(=O)-$G^1$, $A^1$-$NR^{104}$-$G^1$, $A^1$-$NR^{105}$C(=O)-$G^1$, $A^1$-$NR^{106}$S(=O)$_2$-$G^1$, $A^1$-$NR^{107}$C(=O)O-$G^1$, $A^1$-$NR^{108}$C(=O)$NR^{109}$-$G^1$, $A^1$-$NR^{110}$C(=S)-$G^1$, $A^1$-$NR^{111}$C(=S)$NR^{112}$-$G^1$, $A^1$-S-$G^1$, $A^1$-S(=O)-$G^1$, $A^1$-S(=O)$_2$-$G^1$ or $A^1$-S(=O)$_2$$NR^{113}$-$G^1$ (where $R^{101}$-$R^{113}$ each independently represent hydrogen or a $C_{1-4}$ aliphatic hydrocarbon group). As examples of $C_{1-4}$ aliphatic hydrocarbon groups for $R^{101}$ when $A^1$ and $G^1$ are bonded in the form of $A^1$-C(=O)$NR^{101}$-$G^1$, there may be mentioned methyl, ethyl, propyl, isopropyl, butyl, isobutyl, s-butyl, t-butyl, 2-propenyl, 2-butenyl, 3-butenyl, 2-propynyl, 2-butynyl and 3-butynyl. The $C_{1-4}$ aliphatic hydrocarbon group may be optionally substituted with one or more substituent selected from the group consisting of fluorine, chlorine, bromine, iodine, hydroxyl, methoxy, ethoxy, oxo, cyano, carboxyl, carbamoyl, amino, sulfo and phenyl. As preferred examples of $R^{101}$ there may be mentioned hydrogen, methyl, ethyl and propyl, with hydrogen being particularly preferred. As examples of $C_{1-4}$ aliphatic hydrocarbon groups for $R^{102}$ when $A^1$ and $G^1$ are in the form of $A^1$-C(=S)$NR^{102}$-$G^1$, there may be mentioned the same ones as mentioned above for $R^{101}$. As preferred examples of $R^{102}$ there may be mentioned hydrogen, methyl, ethyl and propyl, with hydrogen being particularly preferred. As examples of $C_{1-4}$ aliphatic hydrocarbon groups for $R^{103}$ when $A^1$ and $G^1$ are in the form of $A^1$-C(=$NR^{103}$)-$G^1$, there may be mentioned the same ones as mentioned above for $R^{101}$. As preferred examples of $R^{103}$ there may be mentioned hydrogen, methyl, ethyl and propyl, with hydrogen being particularly preferred. As examples of $C_{1-4}$ aliphatic hydrocarbon groups for $R^{104}$ when $A^1$ and $G^1$ are in the form of $A^1$-$NR^{104}$-$G^1$, there may be mentioned the same ones as mentioned above for $R^{101}$. As preferred examples of $R^{104}$ there may be mentioned hydrogen, methyl, ethyl and propyl, with hydrogen being particularly preferred. As examples of $C_{1-4}$ aliphatic hydrocarbon groups for $R^{105}$ when $A^1$ and $G^1$ are in the form of $A^2$-$NR^{105}$C(=O)-$G^1$, there may be mentioned the same ones as mentioned above for $R^{110}$. As preferred examples of $R^{105}$ there may be mentioned hydrogen, methyl, ethyl and propyl, with hydrogen being particularly preferred. As examples of $C_{1-4}$ aliphatic hydrocarbon groups for $R^{106}$ when $A^1$ and $G^1$ are in the form of A-$NR^{106}$S(=O)$_2$-$G^1$, there may be mentioned the same ones as mentioned above for $R^{101}$. As preferred examples of $R^{106}$ there may be mentioned hydrogen, methyl, ethyl and propyl, with hydrogen being particularly preferred. As examples of $C_{1-4}$ aliphatic hydrocarbon groups for $R^{107}$ when $A^1$ and $G^1$ are in the form of $A^1$-$NR^{107}$C(=O)O-$G^1$, there may be mentioned the same ones as mentioned above for $R^{101}$. As preferred examples of $R^{107}$ there may be mentioned hydrogen, methyl, ethyl and propyl, with hydrogen being particularly preferred. As examples of $C_{1-4}$ aliphatic hydrocarbon groups for $R^{108}$ and $R^{109}$ when $A^1$ and $G^1$ are in the form of $A^1$-$NR^{108}$C(=O)$NR^{109}$-$G^1$, there may be mentioned the same ones as mentioned above for $R^{101}$. As preferred examples of $R^{108}$ and $R^{109}$ there may be mentioned hydrogen, methyl, ethyl and propyl, with hydrogen being particularly preferred. As examples of $C_{1-4}$ aliphatic hydrocarbon groups for $R^{110}$ when $A^1$ and $G^1$ are in the form of $A^1$-$NR^{110}$C(=S)-$G^1$, there may be mentioned the same ones as mentioned above for $R^{101}$. As preferred examples of $R^{110}$ there may be mentioned hydrogen, methyl, ethyl and propyl, with hydrogen being particularly preferred. As examples of $C_{1-4}$ aliphatic hydrocarbon groups for $R^{111}$ and $R^{112}$ when $A^1$ and $G^1$ are in the form of $A^1$-$NR^{111}$C(=S)$NR^{112}$-$G^1$, there may be mentioned the same ones as mentioned above for $R^{101}$. As preferred examples of $R^{111}$ and $R^{112}$ there may be mentioned hydrogen, methyl, ethyl and propyl, with hydrogen being particularly preferred. As examples of $C_{1-4}$ aliphatic hydrocarbon groups for $R^{113}$ when $A^1$ and $G^1$ are in the form of $A^1$-S(=O)$_2$$NR^{113}$-$G^1$, there may be mentioned the same ones as mentioned above for $R^{101}$. As preferred examples of $R^{113}$ there may be mentioned hydrogen, methyl, ethyl and propyl, with hydrogen being particularly preferred. As preferred examples of $A^2$ there may be mentioned groups such that $A^1$ and $G^1$ are bonded in the form of $A^1$-C(=O)-$G^1$, $A^1$-C(=O)$NR^{101}$-$G^1$, $A^1$-O-$G_1$, $A^1$-$NR^{104}$-$G^1$, $A^1$-$NR^{105}$C(=O)-$G^1$, $A^1$-$NR^{109}$C(=O)$NR^{109}$-$G^1$, $A^1$-$NR^{110}$C(=S)-$G^1$ and $A^1$-$NR^{111}$C(=S)$NR^{112}$-$G^1$, with $A^1$-C(=O)-$G^1$, $A^1$-C(=O)$NR^{101}$$G^1$, $A^1$-$NR^{104}$-$G^1$, $A^1$-$NR^{105}$C(=O)-$G^1$ and $A^1$-$NR^{110}$C(=S)-$G^1$ being particularly preferred (wherein $R^{101}$, $R^{104}$, $R^{105}$, $R^{108}$, $R^{109}$, $R^{110}$, $R^{111}$ and $R^{112}$ have the same definitions as above). As even more preferred groups among these there may be mentioned those such that $A^1$ and $G^1$ are bonded in the form of $A^1$-C(=O)-$G^1$, $A^1$-NHC(=O)-$G^1$ and $A^1$-NH-$G^1$. These bonding forms mentioned as preferred and more preferred examples of $A^2$ are even more preferably combined with a structure of formula (I) above wherein X is sulfur and $A^1$ is —(CH$_2$)$_2$—.

In formula (I), $A^3$ represents a single bond, or a $C_{1-6}$ aliphatic hydrocarbon group having $G^1$ and $A^4$ bonded on the same or different carbon atoms. As examples of $C_{1-6}$ aliphatic hydrocarbon groups for $A^3$ there may be mentioned the same ones as mentioned above for $A^1$, as well as —CH=CH—, —C(CH$_3$)=CH—, —C(CH$_3$)=C(CH$_3$)—, —C(CH$_2$CH$_3$)=CH—, —C(CH$_2$CH$_3$)=C(CH$_3$)—, —C(CH$_2$CH$_3$)=C(CH$_2$CH$_3$)—, —C(CH$_2$CH$_2$CH$_3$)=CH—, —C(CH$_2$CH$_2$CH$_3$)=C(CH$_3$)—, —CH=CHCH$_2$—, —C(CH$_3$)=CHCH$_2$—, —CH=C(CH$_3$)CH$_2$—, —CH=CHCH(CH$_3$)—, —C(CH$_3$)=C(CH$_3$)CH$_2$—, —C(CH$_3$)=CHCH(CH$_3$)—, —C(CH$_3$)=C(CH$_3$)CH(CH$_3$)—, —C(CH$_3$)=CHC(CH$_3$)$_2$—, —C(CH$_2$CH$_3$)=CHCH$_2$—, —CH=C(CH$_2$CH$_3$)CH$_2$—, —CH=CHCH(CH$_2$CH$_3$)—, —C(CH$_2$CH$_3$)=C(CH$_3$)CH$_2$—, —C(CH$_2$CH$_3$)=CHCH(CH$_3$)—, —C(CH$_3$)=C(CH$_2$CH$_3$)CH$_2$—, —CH=C(CH$_2$CH$_3$)CH(CH$_3$)—, —CH=CHCH(CH$_2$CH$_3$)—, —C(CH$_3$)=CHCH(CH$_2$CH$_3$)—, —CH=C(CH$_3$)CH(CH$_2$CH$_3$)—, —CH=CH(CH$_2$)$_2$—, —C(CH$_3$)=CH(CH$_2$)$_2$—, —CH=C(CH$_3$)(CH$_2$)$_2$—, —CH=CHC(CH$_3$)CH$_2$—, —CH=CHCH$_2$CH(CH$_3$)—, —C(CH$_3$)=C(CH$_3$)(CH$_2$)$_2$—, —C(CH$_3$)=CHCH(CH$_3$)CH$_2$—, —C(CH$_3$)=CHCH$_2$CH(CH$_3$)—, —CH$_2$CH=CHCH$_2$—, —CH(CH$_3$)CH=CHCH—, —CH$_2$C(CH$_3$)=CHCH$_2$—, —CH(CH$_3$)C(CH$_3$)=CHCH$_2$—, —CH(CH$_3$)CH=CHCH(CH$_3$)—, —CH(CH$_3$)CH=C(CH$_3$)CH$_2$—, —CH$_2$C(CH$_3$)=C(CH$_3$)CH$_2$—, —CH(CH$_2$CH$_3$)CH=CHCH$_2$— and —CH$_2$C(CH$_2$CH$_3$)=CHCH$_2$—. As preferred examples of $A^3$ there may be mentioned a single bond, —CH$_2$—, —(CH$_2$)$_2$—, —(CH$_2$)$_3$—, —(CH$_2$)$_4$—, —CH(CH$_3$)CH$_2$—, —CH(CH$_3$)CH(CH$_3$)—, —CH(CH$_3$)(CH$_2$)$_2$—, —CH=CH— and —CH=CHCH$_2$—. As particularly preferred groups there may be mentioned a single bond, —CH$_2$—, —(CH$_2$)$_2$— and —(CH$_2$)$_3$—.

In formula (I), $A^4$ represents a single bond or a group binding $A^3$ and G in the form of $A^3$-C(=O)-G 2, $A^3$-C(=O)O-$G^2$, $A^3$-C(=O)$NR^{121}$-$G^2$, $A^3$-C(=S)$NR^{122}$-$G^2$, $A^3$-C(=$NR^{123}$)-$G^2$, $A^3$-O-$G^2$, $A^3$-OC(=O)-$G^2$, $A^3$-$NR^{124}$-$G^2$, $A^3$-$NR^{125}$C(=O)-$G^2$, $A^3$-$NR^{126}$S(=O)$_2$-$G^2$, $A^3$-$NR^{127}$C(=O)O-$G^2$, $A^3$-$NR^{128}$C(=O)$NR^{129}$-$G^2$, $A^3$-$NR^{130}$C(=S)-$G^2$, $A^3$-$NR^{131}$C(=S)$NR^{132}$-$G^2$, $A^3$-S-$G^2$, $A^3$-S(=O)-$G^2$, $A^3$-S(=O)$_2$-$G^2$, $A^3$-S(=O)$_2$$NR^{133}$-$G^2$ (where $R^{121}$-$R^{133}$ each independently represent hydrogen or a $C_{1-4}$ aliphatic hydrocarbon group), or $A^3$-S(=O)$_2$O-$G^2$. As examples of $C_{1-4}$ aliphatic hydrocarbon groups for $R^{121}$ when $A^3$ and $G^2$ are bonded in the form of $A^3$-C(=O)$NR^{121}$-$G^2$, there may be mentioned the same ones as mentioned above for $R^{101}$ in $A^2$. As preferred examples of $R^{121}$ there may be mentioned hydrogen, methyl, ethyl and propyl, with hydrogen being particularly preferred. As examples of $C_{1-4}$ aliphatic hydrocarbon groups for $R^{122}$ when $A^3$ and $G^2$ are bonded in the form of $A^3$-C(=S)$NR^{122}$-$G^2$, there may be mentioned the same ones as mentioned above for $R^{101}$ in $A^2$. As preferred examples of $R^{122}$ there may be mentioned hydrogen, methyl, ethyl and propyl, with hydrogen being particularly preferred. As examples of $C_{1-4}$ aliphatic hydrocarbon groups for $R^{123}$ when $A^3$ and $G^2$ are bonded in the form of $A^3$-C(=$NR^{123}$)-$G^2$, there may be mentioned the same ones as mentioned above for $R^{101}$ in $A^2$. As preferred examples of $R^{123}$ there may be mentioned hydrogen, methyl, ethyl and propyl, with hydrogen being particularly preferred. As examples of $C_{1-4}$ aliphatic hydrocarbon groups for $R^{124}$ when $A^3$ and $G^2$ are bonded in the form of $A^3$-$NR^{124}$-$G^2$, there may be mentioned the same ones as mentioned above for $R^{101}$ in $A^2$. As preferred examples of $R^{124}$ there may be mentioned hydrogen, methyl, ethyl and propyl, with hydrogen being particularly preferred. As examples of $C_{1-4}$ aliphatic hydrocarbon groups for $R^{125}$ when $A^3$ and $G^2$ are bonded in the form of $A^3$-$NR^{125}$C(=O)-$G^2$, there may be mentioned the same ones as mentioned above for $R^{101}$ in $A^2$. As preferred examples of $R^{125}$ there may be mentioned hydrogen, methyl, ethyl and propyl, with hydrogen being particularly preferred. As examples of $C_{1-4}$ aliphatic hydrocarbon groups for $R^{126}$ when $A^3$ and $G^2$ are bonded in the form of $A^3$-$NR^{126}$S(=O)$_2$-$G^2$, there may be mentioned the same ones as mentioned above for $R^{101}$ in $A^2$. As preferred examples of $R^{126}$ there may be mentioned hydrogen, methyl, ethyl and propyl, with hydrogen being particularly preferred. As examples of $C_{1-4}$ aliphatic hydrocarbon groups for $R^{127}$ when $A^3$ and $G^2$ are bonded in the form of $A^3$-$NR^{127}$C(=O)O-$G^2$, there may be mentioned the same ones as mentioned above for $R^{101}$ in $A^2$. As preferred examples of $R^{127}$ there may be mentioned hydrogen, methyl, ethyl and propyl, with hydrogen being particularly preferred. As examples of $C_{1-4}$ aliphatic hydrocarbon groups for $R^{128}$ and $R^{129}$ when $A^3$ and $G^2$ are bonded in the form of $A^3$-$NR^{128}$C(=O)$NR^{129}$-$G^2$, there may be mentioned the same ones as mentioned above for $R^{101}$ in $A^2$. As preferred examples of $R^{128}$ and $R^{129}$ there may be mentioned hydrogen, methyl, ethyl and propyl, with hydrogen being particularly preferred. As examples of $C_{1-4}$ aliphatic hydrocarbon groups for $R^{130}$ when $A^3$ and $G^2$ are bonded in the form of $A^3$-$NR^{130}$C(=S)-$G^2$, there may be mentioned the same ones as mentioned above for $R^{101}$ in $A^2$. As preferred examples of $R^{130}$ there may be mentioned hydrogen, methyl, ethyl and propyl, with hydrogen being particularly preferred. As examples of $C_{1-4}$ aliphatic hydrocarbon groups for $R^{131}$ and $R^{132}$ when $A^3$ and $G^2$ are bonded in the form of $A^3$-$NR^{131}$C(=S)$NR^{132}$-$G^2$ there may be mentioned the same ones as mentioned above for $R^{101}$ in $A^2$. As preferred examples of $R^{131}$ and $R^{132}$ there may be mentioned hydrogen, methyl, ethyl and propyl, with hydrogen being particularly preferred. As examples of $C_{1-4}$ aliphatic hydrocarbon groups for $R^{133}$ when $A^3$ and $G^2$ are bonded in the form of $A^3$-S(=O)$_2$$NR^{133}$-$G^2$, there may be mentioned the same ones as mentioned above for $R^{101}$ in $A^2$. As preferred examples of $R^{133}$ there may be mentioned hydrogen, methyl, ethyl and propyl, with hydrogen being particularly preferred. As preferred groups for $A^4$ there may be mentioned a single bond, and groups such that $A^3$ and $G^2$ are bonded in the form of $A^3$-C(=O)-$G^2$, $A^3$-C(=O)O-$G^2$, $A^3$-C(=O)$NR^{121}$-$G^2$, $A^3$-O-$G^2$, $A^3$-$NR^{124}$-$G^2$, $A^3$-$NR^{125}$C(=O)-$G^2$, $A^3$-S(=O)$_{2-G}^2$ and $A^3$-S(=O)$_2$O-$G^2$ (wherein $R^{121}$, $R^{124}$ and $R^{125}$ are as defined above).

In formula (I) above, $G^1$ represents one group selected from among the following 1) to 4):

1) A single bond.

2) A substituted or unsubstituted $C_{3-8}$ alicyclic hydrocarbon group. (As substituents there may be mentioned one or more selected from the group consisting of fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, oxo, $C_{1-6}$ alkylsulfonyloxy, optionally substituted $C_{2-7}$ acyl, carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-8}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbons and optionally substituted $C_{1-6}$ aliphatic hydrocarbons.)

3) A substituted or unsubstituted $C_{6-14}$ aromatic hydrocarbon group. (As substituents there may be mentioned one or more selected from the group consisting of fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, oxo, $C_{1-6}$ alkylsulfonyloxy, optionally substituted $C_{2-7}$ acyl, carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-7}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbons and optionally substituted $C_{1-6}$ aliphatic hydrocarbons.)

4) A substituted or unsubstituted heterocyclic group having in the ring 1 to 4 atoms selected from the group consisting of oxygen, nitrogen and sulfur. (As substituents there may be mentioned one or more selected from the group consisting of fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, oxo, $C_{1-6}$ alkylsulfonyloxy, optionally substituted $C_{2-7}$ acyl, carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-9}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbons and optionally substituted $C_{1-6}$ aliphatic hydrocarbons.)

As examples of preferred $C_{3-8}$ alicyclic hydrocarbon groups when $G^1$ in formula (I) is a substituted or unsubstituted $C_{3-8}$ alicyclic hydrocarbon group, there may be mentioned divalent groups such as cyclopropane, cyclobutane, cyclopentane, cyclopentene, cyclohexane, cyclohexene, cycloheptane, cycloheptene, cyclooctane, bicycle[2.2.1]heptane, bicyclo[2.2.1]heptene, bicyclo[3.1.1]heptane and bicyclo[2.2.2]octane. As preferred $C_{3-8}$ alicyclic hydrocarbon groups for $G^1$ there may be mentioned divalent $C_{3-6}$ monocyclic alicyclic hydrocarbon groups such as cyclopropane, cyclopentane and cyclohexane.

As substituents for the substituted $C_{3-8}$ alicyclic hydrocarbon groups for $G^1$ there may be mentioned fluorine, chlorine, bromine, iodine, hydroxyl, $C_{1-7}$ alkoxy groups composed of linear or branched alkyl or cycloalkyl groups and oxy groups, such as methoxy, ethoxy, propoxy, isopropoxy, butoxy, isobutoxy, s-butoxy, t-butoxy, pentyloxy, isopentyloxy, neopentyloxy, t-pentyloxy, hexyloxy, isohexyloxy, 2-methylpentyloxy, 1-ethylbutoxy, cyclopropyloxy, cyclobutyloxy, cyclopentyloxy, cyclohexyloxy, cyclopropylmethyloxy, cyclopropylethyloxy, cyclopentylmethyloxy and cyclohexylmethyloxy; $C_{6-10}$ aryloxy groups such as phenoxy, 1-naphthoxy and 2-naphthoxy; $C_{7-9}$ aralkoxy groups such as benzyloxy, α-phenethyloxy, β-phenethyloxy and phenylpropyloxy; $C_{2-7}$ acyloxy groups such as acetoxy, propionyloxy, butyryloxy, isobutyryloxy, valeryloxy, isovaleryloxy, pivaloyloxy and hexanoyloxy; oxo; $C_{1-6}$ alkylsulfonyloxy groups composed of linear or branched alkyl and sulfonyloxy groups, such as methylsulfonyloxy, ethylsulfonyloxy, propylsulfonyloxy, butylsulfonyloxy and t-butylsulfonyloxy; $C_{2-7}$ acyl groups such as acetyl, propionyl, butyryl, isobutyryl, valeryl, isovaleryl, pivaloyl and hexanoyl; carboxyl; $C_{2-7}$ alkoxycarbonyl groups composed of linear or branched alkyl and oxycarbonyl groups, such as methoxycarbonyl, ethoxycarbonyl, propoxycarbonyl, isopropoxycarbonyl, butoxycarbonyl, isobutoxycarbonyl, s-butoxycarbonyl and t-butoxycarbonyl; carbamoyl; $C_{2-7}$ alkylcarbamoyl groups composed of linear or branched alkyl or cycloalkyl groups and carbamoyl groups, such as N-methylcarbamoyl, N-ethylcarbamoyl, N-propylcarbamoyl, N-isopropylcarbamoyl, N-butylcarbamoyl, N-isobutylcarbamoyl, N-s-butylcarbamoyl, N-t-butylcarbamoyl, N-pentylcarbamoyl, N-cyclopropylcarbamoyl, N-cyclobutylcarbamoyl, N-cyclopentylcarbamoyl, N-cyclohexylcarbamoyl, N-cycloheptylcarbamoyl, N-cyclopropylmethylcarbamoyl, N,N-dimethylcarbamoyl, N-ethyl-N-methylcarbamoyl, N,N-diethylcarbamoyl and N,N-dipropylcarbamoyl; amino; $C_{1-6}$ alkylamino groups composed of linear or branched alkyl or cycloalkyl groups and amino groups, such as methylamino, ethylamino, propylamino, isopropylamino, butylamino, isobutylamino, s-butylamino, t-butylamino, pentylamino, hexylamino, cyclopropylamino, cyclobutylamino, cyclopentylamino, cyclohexylamino, cyclopropylmethylamino, dimethylamino, N-ethylmethylamino, diethylamino, N-methylpropylamino, N-methylisopropylamino, N-methylbutylamino, N-methyl-t-butylamino, N-ethylisopropylamino, dipropylamino, diisopropylamino and ethylbutylamino; $C_{2-7}$ acylamino groups such as acetylamino, propionylamino, butyrylamino, isobutyrylamino, valerylamino and hexanoylamino; $C_{2-8}$ alkoxycarbonylamino groups such as methoxycarbonylamino, ethoxycarbonylamino and t-butoxycarbonylamino; $C_{1-6}$ alkylsulfonylamino groups such as methylsulfonylamino, ethylsulfonylamino, butylsulfonylamino and t-butylsulfonylamino; cyano; nitro; $C_{1-6}$ alkylthio groups such as methylthio, ethylthio, propylthio, isopropylthio, butylthio, isobutylthio, s-butylthio, t-butylthio, pentylthio and hexylthio; $C_{1-6}$ alkylsulfinyl groups composed of linear or branched alkyl or cycloalkyl groups and sulfinyl groups, such as methylsulfinyl, ethylsulfinyl, propylsulfinyl, isopropylsulfinyl, butylsulfinyl, isobutylsulfinyl, s-butylsulfinyl, t-butylsulfinyl, pentylsulfinyl and cyclopentylsulfinyl; $C_{1-6}$ alkylsulfonyl groups composed of linear or branched alkyl groups or cycloalkyl groups and sulfonyl groups, such as methylsulfonyl, ethylsulfonyl, propylsulfonyl, isopropylsulfonyl, butylsulfonyl, isobutylsulfonyl, s-butylsulfonyl, t-butylsulfonyl, pentylsulfonyl, hexylsulfonyl, cyclopentylsulfonyl and cyclohexylsulfonyl; sulfo; sulfamoyl; $C_{1-6}$ aminosulfonyl groups composed of linear or branched alkyl or cycloalkyl groups and aminosulfonyl groups, such as methylaminosulfonyl, ethylaminosulfonyl, propylaminosulfonyl, isopropylaminosulfonyl, butylaminosulfonyl, isobutylaminosulfonyl, s-butylaminosulfonyl, pentylaminosulfonyl, dimethylaminosulfonyl, N-ethyl-N-methylaminosulfonyl, diethylaminosulfonyl, dipropylaminosulfonyl, cyclopropylaminosulfonyl, cyclopentylaminosulfonyl, cyclohexylaminosulfonyl and cyclopropylmethylaminosulfonyl; $C_{3-6}$ alicyclic hydrocarbons such as cyclopropyl, cyclobutyl, cyclopentyl and cyclohexyl; and linear or branched $C_{1-6}$ aliphatic hydrocarbon groups optionally containing one unsaturated bond, such as methyl, ethyl, vinyl, ethynyl, propyl, 1-propenyl, 2-propenyl, isopropyl, isopropenyl, 1-propynyl, 2-propynyl, butyl, isobutyl, s-butyl, t-butyl, 1-butenyl, 2-butenyl, 3-butenyl, 1-methyl-1-propenyl, 2-methyl-1-propenyl, 1-methyl-2-propenyl, 2-methyl-2-propenyl, 1-butynyl, 2-butynyl, pentyl, isopentyl, neopentyl, t-pentyl, 1-pentenyl, 2-pentenyl, 3-pentenyl, 4-pentenyl, hexyl, 5-hexenyl, 4-methyl-3-pentenyl, isohexyl, 2-methylpentyl and 1-ethylbutyl.

The term "alkyl" according to the invention refers to linear or branched saturated aliphatic hydrocarbon groups such as methyl, ethyl, propyl, butyl, pentyl, hexyl, heptyl, octyl, isopropyl, isobutyl, s-butyl, t-butyl, isopentyl, neopentyl, t-pentyl and isohexyl.

The term "cycloalkyl" according to the invention refers to saturated alicyclic hydrocarbon groups such as cyclopropyl, cyclobutyl and cyclohexyl.

The $C_{1-7}$ alkoxy, $C_{2-7}$ acyl, $C_{2-7}$ alkylcarbamoyl, $C_{1-6}$ alkylamino, $C_{2-7}$ acylamino, $C_{3-6}$ alicyclic hydrocarbon and $C_{1-6}$ aliphatic hydrocarbon groups as substituents for the substituted $C_{3-8}$ alicyclic hydrocarbon groups for $G^1$ may be in turn substituted with one or more substituents selected from the group consisting of fluorine, chlorine, bromine, iodine, hydroxyl; $C_{1-6}$ alkoxy groups such as methoxy, ethoxy, propoxy, isopropoxy, butoxy, isobutoxy, s-butoxy, t-butoxy, pentyloxy and cyclopropyloxy; methoxymethyloxy; 2-methoxyethoxy; formyl; trifluoroacetyl; $C_{2-7}$ acyl groups such as acetyl, propionyl, butyryl, isobutyryl, valeryl and isovaleryl; oxo; carboxyl; $C_{2-7}$ alkoxycarbonyl groups such as methoxycarbonyl, ethoxycarbonyl, propoxycarbonyl, isopropoxycarbonyl, butoxycarbonyl, isobutoxycarbonyl and t-butoxycarbonyl; carbamoyl; $C_{2-7}$ alkylcarbamoyl groups such as N-methylcarbamoyl, N,N-dimethylcarbamoyl, N-ethylcarbamoyl, N-ethyl-N-methylcarbamoyl, N,N-diethylcarbamoyl, N-propylcarbamoyl, N-isopropylcarbamoyl, N-butylcarbamoyl, N-cyclopropylcarbamoyl and N-cyclopropylmethylcarbamoyl; amino; $C_{1-6}$ alkylamino groups such as methylamino, ethylamino, propylamino, isopropylamino, dimethylamino, N-ethylmethylamino, diethylamino, N-methylpropylamino, N-methylisopropylamino, cyclopropylamino and cyclopropylmethylamino; $C_{1-6}$ cyclic amino groups having in the ring 1 or 2 atoms selected from the group consisting of oxygen, nitrogen and sulfur, such as 1-pyrrolidinyl, piperazinyl, 4-methylpiperazinyl, piperidino and morpholino; $C_{1-7}$ acylamino groups such as trifluoroacetylamino, formylamino, acetylamino, propionylamino, butyrylamino, isobutyrylamino and valerylamino; $C_{1-6}$ alkylsulfonylamino groups such as methylsulfonylamino, ethylsulfonylamino, propylsulfonylamino and butylsulfonylamino; nitro; and cyano.

As examples of $C_{6-14}$ aromatic hydrocarbon groups when $G^1$ of formula (I) represents a substituted or unsubstituted $C_{6-14}$ aromatic hydrocarbon group, there may be mentioned divalent groups having at least one aromatic ring in the molecule, such as benzene, indene, indane, naphthalene, 1,2-dihydronaphthalene, 1,2,3,4-tetrahydronaphthalene, azulene, acenaphthylene, acenaphthene, fluorene, phenanthrene and anthracene. As preferred examples of $C_{6-14}$ aromatic hydrocarbon groups for $G^1$, there may be mentioned divalent benzene, naphthalene and indane. Divalent benzene may be mentioned as the most preferred examples of a $C_{6-14}$ aromatic hydrocarbon group for $G^1$.

As substituents for the substituted $C_{6-14}$ aromatic hydrocarbon groups for $G^1$, there may be mentioned fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, oxo, $C_{1-6}$ alkylsulfonyloxy, optionally substituted $C_{2-7}$ acyl, carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-8}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbon groups and optionally substituted $C_{1-6}$ aliphatic hydrocarbon groups.

The definitions of the substituents for the substituted $C_{6-14}$ aromatic hydrocarbon groups for $G^1$ are the same as the definitions of the substituents for the substituted $C_{3-8}$ alicyclic hydrocarbon groups for $G^1$. As specific examples of substituents for the substituted $C_{6-14}$ aromatic hydrocarbon groups for $G^1$, there may be mentioned the same specific substituents mentioned above for the substituted $C_{3-8}$, alicyclic hydrocarbon groups for $G^1$.

The $C_{1-7}$ alkoxy, $C_{2-7}$ acyl, $C_{2-7}$ alkylcarbamoyl, $C_{1-6}$ alkylamino, $C_{2-7}$ acylamino, $C_{3-6}$ alicyclic hydrocarbon and $C_{1-6}$ aliphatic hydrocarbon groups as substituents for the substituted $C_{6-14}$ aromatic hydrocarbon groups for $G^1$ may be in turn substituted with one or more substituents selected from the group consisting of fluorine, chlorine, bromine, iodine, hydroxyl; $C_{1-6}$ alkoxy groups such as methoxy, ethoxy, propoxy, isopropoxy, butoxy, isobutoxy, s-butoxy, t-butoxy, pentyloxy and cyclopropyloxy; methoxymethyloxy; 2-methoxyethoxy; formyl; trifluoroacetyl; $C_{2-7}$ acyl groups such as acetyl, propionyl, butyryl, isobutyryl, valeryl and isovaleryl; oxo; carboxyl; $C_{2-7}$ alkoxycarbonyl groups such as methoxycarbonyl, ethoxycarbonyl, propoxycarbonyl, isopropoxycarbonyl, butoxycarbonyl, isobutoxycarbonyl and t-butoxycarbonyl; carbamoyl; $C_{2-7}$ alkylcarbamoyl groups such as N-methylcarbamoyl, N,N-dimethylcarbamoyl, N-ethylcarbamoyl, N-ethyl-N-methylcarbamoyl, N,N-diethylcarbamoyl, N-propylcarbamoyl, N-isopropylcarbamoyl, N-butylcarbamoyl, N-cyclopropylcarbamoyl and N-cyclopropylmethylcarbamoyl; amino; $C_{1-6}$ alkylamino groups such as methylamino, ethylamino, propylamino, isopropylamino, dimethylamino, N-ethylmethylamino, diethylamino, N-methylpropylamino, N-methylisopropylamino, cyclopropylamino and cyclopropylmethylamino; $C_{4-6}$ cyclic amino groups having in the ring 1 or 2 atoms selected from the group consisting of oxygen, nitrogen and sulfur, such as 1-pyrrolidinyl, piperazinyl, 4-methylpiperazinyl, piperidino and morpholino; $C_{1-7}$ acylamino groups such as trifluoroacetylamino, formylamino, acetylamino, propionylamino, butyrylamino, isobutyrylamino and valerylamino; $C_{1-6}$ alkylsulfonylamino groups such as methylsulfonylamino, ethylsulfonylamino, propylsulfonylamino and butylsulfonylamino; nitro; and cyano.

As preferred examples of substituents for the substituted $C_{6-14}$ aromatic hydrocarbon groups for $G^1$, there may be mentioned fluorine; chlorine; bromine; $C_{1-6}$ alkoxy groups composed of linear or branched alkyl groups and oxy groups, such as methoxy, ethoxy, propoxy, isopropoxy, butoxy, isobutoxy, s-butoxy, t-butoxy, pentyloxy, isopentyloxy, neopentyloxy, t-pentyloxy and hexyloxy; cyano; nitro; carboxyl; hydroxyl; amino; $C_{1-6}$ mono or dialkylamino groups composed of linear or branched alkyl and amino groups, such as methylamino, ethylamino, propylamino, isopropylamino, butylamino, isobutylamino, s-butylamino, t-butylamino, pentylamino, hexylamino, dimethylamino, N-ethylmethylamino, diethylamino, N-methylpropylamino, N-methylisopropylamino, N-methylbutylamino, N-methyl-t-butylamino, N-ethylisopropylamino, dipropylamino, diisopropylamino and ethylbutylamino; carbamoyl; aminosulfonyl; $C_{3-6}$ alicyclic hydrocarbon groups such as cyclopropyl, cyclobutyl, cyclopentyl and cyclohexyl; $C_{2-7}$ acyl groups such as acetyl, propionyl, butyryl, isobutyryl, pivaloyl and hexanoyl; $C_{1-6}$ alkylthio groups such as methylthio, ethylthio, propylthio, isopropylthio, butylthio, isobutylthio, s-butylthio, t-butylthio, pentylthio and hexylthio; $C_{1-6}$ alkylsulfonyl groups such as methylsulfonyl, ethylsulfonyl, propylsulfonyl, isopropylsulfonyl, butylsulfonyl, isobutylsulfonyl, s-butylsulfonyl, t-butylsulfonyl, pentylsulfonyl and hexylsulfonyl; $C_{2-7}$ alkoxycarbonyl groups such as acetoxy, propionyloxy, butyryloxy, isobutyryloxy, valeryloxy, isovaleryloxy, pivaloyloxy and hexanoyloxy; $C_{2-7}$ acylamino groups such as acetylamino, propionylamino, butyrylamino, isobutyrylamino, valerylamino and hexanoylamino; trifluoromethyl; trifluoromethoxy; and linear or branched $C_{1-6}$ aliphatic hydrocarbon groups optionally containing one unsaturated bond, such as methyl, ethyl, vinyl, ethynyl, propyl, 1-propenyl, 2-propenyl, isopropyl, isopropenyl, 1-propynyl, 2-propynyl, butyl, isobutyl, s-butyl, t-butyl, 1-butenyl, 2-butenyl, 3-butenyl, 1-methyl-1-propenyl, 2-methyl-1-propenyl, 1-methyl-2-propenyl, 2-methyl-2-propenyl, 1-butynyl, 2-butynyl, pentyl, isopentyl, neopentyl, t-pentyl, 1-pentenyl, 2-pentenyl, 3-pentenyl, 4-pentenyl, hexyl, 5-hexenyl, 4-methyl-3-pentenyl, isohexyl, 2-methylpentyl and 1-ethylbutyl.

As more preferred examples of substituents for substituted $C_{6-14}$ aromatic hydrocarbon groups for $G^1$ among these groups, there may be mentioned fluorine, chlorine, bromine, $C_{1-6}$ alkoxy, cyano, nitro, carboxyl, hydroxyl, amino, $C_{1-6}$ mono or dialkylamino, carbamoyl, $C_{3-6}$ alicyclic hydrocarbons, $C_{2-7}$ acyl, $C_{1-6}$ alkylsulfonyl, $C_{2-7}$ alkoxycarboxyl, trifluoromethyl, trifluoromethoxy and $C_{1-6}$ alkyl groups such as methyl, ethyl, propyl, isopropyl, butyl, isobutyl, s-butyl, t-butyl, pentyl, isopentyl, neopentyl, t-pentyl, hexyl, isohexyl, 2-methylpentyl and 1-ethylbutyl, and as particularly preferred examples of substituents, there may be mentioned fluorine, chlorine, $C_{1-6}$ alkoxy, cyano, nitro, carboxyl, hydroxyl, amino, $C_{1-6}$ mono or dialkylamino, $C_{3-6}$ alicyclic hydrocarbons, $C_{2-7}$ acyl, trifluoromethyl, trifluoromethoxy and saturated $C_{1-6}$ alkyl groups As examples of heterocyclic groups having in the ring 1 to 4 atoms selected from the group consisting of oxygen, nitrogen and sulfur, when $G^1$ in formula (I) represents a substituted or unsubstituted heterocyclic group having in the ring 1 to 4 atoms selected from the group consisting of oxygen, nitrogen and sulfur, there may be mentioned divalent monocyclic, bicyclic or tricyclic aromaticthetero-cyclic groups such as furan, thiophene, pyrrole, pyrroline, pyrrolidine, oxazole, oxazolidine, isooxazole, isooxazolidine, thiazole, thiazolidine, isothiazole, isothiazolidine, furazan, imidazole, imidazoline, imidazolidine, pyrazole, pyrazoline, pyrazolidine, triazole, thiadiazole, oxadiazole, tetrazole, pyran, tetrahydropyran, thiopyran, tetrahydrothiopyran, tetrahydrofuran, 1,3-dioxolane, 1,4-dioxane, pyridine, pyrazine, pyrimidine, pyridazine, benzofuran, dibenzofuran, 1,4-dioxacycloheptane, benzothiophene, indole, 1,2-methylenedioxybenzene, benzimidazole, benzothiazole, benzoxazole, chromane, isochromane, quinoline, decahydroquinoline, isoquinoline, phthalazine, cinnoline, 1,8-naphthylidine, 1,2,3,4-tetrahydroisoquinoline, quinazoline, quinoxaline, purine, pteridine, azetidine, morpholine, thiomorpholine, piperidine, homopiperidine, piperazine, homopiperazine, indoline, isoindoline, phenoxazine, phenazine, phenothiazine, pyrrolopyrimidine, pyrazolopyrimidine and quinuclidine.

As preferred examples of heterocyclic groups having in the ring 1 to 4 atoms selected from the group consisting of oxygen, nitrogen and sulfur for $G^1$, there may be mentioned divalent monocyclic or bicyclic $C_{2-9}$ aromatic heterocyclic groups having in the ring 1 to 3 atoms selected from the group consisting of oxygen, nitrogen and sulfur, such as furan, pyrrole, thiophene, pyrazole, oxazole, thiazole, isooxazole, isothiazole, pyrazole, imidazole, pyridine, pyrimidine, pyrazine, pyridazine, benzothiophene, benzofuran, 1,2-methylenedioxybenzene, benzimidazole, indole, quinoline, isoquinoline, quinazoline, phthalazine, cinnoline, and 1,8-naphthylidine, or divalent monocyclic $C_{2-9}$ heterocyclic groups having in the ring 1 to 2 atoms selected from the group consisting of oxygen, nitrogen and sulfur, such as pyrrolidine, piperidine, morpholine, thiomorpholine, homopiperidine, homopiperazine, 1,2,3,6-tetrahydropyridine, and piperazine.

A heterocyclic group having in the ring 1 to 4 atoms selected from the group consisting of oxygen, nitrogen and sulfur for $G^1$ bonds to $A^2$ at a carbon atom or nitrogen atom.

As preferred examples of heterocyclic groups having in the ring 1 to 4 atoms selected from the group consisting of oxygen, nitrogen and sulfur, which bond to $A^2$ at a carbon atom, there may be mentioned divalent monocyclic or bicyclic $C_{3-9}$ aromatic heterocyclic groups having in the ring 1 or 2 atoms selected from the group consisting of oxygen, nitrogen and sulfur, such as furan, pyrrole, thiophene, pyrazole, oxazole, thiazole, isooxazole, isothiazole, pyrazole, imidazole, pyridine, pyrimidine, pyrazine, pyridazine, benzothiophene, benzofuran, 1,2-methylenedioxybenzene, benzimidazole, indole, quinoline, isoquinoline and quinazoline.

As preferred examples of heterocyclic groups having in the ring 0.1 to 4 atoms selected from the group consisting of oxygen, nitrogen and sulfur which bond to $A^2$ at a nitrogen atom, there may be mentioned divalent monocyclic $C_{2-9}$ heterocyclic groups having in the ring 1 or 2 atoms selected from the group consisting of oxygen, nitrogen and sulfur, such as pyrrolidine, piperidine, morpholine, thiomorpholine, homopiperidine, homopiperazine, 1,2,3,6-tetrahydropyridine and piperazine. As preferred examples of divalent monocyclic $C_{2-9}$ heterocyclic groups having in the ring 1 or 2 atoms selected from the group consisting of oxygen, nitrogen and sulfur, there may be mentioned piperidine, homopiperidine, morpholine, homopiperazine and piperazine.

As substituents for the substituted heterocyclic groups having in the ring 1 to 4 atoms selected from the group consisting of oxygen, nitrogen and sulfur for $G^1$, there may be mentioned fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, oxo, $C_{1-6}$ alkylsulfonyloxy, optionally substituted $C_{2-7}$ acyl, carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-8}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbon groups and optionally substituted $C_{1-6}$ aliphatic hydrocarbon groups.

The definitions of the substituents for the substituted heterocyclic groups having in the ring 1 to 4 atoms selected from the group consisting of oxygen, nitrogen and sulfur for $G^1$ are the same as the definitions of the substituents for the substituted $C_{3-8}$ alicyclic hydrocarbon groups for $G^1$. As specific examples of substituents for the substituted heterocyclic groups having in the ring 1 to 4 atoms selected from the group-consisting of oxygen, nitrogen and sulfur for $G^1$, there may be mentioned the same specific substituents mentioned above for the substituted $C_{3-8}$ alicyclic hydrocarbon groups for $G^1$.

The $C_{1-7}$ alkoxy, $C_{2-7}$ acyl, $C_{2-7}$ alkylcarbamoyl, $C_{1-6}$ alkylamino, $C_{2-7}$ acylamino, $C_{3-6}$ alicyclic hydrocarbon and $C_{1-6}$ aliphatic hydrocarbon groups as substituents for the substituted heterocyclic groups having in the ring 1 to 4 atoms selected from the group consisting of oxygen, nitrogen and sulfur for $G^1$ may be in turn substituted with one or more substituents selected from the group consisting of fluorine, chlorine, bromine, iodine, hydroxyl; $C_{1-6}$ alkoxy groups such as methoxy, ethoxy, propoxy, isopropoxy, butoxy, isobutoxy, s-butoxy, t-butoxy, pentyloxy and cyclopropyloxy; methoxymethyloxy; 2-methoxyethoxy; formyl; trifluoroacetyl; $C_{2-7}$ acyl groups such as acetyl, propionyl, butyryl, isobutyryl, valeryl and isovaleryl; oxo; carboxyl; $C_{2-7}$ alkoxycarbonyl groups such as methoxycarbonyl, ethoxycarbonyl, propoxycarbonyl, isopropoxycarbonyl, butoxycarbonyl, isobutoxycarbonyl and t-butoxycarbonyl; carbamoyl; $C_{2-7}$ alkylcarbamoyl groups such as N-methylcarbamoyl, N,N-dimethylcarbamoyl, N-ethylcarbamoyl, N-ethyl-N-methylcarbamoyl, N,N-diethylcarbamoyl, N-propylcarbamoyl, N-isopropylcarbamoyl, N-butylcarbamoyl, N-cyclopropylcarbamoyl and N-cyclopropylmethylcarbamoyl; amino; $C_{1-6}$ alkylamino groups such as methylamino, ethylamino, propylamino, isopropylamino, dimethylamino, N-ethylmethylamino, diethylamino, N-methylpropylamino, N-methylisopropylamino, cyclopropylamino and cyclopropylmethylamino; $C_{4-6}$ cyclic amino groups having in the ring 1 or 2 atoms selected from the group consisting of oxygen, nitrogen and sulfur, such as 1-pyrrolidinyl, piperazinyl, 4-methylpiperazinyl, piperidino and morpholino; $C_{1-7}$ acylamino groups such as trifluoroacetylamino, formylamino, acetylamino, propionylamino, butyrylamino, isobutyrylamino and valerylamino; $C_{1-6}$ alkylsulfonylamino groups such as methylsulfonylamino, ethylsulfonylamino, propylsulfonylamino and butylsulfonylamino; nitro; and cyano.

As preferred examples of substituents for the substituted heterocyclic groups having in the ring 1 to 4 atoms selected from the group consisting of oxygen, nitrogen and sulfur for $G^1$, there may be mentioned fluorine; chlorine; bromine; $C_{1-6}$ alkoxy groups composed of linear or branched alkyl groups and oxy groups, such as methoxy, ethoxy, propoxy, isopropoxy, butoxy, isobutoxy, s-butoxy, t-butoxy, pentyloxy, isopentyloxy, neopentyloxy, t-pentyloxy and hexyloxy; cyano; nitro; carboxyl; hydroxyl; amino; $C_{1-6}$ mono or dialkylamino groups composed of linear or branched alkyl and amino groups, such as methylamino, ethylamino, propylamino, isopropylamino, butylamino, isobutylamino, s-butylamino, t-butylamino, pentylamino, hexylamino, dimethylamino, N-ethylmethylamino, diethylamino, N-methylpropylamino, N-methylisopropylamino, N-methylbutylamino, N-methyl-t-butylamino, N-ethylisopropylamino, dipropylamino, diisopropylamino and ethylbutylamino; carbamoyl; aminosulfonyl; $C_{3-6}$ alicyclic hydrocarbon groups such as cyclopropyl, cyclobutyl, cyclopentyl and cyclohexyl; $C_{2-7}$ acyl groups such as acetyl, propionyl, butyryl, isobutyryl, pivaloyl and hexanoyl; $C_{1-6}$ alkylthio groups such as methylthio, ethylthio, propylthio, isopropylthio, butylthio, isobutylthio, s-butylthio, t-butylthio, pentylthio and hexylthio; $C_{1-6}$ alkylsulfonyl groups such as methylsulfonyl, ethylsulfonyl, propylsulfonyl, isopropylsulfonyl, butylsulfonyl, isobutylsulfonyl, s-butylsulfonyl, t-butylsulfonyl, pentylsulfonyl and hexylsulfonyl; $C_{2-7}$ alkoxycarbonyl groups such as acetoxy, propionyloxy, butyryloxy, isobutyryloxy, valeryloxy, isovaleryloxy, pivaloyloxy and hexanoyloxy; $C_{2-7}$ acylamino groups such as acetylamino, propionylamino, butyrylamino, isobutyrylamino, valerylamino and hexanoylamino; trifluoromethyl; trifluoromethoxy; and linear or branched $C_{1-6}$ aliphatic hydrocarbon groups optionally containing one unsaturated bond, such as methyl, ethyl, vinyl, ethynyl, propyl, 1-propenyl, 2-propenyl, isopropyl, isopropenyl, 1-propynyl, 2-propynyl, butyl, isobutyl, s-butyl, t-butyl, 1-butenyl, 2-butenyl, 3-butenyl, 1-methyl-1-propenyl, 2-methyl-1-propenyl, 1-methyl-2-propenyl, 2-methyl-2-propenyl, 1-butynyl, 2-butynyl, pentyl, isopentyl, neopentyl, t-pentyl, 1-pentenyl, 2-pentenyl, 3-pentenyl, 4-pentenyl, hexyl, 5-hexenyl, 4-methyl-3-pentenyl, isohexyl, 2-methylpentyl and 1-ethylbutyl.

As more preferred examples of substituents for substituted heterocyclic groups having in the ring 1 to 4 atoms selected from the group consisting of oxygen, nitrogen and sulfur for $G^1$ among these groups, there may be mentioned fluorine, chlorine, bromine, $C_{1-6}$ alkoxy, cyano, nitro, carboxyl, hydroxyl, amino, $C_{1-6}$ mono or dialkylamino, carbamoyl, $C_{3-6}$ alicyclic hydrocarbons, $C_{2-7}$ acyl, $C_{1-6}$ alkylsulfonyl, $C_{2-7}$ alkoxycarboxyl, trifluoromethyl, trifluoromethoxy and saturated $C_{1-6}$ alkyl groups such as methyl, ethyl, propyl, isopropyl, butyl, isobutyl, s-butyl, t-butyl, pentyl, isopentyl, neopentyl, t-pentyl, hexyl, isohexyl, 2-methylpentyl and 1-ethylbutyl, and as the particularly preferred example of substituents, there may be mentioned fluorine, chlorine, $C_{1-6}$ alkoxy, cyano, nitro, carboxyl, hydroxyl, amino, $C_{1-6}$ mono or dialkylamino, $C_{3-6}$ alicyclic hydrocarbons, $C_{2-7}$ acyl, trifluoromethyl, trifluoromethoxy and $C_{1-6}$ alkyl groups.

As preferred examples for $G^1$, there may be mentioned a benzene, a divalent monocyclic or bicyclic $C_{3-9}$ aromatic heterocyclic group having in the ring 1 to 2 atoms selected from the group consisting of oxygen, nitrogen and sulfur, and a divalent monocyclic $C_{2-9}$ heterocyclic group having in the ring 1 to 2 atoms selected from the group consisting of oxygen, nitrogen and sulfur. A divalent monocyclic or bicyclic $C_{3-9}$ aromatic heterocyclic group having in the ring 1 to 2 atoms selected from the group consisting of oxygen, nitrogen and sulfur may be mentioned as a particularly preferred example for $G^1$.

$G^2$ in formula (I) above represents one group selected from among the following 1) to 5):

1) Hydrogen;

2) A substituted or unsubstituted $C_{1-10}$ aliphatic hydrocarbon group. (As substituents there may be mentioned one or more selected from the group consisting of fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, oxo, $C_{1-6}$ alkylsulfonyloxy, optionally substituted $C_{2-7}$ acyl, carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-7}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbons, optionally substituted $C_{1-6}$ aliphatic hydrocarbons, optionally substituted $C_{6-14}$ aromatic hydrocarbons and optionally substituted heterocyclic groups (having in the ring 1 to 4 atoms selected from the group consisting of oxygen, nitrogen and sulfur).)

3) A substituted or unsubstituted $C_{3-8}$ alicyclic hydrocarbon group. (As substituents there may be mentioned one or more selected from the group consisting of fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, oxo, $C_{1-6}$ alkylsulfonyloxy, optionally substituted $C_{2-7}$ acyl, carboxyl, $C_{2-7}$ alkoxycarbonyl, carbamoyl, optionally substituted $C_{2-8}$ alkylcarbamoyl, amino, optionally substituted $C_{1-6}$ alkylamino, optionally substituted $C_{2-7}$ acylamino, $C_{2-8}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbons, optionally substituted $C_{1-6}$ aliphatic hydrocarbons, optionally substituted $C_{6-14}$ aromatic hydrocarbons and optionally substituted heterocyclic groups (having in the ring 1 to 4 atoms selected from the group consisting of oxygen, nitrogen and sulfur).)

4) A substituted or unsubstituted $C_{6-14}$ aromatic hydrocarbon group. (As substituents there may be mentioned one or more selected from the group consisting of fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, oxo, $C_{1-6}$ alkylsulfonyloxy, optionally substituted $C_{2-7}$ acyl, carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-}$—, alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbons, optionally substituted $C_{1-6}$ aliphatic hydrocarbons, optionally substituted $C_{6-14}$ aromatic hydrocarbons and optionally substituted heterocyclic groups (having in the ring 1 to 4 atoms selected from the group consisting of oxygen, nitrogen and sulfur).)

5) A substituted or unsubstituted heterocyclic group having in the ring 1 to 4 atoms selected from the group consisting of oxygen, nitrogen and sulfur. (As substituents there may be mentioned one or more selected from the group consisting of fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, oxo, $C_{1-6}$ alkylsulfonyloxy, optionally substituted $C_{2-7}$ acyl, carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-7}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbons, optionally substituted $C_{1-6}$ aliphatic hydrocarbons, optionally substituted $C_{6-14}$ aromatic hydrocarbons and optionally substituted heterocyclic groups (having in the ring 1 to 4 atoms selected from the group consisting of oxygen, nitrogen and sulfur).

As examples of $C_{1-10}$ aliphatic hydrocarbon groups for $G^2$ when $G^2$ in formula (I) represents a substituted or unsubstituted $C_{1-10}$ aliphatic hydrocarbon group, there may be mentioned alkyl groups such as methyl, ethyl, propyl, isopropyl, butyl, isobutyl, s-butyl, t-butyl, pentyl, isopentyl, neopentyl, t-pentyl, 2-methylpentyl, 4-methylpentyl, 1-ethylbutyl, hexyl, heptyl, 2-methylhexyl, 5-methylhexyl, 1,1-dimethylpentyl, 6-methylheptyl, octyl, nonyl and decyl; alkenyl groups such as vinyl, 1-methylvinyl, 1-ethylvinyl, 1-propenyl, 2-propenyl, 2-methyl-1-propenyl, 1-butenyl, 2-butenyl, 2-methyl-1-butenyl, 1,3-butadienyl, 1-pentenyl, 2-pentenyl, 4-methyl-1-pentenyl, 1-hexenyl, 2-hexenyl, 3-hexenyl, 4-hexenyl, 5-hexenyl, 1,5-hexadienyl, 2-heptenyl, 2-octenyl, 2-nonenyl and 2-decenyl; and alkynyl groups such as ethynyl, 1-propynyl, 2-propynyl, 1-butynyl, 3-methyl-1-butynyl, 3,3-dimethyl-1-butynyl, 1-pentynyl, 2-pentynyl, 3-pentynyl, 1-hexynyl, 2-hexynyl, 3-hexynyl, 4-hexynyl, 1-methyl-3-pentynyl, 1-methyl-3-hexynyl, 2-heptynyl, 2-octynyl, 2-nonynyl, 2-decynyl.

As preferred $C_{1-10}$ aliphatic hydrocarbon groups for $G^2$, there may be mentioned linear or branched $C_{1-6}$ alkyl groups optionally containing 1 unsaturated bond, such as methyl, ethyl, propyl, isopropyl, butyl, pentyl, hexyl, vinyl, 1-propenyl, 1-butenyl, ethynyl and 1-propynyl, and as particularly preferred groups there may be mentioned linear or branched $C_{1-6}$ alkyl groups such as methyl, ethyl, propyl, isopropyl, butyl and hexyl.

As substituents for the substituted $C_{1-10}$ aliphatic hydrocarbon groups for $G^2$, there may be mentioned fluorine, chlorine, bromine, iodine, hydroxyl, $C_{1-7}$ alkoxy groups composed of linear or branched alkyl or cycloalkyl groups and oxy groups, such as methoxy, ethoxy, propoxy, isopropoxy, butoxy, isobutoxy, s-butoxy, t-butoxy, pentyloxy, isopentyloxy, neopentyloxy, t-pentyloxy, hexyloxy, isohexyloxy, 2-methylpentyloxy, 1-ethylbutoxy, cyclopropyloxy, cyclobutyloxy, cyclopentyloxy, cyclohexyloxy, cyclopropylmethyloxy, cyclopropylethyloxy, cyclopentylmethyloxy and cyclohexylmethyloxy; $C_{6-10}$ aryloxy groups such as phenoxy, 1-naphthoxy and 2-naphthoxy; $C_{7-9}$ aralkoxy groups such as benzyloxy, α-phenethyloxy, β-phenethyloxy and phenylpropyloxy; $C_{2-7}$ acyloxy groups such as acetoxy, propionyloxy, butyryloxy, isobutyryloxy, valeryloxy, isovaleryloxy, pivaloyloxy and hexanoyloxy; oxo; $C_{1-6}$ alkylsulfonyloxy groups composed of linear or branched alkyl groups and sulfonyloxy groups, such as methylsulfonyloxy, ethylsulfonyloxy, propylsulfonyloxy, butylsulfonyloxy and t-butylsulfonyloxy; $C_{2-7}$ acyl groups such as acetyl, propionyl, butyryl, isobutyryl, valeryl, isovaleryl, pivaloyl and hexanoyl; carboxyl; $C_{2-7}$ alkoxycarbonyl groups composed of linear or branched alkyl groups and oxycarbonyl groups, such as methoxycarbonyl, ethoxycarbonyl, propoxycarbonyl, isopropoxycarbonyl, butoxycarbonyl, isobutoxycarbonyl, s-butoxycarbonyl and t-butoxycarbonyl; carbamoyl; $C_{2-7}$ alkylcarbamoyl groups composed of linear or branched alkyl or cycloalkyl groups and carbamoyl groups, such as N-methylcarbamoyl, N-ethylcarbamoyl, N-propylcarbamoyl, N-isopropylcarbamoyl, N-butylcarbamoyl, N-isobutylcarbamoyl, N-s-butylcarbamoyl, N-t-butylcarbamoyl, N-pentylcarbamoyl, N-cyclopropylcarbamoyl, N-cyclobutylcarbamoyl, N-cyclopentylcarbamoyl, N-cyclohexylcarbamoyl, N-cycloheptylcarbamoyl, N-cyclopropylmethylcarbamoyl, N,N-dimethylcarbamoyl, N-ethyl-N-methylcarbamoyl, N,N-diethylcarbamoyl and N,N-dipropylcarbamoyl; amino; $C_{1-6}$ alkylamino groups composed of linear or branched alkyl or cycloalkyl groups and amino groups, such as methylamino, ethylamino, propylamino, isopropylamino, butylamino, isobutylamino, s-butylamino, t-butylamino, pentylamino, hexylamino, cyclopropylamino, cyclobutylamino, cyclopentylamino, cyclohexylamino, cyclopropylmethylamino, dimethylamino, N-ethylmethylamino, diethylamino, N-methylpropylamino, N-methylisopropylamino, N-methylbutylamino, N-methyl-t-butylamino, N-ethylisopropylamino, dipropylamino, diisopropylamino and ethylbutylamino; $C_{2-7}$ acylamino groups such as acetylamino, propionylamino, butyrylamino, isobutyrylamino, valerylamino and hexanoylamino; $C_{2-8}$ alkoxycarbonylamino groups such as methoxycarbonylamino, ethoxycarbonylamino and t-butoxycarbonylamino; $C_{1-6}$ alkylsulfonylamino groups such as methylsulfonylamino, ethylsulfonylamino, butylsulfonylamino and t-butylsulfonylamino; cyano; nitro; $C_{1-6}$ alkylthio groups such as methylthio, ethylthio, propylthio, isopropylthio, butylthio, isobutylthio, s-butylthio, t-butylthio, pentylthio and hexylthio; $C_{1-6}$ alkylsulfinyl groups composed of linear or branched alkyl or cycloalkyl groups and sulfinyl groups, such as methylsulfinyl, ethylsulfinyl, propylsulfinyl, isopropylsulfinyl, butylsulfinyl, isobutylsulfinyl, s-butylsulfinyl, t-butylsulfinyl, pentylsulfinyl and cyclopentylsulfinyl; $C_{1-6}$ alkylsulfonyl groups composed of linear or branched alkyl or cycloalkyl groups and sulfonyl groups, such as methylsulfonyl, ethylsulfonyl, propylsulfonyl, isopropylsulfonyl, butylsulfonyl, isobutylsulfonyl, s-butylsulfonyl, t-butylsulfonyl, pentylsulfonyl, hexylsulfonyl, cyclopentylsulfonyl and cyclohexylsulfonyl; sulfo; sulfamoyl; $C_{1-6}$ aminosulfonyl groups composed of linear or branched alkyl or cycloalkyl groups and aminosulfonyl groups, such as methylaminosulfonyl, ethylaminosulfonyl, propylaminosulfonyl, isopropylaminosulfonyl, butylaminosulfonyl, isobutylaminosulfonyl, s-butylaminosulfonyl, pentylaminosulfonyl, dimethylaminosulfonyl, N-ethyl-N-methylaminosulfonyl, diethylaminosulfonyl, dipropylaminosulfonyl, cyclopropylaminosulfonyl, cyclopentylaminosulfonyl, cyclohexylaminosulfonyl and cyclopropylmethylaminosulfonyl; $C_{3-6}$ alicyclic hydrocarbon groups such as cyclopropyl, cyclobutyl, cyclopentyl and cyclohexyl; linear or branched $C_{1-6}$ aliphatic hydrocarbon groups optionally containing one unsaturated bond, such as methyl, ethyl, vinyl, ethynyl, propyl, 1-propenyl, 2-propenyl, isopropyl, isopropenyl, 1-propynyl, 2-propynyl, butyl, isobutyl, s-butyl, t-butyl, 1-butenyl, 2-butenyl, 3-butenyl, 1-methyl-1-propenyl, 2-methyl-1-propenyl, 1-methyl-2-propenyl, 2-methyl-2-propenyl, 1-butynyl, 2-butynyl, pentyl, isopentyl, neopentyl, t-pentyl, 1-pentenyl, 2-pentenyl, 3-pentenyl, 4-pentenyl, hexyl, 5-hexenyl, 4-methyl-3-pentenyl, isohexyl, 2-methylpentyl and 1-ethylbutyl; monovalent monocyclic, bicyclic or tricyclic $C_{6-14}$ aromatic hydrocarbons such as benzene, naphthalene, indene, indane, 1,2,3,4-tetrahydronaphthalene and fluorene; and heterocyclic groups (having in the ring 1 to 4 atoms selected from the group consisting of oxygen, nitrogen and sulfur) which are monovalent monocyclic, bicyclic or tricyclic heterocycles (having in the ring 1 to 4 atoms selected from the group consisting of oxygen, nitrogen and sulfur), such as furan, thiophene, pyrrole, pyrroline, pyrrolidine, oxazole, oxazolidine, isooxazole, isooxazolidine, thiazole, thiazolidine, isothiazole, isothiazolidine, imidazole, imidazoline, imidazolidine, pyrazole, pyrazoline, pyrazolidine, triazole, thiadiazole, oxadiazole, tetrazole, pyran, tetrahydropyran, thiopyran, tetrahydrothiopyran, pyridine, pyrazine, pyrimidine, pyridazine, benzofuran, dibenzofuran, benzothiophene, indole, benzimidazole, benzothiazole, benzoxazole, chromane, isochromane, quinoline, decahydroquinoline, isoquinoline, quinazoline, quinoxaline, purine, pteridine, azetidine, morpholine, thiomorpholine, piperidine, homopiperidine, piperazine, homopiperazine, indoline, isoindoline, phenoxazine, phenazine, phenothiazine and quinuclidine.

As preferred examples of substituents for the substituted $C_{1-10}$ aliphatic hydrocarbon groups for $G^2$ there may be mentioned hydroxyl, optionally substituted $C_{1-7}$ alkoxy, oxo, optionally substituted $C_{2-7}$ acyl, carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{1-6}$ alkylsulfonylamino, cyano, $C_{1-6}$ alkylsulfonyl, sulfamoyl, optionally substituted $C_{6-14}$ aromatic hydrocarbon groups and optionally substituted heterocyclic groups (having in the ring 1 to 4 atoms selected from the group consisting of oxygen, nitrogen and sulfur).

As more preferred examples of substituents for the substituted $C_{1-10}$ aliphatic hydrocarbon groups for $G^2$ there may be mentioned hydroxyl, optionally substituted $C_{1-7}$ alkoxy, carboxyl, amino, optionally substituted $C_{1-5}$ alkylamino, cyano and optionally substituted heterocyclic groups (having in the ring 1 to 4 atoms selected from the group consisting of oxygen, nitrogen and sulfur).

A heterocyclic group (having in the ring 1 to 4 atoms selected from the group consisting of oxygen, nitrogen and sulfur) as a substituent for a substituted $C_{1-10}$ aliphatic hydrocarbon group for $G^2$ bonds to the $C_{1-10}$ aliphatic hydrocarbon group of $G^2$ at a carbon atom or nitrogen atom.

As more preferred examples of heterocyclic groups (having in the ring 1 to 4 atoms selected from the group consisting of oxygen, nitrogen and sulfur) to bond to the $C_{1-10}$ aliphatic hydrocarbon groups of $G^2$ at a carbon atom, there may be mentioned monovalent monocyclic or bicyclic $C_{3-9}$ aromatic heterocycles having in the ring 1 or 2 atoms selected from the group consisting of oxygen, nitrogen and sulfur, such as furan, pyrrole, thiophene, pyrazole, oxazole, thiazole, isooxazole, isothiazole, pyrazole, imidazole, pyridine, pyrimidine, pyrazine, pyridazine, benzothiophene, benzofuran, 1,2-methylenedioxybenzene, benzimidazole, indole, quinoline, isoquinoline and quinazoline.

As preferred examples of heterocyclic groups (having in the ring 1 to 4 atoms selected from the group consisting of oxygen, nitrogen and sulfur) to bond to the $C_{1-10}$ aliphatic hydrocarbon groups of $G^2$ at a nitrogen atom, there may be mentioned monovalent monocyclic $C_{2-9}$ aromatic heterocycles having in the ring 1 or 2 atoms selected from the group consisting of oxygen, nitrogen and sulfur, such as pyrrolidine, piperidine, morpholine, thiomorpholine, homopiperidine, homopiperazine, 1,2,3,6-tetrahydropyridine and piperazine.

The $C_{1-7}$ alkoxy, $C_{2-7}$ acyl, $C_{2-7}$ alkylcarbamoyl, $C_{1-6}$ alkylamino, $C_{2-7}$ acylamino, $C_{3-6}$ alicyclic hydrocarbon, $C_{1-6}$ aliphatic hydrocarbon, $C_{6-14}$ aromatic hydrocarbon and heterocyclic groups (having in the ring 1 to 4 atoms selected from the group consisting of oxygen, nitrogen and sulfur) as substituents for the substituted $C_{1-10}$ aliphatic hydrocarbon groups for $G^2$ may be in turn substituted with one or more substituents selected from the group consisting of fluorine, chlorine, bromine, iodine, hydroxyl; $C_{1-6}$ alkoxy groups such as methoxy, ethoxy, propoxy, isopropoxy, butoxy, isobutoxy, s-butoxy, t-butoxy, pentyloxy and cyclopropyloxy; methoxymethyloxy; 2-methoxyethoxy; formyl; trifluoroacetyl; $C_{2-7}$ acyl groups such as acetyl, propionyl, butyryl, isobutyryl, valeryl and isovaleryl; oxo; carboxyl; $C_{2-7}$ alkoxycarbonyl groups such as methoxycarbonyl, ethoxycarbonyl, propoxycarbonyl, isopropoxycarbonyl, butoxycarbonyl, isobutoxycarbonyl and t-butoxycarbonyl; carbamoyl; $C_{2-7}$ alkylcarbamoyl groups such as N-methylcarbamoyl, N,N-dimethylcarbamoyl, N-ethylcarbamoyl, N-ethyl-N-methylcarbamoyl, N,N-diethylcarbamoyl, N-propylcarbamoyl, N-isopropylcarbamoyl, N-butylcarbamoyl, N-cyclopropylcarbamoyl and N-cyclopropylmethylcarbamoyl; amino; $C_{1-6}$ alkylamino groups such as methylamino, ethylamino, propylamino, isopropylamino, dimethylamino, N-ethylmethylamino, diethylamino, N-methylpropylamino, N-methylisopropylamino, cyclopropylamino and cyclopropylmethylamino; $C_{4-6}$ cyclic amino groups having in the ring 1 or 2 atoms selected from the group consisting of oxygen, nitrogen and sulfur, such as 1-pyrrolidinyl, piperazinyl, 4-methylpiperazinyl, piperidino and morpholino; $C_{1-7}$ acylamino groups such as trifluoroacetylamino, formylamino, acetylamino, propionylamino, butyrylamino, isobutyrylamino and valerylamino; $C_{1-6}$ alkylsulfonylamino groups such as methylsulfonylamino, ethylsulfonylamino, propylsulfonylamino and butylsulfonylamino; nitro; cyano; $C_{1-6}$ alkyl groups such as methyl, ethyl, propyl, isopropyl, butyl, isobutyl, s-butyl and t-butyl; trifluoromethyl; and trifluoromethoxy.

As examples of $C_{3-8}$ alicyclic hydrocarbon groups for $G^2$ when $G^2$ in formula (I) is a substituted or unsubstituted $C_{3-8}$, alicyclic hydrocarbon group, there may be mentioned monovalent cyclopropane, cyclobutane, cyclopentane, cyclopentene, cyclohexane, cyclohexene, cycloheptane, cycloheptene and cyclooctane. As preferred examples of $C_{3-8}$ alicyclic hydrocarbon groups for $G^2$ there may be mentioned cyclopropyl, cyclobutyl, cyclopentyl, cyclohexyl, 3-cyclopentenyl, 4-cyclopentenyl, 1-cyclohexenyl, 3-cyclohexenyl, 4-cyclohexenyl and 1-cycloheptenyl.

As substituents for the substituted $C_{3-8}$ alicyclic hydrocarbon groups for $G^2$ there may be mentioned one or more selected from the group consisting of fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, oxo, $C_{1-6}$ alkylsulfonyloxy, optionally substituted $C_{2-7}$ acyl, carboxyl, $C_{2-7}$ alkoxycarbonyl, carbamoyl, optionally substituted $C_{2-7}$ alkylcarbamoyl, amino, optionally substituted $C_{1-6}$ alkylaimino, optionally substituted $C_{2-7}$ acylamino, $C_{2-9}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbon, optionally substituted $C_{1-6}$ aliphatic hydrocarbon, optionally substituted $C_{6-14}$ aromatic hydrocarbon and optionally substituted heterocyclic groups (having in the ring 1 to 4 atoms selected from the group consisting of oxygen, nitrogen and sulfur).

The definitions of the substituents for the substituted $C_{3-8}$ alicyclic hydrocarbon groups for $G^2$ are the same as the definitions of the substituents for the substituted $C_{1-10}$ aliphatic hydrocarbon groups for $G^2$. As examples of substituents for the substituted $C_{3-8}$ alicyclic hydrocarbon groups for $G^2$ there may be mentioned the same specific substituents mentioned above for the substituted $C_{1-10}$ aliphatic hydrocarbon groups for $G^2$.

The $C_{1-7}$ alkoxy, $C_{2-7}$ acyl, $C_{2-7}$ alkylcarbamoyl, $C_{1-6}$ alkylamino, $C_{2-7}$ acylamino, $C_{3-6}$ alicyclic hydrocarbon, $C_{1-6}$ aliphatic hydrocarbon, $C_{6-14}$ aromatic hydrocarbon and heterocyclic groups (having in the ring 1 to 4 atoms selected from the group consisting of oxygen, nitrogen and sulfur) as substituents for the substituted $C_{3-8}$ alicyclic hydrocarbon groups for $G^2$ may be in turn substituted with one or more substituents selected from the group consisting of fluorine, chlorine, bromine, iodine, hydroxyl, $C_{1-6}$ alkoxy groups such as methoxy, ethoxy, propoxy, isopropoxy, butoxy, isobutoxy, s-butoxy, t-butoxy, pentyloxy and cyclopropyloxy; methoxymethyloxy; 2-methoxyethoxy; formyl; trifluoroacetyl; $C_{2-7}$ acyl groups such as-acetyl, propionyl, butyryl, isobutyryl, valeryl and isovaleryl; oxo; carboxyl; $C_{2-7}$ alkoxycarbonyl groups such as methoxycarbonyl, ethoxycarbonyl, propoxycarbonyl, isopropoxycarbonyl, butoxycarbonyl, isobutoxycarbonyl and t-butoxycarbonyl; carbamoyl; $C_{2-7}$ alkylcarbamoyl groups such as N-methylcarbamoyl, N,N-dimethylcarbamoyl, N-ethylcarbamoyl, N-ethyl-N-methylcarbamoyl, N,N-diethylcarbamoyl, N-propylcarbamoyl, N-isopropylcarbamoyl, N-butylcarbamoyl, N-cyclopropylcarbamoyl and N-cyclopropylmethylcarbamoyl; amino; $C_{1-6}$ alkylamino groups such as methylamino, ethylamino, propylamino, isopropylamino, dimethylamino, N-ethylmethylamino, diethylamino, N-methylpropylamino, N-methylisopropylamino, cyclopropylamino and cyclopropylmethylamino; $C_{4-6}$ cyclic amino groups having in the ring 1 or 2 atoms selected from the group consisting of oxygen, nitrogen and sulfur, such as 1-pyrrolidinyl, piperazinyl, 4-methylpiperazinyl, piperidino and morpholino; trifluoroacetylamino; $C_{1-7}$ acylamino groups such as formylamino, acetylamino, propionylamino, butyrylamino, isobutyrylamino and valerylamino; $C_{1-6}$ alkylsulfonylamino groups such as methylsulfonylamino, ethylsulfonylamino, propylsulfonylamino and butylsulfonylamino; nitro; cyano; $C_{1-6}$ alkyl groups such as methyl, ethyl, propyl, isopropyl, butyl, isobutyl, s-butyl and t-butyl; trifluoromethyl; and trifluoromethoxy.

As examples of $C_{1-14}$ aromatic hydrocarbon groups for $G^2$ when $G^2$ in formula (I) represents a substituted or unsubstituted $C_{6-14}$ aromatic hydrocarbon group, there may be mentioned monovalent groups having at least one aromatic ring in the molecule, such as benzene, indene, indane, naphthalene, 1,2-dihydronaphthalene, 1,2,3,4-tetrahydronaphthalene, azulene, acenaphthylene, acenaphthene, fluorene, phenanthrene and anthracene. Phenyl may be mentioned as a preferred example of a $C_{6-14}$ aromatic hydrocarbon group for $G^2$.

As substituents for the substituted $C_{6-14}$ aromatic hydrocarbon groups for $G^2$ there may be mentioned one or more selected from the group consisting of fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, oxo, $C_{1-6}$ alkylsulfonyloxy, optionally substituted $C_{2-7}$ acyl, carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-7}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbon, optionally substituted $C_{1-6}$ aliphatic hydrocarbon, optionally substituted $C_{6-14}$ aromatic hydrocarbon and optionally substituted heterocyclic groups (having in the ring 1 to 4 atoms selected from the group consisting of oxygen, nitrogen and sulfur).

The definitions of the substituents for the substituted $C_{6-14}$ aromatic hydrocarbon groups for $G^2$ are the same as the definitions of the substituents for the substituted $C_{1-10}$ aliphatic hydrocarbon groups for $G^2$. As examples of substituents for the substituted $C_{6-14}$ aromatic hydrocarbon groups for $G^2$ there may be mentioned the same specific substituents mentioned above for the substituted $C_{1-1}$ aliphatic hydrocarbon groups for $G^2$ The $C_{1-7}$ alkoxy, $C_{2-7}$ acyl, $C_{2-7}$ alkylcarbamoyl, $C_{1-6}$ alkylamino, $C_{2-7}$ acylamino, $C_{3-6}$ alicyclic hydrocarbon, $C_{1-6}$ aliphatic hydrocarbon, $C_{6-14}$ aromatic hydrocarbon and heterocyclic groups (having in the ring 1 to 4 atoms selected from the group consisting of oxygen, nitrogen and sulfur) as substituents for the substituted $C_{6-14}$ aromatic hydrocarbon groups for $G^2$ may be in turn substituted with one or more substituents selected from the group consisting of fluorine; chlorine; bromine; iodine; hydroxyl; $C_{1-6}$ alkoxy groups such as methoxy, ethoxy, propoxy, isopropoxy, butoxy, isobutoxy, s-butoxy, t-butoxy, pentyloxy and cyclopropyloxy; methoxymethyloxy; 2-methoxyethoxy; formyl; trifluoroacetyl; $C_{2-7}$ acyl groups such-as acetyl, propionfyl, butyryl, isobutyryl, valeryl and isovaleryl; oxo; carboxyl; $C_{2-7}$ alkoxycarbonyl groups such as methoxycarbonyl, ethoxycarbonyl, propoxycarbonyl, isopropoxycarbonyl, butoxycarbonyl, isobutoxycarbonyl and t-butoxycarbonyl; carbamoyl; $C_{2-7}$ alkylcarbamoyl groups such as N-methylcarbamoyl, N,N-dimethylcarbamoyl, N-ethylcarbamoyl, N-ethyl-N-methylcarbamoyl, N,N-diethylcarbamoyl, N-propylcarbamoyl, N-isopropylcarbamoyl, N-butylcarbamoyl, N-cyclopropylcarbamoyl and N-cyclopropylmethylcarbamoyl; amino; $C_{1-6}$ alkylamino groups such as methylamino, ethylamino, propylamino, isopropylamino, dimethylamino, N-ethylmethylamino, diethylamino, N-methylpropylamino, N-methylisopropylamino, cyclopropylamino and cyclopropylmethylamino; $C_{4-6}$ cyclic amino groups having in the ring 1 or 2 atoms selected from the group consisting of oxygen, nitrogen and sulfur, such as 1-pyrrolidinyl, piperazinyl, 4-methylpiperazinyl, piperidino and morpholino; trifluoroacetylamino; $C_{1-7}$ acylamino groups such as formylamino, acetylamino, propionylamino, butyrylamino, isobutyrylamino and valerylamino; $C_{1-6}$ alkylsulfonylamino groups such as methylsulfonylamino, ethylsulfonylamino, propylsulfonylamino and butylsulfonylamino; nitro: cyano; $C_{1-6}$ alkyl groups such as methyl, ethyl, propyl, isopropyl, butyl, isobutyl, s-butyl and t-butyl; trifluoromethyl; and trifluoromethoxy.

As examples of heterocyclic groups having in the ring 1 to 4 atoms selected from the group consisting of oxygen, nitrogen and sulfur for $G^2$ when $G^2$ in formula (I) represents a substituted or unsubstituted heterocyclic group having in the ring 1 to 4 atoms selected from the group consisting of oxygen, nitrogen and sulfur, there may be mentioned monovalent monocyclic, bicyclic or tricyclic groups such as furan, thiophene, pyrrole, pyrroline, pyrrolidine, oxazole, oxazolidine, isooxazole, isooxazolidine, thiazole, thiazolidine, isothiazole, isothiazolidine, imidazole, imidazoline, imidazolidine, pyrazole, pyrazoline, pyrazolidine, triazole, thiadiazole, oxadiazole, tetrazole, pyran, tetrahydropyran, thiopyran, tetrahydrothiopyran, pyridine, pyrazine, pyrimidine, pyridazine, benzofuran, dibenzofuran, benzothiophene, indole, 1,2-methylenedioxybenzene, benzimidazole, benzothiazole, benzoxazole, chromane, isochromane, quinoline, decahydroquinoline, isoquinoline, quinazoline, quinoxaline, purine, pteridine, azetidine, morpholine, thiomorpholine, piperidine, homopiperidine, piperazine, homopiperazine, indoline, isoindoline, phenoxazine, phenazine, phenothiazine and quinuclidine. As preferred examples of heterocyclic groups having in the ring 1 to 4 atoms selected from the group consisting of oxygen, nitrogen and sulfur for $G^2$ there may be mentioned 2-pyridyl, 3-pyridyl, 4-pyridyl, piperidino, 2-piperidyl, 3-piperidyl, 4-piperidyl, morpholino, 1-homopiperidinyl, 1-pyrrolidinyl, 2-thiazolyl, 4-thiazolyl, 5-thiazolyl, 2-oxazolyl, 4-oxazolyl, 5-oxazolyl, 1-imidazolyl, 2-imidazolyl, 4-imidazolyl, 5-imidazolyl, 3-pyrazolyl, 2-furyl, 3-furyl, 2-thienyl, 3-thienyl, 2-pyrrolyl, 3-pyrrolyl, 4-isooxazolyl, 2-pyrimidinyl, 4-pyrimidinyl, 2-pyrazinyl, 4-triazolyl, 5-tetrazolyl, 1-piperazinyl, 4-tetrahydropyranyl, 2-1,3,4-oxadiazolyl, 4-1,2,3-thiadiazolyl, 2-benzofuranyl, 2-benzothiazolyl, 2-indolyl, 3-indolyl, 5-benzimidazolyl and 2-1,2,3,4-tetrahydroisoquinolinyl.

A heterocyclic group having in the ring 1 to 4 atoms selected from the group consisting of oxygen, nitrogen and sulfur for $G^2$ is bonded to $A^4$ at a carbon atom or nitrogen atom.

As more preferred examples of heterocyclic groups for $G^2$ having in the ring 1 to 4 atoms selected from the group consisting of oxygen, nitrogen and sulfur, which bond to $A^4$ at a carbon atom, there may be mentioned monovalent monocyclic or bicyclic $C_{3-9}$ aromatic heterocyclic groups having in the ring 1 or 2 atoms selected from the group consisting of oxygen, nitrogen and sulfur atoms, such as furan, pyrrole, thiophene, pyrazole, oxazole, thiazole, isooxazole, isothiazole, pyrazole, imidazole, pyridine, pyrimidine, pyrazine, pyridazine, benzothiophene, benzofuran, 1,2-methylenedioxybenzene, benzimidazole, indole, quinoline, isoquinoline and quinazoline.

As preferred examples of heterocyclic groups for $G^2$ having in the ring 1 to 4 atoms selected from the group consisting of oxygen, nitrogen and sulfur which bond to $A^2$ at a nitrogen atom, there may be mentioned monovalent monocyclic $C_{2-9}$ heterocyclic groups having in the ring 1 or 2 atoms selected from the group consisting of oxygen, nitrogen and sulfur, such as pyrrolidine, piperidine, morpholine, thiomorpholine, homopiperidine, homopiperazine, 1,2,3,6-tetrahydropyridine and piperazine. As more preferred examples of the heterocyclic groups for $G^2$ there may be mentioned monovalent monocyclic $C_{4-6}$ heterocyclic groups having in the ring 1 or 2 atoms selected from the group consisting of oxygen, nitrogen and sulfur, such as piperidine, homopiperidine, morpholine, homopiperazine and piperazine.

As substituents for the substituted heterocyclic groups having in the ring 1 to 4 atoms selected from the group consisting of oxygen, nitrogen and sulfur for $G^2$, there may be mentioned one or more substituents selected from the group consisting of fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, oxo, $C_{1-6}$ alkylsulfonyloxy, optionally substituted $C_{2-7}$ acyl, carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-7}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbon, optionally substituted $C_{1-6}$ aliphatic hydrocarbon, optionally substituted $C_{6-14}$ aromatic hydrocarbon and optionally substituted heterocyclic groups (having in the ring 1 to 4 atoms selected from the group consisting of oxygen, nitrogen and sulfur).

The definitions of the substituents for the substituted heterocyclic groups having in the ring 1 to 4 atoms selected from the group consisting of oxygen, nitrogen and sulfur for $G^2$ are the same as the definitions of the substituents for the substituted $C_{1-10}$ aliphatic hydrocarbon groups for $G^2$. As specific examples of substituents for the substituted heterocyclic groups having in the ring 1 to 4 atoms selected from the group consisting of oxygen, nitrogen and sulfur for $G^2$ there may be mentioned the same specific substituents mentioned above for the substituted $C_{1-10}$ aliphatic hydrocarbon groups for $G^2$.

The $C_{1-7}$ alkoxy, $C_{2-7}$ acyl, $C_{2-7}$ alkylcarbamoyl, $C_{1-6}$ alkylamino, $C_{2-7}$ acylamino, $C_{3-6}$ alicyclic hydrocarbon, $C_{1-6}$ aliphatic hydrocarbon, $C_{6-14}$ aromatic hydrocarbon and heterocyclic groups (having in the ring 1 to 4 atoms selected from the group consisting of oxygen, nitrogen and sulfur) as substituents for the substituted heterocyclic groups for $G^2$ having in the ring 1 to 4 atoms selected from the group consisting of oxygen, nitrogen and sulfur, may be in turn substituted with one or more substituents selected from the group consisting of fluorine; chlorine; bromine; iodine; hydroxyl; $C_{1-6}$ alkoxy groups such as methoxy, ethoxy, propoxy, isopropoxy, butoxy, isobutoxy, s-butoxy, t-butoxy, pentyloxy and cyclopropyloxy; methoxymethyloxy; 2-methoxyethoxy; formyl; trifluoroacetyl; $C_{2-7}$ acyl groups such as acetyl, propionyl, butyryl, isobutyryl, valeryl and isovaleryl; oxo; carboxyl; $C_{2-7}$ alkoxycarbonyl groups such as methoxycarbonyl, ethoxycarbonyl, propoxycarbonyl, isopropoxycarbonyl, butoxycarbonyl, isobutoxycarbonyl and t-butoxycarbonyl; carbamoyl; $C_{2-7}$ alkylcarbamoyl groups such as N-methylcarbamoyl, N,N-dimethylcarbamoyl, N-ethylcarbamoyl, N-ethyl-N-methylcarbamoyl, N,N-diethylcarbamoyl, N-propylcarbamoyl, N-isopropylcarbamoyl, N-butylcarbamoyl, N-cyclopropylcarbamoyl and N-cyclopropylmethylcarbamoyl; amino; $C_{1-6}$ alkylamino groups such as methylamino, ethylamino, propylamino, isopropylamino, dimethylamino, N-ethylmethylamino, diethylamino, N-methylpropylamino, N-methylisopropylamino, cyclopropylamino and cyclopropylmethylamino; $C_{4-6}$ cyclic amino groups having in the ring 1 or 2 atoms selected from the group consisting of oxygen, nitrogen and sulfur, such as 1-pyrrolidinyl, piperazinyl, 4-methylpiperazinyl, piperidino and morpholino; trifluoroacetylamino; $c_{1-7}$ acylamino groups such as formylamino, acetylamino, propionylamino, butyrylamino, isobutyrylamino and valerylamino; $C_{1-6}$ alkylsulfonylamino groups such as methylsulfonylamino, ethylsulfonylamino, propylsulfonylamino and butylsulfonylamino; nitro; cyano; $C_{1-6}$ alkyl groups such as methyl, ethyl, propyl, isopropyl, butyl, isobutyl, s-butyl and t-butyl; trifluoromethyl; and trifluoromethoxy.

The above is with the proviso that among the combinations of $A^1$, $A^2$, $G^1$, $A^3$, $A^4$ and $G^2$ in formula (I) according to the invention, when $A^1$ is a single bond, $A^2$, $G^1$, $A^3$ and $A^4$ are all single bonds.

Also, among the combinations of $A^1$, $A^2$, $G^1$, $A^3$, $A^4$ and $G^2$ in formula (I) according to the invention, when $A^1$ is not a single bond and $G^1$ and $A^3$ are both single bonds, the combination including $A^2$ and $A^4$ is $A^1$-C(=O)—C(=O)-$G^2$ or $A^1$-C(=O)NR$^{101}$-O-$G^2$ (where $R^{101}$ has the same definition as above).

Also, among the combinations of $G^1$, $A^3$, $A^4$ and $G^2$ in formula (I) according to the invention, when $A^3$ represents a $C_{1-6}$ aliphatic hydrocarbon group having $G^1$ and $A^4$ bonded on the same or different carbon atoms and $G^2$ represents a substituted or unsubstituted $C_{1-10}$ aliphatic hydrocarbon group, $A^4$ is not a single bond.

In formula (I), $A^5$ represents a single bond, or a group binding $R^2$ and the carbon atom of the pyrrole ring to which $A^5$ is bonded in the form of $R^2$—NR$^{201}$-pyrrole ring carbon (where $R^{201}$ represents hydrogen or a $C_{1-4}$ aliphatic hydrocarbon group). As examples of $C_{1-4}$ aliphatic hydrocarbon groups for $R^{201}$ when $A^5$ is a group binding $R^2$ and the carbon atom of the pyrrole ring to which $A^1$ is bonded in the form of $R^2$—NR$^{201}$-pyrrole ring carbon (where $R^{201}$ represents hydrogen or a $C_{1-4}$ aliphatic hydrocarbon group), there may be mentioned the same ones as mentioned above for $R^{101}$ in $A^2$. As preferred examples for $R^{102}$ there may be mentioned hydrogen, methyl, ethyl and propyl, with hydrogen and methyl being particularly preferred.

As preferred examples for $A^5$ there may be mentioned a single bond, —NH— and —N(CH$_3$)—. A single bond may be mentioned as a particularly preferred example for $A^5$.

$R^2$ in formula (I) above represents one group selected from among the following 1) to 6):

1) Hydrogen.

2) Fluorine, chlorine, bromine or iodine.

3) A substituted or unsubstituted $C_{1-10}$ aliphatic hydrocarbon group. (As substituents there may be mentioned one or more selected from the group consisting of fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, oxo, $C_{1-6}$ alkylsulfonyloxy, optionally substituted $C_{2-7}$ acyl, carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-7}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbons, optionally substituted $C_{1-6}$ aliphatic hydrocarbons, optionally substituted $C_{6-14}$ aromatic hydrocarbons and optionally substituted heterocyclic groups (having in the ring 1 to 4 atoms selected from the group consisting of oxygen, nitrogen and sulfur).)

4) A substituted or unsubstituted $C_{3-8}$ alicyclic hydrocarbon group. (As substituents there may be mentioned one or more selected from the group consisting of fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, oxo, $C_{1-6}$ alkylsulfonyloxy, optionally substituted $C_{2-7}$ acyl, carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-8}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbons, optionally substituted $C_{1-6}$ aliphatic hydrocarbons, optionally substituted $C_{6-14}$ aromatic hydrocarbons and optionally substituted heterocyclic groups (having in the ring 1 to 4 atoms selected from the group consisting of oxygen, nitrogen and sulfur).)

5) A substituted or unsubstituted $C_{6-14}$ aromatic hydrocarbon group. (As substituents there may be mentioned one or more selected from the group consisting of fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, oxo, $C_{1-6}$ alkylsulfonyloxy, optionally substituted $C_{2-7}$ acyl, carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-8}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbons, optionally substituted $C_{1-6}$ aliphatic hydrocarbons, optionally substituted $C_{6-14}$ aromatic hydrocarbons and optionally substituted heterocyclic groups (having in the ring 1 to 4 atoms selected from the group consisting of oxygen, nitrogen and sulfur).)

6) A substituted or unsubstituted heterocyclic group having in the ring 1 to 4 atoms selected from the group consisting of oxygen, nitrogen and sulfur. (As substituents there may be mentioned one or more selected from the group consisting of fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, oxo, $C_{1-6}$ alkylsulfonyloxy, optionally substituted $C_{2-7}$ acyl, carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-7}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbons, optionally substituted $C_{1-6}$ aliphatic hydrocarbons, optionally substituted $C_{6-14}$ aromatic hydrocarbons and optionally substituted heterocyclic groups (having in the ring 1 to 4 atoms selected from the group consisting of oxygen, nitrogen and sulfur).)

When $R^2$ in formula (I) is fluorine, chlorine, bromine or iodine, there may be mentioned as preferable chlorine and bromine.

As examples of $C_{1-10}$ aliphatic hydrocarbon groups for $R^2$ when $R^2$ in formula (I) represents a substituted or unsubstituted $C_{1-10}$ aliphatic hydrocarbon group, there may be mentioned the same ones as mentioned above as examples for $C_{1-10}$ aliphatic hydrocarbon groups for $G^2$. As preferred examples of $C_{1-10}$ aliphatic hydrocarbon groups for $R^2$ there may be mentioned methyl, ethyl, isopropyl, butyl, t-butyl, t-pentyl, vinyl, 2-propenyl and 2-propynyl.

As substituents for the substituted $C_{1-10}$ aliphatic hydrocarbon groups for $R^2$ there may be mentioned one or more substituents selected from the group consisting of fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, oxo, $C_{1-6}$ alkylsulfonyloxy, optionally substituted $C_{2-7}$ acyl, carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-7}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbon, optionally substituted $C_{1-6}$ aliphatic hydrocarbon, optionally substituted $C_{6-14}$ aromatic hydrocarbon and optionally substituted heterocyclic groups (having in the ring 1 to 4 atoms selected from the group consisting of oxygen, nitrogen and sulfur).

The definitions of the substituents for the substituted $C_{1-10}$ aliphatic hydrocarbon groups for $R^2$ are the same as the above-mentioned definitions of the substituents for the substituted $C_{1-10}$ aliphatic hydrocarbon groups for $G^2$. As specific examples of substituents for the substituted $C_{1-10}$ aliphatic hydrocarbon groups for $R^2$ there may be mentioned the same specific substituents mentioned above for the substituted $C_{1-10}$ aliphatic hydrocarbon groups for $G^2$.

The $C_{1-7}$ alkoxy, $C_{2-7}$ acyl, $C_{2-7}$ alkylcarbamoyl, $C_{1-6}$ alkylamino, $C_{2-7}$ acylamino, $C_{3-6}$ alicyclic hydrocarbon, $C_{1-6}$ aliphatic hydrocarbon, $C_{6-14}$ aromatic hydrocarbon and heterocyclic groups (having in the ring 1 to 4 atoms selected from the group consisting of oxygen, nitrogen and sulfur) as substituents for the substituted $C_{1-10}$ aliphatic hydrocarbon groups for $R^2$, may be in turn substituted with one or more substituents selected from the group consisting of fluorine; chlorine; bromine; iodine; hydroxyl; $C_{1-6}$ alkoxy groups such as methoxy, ethoxy, propoxy, isopropoxy, butoxy, isobutoxy, s-butoxy, t-butoxy, pentyloxy and cyclopropyloxy; methoxymethyloxy; 2-methoxyethoxy; formyl; trifluoroacetyl; $C_{2-7}$ acyl groups such as acetyl, propionyl, butyryl, isobutyryl, valeryl and isovaleryl; oxo; carboxyl; $C_{2-7}$ alkoxycarbonyl groups such as methoxycarbonyl, ethoxycarbonyl, propoxycarbonyl, isopropoxycarbonyl, butoxycarbonyl, isobutoxycarbonyl and t-butoxycarbonyl; carbamoyl; $C_{2-7}$ alkylcarbamoyl groups such as N-methylcarbamoyl, N,N-dimethylcarbamoyl, N-ethylcarbamoyl, N-ethyl-N-methylcarbamoyl, N,N-diethylcarbamoyl, N-propylcarbamoyl, N-isopropylcarbamoyl, N-butylcarbamoyl, N-cyclopropylcarbamoyl and N-cyclopropylmethylcarbamoyl; amino; $C_{1-6}$ alkylamino groups such as methylamino, ethylamino, propylamino, isopropylamino, dimethylamino, N-ethylmethylamino, diethylamino, N-methylpropylamino, N-methylisopropylamino, cyclopropylamino and cyclopropylmethylamino; $C_{4-6}$ cyclic amino groups having in the ring 1 or 2 atoms selected from the group consisting of oxygen, nitrogen and sulfur, such as 1-pyrrolidinyl, piperazinyl, 4-methylpiperazinyl, piperidino and morpholino; trifluoroacetylamino; $C_{1-7}$ acylamino groups such as formylamino, acetylamino, propionylamino, butyrylamino, isobutyrylamino and valerylamino; $C_{1-6}$ alkylsulfonylamino groups such as methylsulfonylamino, ethylsulfonylamino, propylsulfonylamino and butylsulfonylamino; nitro; cyano; $C_{1-6}$ alkyl groups such as methyl, ethyl, propyl, isopropyl, butyl, isobutyl, s-butyl and t-butyl; trifluoromethyl; and trifluoromethoxy.

As examples of $C_{3-8}$ alicyclic hydrocarbon groups for $R^2$, when $R^2$ in formula (I) represents a substituted or unsubstituted $C_{3-8}$ alicyclic hydrocarbon group, there may be mentioned the same ones as mentioned above as examples for the $C_{3-8}$ alicyclic hydrocarbon groups for $G^2$. As preferred examples of $C_{3-8}$, alicyclic hydrocarbon groups for $R^2$ there may be mentioned cyclopropyl, cyclobutyl, cyclopentyl and cyclohexyl.

As substituents for the substituted $C_{3-8}$ alicyclic hydrocarbon groups for $R^2$ there may be mentioned one or more substituents selected from the group consisting of fluorine, chlorine, bromine, iodine, hydroxyl, optionally substituted $C_{1-7}$ alkoxy, $C_{6-10}$ aryloxy, $C_{1-9}$ aralkoxy, $C_{2-7}$ acyloxy, oxo, $C_{1-6}$ alkylsulfonyloxy, optionally substituted $C_{2-7}$ acyl, carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-7}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbon, optionally substituted $C_{1-6}$ aliphatic hydrocarbon, optionally substituted $C_{6-14}$ aromatic hydrocarbon and optionally substituted heterocyclic groups (having in the ring 1 to 4 atoms selected from the group consisting of oxygen, nitrogen and sulfur).

The definitions of the substituents for the substituted $C_{3-8}$ alicyclic hydrocarbon groups for $R^2$ are the same as the above-mentioned definitions of the substituents for the substituted $C_{1-10}$ aliphatic hydrocarbon groups for $G^2$. As specific examples of substituents for the substituted $C_{3-8}$ alicyclic hydrocarbon groups for $R^2$ there may be mentioned the same specific substituents mentioned above for the substituted $C_{1-10}$ aliphatic hydrocarbon groups for $G^2$.

The $C_{1-7}$ alkoxy, $C_{2-7}$ acyl, $C_{2-7}$ alkylcarbamoyl, $C_{1-6}$ alkylamino, $C_{2-7}$ acylamino, $C_{3-6}$ alicyclic hydrocarbon, $C_{1-6}$ aliphatic hydrocarbon, $C_{6-14}$ aromatic hydrocarbon and heterocyclic groups (having in the ring 1 to 4 atoms selected from the group consisting of oxygen, nitrogen and sulfur) as substituents for the substituted $C_{3-8}$ alicyclic hydrocarbon groups for $R^2$, may be in turn substituted with one or more substituents selected from the group consisting of fluorine; chlorine; bromine; iodine; hydroxyl; $C_{1-6}$ alkoxy groups such as methoxy, ethoxy, propoxy, isopropoxy, butoxy, isobutoxy, s-butoxy, t-butoxy, pentyloxy and cyclopropyloxy; methoxymethyloxy; 2-methoxyethoxy; formyl; trifluoroacetyl; $C_{2-7}$ acyl groups such as acetyl, propionyl, butyryl, isobutyryl, valeryl and isovaleryl; oxo; carboxyl; $C_{2-7}$ alkoxycarbonyl groups such as methoxycarbonyl, ethoxycarbonyl, propoxycarbonyl, isopropoxycarbonyl, butoxycarbonyl, isobutoxycarbonyl and t-butoxycarbonyl; carbamoyl; $C_{2-7}$ alkylcarbamoyl groups such as N-methylcarbamoyl, N,N-dimethylcarbamoyl, N-ethylcarbamoyl, N-ethyl-N-methylcarbamoyl, N,N-diethylcarbamoyl, N-propylcarbamoyl, N-isopropylcarbamoyl, N-butylcarbamoyl, N-cyclopropylcarbamoyl and N-cyclopropylmethylcarbamoyl; amino; $C_{1-6}$ alkylamino groups such as methylamino, ethylamino, propylamino, isopropylamino, dimethylamino, N-ethylmethylamino, diethylamino, N-methylpropylamino, N-methylisopropylamino, cyclopropylamino and cyclopropylmethylamino; $C_{4-6}$ cyclic amino groups having in the ring 1 or 2 atoms selected from the group consisting of oxygen, nitrogen and sulfur, such as 1-pyrrolidinyl, piperazinyl, 4-methylpiperazinyl, piperidino and morpholino; trifluoroacetylamino; $C_{1-7}$ acylamino groups such as formylamino, acetylamino, propionylamino, butyrylamino, isobutyrylamino and valerylamino; $C_{1-6}$ alkylsulfonylamino groups such as methylsulfonylamino, ethylsulfonylamino, propylsulfonylamino and butylsulfonylamino; nitro; cyano; $C_{1-6}$ alkyl groups such as methyl, ethyl, propyl, isopropyl, butyl, isobutyl, s-butyl and t-butyl; trifluoromethyl; and trifluoromethoxy.

As $C_{6-14}$ aromatic hydrocarbon groups for $R^2$ when $R^2$ in formula (I) represents a substituted or unsubstituted $C_{6-14}$ aromatic hydrocarbon group, there may be mentioned the same ones as mentioned above as examples for the $C_{6-14}$ aromatic hydrocarbon groups for $G^2$. Phenyl may be mentioned as a preferred example of a $C_{6-14}$ aromatic hydrocarbon group for $R^2$.

As substituents for the substituted $C_{6-14}$ aromatic hydrocarbon groups for $R^2$ there may be mentioned one or more substituents selected from the group consisting of fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, oxo, $C_{1-6}$ alkylsulfonyloxy, optionally substituted $C_{2-7}$ acyl, carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-8}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbon, optionally substituted $C_{1-6}$ aliphatic hydrocarbon, optionally substituted $C_{6-14}$ aromatic hydrocarbon and optionally substituted heterocyclic groups (having in the ring 1 to 4 atoms selected from the group consisting of oxygen, nitrogen and sulfur).

The definitions of the substituents for the substituted $C_{6-14}$ aromatic hydrocarbon groups for $R^2$ are the same as the above-mentioned definitions of the substituents for the substituted $C_{1-10}$ aliphatic hydrocarbon groups for $G^2$. As specific examples of substituents for the substituted $C_{6-14}$ aromatic hydrocarbon groups for $R^2$ there may be mentioned the same specific substituents mentioned above for the substituted $C_{1-10}$ aliphatic hydrocarbon groups for $G^2$.

The $C_{1-7}$ alkoxy, $C_{2-7}$ acyl, $C_{2-7}$ alkylcarbamoyl, $C_{1-6}$ alkylamino, $C_{2-7}$ acylamino, $C_{3-6}$ alicyclic hydrocarbon, $C_{1-6}$ aliphatic hydrocarbon, $C_{6-14}$ aromatic hydrocarbon and heterocyclic groups (having in the ring 1 to 4 atoms selected from the group consisting of oxygen, nitrogen and sulfur) as substituents for the substituted $C_{6-14}$ aromatic hydrocarbon groups for $R^2$, may be in turn substituted with one or more substituents selected from the group consisting of fluorine; chlorine; bromine; iodine; hydroxyl; $C_{1-6}$ alkoxy groups such as methoxy, ethoxy, propoxy, isopropoxy, butoxy, isobutoxy, s-butoxy, t-butoxy, pentyloxy and cyclopropyloxy; methoxymethyloxy; 2-methoxyethoxy; formyl; trifluoroacetyl; $C_{2-7}$ acyl groups such as acetyl, propionyl, butyryl, isobutyryl, valeryl and isovaleryl; oxo; carboxyl; $C_{2-7}$ alkoxycarbonyl groups such as methoxycarbonyl, ethoxycarbonyl, propoxycarbonyl, isopropoxycarbonyl, butoxycarbonyl, isobutoxycarbonyl and t-butoxycarbonyl; carbamoyl; $C_{2-7}$ alkylcarbamoyl groups such as N-methylcarbamoyl, N,N-dimethylcarbamoyl, N-ethylcarbamoyl, N-ethyl-N-methylcarbamoyl, N,N-diethylcarbamoyl, N-propylcarbamoyl, N-isopropylcarbamoyl, N-butylcarbamoyl, N-cyclopropylcarbamoyl and N-cyclopropylmethylcarbamoyl; amino; $C_{1-6}$ alkylamino groups such as methylamino, ethylamino, propylamino, isopropylamino, dimethylamino, N-ethylmethylamino, diethylamino, N-methylpropylamino, N-methylisopropylamino, cyclopropylamino and cyclopropylmethylamino; $C_{4-6}$ cyclic amino groups having in the ring 1 or 2 atoms selected from the group consisting of oxygen, nitrogen and sulfur, such as 1-pyrrolidinyl, piperazinyl, 4-methylpiperazinyl, piperidino and morpholino; trifluoroacetylamino; $C_{1-7}$ acylamino groups such as formylamino, acetylamino, propionylamino, butyrylamino, isobutyrylamino and valerylamino; $C_{1-6}$ alkylsulfonylamino groups such as methylsulfonylamino, ethylsulfonylamino, propylsulfonylamino and butylsulfonylamino; nitro; cyano; $C_{1-6}$ alkyl groups such as methyl, ethyl, propyl, isopropyl, butyl, isobutyl, s-butyl and t-butyl; trifluoromethyl; and trifluoromethoxy.

As examples of heterocyclic groups having in the ring 1 to 4 atoms selected from the group consisting of oxygen, nitrogen and sulfur for $R^2$, when $R^2$ in formula (I) represents a substituted or unsubstituted heterocyclic group having in the ring 1 to 4 atoms selected from the group consisting of oxygen, nitrogen and sulfur, there may be mentioned the same ones as mentioned above as examples for the heterocyclic group having in the ring 1 to 4 atoms selected from the group consisting of oxygen, nitrogen and sulfur for $G^2$. A heterocyclic group for $R^2$ having in the ring 1 to 4 atoms selected from the group consisting of oxygen, nitrogen and sulfur is bonded to $A^5$ at a carbon atom or nitrogen atom.

As preferred examples of heterocyclic groups having in the ring 1 to 4 atoms selected from the group consisting of oxygen, nitrogen and sulfur, which bond to $A^5$ at a carbon atom, there may be mentioned monocyclic or bicyclic $C_{3-9}$ aromatic heterocyclic groups having in the ring 1 to 3 atoms selected from the group consisting of oxygen, nitrogen and sulfur atoms, such as furyl, thienyl, pyrrolyl, pyrazolyl, oxazolyl, isooxazolyl, thiazolyl, isothiazolyl, imidazolyl, pyridyl, pyrazinyl, pyrimidinyl, pyridazinyl, benzofuranyl, indolyl, benzothienyl, quinolyl, isoquinolyl, quinazolyl, benzimidazolyl and benzooxazolyl. As more preferred groups there may be mentioned monocyclic or bicyclic $C_{3-9}$ aromatic heterocyclic groups having in the ring 1 or 2 atoms selected from the group consisting of oxygen, nitrogen and sulfur atoms, such as 2-furyl, 2-thienyl, 2-pyrrolyl, 2-imidazolyl, 5-imidazolyl, 2-oxazolyl, 5-oxazolyl, 5-isooxazolyl, 2-thiazolyl, 5-thiazolyl, 5-isothiazolyl, 3-isothiazolyl, 2-pyridyl, 2-pyrimidinyl, 2-benzofuranyl and 2-benzothiophenyl. Particularly preferred among these groups are monocyclic $C_{3-5}$ aromatic heterocyclic groups having in the ring 1 to 2 atoms selected from the group consisting of oxygen, nitrogen and sulfur atoms, among which 2-furyl, 2-thienyl and 2-pyrrolyl are especially preferred.

As preferred examples of heterocyclic groups having in the ring 1 to 4 atoms selected from the group consisting of oxygen, nitrogen and sulfur which bond to $A^5$ at a nitrogen atom, there may be mentioned 1-pyrrolidinyl, piperidino, morpholino, 1-homopiperidinyl and 1-piperazinyl. When the heterocyclic group having in the ring 1 to 4 atoms selected from the group consisting of oxygen, nitrogen and sulfur for $R^2$ bonds to $A^5$ at a nitrogen atom, $A^5$ is a single bond.

As substituents for the substituted heterocyclic groups having in the ring 1 to 4 atoms selected from the group consisting of oxygen, nitrogen and sulfur for $R^2$, there may be mentioned one or more substituents selected from the group consisting of fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, oxo, $C_{1-6}$ alkylsulfonyloxy, optionally substituted $C_{2-7}$ acyl, carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-7}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbon, optionally substituted $C_{1-6}$ aliphatic hydrocarbon, optionally substituted $C_{6-14}$ aromatic hydrocarbon and optionally substituted heterocyclic groups (having in the ring 1 to 4 atoms selected from the group consisting of oxygen, nitrogen and sulfur).

The definitions of the substituents for the substituted heterocyclic groups having in the ring 1 to 4 atoms selected from the group consisting of oxygen, nitrogen and sulfur for $R^2$ are the same as the above-mentioned definitions of the substituents for the substituted $C_{1-10}$ aliphatic hydrocarbon groups for $G^2$. As specific examples of substituents for the substituted heterocyclic groups having in the ring 1 to 4 atoms selected from the group consisting of oxygen, nitrogen and sulfur for $R^2$, there may be mentioned the same specific substituents mentioned above for the substituted $C_{1-10}$ aliphatic hydrocarbon groups for $G^2$.

The $C_{1-7}$ alkoxy, $C_{2-7}$ acyl, $C_{2-7}$ alkylcarbamoyl, $C_{1-6}$ alkylamino, $C_{2-7}$ acylamino, $C_{3-6}$ alicyclic hydrocarbon, $C_{1-6}$ aliphatic hydrocarbon, $C_{6-14}$ aromatic hydrocarbon and heterocyclic groups (having in the ring 1 to 4 atoms selected from the group consisting of oxygen, nitrogen and sulfur) as substituents for the substituted heterocyclic groups having in the ring 1 to 4 atoms selected from the group consisting of oxygen, nitrogen and sulfur atoms for $R^2$, may be in turn substituted with one or more substituents selected from the group consisting of fluorine; chlorine; bromine; iodine; hydroxyl; $C_{1-6}$ alkoxy groups such as methoxy, ethoxy, propoxy, isopropoxy, butoxy, isobutoxy, s-butoxy, t-butoxy, pentyloxy and cyclopropyloxy; methoxymethyloxy; 2-methoxyethoxy; formyl; trifluoroacetyl; $C_{2-7}$ acyl groups such as acetyl, propionyl, butyryl, isobutyryl, valeryl and isovaleryl; oxo; carboxyl; $C_{2-7}$ alkoxycarbonyl groups such as methoxycarbonyl, ethoxycarbonyl, propoxycarbonyl, isopropoxycarbonyl, butoxycarbonyl, isobutoxycarbonyl and t-butoxycarbonyl; carbamoyl; $C_{2-7}$ alkylcarbamoyl groups such as N-methylcarbamoyl, N,N-dimethylcarbamoyl, N-ethylcarbamoyl, N-ethyl-N-methylcarbamoyl, N,N-diethylcarbamoyl, N-propylcarbamoyl, N-isopropylcarbamoyl, N-butylcarbamoyl, N-cyclopropylcarbamoyl and N-cyclopropylmethylcarbamoyl; amino; $C_{1-6}$ alkylamino groups such as methylamino, ethylamino, propylamino, isopropylamino, dimethylamino, N-ethylmethylamino, diethylamino, N-methylpropylamino, N-methylisopropylamino, cyclopropylamino and cyclopropylmethylamino; $C_{4-6}$ cyclic amino groups having in the ring 1 or 2 atoms selected from the group consisting of oxygen, nitrogen and sulfur, such as 1-pyrrolidinyl, piperazinyl, 4-methylpiperazinyl, piperidino and morpholino; trifluoroacetylamino; $C_{1-7}$ acylamino groups such as formylamino, acetylamino, propionylamino, butyrylamino, isobutyrylamino and valerylamino; $C_{1-6}$ alkylsulfonylamino groups such as methylsulfonylamino, ethylsulfonylamino, propylsulfonylamino and butylsulfonylamino; nitro; cyano; $C_{1-6}$ alkyl groups such as methyl, ethyl, propyl, isopropyl, butyl, isobutyl, s-butyl and t-butyl; trifluoromethyl; and trifluoromethoxy.

Among the examples mentioned as substituents for the substituted heterocyclic groups having in the ring 1 to 4 atoms selected from the group consisting of oxygen, nitrogen and sulfur for $R^2$ according to the invention, the following may be mentioned as preferred: fluorine; chlorine; bromine; iodine; hydroxyl; cyano; nitro; amino; substituted or unsubstituted $C_{1-6}$ mono or dialkylamino groups composed of linear or branched alkyl groups and amino groups, such as methylamino, ethylamino, propylamino, isopropylamino, butylamino, isobutylamino, s-butylamino, t-butylamino, pentylamino, hexylamino, dimethylamino, N-ethylmethylamino, diethylamino, N-methylpropylamino, N-methylisopropylamino, N-methylbutylamino, N-methyl-t-butylamino, N-ethylisopropylamino, dipropylamino, diisopropylamino and ethylbutylamino; carboxyl; substituted or unsubstituted saturated $C_{1-6}$ alkyl groups such as methyl, ethyl, propyl, isopropyl, butyl, isobutyl, s-butyl, t-butyl, pentyl, isopentyl, neopentyl, t-pentyl, hexyl, isohexyl, 2-methylpentyl and 1-ethylbutyl; $C_{3-6}$ alicyclic hydrocarbons such as cyclopropyl, cyclobutyl, cyclopentyl and cyclohexyl; substituted or unsubstituted $C_{1-6}$ alkoxy groups composed of linear or branched alkyl groups and oxy groups, such as methoxy, ethoxy, propoxy, isopropoxy, butoxy, isobutoxy, s-butoxy, t-butoxy, pentyloxy, isopentyloxy, neopentyloxy, t-pentyloxy and hexyloxy; substituted or unsubstituted $C_{2-7}$ acyl groups such as acetyl, propionyl, butyryl, isobutyryl, pivaloyl and hexanoyl; $C_{1-6}$ alkylthio groups such as methylthio, ethylthio, propylthio, isopropylthio, butylthio, isobutylthio, s-butylthio, t-butylthio, pentylthio and hexylthio; trifluoromethyl; trifluoromethoxy; substituted or unsubstituted $C_{2-7}$ acylamino groups such as acetylamino, propionylamino, butyrylamino, isobutyrylamino, valerylamino and hexanoylamino; and substituted or unsubstituted $C_{2-7}$ alkylcarbamoyl groups composed of linear or branched alkyl groups and carbamoyl groups, such as N-methylcarbamoyl, N-ethylcarbamoyl, N-propylcarbamoyl, N-isopropylcarbamoyl, N-butylcarbamoyl, N-isobutylcarbamoyl, N-s-butylcarbamoyl, N-t-butylcarbamoyl, N-pentylcarbamoyl, N,N-dimethylcarbamoyl, N-ethyl-N-methylcarbamoyl and N,N-diethylcarbamoyl.

As more preferred examples of substituents for the substituted heterocyclic groups having in the ring 1 to 4 atoms selected from the group consisting of oxygen, nitrogen and sulfur for $R^2$, there may be mentioned fluorine, chlorine, bromine, substituted or unsubstituted $C_{1-6}$ alkyl groups, hydroxyl, and substituted or unsubstituted $C_{1-6}$ alkoxy groups.

Among the combinations of $R^2$ and $A^5$ in formula (I) according to the invention, when $R^2$ is fluorine, chlorine, bromine or iodine, $A^5$ is a single bond.

As preferred examples of combinations of $R^2$ and $A^5$ in formula (I) according to the invention, there may be mentioned combinations wherein $A^1$ is a single bond and $R^2$ is a substituted or unsubstituted cyclopropyl, or $A^5$ is a single bond and $R^2$ is a substituted or unsubstituted monocyclic $C_{3-5}$ aromatic heterocyclic group having in the ring 1 or 2 atoms selected from the group consisting of oxygen, nitrogen and sulfur. That is, the group represented by $R^2$-$A^5$- is preferably a substituted or unsubstituted cyclopropyl or a monocyclic $C_{3-5}$ aromatic heterocyclic group having in the ring 1 or 2 atoms selected from the group consisting of oxygen, nitrogen and sulfur, such as substituted or unsubstituted 2-furyl, substituted or unsubstituted 2-thienyl, substituted or unsubstituted 2-pyrrolyl, substituted or unsubstituted 2-imidazolyl, substituted or unsubstituted 5-imidazolyl, substituted or unsubstituted 2-oxazolyl, substituted or unsubstituted 5-oxazolyl, substituted or unsubstituted 5-isooxazolyl, substituted or unsubstituted 2-thiazolyl, substituted or unsubstituted 5-thiazolyl, substituted or unsubstituted 5-isothiazolyl, substituted or unsubstituted 3-isothiazolyl, substituted or unsubstituted 2-pyridyl or substituted or unsubstituted 2-pyrimidinyl. Particularly preferred among these are 2-furyl, 2-thienyl and 2-pyrrolyl, and they are preferably substituted with fluorine, chlorine, bromine, substituted or unsubstituted $C_{1-6}$ alkyl, hydroxyl or substituted or unsubstituted $C_{1-6}$ alkoxy.

As preferred combinations of -$G^1$-$A^3$-$A^4$-$G^2$ in the pyrrolo[3,2-d]pyrimidine derivatives of formula (I) above, there may be mentioned the groups represented by K1-K822 shown in FIGS. 1 to 24 below. In the structural formulas, the symbol "---" indicates the binding site for $A^2$ and -$G^1$-$A^3$-$A^4$-$G^2$.

-continued
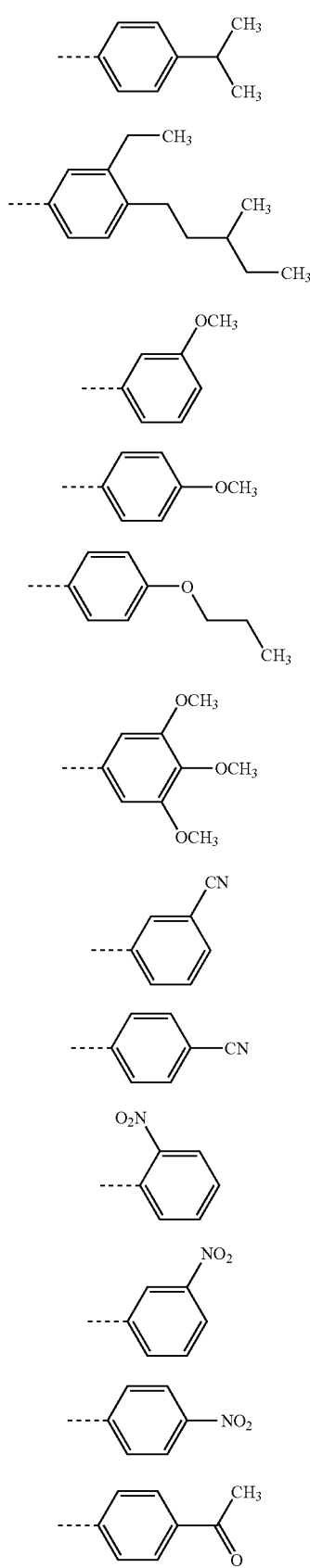
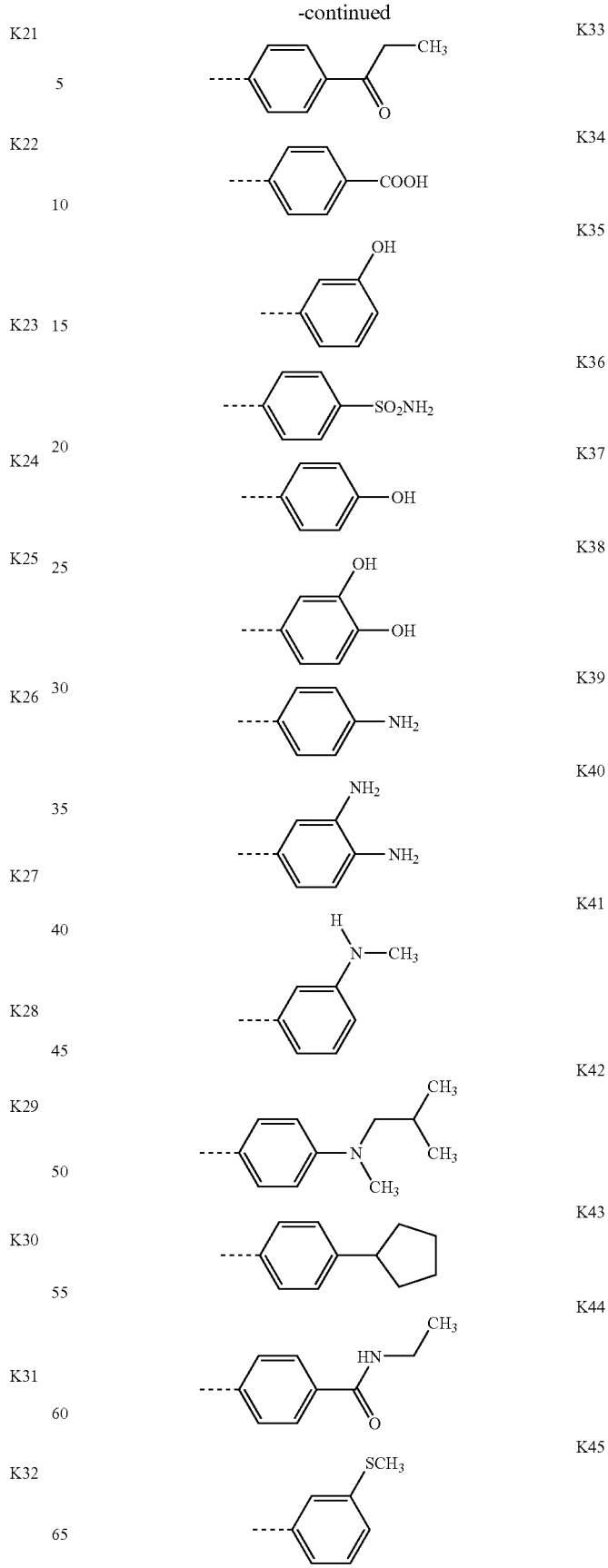

| | |
|---|---|
| 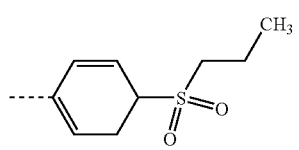 | K46 |
| 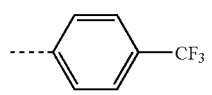 | K47 |
| 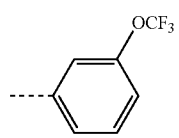 | K48 |
| 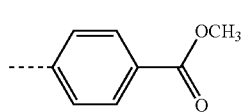 | K49 |
| 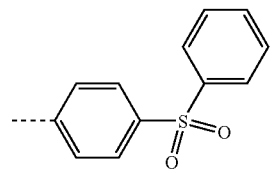 | K50 |
| 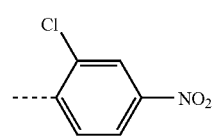 | K51 |
| 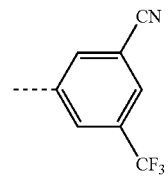 | K52 |
| 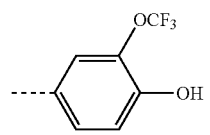 | K53 |
| 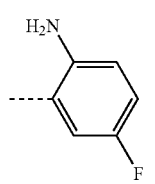 | K54 |
| 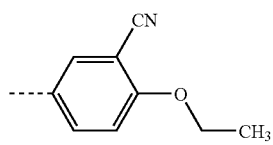 | K55 |
| 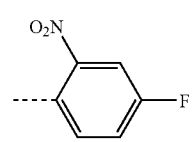 | K56 |
| 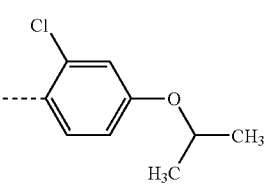 | K57 |
| 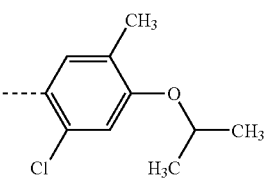 | K58 |
| 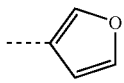 | K59 |
| 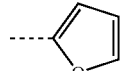 | K60 |
| 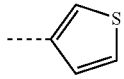 | K61 |
| 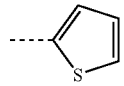 | K62 |
| 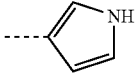 | K63 |
| 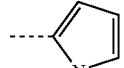 | K64 |
| 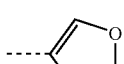 | K65 |
| 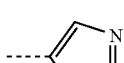 | K66 |
| 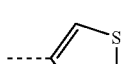 | K67 |
| 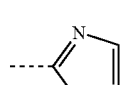 | K68 |
| 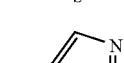 | K69 |
| | K70 |

-continued
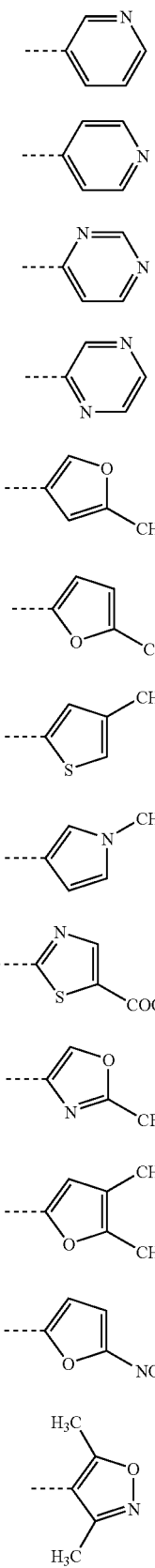
K71
K72
K73
K74
K75
K76
K77
K78
K79
K80
K81
K82
K83
-continued
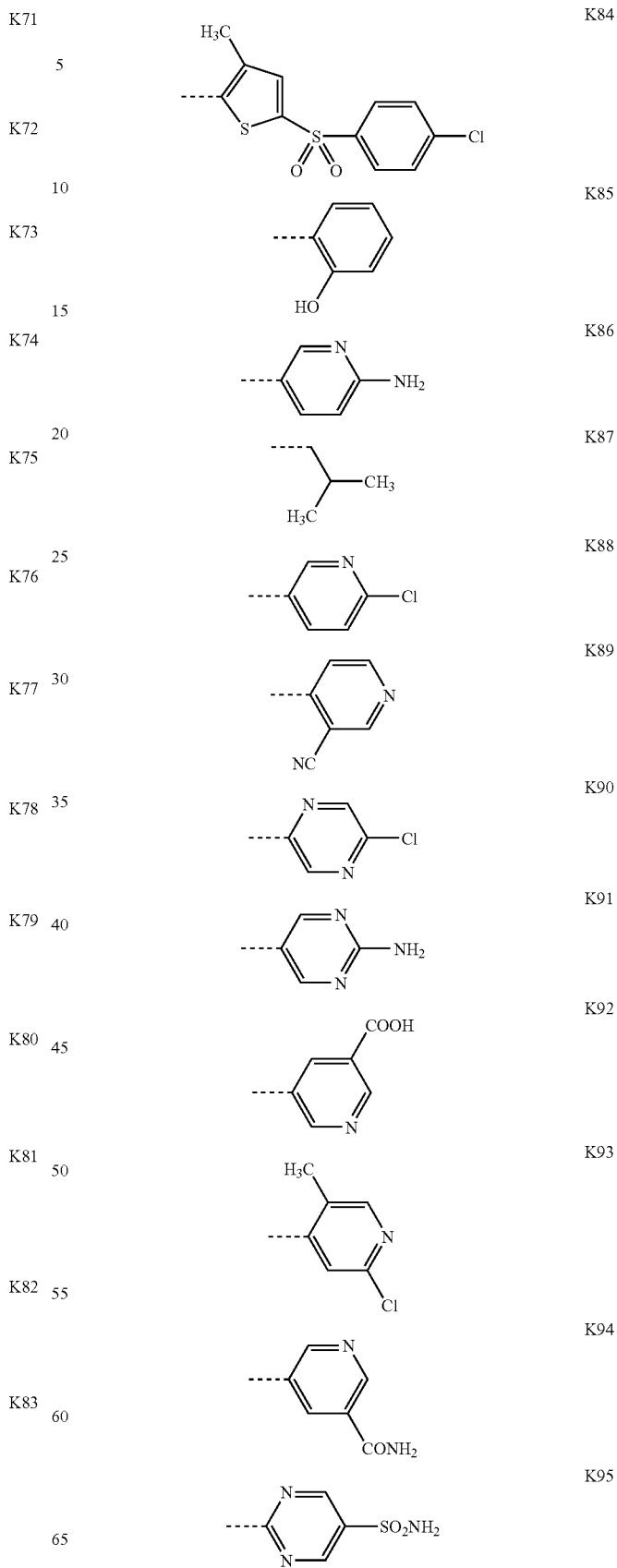
K84
K85
K86
K87
K88
K89
K90
K91
K92
K93
K94
K95

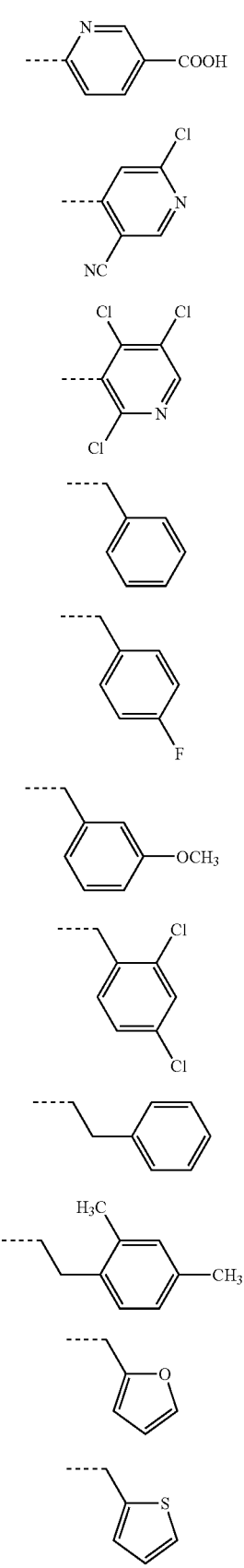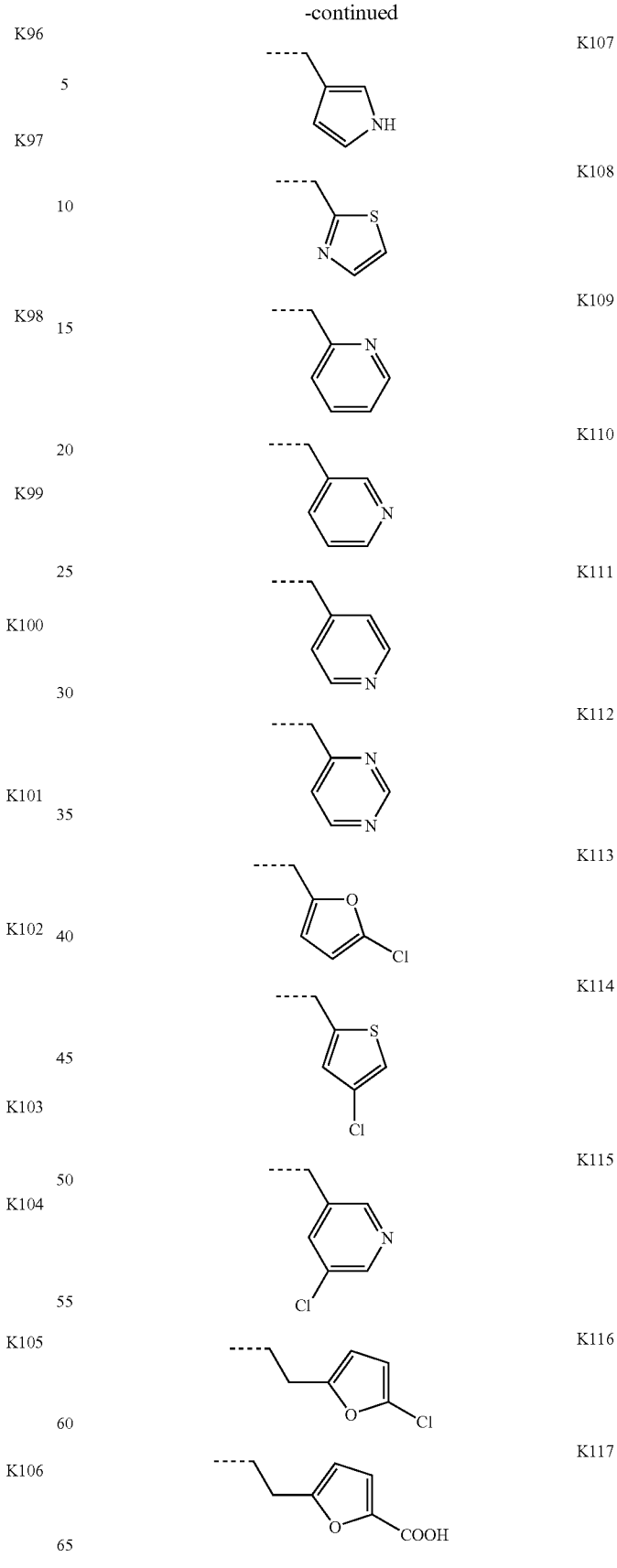

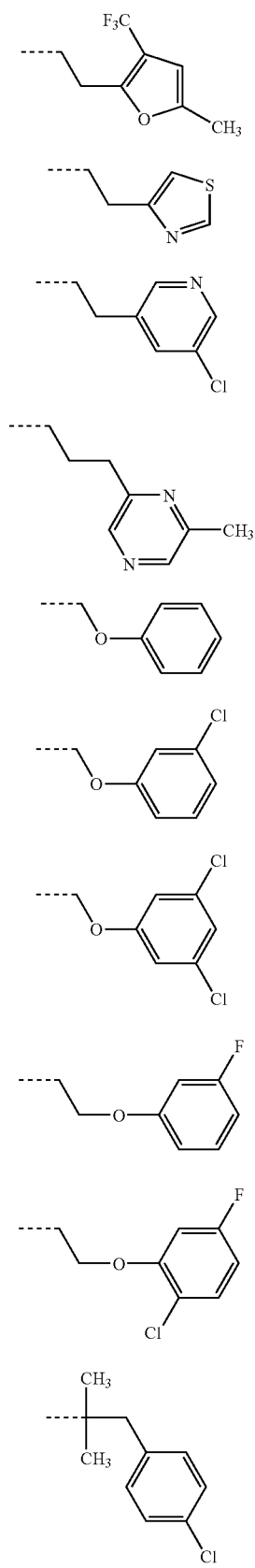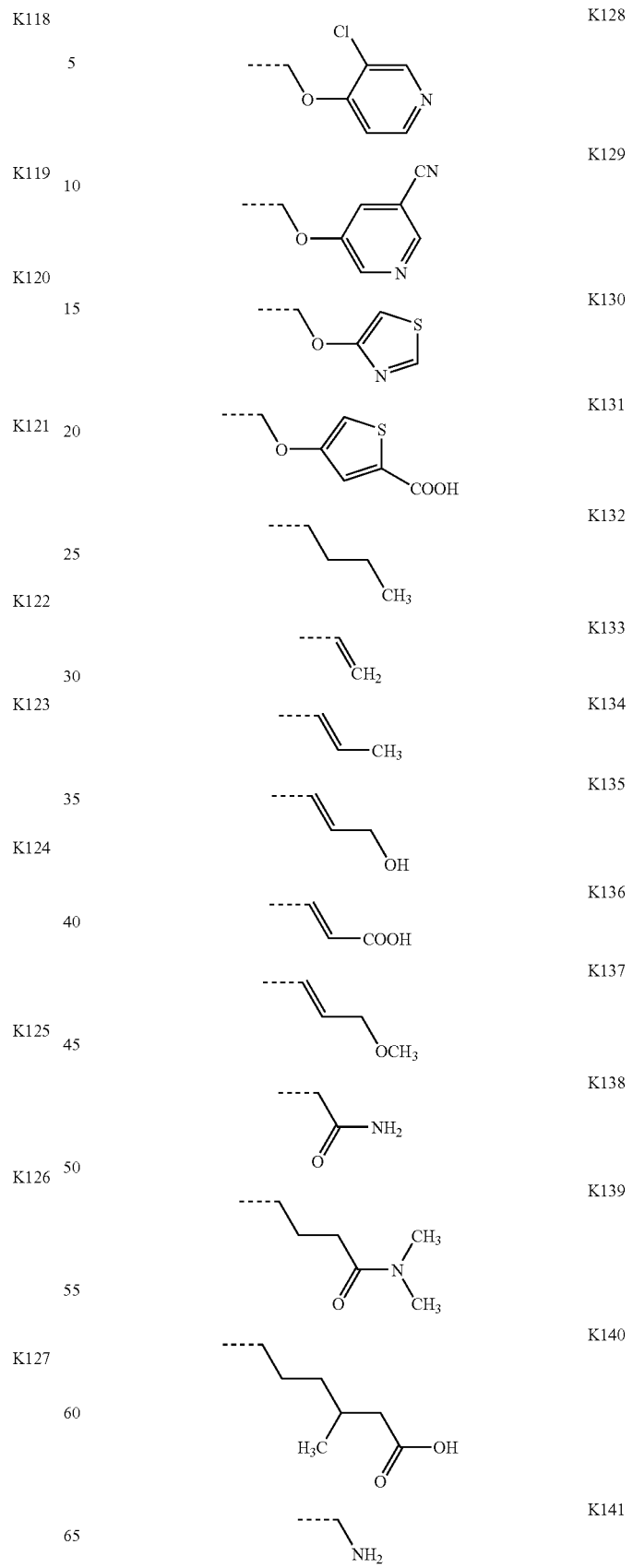

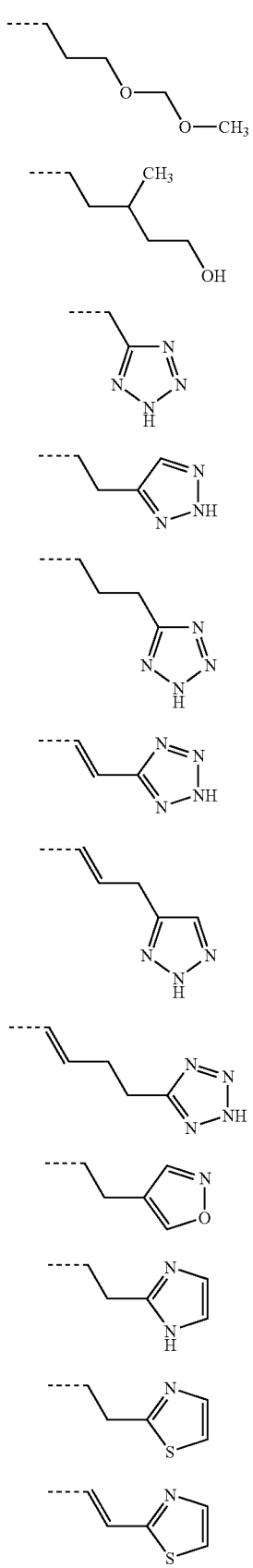
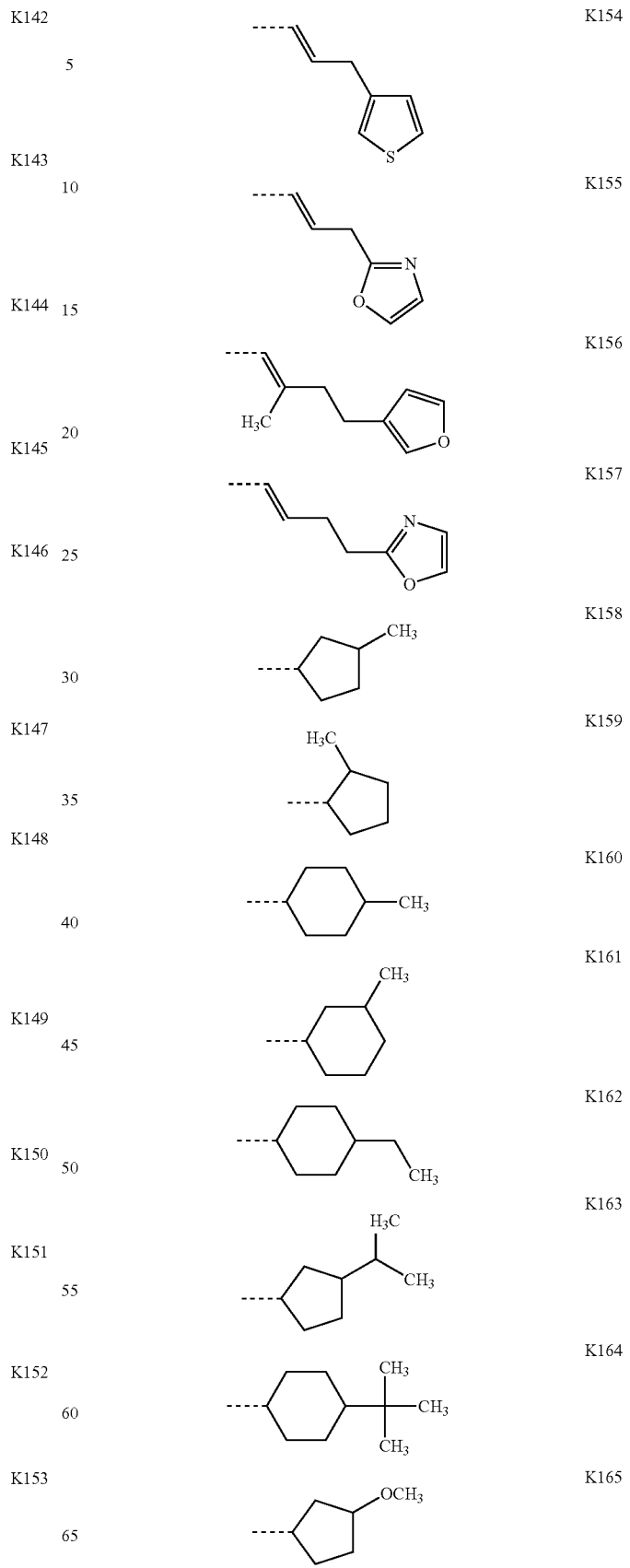

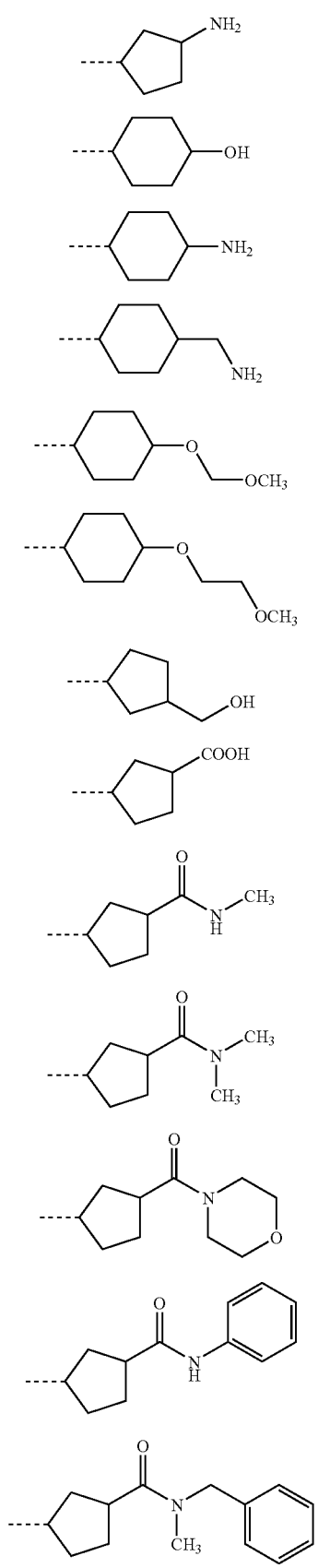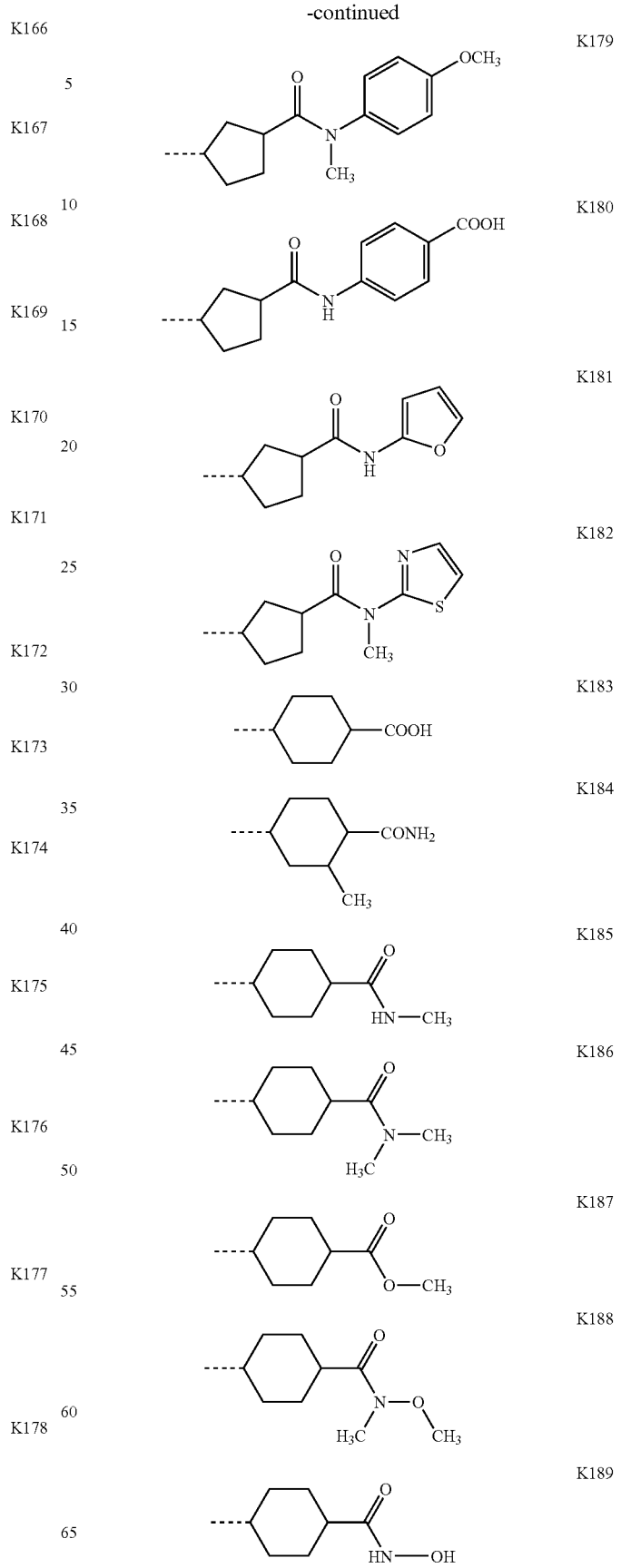

-continued
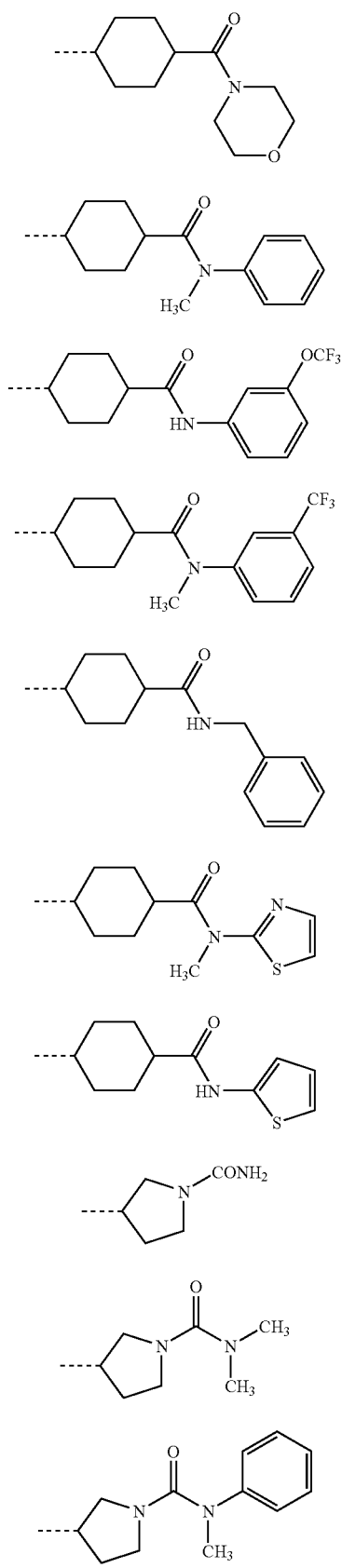
-continued
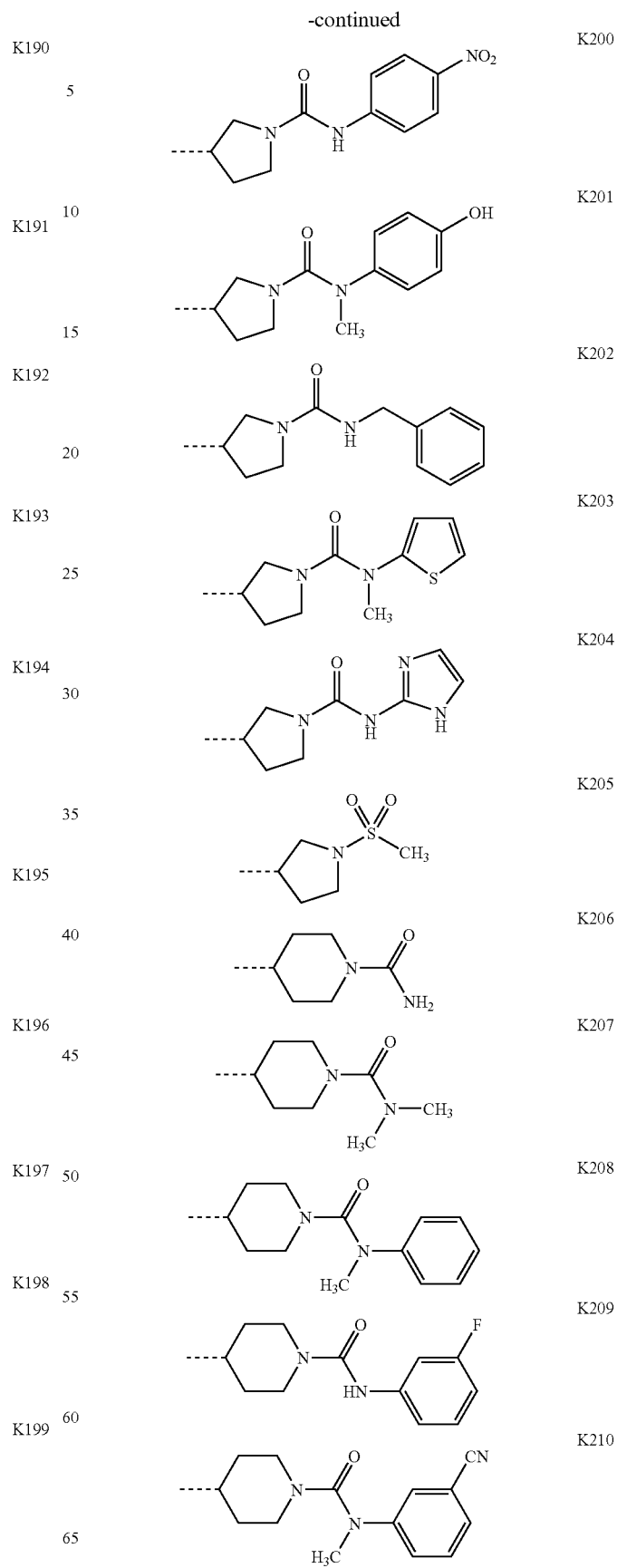

-continued
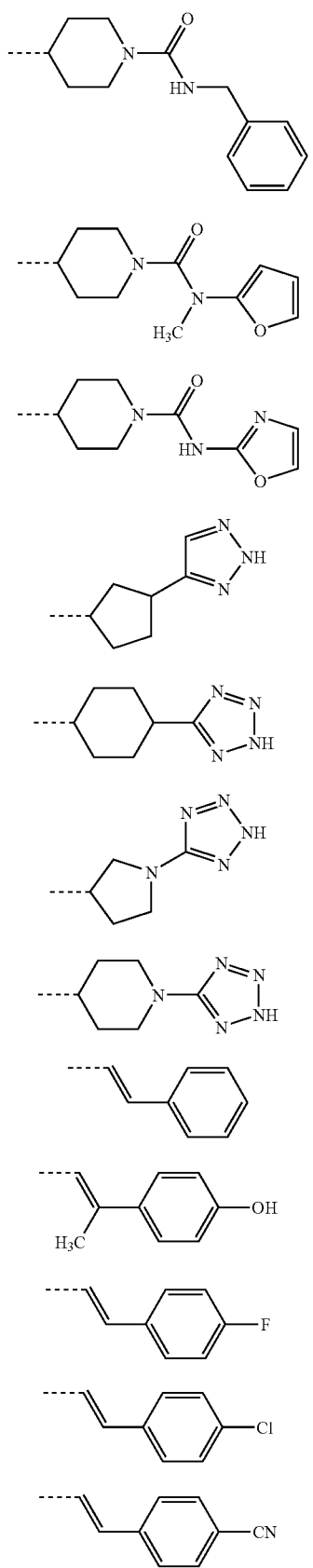
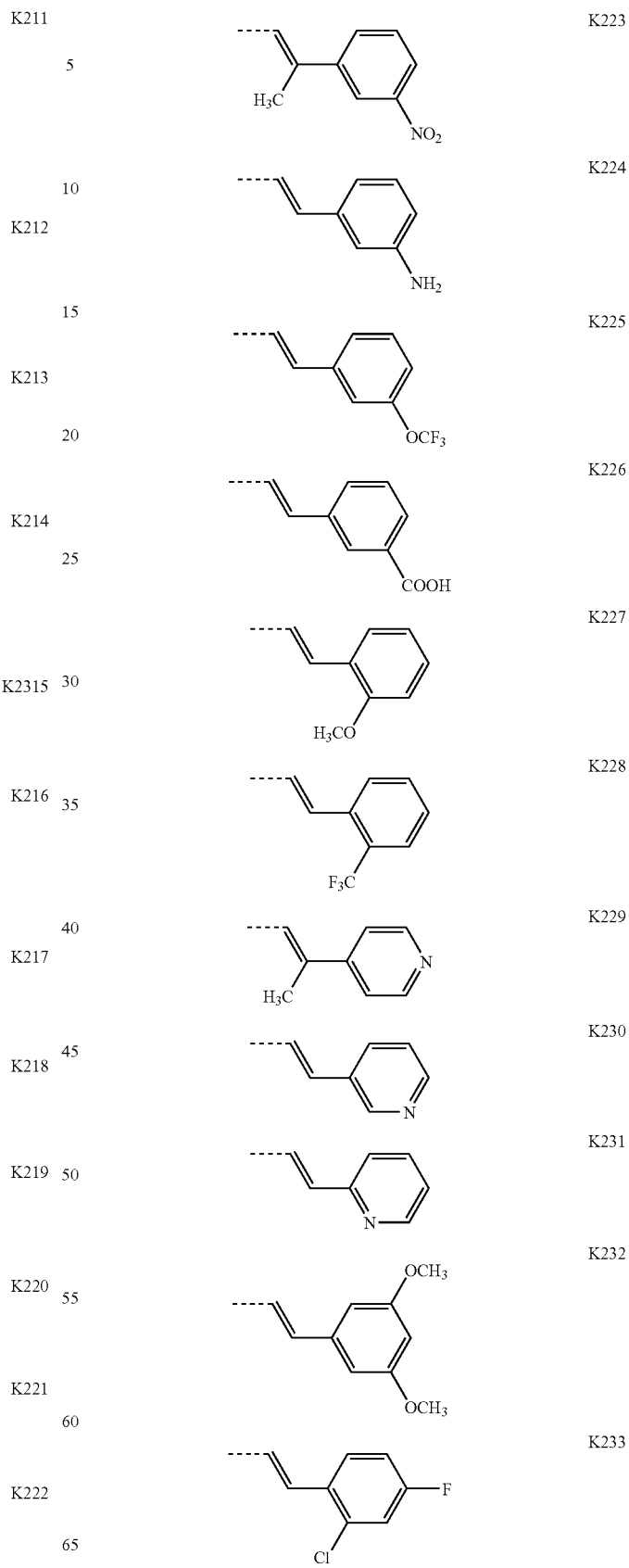
K211
K212
K213
K214
K2315
K216
K217
K218
K219
K220
K221
K222
K223
K224
K225
K226
K227
K228
K229
K230
K231
K232
K233

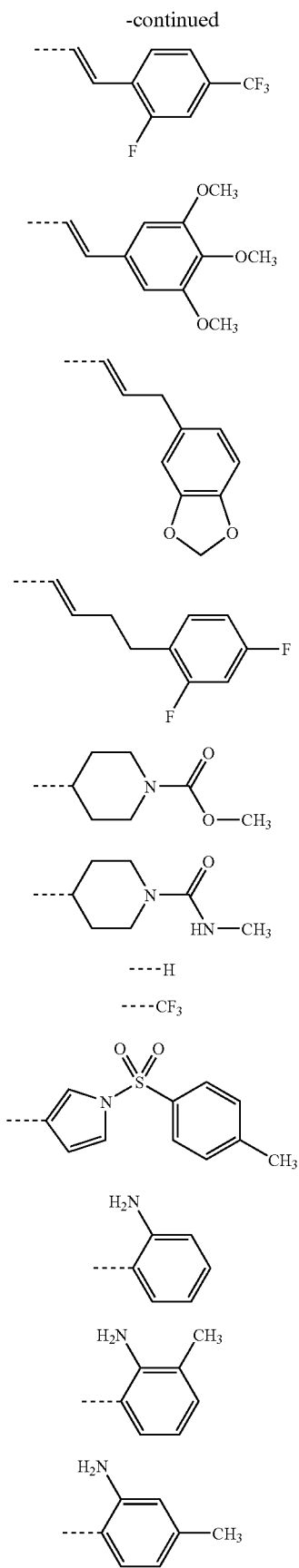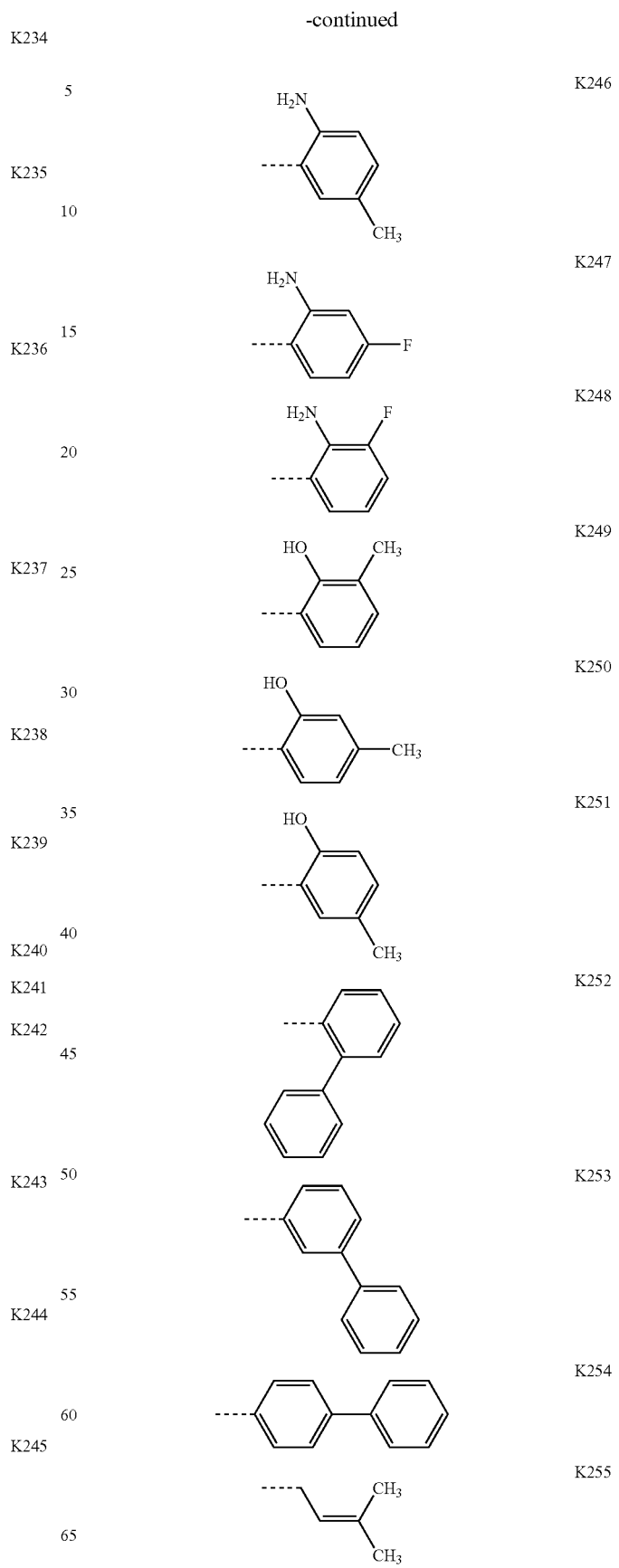

-continued
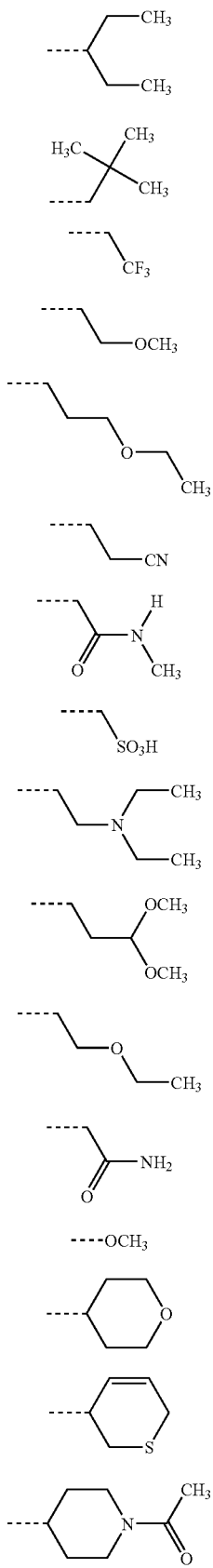
K256
K257
K258
K259
K260
K261
K262
K263
K264
K265
K266
K267
K268
K269
K270
K271
-continued
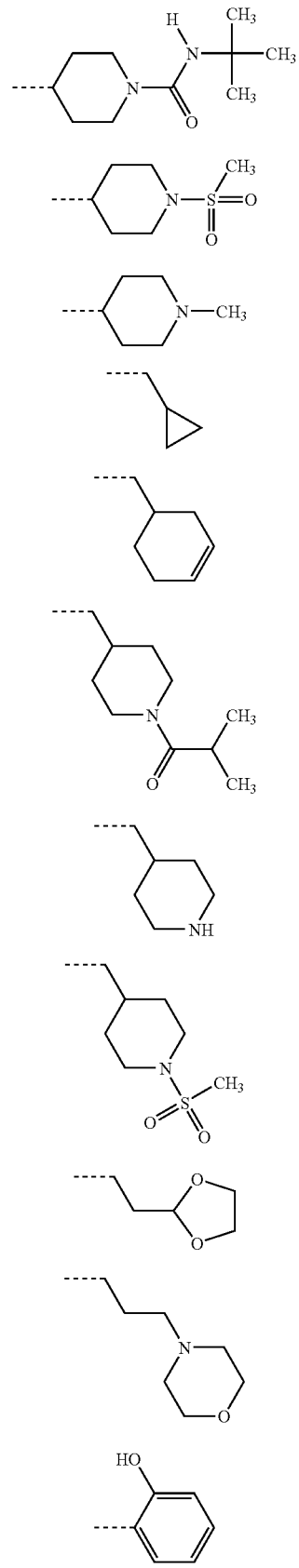
K272
K273
K274
K275
K276
K277
K278
K279
K280
K281
K282

-continued
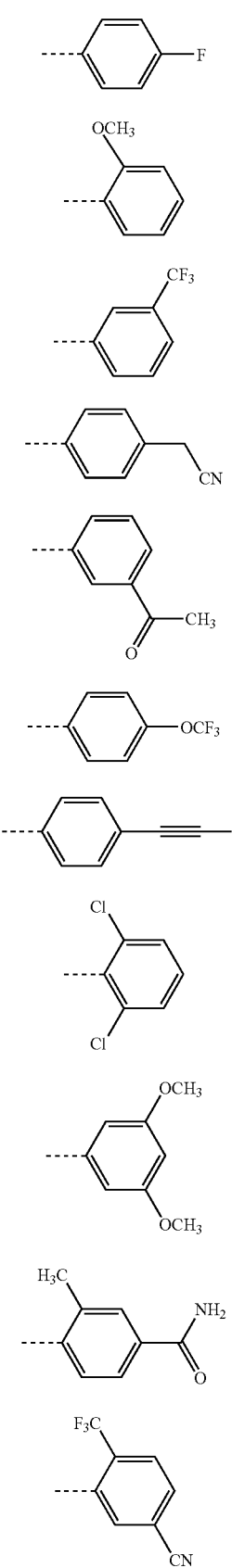
K283
K284
K285
K286
K287
K288
K289
K290
K291
K292
K293
-continued
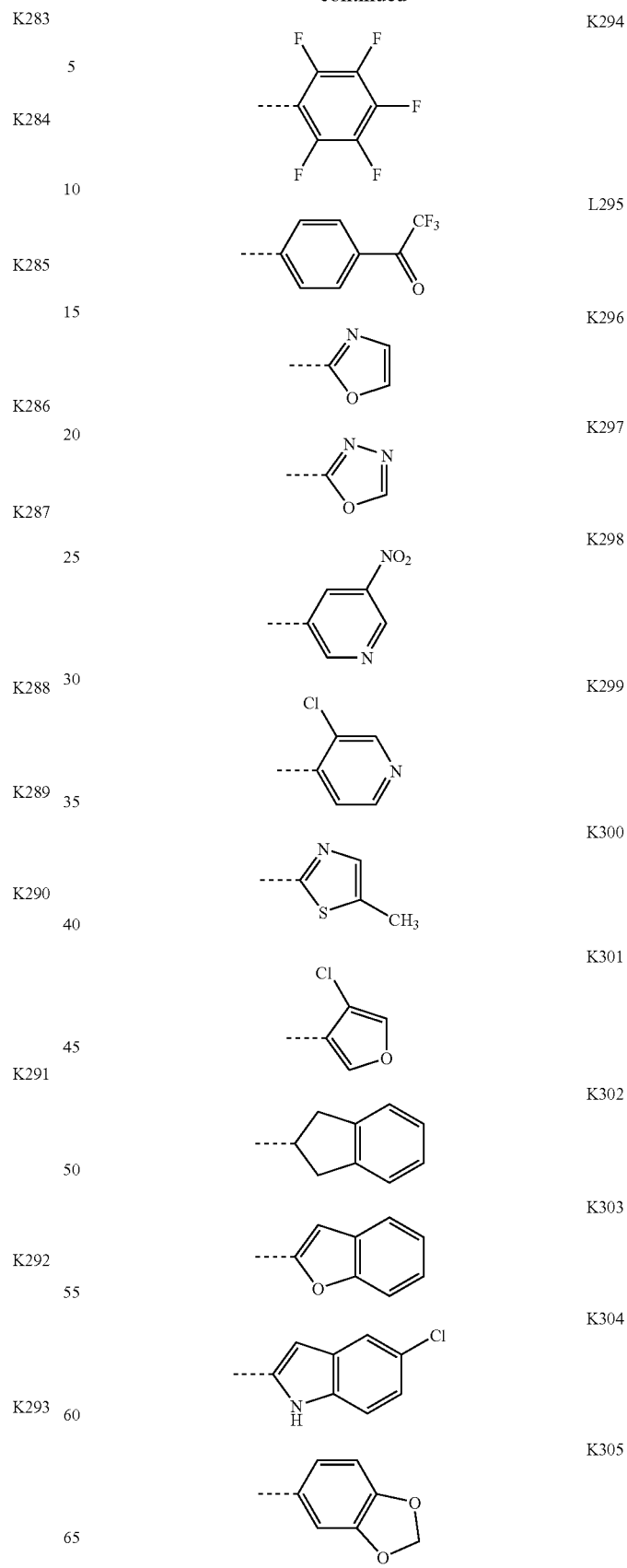
K294
L295
K296
K297
K298
K299
K300
K301
K302
K303
K304
K305

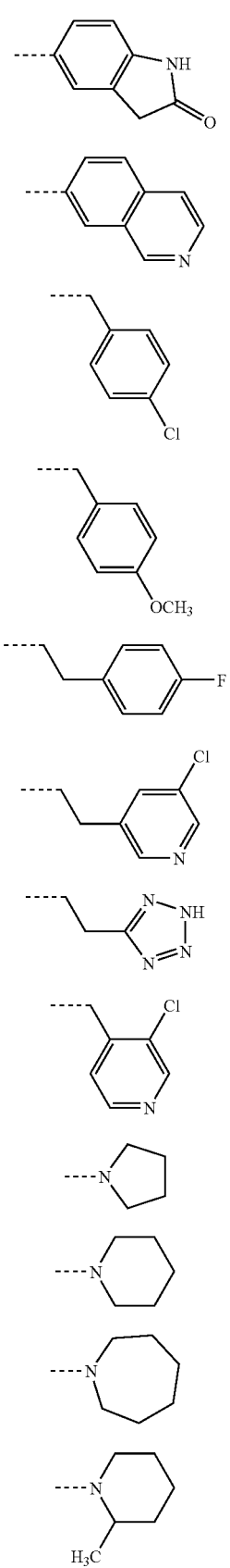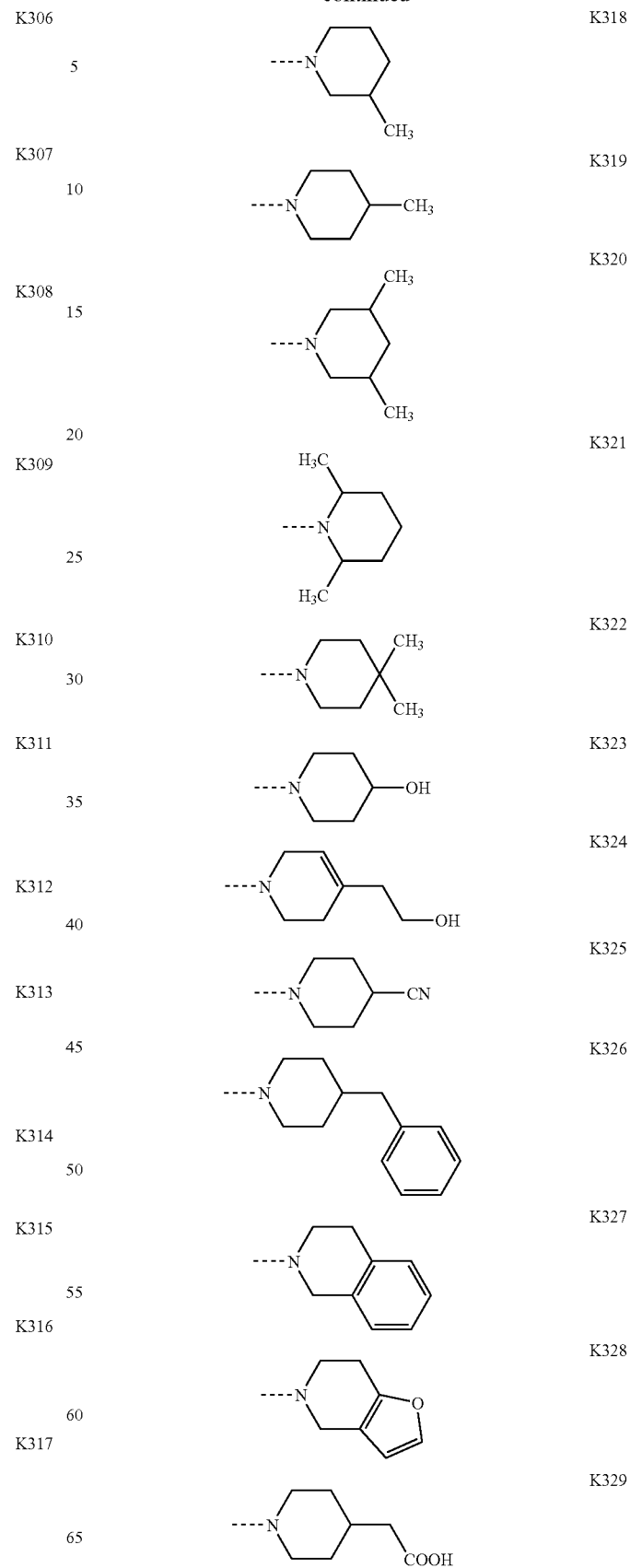

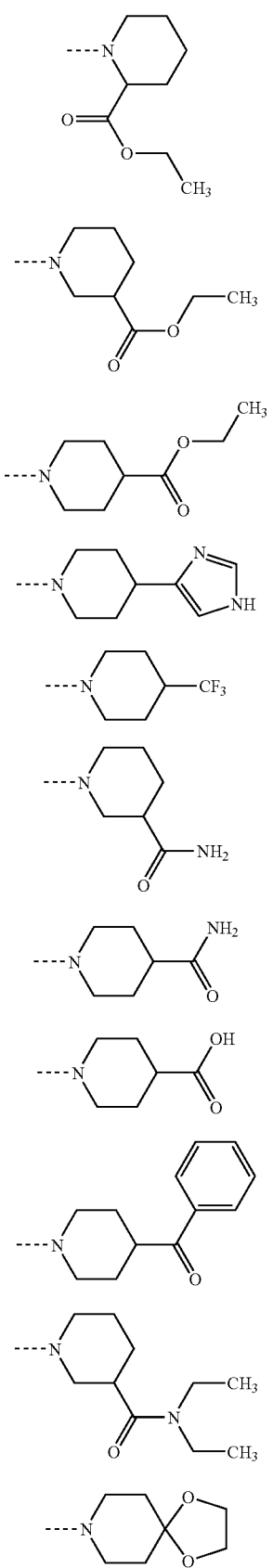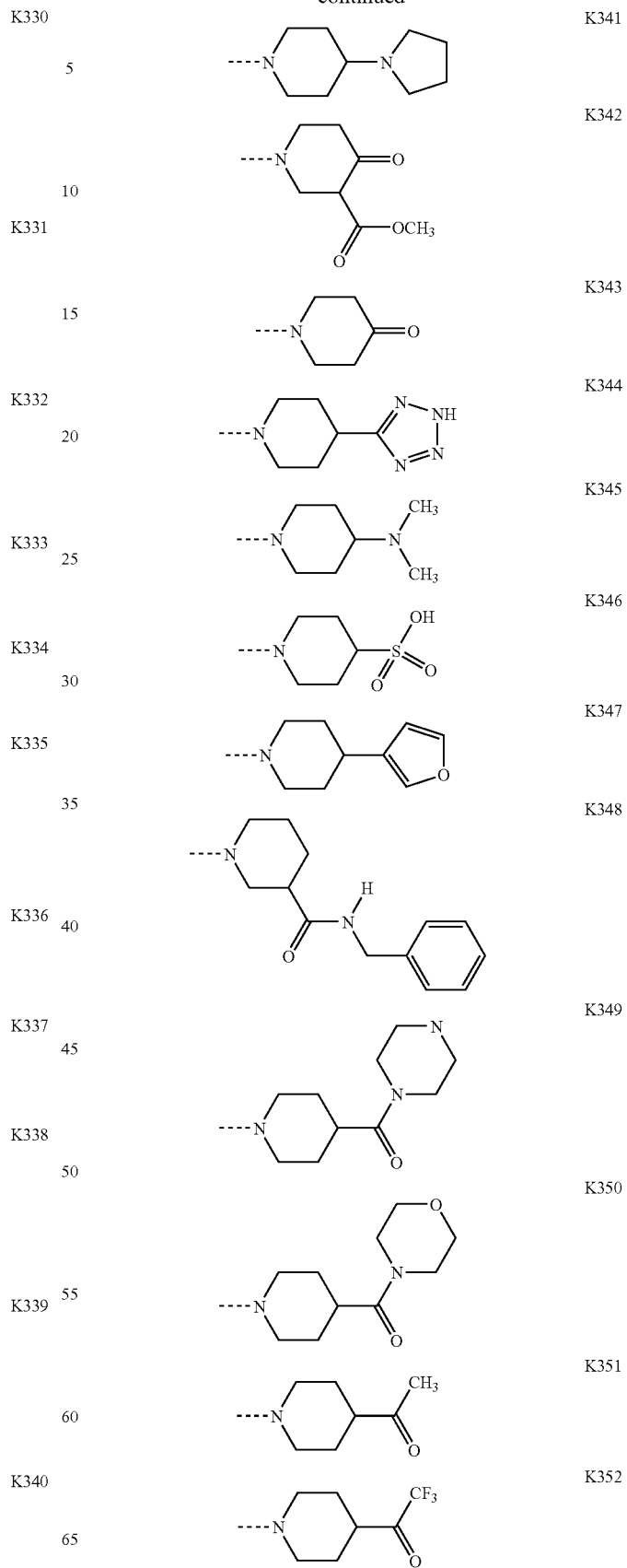

-continued
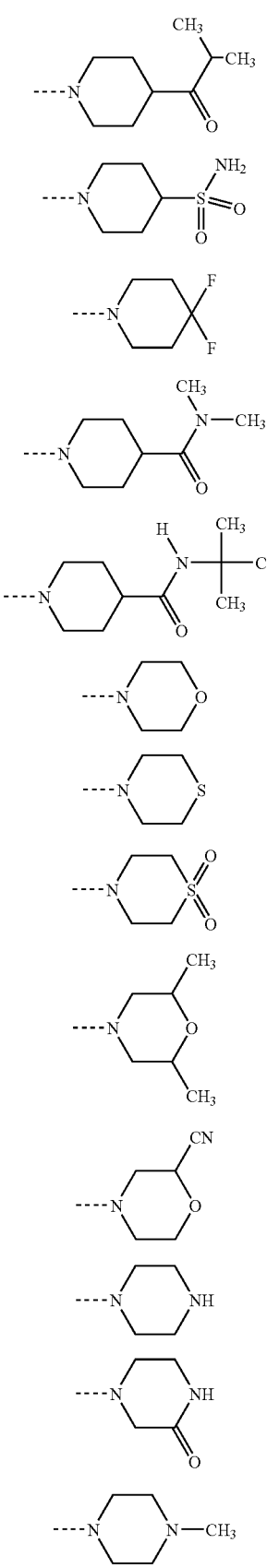
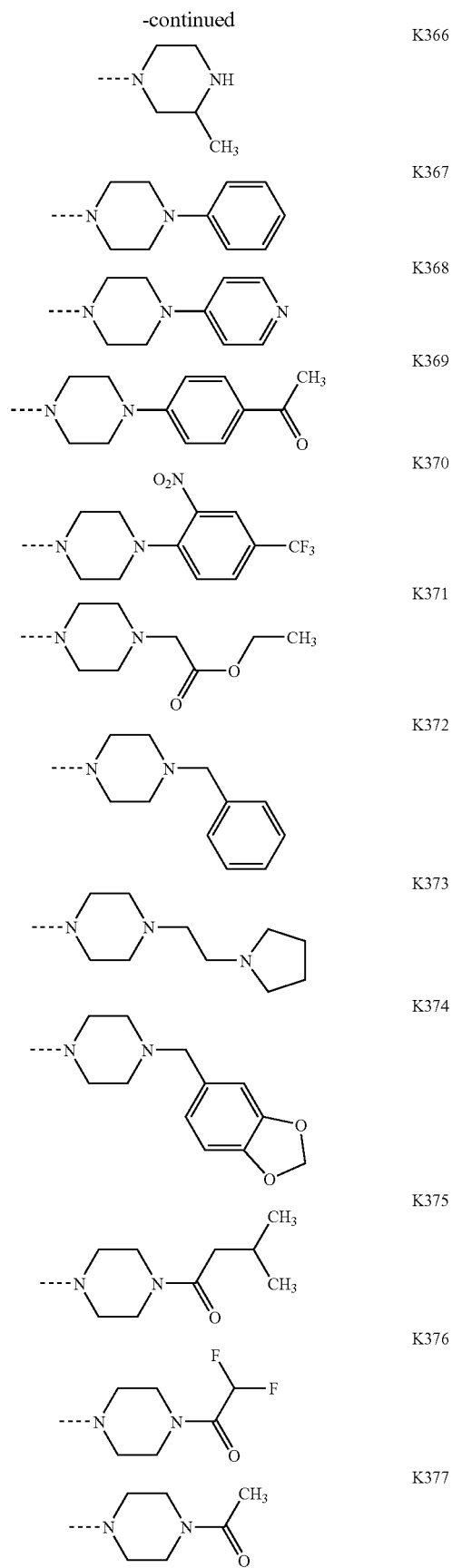

-continued
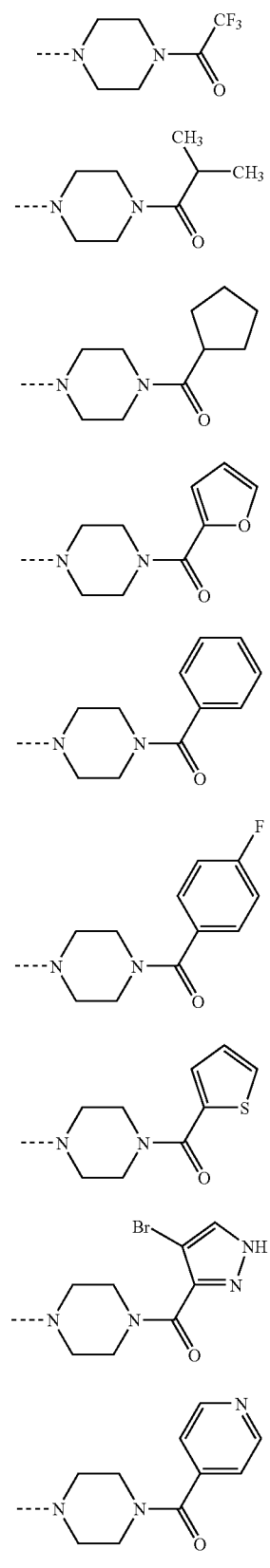
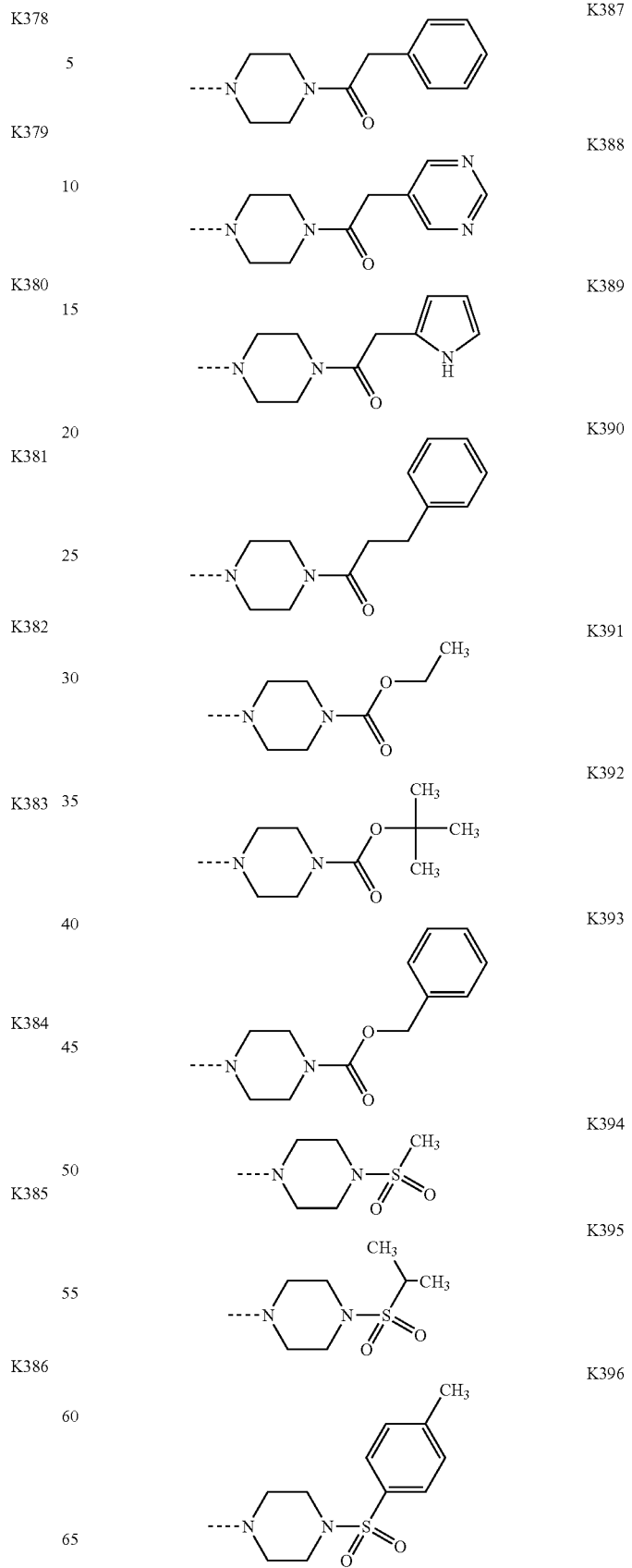

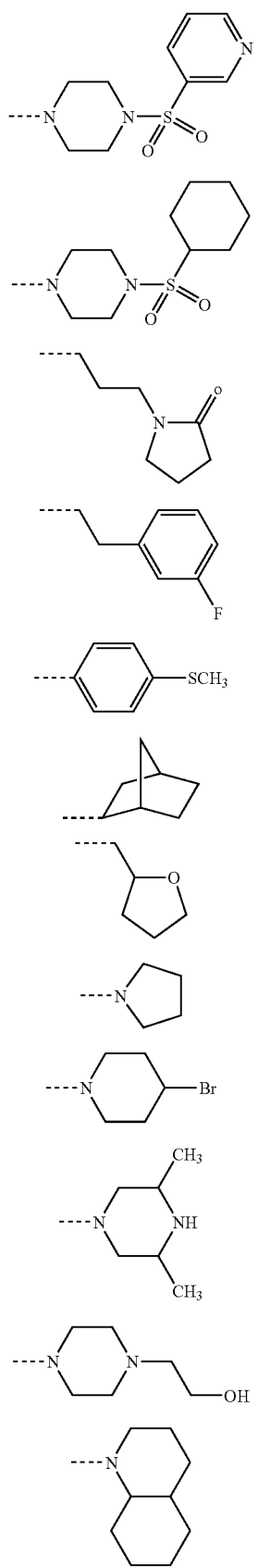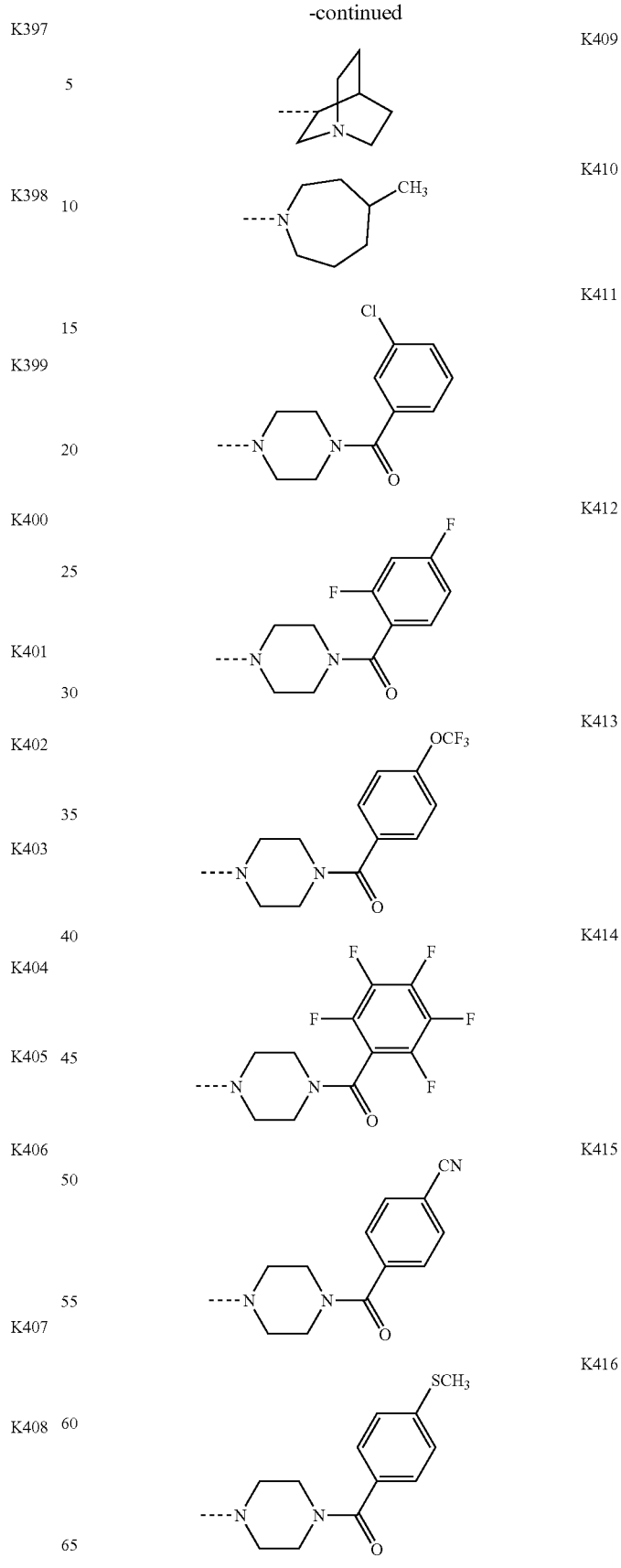

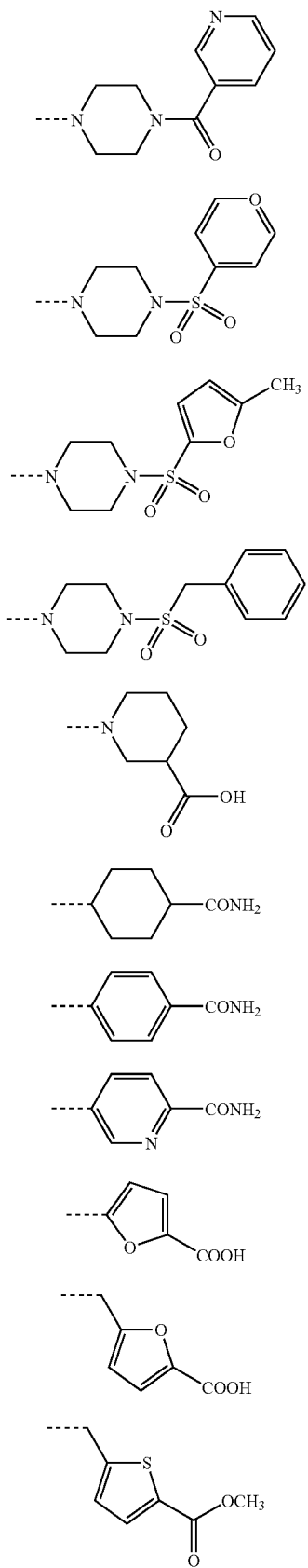
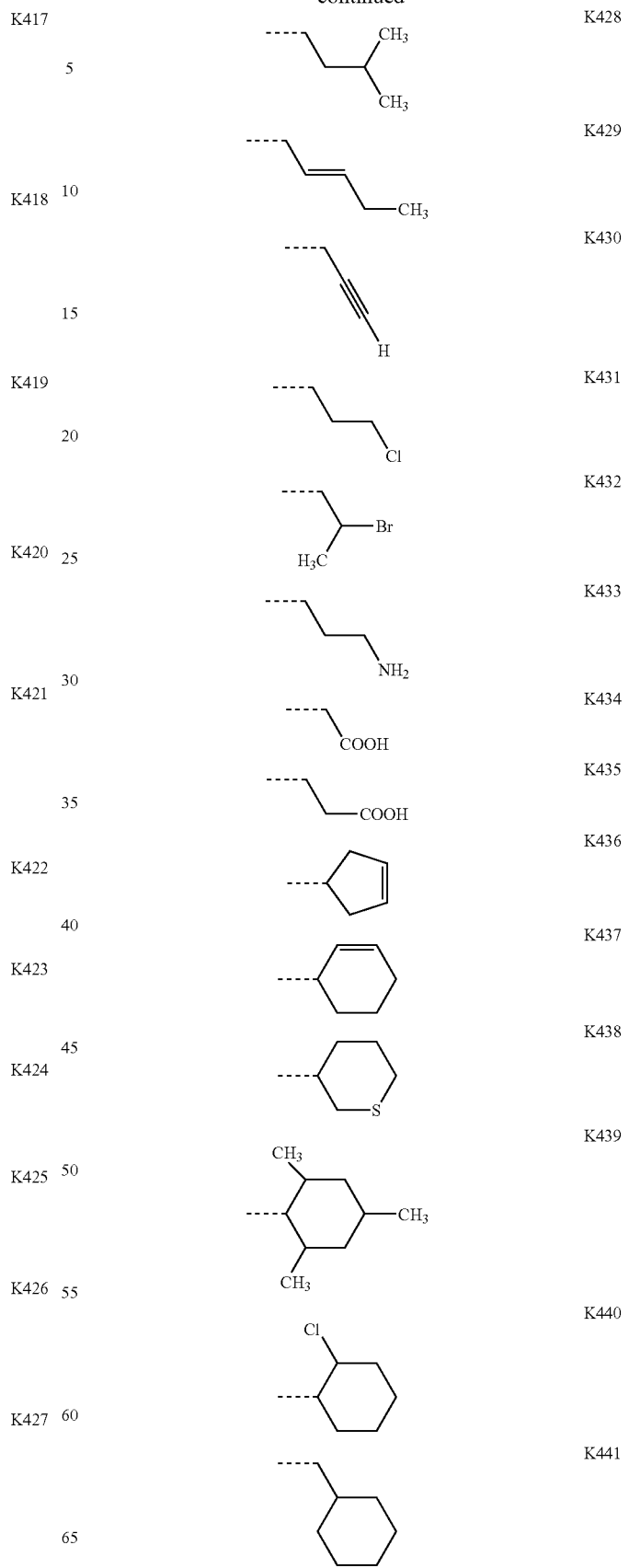

-continued
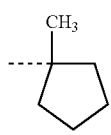 K442
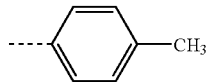 K443
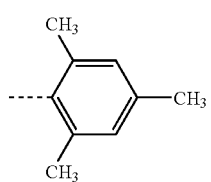 K444
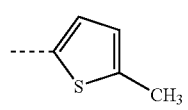 K445
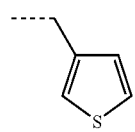 K446
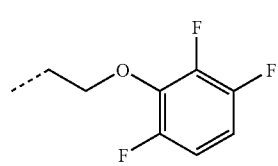 K447
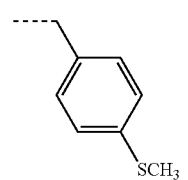 K448
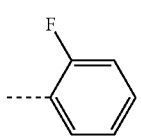 K449
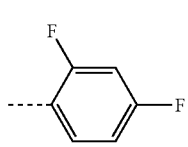 K450
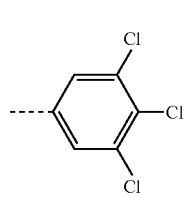 K451
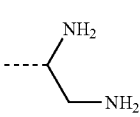 K452
-continued
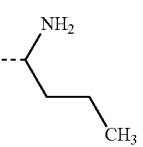 K453
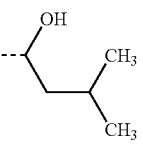 K454
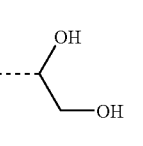 K455
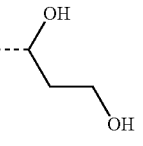 K456
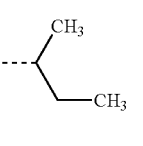 K457
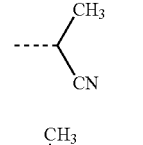 K458
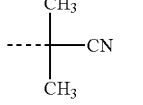 K459
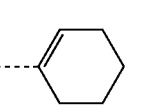 K460
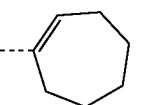 K461
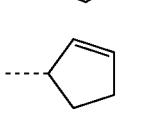 K462
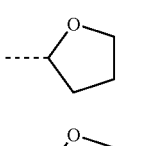 K463
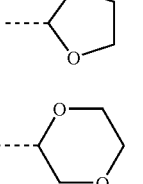 K464
K465

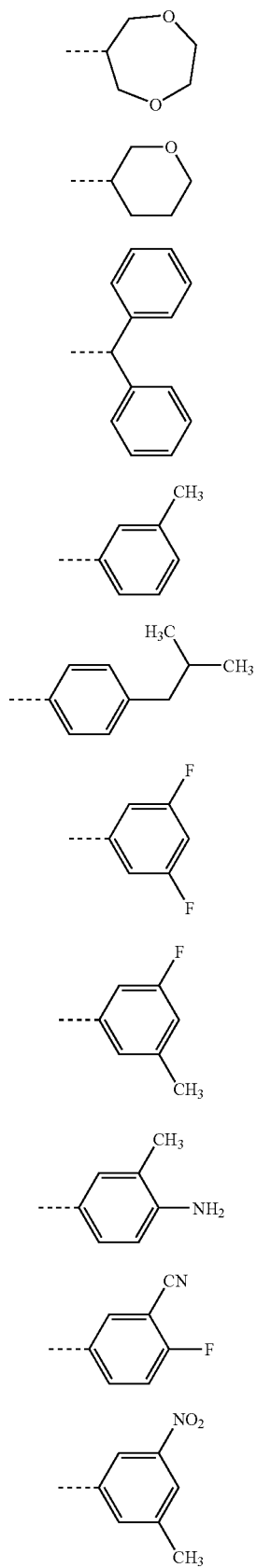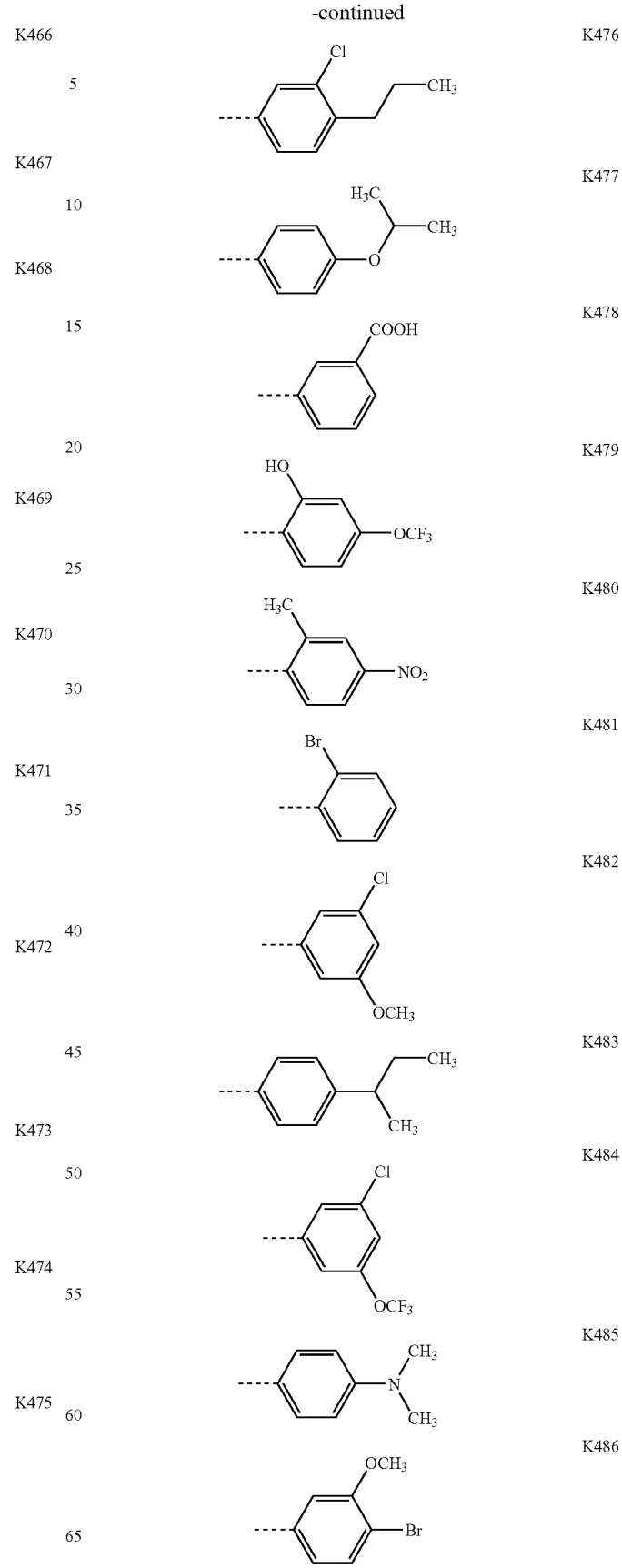

-continued
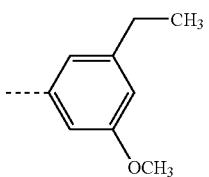 K487
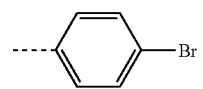 K488
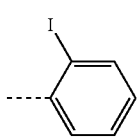 K489
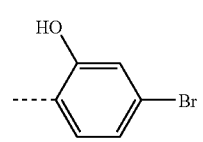 K490
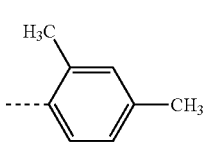 K491
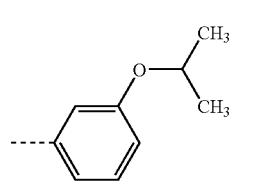 K492
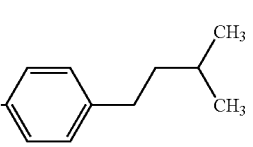 K493
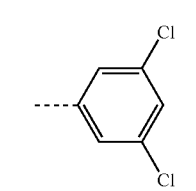 K494
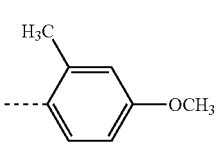 K495
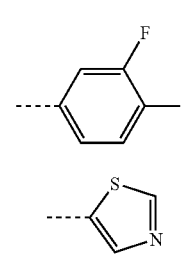 K496
K497
-continued
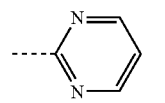 K498
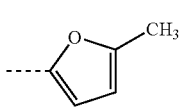 K499
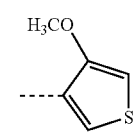 K500
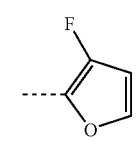 K501
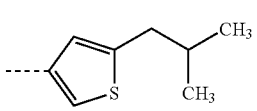 K502
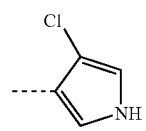 K503
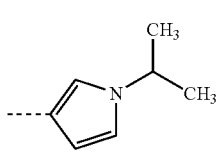 K504
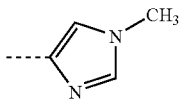 K505
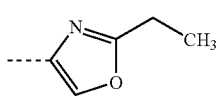 K506
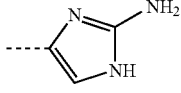 K507
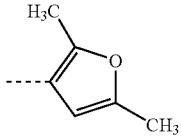 K508
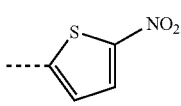 K509
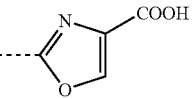 K510

-continued
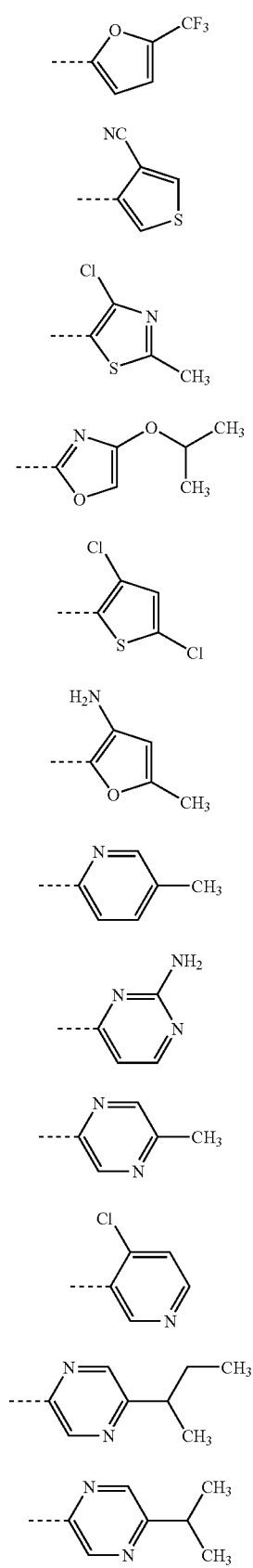
K511
K512
K513
K514
K515
K516
K517
K518
K519
K520
K521
K522
-continued
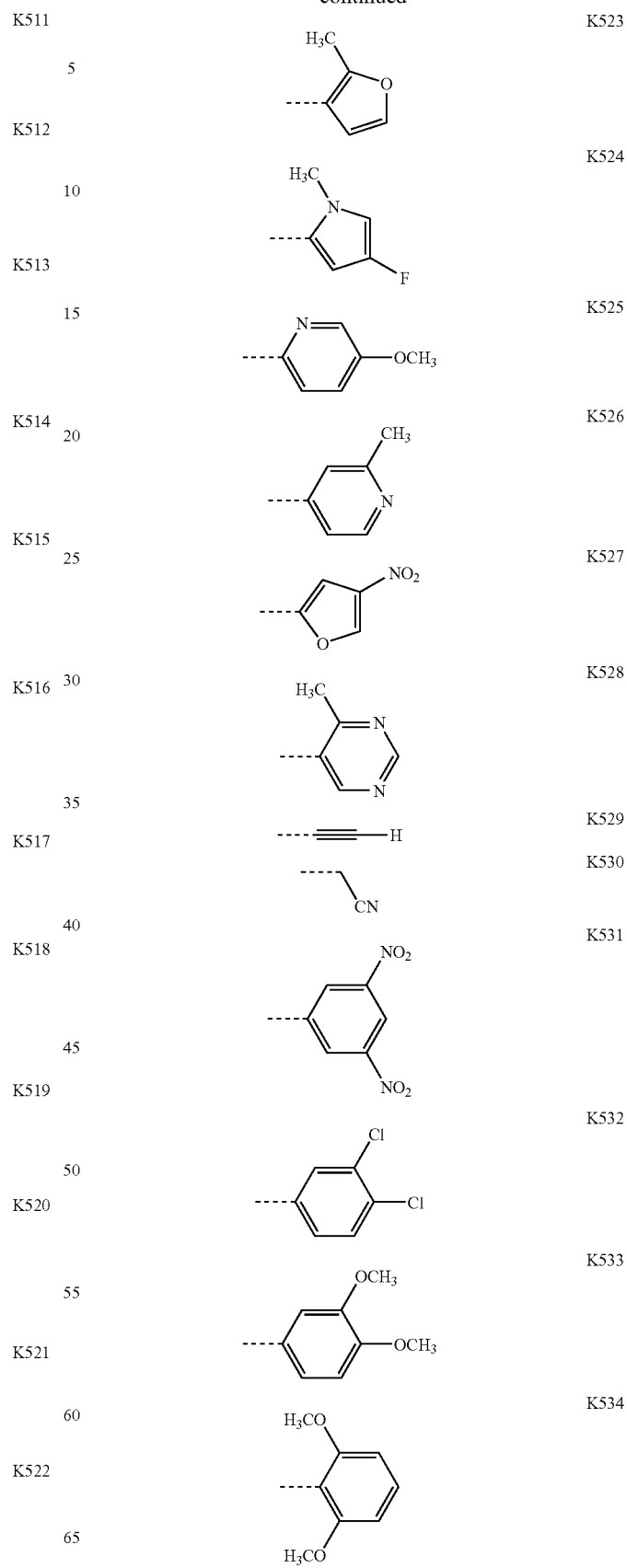
K523
K524
K525
K526
K527
K528
K529
K530
K531
K532
K533
K534

-continued
| | |
|---|---|
| 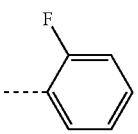 | K535 |
| 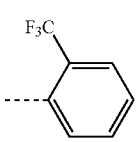 | K536 |
| 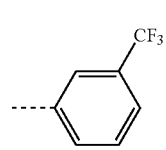 | K537 |
| 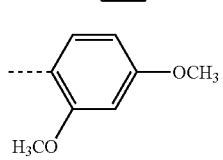 | K538 |
| 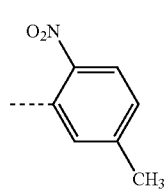 | K539 |
| 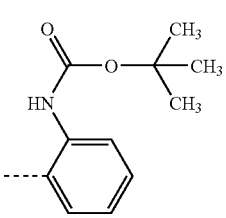 | K540 |
| 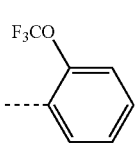 | K541 |
| 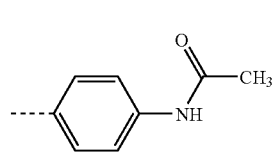 | K542 |
| 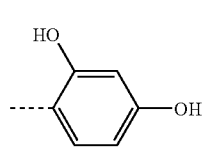 | K543 |
| 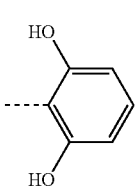 | K544 |
-continued
| | |
|---|---|
| 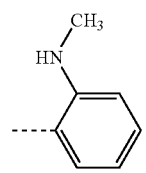 | K545 |
| 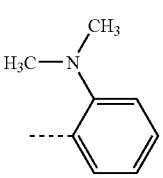 | K546 |
| 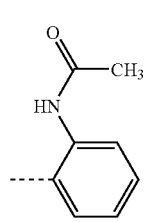 | K547 |
| 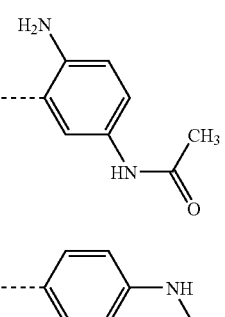 | K548 |
| 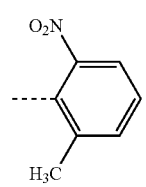 | K549 |
| 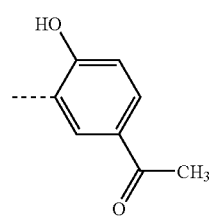 | K550 |
| 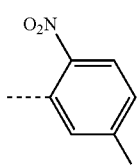 | K551 |
| 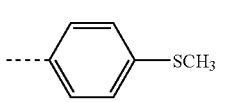 | K552 |
| | K553 |

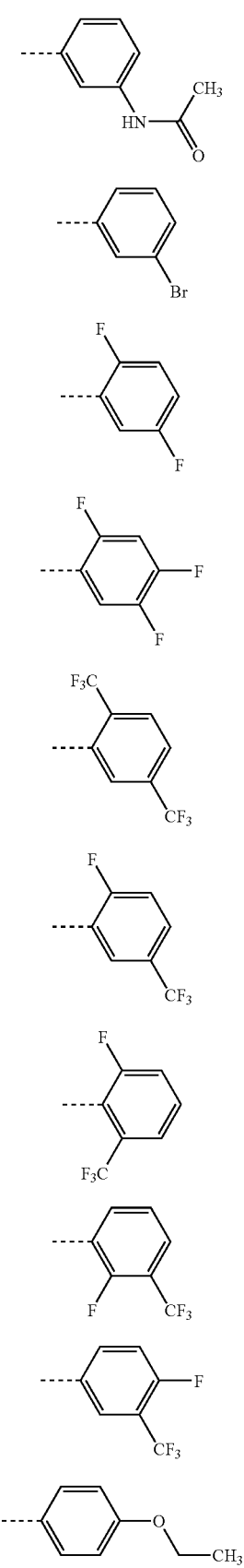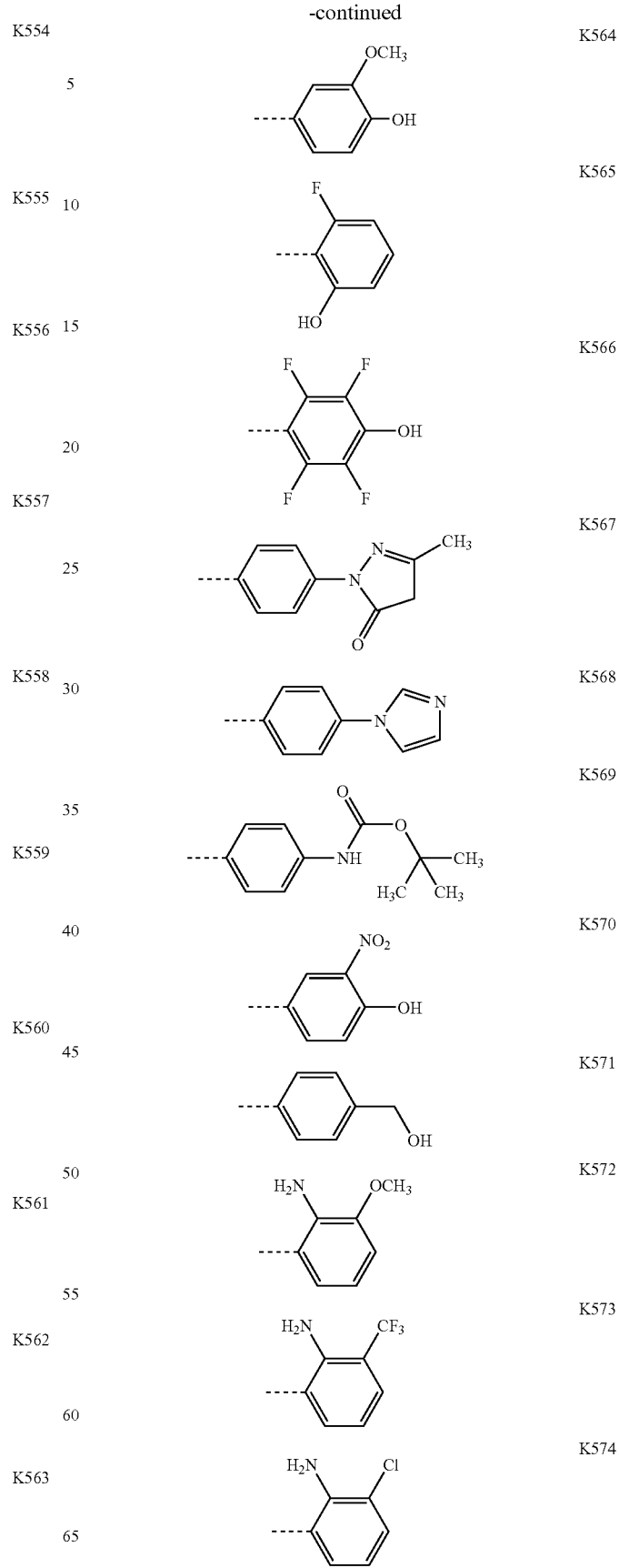

-continued

| | |
|---|---|
| K575 | 2-amino-phenol structure |
| K576 | 4-amino-3-substituted methoxybenzene |
| K577 | 4-fluoroaniline structure |
| K578 | 4-chloroaniline structure |
| K579 | 4-nitroaniline structure |
| K580 | 3-methyl-2-aminobenzene |
| K581 | 4-amino-3-substituted phenol |
| K582 | 3-chloro-2-aminobenzene |
| K583 | 3-fluoro-2-aminobenzene |

-continued

| | |
|---|---|
| K584 | 2-amino-3-methoxybenzene |
| K585 | 3-amino-4-substituted phenol |
| K586 | 4-benzoylphenyl |
| K587 | 3-benzoylphenyl |
| K588 | 4-(cyclohex-2-enyloxy)phenyl |
| K589 | 2-methoxyphenyl |
| K590 | 3-(ethoxycarbonyl)phenyl |
| K591 | 3-carbamoylphenyl |
| K592 | 4-(5-methyl-1,2,4-oxadiazol-3-yl)phenyl |
| K593 | 4-(3-methyl-1,2,4-oxadiazol-5-yl)phenyl |

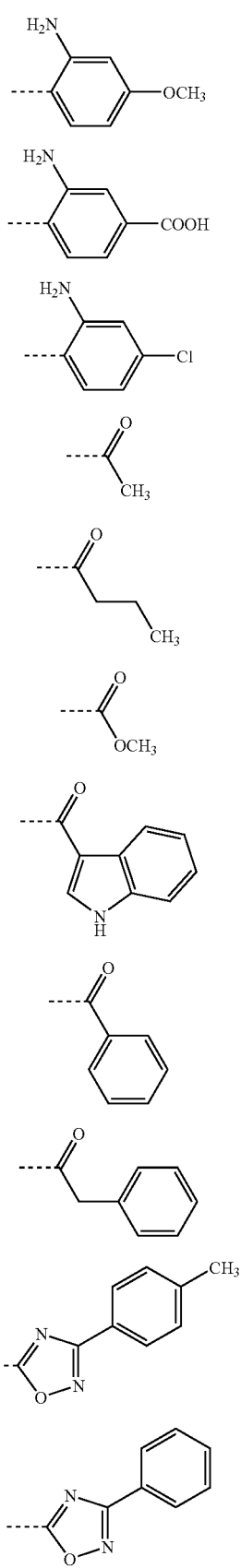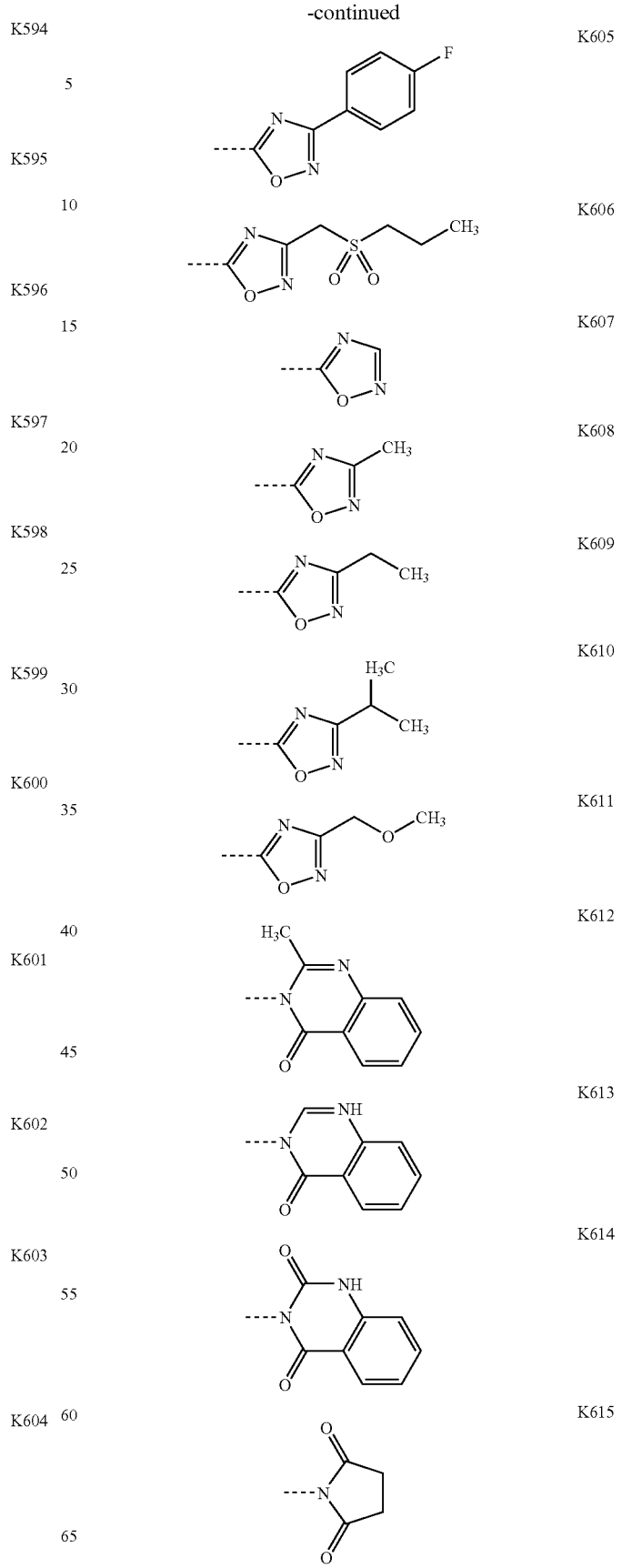

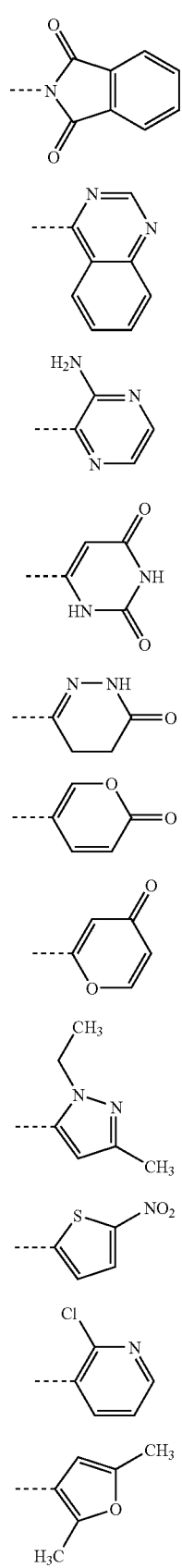
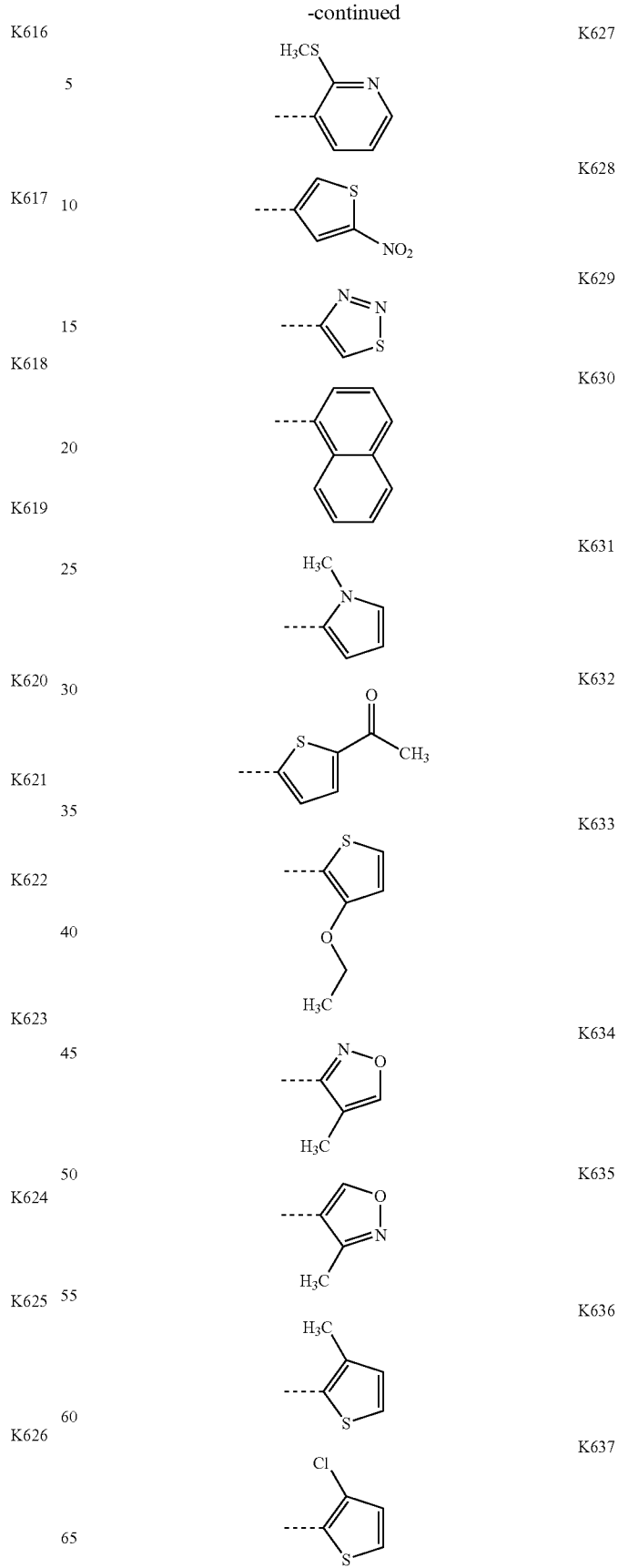

| | |
|---|---|
| 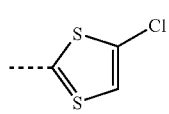 | K638 |
| 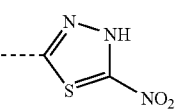 | K639 |
| 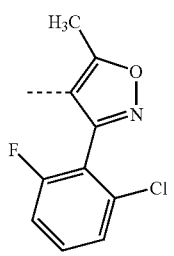 | K640 |
| 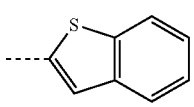 | K641 |
| 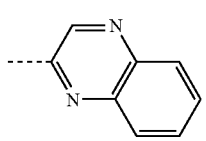 | K642 |
| 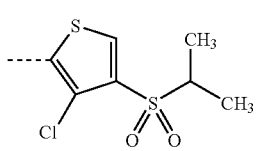 | K643 |
| 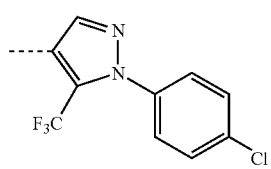 | K644 |
| 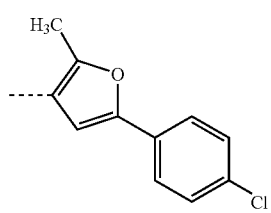 | K645 |
| 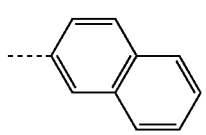 | K646 |
| 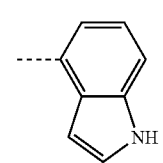 | K647 |
| | |
|---|---|
| 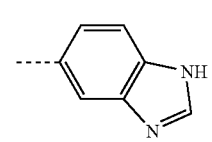 | K648 |
| 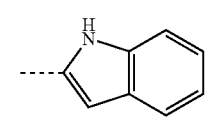 | K649 |
| 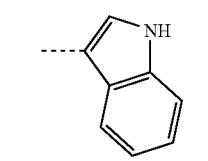 | K650 |
| 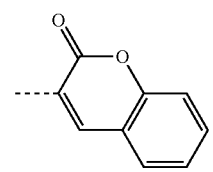 | K651 |
| 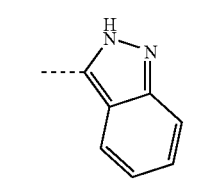 | K652 |
| 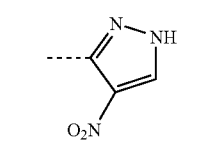 | K653 |
| 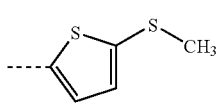 | K654 |
| 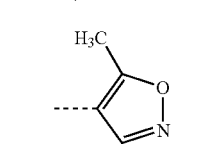 | K655 |
| 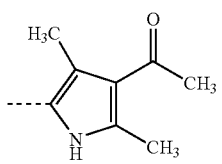 | K656 |
| 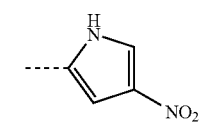 | K657 |
| 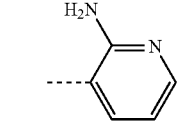 | K658 |

-continued
K659 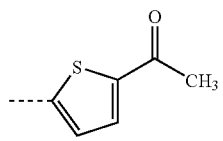
K660 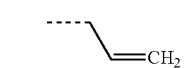
K661 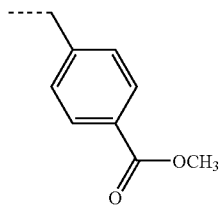
K662 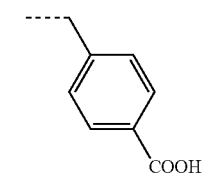
K663 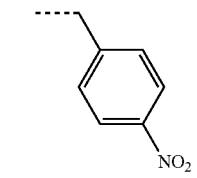
K664 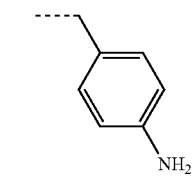
K665 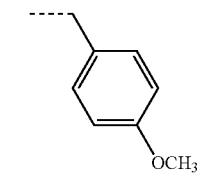
K666 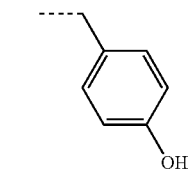
K667 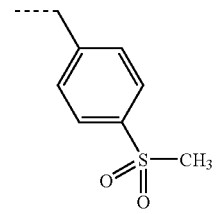
-continued
K668 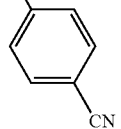
K669 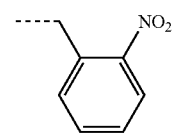
K670 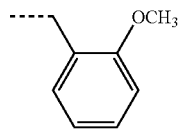
K671 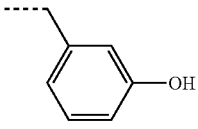
K672 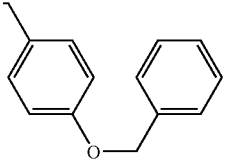
K673 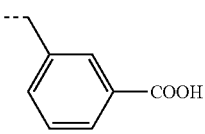
K674 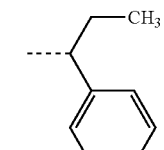
K675 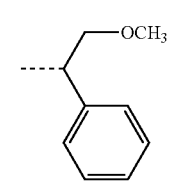
K676 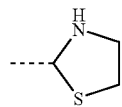
K677 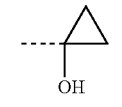
K678 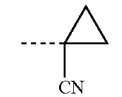

105
-continued
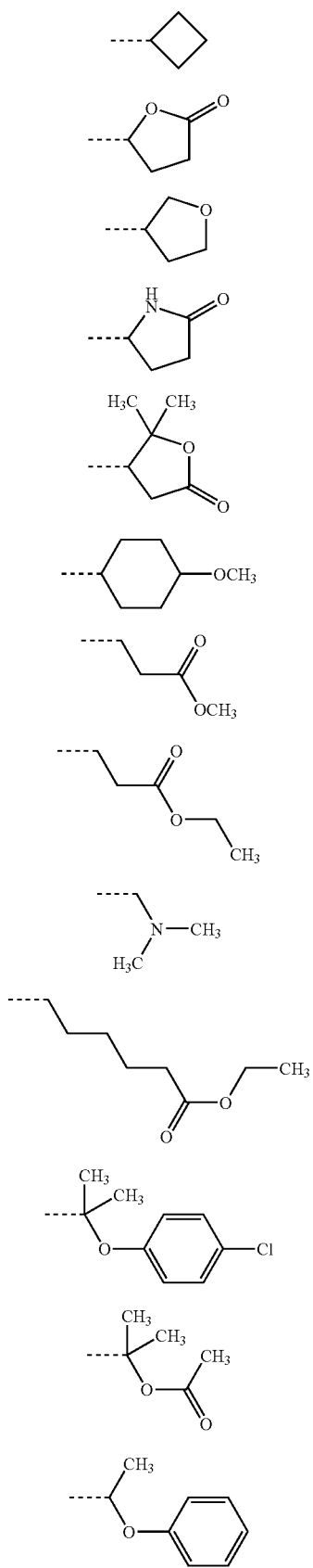
K679
K680
K681
K682
K683
K684
K685
K686
K687
K688
K689
K690
K691
106
-continued
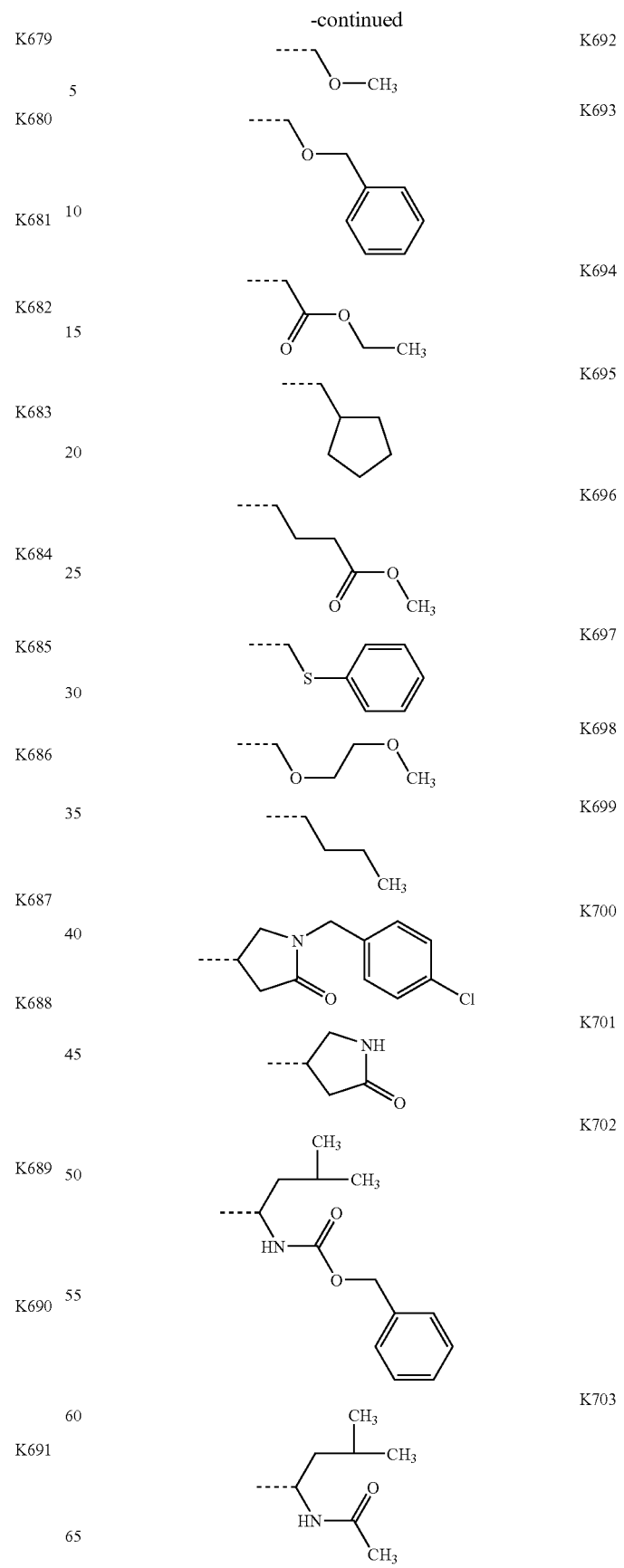
K692
K693
K694
K695
K696
K697
K698
K699
K700
K701
K702
K703

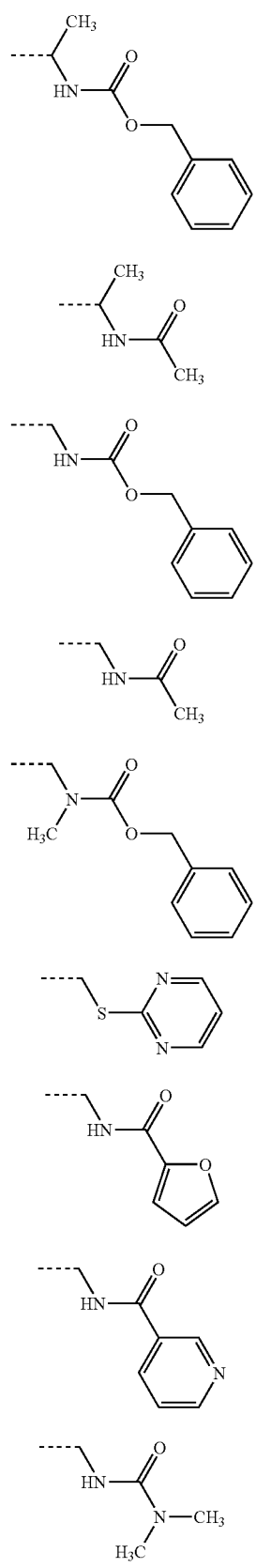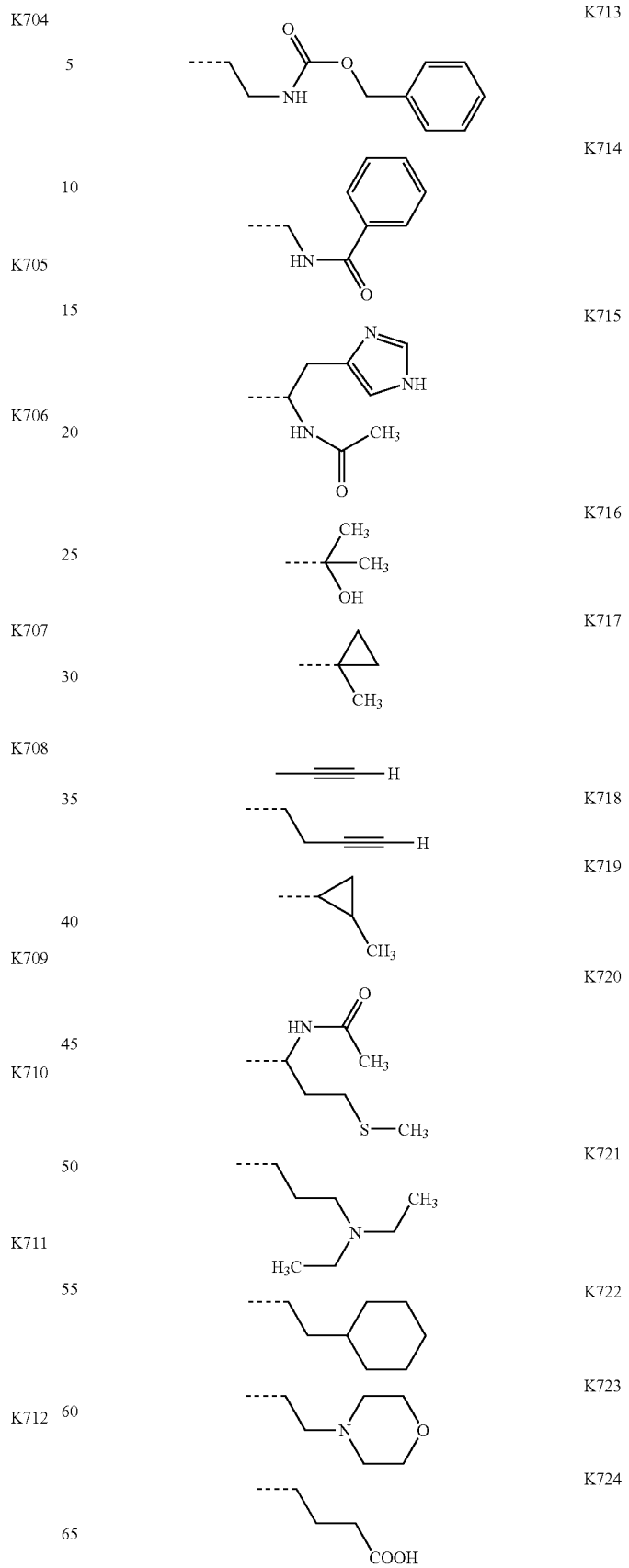

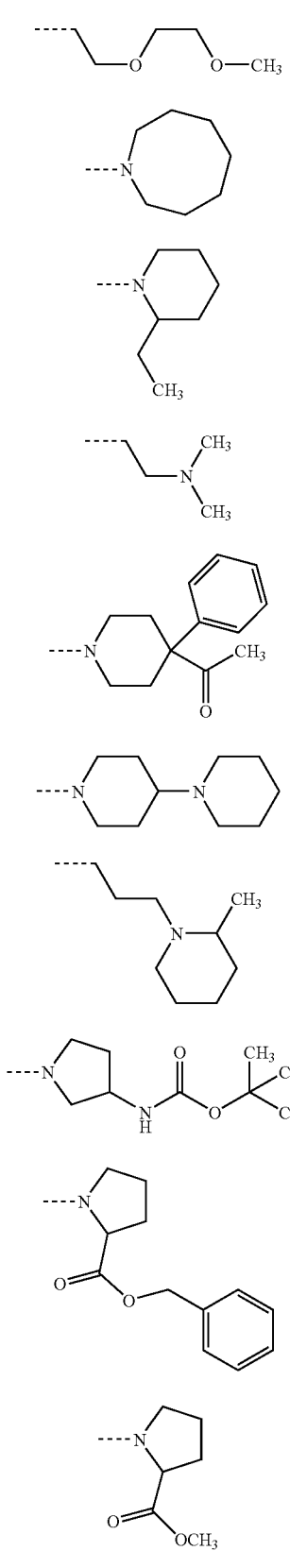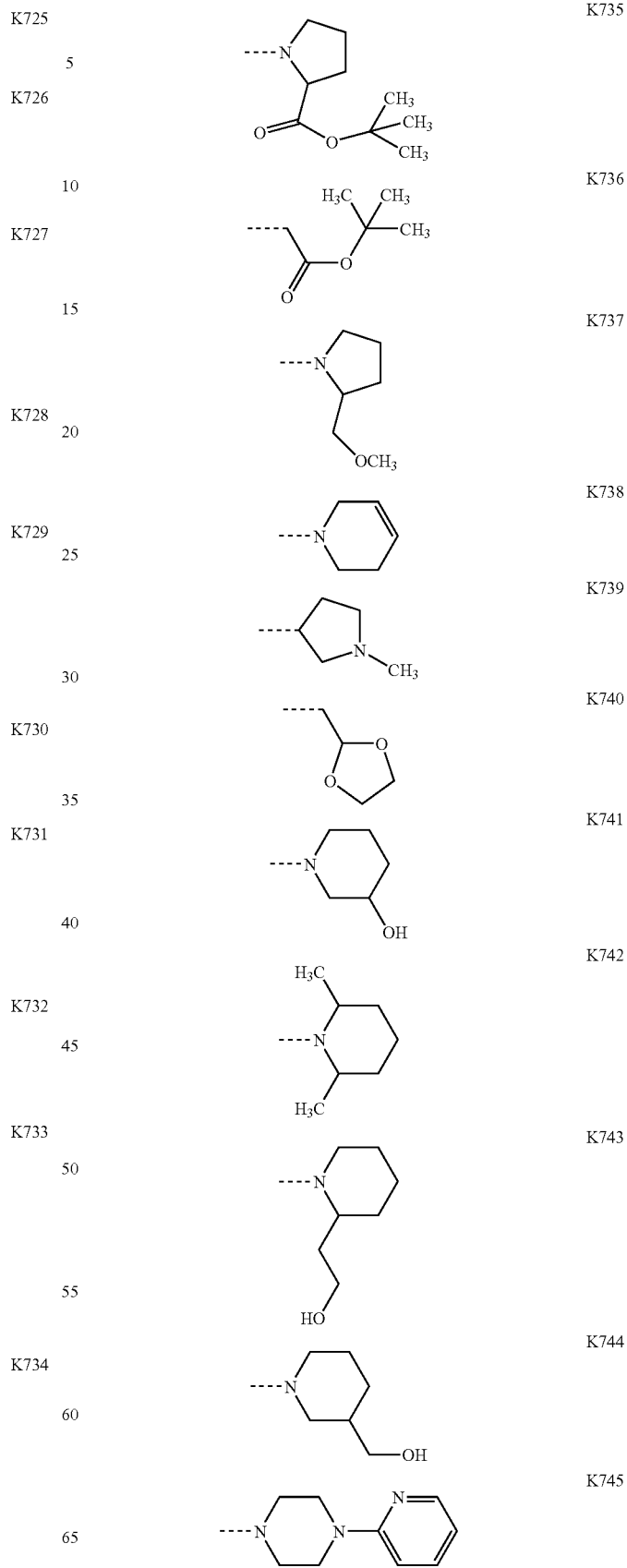

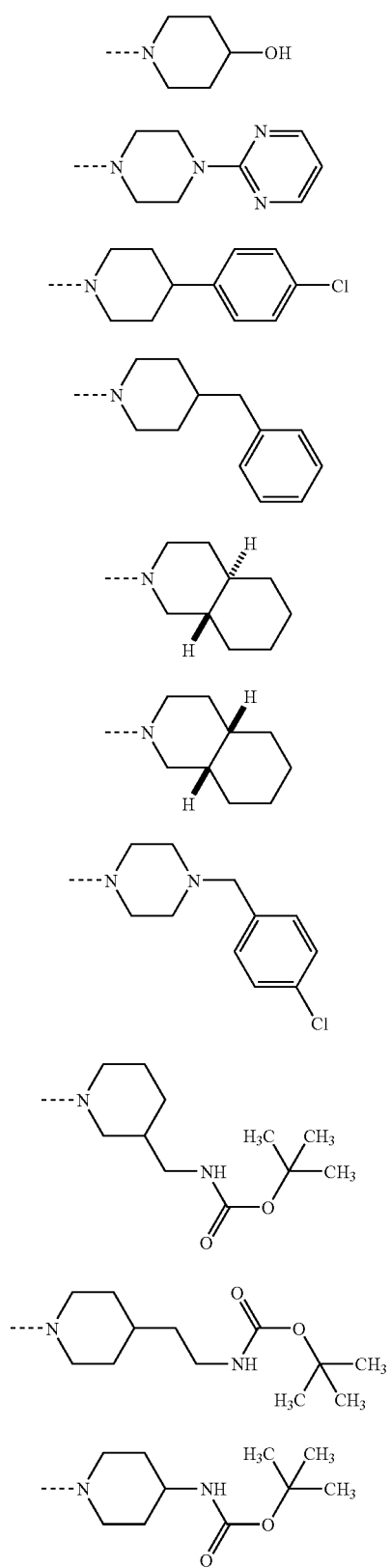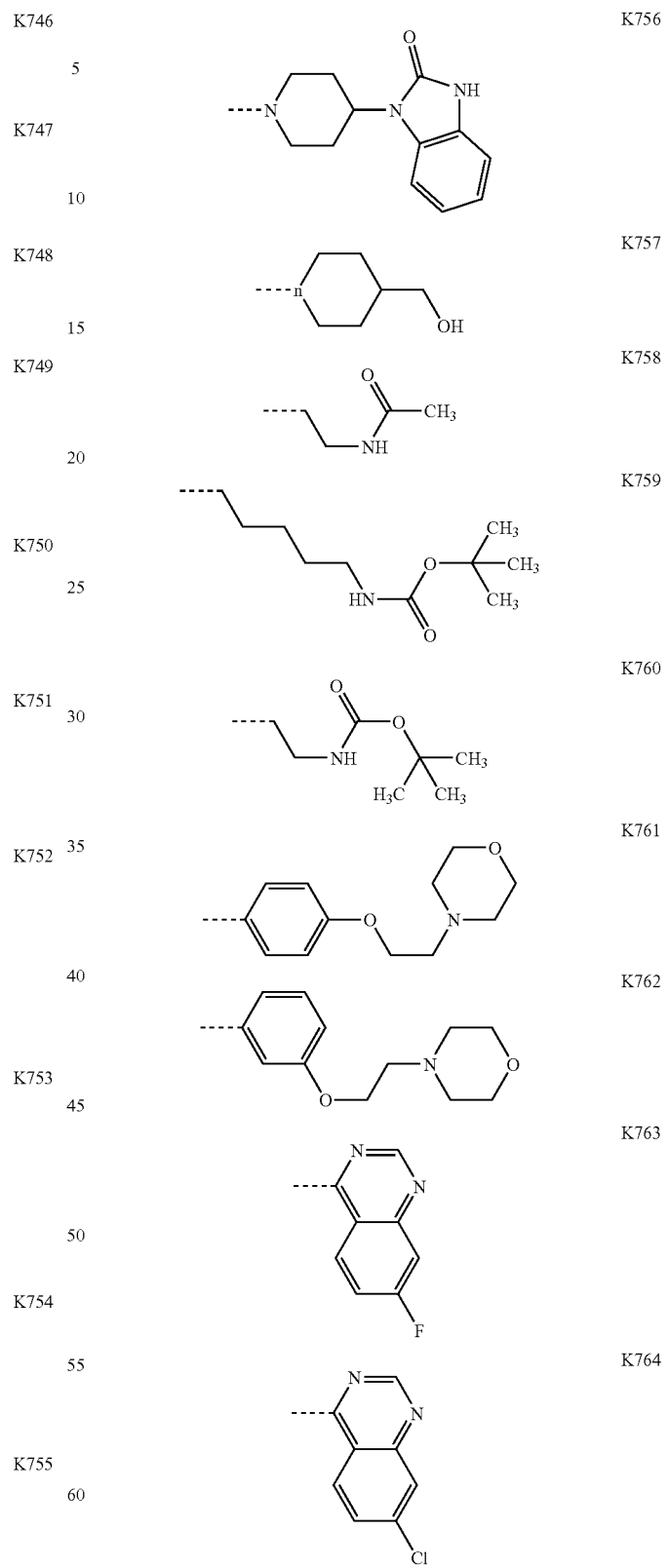

| K765 | 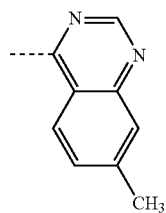 |
| --- | --- |
| K766 | 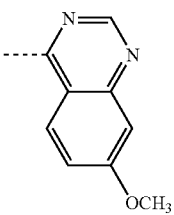 |
| K767 | 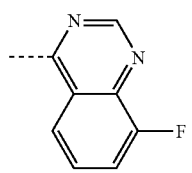 |
| K768 | 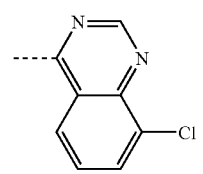 |
| K769 | 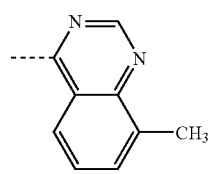 |
| K770 | 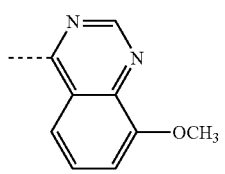 |
| K771 | 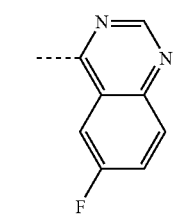 |
| K772 | 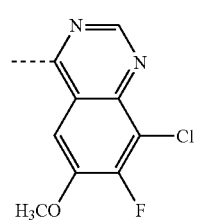 |
| K773 | 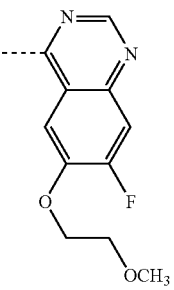 |
| K774 | 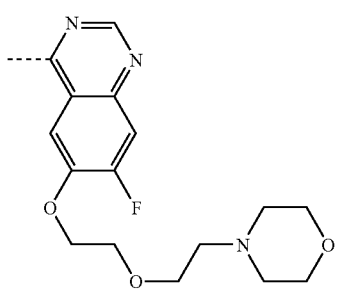 |
| K775 | 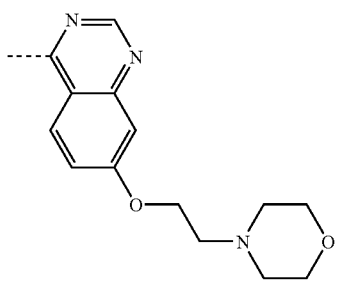 |
| K776 | 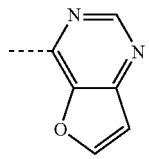 |
| K777 | 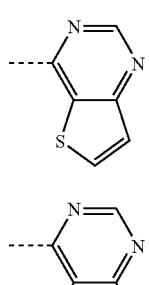 |
| K778 | 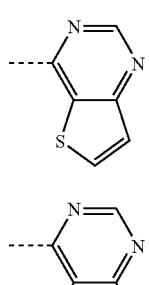 |
| K779 | 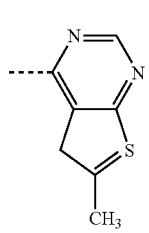 |

-continued
| | |
|---|---|
| 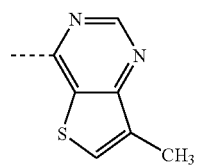 | K780 |
| 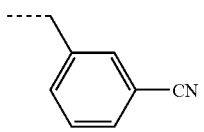 | K781 |
| 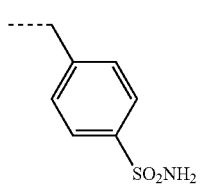 | K782 |
| 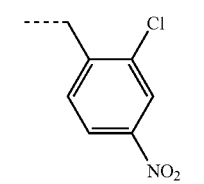 | K783 |
| 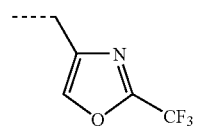 | K784 |
| 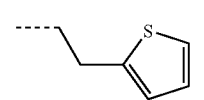 | K785 |
| 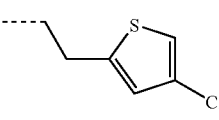 | K786 |
| 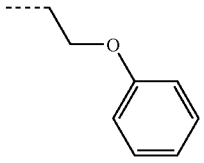 | K787 |
| 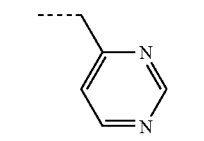 | K788 |
| 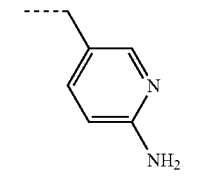 | K789 |
-continued
| | |
|---|---|
| 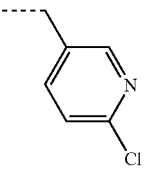 | K790 |
| 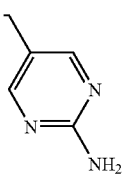 | K791 |
| 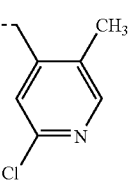 | K792 |
| 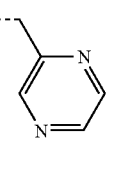 | K793 |
| 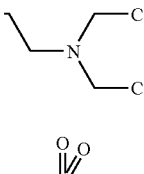 | K794 |
| 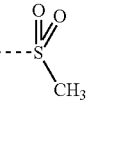 | K795 |
| 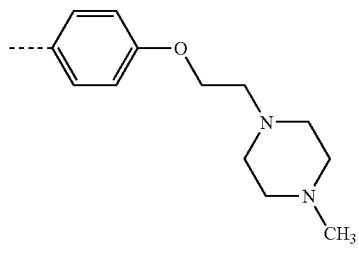 | K796 |
| | K797 |
| 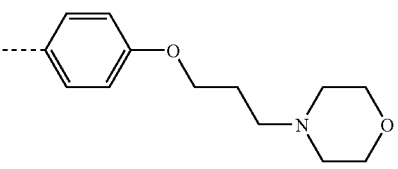 | K798 |

| | |
|---|---|
| 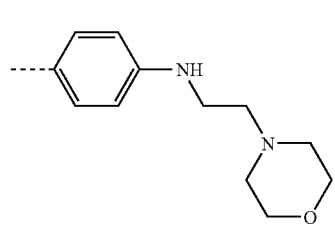 | K799 |
| 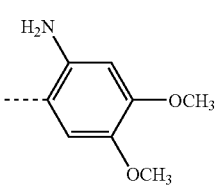 | K800 |
| 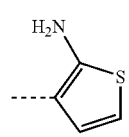 | K801 |
| 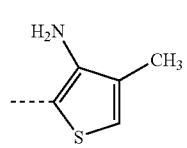 | K802 |
| 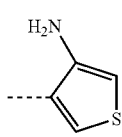 | K803 |
| 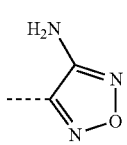 | K804 |
| 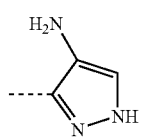 | K805 |
| 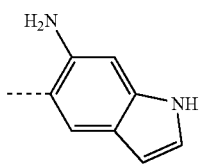 | K806 |
| 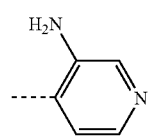 | K807 |
| 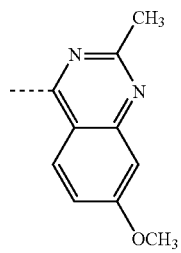 | K808 |
| 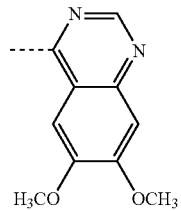 | K809 |
| 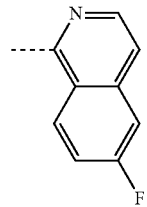 | K810 |
| 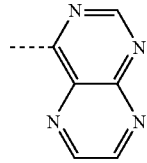 | K811 |
| 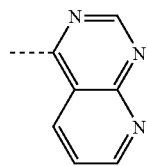 | K812 |
| 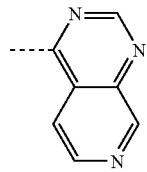 | K813 |
| 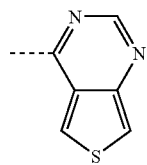 | K814 |
| 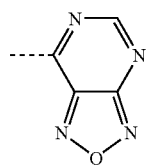 | K815 |

-continued

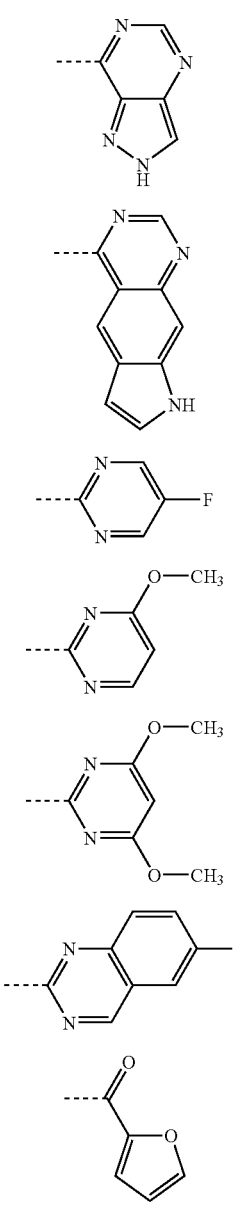

K816
K817
K818
K819
K820
K821
K822

As preferred combinations for -A$^5$-R$^2$ of the pyrrolo[3,2-d]pyrimidine derivatives of formula (I) above, there may be mentioned the groups represented by J1-J243 shown in FIGS. 25 to 31 below, and the groups represented by N1-N158 shown in FIGS. 32 to 36 below. In the structural formulas, the symbol "---" indicates the binding site for a pyrrole ring carbon and -A$^5$-R$^2$.

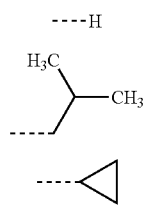

J1
J2
J3

-continued

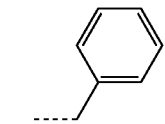 J4

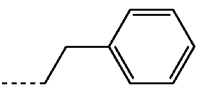 J5

----Br J6

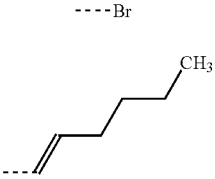 J7

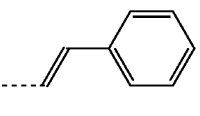 J8

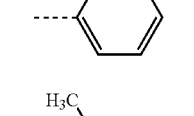 J9

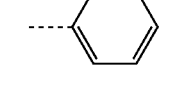 J10

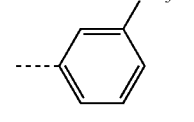 J11

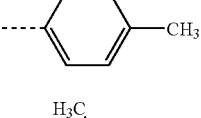 J12

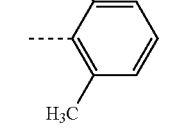 J13

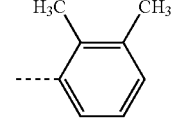 J14

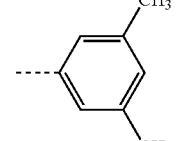 J15

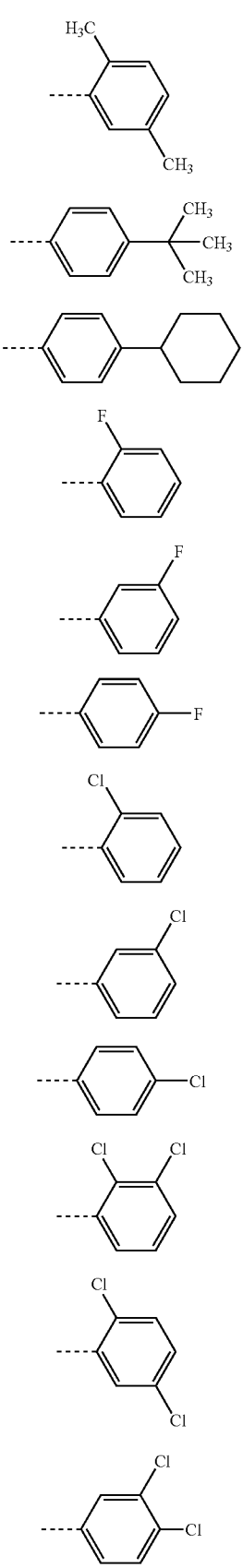
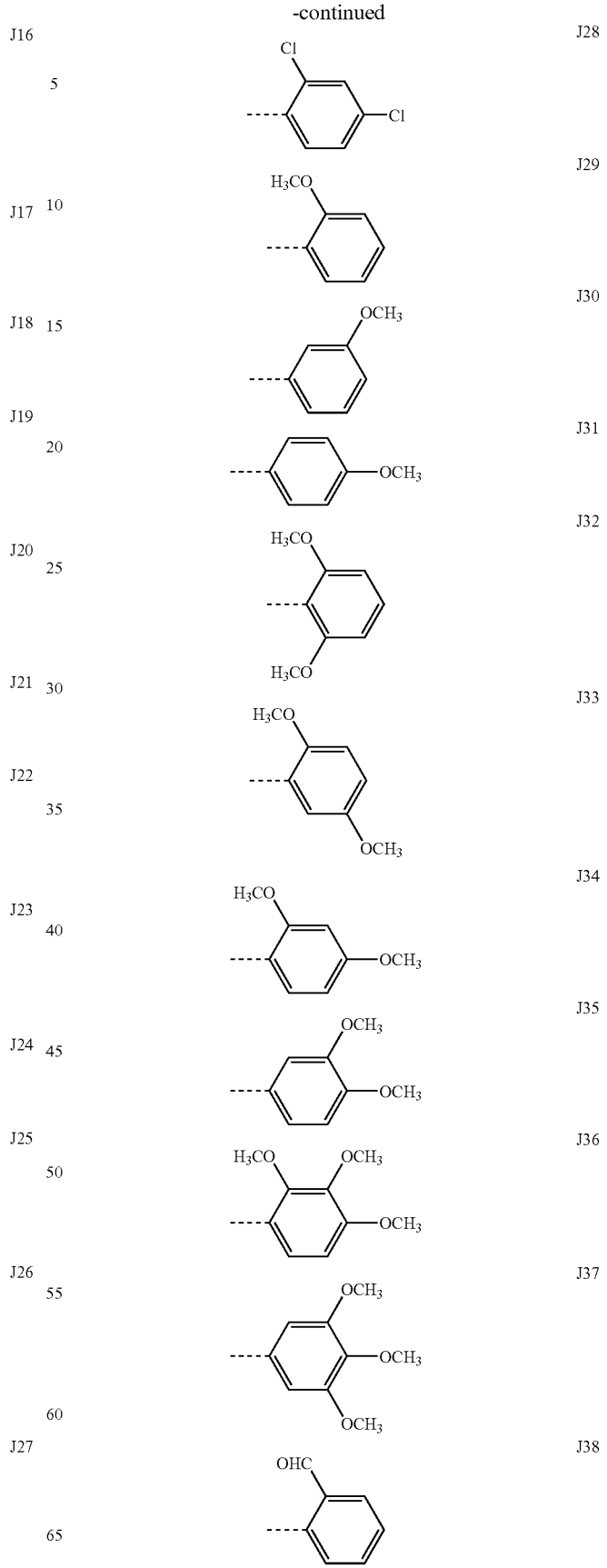

-continued
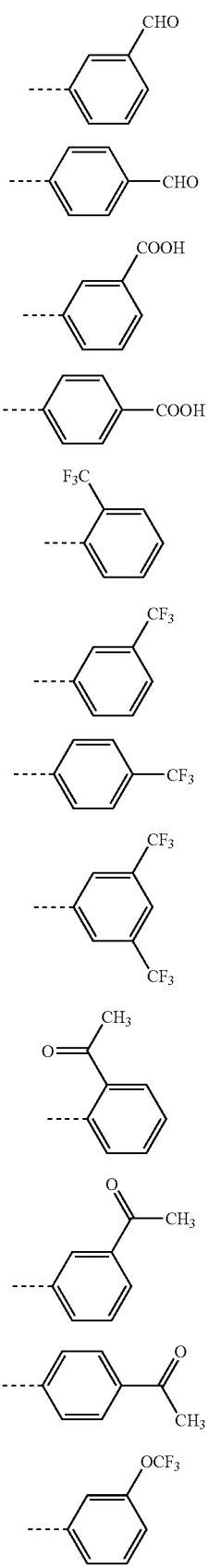
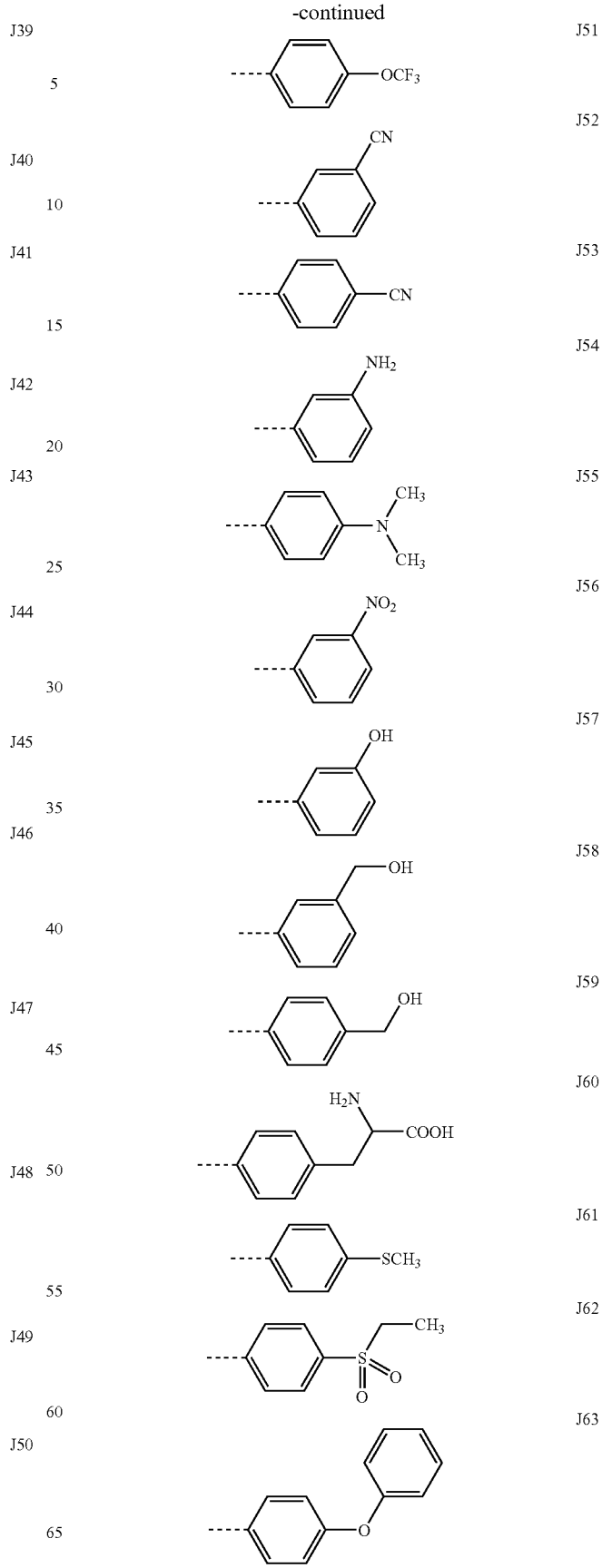

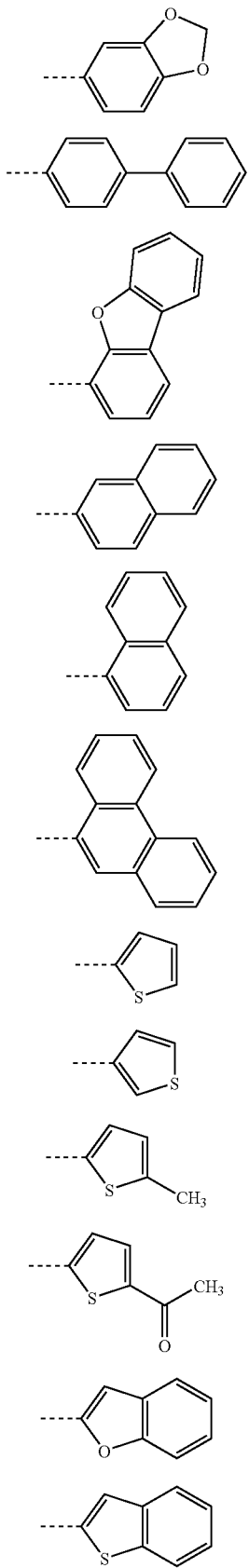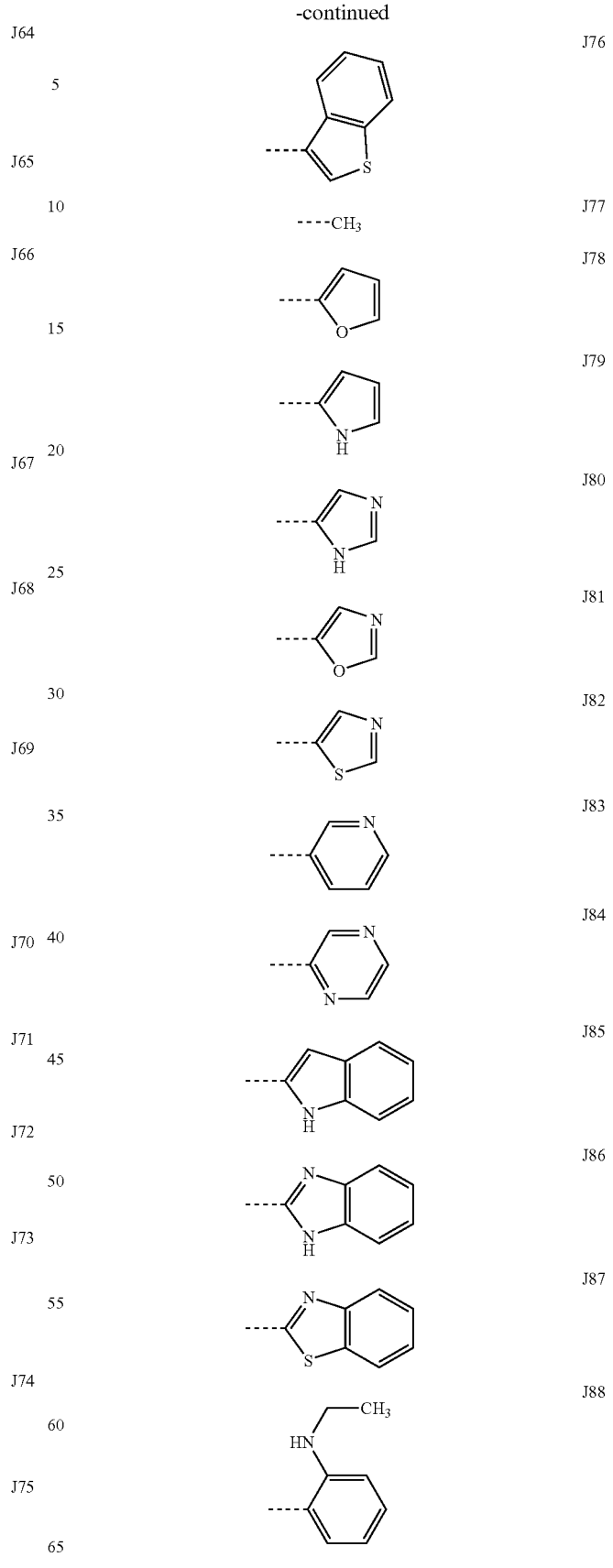

-continued
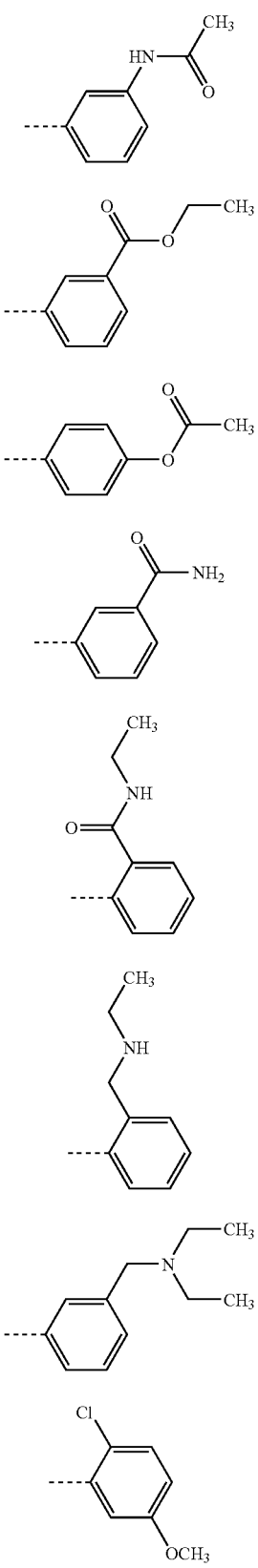
J89
J90
J91
J92
J93
J94
J95
J96
-continued
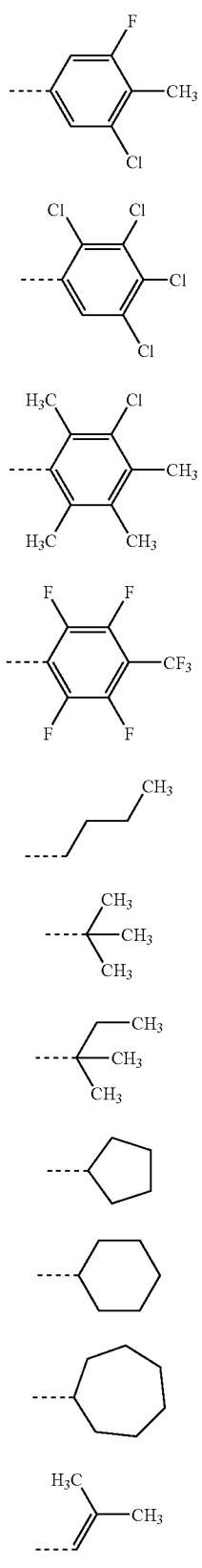
J97
J98
J99
J100
J101
J102
J103
J104
J105
J106
J107

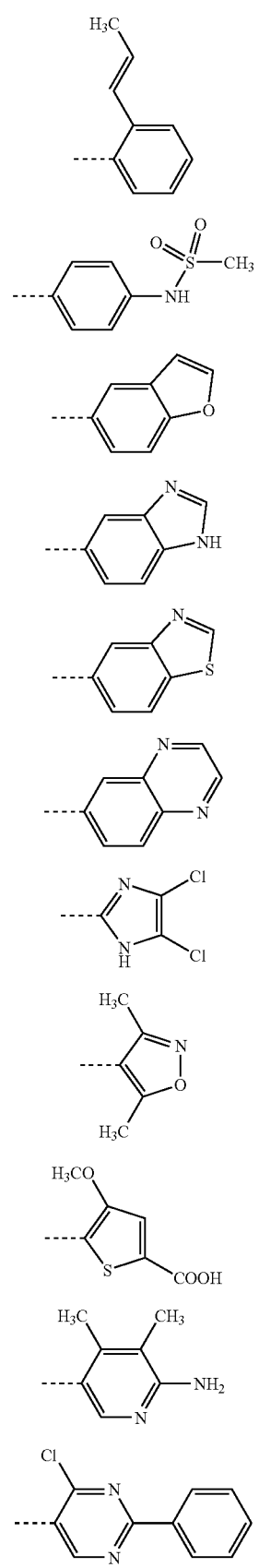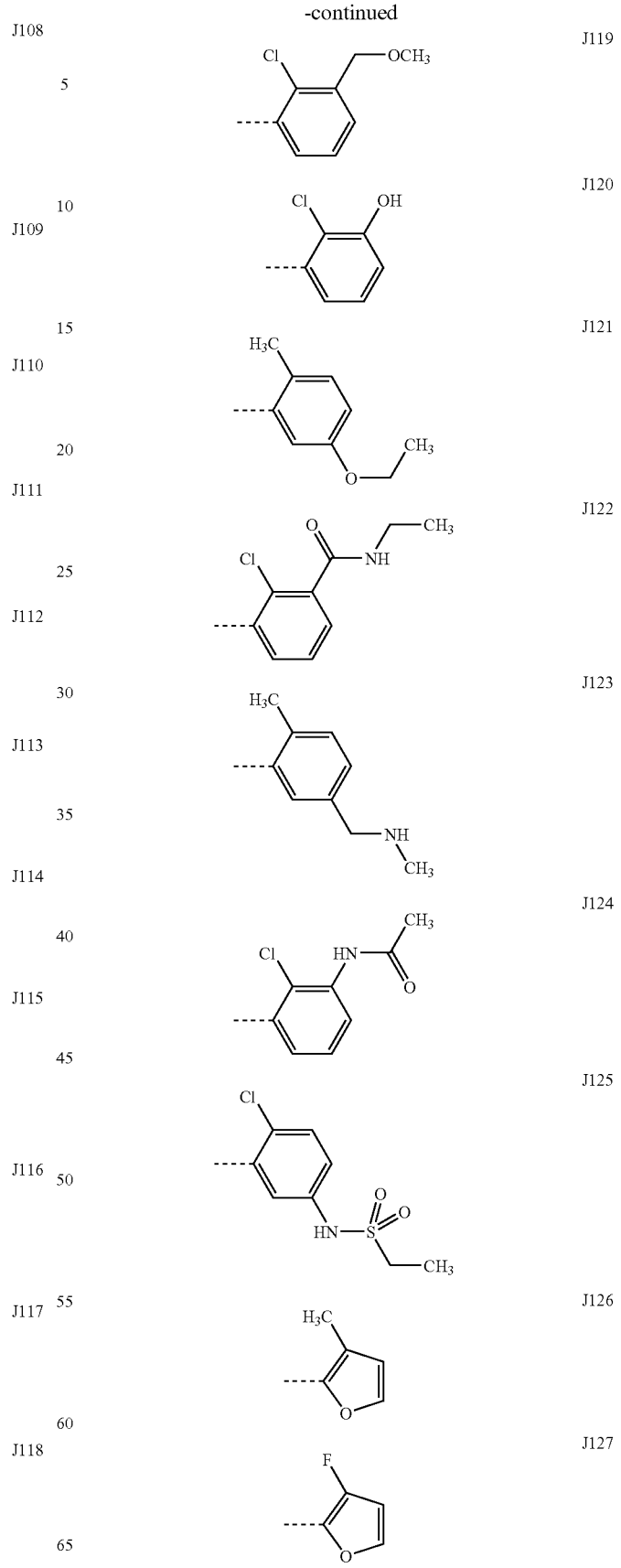

-continued
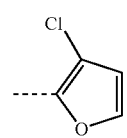 J128
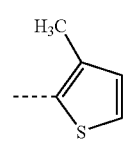 J129
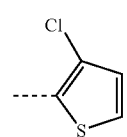 J130
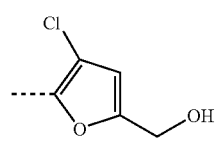 J131
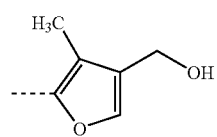 J132
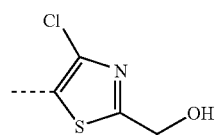 J133
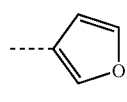 J134
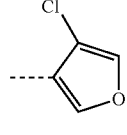 J135
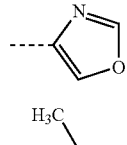 J136
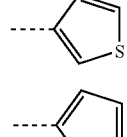 J137
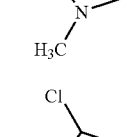 J138
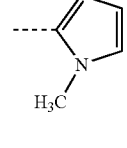 J139
-continued
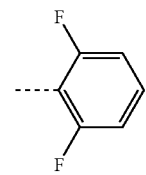 J140
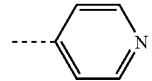 J141
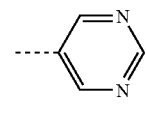 J142
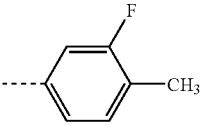 J143
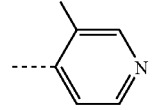 J144
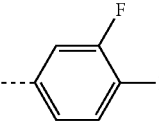 J145
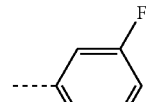 J146
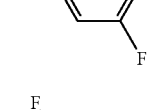 J147
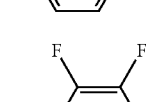 J148
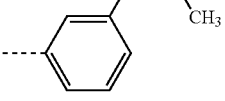 J149
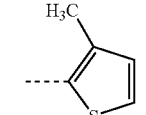 J129

-continued
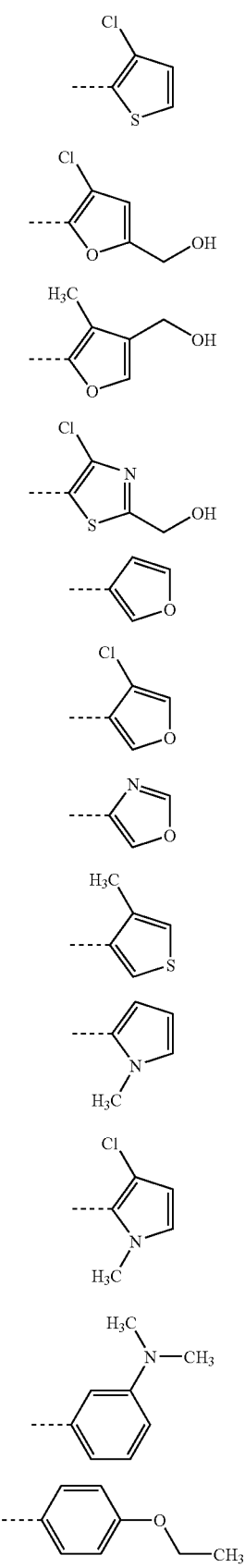
J130
J131
J132
J133
J134
J135
J136
J137
J138
J139
J150
J151
-continued
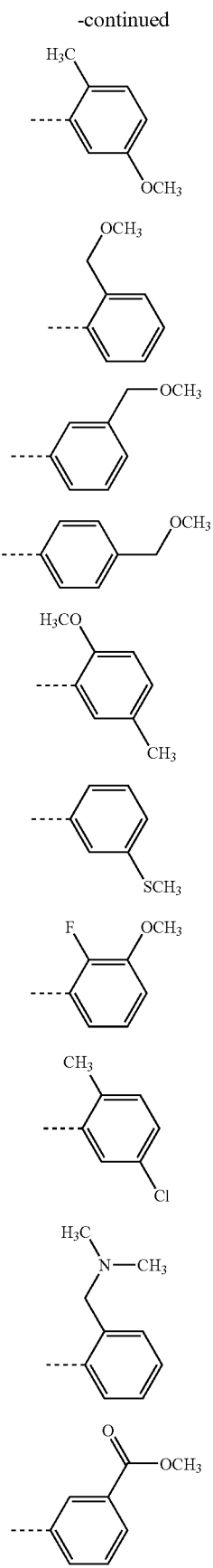
J152
J153
J154
J155
J156
J157
J158
J159
J160
J161

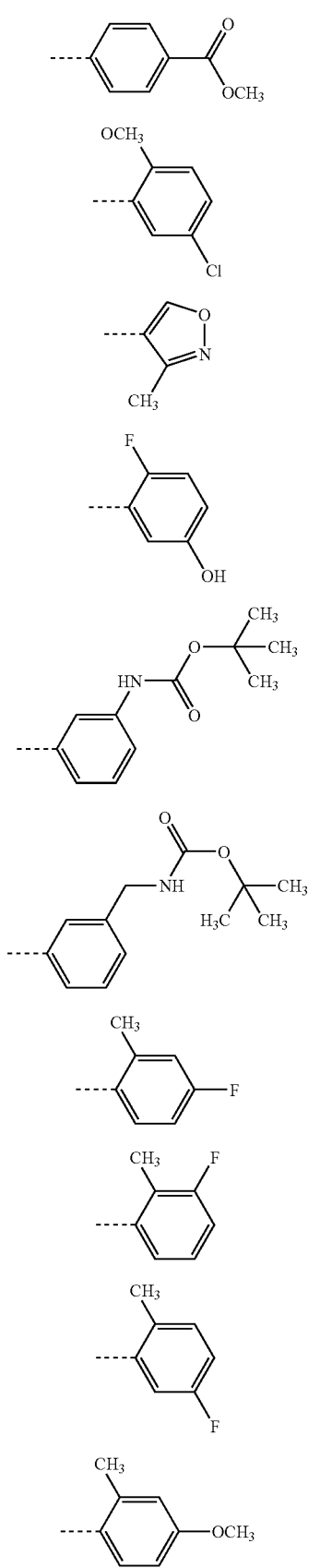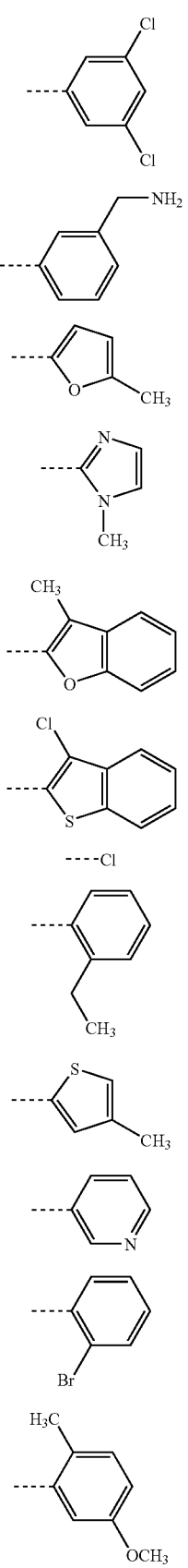

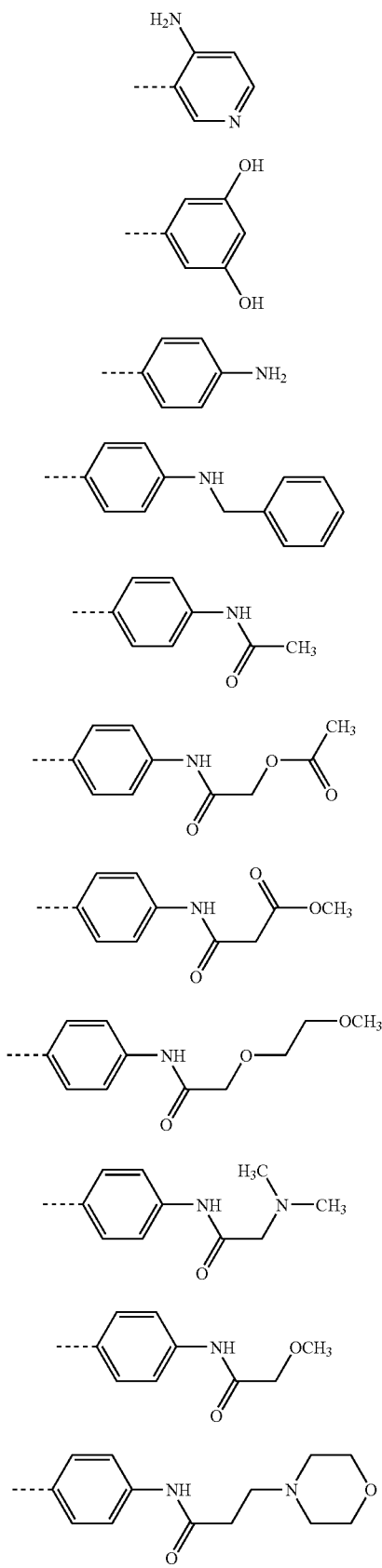
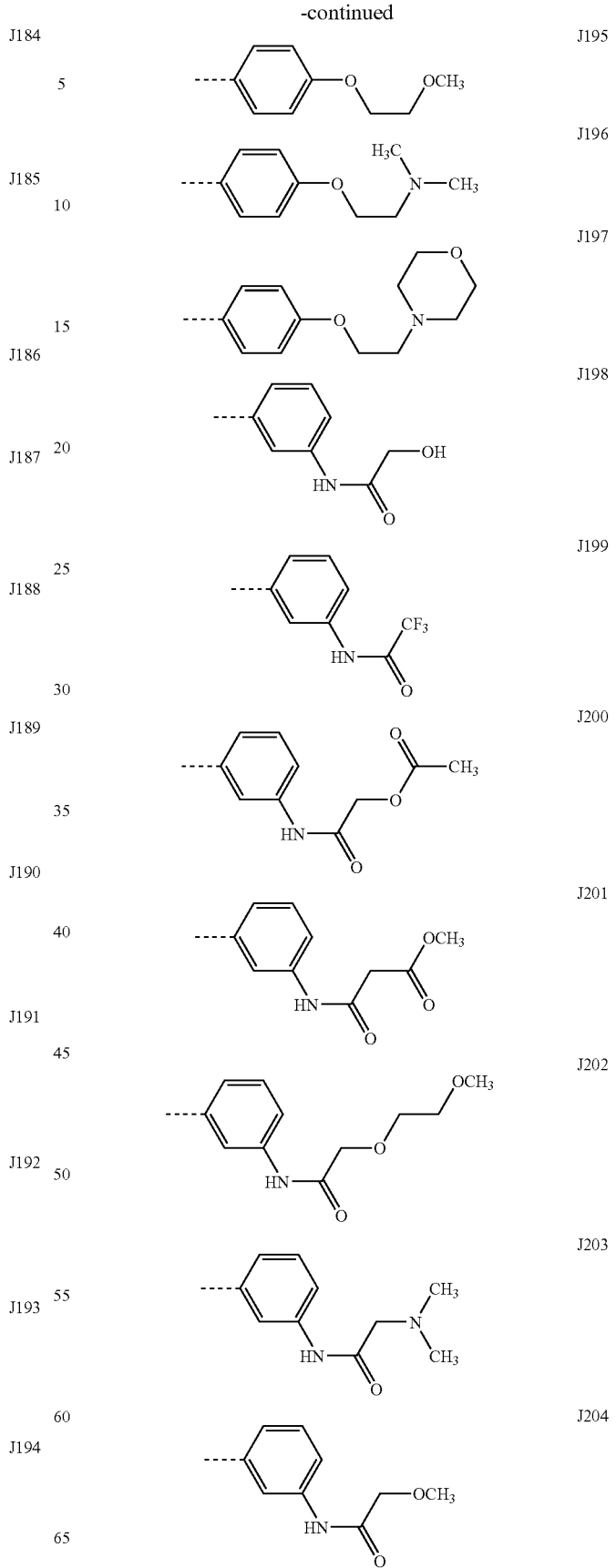

J205 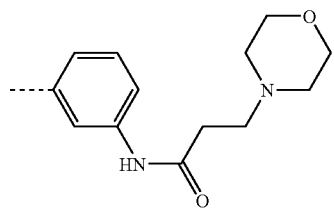
J206 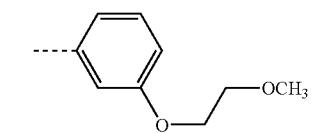
J207 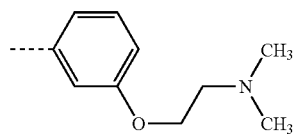
J208 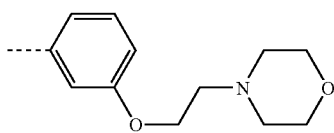
J209 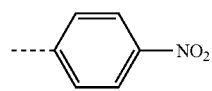
J210 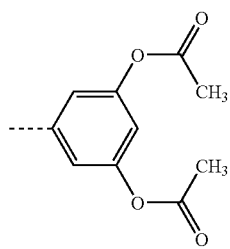
J211 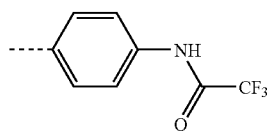
J212 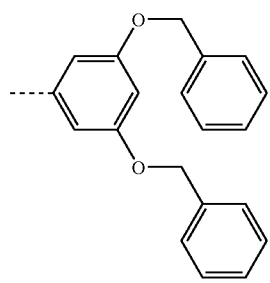
J213 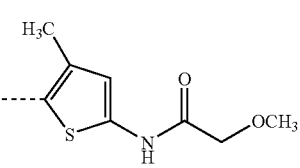
J214 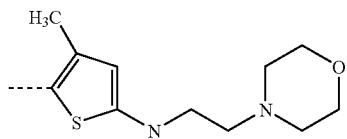
J215 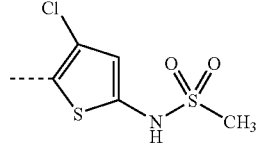
J216 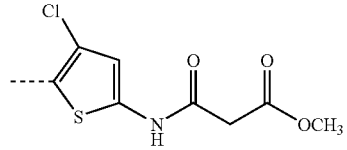
J217 
J218 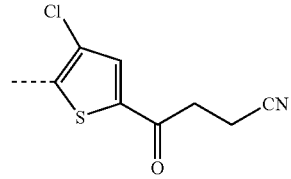
J219 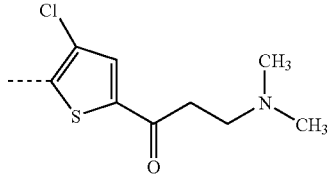
J220 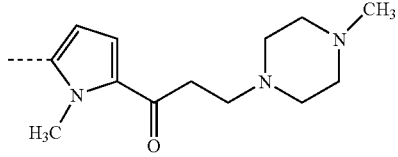
J221 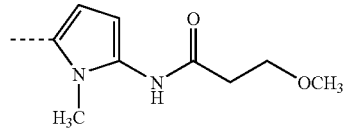
J222 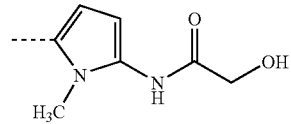

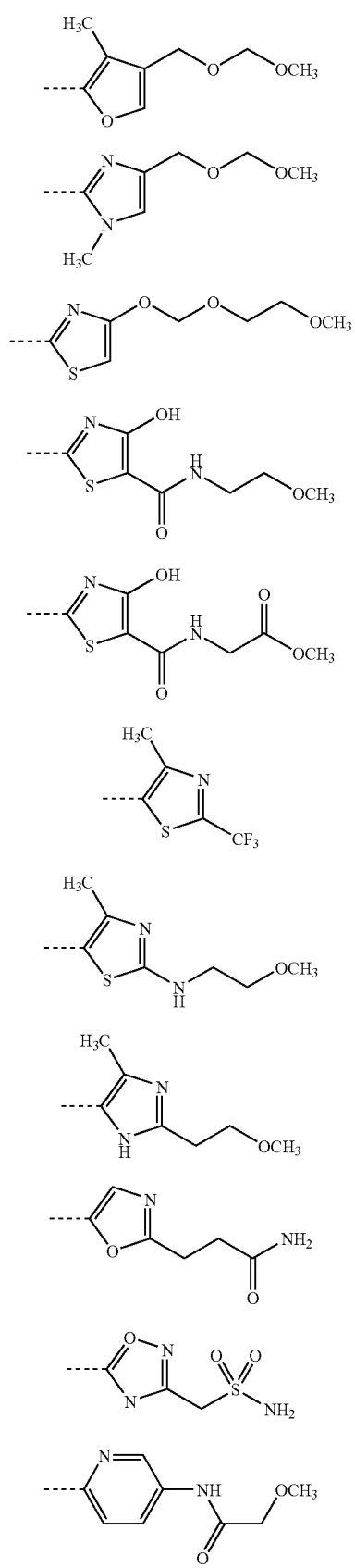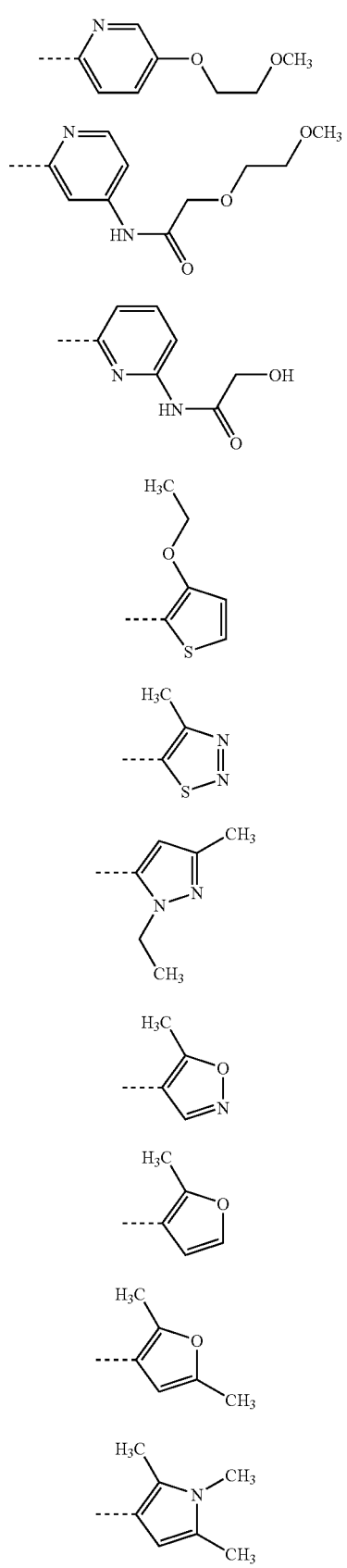

-continued
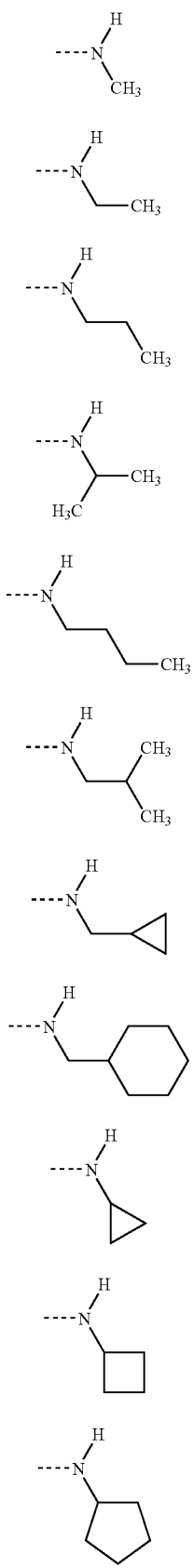
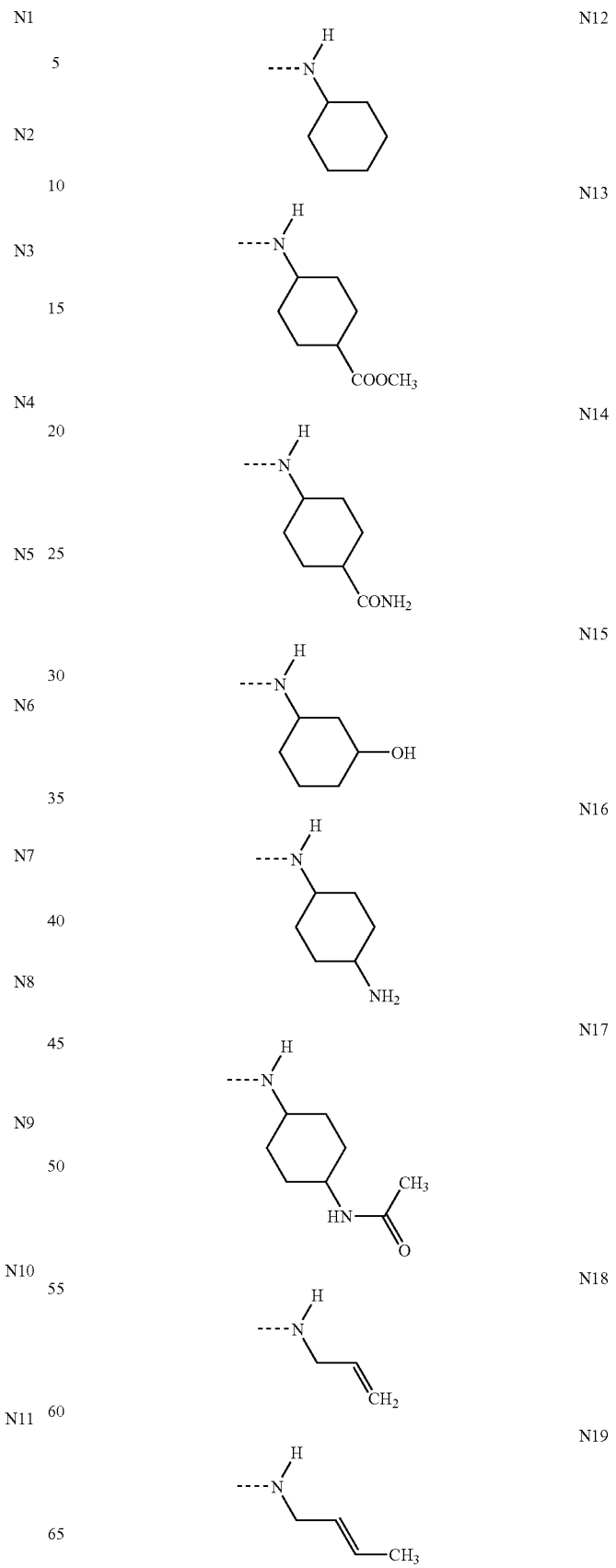

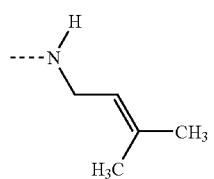 N20
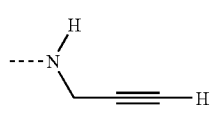 N21
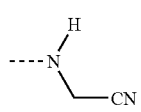 N22
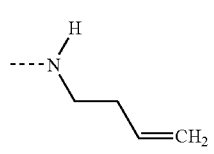 N23
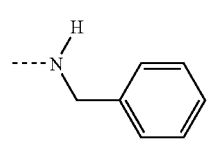 N24
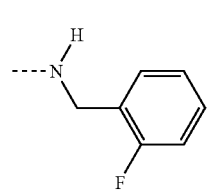 N25
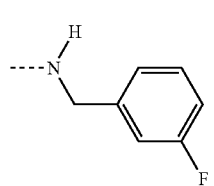 N26
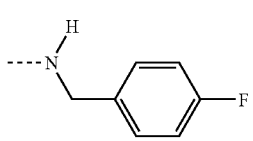 N27
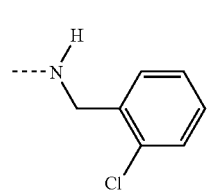 N28
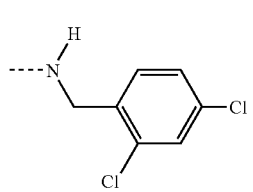 N29
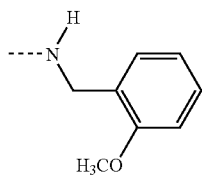 N30
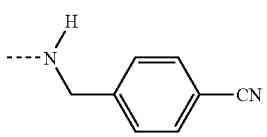 N31
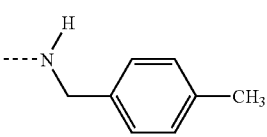 N32
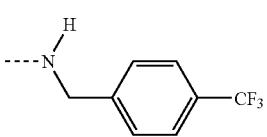 N33
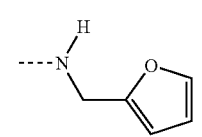 N34
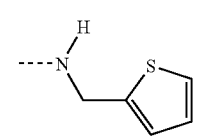 N35
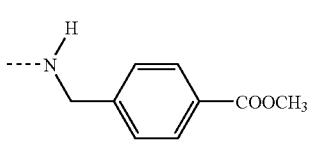 N36
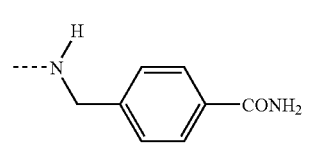 N37
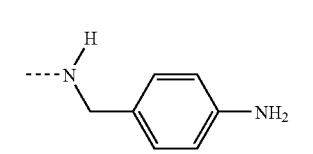 N38
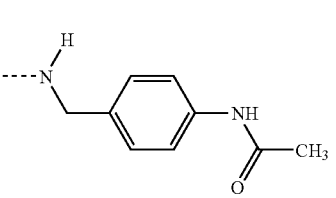 N39

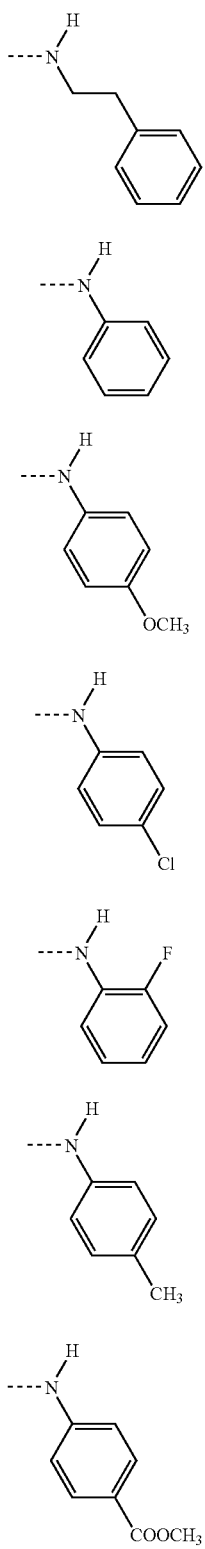
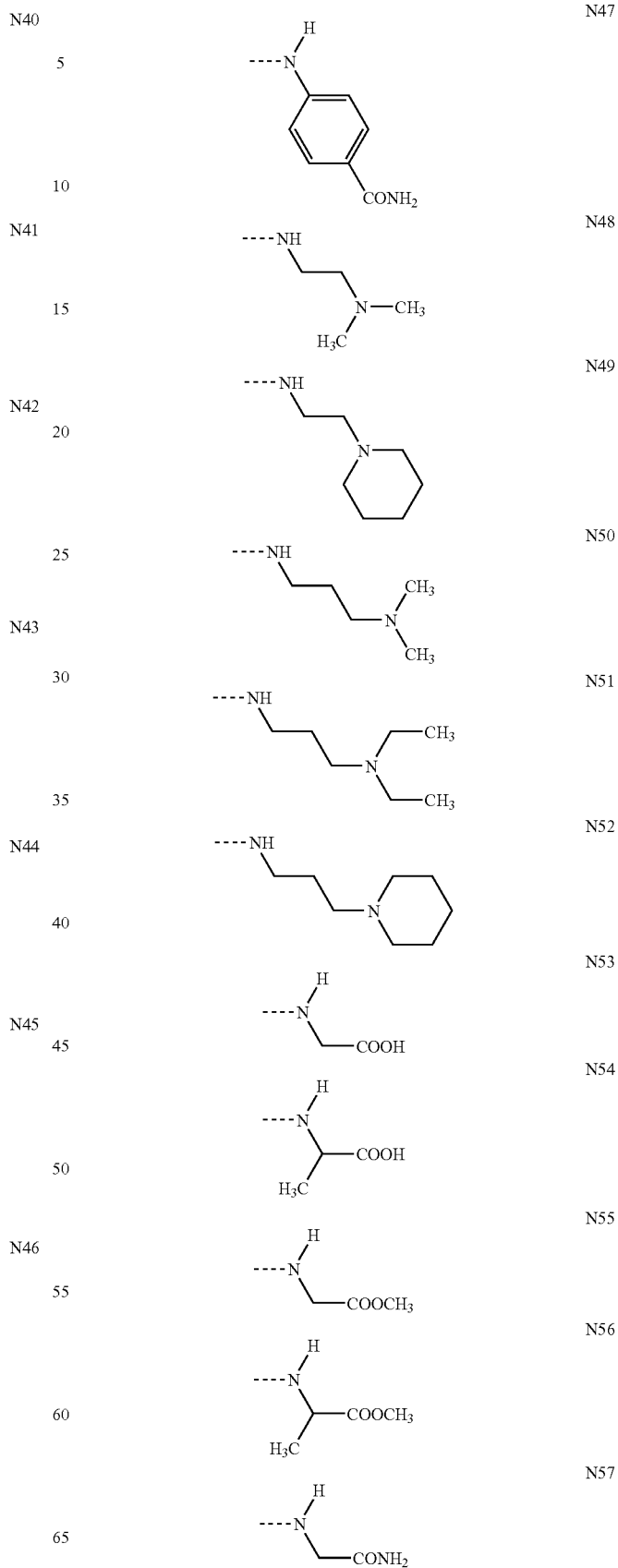

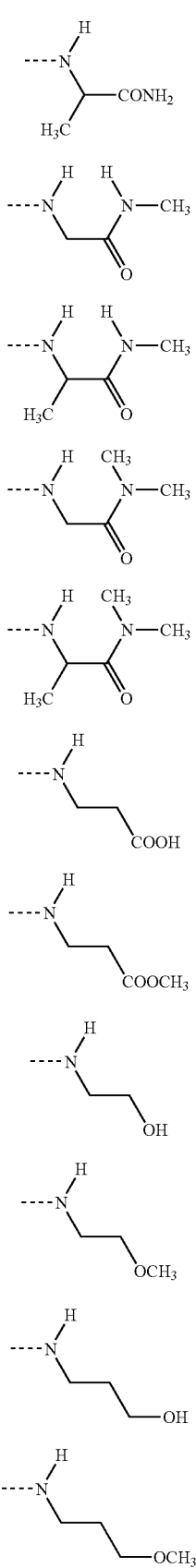
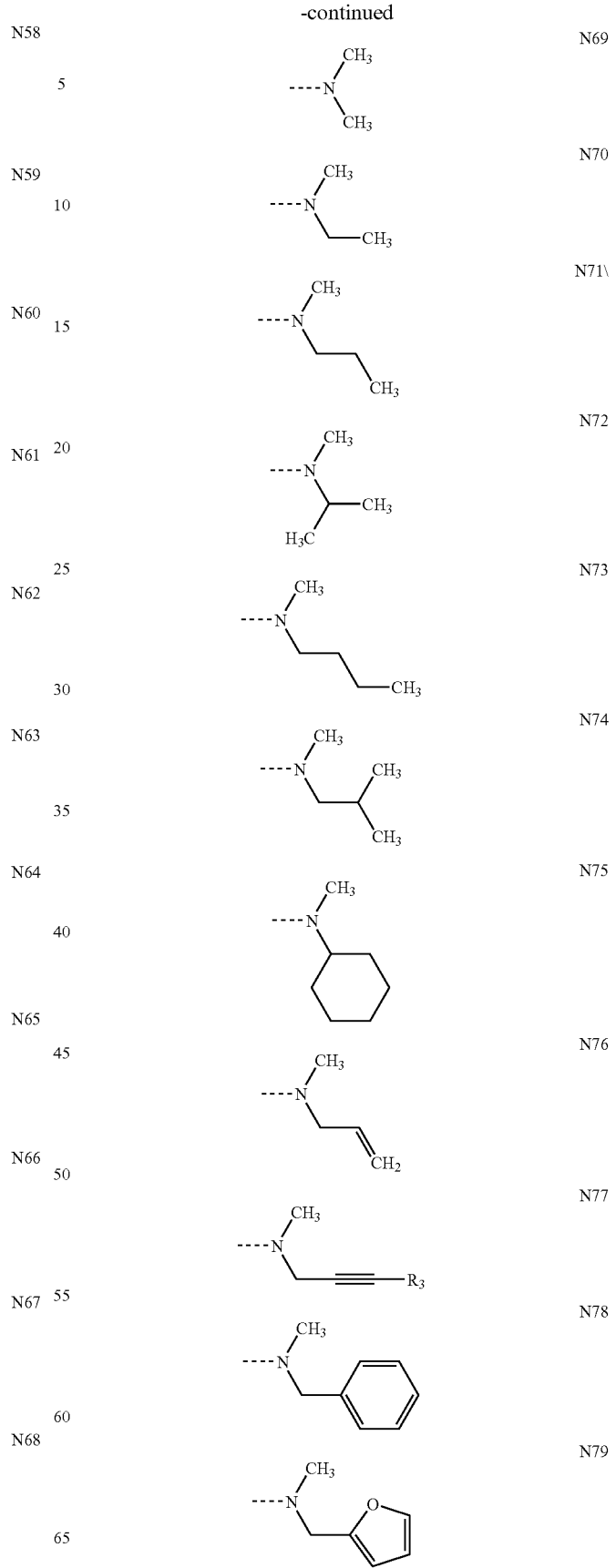

-continued
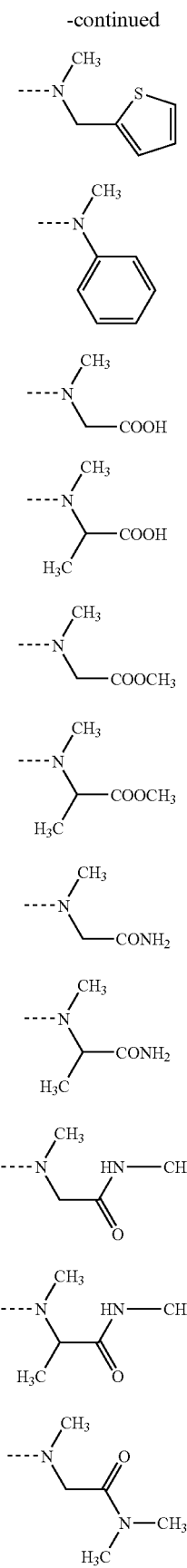
N80
N81
N82
N83
N84
N85
N86
N87
N88
N89
N90
-continued
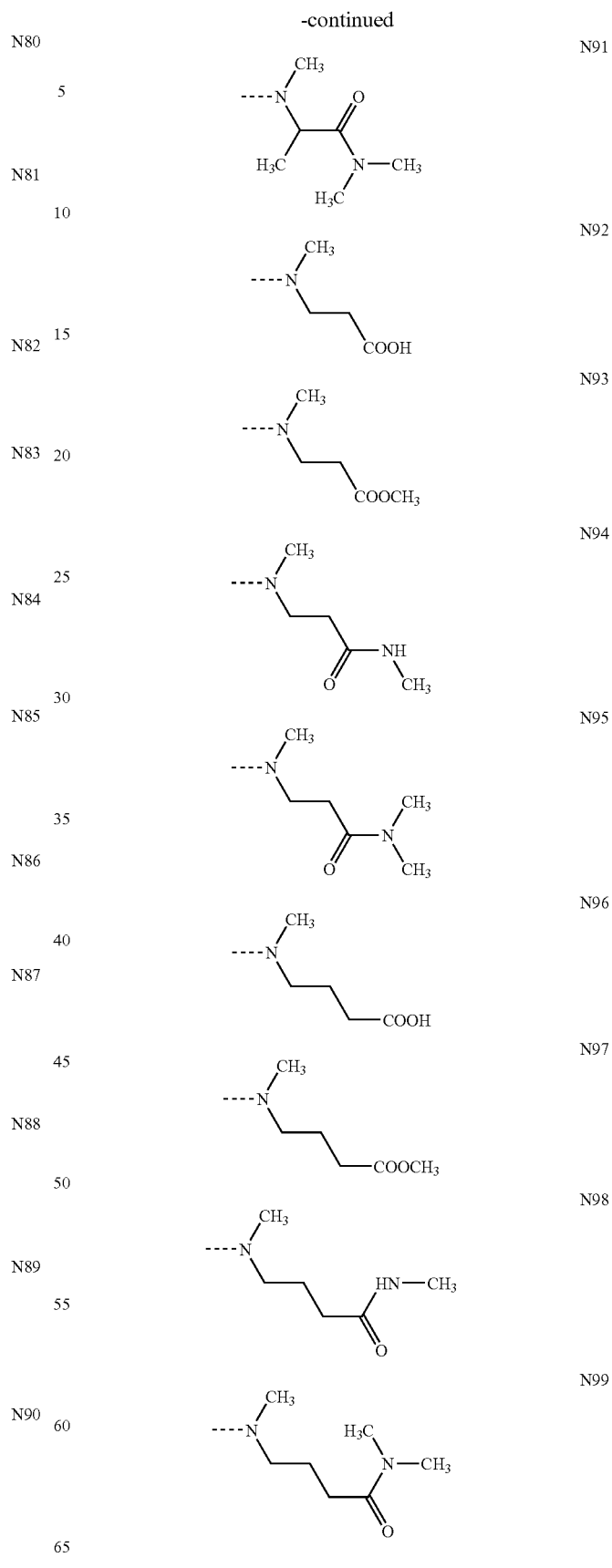
N91
N92
N93
N94
N95
N96
N97
N98
N99

-continued
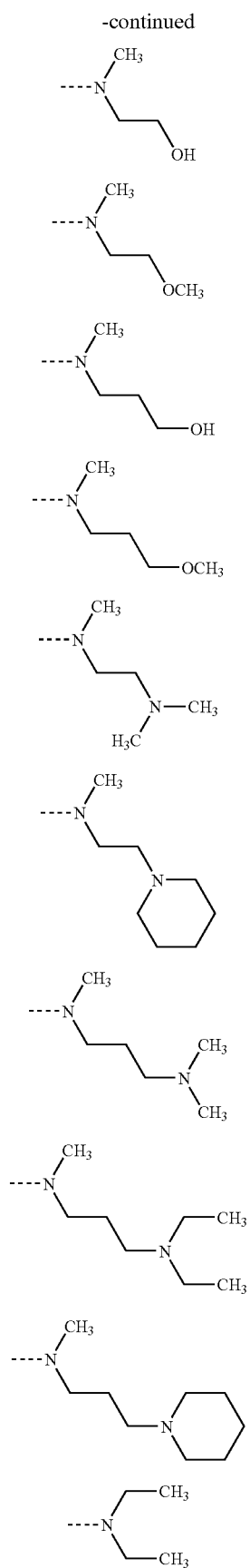
-continued
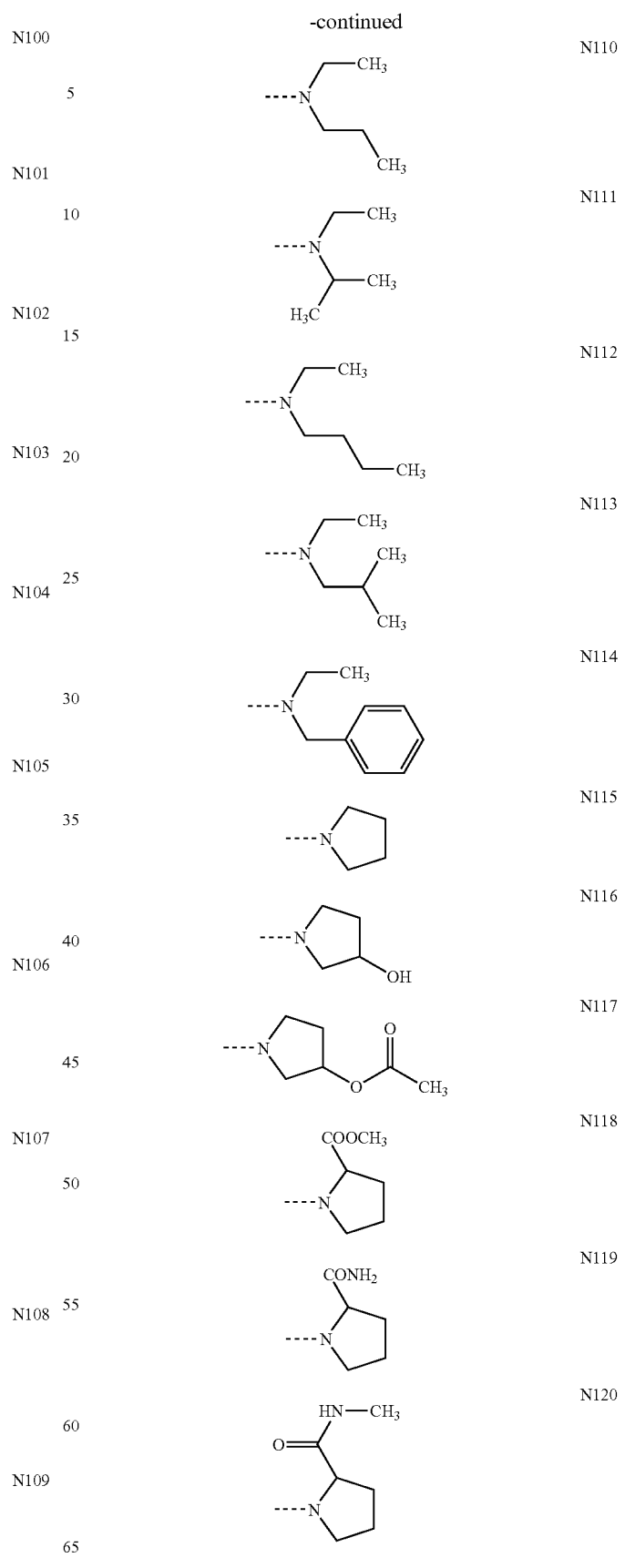

-continued
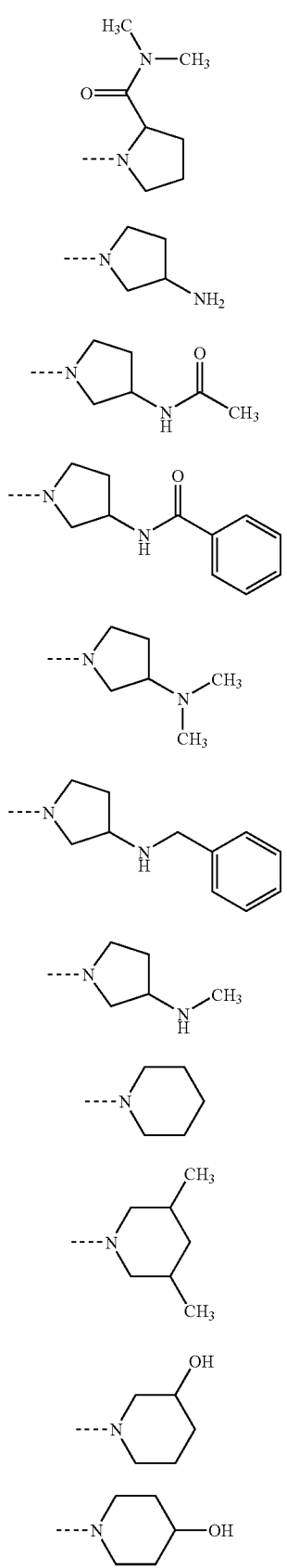
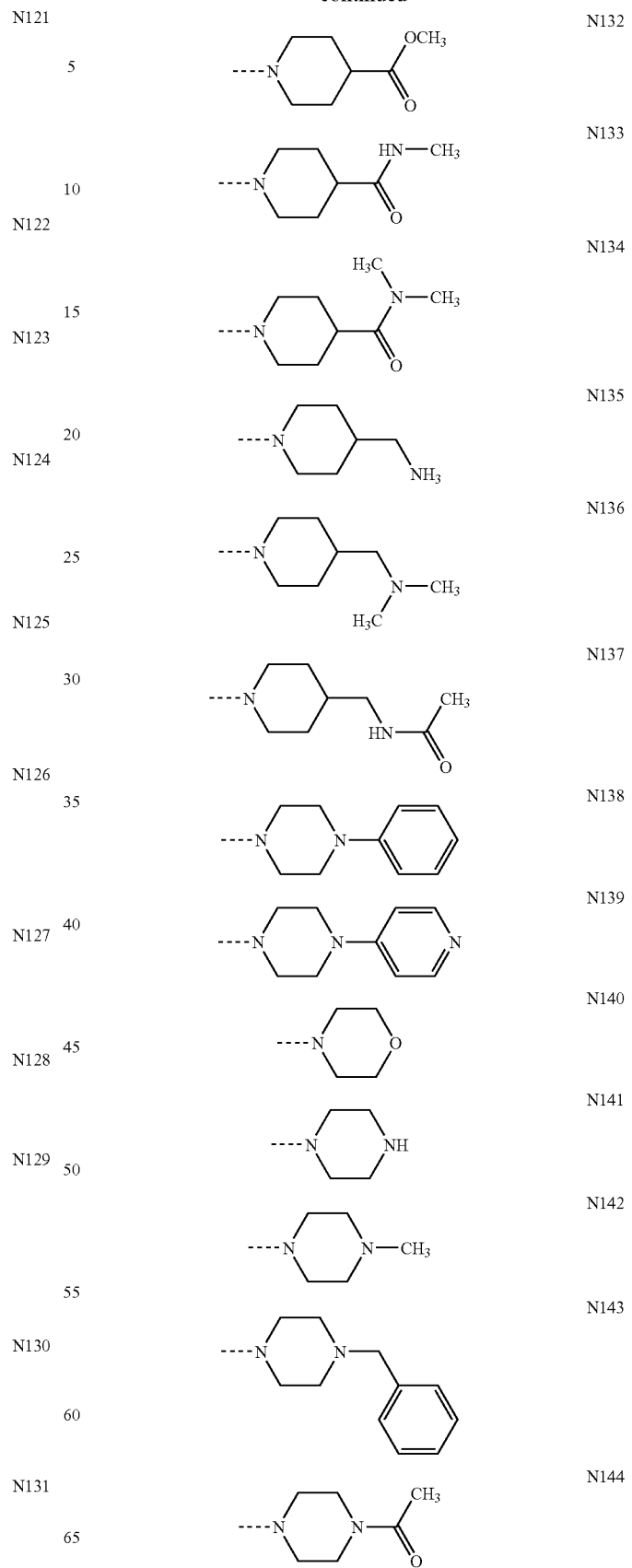

-continued

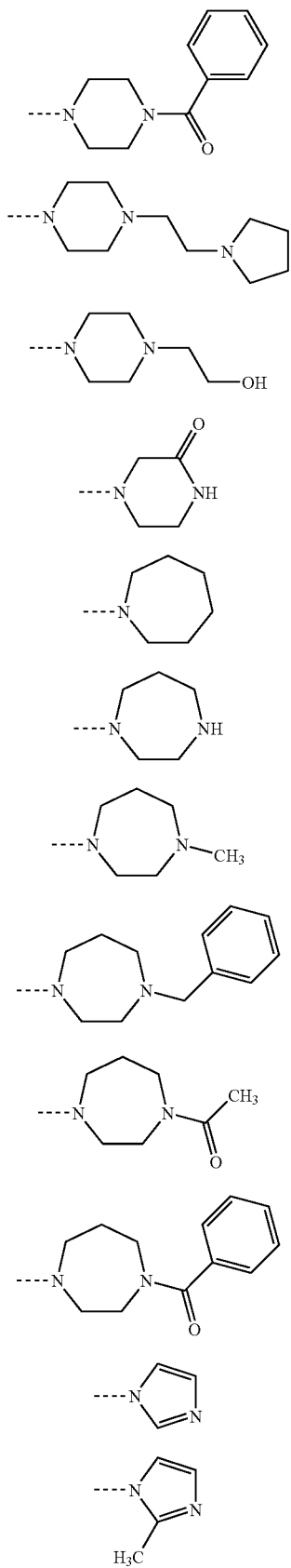

-continued

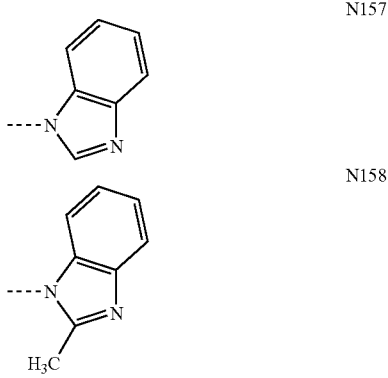

As specific examples of pyrrolo[3,2-d]pyrimidine derivatives of formula (I) above, there may be mentioned compounds having the groups listed in Tables 1 to 214 below as $A^1$, compounds having the groups listed in Tables 1 to 214 below as $A^2$, compounds having the groups represented by K1-K822 shown in FIGS. 1 to 24 above as $-G^1-A^3-A^4-G^2$, compounds having the groups represented by J1-J243 shown in FIGS. 25 to 31 above or the groups represented by N1-N158 shown in FIGS. 32 to 36 above as $-A^5-R^2$, compounds having the groups listed in Tables 1 to 214 below as X, and compounds comprising any desired combinations thereof.

As specific preferred examples there may be mentioned the compounds listed in Tables 1 to 214 below.

The groups K1-K822, J1-J243 and N1-N158 in Tables 1 to 214 below are the respective substituents as defined in FIGS. 1 to 36 above.

TABLE 1

| Compound No. | $-A^1-$ | $-A^2-$ | $-G^1-A^3-A^4-G^2$ | $-A^5-R^2$ | X |
|---|---|---|---|---|---|
| 1-0001 | single bond | single bond | K240 | J1 | O |
| 1-0002 | single bond | single bond | K240 | J3 | O |
| 1-0003 | single bond | single bond | K240 | J3 | S |
| 1-0004 | single bond | single bond | K240 | J6 | O |
| 1-0005 | single bond | single bond | K240 | J7 | O |
| 1-0006 | single bond | single bond | K240 | J8 | O |
| 1-0007 | single bond | single bond | K240 | J9 | O |
| 1-0008 | single bond | single bond | K240 | J9 | S |
| 1-0009 | single bond | single bond | K240 | J10 | O |
| 1-0010 | single bond | single bond | K240 | J10 | S |
| 1-0011 | single bond | single bond | K240 | J11 | S |
| 1-0012 | single bond | single bond | K240 | J11 | O |
| 1-0013 | single bond | single bond | K240 | J12 | O |
| 1-0014 | single bond | single bond | K240 | J13 | O |
| 1-0015 | single bond | single bond | K240 | J14 | O |
| 1-0016 | single bond | single bond | K240 | J14 | S |
| 1-0017 | single bond | single bond | K240 | J15 | O |
| 1-0018 | single bond | single bond | K240 | J16 | O |
| 1-0019 | single bond | single bond | K240 | J16 | S |
| 1-0020 | single bond | single bond | K240 | J17 | O |
| 1-0021 | single bond | single bond | K240 | J18 | O |
| 1-0022 | single bond | single bond | K240 | J19 | O |
| 1-0023 | single bond | single bond | K240 | J20 | O |
| 1-0024 | single bond | single bond | K240 | J21 | O |
| 1-0025 | single bond | single bond | K240 | J22 | O |
| 1-0026 | single bond | single bond | K240 | J22 | S |
| 1-0027 | single bond | single bond | K240 | J23 | S |
| 1-0028 | single bond | single bond | K240 | J23 | O |
| 1-0029 | single bond | single bond | K240 | J24 | O |
| 1-0030 | single bond | single bond | K240 | J24 | S |
| 1-0031 | single bond | single bond | K240 | J25 | O |
| 1-0032 | single bond | single bond | K240 | J25 | S |

TABLE 1-continued

| Compound No. | -A¹- | -A²- | -G¹-A³-A⁴-G² | -A⁵-R² | X |
|---|---|---|---|---|---|

TABLE 2

| Compound No. | -A¹- | -A²- | -G¹-A³-A⁴-G² | -A⁵-R² | X |
|---|---|---|---|---|---|
| 1-0033 | single bond | single bond | K240 | J26 | O |
| 1-0034 | single bond | single bond | K240 | J26 | S |
| 1-0035 | single bond | single bond | K240 | J27 | O |
| 1-0036 | single bond | single bond | K240 | J28 | O |
| 1-0037 | single bond | single bond | K240 | J28 | S |
| 1-0038 | single bond | single bond | K240 | J29 | O |
| 1-0039 | single bond | single bond | K240 | J29 | S |
| 1-0040 | single bond | single bond | K240 | J30 | O |
| 1-0041 | single bond | single bond | K240 | J31 | O |
| 1-0042 | single bond | single bond | K240 | J32 | O |
| 1-0043 | single bond | single bond | K240 | J33 | O |
| 1-0044 | single bond | single bond | K240 | J34 | O |
| 1-0045 | single bond | single bond | K240 | J34 | S |
| 1-0046 | single bond | single bond | K240 | J35 | O |
| 1-0047 | single bond | single bond | K240 | J35 | S |
| 1-0048 | single bond | single bond | K240 | J36 | O |
| 1-0049 | single bond | single bond | K240 | J37 | O |
| 1-0050 | single bond | single bond | K240 | J37 | S |
| 1-0051 | single bond | single bond | K240 | J38 | O |
| 1-0052 | single bond | single bond | K240 | J39 | O |
| 1-0053 | single bond | single bond | K240 | J40 | O |
| 1-0054 | single bond | single bond | K240 | J41 | O |
| 1-0055 | single bond | single bond | K240 | J42 | O |
| 1-0056 | single bond | single bond | K240 | J43 | O |
| 1-0057 | single bond | single bond | K240 | J43 | S |
| 1-0058 | single bond | single bond | K240 | J44 | O |
| 1-0059 | single bond | single bond | K240 | J45 | O |
| 1-0060 | single bond | single bond | K240 | J46 | O |
| 1-0061 | single bond | single bond | K240 | J47 | O |
| 1-0062 | single bond | single bond | K240 | J48 | O |
| 1-0063 | single bond | single bond | K240 | J49 | O |
| 1-0064 | single bond | single bond | K240 | J50 | O |

TABLE 3

| Compound No. | -A¹- | -A²- | -G¹-A³-A⁴-G² | -A⁵-R² | X |
|---|---|---|---|---|---|
| 1-0065 | single bond | single bond | K240 | J51 | O |
| 1-0066 | single bond | single bond | K240 | J52 | O |
| 1-0067 | single bond | single bond | K240 | J53 | O |
| 1-0068 | single bond | single bond | K240 | J54 | O |
| 1-0069 | single bond | single bond | K240 | J55 | O |
| 1-0070 | single bond | single bond | K240 | J56 | O |
| 1-0071 | single bond | single bond | K240 | J56 | S |
| 1-0072 | single bond | single bond | K240 | J57 | O |
| 1-0073 | single bond | single bond | K240 | J58 | O |
| 1-0074 | single bond | single bond | K240 | J59 | O |
| 1-0075 | single bond | single bond | K240 | J60 | O |
| 1-0076 | single bond | single bond | K240 | J61 | O |
| 1-0077 | single bond | single bond | K240 | J62 | O |
| 1-0078 | single bond | single bond | K240 | J63 | O |
| 1-0079 | single bond | single bond | K240 | J63 | S |
| 1-0080 | single bond | single bond | K240 | J64 | O |
| 1-0081 | single bond | single bond | K240 | J65 | O |
| 1-0082 | single bond | single bond | K240 | J66 | O |
| 1-0083 | single bond | single bond | K240 | J67 | O |
| 1-0084 | single bond | single bond | K240 | J68 | O |
| 1-0085 | single bond | single bond | K240 | J69 | O |
| 1-0086 | single bond | single bond | K240 | J70 | O |
| 1-0087 | single bond | single bond | K240 | J70 | S |
| 1-0088 | single bond | single bond | K240 | J71 | O |
| 1-0089 | single bond | single bond | K240 | J72 | O |
| 1-0090 | single bond | single bond | K240 | J73 | O |
| 1-0091 | single bond | single bond | K240 | J74 | O |
| 1-0092 | single bond | single bond | K240 | J75 | O |
| 1-0093 | single bond | single bond | K240 | J76 | O |
| 1-0094 | single bond | single bond | K240 | J84 | O |
| 1-0095 | single bond | single bond | K240 | J84 | S |
| 1-0096 | single bond | single bond | K240 | J92 | O |

TABLE 4

| Compound No. | -A¹- | -A²- | -G¹-A³-A⁴-G² | -A⁵-R² | X |
|---|---|---|---|---|---|
| 1-0097 | single bond | single bond | K240 | J92 | S |
| 1-0098 | —CH₂— | single bond | K240 | J4 | O |
| 1-0099 | —CH₂— | single bond | K240 | J4 | S |
| 1-0100 | —CH₂— | single bond | K240 | J9 | O |
| 1-0101 | —CH₂— | single bond | K240 | J9 | S |
| 1-0102 | —CH₂— | single bond | K240 | J77 | O |
| 1-0103 | —(CH₂)₃— | single bond | K240 | J9 | O |
| 1-0104 | —(CH₂)₃— | single bond | K240 | J77 | O |
| 1-0105 | —(CH₂)₃— | single bond | K240 | J77 | S |
| 1-0106 | —CH₂—CH(CH₃)—CH₂— | single bond | K240 | J9 | O |
| 1-0107 | —CH₂—CH(CH₃)—CH₂— | single bond | K240 | J77 | O |
| 1-0108 | —CH₂—CH(CH₃)—CH₂— | single bond | K240 | J77 | S |
| 1-0109 | —(CH₂)₂—CH(CH₃)—CH₂— | single bond | K240 | J4 | O |
| 1-0110 | —(CH₂)₂—CH(CH₃)—CH₂— | single bond | K240 | J4 | S |
| 1-0111 | —(CH₂)₂—CH(CH₃)—CH₂— | single bond | K240 | J6 | O |
| 1-0112 | —(CH₂)₂—CH(CH₃)—CH₂— | single bond | K240 | J6 | S |
| 1-0113 | —(CH₂)₂—CH(CH₃)—CH₂— | single bond | K240 | J9 | O |
| 1-0114 | —(CH₂)₂—CH(CH₃)—CH₂— | single bond | K240 | J9 | S |
| 1-0115 | —(CH₂)₂—CH(CH₃)—CH₂— | single bond | K240 | J23 | O |
| 1-0116 | —(CH₂)₂—CH(CH₃)—CH₂— | single bond | K240 | J23 | S |
| 1-0117 | —(CH₂)₂—CH(CH₃)—CH₂— | single bond | K240 | J41 | O |
| 1-0118 | —(CH₂)₂—CH(CH₃)—CH₂— | single bond | K240 | J41 | S |
| 1-0119 | —(CH₂)₂—CH(CH₃)—CH₂— | single bond | K240 | J52 | O |
| 1-0120 | —(CH₂)₂—CH(CH₃)—CH₂— | single bond | K240 | J52 | S |
| 1-0121 | —(CH₂)₂—CH(CH₃)—CH₂— | single bond | K240 | J77 | O |
| 1-0122 | —(CH₂)₂—CH(CH₃)—CH₂— | single bond | K240 | J77 | S |

TABLE 4-continued

| Compound No. | -A$^1$- | -A$^2$- | -G$^1$-A$^3$-A$^4$-G$^2$- | -A$^5$-R$^2$ | X |
|---|---|---|---|---|---|
| 1-0123 | —(CH$_2$)$_2$—CH(CH$_3$)—CH$_2$— | single bond | K240 | J84 | O |
| 1-0124 | —(CH$_2$)$_2$—CH(CH$_3$)—CH$_2$— | single bond | K240 | J84 | S |
| 1-0125 | —CH$_2$—CH(CH$_3$)—(CH$_2$)$_2$— | single bond | K240 | J9 | O |
| 1-0126 | —CH$_2$—CH(CH$_3$)—(CH$_2$)$_2$— | single bond | K240 | J9 | S |
| 1-0127 | —CH$_2$—CH(CH$_3$)—(CH$_2$)$_2$— | single bond | K240 | J77 | O |
| 1-0128 | —CH$_2$—C(CH$_3$)$_2$—CH$_2$— | single bond | K240 | J9 | O |

TABLE 5

| Compound No. | -A$^1$- | -A$^2$- | -G$^1$-A$^3$-A$^4$-G$^2$- | -A$^5$-R$^2$ | X |
|---|---|---|---|---|---|
| 1-0129 | —CH$_2$—C(CH$_3$)$_2$—CH$_2$— | single bond | K240 | J9 | S |
| 1-0130 | —(CH$_2$)$_4$— | single bond | K1 | J2 | O |
| 1-0131 | —(CH$_2$)$_4$— | single bond | K1 | J4 | O |
| 1-0132 | —(CH$_2$)$_4$— | single bond | K1 | J9 | O |
| 1-0133 | —(CH$_2$)$_4$— | single bond | K1 | J9 | S |
| 1-0134 | —(CH$_2$)$_4$— | single bond | K1 | J77 | O |
| 1-0135 | —(CH$_2$)$_4$— | single bond | K1 | J77 | S |
| 1-0136 | —(CH$_2$)$_2$—C(CH$_3$)$_2$—CH$_2$— | single bond | K240 | J9 | O |
| 1-0137 | —(CH$_2$)$_2$—C(CH$_3$)$_2$—CH$_2$— | single bond | K240 | J9 | S |
| 1-0138 | —(CH$_2$)$_4$— | single bond | K87 | J96 | O |
| 1-0139 | —(CH$_2$)$_4$— | single bond | K87 | J96 | S |
| 1-0140 | —(CH$_2$)$_4$— | single bond | K87 | J104 | O |
| 1-0141 | —(CH$_2$)$_4$— | single bond | K87 | J104 | S |
| 1-0142 | —(CH$_2$)$_4$— | single bond | K87 | J117 | O |
| 1-0143 | —(CH$_2$)$_4$— | single bond | K87 | J117 | S |
| 1-0144 | single bond | single bond | K6 | J9 | O |
| 1-0145 | single bond | single bond | K6 | J77 | O |
| 1-0146 | single bond | single bond | K14 | J1 | O |
| 1-0147 | —(CH$_2$)$_2$— | —NH— | K240 | J4 | O |
| 1-0148 | —(CH$_2$)$_2$— | —NH— | K240 | J4 | S |
| 1-0149 | —(CH$_2$)$_2$— | —NH— | K240 | J6 | O |
| 1-0150 | —(CH$_2$)$_2$— | —NH— | K240 | J6 | S |
| 1-0151 | —(CH$_2$)$_2$— | —NH— | K240 | J9 | O |
| 1-0152 | —(CH$_2$)$_2$— | —NH— | K240 | J12 | O |
| 1-0153 | —(CH$_2$)$_2$— | —NH— | K240 | J12 | S |
| 1-0154 | —(CH$_2$)$_2$— | —NH— | K240 | J23 | O |
| 1-0155 | —(CH$_2$)$_2$— | —NH— | K240 | J23 | S |
| 1-0156 | —(CH$_2$)$_2$— | —NH— | K240 | J41 | O |
| 1-0157 | —(CH$_2$)$_2$— | —NH— | K240 | J41 | S |
| 1-0158 | —(CH$_2$)$_2$— | —NH— | K240 | J52 | O |
| 1-0159 | —(CH$_2$)$_2$— | —NH— | K240 | J52 | S |
| 1-0160 | —(CH$_2$)$_2$— | —NH— | K240 | J84 | O |

TABLE 6

| Compound No. | -A$^1$- | -A$^2$- | -G$^1$-A$^3$-A$^4$-G$^2$- | -A$^5$-R$^2$ | X |
|---|---|---|---|---|---|
| 1-0161 | —(CH$_2$)$_2$— | —NH— | K240 | J84 | S |
| 1-0162 | —(CH$_2$)$_3$— | —NH— | K240 | J3 | O |
| 1-0163 | —(CH$_2$)$_3$— | —NH— | K240 | J3 | S |
| 1-0164 | —(CH$_2$)$_3$— | —NH— | K240 | J9 | O |
| 1-0165 | —(CH$_2$)$_3$— | —NH— | K240 | J10 | O |
| 1-0166 | —(CH$_2$)$_3$— | —NH— | K240 | J10 | S |
| 1-0167 | —(CH$_2$)$_3$— | —NH— | K240 | J22 | O |
| 1-0168 | —(CH$_2$)$_3$— | —NH— | K240 | J22 | S |
| 1-0169 | —(CH$_2$)$_3$— | —NH— | K240 | J28 | O |
| 1-0170 | —(CH$_2$)$_3$— | —NH— | K240 | J28 | S |
| 1-0171 | —(CH$_2$)$_3$— | —NH— | K240 | J43 | O |
| 1-0172 | —(CH$_2$)$_3$— | —NH— | K240 | J43 | S |
| 1-0173 | —(CH$_2$)$_3$— | —NH— | K240 | J84 | O |
| 1-0174 | —(CH$_2$)$_3$— | —NH— | K240 | J84 | S |
| 1-0175 | —(CH$_2$)$_3$— | —NH— | K240 | J92 | O |
| 1-0176 | —(CH$_2$)$_3$— | —NH— | K240 | J92 | S |
| 1-0177 | —(CH$_2$)$_2$— | —O— | K240 | J4 | O |
| 1-0178 | —(CH$_2$)$_2$— | —O— | K240 | J4 | S |
| 1-0179 | —(CH$_2$)$_2$— | —O— | K240 | J6 | O |
| 1-0180 | —(CH$_2$)$_2$— | —O— | K240 | J6 | S |
| 1-0181 | —(CH$_2$)$_2$— | —O— | K240 | J9 | O |
| 1-0182 | —(CH$_2$)$_2$— | —O— | K240 | J12 | O |
| 1-0183 | —(CH$_2$)$_2$— | —O— | K240 | J12 | S |
| 1-0184 | —(CH$_2$)$_2$— | —O— | K240 | J23 | O |
| 1-0185 | —(CH$_2$)$_2$— | —O— | K240 | J23 | S |
| 1-0186 | —(CH$_2$)$_2$— | —O— | K240 | J41 | O |
| 1-0187 | —(CH$_2$)$_2$— | —O— | K240 | J41 | S |
| 1-0188 | —(CH$_2$)$_2$— | —O— | K240 | J52 | O |
| 1-0189 | —(CH$_2$)$_2$— | —O— | K240 | J52 | S |
| 1-0190 | —(CH$_2$)$_2$— | —O— | K240 | J84 | O |
| 1-0191 | —(CH$_2$)$_2$— | —O— | K240 | J84 | S |
| 1-0192 | —(CH$_2$)$_3$— | —O— | K240 | J3 | O |

TABLE 7

| Compound No. | -A¹- | -A²- | -G¹-A³-A⁴-G² | -A⁵-R² | X |
|---|---|---|---|---|---|
| 1-0193 | —(CH₂)₃— | —O— | K240 | J3 | S |
| 1-0194 | —(CH₂)₃— | —O— | K240 | J9 | O |
| 1-0195 | —(CH₂)₃— | —O— | K240 | J10 | O |
| 1-0196 | —(CH₂)₃— | —O— | K240 | J10 | S |
| 1-0197 | —(CH₂)₃— | —O— | K240 | J22 | O |
| 1-0198 | —(CH₂)₃— | —O— | K240 | J22 | S |
| 1-0199 | —(CH₂)₃— | —O— | K240 | J28 | O |
| 1-0200 | —(CH₂)₃— | —O— | K240 | J28 | S |
| 1-0201 | —(CH₂)₃— | —O— | K240 | J43 | O |
| 1-0202 | —(CH₂)₃— | —O— | K240 | J43 | S |
| 1-0203 | —(CH₂)₃— | —O— | K240 | J84 | O |
| 1-0204 | —(CH₂)₃— | —O— | K240 | J84 | S |
| 1-0205 | —(CH₂)₃— | —O— | K240 | J92 | O |
| 1-0206 | —(CH₂)₃— | —O— | K240 | J92 | S |
| 1-0207 | —(CH₂)₂— | —O— | K1 | J9 | O |
| 1-0208 | —(CH₂)₂— | —O— | K1 | J9 | S |
| 1-0209 | —(CH₂)₂— | —O— | K1 | J77 | O |
| 1-0210 | —(CH₂)₂— | —O— | K2 | J4 | O |
| 1-0211 | —(CH₂)₂— | —O— | K2 | J4 | S |
| 1-0212 | —(CH₂)₂— | —O— | K2 | J6 | O |
| 1-0213 | —(CH₂)₂— | —O— | K2 | J6 | S |
| 1-0214 | —(CH₂)₂— | —O— | K2 | J9 | O |
| 1-0215 | —(CH₂)₂— | —O— | K2 | J9 | S |
| 1-0216 | —(CH₂)₂— | —O— | K2 | J23 | O |
| 1-0217 | —(CH₂)₂— | —O— | K2 | J23 | S |
| 1-0218 | —(CH₂)₂— | —O— | K2 | J41 | O |
| 1-0219 | —(CH₂)₂— | —O— | K2 | J41 | S |
| 1-0220 | —(CH₂)₂— | —O— | K2 | J52 | O |
| 1-0221 | —(CH₂)₂— | —O— | K2 | J52 | S |
| 1-0222 | —(CH₂)₂— | —O— | K2 | J77 | O |
| 1-0223 | —(CH₂)₂— | —O— | K2 | J84 | O |
| 1-0224 | —(CH₂)₂— | —O— | K2 | J84 | S |

TABLE 8

| Compound No. | -A¹- | -A²- | -G¹-A³-A⁴-G² | -A⁵-R² | X |
|---|---|---|---|---|---|
| 1-0225 | —(CH₂)₃— | —O— | K1 | J2 | O |
| 1-0226 | —(CH₂)₃— | —O— | K1 | J4 | O |
| 1-0227 | —(CH₂)₃— | —O— | K1 | J9 | O |
| 1-0228 | —(CH₂)₃— | —O— | K1 | J9 | S |
| 1-0229 | —(CH₂)₃— | —O— | K1 | J77 | O |
| 1-0230 | —(CH₂)₃— | —O— | K1 | J77 | S |
| 1-0231 | —(CH₂)₃— | —O— | K2 | J2 | O |
| 1-0232 | —(CH₂)₃— | —O— | K2 | J4 | O |
| 1-0233 | —(CH₂)₃— | —O— | K2 | J4 | S |
| 1-0234 | —(CH₂)₃— | —O— | K2 | J9 | O |
| 1-0235 | —(CH₂)₃— | —O— | K2 | J9 | S |
| 1-0236 | —(CH₂)₃— | —O— | K2 | J77 | O |
| 1-0237 | —(CH₂)₃— | —O— | K2 | J77 | S |
| 1-0238 | —(CH₂)₃— | —O— | K4 | J2 | O |
| 1-0239 | —(CH₂)₃— | —O— | K4 | J2 | S |
| 1-0240 | —(CH₂)₃— | —O— | K4 | J3 | O |
| 1-0241 | —(CH₂)₃— | —O— | K4 | J3 | S |
| 1-0242 | —(CH₂)₃— | —O— | K4 | J11 | S |
| 1-0243 | —(CH₂)₃— | —O— | K4 | J4 | O |
| 1-0244 | —(CH₂)₃— | —O— | K4 | J4 | S |
| 1-0245 | —(CH₂)₃— | —O— | K4 | J5 | O |
| 1-0246 | —(CH₂)₃— | —O— | K4 | J5 | S |
| 1-0247 | —(CH₂)₃— | —O— | K4 | J9 | O |
| 1-0248 | —(CH₂)₃— | —O— | K4 | J9 | S |
| 1-0249 | —(CH₂)₃— | —O— | K4 | J22 | O |
| 1-0250 | —(CH₂)₃— | —O— | K4 | J22 | S |
| 1-0251 | —(CH₂)₃— | —O— | K4 | J28 | O |
| 1-0252 | —(CH₂)₃— | —O— | K4 | J28 | S |
| 1-0253 | —(CH₂)₃— | —O— | K4 | J77 | O |
| 1-0254 | —(CH₂)₃— | —O— | K4 | J77 | S |
| 1-0255 | —(CH₂)₃— | —O— | K4 | J84 | O |
| 1-0256 | —(CH₂)₃— | —O— | K4 | J84 | S |

TABLE 9

| Compound No. | -A¹- | -A²- | -G¹-A³-A⁴-G² | -A⁵-R² | X |
|---|---|---|---|---|---|
| 1-0257 | —(CH₂)₃— | —O— | K4 | J96 | O |
| 1-0258 | —(CH₂)₃— | —O— | K4 | J96 | S |
| 1-0259 | —(CH₂)₃— | —O— | K4 | J104 | O |
| 1-0260 | —(CH₂)₃— | —O— | K4 | J104 | S |
| 1-0261 | —(CH₂)₃— | —O— | K4 | J117 | O |
| 1-0262 | —(CH₂)₃— | —O— | K4 | J117 | S |
| 1-0263 | —(CH₂)₃— | —S— | K1 | J9 | O |
| 1-0264 | —(CH₂)₃— | —S— | K1 | J9 | S |
| 1-0265 | —(CH₂)₃— | —S— | K1 | J77 | O |
| 1-0266 | —(CH₂)₃— | —S— | K87 | J119 | O |
| 1-0267 | —(CH₂)₃— | —S— | K87 | J119 | S |
| 1-0268 | —(CH₂)₃— | —S— | K87 | J123 | O |
| 1-0269 | —(CH₂)₃— | —S— | K87 | J123 | S |
| 1-0270 | —(CH₂)₃— | —S— | K87 | J125 | O |
| 1-0271 | —(CH₂)₃— | —S— | K87 | J125 | S |
| 1-0272 | —CH₂— | single bond | K530 | J9 | O |
| 1-0273 | —CH₂— | single bond | K530 | J9 | S |
| 1-0274 | —CH₂— | single bond | K6 | J9 | O |
| 1-0275 | —CH₂— | single bond | K6 | J9 | S |
| 1-0276 | —CH₂— | single bond | K8 | J4 | O |
| 1-0277 | —CH₂— | single bond | K8 | J4 | S |
| 1-0278 | —CH₂— | single bond | K8 | J6 | O |
| 1-0279 | —CH₂— | single bond | K8 | J6 | S |
| 1-0280 | —CH₂— | single bond | K8 | J9 | O |
| 1-0281 | —CH₂— | single bond | K8 | J9 | S |
| 1-0282 | —CH₂— | single bond | K8 | J23 | O |
| 1-0283 | —CH₂— | single bond | K8 | J23 | S |
| 1-0284 | —CH₂— | single bond | K8 | J41 | O |
| 1-0285 | —CH₂— | single bond | K8 | J41 | S |
| 1-0286 | —CH₂— | single bond | K8 | J52 | O |
| 1-0287 | —CH₂— | single bond | K8 | J52 | S |
| 1-0288 | —CH₂— | single bond | K8 | J77 | O |

TABLE 10

| Compound No. | -A¹- | -A²- | -G¹-A³-A⁴-G² | -A⁵-R² | X |
|---|---|---|---|---|---|
| 1-0289 | —CH₂— | single bond | K8 | J77 | S |
| 1-0290 | —CH₂— | single bond | K8 | J84 | O |
| 1-0291 | —CH₂— | single bond | K8 | J84 | S |
| 1-0292 | —CH₂— | single bond | K460 | J9 | O |
| 1-0293 | —CH₂— | single bond | K460 | J9 | S |
| 1-0294 | —CH₂— | single bond | K460 | J77 | O |
| 1-0295 | —CH₂— | single bond | K460 | J77 | S |
| 1-0296 | —CH₂— | single bond | K463 | J9 | O |
| 1-0297 | —CH₂— | single bond | K463 | J9 | S |
| 1-0298 | —CH₂— | single bond | K463 | J77 | O |
| 1-0299 | —(CH₂)₂— | single bond | K464 | J9 | O |
| 1-0300 | —CH₂— | single bond | K11 | J1 | O |
| 1-0301 | —CH₂— | single bond | K11 | J1 | S |
| 1-0302 | —CH₂— | single bond | K11 | J2 | O |
| 1-0303 | —CH₂— | single bond | K11 | J3 | O |
| 1-0304 | —CH₂— | single bond | K11 | J3 | S |
| 1-0305 | —CH₂— | single bond | K11 | J4 | O |
| 1-0306 | —CH₂— | single bond | K11 | J5 | O |
| 1-0307 | —CH₂— | single bond | K11 | J9 | O |
| 1-0308 | —CH₂— | single bond | K11 | J9 | S |
| 1-0309 | —CH₂— | single bond | K11 | J77 | O |
| 1-0310 | —CH₂— | single bond | K11 | J77 | S |
| 1-0311 | —(CH₂)₂— | single bond | K11 | J9 | O |
| 1-0312 | —(CH₂)₂— | single bond | K11 | J9 | S |
| 1-0313 | —(CH₂)₂— | single bond | K11 | J77 | O |
| 1-0314 | —(CH₂)₂— | single bond | K11 | J77 | S |
| 1-0315 | —(CH₂)₃— | single bond | K11 | J2 | O |
| 1-0316 | —(CH₂)₃— | single bond | K11 | J2 | S |
| 1-0317 | —(CH₂)₃— | single bond | K11 | J3 | S |
| 1-0318 | —(CH₂)₃— | single bond | K11 | J4 | O |
| 1-0319 | —(CH₂)₃— | single bond | K11 | J5 | S |
| 1-0320 | —(CH₂)₃— | single bond | K11 | J9 | O |

TABLE 11

| Compound No. | -A¹- | -A²- | -G¹-A³-A⁴-G² | -A⁵-R² | X |
|---|---|---|---|---|---|
| 1-0321 | —(CH₂)₃— | single bond | K11 | J9 | S |
| 1-0322 | —(CH₂)₃— | single bond | K11 | J77 | O |
| 1-0323 | —(CH₂)₃— | single bond | K11 | J77 | S |
| 1-0324 | —(CH₂)₃— | single bond | K11 | J3 | O |
| 1-0325 | —(CH₂)₃— | single bond | K11 | J5 | O |
| 1-0326 | —(CH₂)₄— | single bond | K11 | J9 | O |
| 1-0327 | —CH₂— | single bond | K468 | J9 | O |
| 1-0328 | —CH₂— | single bond | K468 | J9 | S |
| 1-0329 | —CH₂— | single bond | K14 | J6 | O |
| 1-0330 | —CH₂— | single bond | K283 | J4 | O |
| 1-0331 | —CH₂— | single bond | K283 | J4 | S |
| 1-0332 | —CH₂— | single bond | K283 | J6 | O |
| 1-0333 | —CH₂— | single bond | K283 | J6 | S |
| 1-0334 | —CH₂— | single bond | K283 | J9 | O |
| 1-0335 | —CH₂— | single bond | K283 | J12 | O |
| 1-0336 | —CH₂— | single bond | K283 | J12 | S |
| 1-0337 | —CH₂— | single bond | K283 | J23 | O |
| 1-0338 | —CH₂— | single bond | K283 | J23 | S |
| 1-0339 | —CH₂— | single bond | K283 | J41 | O |
| 1-0340 | —CH₂— | single bond | K283 | J41 | S |
| 1-0341 | —CH₂— | single bond | K283 | J52 | O |
| 1-0342 | —CH₂— | single bond | K283 | J52 | S |
| 1-0343 | —CH₂— | single bond | K283 | J84 | O |
| 1-0344 | —CH₂— | single bond | K283 | J84 | S |
| 1-0345 | —CH₂— | single bond | K24 | J9 | O |
| 1-0346 | —(CH₂)₂— | single bond | K283 | J9 | O |
| 1-0347 | —(CH₂)₂— | single bond | K14 | J3 | O |
| 1-0348 | —(CH₂)₂— | single bond | K14 | J3 | S |
| 1-0349 | —(CH₂)₂— | single bond | K14 | J9 | O |
| 1-0350 | —(CH₂)₂— | single bond | K14 | J10 | O |
| 1-0351 | —(CH₂)₂— | single bond | K14 | J10 | S |
| 1-0352 | —(CH₂)₂— | single bond | K14 | J22 | O |

TABLE 12

| Compound No. | -A¹- | -A²- | -G¹-A³-A⁴-G² | -A⁵-R² | X |
|---|---|---|---|---|---|
| 1-0353 | —(CH₂)₂— | single bond | K14 | J22 | S |
| 1-0354 | —(CH₂)₂— | single bond | K14 | J28 | O |
| 1-0355 | —(CH₂)₂— | single bond | K14 | J28 | S |
| 1-0356 | —(CH₂)₂— | single bond | K14 | J43 | O |
| 1-0357 | —(CH₂)₂— | single bond | K14 | J43 | S |
| 1-0358 | —(CH₂)₂— | single bond | K14 | J84 | O |
| 1-0359 | —(CH₂)₂— | single bond | K14 | J84 | S |
| 1-0360 | —(CH₂)₂— | single bond | K14 | J92 | O |
| 1-0361 | —(CH₂)₂— | single bond | K14 | J92 | S |
| 1-0362 | —(CH₂)₂— | single bond | K24 | J9 | O |
| 1-0363 | —(CH₂)₂— | single bond | K478 | J119 | O |
| 1-0364 | —(CH₂)₂— | single bond | K478 | J119 | S |
| 1-0365 | —(CH₂)₂— | single bond | K478 | J123 | O |
| 1-0366 | —(CH₂)₂— | single bond | K478 | J123 | S |
| 1-0367 | —(CH₂)₂— | single bond | K478 | J125 | O |
| 1-0368 | —(CH₂)₂— | single bond | K478 | J125 | S |
| 1-0369 | —(CH₂)₂— | —O— | K11 | J2 | O |
| 1-0370 | —(CH₂)₂— | —O— | K11 | J4 | O |
| 1-0371 | —(CH₂)₂— | —O— | K11 | J9 | O |
| 1-0372 | —(CH₂)₂— | —O— | K11 | J9 | S |
| 1-0373 | —(CH₂)₂— | —O— | K37 | J96 | O |
| 1-0374 | —(CH₂)₂— | —O— | K37 | J96 | S |
| 1-0375 | —(CH₂)₂— | —O— | K37 | J104 | O |
| 1-0376 | —(CH₂)₂— | —O— | K37 | J104 | S |
| 1-0377 | —(CH₂)₂— | —O— | K37 | J117 | O |
| 1-0378 | —(CH₂)₂— | —O— | K37 | J117 | S |
| 1-0379 | —(CH₂)₃— | —O— | K477 | J3 | O |
| 1-0380 | —(CH₂)₃— | —O— | K477 | J3 | S |
| 1-0381 | —(CH₂)₃— | —O— | K477 | J10 | O |
| 1-0382 | —(CH₂)₃— | —O— | K477 | J10 | S |
| 1-0383 | —(CH₂)₃— | —O— | K477 | J22 | O |
| 1-0384 | —(CH₂)₃— | —O— | K477 | J22 | S |

TABLE 13

| Compound No. | -A¹- | -A²- | -G¹-A³-A⁴-G² | -A⁵-R² | X |
|---|---|---|---|---|---|
| 1-0385 | —(CH₂)₃— | —O— | K477 | J28 | O |
| 1-0386 | —(CH₂)₃— | —O— | K477 | J28 | S |
| 1-0387 | —(CH₂)₃— | —O— | K477 | J43 | O |
| 1-0388 | —(CH₂)₃— | —O— | K477 | J43 | S |
| 1-0389 | —(CH₂)₃— | —O— | K477 | J84 | O |
| 1-0390 | —(CH₂)₃— | —O— | K477 | J84 | S |
| 1-0391 | —(CH₂)₃— | —O— | K477 | J92 | O |
| 1-0392 | —(CH₂)₃— | —O— | K477 | J92 | S |
| 1-0393 | —CH₂— | single bond | K60 | J9 | O |
| 1-0394 | —CH₂— | single bond | K60 | J9 | S |
| 1-0395 | —CH₂— | single bond | K60 | J77 | O |
| 1-0396 | —CH₂— | single bond | K60 | J77 | S |
| 1-0397 | —CH₂— | single bond | K62 | J9 | O |
| 1-0398 | —CH₂— | single bond | K62 | J77 | O |
| 1-0399 | —CH₂— | single bond | K499 | J9 | O |
| 1-0400 | —CH₂— | single bond | K499 | J77 | O |
| 1-0401 | —CH₂— | single bond | K510 | J3 | O |
| 1-0402 | —CH₂— | single bond | K510 | J3 | S |
| 1-0403 | —CH₂— | single bond | K510 | J10 | O |
| 1-0404 | —CH₂— | single bond | K510 | J10 | S |
| 1-0405 | —CH₂— | single bond | K510 | J22 | O |
| 1-0406 | —CH₂— | single bond | K510 | J22 | S |
| 1-0407 | —CH₂— | single bond | K510 | J28 | O |
| 1-0408 | —CH₂— | single bond | K510 | J28 | S |
| 1-0409 | —CH₂— | single bond | K510 | J43 | O |
| 1-0410 | —CH₂— | single bond | K510 | J43 | S |
| 1-0411 | —CH₂— | single bond | K510 | J84 | O |
| 1-0412 | —CH₂— | single bond | K510 | J84 | S |
| 1-0413 | —CH₂— | single bond | K510 | J92 | O |
| 1-0414 | —CH₂— | single bond | K510 | J92 | S |
| 1-0415 | —(CH₂)₂— | single bond | K62 | J9 | O |
| 1-0416 | —(CH₂)₂— | single bond | K62 | J9 | S |

TABLE 14

| Compound No. | -A¹- | -A²- | -G¹-A³-A⁴-G² | -A⁵-R² | X |
|---|---|---|---|---|---|
| 1-0417 | —(CH₂)₂— | single bond | K62 | J77 | O |
| 1-0418 | —(CH₂)₂— | single bond | K525 | J4 | O |
| 1-0419 | —(CH₂)₂— | single bond | K525 | J4 | S |
| 1-0420 | —(CH₂)₂— | single bond | K525 | J6 | O |
| 1-0421 | —(CH₂)₂— | single bond | K525 | J6 | S |
| 1-0422 | —(CH₂)₂— | single bond | K525 | J12 | O |
| 1-0423 | —(CH₂)₂— | single bond | K525 | J12 | S |
| 1-0424 | —(CH₂)₂— | single bond | K525 | J23 | O |
| 1-0425 | —(CH₂)₂— | single bond | K525 | J23 | S |
| 1-0426 | —(CH₂)₂— | single bond | K525 | J41 | O |
| 1-0427 | —(CH₂)₂— | single bond | K525 | J41 | S |
| 1-0428 | —(CH₂)₂— | single bond | K525 | J52 | O |
| 1-0429 | —(CH₂)₂— | single bond | K525 | J52 | S |
| 1-0430 | —(CH₂)₂— | single bond | K525 | J84 | O |
| 1-0431 | —(CH₂)₂— | single bond | K525 | J84 | S |
| 1-0432 | —(CH₂)₄— | single bond | K528 | J119 | O |
| 1-0433 | —(CH₂)₄— | single bond | K528 | J119 | S |
| 1-0434 | —(CH₂)₄— | single bond | K528 | J123 | O |
| 1-0435 | —(CH₂)₄— | single bond | K528 | J123 | S |
| 1-0436 | —(CH₂)₄— | single bond | K528 | J125 | O |
| 1-0437 | —(CH₂)₄— | single bond | K528 | J125 | S |
| 1-0438 | —CH₂— | single bond | K529 | J9 | O |
| 1-0439 | —(CH₂)₂— | —NH— | K240 | J1 | S |
| 1-0440 | —(CH₂)₂— | —NH— | K240 | J3 | S |
| 1-0441 | —(CH₂)₂— | —NH— | K240 | J9 | S |
| 1-0442 | —(CH₂)₂— | —NH— | K240 | J10 | S |
| 1-0443 | —(CH₂)₂— | —NH— | K240 | J14 | S |
| 1-0444 | —(CH₂)₂— | —NH— | K240 | J19 | S |
| 1-0445 | —(CH₂)₂— | —NH— | K240 | J22 | S |
| 1-0446 | —(CH₂)₂— | —NH— | K240 | J25 | S |
| 1-0447 | —(CH₂)₂— | —NH— | K240 | J29 | S |
| 1-0448 | —(CH₂)₂— | —NH— | K240 | J57 | S |

TABLE 15

| Compound No. | -A¹- | -A²- | -G¹-A³-A⁴-G² | -A⁵-R² | X |
|---|---|---|---|---|---|
| 1-0449 | —(CH$_2$)$_2$— | —NH— | K240 | J59 | S |
| 1-0450 | —(CH$_2$)$_2$— | —NH— | K240 | J70 | S |
| 1-0451 | —(CH$_2$)$_2$— | —NH— | K240 | J72 | S |
| 1-0452 | —(CH$_2$)$_2$— | —NH— | K240 | J74 | S |
| 1-0453 | —(CH$_2$)$_2$— | —NH— | K240 | J75 | S |
| 1-0454 | —(CH$_2$)$_2$— | —NH— | K240 | J77 | S |
| 1-0455 | —(CH$_2$)$_2$— | —NH— | K240 | J78 | S |
| 1-0456 | —(CH$_2$)$_2$— | —NH— | K240 | J126 | S |
| 1-0457 | —(CH$_2$)$_2$— | —NH— | K240 | J129 | S |
| 1-0458 | —(CH$_2$)$_2$— | —NH— | K240 | J130 | S |
| 1-0459 | —(CH$_2$)$_2$— | —NH— | K240 | J138 | S |
| 1-0460 | —(CH$_2$)$_2$— | —NH— | K240 | J140 | S |
| 1-0461 | —(CH$_2$)$_2$— | —NH— | K240 | J151 | S |
| 1-0462 | —(CH$_2$)$_2$— | —NH— | K240 | J165 | S |
| 1-0463 | —(CH$_2$)$_2$— | —NH— | K240 | J168 | S |
| 1-0464 | —(CH$_2$)$_2$— | —NH— | K240 | J174 | S |
| 1-0465 | —(CH$_2$)$_2$— | —NH— | K240 | J176 | S |
| 1-0466 | —(CH$_2$)$_2$— | —NH— | K240 | J177 | S |
| 1-0467 | —(CH$_2$)$_2$— | —NH— | K240 | J178 | S |
| 1-0468 | —(CH$_2$)$_2$— | —NH— | K240 | J185 | S |
| 1-0469 | —(CH$_2$)$_2$— | —NH— | K240 | J191 | S |
| 1-0470 | —(CH$_2$)$_2$— | —NH— | K240 | J193 | S |
| 1-0471 | —(CH$_2$)$_2$— | —NH— | K240 | J195 | S |
| 1-0472 | —(CH$_2$)$_2$— | —NH— | K240 | J197 | S |
| 1-0473 | —(CH$_2$)$_2$— | —O— | K2 | J19 | S |
| 1-0474 | —(CH$_2$)$_2$— | —O— | K2 | J70 | S |
| 1-0475 | —(CH$_2$)$_2$— | —O— | K2 | J78 | S |
| 1-0476 | —(CH$_2$)$_2$— | —O— | K2 | J126 | S |
| 1-0477 | —(CH$_2$)$_2$— | —O— | K2 | J129 | S |
| 1-0478 | —(CH$_2$)$_2$— | —O— | K2 | J130 | S |
| 1-0479 | —(CH$_2$)$_2$— | —O— | K2 | J138 | S |
| 1-0480 | —(CH$_2$)$_2$— | —O— | K2 | J185 | S |

TABLE 16

| Compound No. | -A¹- | -A²- | -G¹-A³-A⁴-G² | -A⁵-R² | X |
|---|---|---|---|---|---|
| 1-0481 | —(CH$_2$)$_2$— | —O— | K4 | J9 | S |
| 1-0482 | —(CH$_2$)$_2$— | —O— | K4 | J126 | S |
| 1-0483 | —(CH$_2$)$_2$— | —O— | K4 | J129 | S |
| 1-0484 | —(CH$_2$)$_2$— | —O— | K4 | J130 | S |
| 1-0485 | —(CH$_2$)$_2$— | —O— | K4 | J138 | S |
| 1-0486 | —(CH$_2$)$_2$— | —O— | K4 | J140 | S |
| 1-0487 | —(CH$_2$)$_2$— | —O— | K240 | J9 | S |
| 1-0488 | —(CH$_2$)$_2$— | —O— | K240 | J70 | S |
| 1-0489 | —(CH$_2$)$_2$— | —O— | K240 | J78 | S |
| 1-0490 | —(CH$_2$)$_2$— | —O— | K240 | J130 | S |
| 1-0491 | —(CH$_2$)$_2$— | —O— | K240 | J138 | S |
| 1-0492 | —(CH$_2$)$_2$— | —O— | K240 | J185 | S |
| 1-0493 | —(CH$_2$)$_2$— | single bond | K603 | J9 | S |
| 1-0494 | —(CH$_2$)$_2$— | single bond | K603 | J140 | S |
| 1-0495 | —(CH$_2$)$_2$— | single bond | K604 | J9 | S |
| 1-0496 | —(CH$_2$)$_2$— | single bond | K604 | J126 | S |
| 1-0497 | —(CH$_2$)$_2$— | single bond | K605 | J9 | S |
| 1-0498 | —(CH$_2$)$_2$— | single bond | K605 | J129 | S |
| 1-0499 | —(CH$_2$)$_2$— | single bond | K615 | J9 | S |
| 1-0500 | —(CH$_2$)$_2$— | single bond | K615 | J130 | S |
| 1-0501 | —(CH$_2$)$_2$— | single bond | K616 | J9 | S |
| 1-0502 | —(CH$_2$)$_2$— | single bond | K616 | J138 | S |
| 1-0503 | —(CH$_2$)$_3$— | —NH— | K240 | J9 | S |
| 1-0504 | —(CH$_2$)$_3$— | —NH— | K240 | J126 | S |
| 1-0505 | —(CH$_2$)$_3$— | —NH— | K240 | J129 | S |
| 1-0506 | —(CH$_2$)$_3$— | —NH— | K240 | J130 | S |
| 1-0507 | —(CH$_2$)$_3$— | —NH— | K240 | J138 | S |
| 1-0508 | —(CH$_2$)$_3$— | —NH— | K240 | J140 | S |
| 1-0509 | —(CH$_2$)$_3$— | —O— | K1 | J22 | S |
| 1-0510 | —(CH$_2$)$_3$— | —O— | K2 | J22 | S |
| 1-0511 | —(CH$_2$)$_3$— | —O— | K4 | J1 | S |
| 1-0512 | —(CH$_2$)$_3$— | —O— | K4 | J10 | S |

TABLE 17

| Compound No. | -A¹- | -A²- | -G¹-A³-A⁴-G² | -A⁵-R² | X |
|---|---|---|---|---|---|
| 1-0513 | —(CH$_2$)$_3$— | —O— | K4 | J10 | O |
| 1-0514 | —(CH$_2$)$_3$— | —O— | K4 | J19 | S |
| 1-0515 | —(CH$_2$)$_3$— | —O— | K4 | J57 | S |
| 1-0516 | —(CH$_2$)$_3$— | —O— | K4 | J70 | S |
| 1-0517 | —(CH$_2$)$_3$— | —O— | K4 | J71 | S |
| 1-0518 | —(CH$_2$)$_3$— | —O— | K4 | J78 | S |
| 1-0519 | —(CH$_2$)$_3$— | —O— | K4 | J126 | S |
| 1-0520 | —(CH$_2$)$_3$— | —O— | K4 | J126 | O |
| 1-0521 | —(CH$_2$)$_3$— | —O— | K4 | J129 | S |
| 1-0522 | —(CH$_2$)$_3$— | —O— | K4 | J129 | O |
| 1-0523 | —(CH$_2$)$_3$— | —O— | K4 | J130 | S |
| 1-0524 | —(CH$_2$)$_3$— | —O— | K4 | J134 | S |
| 1-0525 | —(CH$_2$)$_3$— | —O— | K4 | J138 | S |
| 1-0526 | —(CH$_2$)$_3$— | —O— | K4 | J140 | S |
| 1-0527 | —(CH$_2$)$_3$— | —O— | K4 | J178 | S |
| 1-0528 | —(CH$_2$)$_3$— | —O— | K4 | J178 | S |
| 1-0529 | —(CH$_2$)$_3$— | —O— | K4 | J185 | S |
| 1-0530 | —(CH$_2$)$_3$— | —O— | K4 | J186 | S |
| 1-0531 | —(CH$_2$)$_3$— | —O— | K4 | J187 | S |
| 1-0532 | —(CH$_2$)$_3$— | —O— | K4 | J189 | S |
| 1-0533 | —(CH$_2$)$_3$— | —O— | K4 | J190 | S |
| 1-0534 | —(CH$_2$)$_3$— | —O— | K4 | J191 | S |
| 1-0535 | —(CH$_2$)$_3$— | —O— | K4 | J192 | S |
| 1-0536 | —(CH$_2$)$_3$— | —O— | K4 | J193 | S |
| 1-0537 | —(CH$_2$)$_3$— | —O— | K11 | J9 | S |
| 1-0538 | —(CH$_2$)$_3$— | —O— | K11 | J126 | S |
| 1-0539 | —(CH$_2$)$_3$— | —O— | K11 | J129 | S |
| 1-0540 | —(CH$_2$)$_3$— | —O— | K11 | J130 | S |
| 1-0541 | —(CH$_2$)$_3$— | —O— | K11 | J138 | S |
| 1-0542 | —(CH$_2$)$_3$— | —O— | K11 | J140 | S |
| 1-0543 | —(CH$_2$)$_3$— | —O— | K34 | J9 | S |
| 1-0544 | —(CH$_2$)$_3$— | —O— | K34 | J126 | S |

TABLE 18

| Compound No. | -A¹- | -A²- | -G¹-A³-A⁴-G² | -A⁵-R² | X |
|---|---|---|---|---|---|
| 1-0545 | —(CH$_2$)$_3$— | —O— | K34 | J129 | S |
| 1-0546 | —(CH$_2$)$_3$— | —O— | K34 | J130 | S |
| 1-0547 | —(CH$_2$)$_3$— | —O— | K34 | J138 | S |
| 1-0548 | —(CH$_2$)$_3$— | —O— | K34 | J140 | S |
| 1-0549 | —(CH$_2$)$_3$— | —O— | K49 | J9 | S |
| 1-0550 | —(CH$_2$)$_3$— | —O— | K49 | J126 | S |
| 1-0551 | —(CH$_2$)$_3$— | —O— | K49 | J129 | S |
| 1-0552 | —(CH$_2$)$_3$— | —O— | K49 | J130 | S |
| 1-0553 | —(CH$_2$)$_3$— | —O— | K49 | J138 | S |
| 1-0554 | —(CH$_2$)$_3$— | —O— | K49 | J140 | S |
| 1-0555 | —(CH$_2$)$_3$— | —O— | K103 | J9 | S |
| 1-0556 | —(CH$_2$)$_3$— | —O— | K103 | J126 | S |
| 1-0557 | —(CH$_2$)$_3$— | —O— | K103 | J129 | S |
| 1-0558 | —(CH$_2$)$_3$— | —O— | K103 | J130 | S |
| 1-0559 | —(CH$_2$)$_3$— | —O— | K103 | J138 | S |
| 1-0560 | —(CH$_2$)$_3$— | —O— | K103 | J140 | S |
| 1-0561 | —(CH$_2$)$_3$— | —O— | K240 | J9 | S |
| 1-0562 | —(CH$_2$)$_3$— | —O— | K240 | J70 | S |
| 1-0563 | —(CH$_2$)$_3$— | —O— | K240 | J78 | S |
| 1-0564 | —(CH$_2$)$_3$— | —O— | K240 | J130 | S |
| 1-0565 | —(CH$_2$)$_3$— | —O— | K240 | J138 | S |
| 1-0566 | —(CH$_2$)$_3$— | —O— | K240 | J185 | S |
| 1-0567 | —(CH$_2$)$_3$— | —O— | K723 | J9 | S |
| 1-0568 | —(CH$_2$)$_3$— | —O— | K723 | J126 | S |
| 1-0569 | —(CH$_2$)$_3$— | —O— | K723 | J129 | S |
| 1-0570 | —(CH$_2$)$_3$— | —O— | K723 | J130 | S |
| 1-0571 | —(CH$_2$)$_3$— | —O— | K723 | J138 | S |
| 1-0572 | —(CH$_2$)$_3$— | —O— | K723 | J140 | S |
| 1-0573 | —(CH$_2$)$_3$— | —O— | K725 | J9 | S |
| 1-0574 | —(CH$_2$)$_3$— | —O— | K725 | J126 | S |
| 1-0575 | —(CH$_2$)$_3$— | —O— | K725 | J129 | S |
| 1-0576 | —(CH$_2$)$_3$— | —O— | K725 | J130 | S |

TABLE 19

| Compound No. | -A¹- | -A²- | -G¹-A³-A⁴-G² | -A⁵-R² | X |
|---|---|---|---|---|---|
| 1-0577 | —(CH$_2$)$_3$— | —O— | K725 | J138 | S |
| 1-0578 | —(CH$_2$)$_3$— | —O— | K725 | J140 | S |
| 1-0579 | —(CH$_2$)$_3$— | —O— | K99 | J9 | S |
| 1-0580 | —(CH$_2$)$_3$— | —O— | K99 | J126 | S |
| 1-0581 | —(CH$_2$)$_3$— | —O— | K99 | J129 | S |
| 1-0582 | —(CH$_2$)$_3$— | —O— | K99 | J130 | S |
| 1-0583 | —(CH$_2$)$_3$— | —O— | K99 | J138 | S |
| 1-0584 | —(CH$_2$)$_3$— | —O— | K99 | J140 | S |
| 1-0585 | —(CH$_2$)$_3$— | single bond | K603 | J9 | S |
| 1-0586 | —(CH$_2$)$_3$— | single bond | K604 | J9 | S |
| 1-0587 | —(CH$_2$)$_3$— | single bond | K605 | J9 | S |
| 1-0588 | —(CH$_2$)$_3$— | single bond | K606 | J9 | S |
| 1-0589 | single bond | single bond | K1 | J1 | S |
| 1-0590 | single bond | single bond | K1 | J3 | S |
| 1-0591 | single bond | single bond | K1 | J6 | S |
| 1-0592 | single bond | single bond | K1 | J9 | S |
| 1-0593 | single bond | single bond | K1 | J10 | S |
| 1-0594 | single bond | single bond | K1 | J14 | S |
| 1-0595 | single bond | single bond | K1 | J19 | S |
| 1-0596 | single bond | single bond | K1 | J22 | S |
| 1-0597 | single bond | single bond | K1 | J25 | S |
| 1-0598 | single bond | single bond | K1 | J29 | S |
| 1-0599 | single bond | single bond | K1 | J57 | S |
| 1-0600 | single bond | single bond | K1 | J59 | S |
| 1-0601 | single bond | single bond | K1 | J70 | S |
| 1-0602 | single bond | single bond | K1 | J71 | S |
| 1-0603 | single bond | single bond | K1 | J72 | S |
| 1-0604 | single bond | single bond | K1 | J74 | S |
| 1-0605 | single bond | single bond | K1 | J75 | S |
| 1-0606 | single bond | single bond | K1 | J77 | S |
| 1-0607 | single bond | single bond | K1 | J78 | S |
| 1-0608 | single bond | single bond | K1 | J105 | S |

TABLE 20

| Compound No. | -A¹- | -A²- | -G¹-A³-A⁴-G² | -A⁵-R² | X |
|---|---|---|---|---|---|
| 1-0609 | single bond | single bond | K1 | J126 | S |
| 1-0610 | single bond | single bond | K1 | J129 | S |
| 1-0611 | single bond | single bond | K1 | J130 | S |
| 1-0612 | single bond | single bond | K1 | J134 | S |
| 1-0613 | single bond | single bond | K1 | J138 | S |
| 1-0614 | single bond | single bond | K1 | J140 | S |
| 1-0615 | single bond | single bond | K1 | J151 | S |
| 1-0616 | single bond | single bond | K1 | J165 | S |
| 1-0617 | single bond | single bond | K1 | J168 | S |
| 1-0618 | single bond | single bond | K1 | J174 | S |
| 1-0619 | single bond | single bond | K1 | J176 | S |
| 1-0620 | single bond | single bond | K1 | J177 | S |
| 1-0621 | single bond | single bond | K1 | J178 | S |
| 1-0622 | single bond | single bond | K1 | J185 | S |
| 1-0623 | single bond | single bond | K1 | J191 | S |
| 1-0624 | single bond | single bond | K1 | J194 | S |
| 1-0625 | single bond | single bond | K1 | J195 | S |
| 1-0626 | single bond | single bond | K1 | J197 | S |
| 1-0627 | single bond | single bond | K2 | J9 | S |
| 1-0628 | single bond | single bond | K2 | J10 | S |
| 1-0629 | single bond | single bond | K2 | J14 | S |
| 1-0630 | single bond | single bond | K2 | J19 | S |
| 1-0631 | single bond | single bond | K2 | J22 | S |
| 1-0632 | single bond | single bond | K2 | J57 | S |
| 1-0633 | single bond | single bond | K2 | J59 | S |
| 1-0634 | single bond | single bond | K2 | J70 | S |
| 1-0635 | single bond | single bond | K2 | J72 | S |
| 1-0636 | single bond | single bond | K2 | J74 | S |
| 1-0637 | single bond | single bond | K2 | J75 | S |
| 1-0638 | single bond | single bond | K2 | J77 | S |
| 1-0639 | single bond | single bond | K2 | J78 | S |
| 1-0640 | single bond | single bond | K2 | J126 | S |

TABLE 21

| Compound No. | -A¹- | -A²- | -G¹-A³-A⁴-G² | -A⁵-R² | X |
|---|---|---|---|---|---|
| 1-0641 | single bond | single bond | K2 | J129 | S |
| 1-0642 | single bond | single bond | K2 | J130 | S |
| 1-0643 | single bond | single bond | K2 | J138 | S |
| 1-0644 | single bond | single bond | K2 | J140 | S |
| 1-0645 | single bond | single bond | K2 | J151 | S |
| 1-0646 | single bond | single bond | K2 | J174 | S |
| 1-0647 | single bond | single bond | K2 | J176 | S |
| 1-0648 | single bond | single bond | K2 | J177 | S |
| 1-0649 | single bond | single bond | K2 | J178 | S |
| 1-0650 | single bond | single bond | K2 | J185 | S |
| 1-0651 | single bond | single bond | K2 | J191 | S |
| 1-0652 | single bond | single bond | K2 | J194 | S |
| 1-0653 | single bond | single bond | K2 | J195 | S |
| 1-0654 | single bond | single bond | K2 | J197 | S |
| 1-0655 | single bond | single bond | K3 | J9 | S |
| 1-0656 | single bond | single bond | K3 | J70 | S |
| 1-0657 | single bond | single bond | K3 | J78 | S |
| 1-0658 | single bond | single bond | K3 | J130 | S |
| 1-0659 | single bond | single bond | K3 | J138 | S |
| 1-0660 | single bond | single bond | K3 | J185 | S |
| 1-0661 | single bond | single bond | K4 | J9 | S |
| 1-0662 | single bond | single bond | K4 | J70 | S |
| 1-0663 | single bond | single bond | K4 | J78 | S |
| 1-0664 | single bond | single bond | K4 | J130 | S |
| 1-0665 | single bond | single bond | K4 | J138 | S |
| 1-0666 | single bond | single bond | K4 | J185 | S |
| 1-0667 | single bond | single bond | K99 | J22 | S |
| 1-0668 | single bond | single bond | K103 | J22 | S |
| 1-0669 | single bond | single bond | K240 | J1 | S |
| 1-0670 | single bond | single bond | K240 | J6 | S |
| 1-0671 | single bond | single bond | K240 | J12 | S |
| 1-0672 | single bond | single bond | K240 | J13 | S |

TABLE 22

| Compound No. | -A¹- | -A²- | -G¹-A³-A⁴-G² | -A⁵-R² | X |
|---|---|---|---|---|---|
| 1-0673 | single bond | single bond | K240 | J15 | S |
| 1-0674 | single bond | single bond | K240 | J17 | S |
| 1-0675 | single bond | single bond | K240 | J18 | S |
| 1-0676 | single bond | single bond | K240 | J19 | S |
| 1-0677 | —(CH$_2$)$_3$— | single bond | K240 | J19 | S |
| 1-0678 | single bond | single bond | K240 | J20 | S |
| 1-0679 | single bond | single bond | K240 | J21 | S |
| 1-0680 | single bond | single bond | K240 | J27 | S |
| 1-0681 | single bond | single bond | K240 | J30 | S |
| 1-0682 | single bond | single bond | K240 | J31 | S |
| 1-0683 | single bond | single bond | K240 | J32 | S |
| 1-0684 | single bond | single bond | K240 | J33 | S |
| 1-0685 | single bond | single bond | K240 | J36 | S |
| 1-0686 | single bond | single bond | K240 | J39 | S |
| 1-0687 | single bond | single bond | K240 | J41 | S |
| 1-0688 | single bond | single bond | K240 | J42 | S |
| 1-0689 | single bond | single bond | K240 | J44 | S |
| 1-0690 | single bond | single bond | K240 | J45 | S |
| 1-0691 | single bond | single bond | K240 | J46 | S |
| 1-0692 | single bond | single bond | K240 | J48 | S |
| 1-0693 | single bond | single bond | K240 | J49 | S |
| 1-0694 | single bond | single bond | K240 | J50 | S |
| 1-0695 | single bond | single bond | K240 | J51 | S |
| 1-0696 | single bond | single bond | K240 | J52 | S |
| 1-0697 | single bond | single bond | K240 | J55 | S |
| 1-0698 | single bond | single bond | K240 | J57 | S |
| 1-0699 | single bond | single bond | K240 | J58 | S |
| 1-0700 | single bond | single bond | K240 | J59 | S |
| 1-0701 | single bond | single bond | K240 | J61 | S |
| 1-0702 | single bond | single bond | K240 | J62 | S |
| 1-0703 | single bond | single bond | K240 | J64 | S |
| 1-0704 | single bond | single bond | K240 | J66 | S |

TABLE 23

| Compound No. | -A¹- | -A²- | -G¹-A³-A⁴-G² | -A⁵-R² | X |
|---|---|---|---|---|---|
| 1-0705 | single bond | single bond | K240 | J67 | S |
| 1-0706 | single bond | single bond | K240 | J68 | S |
| 1-0707 | single bond | single bond | K240 | J69 | S |
| 1-0708 | single bond | single bond | K240 | J71 | S |
| 1-0709 | single bond | single bond | K240 | J72 | S |
| 1-0710 | single bond | single bond | K240 | J74 | S |
| 1-0711 | —(CH₂)₃— | single bond | K240 | J74 | S |
| 1-0712 | single bond | single bond | K240 | J75 | S |
| 1-0713 | single bond | single bond | K240 | J77 | S |
| 1-0714 | single bond | single bond | K240 | J78 | S |
| 1-0715 | single bond | single bond | K240 | J90 | S |
| 1-0716 | single bond | single bond | K240 | J126 | S |
| 1-0717 | single bond | single bond | K240 | J129 | S |
| 1-0718 | single bond | single bond | K240 | J130 | S |
| 1-0719 | single bond | single bond | K240 | J138 | S |
| 1-0720 | single bond | single bond | K240 | J140 | S |
| 1-0721 | single bond | single bond | K240 | J143 | S |
| 1-0722 | single bond | single bond | K240 | J145 | S |
| 1-0723 | single bond | single bond | K240 | J146 | S |
| 1-0724 | single bond | single bond | K240 | J147 | S |
| 1-0725 | single bond | single bond | K240 | J148 | S |
| 1-0726 | single bond | single bond | K240 | J149 | S |
| 1-0727 | single bond | single bond | K240 | J150 | S |
| 1-0728 | single bond | single bond | K240 | J151 | S |
| 1-0729 | single bond | single bond | K240 | J153 | S |
| 1-0730 | single bond | single bond | K240 | J154 | S |
| 1-0731 | single bond | single bond | K240 | J155 | S |
| 1-0732 | single bond | single bond | K240 | J156 | S |
| 1-0733 | single bond | single bond | K240 | J157 | S |
| 1-0734 | single bond | single bond | K240 | J158 | S |
| 1-0735 | single bond | single bond | K240 | J159 | S |
| 1-0736 | single bond | single bond | K240 | J163 | S |

TABLE 24

| Compound No. | -A¹- | -A²- | -G¹-A³-A⁴-G² | -A⁵-R² | X |
|---|---|---|---|---|---|
| 1-0737 | single bond | single bond | K240 | J165 | S |
| 1-0738 | single bond | single bond | K240 | J168 | S |
| 1-0739 | single bond | single bond | K240 | J169 | S |
| 1-0740 | single bond | single bond | K240 | J170 | S |
| 1-0741 | single bond | single bond | K240 | J171 | S |
| 1-0742 | single bond | single bond | K240 | J172 | S |
| 1-0743 | single bond | single bond | K240 | J173 | S |
| 1-0744 | single bond | single bond | K240 | J174 | S |
| 1-0745 | single bond | single bond | K240 | J176 | S |
| 1-0746 | single bond | single bond | K240 | J177 | S |
| 1-0747 | single bond | single bond | K240 | J178 | S |
| 1-0748 | single bond | single bond | K240 | J179 | S |
| 1-0749 | single bond | single bond | K240 | J180 | S |
| 1-0750 | single bond | single bond | K240 | J181 | S |
| 1-0751 | single bond | single bond | K240 | J182 | S |
| 1-0752 | single bond | single bond | K240 | J183 | S |
| 1-0753 | single bond | single bond | K240 | J184 | S |
| 1-0754 | single bond | single bond | K240 | J185 | S |
| 1-0755 | single bond | single bond | K240 | J191 | S |
| 1-0756 | single bond | single bond | K240 | J194 | S |
| 1-0757 | single bond | single bond | K240 | J195 | S |
| 1-0758 | single bond | single bond | K240 | J197 | S |
| 1-0759 | single bond | single bond | K281 | J9 | S |
| 1-0760 | single bond | single bond | K660 | J3 | S |
| 1-0761 | —CH₂— | single bond | K11 | J126 | S |
| 1-0762 | —CH₂— | single bond | K11 | J129 | S |
| 1-0763 | —CH₂— | single bond | K11 | J130 | S |
| 1-0764 | —CH₂— | single bond | K11 | J138 | S |
| 1-0765 | —CH₂— | single bond | K11 | J140 | S |
| 1-0766 | —(CH₂)₂— | single bond | K11 | J126 | S |
| 1-0767 | —(CH₂)₂— | single bond | K11 | J129 | S |
| 1-0768 | —(CH₂)₂— | single bond | K11 | J130 | S |

TABLE 25

| Compound No. | -A¹- | -A²- | -G¹-A³-A⁴-G² | -A⁵-R² | X |
|---|---|---|---|---|---|
| 1-0769 | —(CH₂)₂— | single bond | K11 | J138 | S |
| 1-0770 | —(CH₂)₂— | single bond | K11 | J140 | S |
| 1-0771 | —(CH₂)₃— | single bond | K11 | J126 | S |
| 1-0772 | —(CH₂)₃— | single bond | K11 | J129 | S |
| 1-0773 | —(CH₂)₃— | single bond | K11 | J130 | S |
| 1-0774 | —(CH₂)₃— | single bond | K11 | J138 | S |
| 1-0775 | —(CH₂)₃— | single bond | K11 | J140 | S |
| 1-0776 | —(CH₂)₂— | —NH— | K240 | J1 | O |
| 1-0777 | —(CH₂)₂— | —NH— | K240 | J3 | O |
| 1-0778 | —(CH₂)₂— | —NH— | K240 | J10 | O |
| 1-0779 | —(CH₂)₂— | —NH— | K240 | J14 | O |
| 1-0780 | —(CH₂)₂— | —NH— | K240 | J19 | O |
| 1-0781 | —(CH₂)₂— | —NH— | K240 | J22 | O |
| 1-0782 | —(CH₂)₂— | —NH— | K240 | J25 | O |
| 1-0783 | —(CH₂)₂— | —NH— | K240 | J29 | O |
| 1-0784 | —(CH₂)₂— | —NH— | K240 | J57 | O |
| 1-0785 | —(CH₂)₂— | —NH— | K240 | J59 | O |
| 1-0786 | —(CH₂)₂— | —NH— | K240 | J70 | O |
| 1-0787 | —(CH₂)₂— | —NH— | K240 | J72 | O |
| 1-0788 | —(CH₂)₂— | —NH— | K240 | J74 | O |
| 1-0789 | —(CH₂)₂— | —NH— | K240 | J75 | O |
| 1-0790 | —(CH₂)₂— | —NH— | K240 | J77 | O |
| 1-0791 | —(CH₂)₂— | —NH— | K240 | J78 | O |
| 1-0792 | —(CH₂)₂— | —NH— | K240 | J126 | O |
| 1-0793 | —(CH₂)₂— | —NH— | K240 | J129 | O |
| 1-0794 | —(CH₂)₂— | —NH— | K240 | J130 | O |
| 1-0795 | —(CH₂)₂— | —NH— | K240 | J138 | O |
| 1-0796 | —(CH₂)₂— | —NH— | K240 | J140 | O |
| 1-0797 | —(CH₂)₂— | —NH— | K240 | J151 | O |
| 1-0798 | —(CH₂)₂— | —NH— | K240 | J165 | O |
| 1-0799 | —(CH₂)₂— | —NH— | K240 | J168 | O |
| 1-0800 | —(CH₂)₂— | —NH— | K240 | J174 | O |

TABLE 26

| Compound No. | -A¹- | -A²- | -G¹-A³-A⁴-G² | -A⁵-R² | X |
|---|---|---|---|---|---|
| 1-0801 | —(CH₂)₂— | —NH— | K240 | J176 | O |
| 1-0802 | —(CH₂)₂— | —NH— | K240 | J177 | O |
| 1-0803 | —(CH₂)₂— | —NH— | K240 | J178 | O |
| 1-0804 | —(CH₂)₂— | —NH— | K240 | J185 | O |
| 1-0805 | —(CH₂)₂— | —NH— | K240 | J191 | O |
| 1-0806 | —(CH₂)₂— | —NH— | K240 | J193 | O |
| 1-0807 | —(CH₂)₂— | —NH— | K240 | J195 | O |
| 1-0808 | —(CH₂)₂— | —NH— | K240 | J197 | O |
| 1-0809 | —(CH₂)₂— | —O— | K2 | J19 | O |
| 1-0810 | —(CH₂)₂— | —O— | K2 | J70 | O |
| 1-0811 | —(CH₂)₂— | —O— | K2 | J78 | O |
| 1-0812 | —(CH₂)₂— | —O— | K2 | J126 | O |
| 1-0813 | —(CH₂)₂— | —O— | K2 | J129 | O |
| 1-0814 | —(CH₂)₂— | —O— | K2 | J130 | O |
| 1-0815 | —(CH₂)₂— | —O— | K2 | J138 | O |
| 1-0816 | —(CH₂)₂— | —O— | K2 | J185 | O |
| 1-0817 | —(CH₂)₂— | —O— | K4 | J9 | O |
| 1-0818 | —(CH₂)₂— | —O— | K4 | J126 | O |
| 1-0819 | —(CH₂)₂— | —O— | K4 | J129 | O |
| 1-0820 | —(CH₂)₂— | —O— | K4 | J130 | O |
| 1-0821 | —(CH₂)₂— | —O— | K4 | J138 | O |
| 1-0822 | —(CH₂)₂— | —O— | K4 | J140 | O |
| 1-0823 | —(CH₂)₂— | —O— | K240 | J70 | O |
| 1-0824 | —(CH₂)₂— | —O— | K240 | J78 | O |
| 1-0825 | —(CH₂)₂— | —O— | K240 | J130 | O |
| 1-0826 | —(CH₂)₂— | —O— | K240 | J138 | O |
| 1-0827 | —(CH₂)₂— | —O— | K240 | J185 | O |
| 1-0828 | —(CH₂)₂— | single bond | K603 | J9 | O |
| 1-0829 | —(CH₂)₂— | single bond | K603 | J140 | O |
| 1-0830 | —(CH₂)₂— | single bond | K604 | J9 | O |
| 1-0831 | —(CH₂)₂— | single bond | K604 | J126 | O |
| 1-0832 | —(CH₂)₂— | single bond | K605 | J9 | O |

TABLE 27

| Compound No. | -A¹- | -A²- | -G¹-A³-A⁴-G² | -A⁵-R² | X |
|---|---|---|---|---|---|
| 1-0833 | —(CH$_2$)$_2$— | single bond | K605 | J129 | O |
| 1-0834 | —(CH$_2$)$_2$— | single bond | K615 | J9 | O |
| 1-0835 | —(CH$_2$)$_2$— | single bond | K615 | J130 | O |
| 1-0836 | —(CH$_2$)$_2$— | single bond | K616 | J9 | O |
| 1-0837 | —(CH$_2$)$_2$— | single bond | K616 | J138 | O |
| 1-0838 | —(CH$_2$)$_3$— | —NH— | K240 | J126 | O |
| 1-0839 | —(CH$_2$)$_3$— | —NH— | K240 | J129 | O |
| 1-0840 | —(CH$_2$)$_3$— | —NH— | K240 | J130 | O |
| 1-0841 | —(CH$_2$)$_3$— | —NH— | K240 | J138 | O |
| 1-0842 | —(CH$_2$)$_3$— | —NH— | K240 | J140 | O |
| 1-0843 | —(CH$_2$)$_3$— | —O— | K1 | J22 | O |
| 1-0844 | —(CH$_2$)$_3$— | —O— | K2 | J22 | O |
| 1-0845 | —(CH$_2$)$_3$— | —O— | K4 | J1 | O |
| 1-0846 | —(CH$_2$)$_3$— | —O— | K4 | J10 | O |
| 1-0847 | —(CH$_2$)$_3$— | —O— | K4 | J10 | S |
| 1-0848 | —(CH$_2$)$_3$— | —O— | K4 | J19 | O |
| 1-0849 | —(CH$_2$)$_3$— | —O— | K4 | J57 | O |
| 1-0850 | —(CH$_2$)$_3$— | —O— | K4 | J70 | O |
| 1-0851 | —(CH$_2$)$_3$— | —O— | K4 | J71 | O |
| 1-0852 | —(CH$_2$)$_3$— | —O— | K4 | J78 | O |
| 1-0853 | —(CH$_2$)$_3$— | —O— | K4 | J126 | O |
| 1-0854 | —(CH$_2$)$_3$— | —O— | K4 | J126 | S |
| 1-0855 | —(CH$_2$)$_3$— | —O— | K4 | J129 | O |
| 1-0856 | —(CH$_2$)$_3$— | —O— | K4 | J129 | S |
| 1-0857 | —(CH$_2$)$_3$— | —O— | K4 | J130 | O |
| 1-0858 | —(CH$_2$)$_3$— | —O— | K4 | J134 | O |
| 1-0859 | —(CH$_2$)$_3$— | —O— | K4 | J138 | O |
| 1-0860 | —(CH$_2$)$_3$— | —O— | K4 | J140 | O |
| 1-0861 | —(CH$_2$)$_3$— | —O— | K4 | J178 | O |
| 1-0862 | —(CH$_2$)$_2$— | —O— | K4 | J178 | O |
| 1-0863 | —(CH$_2$)$_3$— | —O— | K4 | J185 | O |
| 1-0864 | —(CH$_2$)$_3$— | —O— | K4 | J186 | O |

TABLE 28

| Compound No. | -A¹- | -A²- | -G¹-A³-A⁴-G² | -A⁵-R² | X |
|---|---|---|---|---|---|
| 1-0865 | —(CH$_2$)$_3$— | —O— | K4 | J187 | O |
| 1-0866 | —(CH$_2$)$_3$— | —O— | K4 | J189 | O |
| 1-0867 | —(CH$_2$)$_3$— | —O— | K4 | J190 | O |
| 1-0868 | —(CH$_2$)$_3$— | —O— | K4 | J191 | O |
| 1-0869 | —(CH$_2$)$_3$— | —O— | K4 | J192 | O |
| 1-0870 | —(CH$_2$)$_3$— | —O— | K4 | J193 | O |
| 1-0871 | —(CH$_2$)$_3$— | —O— | K11 | J9 | O |
| 1-0872 | —(CH$_2$)$_3$— | —O— | K11 | J126 | O |
| 1-0873 | —(CH$_2$)$_3$— | —O— | K11 | J129 | O |
| 1-0874 | —(CH$_2$)$_3$— | —O— | K11 | J130 | O |
| 1-0875 | —(CH$_2$)$_3$— | —O— | K11 | J138 | O |
| 1-0876 | —(CH$_2$)$_3$— | —O— | K11 | J140 | O |
| 1-0877 | —(CH$_2$)$_3$— | —O— | K34 | J9 | O |
| 1-0878 | —(CH$_2$)$_3$— | —O— | K34 | J126 | O |
| 1-0879 | —(CH$_2$)$_3$— | —O— | K34 | J129 | O |
| 1-0880 | —(CH$_2$)$_3$— | —O— | K34 | J130 | O |
| 1-0881 | —(CH$_2$)$_3$— | —O— | K34 | J138 | O |
| 1-0882 | —(CH$_2$)$_3$— | —O— | K34 | J140 | O |
| 1-0883 | —(CH$_2$)$_3$— | —O— | K49 | J9 | O |
| 1-0884 | —(CH$_2$)$_3$— | —O— | K49 | J126 | O |
| 1-0885 | —(CH$_2$)$_3$— | —O— | K49 | J129 | O |
| 1-0886 | —(CH$_2$)$_3$— | —O— | K49 | J130 | O |
| 1-0887 | —(CH$_2$)$_3$— | —O— | K49 | J138 | O |
| 1-0888 | —(CH$_2$)$_3$— | —O— | K49 | J140 | O |
| 1-0889 | —(CH$_2$)$_3$— | —O— | K103 | J9 | O |
| 1-0890 | —(CH$_2$)$_3$— | —O— | K103 | J126 | O |
| 1-0891 | —(CH$_2$)$_3$— | —O— | K103 | J129 | O |
| 1-0892 | —(CH$_2$)$_3$— | —O— | K103 | J130 | O |
| 1-0893 | —(CH$_2$)$_3$— | —O— | K103 | J138 | O |
| 1-0894 | —(CH$_2$)$_3$— | —O— | K103 | J140 | O |
| 1-0895 | —(CH$_2$)$_3$— | —O— | K240 | J70 | O |
| 1-0896 | —(CH$_2$)$_3$— | —O— | K240 | J78 | O |

TABLE 29

| Compound No. | -A¹- | -A²- | -G¹-A³-A⁴-G² | -A⁵-R² | X |
|---|---|---|---|---|---|
| 1-0897 | —(CH$_2$)$_3$— | —O— | K240 | J130 | O |
| 1-0898 | —(CH$_2$)$_3$— | —O— | K240 | J138 | O |
| 1-0899 | —(CH$_2$)$_3$— | —O— | K240 | J185 | O |
| 1-0900 | —(CH$_2$)$_3$— | —O— | K723 | J9 | O |
| 1-0901 | —(CH$_2$)$_3$— | —O— | K723 | J126 | O |
| 1-0902 | —(CH$_2$)$_3$— | —O— | K723 | J129 | O |
| 1-0903 | —(CH$_2$)$_3$— | —O— | K723 | J130 | O |
| 1-0904 | —(CH$_2$)$_3$— | —O— | K723 | J138 | O |
| 1-0905 | —(CH$_2$)$_3$— | —O— | K723 | J140 | O |
| 1-0906 | —(CH$_2$)$_3$— | —O— | K725 | J9 | O |
| 1-0907 | —(CH$_2$)$_3$— | —O— | K725 | J126 | O |
| 1-0908 | —(CH$_2$)$_3$— | —O— | K725 | J129 | O |
| 1-0909 | —(CH$_2$)$_3$— | —O— | K725 | J130 | O |
| 1-0910 | —(CH$_2$)$_3$— | —O— | K725 | J138 | O |
| 1-0911 | —(CH$_2$)$_3$— | —O— | K725 | J140 | O |
| 1-0912 | —(CH$_2$)$_3$— | —O— | K99 | J9 | O |
| 1-0913 | —(CH$_2$)$_3$— | —O— | K99 | J126 | O |
| 1-0914 | —(CH$_2$)$_3$— | —O— | K99 | J129 | O |
| 1-0915 | —(CH$_2$)$_3$— | —O— | K99 | J130 | O |
| 1-0916 | —(CH$_2$)$_3$— | —O— | K99 | J138 | O |
| 1-0917 | —(CH$_2$)$_3$— | —O— | K99 | J140 | O |
| 1-0918 | —(CH$_2$)$_3$— | single bond | K603 | J9 | O |
| 1-0919 | —(CH$_2$)$_3$— | single bond | K604 | J9 | O |
| 1-0920 | —(CH$_2$)$_3$— | single bond | K605 | J9 | O |
| 1-0921 | —(CH$_2$)$_3$— | single bond | K606 | J9 | O |
| 1-0922 | single bond | single bond | K1 | J1 | O |
| 1-0923 | single bond | single bond | K1 | J3 | O |
| 1-0924 | single bond | single bond | K1 | J6 | O |
| 1-0925 | single bond | single bond | K1 | J9 | O |
| 1-0926 | single bond | single bond | K1 | J10 | O |
| 1-0927 | single bond | single bond | K1 | J14 | O |
| 1-0928 | single bond | single bond | K1 | J19 | O |

TABLE 30

| Compound No. | -A¹- | -A²- | -G¹-A³-A⁴-G² | -A⁵-R² | X |
|---|---|---|---|---|---|
| 1-0929 | single bond | single bond | K1 | J22 | O |
| 1-0930 | single bond | single bond | K1 | J25 | O |
| 1-0931 | single bond | single bond | K1 | J29 | O |
| 1-0932 | single bond | single bond | K1 | J57 | O |
| 1-0933 | single bond | single bond | K1 | J59 | O |
| 1-0934 | single bond | single bond | K1 | J70 | O |
| 1-0935 | single bond | single bond | K1 | J71 | O |
| 1-0936 | single bond | single bond | K1 | J72 | O |
| 1-0937 | single bond | single bond | K1 | J74 | O |
| 1-0938 | single bond | single bond | K1 | J75 | O |
| 1-0939 | single bond | single bond | K1 | J77 | O |
| 1-0940 | single bond | single bond | K1 | J78 | O |
| 1-0941 | single bond | single bond | K1 | J105 | O |
| 1-0942 | single bond | single bond | K1 | J126 | O |
| 1-0943 | single bond | single bond | K1 | J129 | O |
| 1-0944 | single bond | single bond | K1 | J130 | O |
| 1-0945 | single bond | single bond | K1 | J134 | O |
| 1-0946 | single bond | single bond | K1 | J138 | O |
| 1-0947 | single bond | single bond | K1 | J140 | O |
| 1-0948 | single bond | single bond | K1 | J151 | O |
| 1-0949 | single bond | single bond | K1 | J165 | O |
| 1-0950 | single bond | single bond | K1 | J168 | O |
| 1-0951 | single bond | single bond | K1 | J174 | O |
| 1-0952 | single bond | single bond | K1 | J176 | O |
| 1-0953 | single bond | single bond | K1 | J177 | O |
| 1-0954 | single bond | single bond | K1 | J178 | O |
| 1-0955 | single bond | single bond | K1 | J185 | O |
| 1-0956 | single bond | single bond | K1 | J191 | O |
| 1-0957 | single bond | single bond | K1 | J194 | O |
| 1-0958 | single bond | single bond | K1 | J195 | O |
| 1-0959 | single bond | single bond | K1 | J197 | O |
| 1-0960 | single bond | single bond | K2 | J9 | O |

TABLE 31

| Compound No. | -A¹- | -A²- | -G¹-A³-A⁴-G² | -A⁵-R² | X |
|---|---|---|---|---|---|
| 1-0961 | single bond | single bond | K2 | J10 | O |
| 1-0962 | single bond | single bond | K2 | J14 | O |
| 1-0963 | single bond | single bond | K2 | J19 | O |
| 1-0964 | single bond | single bond | K2 | J22 | O |
| 1-0965 | single bond | single bond | K2 | J57 | O |
| 1-0966 | single bond | single bond | K2 | J59 | O |
| 1-0967 | single bond | single bond | K2 | J70 | O |
| 1-0968 | single bond | single bond | K2 | J72 | O |
| 1-0969 | single bond | single bond | K2 | J74 | O |
| 1-0970 | single bond | single bond | K2 | J75 | O |
| 1-0971 | single bond | single bond | K2 | J77 | O |
| 1-0972 | single bond | single bond | K2 | J78 | O |
| 1-0973 | single bond | single bond | K2 | J126 | O |
| 1-0974 | single bond | single bond | K2 | J129 | O |
| 1-0975 | single bond | single bond | K2 | J130 | O |
| 1-0976 | single bond | single bond | K2 | J138 | O |
| 1-0977 | single bond | single bond | K2 | J140 | O |
| 1-0978 | single bond | single bond | K2 | J151 | O |
| 1-0979 | single bond | single bond | K2 | J174 | O |
| 1-0980 | single bond | single bond | K2 | J176 | O |
| 1-0981 | single bond | single bond | K2 | J177 | O |
| 1-0982 | single bond | single bond | K2 | J178 | O |
| 1-0983 | single bond | single bond | K2 | J185 | O |
| 1-0984 | single bond | single bond | K2 | J191 | O |
| 1-0985 | single bond | single bond | K2 | J194 | O |
| 1-0986 | single bond | single bond | K2 | J195 | O |
| 1-0987 | single bond | single bond | K2 | J197 | O |
| 1-0988 | single bond | single bond | K3 | J9 | O |
| 1-0989 | single bond | single bond | K3 | J70 | O |
| 1-0990 | single bond | single bond | K3 | J78 | O |
| 1-0991 | single bond | single bond | K3 | J130 | O |
| 1-0992 | single bond | single bond | K3 | J138 | O |

TABLE 32

| Compound No. | -A¹- | -A²- | -G¹-A³-A⁴-G² | -A⁵-R² | X |
|---|---|---|---|---|---|
| 1-0993 | single bond | single bond | K3 | J185 | O |
| 1-0994 | single bond | single bond | K4 | J9 | O |
| 1-0995 | single bond | single bond | K4 | J70 | O |
| 1-0996 | single bond | single bond | K4 | J78 | O |
| 1-0997 | single bond | single bond | K4 | J130 | O |
| 1-0998 | single bond | single bond | K4 | J138 | O |
| 1-0999 | single bond | single bond | K4 | J185 | O |
| 1-1000 | single bond | single bond | K99 | J22 | O |
| 1-1001 | single bond | single bond | K103 | J22 | O |
| 1-1002 | single bond | single bond | K240 | J77 | O |
| 1-1003 | single bond | single bond | K240 | J78 | O |
| 1-1004 | single bond | single bond | K240 | J90 | O |
| 1-1005 | single bond | single bond | K240 | J126 | O |
| 1-1006 | single bond | single bond | K240 | J129 | O |
| 1-1007 | single bond | single bond | K240 | J130 | O |
| 1-1008 | single bond | single bond | K240 | J138 | O |
| 1-1009 | single bond | single bond | K240 | J140 | O |
| 1-1010 | single bond | single bond | K240 | J143 | O |
| 1-1011 | single bond | single bond | K240 | J145 | O |
| 1-1012 | single bond | single bond | K240 | J146 | O |
| 1-1013 | single bond | single bond | K240 | J147 | O |
| 1-1014 | single bond | single bond | K240 | J148 | O |
| 1-1015 | single bond | single bond | K240 | J149 | O |
| 1-1016 | single bond | single bond | K240 | J150 | O |
| 1-1017 | single bond | single bond | K240 | J151 | O |
| 1-1018 | single bond | single bond | K240 | J153 | O |
| 1-1019 | single bond | single bond | K240 | J154 | O |
| 1-1020 | single bond | single bond | K240 | J155 | O |
| 1-1021 | single bond | single bond | K240 | J156 | O |
| 1-1022 | single bond | single bond | K240 | J157 | O |
| 1-1023 | single bond | single bond | K240 | J158 | O |
| 1-1024 | single bond | single bond | K240 | J159 | O |

TABLE 33

| Compound No. | -A¹- | -A²- | -G¹-A³-A⁴-G² | -A⁵-R² | X |
|---|---|---|---|---|---|
| 1-1025 | single bond | single bond | K240 | J163 | O |
| 1-1026 | single bond | single bond | K240 | J165 | O |
| 1-1027 | single bond | single bond | K240 | J168 | O |
| 1-1028 | single bond | single bond | K240 | J169 | O |
| 1-1029 | single bond | single bond | K240 | J170 | O |
| 1-1030 | single bond | single bond | K240 | J171 | O |
| 1-1031 | single bond | single bond | K240 | J172 | O |
| 1-1032 | single bond | single bond | K240 | J173 | O |
| 1-1033 | single bond | single bond | K240 | J174 | O |
| 1-1034 | single bond | single bond | K240 | J176 | O |
| 1-1035 | single bond | single bond | K240 | J177 | O |
| 1-1036 | single bond | single bond | K240 | J178 | O |
| 1-1037 | single bond | single bond | K240 | J179 | O |
| 1-1038 | single bond | single bond | K240 | J180 | O |
| 1-1039 | single bond | single bond | K240 | J181 | O |
| 1-1040 | single bond | single bond | K240 | J182 | O |
| 1-1041 | single bond | single bond | K240 | J183 | O |
| 1-1042 | single bond | single bond | K240 | J184 | O |
| 1-1043 | single bond | single bond | K240 | J185 | O |
| 1-1044 | single bond | single bond | K240 | J191 | O |
| 1-1045 | single bond | single bond | K240 | J194 | O |
| 1-1046 | single bond | single bond | K240 | J195 | O |
| 1-1047 | single bond | single bond | K240 | J197 | O |
| 1-1048 | single bond | single bond | K281 | J9 | O |
| 1-1049 | single bond | single bond | K660 | J3 | O |
| 1-1050 | —CH₂— | single bond | K11 | J126 | O |
| 1-1051 | —CH₂— | single bond | K11 | J129 | O |
| 1-1052 | —CH₂— | single bond | K11 | J130 | O |
| 1-1053 | —CH₂— | single bond | K11 | J138 | O |
| 1-1054 | —CH₂— | single bond | K11 | J140 | O |
| 1-1055 | —(CH₂)₂— | single bond | K11 | J126 | O |
| 1-1056 | —(CH₂)₂— | single bond | K11 | J129 | O |

TABLE 34

| Compound No. | -A¹- | -A²- | -G¹-A³-A⁴-G² | -A⁵-R² | X |
|---|---|---|---|---|---|
| 1-1057 | —(CH₂)₂— | single bond | K11 | J130 | O |
| 1-1058 | —(CH₂)₂— | single bond | K11 | J138 | O |
| 1-1059 | —(CH₂)₂— | single bond | K11 | J140 | O |
| 1-1060 | —(CH₂)₃— | single bond | K11 | J126 | O |
| 1-1061 | —(CH₂)₃— | single bond | K11 | J129 | O |
| 1-1062 | —(CH₂)₃— | single bond | K11 | J130 | O |
| 1-1063 | —(CH₂)₃— | single bond | K11 | J138 | O |
| 1-1064 | —(CH₂)₃— | single bond | K11 | J140 | O |
| 1-1065 | —(CH₂)₃— | —O— | K99 | J9 | O |
| 1-1066 | —(CH₂)₃— | —O— | K1 | J12 | O |
| 1-1067 | single bond | single bond | K1 | J12 | O |
| 1-1068 | —(CH₂)₃— | —O— | K4 | J12 | O |
| 1-1069 | —(CH₂)₂— | —O— | K2 | J12 | O |
| 1-1070 | single bond | single bond | K103 | J12 | O |
| 1-1071 | single bond | single bond | K99 | J12 | O |
| 1-1072 | —(CH₂)₃— | —O— | K4 | J6 | O |
| 1-1073 | —(CH₂)₃— | —O— | K4 | J212 | O |
| 1-1074 | —(CH₂)₃— | —O— | K1 | J10 | O |
| 1-1075 | —(CH₂)₃— | —O— | K99 | J9 | S |
| 1-1076 | —(CH₂)₃— | —O— | K2 | J10 | O |
| 1-1077 | —(CH₂)₃— | —O— | K4 | J209 | O |
| 1-1078 | —(CH₂)₃— | —O— | K4 | J210 | S |
| 1-1079 | —(CH₂)₃— | —O— | K4 | J211 | O |
| 1-1080 | —(CH₂)₃— | —O— | K4 | J211 | S |
| 1-1081 | —(CH₂)₃— | —NH— | K240 | J78 | O |
| 1-1082 | —(CH₂)₃— | —NH— | K240 | J78 | S |
| 1-1083 | —(CH₂)₂— | —NH— | K1 | J9 | S |

TABLE 35

| Compound No. | -A¹- | -A²- | -G¹-A³-A⁴-G² | -A⁵-R² | X |
|---|---|---|---|---|---|
| 2-0001 | —(CH$_2$)$_2$— | —NH—C(=O)— | K4 | J4 | O |
| 2-0002 | —(CH$_2$)$_2$— | —NH—C(=O)— | K4 | J4 | S |
| 2-0003 | —(CH$_2$)$_2$— | —NH—C(=O)— | K4 | J23 | O |
| 2-0004 | —(CH$_2$)$_2$— | —NH—C(=O)— | K4 | J23 | S |
| 2-0005 | —(CH$_2$)$_2$— | —NH—C(=O)— | K4 | J71 | O |
| 2-0006 | —(CH$_2$)$_2$— | —NH—C(=O)— | K4 | J71 | S |
| 2-0007 | —(CH$_2$)$_2$— | —NH—C(=O)— | K11 | J9 | O |
| 2-0008 | —(CH$_2$)$_2$— | —NH—C(=O)— | K13 | J4 | O |
| 2-0009 | —(CH$_2$)$_2$— | —NH—C(=O)— | K13 | J4 | S |
| 2-0010 | —(CH$_2$)$_2$— | —NH—C(=O)— | K13 | J9 | O |
| 2-0011 | —(CH$_2$)$_2$— | —NH—C(=O)— | K13 | J23 | O |
| 2-0012 | —(CH$_2$)$_2$— | —NH—C(=O)— | K13 | J23 | S |
| 2-0013 | —(CH$_2$)$_2$— | —NH—C(=O)— | K13 | J71 | O |
| 2-0014 | —(CH$_2$)$_2$— | —NH—C(=O)— | K13 | J71 | S |
| 2-0015 | —(CH$_2$)$_2$— | —NH—C(=O)— | K14 | J9 | O |
| 2-0016 | —(CH$_2$)$_2$— | —NH—C(=O)— | K28 | J9 | O |
| 2-0017 | —(CH$_2$)$_2$— | —NH—C(=O)— | K30 | J9 | O |
| 2-0018 | —(CH$_2$)$_2$— | —NH—C(=O)— | K31 | J9 | O |
| 2-0019 | —(CH$_2$)$_2$— | —NH—C(=O)— | K24 | J9 | O |
| 2-0020 | —(CH$_2$)$_2$— | —NH—C(=O)— | K35 | J4 | O |
| 2-0021 | —(CH$_2$)$_2$— | —NH—C(=O)— | K35 | J4 | S |
| 2-0022 | —(CH$_2$)$_2$— | —NH—C(=O)— | K35 | J23 | O |
| 2-0023 | —(CH$_2$)$_2$— | —NH—C(=O)— | K35 | J23 | S |
| 2-0024 | —(CH$_2$)$_2$— | —NH—C(=O)— | K35 | J71 | O |
| 2-0025 | —(CH$_2$)$_2$— | —NH—C(=O)— | K35 | J71 | S |
| 2-0026 | —(CH$_2$)$_2$— | —NH—C(=O)— | K49 | J9 | O |
| 2-0027 | —(CH$_2$)$_2$— | —NH—C(=O)— | K51 | J102 | O |
| 2-0028 | —(CH$_2$)$_2$— | —NH—C(=O)— | K51 | J102 | S |
| 2-0029 | —(CH$_2$)$_2$— | —NH—C(=O)— | K51 | J105 | O |
| 2-0030 | —(CH$_2$)$_2$— | —NH—C(=O)— | K51 | J105 | S |
| 2-0031 | —(CH$_2$)$_2$— | —NH—C(=O)— | K60 | J9 | O |
| 2-0032 | —(CH$_2$)$_2$— | —NH—C(=O)— | K62 | J9 | O |

TABLE 36

| Compound No. | -A¹- | -A²- | -G¹-A³-A⁴-G² | -A⁵-R² | X |
|---|---|---|---|---|---|
| 2-0033 | —(CH$_2$)$_2$— | —NH—C(=O)— | K71 | J9 | O |
| 2-0034 | —(CH$_2$)$_2$— | —NH—C(=O)— | K72 | J9 | O |
| 2-0035 | —(CH$_2$)$_2$— | —NH—C(=O)— | K82 | J9 | O |
| 2-0036 | —(CH$_2$)$_2$— | —NH—C(=O)— | K83 | J9 | O |
| 2-0037 | —(CH$_2$)$_2$— | —NH—C(=O)— | K84 | J9 | O |
| 2-0038 | —(CH$_2$)$_2$— | —NH—C(=O)— | K110 | J4 | O |
| 2-0039 | —(CH$_2$)$_2$— | —NH—C(=O)— | K110 | J4 | S |
| 2-0040 | —(CH$_2$)$_2$— | —NH—C(=O)— | K110 | J23 | O |
| 2-0041 | —(CH$_2$)$_2$— | —NH—C(=O)— | K110 | J23 | S |
| 2-0042 | —(CH$_2$)$_2$— | —NH—C(=O)— | K110 | J71 | O |
| 2-0043 | —(CH$_2$)$_2$— | —NH—C(=O)— | K110 | J71 | S |
| 2-0044 | —(CH$_2$)$_2$— | —NH—C(=O)— | K114 | J102 | O |
| 2-0045 | —(CH$_2$)$_2$— | —NH—C(=O)— | K114 | J102 | S |
| 2-0046 | —(CH$_2$)$_2$— | —NH—C(=O)— | K114 | J105 | O |
| 2-0047 | —(CH$_2$)$_2$— | —NH—C(=O)— | K114 | J105 | S |
| 2-0048 | —(CH$_2$)$_2$— | —NH—C(=O)— | K116 | J4 | O |
| 2-0049 | —(CH$_2$)$_2$— | —NH—C(=O)— | K116 | J4 | S |
| 2-0050 | —(CH$_2$)$_2$— | —NH—C(=O)— | K116 | J23 | O |
| 2-0051 | —(CH$_2$)$_2$— | —NH—C(=O)— | K116 | J23 | S |
| 2-0052 | —(CH$_2$)$_2$— | —NH—C(=O)— | K116 | J71 | O |
| 2-0053 | —(CH$_2$)$_2$— | —NH—C(=O)— | K116 | J71 | S |
| 2-0054 | —(CH$_2$)$_2$— | —NH—C(=O)— | K122 | J102 | O |
| 2-0055 | —(CH$_2$)$_2$— | —NH—C(=O)— | K122 | J102 | S |
| 2-0056 | —(CH$_2$)$_2$— | —NH—C(=O)— | K122 | J105 | O |
| 2-0057 | —(CH$_2$)$_2$— | —NH—C(=O)— | K122 | J105 | S |
| 2-0058 | —(CH$_2$)$_2$— | —NH—C(=O)— | K127 | J9 | O |
| 2-0059 | —(CH$_2$)$_3$— | —NH—C(=O)— | K7 | J9 | O |
| 2-0060 | —(CH$_2$)$_3$— | —NH—C(=O)— | K11 | J9 | O |
| 2-0061 | —(CH$_2$)$_3$— | —NH—C(=O)— | K12 | J9 | O |
| 2-0062 | —(CH$_2$)$_3$— | —NH—C(=O)— | K13 | J9 | O |
| 2-0063 | —(CH$_2$)$_3$— | —NH—C(=O)— | K14 | J9 | O |
| 2-0064 | —(CH$_2$)$_3$— | —NH—C(=O)— | K24 | J3 | O |

TABLE 37

| Compound No. | -A¹- | -A²- | -G¹-A³-A⁴-G² | -A⁵-R² | X |
|---|---|---|---|---|---|
| 2-0065 | —(CH$_2$)$_3$— | —NH—C(=O)— | K24 | J3 | S |
| 2-0066 | —(CH$_2$)$_3$— | —NH—C(=O)— | K24 | J22 | O |
| 2-0067 | —(CH$_2$)$_3$— | —NH—C(=O)— | K24 | J22 | S |
| 2-0068 | —(CH$_2$)$_3$— | —NH—C(=O)— | K24 | J28 | O |
| 2-0069 | —(CH$_2$)$_3$— | —NH—C(=O)— | K24 | J28 | S |
| 2-0070 | —(CH$_2$)$_3$— | —NH—C(=O)— | K24 | J70 | O |
| 2-0071 | —(CH$_2$)$_3$— | —NH—C(=O)— | K24 | J70 | S |
| 2-0072 | —(CH$_2$)$_3$— | —NH—C(=O)— | K28 | J9 | O |
| 2-0073 | —(CH$_2$)$_3$— | —NH—C(=O)— | K29 | J9 | O |
| 2-0074 | —(CH$_2$)$_3$— | —NH—C(=O)— | K30 | J9 | O |
| 2-0075 | —(CH$_2$)$_3$— | —NH—C(=O)— | K31 | J9 | O |
| 2-0076 | —(CH$_2$)$_3$— | —NH—C(=O)— | K34 | J3 | O |
| 2-0077 | —(CH$_2$)$_3$— | —NH—C(=O)— | K34 | J3 | S |
| 2-0078 | —(CH$_2$)$_3$— | —NH—C(=O)— | K34 | J22 | O |
| 2-0079 | —(CH$_2$)$_3$— | —NH—C(=O)— | K34 | J22 | S |
| 2-0080 | —(CH$_2$)$_3$— | —NH—C(=O)— | K34 | J28 | O |
| 2-0081 | —(CH$_2$)$_3$— | —NH—C(=O)— | K34 | J28 | S |
| 2-0082 | —(CH$_2$)$_3$— | —NH—C(=O)— | K34 | J70 | O |
| 2-0083 | —(CH$_2$)$_3$— | —NH—C(=O)— | K34 | J70 | S |
| 2-0084 | —(CH$_2$)$_3$— | —NH—C(=O)— | K36 | J3 | O |
| 2-0085 | —(CH$_2$)$_3$— | —NH—C(=O)— | K36 | J3 | S |
| 2-0086 | —(CH$_2$)$_3$— | —NH—C(=O)— | K36 | J22 | O |
| 2-0087 | —(CH$_2$)$_3$— | —NH—C(=O)— | K36 | J22 | S |
| 2-0088 | —(CH$_2$)$_3$— | —NH—C(=O)— | K36 | J28 | O |
| 2-0089 | —(CH$_2$)$_3$— | —NH—C(=O)— | K36 | J28 | S |
| 2-0090 | —(CH$_2$)$_3$— | —NH—C(=O)— | K36 | J70 | O |
| 2-0091 | —(CH$_2$)$_3$— | —NH—C(=O)— | K36 | J70 | S |
| 2-0092 | —(CH$_2$)$_3$— | —NH—C(=O)— | K49 | J9 | O |
| 2-0093 | —(CH$_2$)$_3$— | —NH—C(=O)— | K71 | J9 | O |
| 2-0094 | —(CH$_2$)$_3$— | —NH—C(=O)— | K72 | J3 | O |
| 2-0095 | —(CH$_2$)$_3$— | —NH—C(=O)— | K72 | J3 | S |
| 2-0096 | —(CH$_2$)$_3$— | —NH—C(=O)— | K72 | J9 | O |

TABLE 38

| Compound No. | -A¹- | -A²- | -G¹-A³-A⁴-G² | -A⁵-R² | X |
|---|---|---|---|---|---|
| 2-0097 | —(CH$_2$)$_3$— | —NH—C(=O)— | K72 | J22 | O |
| 2-0098 | —(CH$_2$)$_3$— | —NH—C(=O)— | K72 | J22 | S |
| 2-0099 | —(CH$_2$)$_3$— | —NH—C(=O)— | K72 | J28 | O |
| 2-0100 | —(CH$_2$)$_3$— | —NH—C(=O)— | K72 | J28 | S |
| 2-0101 | —(CH$_2$)$_3$— | —NH—C(=O)— | K72 | J70 | O |
| 2-0102 | —(CH$_2$)$_3$— | —NH—C(=O)— | K72 | J70 | S |
| 2-0103 | —(CH$_2$)$_3$— | —NH—C(=O)— | K72 | J103 | O |
| 2-0104 | —(CH$_2$)$_3$— | —NH—C(=O)— | K72 | J103 | S |
| 2-0105 | —(CH$_2$)$_3$— | —NH—C(=O)— | K72 | J120 | O |
| 2-0106 | —(CH$_2$)$_3$— | —NH—C(=O)— | K72 | J120 | S |
| 2-0107 | —(CH$_2$)$_3$— | —NH—C(=O)— | K72 | J122 | O |
| 2-0108 | —(CH$_2$)$_3$— | —NH—C(=O)— | K72 | J122 | S |
| 2-0109 | —(CH$_2$)$_3$— | —NH—C(=O)— | K74 | J3 | O |
| 2-0110 | —(CH$_2$)$_3$— | —NH—C(=O)— | K74 | J3 | S |
| 2-0111 | —(CH$_2$)$_3$— | —NH—C(=O)— | K74 | J22 | O |
| 2-0112 | —(CH$_2$)$_3$— | —NH—C(=O)— | K74 | J22 | S |
| 2-0113 | —(CH$_2$)$_3$— | —NH—C(=O)— | K74 | J28 | O |
| 2-0114 | —(CH$_2$)$_3$— | —NH—C(=O)— | K74 | J28 | S |
| 2-0115 | —(CH$_2$)$_3$— | —NH—C(=O)— | K74 | J70 | O |
| 2-0116 | —(CH$_2$)$_3$— | —NH—C(=O)— | K74 | J70 | S |
| 2-0117 | —(CH$_2$)$_3$— | —NH—C(=O)— | K83 | J9 | O |
| 2-0118 | —(CH$_2$)$_3$— | —NH—C(=O)— | K86 | J3 | O |
| 2-0119 | —(CH$_2$)$_3$— | —NH—C(=O)— | K86 | J3 | S |
| 2-0120 | —(CH$_2$)$_3$— | —NH—C(=O)— | K86 | J22 | O |
| 2-0121 | —(CH$_2$)$_3$— | —NH—C(=O)— | K86 | J22 | S |
| 2-0122 | —(CH$_2$)$_3$— | —NH—C(=O)— | K86 | J28 | O |
| 2-0123 | —(CH$_2$)$_3$— | —NH—C(=O)— | K86 | J28 | S |
| 2-0124 | —(CH$_2$)$_3$— | —NH—C(=O)— | K86 | J70 | O |
| 2-0125 | —(CH$_2$)$_3$— | —NH—C(=O)— | K86 | J70 | S |
| 2-0126 | —(CH$_2$)$_3$— | —NH—C(=O)— | K86 | J103 | O |
| 2-0127 | —(CH$_2$)$_3$— | —NH—C(=O)— | K86 | J103 | S |
| 2-0128 | —(CH$_2$)$_3$— | —NH—C(=O)— | K86 | J120 | O |

TABLE 39

| Compound No. | -A¹- | -A²- | -G¹-A³-A⁴-G² | -A⁵-R² | X |
|---|---|---|---|---|---|
| 2-0129 | —(CH$_2$)$_3$— | —NH—C(=O)— | K86 | J120 | S |
| 2-0130 | —(CH$_2$)$_3$— | —NH—C(=O)— | K86 | J122 | O |
| 2-0131 | —(CH$_2$)$_3$— | —NH—C(=O)— | K86 | J122 | S |
| 2-0132 | —(CH$_2$)$_3$— | —NH—C(=O)— | K91 | J3 | O |
| 2-0133 | —(CH$_2$)$_3$— | —NH—C(=O)— | K91 | J3 | S |
| 2-0134 | —(CH$_2$)$_3$— | —NH—C(=O)— | K91 | J22 | O |
| 2-0135 | —(CH$_2$)$_3$— | —NH—C(=O)— | K91 | J22 | S |
| 2-0136 | —(CH$_2$)$_3$— | —NH—C(=O)— | K91 | J28 | O |
| 2-0137 | —(CH$_2$)$_3$— | —NH—C(=O)— | K91 | J28 | S |
| 2-0138 | —(CH$_2$)$_3$— | —NH—C(=O)— | K91 | J70 | O |
| 2-0139 | —(CH$_2$)$_3$— | —NH—C(=O)— | K91 | J70 | S |
| 2-0140 | —(CH$_2$)$_3$— | —NH—C(=O)— | K91 | J103 | O |
| 2-0141 | —(CH$_2$)$_3$— | —NH—C(=O)— | K91 | J103 | S |
| 2-0142 | —(CH$_2$)$_3$— | —NH—C(=O)— | K91 | J120 | O |
| 2-0143 | —(CH$_2$)$_3$— | —NH—C(=O)— | K91 | J120 | S |
| 2-0144 | —(CH$_2$)$_3$— | —NH—C(=O)— | K91 | J122 | O |
| 2-0145 | —(CH$_2$)$_3$— | —NH—C(=O)— | K91 | J122 | S |
| 2-0146 | —(CH$_2$)$_3$— | —NH—C(=O)— | K100 | J9 | O |
| 2-0147 | —(CH$_2$)$_3$— | —NH—C(=O)— | K106 | J9 | O |
| 2-0148 | —(CH$_2$)$_3$— | —NH—C(=O)— | K114 | J3 | O |
| 2-0149 | —(CH$_2$)$_3$— | —NH—C(=O)— | K114 | J3 | S |
| 2-0150 | —(CH$_2$)$_3$— | —NH—C(=O)— | K114 | J22 | O |
| 2-0151 | —(CH$_2$)$_3$— | —NH—C(=O)— | K114 | J22 | S |
| 2-0152 | —(CH$_2$)$_3$— | —NH—C(=O)— | K114 | J28 | O |
| 2-0153 | —(CH$_2$)$_3$— | —NH—C(=O)— | K114 | J28 | S |
| 2-0154 | —(CH$_2$)$_3$— | —NH—C(=O)— | K114 | J70 | O |
| 2-0155 | —(CH$_2$)$_3$— | —NH—C(=O)— | K114 | J70 | S |
| 2-0156 | —(CH$_2$)$_3$— | —NH—C(=O)— | K127 | J9 | O |
| 2-0157 | —(CH$_2$)$_4$— | —NH—C(=O)— | K8 | J2 | O |
| 2-0158 | —(CH$_2$)$_4$— | —NH—C(=O)— | K8 | J2 | S |
| 2-0159 | —(CH$_2$)$_4$— | —NH—C(=O)— | K8 | J21 | O |
| 2-0160 | —(CH$_2$)$_4$— | —NH—C(=O)— | K8 | J21 | S |

TABLE 40

| Compound No. | -A¹- | -A²- | -G¹-A³-A⁴-G² | -A⁵-R² | X |
|---|---|---|---|---|---|
| 2-0161 | —(CH$_2$)$_4$— | —NH—C(=O)— | K8 | J76 | O |
| 2-0162 | —(CH$_2$)$_4$— | —NH—C(=O)— | K8 | J76 | S |
| 2-0163 | —(CH$_2$)$_4$— | —NH—C(=O)— | K15 | J2 | O |
| 2-0164 | —(CH$_2$)$_4$— | —NH—C(=O)— | K15 | J2 | S |
| 2-0165 | —(CH$_2$)$_4$— | —NH—C(=O)— | K15 | J21 | O |
| 2-0166 | —(CH$_2$)$_4$— | —NH—C(=O)— | K15 | J21 | S |
| 2-0167 | —(CH$_2$)$_4$— | —NH—C(=O)— | K15 | J76 | O |
| 2-0168 | —(CH$_2$)$_4$— | —NH—C(=O)— | K15 | J76 | S |
| 2-0169 | —(CH$_2$)$_4$— | —NH—C(=O)— | K37 | J116 | O |
| 2-0170 | —(CH$_2$)$_4$— | —NH—C(=O)— | K37 | J116 | S |
| 2-0171 | —(CH$_2$)$_4$— | —NH—C(=O)— | K37 | J121 | O |
| 2-0172 | —(CH$_2$)$_4$— | —NH—C(=O)— | K37 | J121 | S |
| 2-0173 | —(CH$_2$)$_4$— | —NH—C(=O)— | K37 | J124 | O |
| 2-0174 | —(CH$_2$)$_4$— | —NH—C(=O)— | K37 | J124 | S |
| 2-0175 | —(CH$_2$)$_4$— | —NH—C(=O)— | K63 | J116 | O |
| 2-0176 | —(CH$_2$)$_4$— | —NH—C(=O)— | K63 | J116 | S |
| 2-0177 | —(CH$_2$)$_4$— | —NH—C(=O)— | K63 | J121 | O |
| 2-0178 | —(CH$_2$)$_4$— | —NH—C(=O)— | K63 | J121 | S |
| 2-0179 | —(CH$_2$)$_4$— | —NH—C(=O)— | K63 | J124 | O |
| 2-0180 | —(CH$_2$)$_4$— | —NH—C(=O)— | K63 | J124 | S |
| 2-0181 | —(CH$_2$)$_4$— | —NH—C(=O)— | K79 | J2 | O |
| 2-0182 | —(CH$_2$)$_4$— | —NH—C(=O)— | K79 | J2 | S |
| 2-0183 | —(CH$_2$)$_4$— | —NH—C(=O)— | K79 | J21 | O |
| 2-0184 | —(CH$_2$)$_4$— | —NH—C(=O)— | K79 | J21 | S |
| 2-0185 | —(CH$_2$)$_4$— | —NH—C(=O)— | K79 | J76 | O |
| 2-0186 | —(CH$_2$)$_4$— | —NH—C(=O)— | K79 | J76 | S |
| 2-0187 | —(CH$_2$)$_4$— | —NH—C(=O)— | K91 | J2 | O |
| 2-0188 | —(CH$_2$)$_4$— | —NH—C(=O)— | K91 | J2 | S |
| 2-0189 | —(CH$_2$)$_4$— | —NH—C(=O)— | K91 | J21 | O |
| 2-0190 | —(CH$_2$)$_4$— | —NH—C(=O)— | K91 | J21 | S |
| 2-0191 | —(CH$_2$)$_4$— | —NH—C(=O)— | K91 | J76 | O |
| 2-0192 | —(CH$_2$)$_4$— | —NH—C(=O)— | K91 | J76 | S |

TABLE 41

| Compound No. | -A¹- | -A²- | -G¹-A³-A⁴-G² | -A⁵-R² | X |
|---|---|---|---|---|---|
| 2-0193 | —(CH$_2$)$_4$— | —NH—C(=O)— | K111 | J2 | O |
| 2-0194 | —(CH$_2$)$_4$— | —NH—C(=O)— | K111 | J2 | S |
| 2-0195 | —(CH$_2$)$_4$— | —NH—C(=O)— | K111 | J21 | O |
| 2-0196 | —(CH$_2$)$_4$— | —NH—C(=O)— | K111 | J21 | S |
| 2-0197 | —(CH$_2$)$_4$— | —NH—C(=O)— | K111 | J76 | O |
| 2-0198 | —(CH$_2$)$_4$— | —NH—C(=O)— | K111 | J76 | S |
| 2-0199 | —(CH$_2$)$_2$— | —NH—C(=O)—O— | K5 | J9 | O |
| 2-0200 | —(CH$_2$)$_2$— | —NH—C(=O)—O— | K24 | J11 | O |
| 2-0201 | —(CH$_2$)$_2$— | —NH—C(=O)—O— | K24 | J11 | S |
| 2-0202 | —(CH$_2$)$_2$— | —NH—C(=O)—O— | K24 | J64 | O |
| 2-0203 | —(CH$_2$)$_2$— | —NH—C(=O)—O— | K24 | J64 | S |
| 2-0204 | —(CH$_2$)$_2$— | —NH—C(=O)—O— | K116 | J11 | O |
| 2-0205 | —(CH$_2$)$_2$— | —NH—C(=O)—O— | K116 | J11 | S |
| 2-0206 | —(CH$_2$)$_2$— | —NH—C(=O)—O— | K116 | J64 | O |
| 2-0207 | —(CH$_2$)$_2$— | —NH—C(=O)—O— | K116 | J64 | S |
| 2-0208 | —(CH$_2$)$_2$— | —NH—C(=O)—O— | K5 | J9 | O |
| 2-0209 | —(CH$_2$)$_3$— | —NH—C(=O)—O— | K34 | J19 | O |
| 2-0210 | —(CH$_2$)$_3$— | —NH—C(=O)—O— | K34 | J19 | S |
| 2-0211 | —(CH$_2$)$_3$— | —NH—C(=O)—O— | K34 | J34 | O |
| 2-0212 | —(CH$_2$)$_3$— | —NH—C(=O)—O— | K34 | J34 | S |
| 2-0213 | —(CH$_2$)$_3$— | —NH—C(=O)—O— | K91 | J19 | O |
| 2-0214 | —(CH$_2$)$_3$— | —NH—C(=O)—O— | K91 | J19 | S |
| 2-0215 | —(CH$_2$)$_3$— | —NH—C(=O)—O— | K91 | J34 | O |
| 2-0216 | —(CH$_2$)$_3$— | —NH—C(=O)—O— | K91 | J34 | S |
| 2-0217 | —(CH$_2$)$_4$— | —NH—C(=O)—O— | K35 | J20 | O |
| 2-0218 | —(CH$_2$)$_4$— | —NH—C(=O)—O— | K35 | J20 | S |
| 2-0219 | —(CH$_2$)$_4$— | —NH—C(=O)—O— | K35 | J82 | O |
| 2-0220 | —(CH$_2$)$_4$— | —NH—C(=O)—O— | K35 | J82 | S |
| 2-0221 | —(CH$_2$)$_4$— | —NH—C(=O)—O— | K94 | J20 | O |
| 2-0222 | —(CH$_2$)$_4$— | —NH—C(=O)—O— | K94 | J20 | S |
| 2-0223 | —(CH$_2$)$_4$— | —NH—C(=O)—O— | K94 | J82 | O |
| 2-0224 | —(CH$_2$)$_4$— | —NH—C(=O)—O— | K94 | J82 | S |

TABLE 42

| Compound No. | -A¹- | -A²- | -G¹-A³-A⁴-G² | -A⁵-R² | X |
|---|---|---|---|---|---|
| 2-0225 | —(CH$_2$)$_2$— | —NH—C(=O)—NH— | K27 | J26 | O |
| 2-0226 | —(CH$_2$)$_2$— | —NH—C(=O)—NH— | K27 | J26 | S |
| 2-0227 | —(CH$_2$)$_2$— | —NH—C(=O)—NH— | K27 | J31 | O |
| 2-0228 | —(CH$_2$)$_2$— | —NH—C(=O)—NH— | K27 | J31 | S |
| 2-0229 | —(CH$_2$)$_2$— | —NH—C(=O)—NH— | K27 | J73 | O |
| 2-0230 | —(CH$_2$)$_2$— | —NH—C(=O)—NH— | K27 | J73 | S |
| 2-0231 | —(CH$_2$)$_2$— | —NH—C(=O)—NH— | K27 | J119 | O |
| 2-0232 | —(CH$_2$)$_2$— | —NH—C(=O)—NH— | K27 | J119 | S |
| 2-0233 | —(CH$_2$)$_2$— | —NH—C(=O)—NH— | K27 | J123 | O |
| 2-0234 | —(CH$_2$)$_2$— | —NH—C(=O)—NH— | K27 | J123 | S |
| 2-0235 | —(CH$_2$)$_2$— | —NH—C(=O)—NH— | K36 | J26 | O |
| 2-0236 | —(CH$_2$)$_2$— | —NH—C(=O)—NH— | K36 | J26 | S |
| 2-0237 | —(CH$_2$)$_2$— | —NH—C(=O)—NH— | K36 | J31 | O |
| 2-0238 | —(CH$_2$)$_2$— | —NH—C(=O)—NH— | K36 | J31 | S |
| 2-0239 | —(CH$_2$)$_2$— | —NH—C(=O)—NH— | K36 | J73 | O |
| 2-0240 | —(CH$_2$)$_2$— | —NH—C(=O)—NH— | K36 | J73 | S |
| 2-0241 | —(CH$_2$)$_2$— | —NH—C(=O)—NH— | K112 | J119 | O |
| 2-0242 | —(CH$_2$)$_2$— | —NH—C(=O)—NH— | K112 | J119 | S |
| 2-0243 | —(CH$_2$)$_2$— | —NH—C(=O)—NH— | K112 | J123 | O |
| 2-0244 | —(CH$_2$)$_2$— | —NH—C(=O)—NH— | K112 | J123 | S |
| 2-0245 | —(CH$_2$)$_2$— | —NH—C(=O)—NH— | K119 | J26 | O |
| 2-0246 | —(CH$_2$)$_2$— | —NH—C(=O)—NH— | K119 | J26 | S |
| 2-0247 | —(CH$_2$)$_2$— | —NH—C(=O)—NH— | K119 | J31 | O |
| 2-0248 | —(CH$_2$)$_2$— | —NH—C(=O)—NH— | K119 | J31 | S |
| 2-0249 | —(CH$_2$)$_2$— | —NH—C(=O)—NH— | K119 | J73 | O |
| 2-0250 | —(CH$_2$)$_2$— | —NH—C(=O)—NH— | K119 | J73 | S |
| 2-0251 | —(CH$_2$)$_3$— | —NH—C(=O)—NH— | K35 | J3 | O |
| 2-0252 | —(CH$_2$)$_3$— | —NH—C(=O)—NH— | K35 | J3 | S |
| 2-0253 | —(CH$_2$)$_3$— | —NH—C(=O)—NH— | K35 | J22 | O |
| 2-0254 | —(CH$_2$)$_3$— | —NH—C(=O)—NH— | K35 | J22 | S |
| 2-0255 | —(CH$_2$)$_3$— | —NH—C(=O)—NH— | K35 | J34 | O |
| 2-0256 | —(CH$_2$)$_3$— | —NH—C(=O)—NH— | K35 | J34 | S |

TABLE 43

| Compound No. | -A$^1$- | -A$^2$- | -G$^1$-A$^3$-A$^4$-G$^2$ | -A$^5$-R$^2$ | X |
|---|---|---|---|---|---|
| 2-0257 | —(CH$_2$)$_3$— | —NH—C(=O)—NH— | K36 | J3 | O |
| 2-0258 | —(CH$_2$)$_3$— | —NH—C(=O)—NH— | K36 | J3 | S |
| 2-0259 | —(CH$_2$)$_3$— | —NH—C(=O)—NH— | K36 | J22 | O |
| 2-0260 | —(CH$_2$)$_3$— | —NH—C(=O)—NH— | K36 | J22 | S |
| 2-0261 | —(CH$_2$)$_3$— | —NH—C(=O)—NH— | K36 | J34 | O |
| 2-0262 | —(CH$_2$)$_3$— | —NH—C(=O)—NH— | K36 | J34 | S |
| 2-0263 | —(CH$_2$)$_3$— | —NH—C(=O)—NH— | K73 | J96 | O |
| 2-0264 | —(CH$_2$)$_3$— | —NH—C(=O)—NH— | K73 | J96 | S |
| 2-0265 | —(CH$_2$)$_3$— | —NH—C(=O)—NH— | K73 | J104 | O |
| 2-0266 | —(CH$_2$)$_3$— | —NH—C(=O)—NH— | K73 | J104 | S |
| 2-0267 | —(CH$_2$)$_3$— | —NH—C(=O)—NH— | K73 | J117 | O |
| 2-0268 | —(CH$_2$)$_3$— | —NH—C(=O)—NH— | K73 | J117 | S |
| 2-0269 | —(CH$_2$)$_3$— | —NH—C(=O)—NH— | K79 | J96 | O |
| 2-0270 | —(CH$_2$)$_3$— | —NH—C(=O)—NH— | K79 | J96 | S |
| 2-0271 | —(CH$_2$)$_3$— | —NH—C(=O)—NH— | K79 | J104 | O |
| 2-0272 | —(CH$_2$)$_3$— | —NH—C(=O)—NH— | K79 | J104 | S |
| 2-0273 | —(CH$_2$)$_3$— | —NH—C(=O)—NH— | K79 | J117 | O |
| 2-0274 | —(CH$_2$)$_3$— | —NH—C(=O)—NH— | K79 | J117 | S |
| 2-0275 | —(CH$_2$)$_3$— | —NH—C(=O)—NH— | K91 | J3 | O |
| 2-0276 | —(CH$_2$)$_3$— | —NH—C(=O)—NH— | K91 | J3 | S |
| 2-0277 | —(CH$_2$)$_3$— | —NH—C(=O)—NH— | K91 | J22 | O |
| 2-0278 | —(CH$_2$)$_3$— | —NH—C(=O)—NH— | K91 | J22 | S |
| 2-0279 | —(CH$_2$)$_3$— | —NH—C(=O)—NH— | K91 | J34 | O |
| 2-0280 | —(CH$_2$)$_3$— | —NH—C(=O)—NH— | K91 | J34 | S |
| 2-0281 | —(CH$_2$)$_3$— | —NH—C(=O)—NH— | K96 | J96 | O |
| 2-0282 | —(CH$_2$)$_3$— | —NH—C(=O)—NH— | K96 | J96 | S |
| 2-0283 | —(CH$_2$)$_3$— | —NH—C(=O)—NH— | K96 | J104 | O |
| 2-0284 | —(CH$_2$)$_3$— | —NH—C(=O)—NH— | K96 | J104 | S |
| 2-0285 | —(CH$_2$)$_3$— | —NH—C(=O)—NH— | K96 | J117 | O |
| 2-0286 | —(CH$_2$)$_3$— | —NH—C(=O)—NH— | K96 | J117 | S |
| 2-0287 | —(CH$_2$)$_3$— | —NH—C(=O)—NH— | K114 | J3 | O |
| 2-0288 | —(CH$_2$)$_3$— | —NH—C(=O)—NH— | K114 | J3 | S |

TABLE 44

| Compound No. | -A$^1$- | -A$^2$- | -G$^1$-A$^3$-A$^4$-G$^2$ | -A$^5$-R$^2$ | X |
|---|---|---|---|---|---|
| 2-0289 | —(CH$_2$)$_3$— | —NH—C(=O)—NH— | K114 | J22 | O |
| 2-0290 | —(CH$_2$)$_3$— | —NH—C(=O)—NH— | K114 | J22 | S |
| 2-0291 | —(CH$_2$)$_3$— | —NH—C(=O)—NH— | K114 | J34 | O |
| 2-0292 | —(CH$_2$)$_3$— | —NH—C(=O)—NH— | K114 | J34 | S |
| 2-0293 | —(CH$_2$)$_4$— | —NH—C(=O)—NH— | K15 | J123 | O |
| 2-0294 | —(CH$_2$)$_4$— | —NH—C(=O)—NH— | K15 | J123 | S |
| 2-0295 | —(CH$_2$)$_4$— | —NH—C(=O)—NH— | K15 | J125 | O |
| 2-0296 | —(CH$_2$)$_4$— | —NH—C(=O)—NH— | K15 | J125 | S |
| 2-0297 | —(CH$_2$)$_4$— | —NH—C(=O)—NH— | K24 | J4 | O |
| 2-0298 | —(CH$_2$)$_4$— | —NH—C(=O)—NH— | K24 | J4 | S |
| 2-0299 | —(CH$_2$)$_4$— | —NH—C(=O)—NH— | K24 | J35 | O |
| 2-0300 | —(CH$_2$)$_4$— | —NH—C(=O)—NH— | K24 | J35 | S |
| 2-0301 | —(CH$_2$)$_4$— | —NH—C(=O)—NH— | K24 | J96 | O |
| 2-0302 | —(CH$_2$)$_4$— | —NH—C(=O)—NH— | K24 | J96 | S |
| 2-0303 | —(CH$_2$)$_4$— | —NH—C(=O)—NH— | K106 | J123 | O |
| 2-0304 | —(CH$_2$)$_4$— | —NH—C(=O)—NH— | K106 | J123 | S |
| 2-0305 | —(CH$_2$)$_4$— | —NH—C(=O)—NH— | K106 | J125 | O |
| 2-0306 | —(CH$_2$)$_4$— | —NH—C(=O)—NH— | K106 | J125 | S |
| 2-0307 | —(CH$_2$)$_4$— | —NH—C(=O)—NH— | K109 | J4 | O |
| 2-0308 | —(CH$_2$)$_4$— | —NH—C(=O)—NH— | K109 | J4 | S |
| 2-0309 | —(CH$_2$)$_4$— | —NH—C(=O)—NH— | K109 | J35 | O |
| 2-0310 | —(CH$_2$)$_4$— | —NH—C(=O)—NH— | K109 | J35 | S |
| 2-0311 | —(CH$_2$)$_4$— | —NH—C(=O)—NH— | K109 | J96 | O |
| 2-0312 | —(CH$_2$)$_4$— | —NH—C(=O)—NH— | K109 | J96 | S |
| 2-0313 | —(CH$_2$)$_4$— | —NH—C(=O)—NH— | K120 | J4 | O |
| 2-0314 | —(CH$_2$)$_4$— | —NH—C(=O)—NH— | K120 | J4 | S |
| 2-0315 | —(CH$_2$)$_4$— | —NH—C(=O)—NH— | K120 | J35 | O |
| 2-0316 | —(CH$_2$)$_4$— | —NH—C(=O)—NH— | K120 | J35 | S |
| 2-0317 | —(CH$_2$)$_4$— | —NH—C(=O)—NH— | K120 | J96 | O |
| 2-0318 | —(CH$_2$)$_4$— | —NH—C(=O)—NH— | K120 | J96 | S |
| 2-0319 | —(CH$_2$)$_2$— | —NH— | K781 | J2 | O |
| 2-0320 | —(CH$_2$)$_2$— | —NH— | K781 | J2 | S |

TABLE 45

| Compound No. | -A$^1$- | -A$^2$- | -G$^1$-A$^3$-A$^4$-G$^2$ | -A$^5$-R$^2$ | X |
|---|---|---|---|---|---|
| 2-0321 | —(CH$_2$)$_2$— | —NH— | K781 | J24 | O |
| 2-0322 | —(CH$_2$)$_2$— | —NH— | K781 | J24 | S |
| 2-0323 | —(CH$_2$)$_2$— | —NH— | K781 | J79 | O |
| 2-0324 | —(CH$_2$)$_2$— | —NH— | K781 | J79 | S |
| 2-0325 | —(CH$_2$)$_2$— | —NH— | K782 | J2 | O |
| 2-0326 | —(CH$_2$)$_2$— | —NH— | K782 | J2 | S |
| 2-0327 | —(CH$_2$)$_2$— | —NH— | K782 | J24 | O |
| 2-0328 | —(CH$_2$)$_2$— | —NH— | K782 | J24 | S |
| 2-0329 | —(CH$_2$)$_2$— | —NH— | K782 | J79 | O |
| 2-0330 | —(CH$_2$)$_2$— | —NH— | K782 | J79 | S |
| 2-0331 | —(CH$_2$)$_2$— | —NH— | K783 | J96 | O |
| 2-0332 | —(CH$_2$)$_2$— | —NH— | K783 | J96 | S |
| 2-0333 | —(CH$_2$)$_2$— | —NH— | K783 | J104 | O |
| 2-0334 | —(CH$_2$)$_2$— | —NH— | K783 | J104 | S |
| 2-0335 | —(CH$_2$)$_2$— | —NH— | K783 | J117 | O |
| 2-0336 | —(CH$_2$)$_2$— | —NH— | K783 | J117 | S |
| 2-0337 | —(CH$_2$)$_2$— | —NH— | K784 | J2 | O |
| 2-0338 | —(CH$_2$)$_2$— | —NH— | K784 | J2 | S |
| 2-0339 | —(CH$_2$)$_2$— | —NH— | K784 | J24 | O |
| 2-0340 | —(CH$_2$)$_2$— | —NH— | K784 | J24 | S |
| 2-0341 | —(CH$_2$)$_2$— | —NH— | K784 | J79 | O |
| 2-0342 | —(CH$_2$)$_2$— | —NH— | K784 | J79 | S |
| 2-0343 | —(CH$_2$)$_2$— | —NH— | K785 | J2 | O |
| 2-0344 | —(CH$_2$)$_2$— | —NH— | K785 | J2 | S |
| 2-0345 | —(CH$_2$)$_2$— | —NH— | K785 | J24 | O |
| 2-0346 | —(CH$_2$)$_2$— | —NH— | K785 | J24 | S |
| 2-0347 | —(CH$_2$)$_2$— | —NH— | K785 | J79 | O |
| 2-0348 | —(CH$_2$)$_2$— | —NH— | K785 | J79 | S |
| 2-0349 | —(CH$_2$)$_2$— | —NH— | K786 | J96 | O |
| 2-0350 | —(CH$_2$)$_2$— | —NH— | K786 | J96 | S |
| 2-0351 | —(CH$_2$)$_2$— | —NH— | K786 | J104 | O |
| 2-0352 | —(CH$_2$)$_2$— | —NH— | K786 | J104 | S |

TABLE 46

| Compound No. | -A$^1$- | -A$^2$- | -G$^1$-A$^3$-A$^4$-G$^2$ | -A$^5$-R$^2$ | X |
|---|---|---|---|---|---|
| 2-0353 | —(CH$_2$)$_2$— | —NH— | K786 | J117 | O |
| 2-0354 | —(CH$_2$)$_2$— | —NH— | K786 | J117 | S |
| 2-0355 | —(CH$_2$)$_2$— | —NH— | K787 | J96 | O |
| 2-0356 | —(CH$_2$)$_2$— | —NH— | K787 | J96 | S |
| 2-0357 | —(CH$_2$)$_2$— | —NH— | K787 | J104 | O |
| 2-0358 | —(CH$_2$)$_2$— | —NH— | K787 | J104 | S |
| 2-0359 | —(CH$_2$)$_2$— | —NH— | K787 | J117 | O |
| 2-0360 | —(CH$_2$)$_2$— | —NH— | K787 | J117 | S |
| 2-0361 | —(CH$_2$)$_3$— | —NH— | K662 | J22 | O |
| 2-0362 | —(CH$_2$)$_3$— | —NH— | K662 | J22 | S |
| 2-0363 | —(CH$_2$)$_3$— | —NH— | K662 | J28 | O |
| 2-0364 | —(CH$_2$)$_3$— | —NH— | K662 | J28 | S |
| 2-0365 | —(CH$_2$)$_3$— | —NH— | K662 | J76 | O |
| 2-0366 | —(CH$_2$)$_3$— | —NH— | K662 | J76 | S |
| 2-0367 | —(CH$_2$)$_3$— | —NH— | K782 | J22 | O |
| 2-0368 | —(CH$_2$)$_3$— | —NH— | K782 | J22 | S |
| 2-0369 | —(CH$_2$)$_3$— | —NH— | K782 | J28 | O |
| 2-0370 | —(CH$_2$)$_3$— | —NH— | K782 | J28 | S |
| 2-0371 | —(CH$_2$)$_3$— | —NH— | K782 | J76 | O |
| 2-0372 | —(CH$_2$)$_3$— | —NH— | K782 | J76 | S |
| 2-0373 | —(CH$_2$)$_3$— | —NH— | K111 | J116 | O |
| 2-0374 | —(CH$_2$)$_3$— | —NH— | K111 | J116 | S |
| 2-0375 | —(CH$_2$)$_3$— | —NH— | K111 | J121 | O |
| 2-0376 | —(CH$_2$)$_3$— | —NH— | K111 | J121 | S |
| 2-0377 | —(CH$_2$)$_3$— | —NH— | K111 | J124 | O |
| 2-0378 | —(CH$_2$)$_3$— | —NH— | K111 | J124 | S |
| 2-0379 | —(CH$_2$)$_3$— | —NH— | K788 | J22 | O |
| 2-0380 | —(CH$_2$)$_3$— | —NH— | K788 | J22 | S |
| 2-0381 | —(CH$_2$)$_3$— | —NH— | K788 | J28 | O |
| 2-0382 | —(CH$_2$)$_3$— | —NH— | K788 | J28 | S |
| 2-0383 | —(CH$_2$)$_3$— | —NH— | K788 | J76 | O |
| 2-0384 | —(CH$_2$)$_3$— | —NH— | K788 | J76 | S |

TABLE 47

| Compound No. | -A¹- | -A²- | -G¹-A³-A⁴-G² | -A⁵-R² | X |
|---|---|---|---|---|---|
| 2-0385 | —(CH$_2$)$_3$— | —NH— | K789 | J116 | O |
| 2-0386 | —(CH$_2$)$_3$— | —NH— | K789 | J116 | S |
| 2-0387 | —(CH$_2$)$_3$— | —NH— | K789 | J121 | O |
| 2-0388 | —(CH$_2$)$_3$— | —NH— | K789 | J121 | S |
| 2-0389 | —(CH$_2$)$_3$— | —NH— | K789 | J124 | O |
| 2-0390 | —(CH$_2$)$_3$— | —NH— | K789 | J124 | S |
| 2-0391 | —(CH$_2$)$_3$— | —NH— | K790 | J22 | O |
| 2-0392 | —(CH$_2$)$_3$— | —NH— | K790 | J22 | S |
| 2-0393 | —(CH$_2$)$_3$— | —NH— | K790 | J28 | O |
| 2-0394 | —(CH$_2$)$_3$— | —NH— | K790 | J28 | S |
| 2-0395 | —(CH$_2$)$_3$— | —NH— | K790 | J76 | O |
| 2-0396 | —(CH$_2$)$_3$— | —NH— | K790 | J76 | S |
| 2-0397 | —(CH$_2$)$_3$— | —NH— | K791 | J22 | O |
| 2-0398 | —(CH$_2$)$_3$— | —NH— | K791 | J22 | S |
| 2-0399 | —(CH$_2$)$_3$— | —NH— | K791 | J28 | O |
| 2-0400 | —(CH$_2$)$_3$— | —NH— | K791 | J28 | S |
| 2-0401 | —(CH$_2$)$_3$— | —NH— | K791 | J76 | O |
| 2-0402 | —(CH$_2$)$_3$— | —NH— | K791 | J76 | S |
| 2-0403 | —(CH$_2$)$_3$— | —NH— | K791 | J116 | O |
| 2-0404 | —(CH$_2$)$_3$— | —NH— | K791 | J116 | S |
| 2-0405 | —(CH$_2$)$_3$— | —NH— | K791 | J121 | O |
| 2-0406 | —(CH$_2$)$_3$— | —NH— | K791 | J121 | S |
| 2-0407 | —(CH$_2$)$_3$— | —NH— | K791 | J124 | O |
| 2-0408 | —(CH$_2$)$_3$— | —NH— | K791 | J124 | S |
| 2-0409 | —(CH$_2$)$_3$— | —NH— | K792 | J22 | O |
| 2-0410 | —(CH$_2$)$_3$— | —NH— | K792 | J22 | S |
| 2-0411 | —(CH$_2$)$_3$— | —NH— | K792 | J28 | O |
| 2-0412 | —(CH$_2$)$_3$— | —NH— | K792 | J28 | S |
| 2-0413 | —(CH$_2$)$_3$— | —NH— | K792 | J76 | O |
| 2-0414 | —(CH$_2$)$_3$— | —NH— | K792 | J76 | S |
| 2-0415 | —(CH$_2$)$_3$— | —NH— | K786 | J22 | O |
| 2-0416 | —(CH$_2$)$_3$— | —NH— | K786 | J22 | S |

TABLE 48

| Compound No. | -A¹- | -A²- | -G¹-A³-A⁴-G² | -A⁵-R² | X |
|---|---|---|---|---|---|
| 2-0417 | —(CH$_2$)$_3$— | —NH— | K786 | J28 | O |
| 2-0418 | —(CH$_2$)$_3$— | —NH— | K786 | J28 | S |
| 2-0419 | —(CH$_2$)$_3$— | —NH— | K786 | J76 | O |
| 2-0420 | —(CH$_2$)$_3$— | —NH— | K786 | J76 | S |
| 2-0421 | —(CH$_2$)$_3$— | —NH— | K793 | J22 | O |
| 2-0422 | —(CH$_2$)$_3$— | —NH— | K793 | J22 | S |
| 2-0423 | —(CH$_2$)$_3$— | —NH— | K793 | J28 | O |
| 2-0424 | —(CH$_2$)$_3$— | —NH— | K793 | J28 | S |
| 2-0425 | —(CH$_2$)$_3$— | —NH— | K793 | J76 | O |
| 2-0426 | —(CH$_2$)$_3$— | —NH— | K793 | J76 | S |
| 2-0427 | —(CH$_2$)$_4$— | —NH— | K695 | J16 | O |
| 2-0428 | —(CH$_2$)$_4$— | —NH— | K695 | J16 | S |
| 2-0429 | —(CH$_2$)$_4$— | —NH— | K695 | J37 | O |
| 2-0430 | —(CH$_2$)$_4$— | —NH— | K695 | J37 | S |
| 2-0431 | —(CH$_2$)$_4$— | —NH— | K695 | J87 | O |
| 2-0432 | —(CH$_2$)$_4$— | —NH— | K695 | J87 | S |
| 2-0433 | —(CH$_2$)$_4$— | —NH— | K101 | J16 | O |
| 2-0434 | —(CH$_2$)$_4$— | —NH— | K101 | J16 | S |
| 2-0435 | —(CH$_2$)$_4$— | —NH— | K101 | J37 | O |
| 2-0436 | —(CH$_2$)$_4$— | —NH— | K101 | J37 | S |
| 2-0437 | —(CH$_2$)$_4$— | —NH— | K101 | J87 | O |
| 2-0438 | —(CH$_2$)$_4$— | —NH— | K101 | J87 | S |
| 2-0439 | —(CH$_2$)$_4$— | —NH— | K666 | J120 | O |
| 2-0440 | —(CH$_2$)$_4$— | —NH— | K666 | J120 | S |
| 2-0441 | —(CH$_2$)$_4$— | —NH— | K666 | J122 | O |
| 2-0442 | —(CH$_2$)$_4$— | —NH— | K666 | J122 | S |
| 2-0443 | —(CH$_2$)$_4$— | —NH— | K107 | J120 | O |
| 2-0444 | —(CH$_2$)$_4$— | —NH— | K107 | J120 | S |
| 2-0445 | —(CH$_2$)$_4$— | —NH— | K107 | J122 | O |
| 2-0446 | —(CH$_2$)$_4$— | —NH— | K107 | J122 | S |
| 2-0447 | —(CH$_2$)$_4$— | —NH— | K794 | J16 | O |
| 2-0448 | —(CH$_2$)$_4$— | —NH— | K794 | J16 | S |

TABLE 49

| Compound No. | -A¹- | -A²- | -G¹-A³-A⁴-G² | -A⁵-R² | X |
|---|---|---|---|---|---|
| 2-0449 | —(CH$_2$)$_4$— | —NH— | K794 | J37 | O |
| 2-0450 | —(CH$_2$)$_4$— | —NH— | K794 | J37 | S |
| 2-0451 | —(CH$_2$)$_4$— | —NH— | K794 | J87 | O |
| 2-0452 | —(CH$_2$)$_4$— | —NH— | K794 | J87 | S |
| 2-0453 | —(CH$_2$)$_4$— | —NH— | K791 | J16 | O |
| 2-0454 | —(CH$_2$)$_4$— | —NH— | K791 | J16 | S |
| 2-0455 | —(CH$_2$)$_4$— | —NH— | K791 | J37 | O |
| 2-0456 | —(CH$_2$)$_4$— | —NH— | K791 | J37 | S |
| 2-0457 | —(CH$_2$)$_4$— | —NH— | K791 | J87 | O |
| 2-0458 | —(CH$_2$)$_4$— | —NH— | K791 | J87 | S |
| 2-0459 | —(CH$_2$)$_2$— | —NH—S(=O)$_2$— | K13 | J30 | O |
| 2-0460 | —(CH$_2$)$_2$— | —NH—S(=O)$_2$— | K13 | J30 | S |
| 2-0461 | —(CH$_2$)$_2$— | —NH—S(=O)$_2$— | K13 | J72 | O |
| 2-0462 | —(CH$_2$)$_2$— | —NH—S(=O)$_2$— | K13 | J72 | S |
| 2-0463 | —(CH$_2$)$_2$— | —NH—S(=O)$_2$— | K34 | J3 | O |
| 2-0464 | —(CH$_2$)$_2$— | —NH—S(=O)$_2$— | K34 | J3 | S |
| 2-0465 | —(CH$_2$)$_2$— | —NH—S(=O)$_2$— | K36 | J30 | O |
| 2-0466 | —(CH$_2$)$_2$— | —NH—S(=O)$_2$— | K36 | J30 | S |
| 2-0467 | —(CH$_2$)$_2$— | —NH—S(=O)$_2$— | K36 | J72 | O |
| 2-0468 | —(CH$_2$)$_2$— | —NH—S(=O)$_2$— | K36 | J72 | S |
| 2-0469 | —(CH$_2$)$_2$— | —NH—S(=O)$_2$— | K109 | J30 | O |
| 2-0470 | —(CH$_2$)$_2$— | —NH—S(=O)$_2$— | K109 | J30 | S |
| 2-0471 | —(CH$_2$)$_2$— | —NH—S(=O)$_2$— | K109 | J72 | O |
| 2-0472 | —(CH$_2$)$_2$— | —NH—S(=O)$_2$— | K109 | J72 | S |
| 2-0473 | —(CH$_2$)$_3$— | —NH—S(=O)$_2$— | K34 | J28 | O |
| 2-0474 | —(CH$_2$)$_3$— | —NH—S(=O)$_2$— | K34 | J28 | S |
| 2-0475 | —(CH$_2$)$_3$— | —NH—S(=O)$_2$— | K34 | J64 | O |
| 2-0476 | —(CH$_2$)$_3$— | —NH—S(=O)$_2$— | K34 | J64 | S |
| 2-0477 | —(CH$_2$)$_3$— | —NH—S(=O)$_2$— | K73 | J3 | O |
| 2-0478 | —(CH$_2$)$_3$— | —NH—S(=O)$_2$— | K73 | J3 | S |
| 2-0479 | —(CH$_2$)$_3$— | —NH—S(=O)$_2$— | K73 | J28 | O |
| 2-0480 | —(CH$_2$)$_3$— | —NH—S(=O)$_2$— | K73 | J28 | S |

TABLE 50

| Compound No. | -A¹- | -A²- | -G¹-A³-A⁴-G² | -A⁵-R² | X |
|---|---|---|---|---|---|
| 2-0481 | —(CH$_2$)$_3$— | —NH—S(=O)$_2$— | K73 | J64 | O |
| 2-0482 | —(CH$_2$)$_3$— | —NH—S(=O)$_2$— | K73 | J64 | S |
| 2-0483 | —(CH$_2$)$_3$— | —NH—S(=O)$_2$— | K107 | J3 | O |
| 2-0484 | —(CH$_2$)$_3$— | —NH—S(=O)$_2$— | K107 | J3 | S |
| 2-0485 | —(CH$_2$)$_3$— | —NH—S(=O)$_2$— | K107 | J28 | O |
| 2-0486 | —(CH$_2$)$_3$— | —NH—S(=O)$_2$— | K107 | J28 | S |
| 2-0487 | —(CH$_2$)$_3$— | —NH—S(=O)$_2$— | K107 | J64 | O |
| 2-0488 | —(CH$_2$)$_3$— | —NH—S(=O)$_2$— | K107 | J64 | S |
| 2-0489 | —(CH$_2$)$_3$— | —NH—S(=O)$_2$— | K114 | J3 | O |
| 2-0490 | —(CH$_2$)$_3$— | —NH—S(=O)$_2$— | K114 | J3 | S |
| 2-0491 | —(CH$_2$)$_3$— | —NH—S(=O)$_2$— | K114 | J28 | O |
| 2-0492 | —(CH$_2$)$_3$— | —NH—S(=O)$_2$— | K114 | J28 | S |
| 2-0493 | —(CH$_2$)$_3$— | —NH—S(=O)$_2$— | K114 | J64 | O |
| 2-0494 | —(CH$_2$)$_3$— | —NH—S(=O)$_2$— | K114 | J64 | S |
| 2-0495 | —(CH$_2$)$_4$— | —NH—S(=O)$_2$— | K15 | J27 | O |
| 2-0496 | —(CH$_2$)$_4$— | —NH—S(=O)$_2$— | K15 | J27 | S |
| 2-0497 | —(CH$_2$)$_4$— | —NH—S(=O)$_2$— | K15 | J89 | O |
| 2-0498 | —(CH$_2$)$_4$— | —NH—S(=O)$_2$— | K15 | J89 | S |
| 2-0499 | —(CH$_2$)$_4$— | —NH—S(=O)$_2$— | K79 | J27 | O |
| 2-0500 | —(CH$_2$)$_4$— | —NH—S(=O)$_2$— | K79 | J27 | S |
| 2-0501 | —(CH$_2$)$_4$— | —NH—S(=O)$_2$— | K79 | J89 | O |
| 2-0502 | —(CH$_2$)$_4$— | —NH—S(=O)$_2$— | K79 | J89 | S |
| 2-0503 | —(CH$_2$)$_4$— | —NH—S(=O)$_2$— | K106 | J27 | O |
| 2-0504 | —(CH$_2$)$_4$— | —NH—S(=O)$_2$— | K106 | J27 | S |
| 2-0505 | —(CH$_2$)$_4$— | —NH—S(=O)$_2$— | K106 | J89 | O |
| 2-0506 | —(CH$_2$)$_4$— | —NH—S(=O)$_2$— | K106 | J89 | S |
| 2-0507 | —(CH$_2$)$_2$— | —O—C(=O)— | K1 | J9 | O |
| 2-0508 | —(CH$_2$)$_2$— | —O—C(=O)— | K11 | J9 | O |
| 2-0509 | —(CH$_2$)$_2$— | —O—C(=O)— | K13 | J9 | O |
| 2-0510 | —(CH$_2$)$_2$— | —O—C(=O)— | K24 | J2 | O |
| 2-0511 | —(CH$_2$)$_2$— | —O—C(=O)— | K24 | J2 | S |
| 2-0512 | —(CH$_2$)$_2$— | —O—C(=O)— | K24 | J27 | O |

TABLE 51

| Compound No. | -A¹- | -A²- | -G¹-A³-A⁴-G² | -A⁵-R² | X |
|---|---|---|---|---|---|
| 2-0513 | —(CH$_2$)$_2$— | —O—C(=O)— | K24 | J27 | S |
| 2-0514 | —(CH$_2$)$_2$— | —O—C(=O)— | K49 | J9 | O |
| 2-0515 | —(CH$_2$)$_2$— | —O—C(=O)— | K109 | J2 | O |
| 2-0516 | —(CH$_2$)$_2$— | —O—C(=O)— | K109 | J2 | S |
| 2-0517 | —(CH$_2$)$_2$— | —O—C(=O)— | K109 | J27 | O |
| 2-0518 | —(CH$_2$)$_2$— | —O—C(=O)— | K109 | J27 | S |
| 2-0519 | —(CH$_2$)$_3$— | —O—C(=O)— | K1 | J9 | O |
| 2-0520 | —(CH$_2$)$_3$— | —O—C(=O)— | K7 | J9 | O |
| 2-0521 | —(CH$_2$)$_3$— | —O—C(=O)— | K11 | J9 | O |
| 2-0522 | —(CH$_2$)$_3$— | —O—C(=O)— | K12 | J9 | O |
| 2-0523 | —(CH$_2$)$_3$— | —O—C(=O)— | K13 | J9 | O |
| 2-0524 | —(CH$_2$)$_3$— | —O—C(=O)— | K14 | J9 | O |
| 2-0525 | —(CH$_2$)$_3$— | —O—C(=O)— | K28 | J9 | O |
| 2-0526 | —(CH$_2$)$_3$— | —O—C(=O)— | K30 | J9 | O |
| 2-0527 | —(CH$_2$)$_3$— | —O—C(=O)— | K31 | J9 | O |
| 2-0528 | —(CH$_2$)$_3$— | —O—C(=O)— | K24 | J9 | O |
| 2-0529 | —(CH$_2$)$_3$— | —O—C(=O)— | K49 | J9 | O |
| 2-0530 | —(CH$_2$)$_3$— | —O—C(=O)— | K60 | J9 | O |
| 2-0531 | —(CH$_2$)$_3$— | —O—C(=O)— | K62 | J9 | O |
| 2-0532 | —(CH$_2$)$_3$— | —O—C(=O)— | K63 | J43 | O |
| 2-0533 | —(CH$_2$)$_3$— | —O—C(=O)— | K63 | J43 | S |
| 2-0534 | —(CH$_2$)$_3$— | —O—C(=O)— | K63 | J82 | O |
| 2-0535 | —(CH$_2$)$_3$— | —O—C(=O)— | K63 | J82 | S |
| 2-0536 | —(CH$_2$)$_3$— | —O—C(=O)— | K71 | J9 | O |
| 2-0537 | —(CH$_2$)$_3$— | —O—C(=O)— | K72 | J9 | O |
| 2-0538 | —(CH$_2$)$_3$— | —O—C(=O)— | K82 | J9 | O |
| 2-0539 | —(CH$_2$)$_3$— | —O—C(=O)— | K83 | J9 | O |
| 2-0540 | —(CH$_2$)$_3$— | —O—C(=O)— | K88 | J43 | O |
| 2-0541 | —(CH$_2$)$_3$— | —O—C(=O)— | K88 | J43 | S |
| 2-0542 | —(CH$_2$)$_3$— | —O—C(=O)— | K88 | J82 | O |
| 2-0543 | —(CH$_2$)$_3$— | —O—C(=O)— | K88 | J82 | S |
| 2-0544 | —(CH$_2$)$_4$— | —O—C(=O)— | K23 | J28 | O |

TABLE 52

| Compound No. | -A¹- | -A²- | -G¹-A³-A⁴-G² | -A⁵-R² | X |
|---|---|---|---|---|---|
| 2-0545 | —(CH$_2$)$_4$— | —O—C(=O)— | K23 | J28 | S |
| 2-0546 | —(CH$_2$)$_4$— | —O—C(=O)— | K23 | J84 | O |
| 2-0547 | —(CH$_2$)$_4$— | —O—C(=O)— | K23 | J84 | S |
| 2-0548 | —(CH$_2$)$_4$— | —O—C(=O)— | K73 | J28 | O |
| 2-0549 | —(CH$_2$)$_4$— | —O—C(=O)— | K73 | J28 | S |
| 2-0550 | —(CH$_2$)$_4$— | —O—C(=O)— | K73 | J84 | O |
| 2-0551 | —(CH$_2$)$_4$— | —O—C(=O)— | K73 | J84 | S |
| 2-0552 | —(CH$_2$)$_2$— | —NH—C(=O)— | K1 | J9 | S |
| 2-0553 | —(CH$_2$)$_2$— | —NH—C(=O)— | K1 | J126 | S |
| 2-0554 | —(CH$_2$)$_2$— | —NH—C(=O)— | K1 | J129 | S |
| 2-0555 | —(CH$_2$)$_2$— | —NH—C(=O)— | K1 | J130 | S |
| 2-0556 | —(CH$_2$)$_2$— | —NH—C(=O)— | K1 | J138 | S |
| 2-0557 | —(CH$_2$)$_2$— | —NH—C(=O)— | K103 | J9 | S |
| 2-0558 | —(CH$_2$)$_2$— | —NH—C(=O)— | K11 | J9 | S |
| 2-0559 | —(CH$_2$)$_2$— | —NH—C(=O)— | K11 | J126 | S |
| 2-0560 | —(CH$_2$)$_2$— | —NH—C(=O)— | K11 | J129 | S |
| 2-0561 | —(CH$_2$)$_2$— | —NH—C(=O)— | K11 | J130 | S |
| 2-0562 | —(CH$_2$)$_2$— | —NH—C(=O)— | K11 | J138 | S |
| 2-0563 | —(CH$_2$)$_2$— | —NH—C(=O)— | K12 | J9 | S |
| 2-0564 | —(CH$_2$)$_2$— | —NH—C(=O)— | K12 | J126 | S |
| 2-0565 | —(CH$_2$)$_2$— | —NH—C(=O)— | K12 | J129 | S |
| 2-0566 | —(CH$_2$)$_2$— | —NH—C(=O)— | K12 | J130 | S |
| 2-0567 | —(CH$_2$)$_2$— | —NH—C(=O)— | K12 | J138 | S |
| 2-0568 | —(CH$_2$)$_2$— | —NH—C(=O)— | K13 | J9 | S |
| 2-0569 | —(CH$_2$)$_2$— | —NH—C(=O)— | K13 | J126 | S |
| 2-0570 | —(CH$_2$)$_2$— | —NH—C(=O)— | K13 | J129 | S |
| 2-0571 | —(CH$_2$)$_2$— | —NH—C(=O)— | K13 | J130 | S |
| 2-0572 | —(CH$_2$)$_2$— | —NH—C(=O)— | K13 | J138 | S |
| 2-0573 | —(CH$_2$)$_2$— | —NH—C(=O)— | K14 | J9 | S |
| 2-0574 | —(CH$_2$)$_2$— | —NH—C(=O)— | K14 | J126 | S |
| 2-0575 | —(CH$_2$)$_2$— | —NH—C(=O)— | K14 | J129 | S |
| 2-0576 | —(CH$_2$)$_2$— | —NH—C(=O)— | K14 | J130 | S |

TABLE 53

| Compound No. | -A¹- | -A²- | -G¹-A³-A⁴-G² | -A⁵-R² | X |
|---|---|---|---|---|---|
| 2-0577 | —(CH$_2$)$_2$— | —NH—C(=O)— | K14 | J138 | S |
| 2-0578 | —(CH$_2$)$_2$— | —NH—C(=O)— | K15 | J9 | S |
| 2-0579 | —(CH$_2$)$_2$— | —NH—C(=O)— | K15 | J126 | S |
| 2-0580 | —(CH$_2$)$_2$— | —NH—C(=O)— | K15 | J129 | S |
| 2-0581 | —(CH$_2$)$_2$— | —NH—C(=O)— | K15 | J130 | S |
| 2-0582 | —(CH$_2$)$_2$— | —NH—C(=O)— | K15 | J138 | S |
| 2-0583 | —(CH$_2$)$_2$— | —NH—C(=O)— | K16 | J9 | S |
| 2-0584 | —(CH$_2$)$_2$— | —NH—C(=O)— | K17 | J9 | S |
| 2-0585 | —(CH$_2$)$_2$— | —NH—C(=O)— | K18 | J9 | S |
| 2-0586 | —(CH$_2$)$_2$— | —NH—C(=O)— | K19 | J9 | S |
| 2-0587 | —(CH$_2$)$_2$— | —NH—C(=O)— | K20 | J9 | S |
| 2-0588 | —(CH$_2$)$_2$— | —NH—C(=O)— | K21 | J9 | S |
| 2-0589 | —(CH$_2$)$_2$— | —NH—C(=O)— | K22 | J9 | S |
| 2-0590 | —(CH$_2$)$_2$— | —NH—C(=O)— | K23 | J9 | S |
| 2-0591 | —(CH$_2$)$_2$— | —NH—C(=O)— | K23 | J126 | S |
| 2-0592 | —(CH$_2$)$_2$— | —NH—C(=O)— | K23 | J129 | S |
| 2-0593 | —(CH$_2$)$_2$— | —NH—C(=O)— | K23 | J130 | S |
| 2-0594 | —(CH$_2$)$_2$— | —NH—C(=O)— | K23 | J138 | S |
| 2-0595 | —(CH$_2$)$_2$— | —NH—C(=O)— | K24 | J9 | S |
| 2-0596 | —(CH$_2$)$_2$— | —NH—C(=O)— | K24 | J126 | S |
| 2-0597 | —(CH$_2$)$_2$— | —NH—C(=O)— | K24 | J129 | S |
| 2-0598 | —(CH$_2$)$_2$— | —NH—C(=O)— | K24 | J130 | S |
| 2-0599 | —(CH$_2$)$_2$— | —NH—C(=O)— | K24 | J138 | S |
| 2-0600 | —(CH$_2$)$_2$— | —NH—C(=O)— | K241 | J9 | S |
| 2-0601 | —(CH$_2$)$_2$— | —NH—C(=O)— | K241 | J126 | S |
| 2-0602 | —(CH$_2$)$_2$— | —NH—C(=O)— | K241 | J129 | S |
| 2-0603 | —(CH$_2$)$_2$— | —NH—C(=O)— | K241 | J130 | S |
| 2-0604 | —(CH$_2$)$_2$— | —NH—C(=O)— | K241 | J138 | S |
| 2-0605 | —(CH$_2$)$_2$— | —NH—C(=O)— | K241 | J14 | S |
| 2-0606 | —(CH$_2$)$_2$— | —NH—C(=O)— | K241 | J150 | S |
| 2-0607 | —(CH$_2$)$_2$— | —NH—C(=O)— | K242 | J9 | S |
| 2-0608 | —(CH$_2$)$_2$— | —NH—C(=O)— | K242 | J126 | S |

TABLE 54

| Compound No. | -A¹- | -A²- | -G¹-A³-A⁴-G² | -A⁵-R² | X |
|---|---|---|---|---|---|
| 2-0609 | —(CH$_2$)$_2$— | —NH—C(=O)— | K242 | J129 | S |
| 2-0610 | —(CH$_2$)$_2$— | —NH—C(=O)— | K242 | J130 | S |
| 2-0611 | —(CH$_2$)$_2$— | —NH—C(=O)— | K242 | J138 | S |
| 2-0612 | —(CH$_2$)$_2$— | —NH—C(=O)— | K242 | J16 | S |
| 2-0613 | —(CH$_2$)$_2$— | —NH—C(=O)— | K242 | J151 | S |
| 2-0614 | —(CH$_2$)$_2$— | —NH—C(=O)— | K243 | J9 | S |
| 2-0615 | —(CH$_2$)$_2$— | —NH—C(=O)— | K243 | J126 | S |
| 2-0616 | —(CH$_2$)$_2$— | —NH—C(=O)— | K243 | J129 | S |
| 2-0617 | —(CH$_2$)$_2$— | —NH—C(=O)— | K243 | J130 | S |
| 2-0618 | —(CH$_2$)$_2$— | —NH—C(=O)— | K243 | J138 | S |
| 2-0619 | —(CH$_2$)$_2$— | —NH—C(=O)— | K243 | J16 | S |
| 2-0620 | —(CH$_2$)$_2$— | —NH—C(=O)— | K243 | J151 | S |
| 2-0621 | —(CH$_2$)$_2$— | —NH—C(=O)— | K244 | J9 | S |
| 2-0622 | —(CH$_2$)$_2$— | —NH—C(=O)— | K244 | J126 | S |
| 2-0623 | —(CH$_2$)$_2$— | —NH—C(=O)— | K244 | J129 | S |
| 2-0624 | —(CH$_2$)$_2$— | —NH—C(=O)— | K244 | J130 | S |
| 2-0625 | —(CH$_2$)$_2$— | —NH—C(=O)— | K244 | J138 | S |
| 2-0626 | —(CH$_2$)$_2$— | —NH—C(=O)— | K244 | J19 | S |
| 2-0627 | —(CH$_2$)$_2$— | —NH—C(=O)— | K244 | J152 | S |
| 2-0628 | —(CH$_2$)$_2$— | —NH—C(=O)— | K245 | J9 | S |
| 2-0629 | —(CH$_2$)$_2$— | —NH—C(=O)— | K245 | J126 | S |
| 2-0630 | —(CH$_2$)$_2$— | —NH—C(=O)— | K245 | J129 | S |
| 2-0631 | —(CH$_2$)$_2$— | —NH—C(=O)— | K245 | J130 | S |
| 2-0632 | —(CH$_2$)$_2$— | —NH—C(=O)— | K245 | J138 | S |
| 2-0633 | —(CH$_2$)$_2$— | —NH—C(=O)— | K245 | J19 | S |
| 2-0634 | —(CH$_2$)$_2$— | —NH—C(=O)— | K245 | J152 | S |
| 2-0635 | —(CH$_2$)$_2$— | —NH—C(=O)— | K246 | J9 | S |
| 2-0636 | —(CH$_2$)$_2$— | —NH—C(=O)— | K246 | J126 | S |
| 2-0637 | —(CH$_2$)$_2$— | —NH—C(=O)— | K246 | J129 | S |
| 2-0638 | —(CH$_2$)$_2$— | —NH—C(=O)— | K246 | J130 | S |
| 2-0639 | —(CH$_2$)$_2$— | —NH—C(=O)— | K246 | J138 | S |
| 2-0640 | —(CH$_2$)$_2$— | —NH—C(=O)— | K246 | J22 | S |

TABLE 55

| Compound No. | -A$^1$- | -A$^2$- | -G$^1$-A$^3$-A$^4$-G$^2$ | -A$^5$-R$^2$ | X |
|---|---|---|---|---|---|
| 2-0641 | —(CH$_2$)$_2$— | —NH—C(=O)— | K246 | J153 | S |
| 2-0642 | —(CH$_2$)$_2$— | —NH—C(=O)— | K247 | J9 | S |
| 2-0643 | —(CH$_2$)$_2$— | —NH—C(=O)— | K247 | J126 | S |
| 2-0644 | —(CH$_2$)$_2$— | —NH—C(=O)— | K247 | J129 | S |
| 2-0645 | —(CH$_2$)$_2$— | —NH—C(=O)— | K247 | J130 | S |
| 2-0646 | —(CH$_2$)$_2$— | —NH—C(=O)— | K247 | J138 | S |
| 2-0647 | —(CH$_2$)$_2$— | —NH—C(=O)— | K247 | J22 | S |
| 2-0648 | —(CH$_2$)$_2$— | —NH—C(=O)— | K247 | J153 | S |
| 2-0649 | —(CH$_2$)$_2$— | —NH—C(=O)— | K248 | J9 | S |
| 2-0650 | —(CH$_2$)$_2$— | —NH—C(=O)— | K248 | J126 | S |
| 2-0651 | —(CH$_2$)$_2$— | —NH—C(=O)— | K248 | J129 | S |
| 2-0652 | —(CH$_2$)$_2$— | —NH—C(=O)— | K248 | J130 | S |
| 2-0653 | —(CH$_2$)$_2$— | —NH—C(=O)— | K248 | J138 | S |
| 2-0654 | —(CH$_2$)$_2$— | —NH—C(=O)— | K248 | J25 | S |
| 2-0655 | —(CH$_2$)$_2$— | —NH—C(=O)— | K248 | J154 | S |
| 2-0656 | —(CH$_2$)$_2$— | —NH—C(=O)— | K249 | J9 | S |
| 2-0657 | —(CH$_2$)$_2$— | —NH—C(=O)— | K249 | J126 | S |
| 2-0658 | —(CH$_2$)$_2$— | —NH—C(=O)— | K249 | J129 | S |
| 2-0659 | —(CH$_2$)$_2$— | —NH—C(=O)— | K249 | J130 | S |
| 2-0660 | —(CH$_2$)$_2$— | —NH—C(=O)— | K249 | J138 | S |
| 2-0661 | —(CH$_2$)$_2$— | —NH—C(=O)— | K249 | J25 | S |
| 2-0662 | —(CH$_2$)$_2$— | —NH—C(=O)— | K249 | J154 | S |
| 2-0663 | —(CH$_2$)$_2$— | —NH—C(=O)— | K25 | J9 | S |
| 2-0664 | —(CH$_2$)$_2$— | —NH—C(=O)— | K250 | J9 | S |
| 2-0665 | —(CH$_2$)$_2$— | —NH—C(=O)— | K250 | J126 | S |
| 2-0666 | —(CH$_2$)$_2$— | —NH—C(=O)— | K250 | J129 | S |
| 2-0667 | —(CH$_2$)$_2$— | —NH—C(=O)— | K250 | J130 | S |
| 2-0668 | —(CH$_2$)$_2$— | —NH—C(=O)— | K250 | J138 | S |
| 2-0669 | —(CH$_2$)$_2$— | —NH—C(=O)— | K250 | J26 | S |
| 2-0670 | —(CH$_2$)$_2$— | —NH—C(=O)— | K250 | J155 | S |
| 2-0671 | —(CH$_2$)$_2$— | —NH—C(=O)— | K251 | J9 | S |
| 2-0672 | —(CH$_2$)$_2$— | —NH—C(=O)— | K251 | J126 | S |

TABLE 56

| Compound No. | -A$^1$- | -A$^2$- | -G$^1$-A$^3$-A$^4$-G$^2$ | -A$^5$-R$^2$ | X |
|---|---|---|---|---|---|
| 2-0673 | —(CH$_2$)$_2$— | —NH—C(=O)— | K251 | J129 | S |
| 2-0674 | —(CH$_2$)$_2$— | —NH—C(=O)— | K251 | J130 | S |
| 2-0675 | —(CH$_2$)$_2$— | —NH—C(=O)— | K251 | J138 | S |
| 2-0676 | —(CH$_2$)$_2$— | —NH—C(=O)— | K251 | J26 | S |
| 2-0677 | —(CH$_2$)$_2$— | —NH—C(=O)— | K251 | J155 | S |
| 2-0678 | —(CH$_2$)$_2$— | —NH—C(=O)— | K252 | J9 | S |
| 2-0679 | —(CH$_2$)$_2$— | —NH—C(=O)— | K253 | J9 | S |
| 2-0680 | —(CH$_2$)$_2$— | —NH—C(=O)— | K254 | J9 | S |
| 2-0681 | —(CH$_2$)$_2$— | —NH—C(=O)— | K26 | J9 | S |
| 2-0682 | —(CH$_2$)$_2$— | —NH—C(=O)— | K27 | J9 | S |
| 2-0683 | —(CH$_2$)$_2$— | —NH—C(=O)— | K27 | J126 | S |
| 2-0684 | —(CH$_2$)$_2$— | —NH—C(=O)— | K27 | J129 | S |
| 2-0685 | —(CH$_2$)$_2$— | —NH—C(=O)— | K27 | J130 | S |
| 2-0686 | —(CH$_2$)$_2$— | —NH—C(=O)— | K27 | J138 | S |
| 2-0687 | —(CH$_2$)$_2$— | —NH—C(=O)— | K28 | J9 | S |
| 2-0688 | —(CH$_2$)$_2$— | —NH—C(=O)— | K282 | J9 | S |
| 2-0689 | —(CH$_2$)$_2$— | —NH—C(=O)— | K282 | J126 | S |
| 2-0690 | —(CH$_2$)$_2$— | —NH—C(=O)— | K282 | J129 | S |
| 2-0691 | —(CH$_2$)$_2$— | —NH—C(=O)— | K282 | J130 | S |
| 2-0692 | —(CH$_2$)$_2$— | —NH—C(=O)— | K282 | J138 | S |
| 2-0693 | —(CH$_2$)$_2$— | —NH—C(=O)— | K283 | J9 | S |
| 2-0694 | —(CH$_2$)$_2$— | —NH—C(=O)— | K283 | J126 | S |
| 2-0695 | —(CH$_2$)$_2$— | —NH—C(=O)— | K283 | J129 | S |
| 2-0696 | —(CH$_2$)$_2$— | —NH—C(=O)— | K283 | J130 | S |
| 2-0697 | —(CH$_2$)$_2$— | —NH—C(=O)— | K283 | J138 | S |
| 2-0698 | —(CH$_2$)$_2$— | —NH—C(=O)— | K284 | J9 | S |
| 2-0699 | —(CH$_2$)$_2$— | —NH—C(=O)— | K284 | J126 | S |
| 2-0700 | —(CH$_2$)$_2$— | —NH—C(=O)— | K284 | J129 | S |
| 2-0701 | —(CH$_2$)$_2$— | —NH—C(=O)— | K284 | J130 | S |
| 2-0702 | —(CH$_2$)$_2$— | —NH—C(=O)— | K284 | J138 | S |
| 2-0703 | —(CH$_2$)$_2$— | —NH—C(=O)— | K285 | J9 | S |
| 2-0704 | —(CH$_2$)$_2$— | —NH—C(=O)— | K286 | J9 | S |

TABLE 57

| Compound No. | -A$^1$- | -A$^2$- | -G$^1$-A$^3$-A$^4$-G$^2$ | -A$^5$-R$^2$ | X |
|---|---|---|---|---|---|
| 2-0705 | —(CH$_2$)$_2$— | —NH—C(=O)— | K287 | J9 | S |
| 2-0706 | —(CH$_2$)$_2$— | —NH—C(=O)— | K288 | J9 | S |
| 2-0707 | —(CH$_2$)$_2$— | —NH—C(=O)— | K289 | J9 | S |
| 2-0708 | —(CH$_2$)$_2$— | —NH—C(=O)— | K29 | J9 | S |
| 2-0709 | —(CH$_2$)$_2$— | —NH—C(=O)— | K290 | J9 | S |
| 2-0710 | —(CH$_2$)$_2$— | —NH—C(=O)— | K291 | J9 | S |
| 2-0711 | —(CH$_2$)$_2$— | —NH—C(=O)— | K292 | J9 | S |
| 2-0712 | —(CH$_2$)$_2$— | —NH—C(=O)— | K292 | J28 | S |
| 2-0713 | —(CH$_2$)$_2$— | —NH—C(=O)— | K292 | J156 | S |
| 2-0714 | —(CH$_2$)$_2$— | —NH—C(=O)— | K293 | J9 | S |
| 2-0715 | —(CH$_2$)$_2$— | —NH—C(=O)— | K294 | J9 | S |
| 2-0716 | —(CH$_2$)$_2$— | —NH—C(=O)— | K295 | J9 | S |
| 2-0717 | —(CH$_2$)$_2$— | —NH—C(=O)— | K295 | J28 | S |
| 2-0718 | —(CH$_2$)$_2$— | —NH—C(=O)— | K295 | J156 | S |
| 2-0719 | —(CH$_2$)$_2$— | —NH—C(=O)— | K296 | J9 | S |
| 2-0720 | —(CH$_2$)$_2$— | —NH—C(=O)— | K296 | J126 | S |
| 2-0721 | —(CH$_2$)$_2$— | —NH—C(=O)— | K296 | J129 | S |
| 2-0722 | —(CH$_2$)$_2$— | —NH—C(=O)— | K296 | J130 | S |
| 2-0723 | —(CH$_2$)$_2$— | —NH—C(=O)— | K296 | J138 | S |
| 2-0724 | —(CH$_2$)$_2$— | —NH—C(=O)— | K297 | J9 | S |
| 2-0725 | —(CH$_2$)$_2$— | —NH—C(=O)— | K297 | J126 | S |
| 2-0726 | —(CH$_2$)$_2$— | —NH—C(=O)— | K297 | J129 | S |
| 2-0727 | —(CH$_2$)$_2$— | —NH—C(=O)— | K297 | J130 | S |
| 2-0728 | —(CH$_2$)$_2$— | —NH—C(=O)— | K297 | J138 | S |
| 2-0729 | —(CH$_2$)$_2$— | —NH—C(=O)— | K298 | J9 | S |
| 2-0730 | —(CH$_2$)$_2$— | —NH—C(=O)— | K299 | J9 | S |
| 2-0731 | —(CH$_2$)$_2$— | —NH—C(=O)— | K30 | J9 | S |
| 2-0732 | —(CH$_2$)$_2$— | —NH—C(=O)— | K300 | J9 | S |
| 2-0733 | —(CH$_2$)$_2$— | —NH—C(=O)— | K300 | J29 | S |
| 2-0734 | —(CH$_2$)$_2$— | —NH—C(=O)— | K300 | J157 | S |
| 2-0735 | —(CH$_2$)$_2$— | —NH—C(=O)— | K301 | J9 | S |
| 2-0736 | —(CH$_2$)$_2$— | —NH—C(=O)— | K301 | J29 | S |

TABLE 58

| Compound No. | -A$^1$- | -A$^2$- | -G$^1$-A$^3$-A$^4$-G$^2$ | -A$^5$-R$^2$ | X |
|---|---|---|---|---|---|
| 2-0737 | —(CH$_2$)$_2$— | —NH—C(=O)— | K301 | J157 | S |
| 2-0738 | —(CH$_2$)$_2$— | —NH—C(=O)— | K303 | J9 | S |
| 2-0739 | —(CH$_2$)$_2$— | —NH—C(=O)— | K304 | J9 | S |
| 2-0740 | —(CH$_2$)$_2$— | —NH—C(=O)— | K305 | J9 | S |
| 2-0741 | —(CH$_2$)$_2$— | —NH—C(=O)— | K305 | J126 | S |
| 2-0742 | —(CH$_2$)$_2$— | —NH—C(=O)— | K305 | J129 | S |
| 2-0743 | —(CH$_2$)$_2$— | —NH—C(=O)— | K305 | J130 | S |
| 2-0744 | —(CH$_2$)$_2$— | —NH—C(=O)— | K305 | J138 | S |
| 2-0745 | —(CH$_2$)$_2$— | —NH—C(=O)— | K305 | J31 | S |
| 2-0746 | —(CH$_2$)$_2$— | —NH—C(=O)— | K305 | J158 | S |
| 2-0747 | —(CH$_2$)$_2$— | —NH—C(=O)— | K306 | J9 | S |
| 2-0748 | —(CH$_2$)$_2$— | —NH—C(=O)— | K306 | J126 | S |
| 2-0749 | —(CH$_2$)$_2$— | —NH—C(=O)— | K306 | J129 | S |
| 2-0750 | —(CH$_2$)$_2$— | —NH—C(=O)— | K306 | J130 | S |
| 2-0751 | —(CH$_2$)$_2$— | —NH—C(=O)— | K306 | J138 | S |
| 2-0752 | —(CH$_2$)$_2$— | —NH—C(=O)— | K306 | J31 | S |
| 2-0753 | —(CH$_2$)$_2$— | —NH—C(=O)— | K306 | J158 | S |
| 2-0754 | —(CH$_2$)$_2$— | —NH—C(=O)— | K307 | J9 | S |
| 2-0755 | —(CH$_2$)$_2$— | —NH—C(=O)— | K307 | J126 | S |
| 2-0756 | —(CH$_2$)$_2$— | —NH—C(=O)— | K307 | J129 | S |
| 2-0757 | —(CH$_2$)$_2$— | —NH—C(=O)— | K307 | J130 | S |
| 2-0758 | —(CH$_2$)$_2$— | —NH—C(=O)— | K307 | J138 | S |
| 2-0759 | —(CH$_2$)$_2$— | —NH—C(=O)— | K307 | J33 | S |
| 2-0760 | —(CH$_2$)$_2$— | —NH—C(=O)— | K307 | J159 | S |
| 2-0761 | —(CH$_2$)$_2$— | —NH—C(=O)— | K31 | J9 | S |
| 2-0762 | —(CH$_2$)$_2$— | —NH—C(=O)— | K31 | J126 | S |
| 2-0763 | —(CH$_2$)$_2$— | —NH—C(=O)— | K31 | J129 | S |
| 2-0764 | —(CH$_2$)$_2$— | —NH—C(=O)— | K31 | J130 | S |
| 2-0765 | —(CH$_2$)$_2$— | —NH—C(=O)— | K31 | J138 | S |
| 2-0766 | —(CH$_2$)$_2$— | —NH—C(=O)— | K32 | J9 | S |
| 2-0767 | —(CH$_2$)$_2$— | —NH—C(=O)— | K32 | J126 | S |
| 2-0768 | —(CH$_2$)$_2$— | —NH—C(=O)— | K32 | J129 | S |

TABLE 59

| Compound No. | -A¹- | -A²- | -G¹-A³-A⁴-G² | -A⁵-R² | X |
|---|---|---|---|---|---|
| 2-0769 | —(CH$_2$)$_2$— | —NH—C(=O)— | K32 | J130 | S |
| 2-0770 | —(CH$_2$)$_2$— | —NH—C(=O)— | K32 | J138 | S |
| 2-0771 | —(CH$_2$)$_2$— | —NH—C(=O)— | K33 | J9 | S |
| 2-0772 | —(CH$_2$)$_2$— | —NH—C(=O)— | K34 | J9 | S |
| 2-0773 | —(CH$_2$)$_2$— | —NH—C(=O)— | K34 | J126 | S |
| 2-0774 | —(CH$_2$)$_2$— | —NH—C(=O)— | K34 | J129 | S |
| 2-0775 | —(CH$_2$)$_2$— | —NH—C(=O)— | K34 | J130 | S |
| 2-0776 | —(CH$_2$)$_2$— | —NH—C(=O)— | K34 | J138 | S |
| 2-0777 | —(CH$_2$)$_2$— | —NH—C(=O)— | K35 | J9 | S |
| 2-0778 | —(CH$_2$)$_2$— | —NH—C(=O)— | K35 | J126 | S |
| 2-0779 | —(CH$_2$)$_2$— | —NH—C(=O)— | K35 | J129 | S |
| 2-0780 | —(CH$_2$)$_2$— | —NH—C(=O)— | K35 | J130 | S |
| 2-0781 | —(CH$_2$)$_2$— | —NH—C(=O)— | K35 | J138 | S |
| 2-0782 | —(CH$_2$)$_2$— | —NH—C(=O)— | K36 | J9 | S |
| 2-0783 | —(CH$_2$)$_2$— | —NH—C(=O)— | K36 | J126 | S |
| 2-0784 | —(CH$_2$)$_2$— | —NH—C(=O)— | K36 | J129 | S |
| 2-0785 | —(CH$_2$)$_2$— | —NH—C(=O)— | K36 | J130 | S |
| 2-0786 | —(CH$_2$)$_2$— | —NH—C(=O)— | K36 | J138 | S |
| 2-0787 | —(CH$_2$)$_2$— | —NH—C(=O)— | K37 | J9 | S |
| 2-0788 | —(CH$_2$)$_2$— | —NH—C(=O)— | K37 | J126 | S |
| 2-0789 | —(CH$_2$)$_2$— | —NH—C(=O)— | K37 | J129 | S |
| 2-0790 | —(CH$_2$)$_2$— | —NH—C(=O)— | K37 | J130 | S |
| 2-0791 | —(CH$_2$)$_2$— | —NH—C(=O)— | K37 | J138 | S |
| 2-0792 | —(CH$_2$)$_2$— | —NH—C(=O)— | K38 | J9 | S |
| 2-0793 | —(CH$_2$)$_2$— | —NH—C(=O)— | K38 | J126 | S |
| 2-0794 | —(CH$_2$)$_2$— | —NH—C(=O)— | K38 | J129 | S |
| 2-0795 | —(CH$_2$)$_2$— | —NH—C(=O)— | K38 | J130 | S |
| 2-0796 | —(CH$_2$)$_2$— | —NH—C(=O)— | K38 | J138 | S |
| 2-0797 | —(CH$_2$)$_2$— | —NH—C(=O)— | K39 | J9 | S |
| 2-0798 | —(CH$_2$)$_2$— | —NH—C(=O)— | K39 | J126 | S |
| 2-0799 | —(CH$_2$)$_2$— | —NH—C(=O)— | K39 | J129 | S |
| 2-0800 | —(CH$_2$)$_2$— | —NH—C(=O)— | K39 | J130 | S |

TABLE 60

| Compound No. | -A¹- | -A²- | -G¹-A³-A⁴-G² | -A⁵-R² | X |
|---|---|---|---|---|---|
| 2-0801 | —(CH$_2$)$_2$— | —NH—C(=O)— | K39 | J138 | S |
| 2-0802 | —(CH$_2$)$_2$— | —NH—C(=O)— | K4 | J9 | S |
| 2-0803 | —(CH$_2$)$_2$— | —NH—C(=O)— | K40 | J9 | S |
| 2-0804 | —(CH$_2$)$_2$— | —NH—C(=O)— | K41 | J9 | S |
| 2-0805 | —(CH$_2$)$_2$— | —NH—C(=O)— | K42 | J9 | S |
| 2-0806 | —(CH$_2$)$_2$— | —NH—C(=O)— | K423 | J9 | S |
| 2-0807 | —(CH$_2$)$_2$— | —NH—C(=O)— | K423 | J33 | S |
| 2-0808 | —(CH$_2$)$_2$— | —NH—C(=O)— | K423 | J159 | S |
| 2-0809 | —(CH$_2$)$_2$— | —NH—C(=O)— | K424 | J9 | S |
| 2-0810 | —(CH$_2$)$_2$— | —NH—C(=O)— | K424 | J34 | S |
| 2-0811 | —(CH$_2$)$_2$— | —NH—C(=O)— | K424 | J163 | S |
| 2-0812 | —(CH$_2$)$_2$— | —NH—C(=O)— | K425 | J9 | S |
| 2-0813 | —(CH$_2$)$_2$— | —NH—C(=O)— | K425 | J34 | S |
| 2-0814 | —(CH$_2$)$_2$— | —NH—C(=O)— | K425 | J163 | S |
| 2-0815 | —(CH$_2$)$_2$— | —NH—C(=O)— | K43 | J9 | S |
| 2-0816 | —(CH$_2$)$_2$— | —NH—C(=O)— | K44 | J9 | S |
| 2-0817 | —(CH$_2$)$_2$— | —NH—C(=O)— | K443 | J9 | S |
| 2-0818 | —(CH$_2$)$_2$— | —NH—C(=O)— | K443 | J126 | S |
| 2-0819 | —(CH$_2$)$_2$— | —NH—C(=O)— | K443 | J129 | S |
| 2-0820 | —(CH$_2$)$_2$— | —NH—C(=O)— | K443 | J130 | S |
| 2-0821 | —(CH$_2$)$_2$— | —NH—C(=O)— | K443 | J138 | S |
| 2-0822 | —(CH$_2$)$_2$— | —NH—C(=O)— | K444 | J9 | S |
| 2-0823 | —(CH$_2$)$_2$— | —NH—C(=O)— | K445 | J9 | S |
| 2-0824 | —(CH$_2$)$_2$— | —NH—C(=O)— | K445 | J126 | S |
| 2-0825 | —(CH$_2$)$_2$— | —NH—C(=O)— | K445 | J129 | S |
| 2-0826 | —(CH$_2$)$_2$— | —NH—C(=O)— | K445 | J130 | S |
| 2-0827 | —(CH$_2$)$_2$— | —NH—C(=O)— | K445 | J138 | S |
| 2-0828 | —(CH$_2$)$_2$— | —NH—C(=O)— | K449 | J9 | S |
| 2-0829 | —(CH$_2$)$_2$— | —NH—C(=O)— | K449 | J126 | S |
| 2-0830 | —(CH$_2$)$_2$— | —NH—C(=O)— | K449 | J129 | S |
| 2-0831 | —(CH$_2$)$_2$— | —NH—C(=O)— | K449 | J130 | S |
| 2-0832 | —(CH$_2$)$_2$— | —NH—C(=O)— | K449 | J138 | S |

TABLE 61

| Compound No. | -A¹- | -A²- | -G¹-A³-A⁴-G² | -A⁵-R² | X |
|---|---|---|---|---|---|
| 2-0833 | —(CH$_2$)$_2$— | —NH—C(=O)— | K45 | J9 | S |
| 2-0834 | —(CH$_2$)$_2$— | —NH—C(=O)— | K450 | J9 | S |
| 2-0835 | —(CH$_2$)$_2$— | —NH—C(=O)— | K450 | J126 | S |
| 2-0836 | —(CH$_2$)$_2$— | —NH—C(=O)— | K450 | J129 | S |
| 2-0837 | —(CH$_2$)$_2$— | —NH—C(=O)— | K450 | J130 | S |
| 2-0838 | —(CH$_2$)$_2$— | —NH—C(=O)— | K450 | J138 | S |
| 2-0839 | —(CH$_2$)$_2$— | —NH—C(=O)— | K46 | J9 | S |
| 2-0840 | —(CH$_2$)$_2$— | —NH—C(=O)— | K469 | J126 | S |
| 2-0841 | —(CH$_2$)$_2$— | —NH—C(=O)— | K469 | J129 | S |
| 2-0842 | —(CH$_2$)$_2$— | —NH—C(=O)— | K469 | J130 | S |
| 2-0843 | —(CH$_2$)$_2$— | —NH—C(=O)— | K469 | J138 | S |
| 2-0844 | —(CH$_2$)$_2$— | —NH—C(=O)— | K47 | J9 | S |
| 2-0845 | —(CH$_2$)$_2$— | —NH—C(=O)— | K471 | J126 | S |
| 2-0846 | —(CH$_2$)$_2$— | —NH—C(=O)— | K471 | J129 | S |
| 2-0847 | —(CH$_2$)$_2$— | —NH—C(=O)— | K471 | J130 | S |
| 2-0848 | —(CH$_2$)$_2$— | —NH—C(=O)— | K471 | J138 | S |
| 2-0849 | —(CH$_2$)$_2$— | —NH—C(=O)— | K472 | J9 | S |
| 2-0850 | —(CH$_2$)$_2$— | —NH—C(=O)— | K473 | J9 | S |
| 2-0851 | —(CH$_2$)$_2$— | —NH—C(=O)— | K474 | J9 | S |
| 2-0852 | —(CH$_2$)$_2$— | —NH—C(=O)— | K475 | J9 | S |
| 2-0853 | —(CH$_2$)$_2$— | —NH—C(=O)— | K476 | J9 | S |
| 2-0854 | —(CH$_2$)$_2$— | —NH—C(=O)— | K477 | J9 | S |
| 2-0855 | —(CH$_2$)$_2$— | —NH—C(=O)— | K478 | J9 | S |
| 2-0856 | —(CH$_2$)$_2$— | —NH—C(=O)— | K478 | J126 | S |
| 2-0857 | —(CH$_2$)$_2$— | —NH—C(=O)— | K478 | J129 | S |
| 2-0858 | —(CH$_2$)$_2$— | —NH—C(=O)— | K478 | J130 | S |
| 2-0859 | —(CH$_2$)$_2$— | —NH—C(=O)— | K478 | J138 | S |
| 2-0860 | —(CH$_2$)$_2$— | —NH—C(=O)— | K478 | J37 | S |
| 2-0861 | —(CH$_2$)$_2$— | —NH—C(=O)— | K478 | J165 | S |
| 2-0862 | —(CH$_2$)$_2$— | —NH—C(=O)— | K479 | J9 | S |
| 2-0863 | —(CH$_2$)$_2$— | —NH—C(=O)— | K479 | J126 | S |
| 2-0864 | —(CH$_2$)$_2$— | —NH—C(=O)— | K479 | J129 | S |

TABLE 62

| Compound No. | -A¹- | -A²- | -G¹-A³-A⁴-G² | -A⁵-R² | X |
|---|---|---|---|---|---|
| 2-0865 | —(CH$_2$)$_2$— | —NH—C(=O)— | K479 | J130 | S |
| 2-0866 | —(CH$_2$)$_2$— | —NH—C(=O)— | K479 | J138 | S |
| 2-0867 | —(CH$_2$)$_2$— | —NH—C(=O)— | K48 | J9 | S |
| 2-0868 | —(CH$_2$)$_2$— | —NH—C(=O)— | K480 | J9 | S |
| 2-0869 | —(CH$_2$)$_2$— | —NH—C(=O)— | K481 | J9 | S |
| 2-0870 | —(CH$_2$)$_2$— | —NH—C(=O)— | K482 | J9 | S |
| 2-0871 | —(CH$_2$)$_2$— | —NH—C(=O)— | K483 | J9 | S |
| 2-0872 | —(CH$_2$)$_2$— | —NH—C(=O)— | K484 | J9 | S |
| 2-0873 | —(CH$_2$)$_2$— | —NH—C(=O)— | K485 | J9 | S |
| 2-0874 | —(CH$_2$)$_2$— | —NH—C(=O)— | K485 | J126 | S |
| 2-0875 | —(CH$_2$)$_2$— | —NH—C(=O)— | K485 | J129 | S |
| 2-0876 | —(CH$_2$)$_2$— | —NH—C(=O)— | K485 | J130 | S |
| 2-0877 | —(CH$_2$)$_2$— | —NH—C(=O)— | K485 | J138 | S |
| 2-0878 | —(CH$_2$)$_2$— | —NH—C(=O)— | K485 | J37 | S |
| 2-0879 | —(CH$_2$)$_2$— | —NH—C(=O)— | K485 | J165 | S |
| 2-0880 | —(CH$_2$)$_2$— | —NH—C(=O)— | K486 | J9 | S |
| 2-0881 | —(CH$_2$)$_2$— | —NH—C(=O)— | K487 | J9 | S |
| 2-0882 | —(CH$_2$)$_2$— | —NH—C(=O)— | K488 | J9 | S |
| 2-0883 | —(CH$_2$)$_2$— | —NH—C(=O)— | K489 | J9 | S |
| 2-0884 | —(CH$_2$)$_2$— | —NH—C(=O)— | K49 | J9 | S |
| 2-0885 | —(CH$_2$)$_2$— | —NH—C(=O)— | K49 | J126 | S |
| 2-0886 | —(CH$_2$)$_2$— | —NH—C(=O)— | K49 | J129 | S |
| 2-0887 | —(CH$_2$)$_2$— | —NH—C(=O)— | K49 | J130 | S |
| 2-0888 | —(CH$_2$)$_2$— | —NH—C(=O)— | K49 | J138 | S |
| 2-0889 | —(CH$_2$)$_2$— | —NH—C(=O)— | K490 | J9 | S |
| 2-0890 | —(CH$_2$)$_2$— | —NH—C(=O)— | K491 | J9 | S |
| 2-0891 | —(CH$_2$)$_2$— | —NH—C(=O)— | K492 | J9 | S |
| 2-0892 | —(CH$_2$)$_2$— | —NH—C(=O)— | K493 | J9 | S |
| 2-0893 | —(CH$_2$)$_2$— | —NH—C(=O)— | K494 | J9 | S |
| 2-0894 | —(CH$_2$)$_2$— | —NH—C(=O)— | K495 | J9 | S |
| 2-0895 | —(CH$_2$)$_2$— | —NH—C(=O)— | K496 | J9 | S |
| 2-0896 | —(CH$_2$)$_2$— | —NH—C(=O)— | K497 | J9 | S |

TABLE 63

| Compound No. | -A$^1$- | -A$^2$- | -G$^1$-A$^3$-A$^4$-G$^2$ | -A$^5$-R$^2$ | X |
|---|---|---|---|---|---|
| 2-0897 | —(CH$_2$)$_2$— | —NH—C(=O)— | K497 | J126 | S |
| 2-0898 | —(CH$_2$)$_2$— | —NH—C(=O)— | K497 | J129 | S |
| 2-0899 | —(CH$_2$)$_2$— | —NH—C(=O)— | K497 | J130 | S |
| 2-0900 | —(CH$_2$)$_2$— | —NH—C(=O)— | K497 | J138 | S |
| 2-0901 | —(CH$_2$)$_2$— | —NH—C(=O)— | K498 | J9 | S |
| 2-0902 | —(CH$_2$)$_2$— | —NH—C(=O)— | K498 | J126 | S |
| 2-0903 | —(CH$_2$)$_2$— | —NH—C(=O)— | K498 | J129 | S |
| 2-0904 | —(CH$_2$)$_2$— | —NH—C(=O)— | K498 | J130 | S |
| 2-0905 | —(CH$_2$)$_2$— | —NH—C(=O)— | K498 | J138 | S |
| 2-0906 | —(CH$_2$)$_2$— | —NH—C(=O)— | K499 | J9 | S |
| 2-0907 | —(CH$_2$)$_2$— | —NH—C(=O)— | K499 | J126 | S |
| 2-0908 | —(CH$_2$)$_2$— | —NH—C(=O)— | K499 | J129 | S |
| 2-0909 | —(CH$_2$)$_2$— | —NH—C(=O)— | K499 | J130 | S |
| 2-0910 | —(CH$_2$)$_2$— | —NH—C(=O)— | K499 | J138 | S |
| 2-0911 | —(CH$_2$)$_2$— | —NH—C(=O)— | K499 | J57 | S |
| 2-0912 | —(CH$_2$)$_2$— | —NH—C(=O)— | K499 | J166 | S |
| 2-0913 | —(CH$_2$)$_2$— | —NH—C(=O)— | K50 | J9 | S |
| 2-0914 | —(CH$_2$)$_2$— | —NH—C(=O)— | K500 | J9 | S |
| 2-0915 | —(CH$_2$)$_2$— | —NH—C(=O)— | K500 | J126 | S |
| 2-0916 | —(CH$_2$)$_2$— | —NH—C(=O)— | K500 | J129 | S |
| 2-0917 | —(CH$_2$)$_2$— | —NH—C(=O)— | K500 | J130 | S |
| 2-0918 | —(CH$_2$)$_2$— | —NH—C(=O)— | K500 | J138 | S |
| 2-0919 | —(CH$_2$)$_2$— | —NH—C(=O)— | K500 | J57 | S |
| 2-0920 | —(CH$_2$)$_2$— | —NH—C(=O)— | K500 | J166 | S |
| 2-0921 | —(CH$_2$)$_2$— | —NH—C(=O)— | K501 | J9 | S |
| 2-0922 | —(CH$_2$)$_2$— | —NH—C(=O)— | K501 | J126 | S |
| 2-0923 | —(CH$_2$)$_2$— | —NH—C(=O)— | K501 | J129 | S |
| 2-0924 | —(CH$_2$)$_2$— | —NH—C(=O)— | K501 | J130 | S |
| 2-0925 | —(CH$_2$)$_2$— | —NH—C(=O)— | K501 | J138 | S |
| 2-0926 | —(CH$_2$)$_2$— | —NH—C(=O)— | K501 | J58 | S |
| 2-0927 | —(CH$_2$)$_2$— | —NH—C(=O)— | K501 | J167 | S |
| 2-0928 | —(CH$_2$)$_2$— | —NH—C(=O)— | K502 | J9 | S |

TABLE 64

| Compound No. | -A$^1$- | -A$^2$- | -G$^1$-A$^3$-A$^4$-G$^2$ | -A$^5$-R$^2$ | X |
|---|---|---|---|---|---|
| 2-0929 | —(CH$_2$)$_2$— | —NH—C(=O)— | K502 | J58 | S |
| 2-0930 | —(CH$_2$)$_2$— | —NH—C(=O)— | K502 | J167 | S |
| 2-0931 | —(CH$_2$)$_2$— | —NH—C(=O)— | K503 | J9 | S |
| 2-0932 | —(CH$_2$)$_2$— | —NH—C(=O)— | K503 | J126 | S |
| 2-0933 | —(CH$_2$)$_2$— | —NH—C(=O)— | K503 | J129 | S |
| 2-0934 | —(CH$_2$)$_2$— | —NH—C(=O)— | K503 | J130 | S |
| 2-0935 | —(CH$_2$)$_2$— | —NH—C(=O)— | K503 | J138 | S |
| 2-0936 | —(CH$_2$)$_2$— | —NH—C(=O)— | K503 | J59 | S |
| 2-0937 | —(CH$_2$)$_2$— | —NH—C(=O)— | K503 | J168 | S |
| 2-0938 | —(CH$_2$)$_2$— | —NH—C(=O)— | K504 | J9 | S |
| 2-0939 | —(CH$_2$)$_2$— | —NH—C(=O)— | K504 | J59 | S |
| 2-0940 | —(CH$_2$)$_2$— | —NH—C(=O)— | K504 | J168 | S |
| 2-0941 | —(CH$_2$)$_2$— | —NH—C(=O)— | K505 | J9 | S |
| 2-0942 | —(CH$_2$)$_2$— | —NH—C(=O)— | K505 | J126 | S |
| 2-0943 | —(CH$_2$)$_2$— | —NH—C(=O)— | K505 | J129 | S |
| 2-0944 | —(CH$_2$)$_2$— | —NH—C(=O)— | K505 | J130 | S |
| 2-0945 | —(CH$_2$)$_2$— | —NH—C(=O)— | K505 | J138 | S |
| 2-0946 | —(CH$_2$)$_2$— | —NH—C(=O)— | K505 | J70 | S |
| 2-0947 | —(CH$_2$)$_2$— | —NH—C(=O)— | K505 | J169 | S |
| 2-0948 | —(CH$_2$)$_2$— | —NH—C(=O)— | K506 | J9 | S |
| 2-0949 | —(CH$_2$)$_2$— | —NH—C(=O)— | K506 | J126 | S |
| 2-0950 | —(CH$_2$)$_2$— | —NH—C(=O)— | K506 | J129 | S |
| 2-0951 | —(CH$_2$)$_2$— | —NH—C(=O)— | K506 | J130 | S |
| 2-0952 | —(CH$_2$)$_2$— | —NH—C(=O)— | K506 | J138 | S |
| 2-0953 | —(CH$_2$)$_2$— | —NH—C(=O)— | K506 | J70 | S |
| 2-0954 | —(CH$_2$)$_2$— | —NH—C(=O)— | K506 | J169 | S |
| 2-0955 | —(CH$_2$)$_2$— | —NH—C(=O)— | K507 | J9 | S |
| 2-0956 | —(CH$_2$)$_2$— | —NH—C(=O)— | K507 | J126 | S |
| 2-0957 | —(CH$_2$)$_2$— | —NH—C(=O)— | K507 | J129 | S |
| 2-0958 | —(CH$_2$)$_2$— | —NH—C(=O)— | K507 | J130 | S |
| 2-0959 | —(CH$_2$)$_2$— | —NH—C(=O)— | K507 | J138 | S |
| 2-0960 | —(CH$_2$)$_2$— | —NH—C(=O)— | K507 | J71 | S |

TABLE 65

| Compound No. | -A$^1$- | -A$^2$- | -G$^1$-A$^3$-A$^4$-G$^2$ | -A$^5$-R$^2$ | X |
|---|---|---|---|---|---|
| 2-0961 | —(CH$_2$)$_2$— | —NH—C(=O)— | K507 | J170 | S |
| 2-0962 | —(CH$_2$)$_2$— | —NH—C(=O)— | K508 | J9 | S |
| 2-0963 | —(CH$_2$)$_2$— | —NH—C(=O)— | K508 | J126 | S |
| 2-0964 | —(CH$_2$)$_2$— | —NH—C(=O)— | K508 | J129 | S |
| 2-0965 | —(CH$_2$)$_2$— | —NH—C(=O)— | K508 | J130 | S |
| 2-0966 | —(CH$_2$)$_2$— | —NH—C(=O)— | K508 | J138 | S |
| 2-0967 | —(CH$_2$)$_2$— | —NH—C(=O)— | K508 | J71 | S |
| 2-0968 | —(CH$_2$)$_2$— | —NH—C(=O)— | K508 | J170 | S |
| 2-0969 | —(CH$_2$)$_2$— | —NH—C(=O)— | K509 | J9 | S |
| 2-0970 | —(CH$_2$)$_2$— | —NH—C(=O)— | K509 | J72 | S |
| 2-0971 | —(CH$_2$)$_2$— | —NH—C(=O)— | K509 | J171 | S |
| 2-0972 | —(CH$_2$)$_2$— | —NH—C(=O)— | K51 | J9 | S |
| 2-0973 | —(CH$_2$)$_2$— | —NH—C(=O)— | K510 | J9 | S |
| 2-0974 | —(CH$_2$)$_2$— | —NH—C(=O)— | K510 | J126 | S |
| 2-0975 | —(CH$_2$)$_2$— | —NH—C(=O)— | K510 | J129 | S |
| 2-0976 | —(CH$_2$)$_2$— | —NH—C(=O)— | K510 | J130 | S |
| 2-0977 | —(CH$_2$)$_2$— | —NH—C(=O)— | K510 | J138 | S |
| 2-0978 | —(CH$_2$)$_2$— | —NH—C(=O)— | K510 | J72 | S |
| 2-0979 | —(CH$_2$)$_2$— | —NH—C(=O)— | K510 | J171 | S |
| 2-0980 | —(CH$_2$)$_2$— | —NH—C(=O)— | K511 | J9 | S |
| 2-0981 | —(CH$_2$)$_2$— | —NH—C(=O)— | K511 | J74 | S |
| 2-0982 | —(CH$_2$)$_2$— | —NH—C(=O)— | K511 | J174 | S |
| 2-0983 | —(CH$_2$)$_2$— | —NH—C(=O)— | K512 | J9 | S |
| 2-0984 | —(CH$_2$)$_2$— | —NH—C(=O)— | K512 | J74 | S |
| 2-0985 | —(CH$_2$)$_2$— | —NH—C(=O)— | K512 | J174 | S |
| 2-0986 | —(CH$_2$)$_2$— | —NH—C(=O)— | K513 | J9 | S |
| 2-0987 | —(CH$_2$)$_2$— | —NH—C(=O)— | K513 | J75 | S |
| 2-0988 | —(CH$_2$)$_2$— | —NH—C(=O)— | K513 | J175 | S |
| 2-0989 | —(CH$_2$)$_2$— | —NH—C(=O)— | K514 | J9 | S |
| 2-0990 | —(CH$_2$)$_2$— | —NH—C(=O)— | K514 | J75 | S |
| 2-0991 | —(CH$_2$)$_2$— | —NH—C(=O)— | K514 | J175 | S |
| 2-0992 | —(CH$_2$)$_2$— | —NH—C(=O)— | K515 | J9 | S |

TABLE 66

| Compound No. | -A$^1$- | -A$^2$- | -G$^1$-A$^3$-A$^4$-G$^2$ | -A$^5$-R$^2$ | X |
|---|---|---|---|---|---|
| 2-0993 | —(CH$_2$)$_2$— | —NH—C(=O)— | K516 | J9 | S |
| 2-0994 | —(CH$_2$)$_2$— | —NH—C(=O)— | K516 | J76 | S |
| 2-0995 | —(CH$_2$)$_2$— | —NH—C(=O)— | K516 | J176 | S |
| 2-0996 | —(CH$_2$)$_2$— | —NH—C(=O)— | K517 | J9 | S |
| 2-0997 | —(CH$_2$)$_2$— | —NH—C(=O)— | K517 | J126 | S |
| 2-0998 | —(CH$_2$)$_2$— | —NH—C(=O)— | K517 | J129 | S |
| 2-0999 | —(CH$_2$)$_2$— | —NH—C(=O)— | K517 | J130 | S |
| 2-1000 | —(CH$_2$)$_2$— | —NH—C(=O)— | K517 | J138 | S |
| 2-1001 | —(CH$_2$)$_2$— | —NH—C(=O)— | K517 | J76 | S |
| 2-1002 | —(CH$_2$)$_2$— | —NH—C(=O)— | K517 | J176 | S |
| 2-1003 | —(CH$_2$)$_2$— | —NH—C(=O)— | K518 | J9 | S |
| 2-1004 | —(CH$_2$)$_2$— | —NH—C(=O)— | K518 | J126 | S |
| 2-1005 | —(CH$_2$)$_2$— | —NH—C(=O)— | K518 | J129 | S |
| 2-1006 | —(CH$_2$)$_2$— | —NH—C(=O)— | K518 | J130 | S |
| 2-1007 | —(CH$_2$)$_2$— | —NH—C(=O)— | K518 | J138 | S |
| 2-1008 | —(CH$_2$)$_2$— | —NH—C(=O)— | K518 | J77 | S |
| 2-1009 | —(CH$_2$)$_2$— | —NH—C(=O)— | K518 | J177 | S |
| 2-1010 | —(CH$_2$)$_2$— | —NH—C(=O)— | K519 | J9 | S |
| 2-1011 | —(CH$_2$)$_2$— | —NH—C(=O)— | K519 | J126 | S |
| 2-1012 | —(CH$_2$)$_2$— | —NH—C(=O)— | K519 | J129 | S |
| 2-1013 | —(CH$_2$)$_2$— | —NH—C(=O)— | K519 | J130 | S |
| 2-1014 | —(CH$_2$)$_2$— | —NH—C(=O)— | K519 | J138 | S |
| 2-1015 | —(CH$_2$)$_2$— | —NH—C(=O)— | K519 | J77 | S |
| 2-1016 | —(CH$_2$)$_2$— | —NH—C(=O)— | K519 | J177 | S |
| 2-1017 | —(CH$_2$)$_2$— | —NH—C(=O)— | K52 | J9 | S |
| 2-1018 | —(CH$_2$)$_2$— | —NH—C(=O)— | K520 | J9 | S |
| 2-1019 | —(CH$_2$)$_2$— | —NH—C(=O)— | K521 | J9 | S |
| 2-1020 | —(CH$_2$)$_2$— | —NH—C(=O)— | K522 | J9 | S |
| 2-1021 | —(CH$_2$)$_2$— | —NH—C(=O)— | K523 | J9 | S |
| 2-1022 | —(CH$_2$)$_2$— | —NH—C(=O)— | K523 | J126 | S |
| 2-1023 | —(CH$_2$)$_2$— | —NH—C(=O)— | K523 | J129 | S |
| 2-1024 | —(CH$_2$)$_2$— | —NH—C(=O)— | K523 | J130 | S |

TABLE 67

| Compound No. | -A¹- | -A²- | -G¹-A³-A⁴-G² | -A⁵-R² | X |
|---|---|---|---|---|---|
| 2-1025 | —(CH$_2$)$_2$— | —NH—C(=O)— | K523 | J138 | S |
| 2-1026 | —(CH$_2$)$_2$— | —NH—C(=O)— | K523 | J78 | S |
| 2-1027 | —(CH$_2$)$_2$— | —NH—C(=O)— | K523 | J178 | S |
| 2-1028 | —(CH$_2$)$_2$— | —NH—C(=O)— | K524 | J9 | S |
| 2-1029 | —(CH$_2$)$_2$— | —NH—C(=O)— | K525 | J9 | S |
| 2-1030 | —(CH$_2$)$_2$— | —NH—C(=O)— | K525 | J126 | S |
| 2-1031 | —(CH$_2$)$_2$— | —NH—C(=O)— | K525 | J129 | S |
| 2-1032 | —(CH$_2$)$_2$— | —NH—C(=O)— | K525 | J130 | S |
| 2-1033 | —(CH$_2$)$_2$— | —NH—C(=O)— | K525 | J138 | S |
| 2-1034 | —(CH$_2$)$_2$— | —NH—C(=O)— | K525 | J78 | S |
| 2-1035 | —(CH$_2$)$_2$— | —NH—C(=O)— | K525 | J178 | S |
| 2-1036 | —(CH$_2$)$_2$— | —NH—C(=O)— | K526 | J9 | S |
| 2-1037 | —(CH$_2$)$_2$— | —NH—C(=O)— | K526 | J126 | S |
| 2-1038 | —(CH$_2$)$_2$— | —NH—C(=O)— | K526 | J129 | S |
| 2-1039 | —(CH$_2$)$_2$— | —NH—C(=O)— | K526 | J130 | S |
| 2-1040 | —(CH$_2$)$_2$— | —NH—C(=O)— | K526 | J138 | S |
| 2-1041 | —(CH$_2$)$_2$— | —NH—C(=O)— | K526 | J79 | S |
| 2-1042 | —(CH$_2$)$_2$— | —NH—C(=O)— | K526 | J179 | S |
| 2-1043 | —(CH$_2$)$_2$— | —NH—C(=O)— | K527 | J9 | S |
| 2-1044 | —(CH$_2$)$_2$— | —NH—C(=O)— | K528 | J9 | S |
| 2-1045 | —(CH$_2$)$_2$— | —NH—C(=O)— | K528 | J79 | S |
| 2-1046 | —(CH$_2$)$_2$— | —NH—C(=O)— | K528 | J179 | S |
| 2-1047 | —(CH$_2$)$_2$— | —NH—C(=O)— | K53 | J9 | S |
| 2-1048 | —(CH$_2$)$_2$— | —NH—C(=O)— | K53 | J126 | S |
| 2-1049 | —(CH$_2$)$_2$— | —NH—C(=O)— | K53 | J129 | S |
| 2-1050 | —(CH$_2$)$_2$— | —NH—C(=O)— | K53 | J130 | S |
| 2-1051 | —(CH$_2$)$_2$— | —NH—C(=O)— | K53 | J138 | S |
| 2-1052 | —(CH$_2$)$_2$— | —NH—C(=O)— | K531 | J9 | S |
| 2-1053 | —(CH$_2$)$_2$— | —NH—C(=O)— | K532 | J9 | S |
| 2-1054 | —(CH$_2$)$_2$— | —NH—C(=O)— | K533 | J9 | S |
| 2-1055 | —(CH$_2$)$_2$— | —NH—C(=O)— | K533 | J126 | S |
| 2-1056 | —(CH$_2$)$_2$— | —NH—C(=O)— | K533 | J129 | S |

TABLE 68

| Compound No. | -A¹- | -A²- | -G¹-A³-A⁴-G² | -A⁵-R² | X |
|---|---|---|---|---|---|
| 2-1057 | —(CH$_2$)$_2$— | —NH—C(=O)— | K533 | J130 | S |
| 2-1058 | —(CH$_2$)$_2$— | —NH—C(=O)— | K533 | J138 | S |
| 2-1059 | —(CH$_2$)$_2$— | —NH—C(=O)— | K534 | J9 | S |
| 2-1060 | —(CH$_2$)$_2$— | —NH—C(=O)— | K535 | J9 | S |
| 2-1061 | —(CH$_2$)$_2$— | —NH—C(=O)— | K535 | J126 | S |
| 2-1062 | —(CH$_2$)$_2$— | —NH—C(=O)— | K535 | J129 | S |
| 2-1063 | —(CH$_2$)$_2$— | —NH—C(=O)— | K535 | J130 | S |
| 2-1064 | —(CH$_2$)$_2$— | —NH—C(=O)— | K535 | J138 | S |
| 2-1065 | —(CH$_2$)$_2$— | —NH—C(=O)— | K536 | J9 | S |
| 2-1066 | —(CH$_2$)$_2$— | —NH—C(=O)— | K537 | J9 | S |
| 2-1067 | —(CH$_2$)$_2$— | —NH—C(=O)— | K538 | J9 | S |
| 2-1068 | —(CH$_2$)$_2$— | —NH—C(=O)— | K539 | J9 | S |
| 2-1069 | —(CH$_2$)$_2$— | —NH—C(=O)— | K54 | J9 | S |
| 2-1070 | —(CH$_2$)$_2$— | —NH—C(=O)— | K54 | J126 | S |
| 2-1071 | —(CH$_2$)$_2$— | —NH—C(=O)— | K54 | J129 | S |
| 2-1072 | —(CH$_2$)$_2$— | —NH—C(=O)— | K54 | J130 | S |
| 2-1073 | —(CH$_2$)$_2$— | —NH—C(=O)— | K54 | J138 | S |
| 2-1074 | —(CH$_2$)$_2$— | —NH—C(=O)— | K540 | J9 | S |
| 2-1075 | —(CH$_2$)$_2$— | —NH—C(=O)— | K541 | J9 | S |
| 2-1076 | —(CH$_2$)$_2$— | —NH—C(=O)— | K542 | J9 | S |
| 2-1077 | —(CH$_2$)$_2$— | —NH—C(=O)— | K542 | J126 | S |
| 2-1078 | —(CH$_2$)$_2$— | —NH—C(=O)— | K542 | J129 | S |
| 2-1079 | —(CH$_2$)$_2$— | —NH—C(=O)— | K542 | J130 | S |
| 2-1080 | —(CH$_2$)$_2$— | —NH—C(=O)— | K542 | J138 | S |
| 2-1081 | —(CH$_2$)$_2$— | —NH—C(=O)— | K542 | J81 | S |
| 2-1082 | —(CH$_2$)$_2$— | —NH—C(=O)— | K542 | J180 | S |
| 2-1083 | —(CH$_2$)$_2$— | —NH—C(=O)— | K543 | J9 | S |
| 2-1084 | —(CH$_2$)$_2$— | —NH—C(=O)— | K543 | J81 | S |
| 2-1085 | —(CH$_2$)$_2$— | —NH—C(=O)— | K543 | J180 | S |
| 2-1086 | —(CH$_2$)$_2$— | —NH—C(=O)— | K544 | J9 | S |
| 2-1087 | —(CH$_2$)$_2$— | —NH—C(=O)— | K545 | J9 | S |
| 2-1088 | —(CH$_2$)$_2$— | —NH—C(=O)— | K545 | J126 | S |

TABLE 69

| Compound No. | -A¹- | -A²- | -G¹-A³-A⁴-G² | -A⁵-R² | X |
|---|---|---|---|---|---|
| 2-1089 | —(CH$_2$)$_2$— | —NH—C(=O)— | K545 | J129 | S |
| 2-1090 | —(CH$_2$)$_2$— | —NH—C(=O)— | K545 | J130 | S |
| 2-1091 | —(CH$_2$)$_2$— | —NH—C(=O)— | K545 | J138 | S |
| 2-1092 | —(CH$_2$)$_2$— | —NH—C(=O)— | K545 | J83 | S |
| 2-1093 | —(CH$_2$)$_2$— | —NH—C(=O)— | K545 | J181 | S |
| 2-1094 | —(CH$_2$)$_2$— | —NH—C(=O)— | K546 | J9 | S |
| 2-1095 | —(CH$_2$)$_2$— | —NH—C(=O)— | K546 | J126 | S |
| 2-1096 | —(CH$_2$)$_2$— | —NH—C(=O)— | K546 | J129 | S |
| 2-1097 | —(CH$_2$)$_2$— | —NH—C(=O)— | K546 | J130 | S |
| 2-1098 | —(CH$_2$)$_2$— | —NH—C(=O)— | K546 | J138 | S |
| 2-1099 | —(CH$_2$)$_2$— | —NH—C(=O)— | K546 | J83 | S |
| 2-1100 | —(CH$_2$)$_2$— | —NH—C(=O)— | K546 | J181 | S |
| 2-1101 | —(CH$_2$)$_2$— | —NH—C(=O)— | K547 | J9 | S |
| 2-1102 | —(CH$_2$)$_2$— | —NH—C(=O)— | K547 | J126 | S |
| 2-1103 | —(CH$_2$)$_2$— | —NH—C(=O)— | K547 | J129 | S |
| 2-1104 | —(CH$_2$)$_2$— | —NH—C(=O)— | K547 | J130 | S |
| 2-1105 | —(CH$_2$)$_2$— | —NH—C(=O)— | K547 | J138 | S |
| 2-1106 | —(CH$_2$)$_2$— | —NH—C(=O)— | K547 | J84 | S |
| 2-1107 | —(CH$_2$)$_2$— | —NH—C(=O)— | K547 | J182 | S |
| 2-1108 | —(CH$_2$)$_2$— | —NH—C(=O)— | K548 | J9 | S |
| 2-1109 | —(CH$_2$)$_2$— | —NH—C(=O)— | K548 | J126 | S |
| 2-1110 | —(CH$_2$)$_2$— | —NH—C(=O)— | K548 | J129 | S |
| 2-1111 | —(CH$_2$)$_2$— | —NH—C(=O)— | K548 | J130 | S |
| 2-1112 | —(CH$_2$)$_2$— | —NH—C(=O)— | K548 | J138 | S |
| 2-1113 | —(CH$_2$)$_2$— | —NH—C(=O)— | K548 | J84 | S |
| 2-1114 | —(CH$_2$)$_2$— | —NH—C(=O)— | K548 | J182 | S |
| 2-1115 | —(CH$_2$)$_2$— | —NH—C(=O)— | K549 | J9 | S |
| 2-1116 | —(CH$_2$)$_2$— | —NH—C(=O)— | K549 | J126 | S |
| 2-1117 | —(CH$_2$)$_2$— | —NH—C(=O)— | K549 | J129 | S |
| 2-1118 | —(CH$_2$)$_2$— | —NH—C(=O)— | K549 | J130 | S |
| 2-1119 | —(CH$_2$)$_2$— | —NH—C(=O)— | K549 | J138 | S |
| 2-1120 | —(CH$_2$)$_2$— | —NH—C(=O)— | K549 | J87 | S |

TABLE 70

| Compound No. | -A¹- | -A²- | -G¹-A³-A⁴-G² | -A⁵-R² | X |
|---|---|---|---|---|---|
| 2-1121 | —(CH$_2$)$_2$— | —NH—C(=O)— | K549 | J185 | S |
| 2-1122 | —(CH$_2$)$_2$— | —NH—C(=O)— | K55 | J9 | S |
| 2-1123 | —(CH$_2$)$_2$— | —NH—C(=O)— | K550 | J9 | S |
| 2-1124 | —(CH$_2$)$_2$— | —NH—C(=O)— | K550 | J126 | S |
| 2-1125 | —(CH$_2$)$_2$— | —NH—C(=O)— | K550 | J129 | S |
| 2-1126 | —(CH$_2$)$_2$— | —NH—C(=O)— | K550 | J130 | S |
| 2-1127 | —(CH$_2$)$_2$— | —NH—C(=O)— | K550 | J138 | S |
| 2-1128 | —(CH$_2$)$_2$— | —NH—C(=O)— | K551 | J9 | S |
| 2-1129 | —(CH$_2$)$_2$— | —NH—C(=O)— | K551 | J126 | S |
| 2-1130 | —(CH$_2$)$_2$— | —NH—C(=O)— | K551 | J129 | S |
| 2-1131 | —(CH$_2$)$_2$— | —NH—C(=O)— | K551 | J130 | S |
| 2-1132 | —(CH$_2$)$_2$— | —NH—C(=O)— | K551 | J138 | S |
| 2-1133 | —(CH$_2$)$_2$— | —NH—C(=O)— | K552 | J9 | S |
| 2-1134 | —(CH$_2$)$_2$— | —NH—C(=O)— | K553 | J9 | S |
| 2-1135 | —(CH$_2$)$_2$— | —NH—C(=O)— | K554 | J9 | S |
| 2-1136 | —(CH$_2$)$_2$— | —NH—C(=O)— | K554 | J126 | S |
| 2-1137 | —(CH$_2$)$_2$— | —NH—C(=O)— | K554 | J129 | S |
| 2-1138 | —(CH$_2$)$_2$— | —NH—C(=O)— | K554 | J130 | S |
| 2-1139 | —(CH$_2$)$_2$— | —NH—C(=O)— | K554 | J138 | S |
| 2-1140 | —(CH$_2$)$_2$— | —NH—C(=O)— | K554 | J87 | S |
| 2-1141 | —(CH$_2$)$_2$— | —NH—C(=O)— | K554 | J185 | S |
| 2-1142 | —(CH$_2$)$_2$— | —NH—C(=O)— | K555 | J9 | S |
| 2-1143 | —(CH$_2$)$_2$— | —NH—C(=O)— | K556 | J9 | S |
| 2-1144 | —(CH$_2$)$_2$— | —NH—C(=O)— | K557 | J9 | S |
| 2-1145 | —(CH$_2$)$_2$— | —NH—C(=O)— | K558 | J9 | S |
| 2-1146 | —(CH$_2$)$_2$— | —NH—C(=O)— | K559 | J9 | S |
| 2-1147 | —(CH$_2$)$_2$— | —NH—C(=O)— | K56 | J9 | S |
| 2-1148 | —(CH$_2$)$_2$— | —NH—C(=O)— | K560 | J9 | S |
| 2-1149 | —(CH$_2$)$_2$— | —NH—C(=O)— | K561 | J9 | S |
| 2-1150 | —(CH$_2$)$_2$— | —NH—C(=O)— | K562 | J9 | S |
| 2-1151 | —(CH$_2$)$_2$— | —NH—C(=O)— | K563 | J9 | S |
| 2-1152 | —(CH$_2$)$_2$— | —NH—C(=O)— | K563 | J89 | S |

TABLE 71

| Compound No. | -A¹- | -A²- | -G¹-A³-A⁴-G² | -A⁵-R² | X |
|---|---|---|---|---|---|
| 2-1153 | —(CH$_2$)$_2$— | —NH—C(=O)— | K563 | J188 | S |
| 2-1154 | —(CH$_2$)$_2$— | —NH—C(=O)— | K564 | J9 | S |
| 2-1155 | —(CH$_2$)$_2$— | —NH—C(=O)— | K564 | J126 | S |
| 2-1156 | —(CH$_2$)$_2$— | —NH—C(=O)— | K564 | J129 | S |
| 2-1157 | —(CH$_2$)$_2$— | —NH—C(=O)— | K564 | J130 | S |
| 2-1158 | —(CH$_2$)$_2$— | —NH—C(=O)— | K564 | J138 | S |
| 2-1159 | —(CH$_2$)$_2$— | —NH—C(=O)— | K564 | J89 | S |
| 2-1160 | —(CH$_2$)$_2$— | —NH—C(=O)— | K564 | J188 | S |
| 2-1161 | —(CH$_2$)$_2$— | —NH—C(=O)— | K565 | J9 | S |
| 2-1162 | —(CH$_2$)$_2$— | —NH—C(=O)— | K566 | J9 | S |
| 2-1163 | —(CH$_2$)$_2$— | —NH—C(=O)— | K567 | J9 | S |
| 2-1164 | —(CH$_2$)$_2$— | —NH—C(=O)— | K567 | J126 | S |
| 2-1165 | —(CH$_2$)$_2$— | —NH—C(=O)— | K567 | J129 | S |
| 2-1166 | —(CH$_2$)$_2$— | —NH—C(=O)— | K567 | J130 | S |
| 2-1167 | —(CH$_2$)$_2$— | —NH—C(=O)— | K567 | J138 | S |
| 2-1168 | —(CH$_2$)$_2$— | —NH—C(=O)— | K567 | J120 | S |
| 2-1169 | —(CH$_2$)$_2$— | —NH—C(=O)— | K567 | J189 | S |
| 2-1170 | —(CH$_2$)$_2$— | —NH—C(=O)— | K568 | J9 | S |
| 2-1171 | —(CH$_2$)$_2$— | —NH—C(=O)— | K568 | J126 | S |
| 2-1172 | —(CH$_2$)$_2$— | —NH—C(=O)— | K568 | J129 | S |
| 2-1173 | —(CH$_2$)$_2$— | —NH—C(=O)— | K568 | J130 | S |
| 2-1174 | —(CH$_2$)$_2$— | —NH—C(=O)— | K568 | J138 | S |
| 2-1175 | —(CH$_2$)$_2$— | —NH—C(=O)— | K568 | J120 | S |
| 2-1176 | —(CH$_2$)$_2$— | —NH—C(=O)— | K568 | J189 | S |
| 2-1177 | —(CH$_2$)$_2$— | —NH—C(=O)— | K569 | J9 | S |
| 2-1178 | —(CH$_2$)$_2$— | —NH—C(=O)— | K569 | J126 | S |
| 2-1179 | —(CH$_2$)$_2$— | —NH—C(=O)— | K569 | J129 | S |
| 2-1180 | —(CH$_2$)$_2$— | —NH—C(=O)— | K569 | J130 | S |
| 2-1181 | —(CH$_2$)$_2$— | —NH—C(=O)— | K569 | J138 | S |
| 2-1182 | —(CH$_2$)$_2$— | —NH—C(=O)— | K569 | J121 | S |
| 2-1183 | —(CH$_2$)$_2$— | —NH—C(=O)— | K569 | J190 | S |
| 2-1184 | —(CH$_2$)$_2$— | —NH—C(=O)— | K57 | J9 | S |

TABLE 72

| Compound No. | -A¹- | -A²- | -G¹-A³-A⁴-G² | -A⁵-R² | X |
|---|---|---|---|---|---|
| 2-1185 | —(CH$_2$)$_2$— | —NH—C(=O)— | K570 | J9 | S |
| 2-1186 | —(CH$_2$)$_2$— | —NH—C(=O)— | K570 | J121 | S |
| 2-1187 | —(CH$_2$)$_2$— | —NH—C(=O)— | K570 | J190 | S |
| 2-1188 | —(CH$_2$)$_2$— | —NH—C(=O)— | K571 | J9 | S |
| 2-1189 | —(CH$_2$)$_2$— | —NH—C(=O)— | K571 | J126 | S |
| 2-1190 | —(CH$_2$)$_2$— | —NH—C(=O)— | K571 | J129 | S |
| 2-1191 | —(CH$_2$)$_2$— | —NH—C(=O)— | K571 | J130 | S |
| 2-1192 | —(CH$_2$)$_2$— | —NH—C(=O)— | K571 | J138 | S |
| 2-1193 | —(CH$_2$)$_2$— | —NH—C(=O)— | K571 | J122 | S |
| 2-1194 | —(CH$_2$)$_2$— | —NH—C(=O)— | K571 | J191 | S |
| 2-1195 | —(CH$_2$)$_2$— | —NH—C(=O)— | K572 | J9 | S |
| 2-1196 | —(CH$_2$)$_2$— | —NH—C(=O)— | K572 | J126 | S |
| 2-1197 | —(CH$_2$)$_2$— | —NH—C(=O)— | K572 | J129 | S |
| 2-1198 | —(CH$_2$)$_2$— | —NH—C(=O)— | K572 | J130 | S |
| 2-1199 | —(CH$_2$)$_2$— | —NH—C(=O)— | K572 | J138 | S |
| 2-1200 | —(CH$_2$)$_2$— | —NH—C(=O)— | K572 | J122 | S |
| 2-1201 | —(CH$_2$)$_2$— | —NH—C(=O)— | K572 | J191 | S |
| 2-1202 | —(CH$_2$)$_2$— | —NH—C(=O)— | K573 | J9 | S |
| 2-1203 | —(CH$_2$)$_2$— | —NH—C(=O)— | K573 | J126 | S |
| 2-1204 | —(CH$_2$)$_2$— | —NH—C(=O)— | K573 | J129 | S |
| 2-1205 | —(CH$_2$)$_2$— | —NH—C(=O)— | K573 | J130 | S |
| 2-1206 | —(CH$_2$)$_2$— | —NH—C(=O)— | K573 | J138 | S |
| 2-1207 | —(CH$_2$)$_2$— | —NH—C(=O)— | K573 | J123 | S |
| 2-1208 | —(CH$_2$)$_2$— | —NH—C(=O)— | K573 | J192 | S |
| 2-1209 | —(CH$_2$)$_2$— | —NH—C(=O)— | K574 | J9 | S |
| 2-1210 | —(CH$_2$)$_2$— | —NH—C(=O)— | K574 | J126 | S |
| 2-1211 | —(CH$_2$)$_2$— | —NH—C(=O)— | K574 | J129 | S |
| 2-1212 | —(CH$_2$)$_2$— | —NH—C(=O)— | K574 | J130 | S |
| 2-1213 | —(CH$_2$)$_2$— | —NH—C(=O)— | K574 | J138 | S |
| 2-1214 | —(CH$_2$)$_2$— | —NH—C(=O)— | K574 | J123 | S |
| 2-1215 | —(CH$_2$)$_2$— | —NH—C(=O)— | K574 | J192 | S |
| 2-1216 | —(CH$_2$)$_2$— | —NH—C(=O)— | K575 | J9 | S |

TABLE 73

| Compound No. | -A¹- | -A²- | -G¹-A³-A⁴-G² | -A⁵-R² | X |
|---|---|---|---|---|---|
| 2-1217 | —(CH$_2$)$_2$— | —NH—C(=O)— | K575 | J126 | S |
| 2-1218 | —(CH$_2$)$_2$— | —NH—C(=O)— | K575 | J129 | S |
| 2-1219 | —(CH$_2$)$_2$— | —NH—C(=O)— | K575 | J130 | S |
| 2-1220 | —(CH$_2$)$_2$— | —NH—C(=O)— | K575 | J138 | S |
| 2-1221 | —(CH$_2$)$_2$— | —NH—C(=O)— | K575 | J124 | S |
| 2-1222 | —(CH$_2$)$_2$— | —NH—C(=O)— | K575 | J193 | S |
| 2-1223 | —(CH$_2$)$_2$— | —NH—C(=O)— | K576 | J9 | S |
| 2-1224 | —(CH$_2$)$_2$— | —NH—C(=O)— | K576 | J124 | S |
| 2-1225 | —(CH$_2$)$_2$— | —NH—C(=O)— | K576 | J193 | S |
| 2-1226 | —(CH$_2$)$_2$— | —NH—C(=O)— | K577 | J9 | S |
| 2-1227 | —(CH$_2$)$_2$— | —NH—C(=O)— | K577 | J125 | S |
| 2-1228 | —(CH$_2$)$_2$— | —NH—C(=O)— | K577 | J194 | S |
| 2-1229 | —(CH$_2$)$_2$— | —NH—C(=O)— | K578 | J9 | S |
| 2-1230 | —(CH$_2$)$_2$— | —NH—C(=O)— | K578 | J125 | S |
| 2-1231 | —(CH$_2$)$_2$— | —NH—C(=O)— | K578 | J194 | S |
| 2-1232 | —(CH$_2$)$_2$— | —NH—C(=O)— | K579 | J9 | S |
| 2-1233 | —(CH$_2$)$_2$— | —NH—C(=O)— | K579 | J126 | S |
| 2-1234 | —(CH$_2$)$_2$— | —NH—C(=O)— | K579 | J129 | S |
| 2-1235 | —(CH$_2$)$_2$— | —NH—C(=O)— | K579 | J130 | S |
| 2-1236 | —(CH$_2$)$_2$— | —NH—C(=O)— | K579 | J138 | S |
| 2-1237 | —(CH$_2$)$_2$— | —NH—C(=O)— | K579 | J127 | S |
| 2-1238 | —(CH$_2$)$_2$— | —NH—C(=O)— | K579 | J195 | S |
| 2-1239 | —(CH$_2$)$_2$— | —NH—C(=O)— | K58 | J9 | S |
| 2-1240 | —(CH$_2$)$_2$— | —NH—C(=O)— | K580 | J9 | S |
| 2-1241 | —(CH$_2$)$_2$— | —NH—C(=O)— | K580 | J126 | S |
| 2-1242 | —(CH$_2$)$_2$— | —NH—C(=O)— | K580 | J129 | S |
| 2-1243 | —(CH$_2$)$_2$— | —NH—C(=O)— | K580 | J130 | S |
| 2-1244 | —(CH$_2$)$_2$— | —NH—C(=O)— | K580 | J138 | S |
| 2-1245 | —(CH$_2$)$_2$— | —NH—C(=O)— | K580 | J127 | S |
| 2-1246 | —(CH$_2$)$_2$— | —NH—C(=O)— | K580 | J195 | S |
| 2-1247 | —(CH$_2$)$_2$— | —NH—C(=O)— | K581 | J9 | S |
| 2-1248 | —(CH$_2$)$_2$— | —NH—C(=O)— | K581 | J126 | S |

TABLE 74

| Compound No. | -A¹- | -A²- | -G¹-A³-A⁴-G² | -A⁵-R² | X |
|---|---|---|---|---|---|
| 2-1249 | —(CH$_2$)$_2$— | —NH—C(=O)— | K581 | J129 | S |
| 2-1250 | —(CH$_2$)$_2$— | —NH—C(=O)— | K581 | J130 | S |
| 2-1251 | —(CH$_2$)$_2$— | —NH—C(=O)— | K581 | J138 | S |
| 2-1252 | —(CH$_2$)$_2$— | —NH—C(=O)— | K581 | J128 | S |
| 2-1253 | —(CH$_2$)$_2$— | —NH—C(=O)— | K581 | J196 | S |
| 2-1254 | —(CH$_2$)$_2$— | —NH—C(=O)— | K582 | J9 | S |
| 2-1255 | —(CH$_2$)$_2$— | —NH—C(=O)— | K582 | J126 | S |
| 2-1256 | —(CH$_2$)$_2$— | —NH—C(=O)— | K582 | J129 | S |
| 2-1257 | —(CH$_2$)$_2$— | —NH—C(=O)— | K582 | J130 | S |
| 2-1258 | —(CH$_2$)$_2$— | —NH—C(=O)— | K582 | J138 | S |
| 2-1259 | —(CH$_2$)$_2$— | —NH—C(=O)— | K582 | J128 | S |
| 2-1260 | —(CH$_2$)$_2$— | —NH—C(=O)— | K582 | J196 | S |
| 2-1261 | —(CH$_2$)$_2$— | —NH—C(=O)— | K583 | J9 | S |
| 2-1262 | —(CH$_2$)$_2$— | —NH—C(=O)— | K583 | J126 | S |
| 2-1263 | —(CH$_2$)$_2$— | —NH—C(=O)— | K583 | J129 | S |
| 2-1264 | —(CH$_2$)$_2$— | —NH—C(=O)— | K583 | J130 | S |
| 2-1265 | —(CH$_2$)$_2$— | —NH—C(=O)— | K583 | J138 | S |
| 2-1266 | —(CH$_2$)$_2$— | —NH—C(=O)— | K583 | J131 | S |
| 2-1267 | —(CH$_2$)$_2$— | —NH—C(=O)— | K583 | J197 | S |
| 2-1268 | —(CH$_2$)$_2$— | —NH—C(=O)— | K584 | J9 | S |
| 2-1269 | —(CH$_2$)$_2$— | —NH—C(=O)— | K584 | J126 | S |
| 2-1270 | —(CH$_2$)$_2$— | —NH—C(=O)— | K584 | J129 | S |
| 2-1271 | —(CH$_2$)$_2$— | —NH—C(=O)— | K584 | J130 | S |
| 2-1272 | —(CH$_2$)$_2$— | —NH—C(=O)— | K584 | J138 | S |
| 2-1273 | —(CH$_2$)$_2$— | —NH—C(=O)— | K584 | J131 | S |
| 2-1274 | —(CH$_2$)$_2$— | —NH—C(=O)— | K584 | J197 | S |
| 2-1275 | —(CH$_2$)$_2$— | —NH—C(=O)— | K585 | J9 | S |
| 2-1276 | —(CH$_2$)$_2$— | —NH—C(=O)— | K585 | J126 | S |
| 2-1277 | —(CH$_2$)$_2$— | —NH—C(=O)— | K585 | J129 | S |
| 2-1278 | —(CH$_2$)$_2$— | —NH—C(=O)— | K585 | J130 | S |
| 2-1279 | —(CH$_2$)$_2$— | —NH—C(=O)— | K585 | J138 | S |
| 2-1280 | —(CH$_2$)$_2$— | —NH—C(=O)— | K585 | J132 | S |

TABLE 75

| Compound No. | -A¹- | -A²- | -G¹-A³-A⁴-G² | -A⁵-R² | X |
|---|---|---|---|---|---|
| 2-1281 | —(CH$_2$)$_2$— | —NH—C(=O)— | K585 | J198 | S |
| 2-1282 | —(CH$_2$)$_2$— | —NH—C(=O)— | K586 | J9 | S |
| 2-1283 | —(CH$_2$)$_2$— | —NH—C(=O)— | K587 | J9 | S |
| 2-1284 | —(CH$_2$)$_2$— | —NH—C(=O)— | K588 | J9 | S |
| 2-1285 | —(CH$_2$)$_2$— | —NH—C(=O)— | K589 | J9 | S |
| 2-1286 | —(CH$_2$)$_2$— | —NH—C(=O)— | K589 | J126 | S |
| 2-1287 | —(CH$_2$)$_2$— | —NH—C(=O)— | K589 | J129 | S |
| 2-1288 | —(CH$_2$)$_2$— | —NH—C(=O)— | K589 | J130 | S |
| 2-1289 | —(CH$_2$)$_2$— | —NH—C(=O)— | K589 | J138 | S |
| 2-1290 | —(CH$_2$)$_2$— | —NH—C(=O)— | K59 | J9 | S |
| 2-1291 | —(CH$_2$)$_2$— | —NH—C(=O)— | K59 | J126 | S |
| 2-1292 | —(CH$_2$)$_2$— | —NH—C(=O)— | K59 | J129 | S |
| 2-1293 | —(CH$_2$)$_2$— | —NH—C(=O)— | K59 | J130 | S |
| 2-1294 | —(CH$_2$)$_2$— | —NH—C(=O)— | K59 | J138 | S |
| 2-1295 | —(CH$_2$)$_2$— | —NH—C(=O)— | K590 | J9 | S |
| 2-1296 | —(CH$_2$)$_2$— | —NH—C(=O)— | K590 | J126 | S |
| 2-1297 | —(CH$_2$)$_2$— | —NH—C(=O)— | K590 | J129 | S |
| 2-1298 | —(CH$_2$)$_2$— | —NH—C(=O)— | K590 | J130 | S |
| 2-1299 | —(CH$_2$)$_2$— | —NH—C(=O)— | K590 | J138 | S |
| 2-1300 | —(CH$_2$)$_2$— | —NH—C(=O)— | K590 | J132 | S |
| 2-1301 | —(CH$_2$)$_2$— | —NH—C(=O)— | K590 | J198 | S |
| 2-1302 | —(CH$_2$)$_2$— | —NH—C(=O)— | K591 | J9 | S |
| 2-1303 | —(CH$_2$)$_2$— | —NH—C(=O)— | K591 | J126 | S |
| 2-1304 | —(CH$_2$)$_2$— | —NH—C(=O)— | K591 | J129 | S |
| 2-1305 | —(CH$_2$)$_2$— | —NH—C(=O)— | K591 | J130 | S |
| 2-1306 | —(CH$_2$)$_2$— | —NH—C(=O)— | K591 | J138 | S |
| 2-1307 | —(CH$_2$)$_2$— | —NH—C(=O)— | K591 | J133 | S |
| 2-1308 | —(CH$_2$)$_2$— | —NH—C(=O)— | K591 | J199 | S |
| 2-1309 | —(CH$_2$)$_2$— | —NH—C(=O)— | K592 | J9 | S |
| 2-1310 | —(CH$_2$)$_2$— | —NH—C(=O)— | K592 | J126 | S |
| 2-1311 | —(CH$_2$)$_2$— | —NH—C(=O)— | K592 | J129 | S |
| 2-1312 | —(CH$_2$)$_2$— | —NH—C(=O)— | K592 | J130 | S |

TABLE 76

| Compound No. | -A¹- | -A²- | -G¹-A³-A⁴-G² | -A⁵-R² | X |
|---|---|---|---|---|---|
| 2-1313 | —(CH$_2$)$_2$— | —NH—C(=O)— | K592 | J138 | S |
| 2-1314 | —(CH$_2$)$_2$— | —NH—C(=O)— | K592 | J133 | S |
| 2-1315 | —(CH$_2$)$_2$— | —NH—C(=O)— | K592 | J199 | S |
| 2-1316 | —(CH$_2$)$_2$— | —NH—C(=O)— | K593 | J9 | S |
| 2-1317 | —(CH$_2$)$_2$— | —NH—C(=O)— | K593 | J126 | S |
| 2-1318 | —(CH$_2$)$_2$— | —NH—C(=O)— | K593 | J129 | S |
| 2-1319 | —(CH$_2$)$_2$— | —NH—C(=O)— | K593 | J130 | S |
| 2-1320 | —(CH$_2$)$_2$— | —NH—C(=O)— | K593 | J138 | S |
| 2-1321 | —(CH$_2$)$_2$— | —NH—C(=O)— | K593 | J134 | S |
| 2-1322 | —(CH$_2$)$_2$— | —NH—C(=O)— | K593 | J200 | S |
| 2-1323 | —(CH$_2$)$_2$— | —NH—C(=O)— | K594 | J9 | S |
| 2-1324 | —(CH$_2$)$_2$— | —NH—C(=O)— | K594 | J126 | S |
| 2-1325 | —(CH$_2$)$_2$— | —NH—C(=O)— | K594 | J129 | S |
| 2-1326 | —(CH$_2$)$_2$— | —NH—C(=O)— | K594 | J130 | S |
| 2-1327 | —(CH$_2$)$_2$— | —NH—C(=O)— | K594 | J138 | S |
| 2-1328 | —(CH$_2$)$_2$— | —NH—C(=O)— | K594 | J134 | S |
| 2-1329 | —(CH$_2$)$_2$— | —NH—C(=O)— | K594 | J200 | S |
| 2-1330 | —(CH$_2$)$_2$— | —NH—C(=O)— | K595 | J9 | S |
| 2-1331 | —(CH$_2$)$_2$— | —NH—C(=O)— | K595 | J126 | S |
| 2-1332 | —(CH$_2$)$_2$— | —NH—C(=O)— | K595 | J129 | S |
| 2-1333 | —(CH$_2$)$_2$— | —NH—C(=O)— | K595 | J130 | S |
| 2-1334 | —(CH$_2$)$_2$— | —NH—C(=O)— | K595 | J138 | S |
| 2-1335 | —(CH$_2$)$_2$— | —NH—C(=O)— | K595 | J135 | S |
| 2-1336 | —(CH$_2$)$_2$— | —NH—C(=O)— | K595 | J201 | S |
| 2-1337 | —(CH$_2$)$_2$— | —NH—C(=O)— | K596 | J9 | S |
| 2-1338 | —(CH$_2$)$_2$— | —NH—C(=O)— | K596 | J126 | S |
| 2-1339 | —(CH$_2$)$_2$— | —NH—C(=O)— | K596 | J129 | S |
| 2-1340 | —(CH$_2$)$_2$— | —NH—C(=O)— | K596 | J130 | S |
| 2-1341 | —(CH$_2$)$_2$— | —NH—C(=O)— | K596 | J138 | S |
| 2-1342 | —(CH$_2$)$_2$— | —NH—C(=O)— | K596 | J135 | S |
| 2-1343 | —(CH$_2$)$_2$— | —NH—C(=O)— | K596 | J201 | S |
| 2-1344 | —(CH$_2$)$_2$— | —NH—C(=O)— | K597 | J9 | S |

TABLE 77

| Compound No. | -A¹- | -A²- | -G¹-A³-A⁴-G² | -A⁵-R² | X |
|---|---|---|---|---|---|
| 2-1345 | —(CH$_2$)$_2$— | —NH—C(=O)— | K598 | J9 | S |
| 2-1346 | —(CH$_2$)$_2$— | —NH—C(=O)— | K599 | J9 | S |
| 2-1347 | —(CH$_2$)$_2$— | —NH—C(=O)— | K6 | J9 | S |
| 2-1348 | —(CH$_2$)$_2$— | —NH—C(=O)— | K60 | J9 | S |
| 2-1349 | —(CH$_2$)$_2$— | —NH—C(=O)— | K60 | J126 | S |
| 2-1350 | —(CH$_2$)$_2$— | —NH—C(=O)— | K60 | J129 | S |
| 2-1351 | —(CH$_2$)$_2$— | —NH—C(=O)— | K60 | J130 | S |
| 2-1352 | —(CH$_2$)$_2$— | —NH—C(=O)— | K60 | J138 | S |
| 2-1353 | —(CH$_2$)$_2$— | —NH—C(=O)— | K600 | J9 | S |
| 2-1354 | —(CH$_2$)$_2$— | —NH—C(=O)— | K601 | J9 | S |
| 2-1355 | —(CH$_2$)$_2$— | —NH—C(=O)— | K602 | J9 | S |
| 2-1356 | —(CH$_2$)$_2$— | —NH—C(=O)— | K608 | J136 | S |
| 2-1357 | —(CH$_2$)$_2$— | —NH—C(=O)— | K608 | J202 | S |
| 2-1358 | —(CH$_2$)$_2$— | —NH—C(=O)— | K61 | J9 | S |
| 2-1359 | —(CH$_2$)$_2$— | —NH—C(=O)— | K61 | J126 | S |
| 2-1360 | —(CH$_2$)$_2$— | —NH—C(=O)— | K61 | J129 | S |
| 2-1361 | —(CH$_2$)$_2$— | —NH—C(=O)— | K61 | J130 | S |
| 2-1362 | —(CH$_2$)$_2$— | —NH—C(=O)— | K61 | J138 | S |
| 2-1363 | —(CH$_2$)$_2$— | —NH—C(=O)— | K611 | J136 | S |
| 2-1364 | —(CH$_2$)$_2$— | —NH—C(=O)— | K611 | J202 | S |
| 2-1365 | —(CH$_2$)$_2$— | —NH—C(=O)— | K618 | J9 | S |
| 2-1366 | —(CH$_2$)$_2$— | —NH—C(=O)— | K618 | J126 | S |
| 2-1367 | —(CH$_2$)$_2$— | —NH—C(=O)— | K618 | J129 | S |
| 2-1368 | —(CH$_2$)$_2$— | —NH—C(=O)— | K618 | J130 | S |
| 2-1369 | —(CH$_2$)$_2$— | —NH—C(=O)— | K618 | J138 | S |
| 2-1370 | —(CH$_2$)$_2$— | —NH—C(=O)— | K618 | J137 | S |
| 2-1371 | —(CH$_2$)$_2$— | —NH—C(=O)— | K618 | J203 | S |
| 2-1372 | —(CH$_2$)$_2$— | —NH—C(=O)— | K619 | J9 | S |
| 2-1373 | —(CH$_2$)$_2$— | —NH—C(=O)— | K619 | J126 | S |
| 2-1374 | —(CH$_2$)$_2$— | —NH—C(=O)— | K619 | J129 | S |
| 2-1375 | —(CH$_2$)$_2$— | —NH—C(=O)— | K619 | J130 | S |
| 2-1376 | —(CH$_2$)$_2$— | —NH—C(=O)— | K619 | J138 | S |

TABLE 78

| Compound No. | -A¹- | -A²- | -G¹-A³-A⁴-G² | -A⁵-R² | X |
|---|---|---|---|---|---|
| 2-1377 | —(CH$_2$)$_2$— | —NH—C(=O)— | K62 | J9 | S |
| 2-1378 | —(CH$_2$)$_2$— | —NH—C(=O)— | K62 | J126 | S |
| 2-1379 | —(CH$_2$)$_2$— | —NH—C(=O)— | K62 | J129 | S |
| 2-1380 | —(CH$_2$)$_2$— | —NH—C(=O)— | K62 | J130 | S |
| 2-1381 | —(CH$_2$)$_2$— | —NH—C(=O)— | K62 | J138 | S |
| 2-1382 | —(CH$_2$)$_2$— | —NH—C(=O)— | K620 | J9 | S |
| 2-1383 | —(CH$_2$)$_2$— | —NH—C(=O)— | K620 | J126 | S |
| 2-1384 | —(CH$_2$)$_2$— | —NH—C(=O)— | K620 | J129 | S |
| 2-1385 | —(CH$_2$)$_2$— | —NH—C(=O)— | K620 | J130 | S |
| 2-1386 | —(CH$_2$)$_2$— | —NH—C(=O)— | K620 | J138 | S |
| 2-1387 | —(CH$_2$)$_2$— | —NH—C(=O)— | K621 | J9 | S |
| 2-1388 | —(CH$_2$)$_2$— | —NH—C(=O)— | K622 | J9 | S |
| 2-1389 | —(CH$_2$)$_2$— | —NH—C(=O)— | K623 | J9 | S |
| 2-1390 | —(CH$_2$)$_2$— | —NH—C(=O)— | K623 | J126 | S |
| 2-1391 | —(CH$_2$)$_2$— | —NH—C(=O)— | K623 | J129 | S |
| 2-1392 | —(CH$_2$)$_2$— | —NH—C(=O)— | K623 | J130 | S |
| 2-1393 | —(CH$_2$)$_2$— | —NH—C(=O)— | K623 | J138 | S |
| 2-1394 | —(CH$_2$)$_2$— | —NH—C(=O)— | K623 | J137 | S |
| 2-1395 | —(CH$_2$)$_2$— | —NH—C(=O)— | K623 | J203 | S |
| 2-1396 | —(CH$_2$)$_2$— | —NH—C(=O)— | K624 | J9 | S |
| 2-1397 | —(CH$_2$)$_2$— | —NH—C(=O)— | K624 | J126 | S |
| 2-1398 | —(CH$_2$)$_2$— | —NH—C(=O)— | K624 | J129 | S |
| 2-1399 | —(CH$_2$)$_2$— | —NH—C(=O)— | K624 | J130 | S |
| 2-1400 | —(CH$_2$)$_2$— | —NH—C(=O)— | K624 | J138 | S |
| 2-1401 | —(CH$_2$)$_2$— | —NH—C(=O)— | K625 | J9 | S |
| 2-1402 | —(CH$_2$)$_2$— | —NH—C(=O)— | K625 | J126 | S |
| 2-1403 | —(CH$_2$)$_2$— | —NH—C(=O)— | K625 | J129 | S |
| 2-1404 | —(CH$_2$)$_2$— | —NH—C(=O)— | K625 | J130 | S |
| 2-1405 | —(CH$_2$)$_2$— | —NH—C(=O)— | K625 | J138 | S |
| 2-1406 | —(CH$_2$)$_2$— | —NH—C(=O)— | K626 | J9 | S |
| 2-1407 | —(CH$_2$)$_2$— | —NH—C(=O)— | K626 | J126 | S |
| 2-1408 | —(CH$_2$)$_2$— | —NH—C(=O)— | K626 | J129 | S |

TABLE 79

| Compound No. | -A$^1$- | -A$^2$- | -G$^1$-A$^3$-A$^4$-G$^2$ | -A$^5$-R$^2$ | X |
|---|---|---|---|---|---|
| 2-1409 | —(CH$_2$)$_2$— | —NH—C(=O)— | K626 | J130 | S |
| 2-1410 | —(CH$_2$)$_2$— | —NH—C(=O)— | K626 | J138 | S |
| 2-1411 | —(CH$_2$)$_2$— | —NH—C(=O)— | K627 | J9 | S |
| 2-1412 | —(CH$_2$)$_2$— | —NH—C(=O)— | K627 | J126 | S |
| 2-1413 | —(CH$_2$)$_2$— | —NH—C(=O)— | K627 | J129 | S |
| 2-1414 | —(CH$_2$)$_2$— | —NH—C(=O)— | K627 | J130 | S |
| 2-1415 | —(CH$_2$)$_2$— | —NH—C(=O)— | K627 | J138 | S |
| 2-1416 | —(CH$_2$)$_2$— | —NH—C(=O)— | K628 | J9 | S |
| 2-1417 | —(CH$_2$)$_2$— | —NH—C(=O)— | K629 | J9 | S |
| 2-1418 | —(CH$_2$)$_2$— | —NH—C(=O)— | K63 | J9 | S |
| 2-1419 | —(CH$_2$)$_2$— | —NH—C(=O)— | K63 | J126 | S |
| 2-1420 | —(CH$_2$)$_2$— | —NH—C(=O)— | K63 | J129 | S |
| 2-1421 | —(CH$_2$)$_2$— | —NH—C(=O)— | K63 | J130 | S |
| 2-1422 | —(CH$_2$)$_2$— | —NH—C(=O)— | K63 | J138 | S |
| 2-1423 | —(CH$_2$)$_2$— | —NH—C(=O)— | K630 | J9 | S |
| 2-1424 | —(CH$_2$)$_2$— | —NH—C(=O)— | K631 | J9 | S |
| 2-1425 | —(CH$_2$)$_2$— | —NH—C(=O)— | K632 | J9 | S |
| 2-1426 | —(CH$_2$)$_2$— | —NH—C(=O)— | K633 | J9 | S |
| 2-1427 | —(CH$_2$)$_2$— | —NH—C(=O)— | K633 | J126 | S |
| 2-1428 | —(CH$_2$)$_2$— | —NH—C(=O)— | K633 | J129 | S |
| 2-1429 | —(CH$_2$)$_2$— | —NH—C(=O)— | K633 | J130 | S |
| 2-1430 | —(CH$_2$)$_2$— | —NH—C(=O)— | K633 | J138 | S |
| 2-1431 | —(CH$_2$)$_2$— | —NH—C(=O)— | K634 | J9 | S |
| 2-1432 | —(CH$_2$)$_2$— | —NH—C(=O)— | K634 | J126 | S |
| 2-1433 | —(CH$_2$)$_2$— | —NH—C(=O)— | K634 | J129 | S |
| 2-1434 | —(CH$_2$)$_2$— | —NH—C(=O)— | K634 | J130 | S |
| 2-1435 | —(CH$_2$)$_2$— | —NH—C(=O)— | K634 | J138 | S |
| 2-1436 | —(CH$_2$)$_2$— | —NH—C(=O)— | K634 | J139 | S |
| 2-1437 | —(CH$_2$)$_2$— | —NH—C(=O)— | K634 | J204 | S |
| 2-1438 | —(CH$_2$)$_2$— | —NH—C(=O)— | K635 | J9 | S |
| 2-1439 | —(CH$_2$)$_2$— | —NH—C(=O)— | K635 | J126 | S |
| 2-1440 | —(CH$_2$)$_2$— | —NH—C(=O)— | K635 | J129 | S |

TABLE 80

| Compound No. | -A$^1$- | -A$^2$- | -G$^1$-A$^3$-A$^4$-G$^2$ | -A$^5$-R$^2$ | X |
|---|---|---|---|---|---|
| 2-1441 | —(CH$_2$)$_2$— | —NH—C(=O)— | K635 | J130 | S |
| 2-1442 | —(CH$_2$)$_2$— | —NH—C(=O)— | K635 | J138 | S |
| 2-1443 | —(CH$_2$)$_2$— | —NH—C(=O)— | K635 | J139 | S |
| 2-1444 | —(CH$_2$)$_2$— | —NH—C(=O)— | K635 | J204 | S |
| 2-1445 | —(CH$_2$)$_2$— | —NH—C(=O)— | K636 | J9 | S |
| 2-1446 | —(CH$_2$)$_2$— | —NH—C(=O)— | K636 | J126 | S |
| 2-1447 | —(CH$_2$)$_2$— | —NH—C(=O)— | K636 | J129 | S |
| 2-1448 | —(CH$_2$)$_2$— | —NH—C(=O)— | K636 | J130 | S |
| 2-1449 | —(CH$_2$)$_2$— | —NH—C(=O)— | K636 | J138 | S |
| 2-1450 | —(CH$_2$)$_2$— | —NH—C(=O)— | K636 | J140 | S |
| 2-1451 | —(CH$_2$)$_2$— | —NH—C(=O)— | K636 | J205 | S |
| 2-1452 | —(CH$_2$)$_2$— | —NH—C(=O)— | K637 | J9 | S |
| 2-1453 | —(CH$_2$)$_2$— | —NH—C(=O)— | K637 | J140 | S |
| 2-1454 | —(CH$_2$)$_2$— | —NH—C(=O)— | K637 | J205 | S |
| 2-1455 | —(CH$_2$)$_2$— | —NH—C(=O)— | K638 | J9 | S |
| 2-1456 | —(CH$_2$)$_2$— | —NH—C(=O)— | K638 | J144 | S |
| 2-1457 | —(CH$_2$)$_2$— | —NH—C(=O)— | K638 | J206 | S |
| 2-1458 | —(CH$_2$)$_2$— | —NH—C(=O)— | K639 | J9 | S |
| 2-1459 | —(CH$_2$)$_2$— | —NH—C(=O)— | K639 | J144 | S |
| 2-1460 | —(CH$_2$)$_2$— | —NH—C(=O)— | K639 | J206 | S |
| 2-1461 | —(CH$_2$)$_2$— | —NH—C(=O)— | K64 | J9 | S |
| 2-1462 | —(CH$_2$)$_2$— | —NH—C(=O)— | K64 | J126 | S |
| 2-1463 | —(CH$_2$)$_2$— | —NH—C(=O)— | K64 | J129 | S |
| 2-1464 | —(CH$_2$)$_2$— | —NH—C(=O)— | K64 | J130 | S |
| 2-1465 | —(CH$_2$)$_2$— | —NH—C(=O)— | K64 | J138 | S |
| 2-1466 | —(CH$_2$)$_2$— | —NH—C(=O)— | K640 | J9 | S |
| 2-1467 | —(CH$_2$)$_2$— | —NH—C(=O)— | K641 | J9 | S |
| 2-1468 | —(CH$_2$)$_2$— | —NH—C(=O)— | K642 | J9 | S |
| 2-1469 | —(CH$_2$)$_2$— | —NH—C(=O)— | K643 | J9 | S |
| 2-1470 | —(CH$_2$)$_2$— | —NH—C(=O)— | K644 | J9 | S |
| 2-1471 | —(CH$_2$)$_2$— | —NH—C(=O)— | K645 | J9 | S |
| 2-1472 | —(CH$_2$)$_2$— | —NH—C(=O)— | K646 | J9 | S |

TABLE 81

| Compound No. | -A$^1$- | -A$^2$- | -G$^1$-A$^3$-A$^4$-G$^2$ | -A$^5$-R$^2$ | X |
|---|---|---|---|---|---|
| 2-1473 | —(CH$_2$)$_2$— | —NH—C(=O)— | K647 | J9 | S |
| 2-1474 | —(CH$_2$)$_2$— | —NH—C(=O)— | K648 | J9 | S |
| 2-1475 | —(CH$_2$)$_2$— | —NH—C(=O)— | K648 | J126 | S |
| 2-1476 | —(CH$_2$)$_2$— | —NH—C(=O)— | K648 | J129 | S |
| 2-1477 | —(CH$_2$)$_2$— | —NH—C(=O)— | K648 | J130 | S |
| 2-1478 | —(CH$_2$)$_2$— | —NH—C(=O)— | K648 | J138 | S |
| 2-1479 | —(CH$_2$)$_2$— | —NH—C(=O)— | K649 | J9 | S |
| 2-1480 | —(CH$_2$)$_2$— | —NH—C(=O)— | K65 | J9 | S |
| 2-1481 | —(CH$_2$)$_2$— | —NH—C(=O)— | K65 | J126 | S |
| 2-1482 | —(CH$_2$)$_2$— | —NH—C(=O)— | K65 | J129 | S |
| 2-1483 | —(CH$_2$)$_2$— | —NH—C(=O)— | K65 | J130 | S |
| 2-1484 | —(CH$_2$)$_2$— | —NH—C(=O)— | K65 | J138 | S |
| 2-1485 | —(CH$_2$)$_2$— | —NH—C(=O)— | K650 | J9 | S |
| 2-1486 | —(CH$_2$)$_2$— | —NH—C(=O)— | K651 | J9 | S |
| 2-1487 | —(CH$_2$)$_2$— | —NH—C(=O)— | K652 | J9 | S |
| 2-1488 | —(CH$_2$)$_2$— | —NH—C(=O)— | K653 | J9 | S |
| 2-1489 | —(CH$_2$)$_2$— | —NH—C(=O)— | K654 | J9 | S |
| 2-1490 | —(CH$_2$)$_2$— | —NH—C(=O)— | K655 | J9 | S |
| 2-1491 | —(CH$_2$)$_2$— | —NH—C(=O)— | K655 | J126 | S |
| 2-1492 | —(CH$_2$)$_2$— | —NH—C(=O)— | K655 | J129 | S |
| 2-1493 | —(CH$_2$)$_2$— | —NH—C(=O)— | K655 | J130 | S |
| 2-1494 | —(CH$_2$)$_2$— | —NH—C(=O)— | K655 | J138 | S |
| 2-1495 | —(CH$_2$)$_2$— | —NH—C(=O)— | K655 | J147 | S |
| 2-1496 | —(CH$_2$)$_2$— | —NH—C(=O)— | K655 | J207 | S |
| 2-1497 | —(CH$_2$)$_2$— | —NH—C(=O)— | K656 | J9 | S |
| 2-1498 | —(CH$_2$)$_2$— | —NH—C(=O)— | K657 | J9 | S |
| 2-1499 | —(CH$_2$)$_2$— | —NH—C(=O)— | K658 | J9 | S |
| 2-1500 | —(CH$_2$)$_2$— | —NH—C(=O)— | K659 | J9 | S |
| 2-1501 | —(CH$_2$)$_2$— | —NH—C(=O)— | K66 | J9 | S |
| 2-1502 | —(CH$_2$)$_2$— | —NH—C(=O)— | K66 | J126 | S |
| 2-1503 | —(CH$_2$)$_2$— | —NH—C(=O)— | K66 | J129 | S |
| 2-1504 | —(CH$_2$)$_2$— | —NH—C(=O)— | K66 | J130 | S |

TABLE 82

| Compound No. | -A$^1$- | -A$^2$- | -G$^1$-A$^3$-A$^4$-G$^2$ | -A$^5$-R$^2$ | X |
|---|---|---|---|---|---|
| 2-1505 | —(CH$_2$)$_2$— | —NH—C(=O)— | K66 | J138 | S |
| 2-1506 | —(CH$_2$)$_2$— | —NH—C(=O)— | K67 | J9 | S |
| 2-1507 | —(CH$_2$)$_2$— | —NH—C(=O)— | K67 | J126 | S |
| 2-1508 | —(CH$_2$)$_2$— | —NH—C(=O)— | K67 | J129 | S |
| 2-1509 | —(CH$_2$)$_2$— | —NH—C(=O)— | K67 | J130 | S |
| 2-1510 | —(CH$_2$)$_2$— | —NH—C(=O)— | K67 | J138 | S |
| 2-1511 | —(CH$_2$)$_2$— | —NH—C(=O)— | K68 | J9 | S |
| 2-1512 | —(CH$_2$)$_2$— | —NH—C(=O)— | K68 | J126 | S |
| 2-1513 | —(CH$_2$)$_2$— | —NH—C(=O)— | K68 | J129 | S |
| 2-1514 | —(CH$_2$)$_2$— | —NH—C(=O)— | K68 | J130 | S |
| 2-1515 | —(CH$_2$)$_2$— | —NH—C(=O)— | K68 | J138 | S |
| 2-1516 | —(CH$_2$)$_2$— | —NH—C(=O)— | K69 | J9 | S |
| 2-1517 | —(CH$_2$)$_2$— | —NH—C(=O)— | K69 | J126 | S |
| 2-1518 | —(CH$_2$)$_2$— | —NH—C(=O)— | K69 | J129 | S |
| 2-1519 | —(CH$_2$)$_2$— | —NH—C(=O)— | K69 | J130 | S |
| 2-1520 | —(CH$_2$)$_2$— | —NH—C(=O)— | K69 | J138 | S |
| 2-1521 | —(CH$_2$)$_2$— | —NH—C(=O)— | K70 | J9 | S |
| 2-1522 | —(CH$_2$)$_2$— | —NH—C(=O)— | K70 | J126 | S |
| 2-1523 | —(CH$_2$)$_2$— | —NH—C(=O)— | K70 | J129 | S |
| 2-1524 | —(CH$_2$)$_2$— | —NH—C(=O)— | K70 | J130 | S |
| 2-1525 | —(CH$_2$)$_2$— | —NH—C(=O)— | K70 | J138 | S |
| 2-1526 | —(CH$_2$)$_2$— | —NH—C(=O)— | K71 | J9 | S |
| 2-1527 | —(CH$_2$)$_2$— | —NH—C(=O)— | K71 | J126 | S |
| 2-1528 | —(CH$_2$)$_2$— | —NH—C(=O)— | K71 | J129 | S |
| 2-1529 | —(CH$_2$)$_2$— | —NH—C(=O)— | K71 | J130 | S |
| 2-1530 | —(CH$_2$)$_2$— | —NH—C(=O)— | K71 | J138 | S |
| 2-1531 | —(CH$_2$)$_2$— | —NH—C(=O)— | K72 | J9 | S |
| 2-1532 | —(CH$_2$)$_2$— | —NH—C(=O)— | K72 | J126 | S |
| 2-1533 | —(CH$_2$)$_2$— | —NH—C(=O)— | K72 | J129 | S |
| 2-1534 | —(CH$_2$)$_2$— | —NH—C(=O)— | K72 | J130 | S |
| 2-1535 | —(CH$_2$)$_2$— | —NH—C(=O)— | K72 | J138 | S |
| 2-1536 | —(CH$_2$)$_2$— | —NH—C(=O)— | K73 | J9 | S |

TABLE 83

| Compound No. | -A¹- | -A²- | -G¹-A³-A⁴-G² | -A⁵-R² | X |
|---|---|---|---|---|---|
| 2-1537 | —(CH$_2$)$_2$— | —NH—C(=O)— | K73 | J126 | S |
| 2-1538 | —(CH$_2$)$_2$— | —NH—C(=O)— | K73 | J129 | S |
| 2-1539 | —(CH$_2$)$_2$— | —NH—C(=O)— | K73 | J130 | S |
| 2-1540 | —(CH$_2$)$_2$— | —NH—C(=O)— | K73 | J138 | S |
| 2-1541 | —(CH$_2$)$_2$— | —NH—C(=O)— | K74 | J9 | S |
| 2-1542 | —(CH$_2$)$_2$— | —NH—C(=O)— | K74 | J126 | S |
| 2-1543 | —(CH$_2$)$_2$— | —NH—C(=O)— | K74 | J129 | S |
| 2-1544 | —(CH$_2$)$_2$— | —NH—C(=O)— | K74 | J130 | S |
| 2-1545 | —(CH$_2$)$_2$— | —NH—C(=O)— | K74 | J138 | S |
| 2-1546 | —(CH$_2$)$_2$— | —NH—C(=O)— | K75 | J9 | S |
| 2-1547 | —(CH$_2$)$_2$— | —NH—C(=O)— | K75 | J126 | S |
| 2-1548 | —(CH$_2$)$_2$— | —NH—C(=O)— | K75 | J129 | S |
| 2-1549 | —(CH$_2$)$_2$— | —NH—C(=O)— | K75 | J130 | S |
| 2-1550 | —(CH$_2$)$_2$— | —NH—C(=O)— | K75 | J138 | S |
| 2-1551 | —(CH$_2$)$_2$— | —NH—C(=O)— | K75 | J3 | S |
| 2-1552 | —(CH$_2$)$_2$— | —NH—C(=O)— | K75 | J148 | S |
| 2-1553 | —(CH$_2$)$_2$— | —NH—C(=O)— | K76 | J9 | S |
| 2-1554 | —(CH$_2$)$_2$— | —NH—C(=O)— | K76 | J126 | S |
| 2-1555 | —(CH$_2$)$_2$— | —NH—C(=O)— | K76 | J129 | S |
| 2-1556 | —(CH$_2$)$_2$— | —NH—C(=O)— | K76 | J130 | S |
| 2-1557 | —(CH$_2$)$_2$— | —NH—C(=O)— | K76 | J138 | S |
| 2-1558 | —(CH$_2$)$_2$— | —NH—C(=O)— | K761 | J126 | S |
| 2-1559 | —(CH$_2$)$_2$— | —NH—C(=O)— | K761 | J129 | S |
| 2-1560 | —(CH$_2$)$_2$— | —NH—C(=O)— | K761 | J130 | S |
| 2-1561 | —(CH$_2$)$_2$— | —NH—C(=O)— | K761 | J138 | S |
| 2-1562 | —(CH$_2$)$_2$— | —NH—C(=O)— | K761 | J147 | S |
| 2-1563 | —(CH$_2$)$_2$— | —NH—C(=O)— | K761 | J207 | S |
| 2-1564 | —(CH$_2$)$_2$— | —NH—C(=O)— | K762 | J126 | S |
| 2-1565 | —(CH$_2$)$_2$— | —NH—C(=O)— | K762 | J129 | S |
| 2-1566 | —(CH$_2$)$_2$— | —NH—C(=O)— | K762 | J130 | S |
| 2-1567 | —(CH$_2$)$_2$— | —NH—C(=O)— | K762 | J138 | S |
| 2-1568 | —(CH$_2$)$_2$— | —NH—C(=O)— | K77 | J9 | S |

TABLE 84

| Compound No. | -A¹- | -A²- | -G¹-A³-A⁴-G² | -A⁵-R² | X |
|---|---|---|---|---|---|
| 2-1569 | —(CH$_2$)$_2$— | —NH—C(=O)— | K77 | J126 | S |
| 2-1570 | —(CH$_2$)$_2$— | —NH—C(=O)— | K77 | J129 | S |
| 2-1571 | —(CH$_2$)$_2$— | —NH—C(=O)— | K77 | J130 | S |
| 2-1572 | —(CH$_2$)$_2$— | —NH—C(=O)— | K77 | J138 | S |
| 2-1573 | —(CH$_2$)$_2$— | —NH—C(=O)— | K77 | J3 | S |
| 2-1574 | —(CH$_2$)$_2$— | —NH—C(=O)— | K77 | J148 | S |
| 2-1575 | —(CH$_2$)$_2$— | —NH—C(=O)— | K78 | J9 | S |
| 2-1576 | —(CH$_2$)$_2$— | —NH—C(=O)— | K78 | J126 | S |
| 2-1577 | —(CH$_2$)$_2$— | —NH—C(=O)— | K78 | J129 | S |
| 2-1578 | —(CH$_2$)$_2$— | —NH—C(=O)— | K78 | J130 | S |
| 2-1579 | —(CH$_2$)$_2$— | —NH—C(=O)— | K78 | J138 | S |
| 2-1580 | —(CH$_2$)$_2$— | —NH—C(=O)— | K78 | J10 | S |
| 2-1581 | —(CH$_2$)$_2$— | —NH—C(=O)— | K78 | J149 | S |
| 2-1582 | —(CH$_2$)$_2$— | —NH—C(=O)— | K79 | J9 | S |
| 2-1583 | —(CH$_2$)$_2$— | —NH—C(=O)— | K79 | J126 | S |
| 2-1584 | —(CH$_2$)$_2$— | —NH—C(=O)— | K79 | J129 | S |
| 2-1585 | —(CH$_2$)$_2$— | —NH—C(=O)— | K79 | J130 | S |
| 2-1586 | —(CH$_2$)$_2$— | —NH—C(=O)— | K79 | J138 | S |
| 2-1587 | —(CH$_2$)$_2$— | —NH—C(=O)— | K79 | J10 | S |
| 2-1588 | —(CH$_2$)$_2$— | —NH—C(=O)— | K79 | J149 | S |
| 2-1589 | —(CH$_2$)$_2$— | —NH—C(=O)— | K8 | J9 | S |
| 2-1590 | —(CH$_2$)$_2$— | —NH—C(=O)— | K80 | J9 | S |
| 2-1591 | —(CH$_2$)$_2$— | —NH—C(=O)— | K80 | J126 | S |
| 2-1592 | —(CH$_2$)$_2$— | —NH—C(=O)— | K80 | J129 | S |
| 2-1593 | —(CH$_2$)$_2$— | —NH—C(=O)— | K80 | J130 | S |
| 2-1594 | —(CH$_2$)$_2$— | —NH—C(=O)— | K80 | J138 | S |
| 2-1595 | —(CH$_2$)$_2$— | —NH—C(=O)— | K81 | J9 | S |
| 2-1596 | —(CH$_2$)$_2$— | —NH—C(=O)— | K81 | J126 | S |
| 2-1597 | —(CH$_2$)$_2$— | —NH—C(=O)— | K81 | J129 | S |
| 2-1598 | —(CH$_2$)$_2$— | —NH—C(=O)— | K81 | J130 | S |
| 2-1599 | —(CH$_2$)$_2$— | —NH—C(=O)— | K81 | J138 | S |
| 2-1600 | —(CH$_2$)$_2$— | —NH—C(=O)— | K82 | J9 | S |

TABLE 85

| Compound No. | -A¹- | -A²- | -G¹-A³-A⁴-G² | -A⁵-R² | X |
|---|---|---|---|---|---|
| 2-1601 | —(CH$_2$)$_2$— | —NH—C(=O)— | K83 | J9 | S |
| 2-1602 | —(CH$_2$)$_2$— | —NH—C(=O)— | K83 | J126 | S |
| 2-1603 | —(CH$_2$)$_2$— | —NH—C(=O)— | K83 | J129 | S |
| 2-1604 | —(CH$_2$)$_2$— | —NH—C(=O)— | K83 | J130 | S |
| 2-1605 | —(CH$_2$)$_2$— | —NH—C(=O)— | K83 | J138 | S |
| 2-1606 | —(CH$_2$)$_2$— | —NH—C(=O)— | K83 | J14 | S |
| 2-1607 | —(CH$_2$)$_2$— | —NH—C(=O)— | K83 | J150 | S |
| 2-1608 | —(CH$_2$)$_2$— | —NH—C(=O)— | K84 | J9 | S |
| 2-1609 | —(CH$_2$)$_2$— | —NH—C(=O)— | K85 | J9 | S |
| 2-1610 | —(CH$_2$)$_2$— | —NH—C(=O)— | K85 | J126 | S |
| 2-1611 | —(CH$_2$)$_2$— | —NH—C(=O)— | K85 | J129 | S |
| 2-1612 | —(CH$_2$)$_2$— | —NH—C(=O)— | K85 | J130 | S |
| 2-1613 | —(CH$_2$)$_2$— | —NH—C(=O)— | K85 | J138 | S |
| 2-1614 | —(CH$_2$)$_2$— | —NH—C(=O)— | K86 | J9 | S |
| 2-1615 | —(CH$_2$)$_2$— | —NH—C(=O)— | K86 | J126 | S |
| 2-1616 | —(CH$_2$)$_2$— | —NH—C(=O)— | K86 | J129 | S |
| 2-1617 | —(CH$_2$)$_2$— | —NH—C(=O)— | K86 | J130 | S |
| 2-1618 | —(CH$_2$)$_2$— | —NH—C(=O)— | K86 | J138 | S |
| 2-1619 | —(CH$_2$)$_2$— | —NH—C(=O)— | K88 | J126 | S |
| 2-1620 | —(CH$_2$)$_2$— | —NH—C(=O)— | K88 | J129 | S |
| 2-1621 | —(CH$_2$)$_2$— | —NH—C(=O)— | K88 | J130 | S |
| 2-1622 | —(CH$_2$)$_2$— | —NH—C(=O)— | K88 | J138 | S |
| 2-1623 | —(CH$_2$)$_2$— | —NH—C(=O)— | K89 | J9 | S |
| 2-1624 | —(CH$_2$)$_2$— | —NH—C(=O)— | K89 | J126 | S |
| 2-1625 | —(CH$_2$)$_2$— | —NH—C(=O)— | K89 | J129 | S |
| 2-1626 | —(CH$_2$)$_2$— | —NH—C(=O)— | K89 | J130 | S |
| 2-1627 | —(CH$_2$)$_2$— | —NH—C(=O)— | K89 | J138 | S |
| 2-1628 | —(CH$_2$)$_2$— | —NH—C(=O)— | K90 | J9 | S |
| 2-1629 | —(CH$_2$)$_2$— | —NH—C(=O)— | K90 | J126 | S |
| 2-1630 | —(CH$_2$)$_2$— | —NH—C(=O)— | K90 | J129 | S |
| 2-1631 | —(CH$_2$)$_2$— | —NH—C(=O)— | K90 | J130 | S |
| 2-1632 | —(CH$_2$)$_2$— | —NH—C(=O)— | K90 | J138 | S |

TABLE 86

| Compound No. | -A¹- | -A²- | -G¹-A³-A⁴-G² | -A⁵-R² | X |
|---|---|---|---|---|---|
| 2-1633 | —(CH$_2$)$_2$— | —NH—C(=O)— | K91 | J9 | S |
| 2-1634 | —(CH$_2$)$_2$— | —NH—C(=O)— | K91 | J126 | S |
| 2-1635 | —(CH$_2$)$_2$— | —NH—C(=O)— | K91 | J129 | S |
| 2-1636 | —(CH$_2$)$_2$— | —NH—C(=O)— | K91 | J130 | S |
| 2-1637 | —(CH$_2$)$_2$— | —NH—C(=O)— | K91 | J138 | S |
| 2-1638 | —(CH$_2$)$_2$— | —NH—C(=O)— | K92 | J9 | S |
| 2-1639 | —(CH$_2$)$_2$— | —NH—C(=O)— | K92 | J126 | S |
| 2-1640 | —(CH$_2$)$_2$— | —NH—C(=O)— | K92 | J129 | S |
| 2-1641 | —(CH$_2$)$_2$— | —NH—C(=O)— | K92 | J130 | S |
| 2-1642 | —(CH$_2$)$_2$— | —NH—C(=O)— | K92 | J138 | S |
| 2-1643 | —(CH$_2$)$_2$— | —NH—C(=O)— | K93 | J9 | S |
| 2-1644 | —(CH$_2$)$_2$— | —NH—C(=O)— | K93 | J126 | S |
| 2-1645 | —(CH$_2$)$_2$— | —NH—C(=O)— | K93 | J129 | S |
| 2-1646 | —(CH$_2$)$_2$— | —NH—C(=O)— | K93 | J130 | S |
| 2-1647 | —(CH$_2$)$_2$— | —NH—C(=O)— | K93 | J138 | S |
| 2-1648 | —(CH$_2$)$_2$— | —NH—C(=O)— | K94 | J9 | S |
| 2-1649 | —(CH$_2$)$_2$— | —NH—C(=O)— | K94 | J126 | S |
| 2-1650 | —(CH$_2$)$_2$— | —NH—C(=O)— | K94 | J129 | S |
| 2-1651 | —(CH$_2$)$_2$— | —NH—C(=O)— | K94 | J130 | S |
| 2-1652 | —(CH$_2$)$_2$— | —NH—C(=O)— | K94 | J138 | S |
| 2-1653 | —(CH$_2$)$_2$— | —NH—C(=O)— | K95 | J126 | S |
| 2-1654 | —(CH$_2$)$_2$— | —NH—C(=O)— | K95 | J129 | S |
| 2-1655 | —(CH$_2$)$_2$— | —NH—C(=O)— | K95 | J130 | S |
| 2-1656 | —(CH$_2$)$_2$— | —NH—C(=O)— | K95 | J138 | S |
| 2-1657 | —(CH$_2$)$_2$— | —NH—C(=O)— | K96 | J9 | S |
| 2-1658 | —(CH$_2$)$_2$— | —NH—C(=O)— | K96 | J126 | S |
| 2-1659 | —(CH$_2$)$_2$— | —NH—C(=O)— | K96 | J129 | S |
| 2-1660 | —(CH$_2$)$_2$— | —NH—C(=O)— | K96 | J130 | S |
| 2-1661 | —(CH$_2$)$_2$— | —NH—C(=O)— | K96 | J138 | S |
| 2-1662 | —(CH$_2$)$_2$— | —NH—C(=O)— | K99 | J9 | S |
| 2-1663 | —(CH$_2$)$_2$— | —NH—C(=O)— | K241 | J9 | O |
| 2-1664 | —(CH$_2$)$_2$— | —NH—C(=O)— | K241 | J126 | O |

TABLE 87

| Compound No. | -A¹- | -A²- | -G¹-A³-A⁴-G² | -A⁵-R² | X |
|---|---|---|---|---|---|
| 2-1665 | —(CH$_2$)$_2$— | —NH—C(=O)— | K241 | J129 | O |
| 2-1666 | —(CH$_2$)$_2$— | —NH—C(=O)— | K241 | J130 | O |
| 2-1667 | —(CH$_2$)$_2$— | —NH—C(=O)— | K241 | J138 | O |
| 2-1668 | —(CH$_2$)$_2$— | —NH—C(=O)— | K241 | J3 | O |
| 2-1669 | —(CH$_2$)$_2$— | —NH—C(=O)— | K241 | J10 | O |
| 2-1670 | —(CH$_2$)$_2$— | —NH—C(=O)— | K241 | J14 | O |
| 2-1671 | —(CH$_2$)$_2$— | —NH—C(=O)— | K241 | J16 | O |
| 2-1672 | —(CH$_2$)$_2$— | —NH—C(=O)— | K241 | J19 | O |
| 2-1673 | —(CH$_2$)$_2$— | —NH—C(=O)— | K241 | J22 | O |
| 2-1674 | —(CH$_2$)$_2$— | —NH—C(=O)— | K241 | J25 | O |
| 2-1675 | —(CH$_2$)$_2$— | —NH—C(=O)— | K241 | J26 | O |
| 2-1676 | —(CH$_2$)$_2$— | —NH—C(=O)— | K241 | J28 | O |
| 2-1677 | —(CH$_2$)$_2$— | —NH—C(=O)— | K241 | J29 | O |
| 2-1678 | —(CH$_2$)$_2$— | —NH—C(=O)— | K241 | J31 | O |
| 2-1679 | —(CH$_2$)$_2$— | —NH—C(=O)— | K241 | J33 | O |
| 2-1680 | —(CH$_2$)$_2$— | —NH—C(=O)— | K241 | J34 | O |
| 2-1681 | —(CH$_2$)$_2$— | —NH—C(=O)— | K241 | J37 | O |
| 2-1682 | —(CH$_2$)$_2$— | —NH—C(=O)— | K241 | J57 | O |
| 2-1683 | —(CH$_2$)$_2$— | —NH—C(=O)— | K241 | J58 | O |
| 2-1684 | —(CH$_2$)$_2$— | —NH—C(=O)— | K241 | J59 | O |
| 2-1685 | —(CH$_2$)$_2$— | —NH—C(=O)— | K241 | J70 | O |
| 2-1686 | —(CH$_2$)$_2$— | —NH—C(=O)— | K241 | J71 | O |
| 2-1687 | —(CH$_2$)$_2$— | —NH—C(=O)— | K241 | J72 | O |
| 2-1688 | —(CH$_2$)$_2$— | —NH—C(=O)— | K241 | J74 | O |
| 2-1689 | —(CH$_2$)$_2$— | —NH—C(=O)— | K241 | J75 | O |
| 2-1690 | —(CH$_2$)$_2$— | —NH—C(=O)— | K241 | J76 | O |
| 2-1691 | —(CH$_2$)$_2$— | —NH—C(=O)— | K241 | J77 | O |
| 2-1692 | —(CH$_2$)$_2$— | —NH—C(=O)— | K241 | J78 | O |
| 2-1693 | —(CH$_2$)$_2$— | —NH—C(=O)— | K241 | J79 | O |
| 2-1694 | —(CH$_2$)$_2$— | —NH—C(=O)— | K241 | J81 | O |
| 2-1695 | —(CH$_2$)$_2$— | —NH—C(=O)— | K241 | J83 | O |
| 2-1696 | —(CH$_2$)$_2$— | —NH—C(=O)— | K241 | J84 | O |

TABLE 88

| Compound No. | -A¹- | -A²- | -G¹-A³-A⁴-G² | -A⁵-R² | X |
|---|---|---|---|---|---|
| 2-1697 | —(CH$_2$)$_2$— | —NH—C(=O)— | K241 | J87 | O |
| 2-1698 | —(CH$_2$)$_2$— | —NH—C(=O)— | K241 | J89 | O |
| 2-1699 | —(CH$_2$)$_2$— | —NH—C(=O)— | K241 | J120 | O |
| 2-1700 | —(CH$_2$)$_2$— | —NH—C(=O)— | K241 | J121 | O |
| 2-1701 | —(CH$_2$)$_2$— | —NH—C(=O)— | K241 | J122 | O |
| 2-1702 | —(CH$_2$)$_2$— | —NH—C(=O)— | K241 | J123 | O |
| 2-1703 | —(CH$_2$)$_2$— | —NH—C(=O)— | K241 | J124 | O |
| 2-1704 | —(CH$_2$)$_2$— | —NH—C(=O)— | K241 | J125 | O |
| 2-1705 | —(CH$_2$)$_2$— | —NH—C(=O)— | K241 | J127 | O |
| 2-1706 | —(CH$_2$)$_2$— | —NH—C(=O)— | K241 | J128 | O |
| 2-1707 | —(CH$_2$)$_2$— | —NH—C(=O)— | K241 | J131 | O |
| 2-1708 | —(CH$_2$)$_2$— | —NH—C(=O)— | K241 | J132 | O |
| 2-1709 | —(CH$_2$)$_2$— | —NH—C(=O)— | K241 | J133 | O |
| 2-1710 | —(CH$_2$)$_2$— | —NH—C(=O)— | K241 | J134 | O |
| 2-1711 | —(CH$_2$)$_2$— | —NH—C(=O)— | K241 | J135 | O |
| 2-1712 | —(CH$_2$)$_2$— | —NH—C(=O)— | K241 | J136 | O |
| 2-1713 | —(CH$_2$)$_2$— | —NH—C(=O)— | K241 | J137 | O |
| 2-1714 | —(CH$_2$)$_2$— | —NH—C(=O)— | K241 | J139 | O |
| 2-1715 | —(CH$_2$)$_2$— | —NH—C(=O)— | K241 | J140 | O |
| 2-1716 | —(CH$_2$)$_2$— | —NH—C(=O)— | K241 | J144 | O |
| 2-1717 | —(CH$_2$)$_2$— | —NH—C(=O)— | K241 | J147 | O |
| 2-1718 | —(CH$_2$)$_2$— | —NH—C(=O)— | K241 | J148 | O |
| 2-1719 | —(CH$_2$)$_2$— | —NH—C(=O)— | K241 | J149 | O |
| 2-1720 | —(CH$_2$)$_2$— | —NH—C(=O)— | K241 | J150 | O |
| 2-1721 | —(CH$_2$)$_2$— | —NH—C(=O)— | K241 | J151 | O |
| 2-1722 | —(CH$_2$)$_2$— | —NH—C(=O)— | K241 | J152 | O |
| 2-1723 | —(CH$_2$)$_2$— | —NH—C(=O)— | K241 | J153 | O |
| 2-1724 | —(CH$_2$)$_2$— | —NH—C(=O)— | K241 | J154 | O |
| 2-1725 | —(CH$_2$)$_2$— | —NH—C(=O)— | K241 | J155 | O |
| 2-1726 | —(CH$_2$)$_2$— | —NH—C(=O)— | K241 | J156 | O |
| 2-1727 | —(CH$_2$)$_2$— | —NH—C(=O)— | K241 | J157 | O |
| 2-1728 | —(CH$_2$)$_2$— | —NH—C(=O)— | K241 | J158 | O |

TABLE 89

| Compound No. | -A¹- | -A²- | -G¹-A³-A⁴-G² | -A⁵-R² | X |
|---|---|---|---|---|---|
| 2-1729 | —(CH$_2$)$_2$— | —NH—C(=O)— | K241 | J159 | O |
| 2-1730 | —(CH$_2$)$_2$— | —NH—C(=O)— | K241 | J163 | O |
| 2-1731 | —(CH$_2$)$_2$— | —NH—C(=O)— | K241 | J165 | O |
| 2-1732 | —(CH$_2$)$_2$— | —NH—C(=O)— | K241 | J166 | O |
| 2-1733 | —(CH$_2$)$_2$— | —NH—C(=O)— | K241 | J167 | O |
| 2-1734 | —(CH$_2$)$_2$— | —NH—C(=O)— | K241 | J168 | O |
| 2-1735 | —(CH$_2$)$_2$— | —NH—C(=O)— | K241 | J169 | O |
| 2-1736 | —(CH$_2$)$_2$— | —NH—C(=O)— | K241 | J170 | O |
| 2-1737 | —(CH$_2$)$_2$— | —NH—C(=O)— | K241 | J171 | O |
| 2-1738 | —(CH$_2$)$_2$— | —NH—C(=O)— | K241 | J174 | O |
| 2-1739 | —(CH$_2$)$_2$— | —NH—C(=O)— | K241 | J175 | O |
| 2-1740 | —(CH$_2$)$_2$— | —NH—C(=O)— | K241 | J176 | O |
| 2-1741 | —(CH$_2$)$_2$— | —NH—C(=O)— | K241 | J177 | O |
| 2-1742 | —(CH$_2$)$_2$— | —NH—C(=O)— | K241 | J178 | O |
| 2-1743 | —(CH$_2$)$_2$— | —NH—C(=O)— | K241 | J179 | O |
| 2-1744 | —(CH$_2$)$_2$— | —NH—C(=O)— | K241 | J180 | O |
| 2-1745 | —(CH$_2$)$_2$— | —NH—C(=O)— | K241 | J181 | O |
| 2-1746 | —(CH$_2$)$_2$— | —NH—C(=O)— | K241 | J182 | O |
| 2-1747 | —(CH$_2$)$_2$— | —NH—C(=O)— | K241 | J185 | O |
| 2-1748 | —(CH$_2$)$_2$— | —NH—C(=O)— | K241 | J188 | O |
| 2-1749 | —(CH$_2$)$_2$— | —NH—C(=O)— | K241 | J189 | O |
| 2-1750 | —(CH$_2$)$_2$— | —NH—C(=O)— | K241 | J190 | O |
| 2-1751 | —(CH$_2$)$_2$— | —NH—C(=O)— | K241 | J191 | O |
| 2-1752 | —(CH$_2$)$_2$— | —NH—C(=O)— | K241 | J192 | O |
| 2-1753 | —(CH$_2$)$_2$— | —NH—C(=O)— | K241 | J193 | O |
| 2-1754 | —(CH$_2$)$_2$— | —NH—C(=O)— | K241 | J194 | O |
| 2-1755 | —(CH$_2$)$_2$— | —NH—C(=O)— | K241 | J195 | O |
| 2-1756 | —(CH$_2$)$_2$— | —NH—C(=O)— | K241 | J196 | O |
| 2-1757 | —(CH$_2$)$_2$— | —NH—C(=O)— | K241 | J197 | O |
| 2-1758 | —(CH$_2$)$_2$— | —NH—C(=O)— | K241 | J198 | O |
| 2-1759 | —(CH$_2$)$_2$— | —NH—C(=O)— | K241 | J199 | O |
| 2-1760 | —(CH$_2$)$_2$— | —NH—C(=O)— | K241 | J200 | O |

TABLE 90

| Compound No. | -A¹- | -A²- | -G¹-A³-A⁴-G² | -A⁵-R² | X |
|---|---|---|---|---|---|
| 2-1761 | —(CH$_2$)$_2$— | —NH—C(=O)— | K241 | J201 | O |
| 2-1762 | —(CH$_2$)$_2$— | —NH—C(=O)— | K241 | J202 | O |
| 2-1763 | —(CH$_2$)$_2$— | —NH—C(=O)— | K241 | J203 | O |
| 2-1764 | —(CH$_2$)$_2$— | —NH—C(=O)— | K241 | J204 | O |
| 2-1765 | —(CH$_2$)$_2$— | —NH—C(=O)— | K241 | J205 | O |
| 2-1766 | —(CH$_2$)$_2$— | —NH—C(=O)— | K241 | J206 | O |
| 2-1767 | —(CH$_2$)$_2$— | —NH—C(=O)— | K241 | J207 | O |
| 2-1768 | —(CH$_2$)$_2$— | —NH—C(=O)— | K11 | J9 | S |
| 2-1769 | —(CH$_2$)$_3$— | —NH—C(=O)— | K49 | J9 | S |
| 2-1770 | —(CH$_2$)$_3$— | —NH—C(=O)— | K34 | J9 | S |
| 2-1771 | —(CH$_2$)$_3$— | —NH— | K661 | J9 | S |
| 2-1772 | —(CH$_2$)$_3$— | —NH— | K663 | J9 | S |
| 2-1773 | —(CH$_2$)$_3$— | —NH— | K665 | J9 | S |
| 2-1774 | —(CH$_2$)$_3$— | —NH— | K667 | J9 | S |
| 2-1775 | —(CH$_2$)$_2$— | —NH— | K99 | J9 | S |
| 2-1776 | —(CH$_2$)$_2$— | —NH—C(=O)—NH— | K11 | J9 | S |
| 2-1777 | —(CH$_2$)$_2$— | —NH—C(=O)—NH— | K478 | J9 | S |
| 2-1778 | —(CH$_2$)$_3$— | —NH—C(=O)—NH— | K11 | J9 | S |
| 2-1779 | —(CH$_2$)$_3$— | —NH—C(=O)—NH— | K478 | J9 | S |
| 2-1780 | —(CH$_2$)$_2$— | —NH—C(=O)—NH— | K721 | J9 | S |
| 2-1781 | —(CH$_2$)$_2$— | —NH—C(=O)—NH— | K722 | J9 | S |
| 2-1782 | —(CH$_2$)$_2$— | —NH—C(=O)—NH— | K723 | J9 | S |
| 2-1783 | —(CH$_2$)$_2$— | —NH—C(=O)—NH— | K281 | J9 | S |
| 2-1784 | —(CH$_2$)$_3$— | —NH—C(=O)—NH— | K721 | J9 | S |
| 2-1785 | —(CH$_2$)$_3$— | —NH—C(=O)—NH— | K722 | J9 | S |
| 2-1786 | —(CH$_2$)$_3$— | —NH—C(=O)—NH— | K723 | J9 | S |
| 2-1787 | —(CH$_2$)$_3$— | —NH—C(=S)—NH— | K281 | J9 | S |
| 2-1788 | —(CH$_2$)$_2$— | —NH—C(=O)—NH— | K435 | J9 | S |
| 2-1789 | —(CH$_2$)$_3$— | —NH—C(=O)—NH— | K434 | J9 | S |
| 2-1790 | —(CH$_2$)$_3$— | —NH—C(=O)—NH— | K435 | J9 | S |
| 2-1791 | —(CH$_2$)$_3$— | —NH—C(=O)—NH— | K724 | J9 | S |
| 2-1792 | —(CH$_2$)$_2$— | —NH—C(=S)—NH— | K34 | J9 | S |

TABLE 91

| Compound No. | -A¹- | -A²- | -G¹-A³-A⁴-G² | -A⁵-R² | X |
|---|---|---|---|---|---|
| 2-1793 | —(CH₂)₂— | —NH—C(=O)—NH— | K15 | J9 | S |
| 2-1794 | —(CH₂)₂— | —NH—C(=O)—NH— | K283 | J9 | S |
| 2-1795 | —(CH₂)₂— | —NH—C(=O)—NH— | K469 | J9 | S |
| 2-1796 | —(CH₂)₂— | —NH—C(=O)—NH— | K19 | J9 | S |
| 2-1797 | —(CH₂)₂— | —NH—C(=O)—NH— | K589 | J9 | S |
| 2-1798 | —(CH₂)₂— | —NH—C(=O)—NH— | K630 | J9 | S |
| 2-1799 | —(CH₂)₂— | —NH—C(=O)—NH— | K47 | J9 | S |
| 2-1800 | —(CH₂)₂— | —NH—C(=O)—NH— | K285 | J9 | S |
| 2-1801 | —(CH₂)₂— | —NH—C(=O)—NH— | K535 | J9 | S |
| 2-1802 | —(CH₂)₂— | —NH—C(=O)—NH— | K646 | J9 | S |
| 2-1803 | —(CH₂)₃— | —NH—C(=O)— | K1 | J9 | S |
| 2-1804 | —(CH₂)₂— | —NH—C(=O)— | K241 | J78 | S |
| 2-1805 | —(CH₂)₃— | —NH—C(=O)— | K241 | J78 | S |
| 2-1806 | —(CH₂)₂— | —NH—C(=O)— | K7 | J9 | S |
| 2-1807 | —(CH₂)₂— | —NH—C(=O)— | K11 | J78 | S |
| 2-1808 | —(CH₂)₂— | —NH—C(=O)— | K99 | J78 | S |
| 2-1809 | —(CH₂)₂— | —NH—C(=O)— | K24 | J78 | S |
| 2-1810 | —(CH₂)₂— | —NH—C(=O)— | K62 | J78 | S |
| 2-1811 | —(CH₂)₂— | —NH—C(=O)— | K72 | J78 | S |
| 2-1812 | —(CH₂)₂— | —NH—C(=O)—NH— | K11 | J78 | S |
| 2-1813 | —(CH₂)₂— | —NH—C(=O)—NH— | K49 | J78 | S |
| 2-1814 | —(CH₂)₃— | —NH—C(=O)— | K11 | J78 | S |
| 2-1815 | —(CH₂)₃— | —NH—C(=O)— | K99 | J78 | S |
| 2-1816 | —(CH₂)₃— | —NH—C(=O)— | K24 | J78 | S |
| 2-1817 | —(CH₂)₃— | —NH—C(=O)— | K62 | J78 | S |
| 2-1818 | —(CH₂)₃— | —NH—C(=O)— | K72 | J78 | S |
| 2-1819 | —(CH₂)₂— | —NH—C(=O)— | K679 | J9 | S |
| 2-1820 | —(CH₂)₂— | —NH—C(=O)— | K106 | J9 | S |
| 2-1821 | —(CH₂)₂— | —NH—C(=O)— | K271 | J9 | S |
| 2-1822 | —(CH₂)₂— | —NH—C(=O)— | K283 | K283 | S |
| 2-1823 | —(CH₂)₂— | —NH—C(=O)— | K5 | J9 | S |
| 2-1824 | —(CH₂)₂— | —NH—C(=O)— | K29 | J126 | S |

TABLE 92

| Compound No. | -A¹- | -A²- | -G¹-A³-A⁴-G² | -A⁵-R² | X |
|---|---|---|---|---|---|
| 2-1825 | —(CH₂)₂— | —NH—C(=O)— | K28 | J126 | S |
| 2-1826 | —(CH₂)₂— | —NH—C(=O)— | K99 | J126 | S |
| 2-1827 | —(CH₂)₂— | —NH—C(=O)— | K309 | J9 | S |
| 2-1828 | —(CH₂)₂— | —NH—C(=O)— | K469 | J9 | S |
| 2-1829 | —(CH₂)₂— | —NH—C(=O)— | K11 | J57 | S |
| 2-1830 | —(CH₂)₂— | —NH—C(=O)— | K463 | J9 | S |
| 2-1831 | —(CH₂)₂— | —NH—C(=O)— | K680 | J9 | S |
| 2-1832 | —(CH₂)₂— | —NH—C(=O)— | K681 | J9 | S |
| 2-1833 | —(CH₂)₂— | —NH—C(=O)— | K682 | J9 | S |
| 2-1834 | —(CH₂)₂— | —NH—C(=O)— | K683 | J9 | S |
| 2-1835 | —(CH₂)₂— | —NH—C(=O)— | K283 | J78 | S |
| 2-1836 | —(CH₂)₂— | —NH—C(=S)— | K11 | J57 | S |
| 2-1837 | —(CH₂)₂— | —NH—C(=O)— | K684 | J9 | S |
| 2-1838 | —(CH₂)₂— | —NH—C(=O)— | K685 | J9 | S |
| 2-1839 | —(CH₂)₂— | —NH—C(=O)— | K686 | J9 | S |
| 2-1840 | —(CH₂)₂— | —NH—C(=O)— | K687 | J9 | S |
| 2-1841 | —(CH₂)₂— | —NH—C(=O)— | K688 | J9 | S |
| 2-1842 | —(CH₂)₂— | single bond | K612 | J9 | S |
| 2-1843 | —(CH₂)₂— | —NH—C(=O)— | K613 | J9 | S |
| 2-1844 | —(CH₂)₂— | —NH—C(=O)— | K675 | J9 | S |
| 2-1845 | —(CH₂)₂— | —NH—C(=O)— | K676 | J9 | S |
| 2-1846 | —(CH₂)₂— | —NH—C(=O)— | K677 | J9 | S |
| 2-1847 | —(CH₂)₂— | —NH—C(=O)— | K678 | J9 | S |
| 2-1848 | —(CH₂)₂— | single bond | K613 | J9 | S |
| 2-1849 | —(CH₂)₃— | single bond | K614 | J9 | S |
| 2-1850 | —(CH₂)₃— | —NH—C(=O)— | K676 | J9 | S |
| 2-1851 | —(CH₂)₃— | —NH—C(=O)— | K546 | J9 | S |
| 2-1852 | —(CH₂)₃— | —NH—C(=O)— | K677 | J9 | S |
| 2-1853 | —(CH₂)₃— | —NH—C(=O)— | K678 | J9 | S |
| 2-1854 | —(CH₂)₃— | single bond | K612 | J9 | S |
| 2-1855 | —(CH₂)₂— | —N(CH₃)—C(=O)— | K241 | J9 | S |
| 2-1856 | —(CH₂)₂— | —N(CH₃)—C(=O)— | K11 | J9 | S |

TABLE 93

| Compound No. | -A¹- | -A²- | -G¹-A³-A⁴-G² | -A⁵-R² | X |
|---|---|---|---|---|---|
| 2-1857 | —(CH₂)₂— | —N(CH₃)—C(=O)— | K243 | J9 | S |
| 2-1858 | —(CH₂)₂— | —N(CH₃)—C(=O)— | K545 | J9 | S |
| 2-1859 | —(CH₂)₂— | —N(CH₃)—C(=O)— | K284 | J9 | S |
| 2-1860 | —(CH₂)₂— | —NH—C(=O)— | K689 | J9 | S |
| 2-1861 | —(CH₂)₂— | —NH—C(=O)— | K468 | J9 | S |
| 2-1862 | —(CH₂)₂— | —NH—C(=O)— | K134 | J9 | S |
| 2-1863 | —(CH₂)₂— | —NH—C(=O)— | K690 | J9 | S |
| 2-1864 | —(CH₂)₂— | —NH—C(=O)— | K218 | J9 | S |
| 2-1865 | —(CH₂)₂— | —NH—C(=O)— | K691 | J9 | S |
| 2-1866 | —(CH₂)₂— | —NH—C(=O)— | K692 | J9 | S |
| 2-1867 | —(CH₂)₂— | —NH—C(=O)— | K122 | J9 | S |
| 2-1868 | —(CH₂)₂— | —NH—C(=O)— | K693 | J9 | S |
| 2-1869 | —(CH₂)₂— | —NH—C(=O)— | K694 | J9 | S |
| 2-1870 | —(CH₂)₂— | —NH—C(=O)— | K100 | J9 | S |
| 2-1871 | —(CH₂)₂— | —NH—C(=O)— | K695 | J9 | S |
| 2-1872 | —(CH₂)₂— | —NH—C(=O)— | K273 | J9 | S |
| 2-1873 | —(CH₂)₂— | —NH—C(=O)— | K101 | J9 | S |
| 2-1874 | —(CH₂)₂— | —NH—C(=O)— | K672 | J9 | S |
| 2-1875 | —(CH₂)₂— | —NH—C(=O)— | K471 | J9 | S |
| 2-1876 | —(CH₂)₂— | —NH—C(=O)— | K674 | J9 | S |
| 2-1877 | —(CH₂)₂— | —NH—C(=O)— | K697 | J9 | S |
| 2-1878 | —(CH₂)₂— | —NH—C(=O)— | K698 | J9 | S |
| 2-1879 | —(CH₂)₂— | —NH—C(=O)— | K3 | J9 | S |
| 2-1880 | —(CH₂)₂— | —NH—C(=O)— | K87 | J9 | S |
| 2-1881 | —(CH₂)₂— | —NH—C(=O)— | K700 | J9 | S |
| 2-1882 | —(CH₂)₂— | —NH—C(=O)— | K702 | J9 | S |
| 2-1883 | —(CH₂)₂— | —NH—C(=O)— | K704 | J9 | S |
| 2-1884 | —(CH₂)₂— | —NH—C(=O)— | K706 | J9 | S |
| 2-1885 | —(CH₂)₂— | —NH—C(=O)— | K705 | J9 | S |
| 2-1886 | —(CH₂)₂— | —NH—C(=O)— | K703 | J9 | S |
| 2-1887 | —(CH₂)₂— | —NH—C(=O)— | K708 | J9 | S |
| 2-1888 | —(CH₂)₂— | —NH—C(=O)— | K709 | J9 | S |

TABLE 94

| Compound No. | -A¹- | -A²- | -G¹-A³-A⁴-G² | -A⁵-R² | X |
|---|---|---|---|---|---|
| 2-1889 | —(CH₂)₂— | —NH—C(=O)— | K710 | J9 | S |
| 2-1890 | —(CH₂)₂— | —NH—C(=O)— | K711 | J9 | S |
| 2-1891 | —(CH₂)₂— | —NH—C(=O)— | K712 | J9 | S |
| 2-1892 | —(CH₂)₂— | —NH—C(=O)— | K718 | J9 | S |
| 2-1893 | —(CH₂)₂— | —NH—C(=O)— | K714 | J9 | S |
| 2-1894 | —(CH₂)₂— | —NH—C(=O)— | K715 | J9 | S |
| 2-1895 | —(CH₂)₂— | —NH—C(=O)— | K11 | J1 | S |
| 2-1896 | —(CH₂)₂— | —NH—C(=O)— | K11 | J178 | S |
| 2-1897 | —(CH₂)₂— | —NH—C(=O)— | K11 | J22 | S |
| 2-1898 | —(CH₂)₂— | —NH—C(=O)— | K669 | J9 | S |
| 2-1899 | —(CH₂)₂— | —NH—C(=O)— | K716 | J9 | S |
| 2-1900 | —(CH₂)₂— | —NH—C(=O)— | K717 | J9 | S |
| 2-1901 | —(CH₂)₂— | —NH—C(=O)— | K713 | J9 | S |
| 2-1902 | —(CH₂)₂— | —NH—C(=O)— | K719 | J9 | S |
| 2-1903 | —(CH₂)₂— | —NH—C(=O)— | K435 | J9 | S |
| 2-1904 | —(CH₂)₂— | —NH—C(=O)— | K720 | J9 | S |
| 2-1905 | —(CH₂)₂— | —NH—S(=O)₂— | K11 | J9 | S |
| 2-1906 | —(CH₂)₂— | —NH—C(=O)— | K11 | J19 | S |
| 2-1907 | —(CH₂)₂— | —NH—C(=S)— | K11 | J19 | S |
| 2-1908 | —(CH₂)₂— | —NH—C(=O)— | K11 | J151 | S |
| 2-1909 | —(CH₂)₂— | —NH—C(=O)— | K11 | J140 | S |
| 2-1910 | —(CH₂)₂— | —NH—C(=O)— | K283 | J140 | S |
| 2-1911 | —(CH₂)₂— | —NH—C(=O)— | K49 | J140 | S |
| 2-1912 | —(CH₂)₂— | —NH—C(=O)— | K24 | J140 | S |
| 2-1913 | —(CH₂)₂— | —NH—C(=O)— | K243 | J140 | S |
| 2-1914 | —(CH₂)₂— | —NH—C(=O)— | K247 | J140 | S |
| 2-1915 | —(CH₂)₂— | —NH—C(=O)— | K244 | J140 | S |
| 2-1916 | —(CH₂)₂— | —NH—C(=O)— | K60 | J140 | S |
| 2-1917 | —(CH₂)₂— | —NH—C(=O)— | K62 | J140 | S |
| 2-1918 | —(CH₂)₂— | —NH—C(=O)— | K64 | J140 | S |
| 2-1919 | —(CH₂)₂— | —NH—C(=O)— | K11 | J176 | S |
| 2-1920 | —(CH₂)₂— | —NH—C(=S)— | K11 | J176 | S |

TABLE 95

| Compound No. | -A¹- | -A²- | -G¹-A³-A⁴-G² | -A⁵-R² | X |
|---|---|---|---|---|---|
| 2-1921 | —(CH₂)₂— | —NH—C(=O)— | K11 | J185 | S |
| 2-1922 | —(CH₂)₂— | —NH—C(=O)— | K11 | J49 | S |
| 2-1923 | —(CH₂)₂— | —NH—C(=O)— | K11 | J150 | S |
| 2-1924 | —(CH₂)₂— | —NH—C(=O)— | K11 | J37 | S |
| 2-1925 | —(CH₂)₂— | —NH—C(=O)— | K11 | J169 | S |
| 2-1926 | —(CH₂)₂— | —NH—C(=O)— | K11 | J171 | S |
| 2-1927 | —(CH₂)₂— | —NH—C(=O)— | K658 | J130 | S |
| 2-1928 | —(CH₂)₂— | —NH—C(=O)— | K543 | J130 | S |
| 2-1929 | —(CH₂)₂— | —NH—C(=O)— | K632 | J130 | S |
| 2-1930 | —(CH₂)₂— | —NH—C(=O)— | K761 | J9 | S |
| 2-1931 | —(CH₂)₂— | —NH— | K661 | J9 | S |
| 2-1932 | —(CH₂)₂— | —NH— | K663 | J9 | S |
| 2-1933 | —(CH₂)₂— | —NH— | K665 | J9 | S |
| 2-1934 | —(CH₂)₂— | —NH— | K667 | J9 | S |
| 2-1935 | —(CH₂)₂— | —NH— | K668 | J9 | S |
| 2-1936 | —(CH₂)₂— | —NH— | K669 | J9 | S |
| 2-1937 | —(CH₂)₂— | —NH— | K670 | J9 | S |
| 2-1938 | —(CH₂)₂— | —NH—C(=O)—NH— | K434 | J9 | S |
| 2-1939 | —(CH₂)₂— | —NH—C(=O)—NH— | K724 | J9 | S |
| 2-1940 | —(CH₂)₂— | —NH—C(=O)—NH— | K34 | J9 | S |
| 2-1941 | —(CH₂)₂— | —NH—C(=O)—NH— | K443 | J9 | S |
| 2-1942 | —(CH₂)₂— | —NH—C(=O)—NH— | K32 | J9 | S |
| 2-1943 | —(CH₂)₂— | —NH—C(=O)—NH— | K287 | J9 | S |
| 2-1944 | —(CH₂)₃— | —NH—C(=O)— | K243 | J9 | S |
| 2-1945 | —(CH₂)₃— | —NH—C(=O)— | K241 | J9 | S |
| 2-1946 | —(CH₂)₂— | —NH— | K617 | J129 | S |
| 2-1947 | —(CH₂)₃— | —NH—C(=O)— | K241 | J9 | O |
| 2-1948 | —(CH₂)₂— | —NH—C(=O)— | K283 | J9 | O |
| 2-1949 | —(CH₂)₂— | —NH—C(=O)— | K283 | J126 | O |
| 2-1950 | —(CH₂)₂— | —NH—C(=O)— | K283 | J129 | O |
| 2-1951 | —(CH₂)₂— | —NH— | K617 | J129 | O |
| 2-1952 | —(CH₂)₂— | —NH—C(=O)— | K283 | J1 | O |

TABLE 96

| Compound No. | -A¹- | -A²- | -G¹-A³-A⁴-G² | -A⁵-R² | X |
|---|---|---|---|---|---|
| 2-1953 | —(CH₂)₂— | —NH—C(=O)— | K11 | J1 | O |
| 2-1954 | —(CH₂)₂— | —NH—C(=O)— | K11 | J178 | O |
| 2-1955 | —(CH₂)₃— | —NH—C(=O)— | K241 | J78 | O |
| 2-1956 | —(CH₂)₂— | —NH—C(=O)— | K283 | J19 | S |
| 2-1957 | —(CH₂)₂— | —NH—C(=O)— | K283 | J151 | S |
| 2-1958 | —(CH₂)₂— | —NH—C(=O)—O— | K5 | J138 | O |
| 2-1959 | —(CH₂)₂— | —NH—C(=O)—O— | K5 | J78 | O |
| 2-1960 | —(CH₂)₂— | —NH—C(=O)—O— | K5 | J126 | O |
| 2-1961 | —(CH₂)₂— | —NH—C(=O)—O— | K5 | J129 | O |
| 2-1962 | —(CH₂)₂— | —NH—C(=O)—O— | K5 | J130 | O |
| 2-1963 | —(CH₂)₃— | —NH—C(=O)—O— | K5 | J78 | O |
| 2-1964 | —(CH₂)₂— | —NH—C(=O)—O— | K5 | J1 | O |
| 2-1965 | —(CH₂)₂— | —NH— | K767 | J213 | S |
| 2-1966 | —(CH₂)₂— | —NH— | K775 | J214 | S |
| 2-1967 | —(CH₂)₂— | —NH— | K763 | J215 | S |
| 2-1968 | —(CH₂)₂— | —NH— | K766 | J216 | S |
| 2-1969 | —(CH₂)₂— | —NH— | K813 | J217 | S |
| 2-1970 | —(CH₂)₂— | —NH— | K774 | J218 | S |
| 2-1971 | —(CH₂)₂— | —NH— | K764 | J219 | S |
| 2-1972 | —(CH₂)₂— | —NH— | K769 | J220 | S |
| 2-1973 | —(CH₂)₂— | —NH— | K821 | J221 | S |
| 2-1974 | —(CH₂)₂— | —NH— | K776 | J222 | S |
| 2-1975 | —(CH₂)₂— | —NH— | K778 | J223 | S |
| 2-1976 | —(CH₂)₂— | —NH— | K777 | J224 | S |
| 2-1977 | —(CH₂)₂— | —NH— | K767 | J225 | S |
| 2-1978 | —(CH₂)₂— | —NH— | K766 | J226 | S |
| 2-1979 | —(CH₂)₂— | —NH— | K819 | J227 | S |
| 2-1980 | —(CH₂)₂— | —NH— | K765 | J228 | S |
| 2-1981 | —(CH₂)₂— | —NH— | K780 | J229 | S |
| 2-1982 | —(CH₂)₂— | —NH— | K776 | J230 | S |
| 2-1983 | —(CH₂)₂— | —NH— | K814 | J231 | S |
| 2-1984 | —(CH₂)₂— | —NH— | K775 | J232 | S |

TABLE 97

| Compound No. | -A¹- | -A²- | -G¹-A³-A⁴-G² | -A⁵-R² | X |
|---|---|---|---|---|---|
| 2-1985 | —(CH₂)₂— | —NH— | K771 | J233 | S |
| 2-1986 | —(CH₂)₂— | —NH— | K765 | J234 | S |
| 2-1987 | —(CH₂)₂— | —NH— | K779 | J235 | S |
| 2-1988 | —(CH₂)₂— | —NH— | K773 | J236 | S |
| 2-1989 | —(CH₂)₂— | —NH— | K768 | J237 | S |
| 2-1990 | —(CH₂)₂— | —NH— | K770 | J238 | S |
| 2-1991 | —(CH₂)₂— | —NH— | K767 | J239 | S |
| 2-1992 | —(CH₂)₂— | —NH— | K811 | J240 | S |
| 2-1993 | —(CH₂)₂— | —NH— | K808 | J241 | S |
| 2-1994 | —(CH₂)₂— | —NH— | K763 | J242 | S |
| 2-1995 | —(CH₂)₂— | —NH— | K772 | J243 | S |
| 2-1996 | —(CH₂)₂— | —NH—C(=O)— | K585 | J213 | S |
| 2-1997 | —(CH₂)₂— | —NH—C(=O)— | K577 | J213 | S |
| 2-1998 | —(CH₂)₂— | —NH—C(=O)— | K516 | J214 | S |
| 2-1999 | —(CH₂)₂— | —NH—C(=O)— | K634 | J214 | S |
| 2-2000 | —(CH₂)₂— | —NH—C(=O)— | K581 | J215 | S |
| 2-2001 | —(CH₂)₂— | —NH—C(=O)— | K618 | J215 | S |
| 2-2002 | —(CH₂)₂— | —NH—C(=O)— | K573 | J216 | S |
| 2-2003 | —(CH₂)₂— | —NH—C(=O)— | K500 | J216 | S |
| 2-2004 | —(CH₂)₂— | —NH—C(=O)— | K513 | J217 | S |
| 2-2005 | —(CH₂)₂— | —NH—C(=O)— | K548 | J217 | S |
| 2-2006 | —(CH₂)₂— | —NH—C(=O)— | K577 | J218 | S |
| 2-2007 | —(CH₂)₂— | —NH—C(=O)— | K629 | J218 | S |
| 2-2008 | —(CH₂)₂— | —NH—C(=O)— | K618 | J219 | S |
| 2-2009 | —(CH₂)₂— | —NH—C(=O)— | K578 | J219 | S |
| 2-2010 | —(CH₂)₂— | —NH—C(=O)— | K585 | J220 | S |
| 2-2011 | —(CH₂)₂— | —NH—C(=O)— | K594 | J220 | S |
| 2-2012 | —(CH₂)₂— | —NH—C(=O)— | K427 | J221 | S |
| 2-2013 | —(CH₂)₂— | —NH—C(=O)— | K583 | J221 | S |
| 2-2014 | —(CH₂)₂— | —NH—C(=O)— | K607 | J222 | S |
| 2-2015 | —(CH₂)₂— | —NH—C(=O)— | K580 | J222 | S |
| 2-2016 | —(CH₂)₂— | —NH—C(=O)— | K297 | J223 | S |

TABLE 98

| Compound No. | -A¹- | -A²- | -G¹-A³-A⁴-G² | -A⁵-R² | X |
|---|---|---|---|---|---|
| 2-2017 | —(CH₂)₂— | —NH—C(=O)— | K575 | J223 | S |
| 2-2018 | —(CH₂)₂— | —NH—C(=O)— | K247 | J224 | S |
| 2-2019 | —(CH₂)₂— | —NH—C(=O)— | K627 | J224 | S |
| 2-2020 | —(CH₂)₂— | —NH—C(=O)— | K246 | J225 | S |
| 2-2021 | —(CH₂)₂— | —NH—C(=O)— | K243 | J225 | S |
| 2-2022 | —(CH₂)₂— | —NH—C(=O)— | K80 | J226 | S |
| 2-2023 | —(CH₂)₂— | —NH—C(=O)— | K54 | J226 | S |
| 2-2024 | —(CH₂)₂— | —NH—C(=O)— | K623 | J227 | S |
| 2-2025 | —(CH₂)₂— | —NH—C(=O)— | K245 | J227 | S |
| 2-2026 | —(CH₂)₂— | —NH—C(=O)— | K246 | J228 | S |
| 2-2027 | —(CH₂)₂— | —NH—C(=O)— | K582 | J228 | S |
| 2-2028 | —(CH₂)₂— | —NH—C(=O)— | K609 | J229 | S |
| 2-2029 | —(CH₂)₂— | —NH—C(=O)— | K611 | J229 | S |
| 2-2030 | —(CH₂)₂— | —NH—C(=O)— | K576 | J230 | S |
| 2-2031 | —(CH₂)₂— | —NH—C(=O)— | K585 | J230 | S |
| 2-2032 | —(CH₂)₂— | —NH—C(=O)— | K244 | J231 | S |
| 2-2033 | —(CH₂)₂— | —NH—C(=O)— | K82 | J231 | S |
| 2-2034 | —(CH₂)₂— | —NH—C(=O)— | K66 | J232 | S |
| 2-2035 | —(CH₂)₂— | —NH—C(=O)— | K248 | J232 | S |
| 2-2036 | —(CH₂)₂— | —NH—C(=O)— | K639 | J233 | S |
| 2-2037 | —(CH₂)₂— | —NH—C(=O)— | K85 | J233 | S |
| 2-2038 | —(CH₂)₂— | —NH—C(=O)— | K249 | J234 | S |
| 2-2039 | —(CH₂)₂— | —NH—C(=O)— | K245 | J234 | S |
| 2-2040 | —(CH₂)₂— | —NH—C(=O)— | K632 | J235 | S |
| 2-2041 | —(CH₂)₂— | —NH—C(=O)— | K246 | J235 | S |
| 2-2042 | —(CH₂)₂— | —NH—C(=O)— | K242 | J236 | S |
| 2-2043 | —(CH₂)₂— | —NH—C(=O)— | K618 | J236 | S |
| 2-2044 | —(CH₂)₂— | —NH—C(=O)— | K60 | J237 | S |
| 2-2045 | —(CH₂)₂— | —NH—C(=O)— | K581 | J237 | S |
| 2-2046 | —(CH₂)₂— | —NH—C(=O)— | K64 | J238 | S |
| 2-2047 | —(CH₂)₂— | —NH—C(=O)— | K247 | J238 | S |
| 2-2048 | —(CH₂)₂— | —NH—C(=O)— | K577 | J239 | S |

TABLE 99

| Compound No. | -A¹- | -A²- | -G¹-A³-A⁴-G² | -A⁵-R² | X |
|---|---|---|---|---|---|
| 2-2049 | —(CH$_2$)$_2$— | —NH—C(=O)— | K67 | J239 | S |
| 2-2050 | —(CH$_2$)$_2$— | —NH—C(=O)— | K573 | J240 | S |
| 2-2051 | —(CH$_2$)$_2$— | —NH—C(=O)— | K244 | J240 | S |
| 2-2052 | —(CH$_2$)$_2$— | —NH—C(=O)— | K69 | J241 | S |
| 2-2053 | —(CH$_2$)$_2$— | —NH—C(=O)— | K583 | J241 | S |
| 2-2054 | —(CH$_2$)$_2$— | —NH—C(=O)— | K580 | J242 | S |
| 2-2055 | —(CH$_2$)$_2$— | —NH—C(=O)— | K68 | J242 | S |
| 2-2056 | —(CH$_2$)$_2$— | —NH—C(=O)— | K245 | J243 | S |
| 2-2057 | —(CH$_2$)$_2$— | —NH—C(=O)— | K578 | J243 | S |
| 2-2058 | —(CH$_2$)$_2$— | —NH— | K808 | J126 | S |
| 2-2059 | —(CH$_2$)$_2$— | —NH— | K808 | J129 | S |
| 2-2060 | —(CH$_2$)$_2$— | —NH— | K808 | J130 | S |
| 2-2061 | —(CH$_2$)$_2$— | —NH— | K808 | J138 | S |
| 2-2062 | —(CH$_2$)$_2$— | —NH— | K809 | J126 | S |
| 2-2063 | —(CH$_2$)$_2$— | —NH— | K809 | J129 | S |
| 2-2064 | —(CH$_2$)$_2$— | —NH— | K809 | J130 | S |
| 2-2065 | —(CH$_2$)$_2$— | —NH— | K809 | J138 | S |
| 2-2066 | —(CH$_2$)$_2$— | —NH— | K810 | J126 | S |
| 2-2067 | —(CH$_2$)$_2$— | —NH— | K810 | J129 | S |
| 2-2068 | —(CH$_2$)$_2$— | —NH— | K810 | J130 | S |
| 2-2069 | —(CH$_2$)$_2$— | —NH— | K810 | J138 | S |
| 2-2070 | —(CH$_2$)$_2$— | —NH— | K811 | J126 | S |
| 2-2071 | —(CH$_2$)$_2$— | —NH— | K811 | J129 | S |
| 2-2072 | —(CH$_2$)$_2$— | —NH— | K811 | J130 | S |
| 2-2073 | —(CH$_2$)$_2$— | —NH— | K811 | J138 | S |
| 2-2074 | —(CH$_2$)$_2$— | —NH— | K812 | J126 | S |
| 2-2075 | —(CH$_2$)$_2$— | —NH— | K812 | J129 | S |
| 2-2076 | —(CH$_2$)$_2$— | —NH— | K812 | J130 | S |
| 2-2077 | —(CH$_2$)$_2$— | —NH— | K812 | J138 | S |
| 2-2078 | —(CH$_2$)$_2$— | —NH— | K813 | J126 | S |
| 2-2079 | —(CH$_2$)$_2$— | —NH— | K813 | J129 | S |
| 2-2080 | —(CH$_2$)$_2$— | —NH— | K813 | J130 | S |

TABLE 100

| Compound No. | -A¹- | -A²- | -G¹-A³-A⁴-G² | -A⁵-R² | X |
|---|---|---|---|---|---|
| 2-2081 | —(CH$_2$)$_2$— | —NH— | K813 | J138 | S |
| 2-2082 | —(CH$_2$)$_2$— | —NH— | K814 | J126 | S |
| 2-2083 | —(CH$_2$)$_2$— | —NH— | K814 | J129 | S |
| 2-2084 | —(CH$_2$)$_2$— | —NH— | K814 | J130 | S |
| 2-2085 | —(CH$_2$)$_2$— | —NH— | K814 | J138 | S |
| 2-2086 | —(CH$_2$)$_2$— | —NH— | K815 | J126 | S |
| 2-2087 | —(CH$_2$)$_2$— | —NH— | K815 | J129 | S |
| 2-2088 | —(CH$_2$)$_2$— | —NH— | K815 | J130 | S |
| 2-2089 | —(CH$_2$)$_2$— | —NH— | K815 | J138 | S |
| 2-2090 | —(CH$_2$)$_2$— | —NH— | K816 | J126 | S |
| 2-2091 | —(CH$_2$)$_2$— | —NH— | K816 | J129 | S |
| 2-2092 | —(CH$_2$)$_2$— | —NH— | K816 | J130 | S |
| 2-2093 | —(CH$_2$)$_2$— | —NH— | K816 | J138 | S |
| 2-2094 | —(CH$_2$)$_2$— | —NH— | K817 | J126 | S |
| 2-2095 | —(CH$_2$)$_2$— | —NH— | K817 | J129 | S |
| 2-2096 | —(CH$_2$)$_2$— | —NH— | K817 | J130 | S |
| 2-2097 | —(CH$_2$)$_2$— | —NH— | K817 | J138 | S |
| 2-2098 | —(CH$_2$)$_2$— | —NH— | K818 | J126 | S |
| 2-2099 | —(CH$_2$)$_2$— | —NH— | K818 | J129 | S |
| 2-2100 | —(CH$_2$)$_2$— | —NH— | K818 | J130 | S |
| 2-2101 | —(CH$_2$)$_2$— | —NH— | K818 | J138 | S |
| 2-2102 | —(CH$_2$)$_2$— | —NH— | K819 | J126 | S |
| 2-2103 | —(CH$_2$)$_2$— | —NH— | K819 | J129 | S |
| 2-2104 | —(CH$_2$)$_2$— | —NH— | K819 | J130 | S |
| 2-2105 | —(CH$_2$)$_2$— | —NH— | K819 | J138 | S |
| 2-2106 | —(CH$_2$)$_2$— | —NH— | K820 | J126 | S |
| 2-2107 | —(CH$_2$)$_2$— | —NH— | K820 | J129 | S |
| 2-2108 | —(CH$_2$)$_2$— | —NH— | K820 | J130 | S |
| 2-2109 | —(CH$_2$)$_2$— | —NH— | K820 | J138 | S |
| 2-2110 | —(CH$_2$)$_2$— | —NH— | K821 | J126 | S |
| 2-2111 | —(CH$_2$)$_2$— | —NH— | K821 | J129 | S |
| 2-2112 | —(CH$_2$)$_2$— | —NH— | K821 | J130 | S |

TABLE 101

| Compound No. | -A¹- | -A²- | -G¹-A³-A⁴-G² | -A⁵-R² | X |
|---|---|---|---|---|---|
| 2-2113 | —(CH$_2$)$_2$— | —NH— | K821 | J138 | S |
| 2-2114 | —(CH$_2$)$_2$— | —NH—C(=O)— | K797 | J126 | S |
| 2-2115 | —(CH$_2$)$_2$— | —NH—C(=O)— | K797 | J129 | S |
| 2-2116 | —(CH$_2$)$_2$— | —NH—C(=O)— | K797 | J130 | S |
| 2-2117 | —(CH$_2$)$_2$— | —NH—C(=O)— | K797 | J138 | S |
| 2-2118 | —(CH$_2$)$_2$— | —NH—C(=O)— | K798 | J126 | S |
| 2-2119 | —(CH$_2$)$_2$— | —NH—C(=O)— | K798 | J129 | S |
| 2-2120 | —(CH$_2$)$_2$— | —NH—C(=O)— | K798 | J130 | S |
| 2-2121 | —(CH$_2$)$_2$— | —NH—C(=O)— | K798 | J138 | S |
| 2-2122 | —(CH$_2$)$_2$— | —NH—C(=O)— | K799 | J126 | S |
| 2-2123 | —(CH$_2$)$_2$— | —NH—C(=O)— | K799 | J129 | S |
| 2-2124 | —(CH$_2$)$_2$— | —NH—C(=O)— | K799 | J130 | S |
| 2-2125 | —(CH$_2$)$_2$— | —NH—C(=O)— | K799 | J138 | S |
| 2-2126 | —(CH$_2$)$_2$— | —NH—C(=O)— | K800 | J126 | S |
| 2-2127 | —(CH$_2$)$_2$— | —NH—C(=O)— | K800 | J129 | S |
| 2-2128 | —(CH$_2$)$_2$— | —NH—C(=O)— | K800 | J130 | S |
| 2-2129 | —(CH$_2$)$_2$— | —NH—C(=O)— | K800 | J138 | S |
| 2-2130 | —(CH$_2$)$_2$— | —NH—C(=O)— | K801 | J126 | S |
| 2-2131 | —(CH$_2$)$_2$— | —NH—C(=O)— | K801 | J129 | S |
| 2-2132 | —(CH$_2$)$_2$— | —NH—C(=O)— | K801 | J130 | S |
| 2-2133 | —(CH$_2$)$_2$— | —NH—C(=O)— | K801 | J138 | S |
| 2-2134 | —(CH$_2$)$_2$— | —NH—C(=O)— | K802 | J126 | S |
| 2-2135 | —(CH$_2$)$_2$— | —NH—C(=O)— | K802 | J129 | S |
| 2-2136 | —(CH$_2$)$_2$— | —NH—C(=O)— | K802 | J130 | S |
| 2-2137 | —(CH$_2$)$_2$— | —NH—C(=O)— | K802 | J138 | S |
| 2-2138 | —(CH$_2$)$_2$— | —NH—C(=O)— | K803 | J126 | S |
| 2-2139 | —(CH$_2$)$_2$— | —NH—C(=O)— | K803 | J129 | S |
| 2-2140 | —(CH$_2$)$_2$— | —NH—C(=O)— | K803 | J130 | S |
| 2-2141 | —(CH$_2$)$_2$— | —NH—C(=O)— | K803 | J138 | S |
| 2-2142 | —(CH$_2$)$_2$— | —NH—C(=O)— | K804 | J126 | S |
| 2-2143 | —(CH$_2$)$_2$— | —NH—C(=O)— | K804 | J129 | S |
| 2-2144 | —(CH$_2$)$_2$— | —NH—C(=O)— | K804 | J130 | S |

TABLE 102

| Compound No. | -A¹- | -A²- | -G¹-A³-A⁴-G² | -A⁵-R² | X |
|---|---|---|---|---|---|
| 2-2145 | —(CH$_2$)$_2$— | —NH—C(=O)— | K804 | J138 | S |
| 2-2146 | —(CH$_2$)$_2$— | —NH—C(=O)— | K805 | J126 | S |
| 2-2147 | —(CH$_2$)$_2$— | —NH—C(=O)— | K805 | J129 | S |
| 2-2148 | —(CH$_2$)$_2$— | —NH—C(=O)— | K805 | J130 | S |
| 2-2149 | —(CH$_2$)$_2$— | —NH—C(=O)— | K805 | J138 | S |
| 2-2150 | —(CH$_2$)$_2$— | —NH—C(=O)— | K806 | J126 | S |
| 2-2151 | —(CH$_2$)$_2$— | —NH—C(=O)— | K806 | J129 | S |
| 2-2152 | —(CH$_2$)$_2$— | —NH—C(=O)— | K806 | J130 | S |
| 2-2153 | —(CH$_2$)$_2$— | —NH—C(=O)— | K806 | J138 | S |
| 2-2154 | —(CH$_2$)$_2$— | —NH—C(=O)— | K807 | J126 | S |
| 2-2155 | —(CH$_2$)$_2$— | —NH—C(=O)— | K807 | J129 | S |
| 2-2156 | —(CH$_2$)$_2$— | —NH—C(=O)— | K807 | J130 | S |
| 2-2157 | —(CH$_2$)$_2$— | —NH—C(=O)— | K807 | J138 | S |
| 2-2158 | —(CH$_2$)$_2$— | —NH—C(=O)— | K822 | J9 | S |
| 2-2159 | —(CH$_2$)$_2$— | —NH—C(=O)— | K88 | J9 | S |

TABLE 103

| Compound No. | -A¹- | -A²- | -G¹-A³-A⁴-G² | -A⁵-R² | X |
|---|---|---|---|---|---|
| 3-0001 | —(CH$_2$)$_2$— | —C(=O)—NH— | K240 | J9 | S |
| 3-0002 | —(CH$_2$)$_2$— | —C(=O)—N(CH$_2$CH$_3$)— | K2 | J1 | S |
| 3-0003 | —(CH$_2$)$_2$— | —C(=O)—N(CH$_2$CH$_3$)— | K2 | J6 | S |
| 3-0004 | —(CH$_2$)$_2$— | —C(=O)—N(CH$_2$CH$_3$)— | K2 | J9 | S |
| 3-0005 | —(CH$_2$)$_2$— | —C(=O)—N(CH$_2$CH$_3$)— | K2 | J22 | S |
| 3-0006 | —(CH$_2$)$_2$— | —C(=O)—N(CH$_2$CH$_3$)— | K2 | J30 | S |
| 3-0007 | —(CH$_2$)$_2$— | —C(=O)—N(CH$_2$CH$_3$)— | K2 | J70 | S |
| 3-0008 | —(CH$_2$)$_2$— | —C(=O)—N(CH$_2$CH$_3$)— | K2 | J77 | S |
| 3-0009 | —(CH$_2$)$_2$— | —C(=O)—NH— | K4 | J9 | S |
| 3-0010 | —(CH$_2$)$_2$— | —C(=O)—NH— | K4 | J10 | S |
| 3-0011 | —(CH$_2$)$_2$— | —C(=O)—NH— | K4 | J13 | S |

TABLE 103-continued

| Compound No. | -A¹- | -A²- | -G¹-A³-A⁴-G² | -A⁵-R² | X |
|---|---|---|---|---|---|
| 3-0012 | —(CH₂)₂— | —C(=O)—NH— | K256 | J9 | S |
| 3-0013 | —(CH₂)₂— | —C(=O)—NH— | K256 | J42 | S |
| 3-0014 | —(CH₂)₂— | —C(=O)—NH— | K256 | J43 | S |
| 3-0015 | —(CH₂)₂— | —C(=O)—NH— | K256 | J59 | S |
| 3-0016 | —(CH₂)₂— | —C(=O)—NH— | K257 | J9 | S |
| 3-0017 | —(CH₂)₂— | —C(=O)—NH— | K257 | J132 | S |
| 3-0018 | —(CH₂)₂— | —C(=O)—NH— | K257 | J133 | S |
| 3-0019 | —(CH₂)₂— | —C(=O)—NH— | K258 | J9 | S |
| 3-0020 | —(CH₂)₂— | —C(=O)—NH— | K260 | J9 | S |
| 3-0021 | —(CH₂)₂— | —C(=O)—NH— | K262 | J9 | S |
| 3-0022 | —(CH₂)₂— | —C(=O)—NH— | K262 | J134 | S |
| 3-0023 | —(CH₂)₂— | —C(=O)—NH— | K262 | J137 | S |
| 3-0024 | —(CH₂)₂— | —C(=O)—NH— | K262 | J154 | S |
| 3-0025 | —(CH₂)₂— | —C(=O)—NH— | K262 | J157 | S |
| 3-0026 | —(CH₂)₂— | —C(=O)—NH— | K262 | J168 | S |
| 3-0027 | —(CH₂)₂— | —C(=O)—NH— | K262 | J174 | O |
| 3-0028 | —(CH₂)₂— | —C(=O)—NH— | K262 | J177 | S |
| 3-0029 | —(CH₂)₂— | —C(=O)—NH— | K263 | J9 | S |
| 3-0030 | —(CH₂)₂— | —C(=O)—NH— | K263 | J11 | S |
| 3-0031 | —(CH₂)₂— | —C(=O)—NH— | K263 | J20 | O |
| 3-0032 | —(CH₂)₂— | —C(=O)—NH— | K263 | J48 | O |

TABLE 104

| Compound No. | -A¹- | -A²- | -G¹-A³-A⁴-G² | -A⁵-R² | X |
|---|---|---|---|---|---|
| 3-0033 | —(CH₂)₂— | —C(=O)—NH— | K263 | J51 | S |
| 3-0034 | —(CH₂)₂— | —C(=O)—NH— | K263 | J52 | S |
| 3-0035 | —(CH₂)₂— | —C(=O)—NH— | K263 | J87 | O |
| 3-0036 | —(CH₂)₂— | —C(=O)—NH— | K264 | J9 | S |
| 3-0037 | —(CH₂)₂— | —C(=O)—N(CH₃)— | K268 | J9 | S |
| 3-0038 | —(CH₂)₂— | —C(=O)—NH— | K7 | J9 | S |
| 3-0039 | —(CH₂)₂— | —C(=O)—NH— | K7 | J105 | S |
| 3-0040 | —(CH₂)₂— | —C(=O)—NH— | K7 | J127 | S |
| 3-0041 | —(CH₂)₂— | —C(=O)—NH— | K7 | J129 | O |
| 3-0042 | —(CH₂)₂— | —C(=O)—NH— | K7 | J138 | O |
| 3-0043 | —(CH₂)₂— | —C(=O)—NH— | K7 | J147 | S |
| 3-0044 | —(CH₂)₂— | —C(=O)—NH— | K7 | J165 | S |
| 3-0045 | —(CH₂)₂— | —C(=O)—NH— | K7 | J178 | O |
| 3-0046 | —(CH₂)₂— | —C(=O)—NH— | K8 | J73 | S |
| 3-0047 | —(CH₂)₂— | —C(=O)—NH— | K8 | J74 | S |
| 3-0048 | —(CH₂)₂— | —C(=O)—NH— | K8 | J75 | O |
| 3-0049 | —(CH₂)₂— | —C(=O)—NH— | K8 | J81 | O |
| 3-0050 | —(CH₂)₂— | —C(=O)—NH— | K8 | J82 | S |
| 3-0051 | —(CH₂)₂— | —C(=O)—NH— | K8 | J83 | S |
| 3-0052 | —(CH₂)₂— | —C(=O)—NH— | K8 | J92 | O |
| 3-0053 | —(CH₂)₂— | —C(=O)—NH— | K9 | J9 | S |
| 3-0054 | —(CH₂)₂— | —C(=O)—NH— | K271 | J1 | S |
| 3-0055 | —(CH₂)₂— | —C(=O)—NH— | K271 | J6 | S |
| 3-0056 | —(CH₂)₂— | —C(=O)—NH— | K271 | J22 | S |
| 3-0057 | —(CH₂)₂— | —C(=O)—NH— | K271 | J30 | S |
| 3-0058 | —(CH₂)₂— | —C(=O)—NH— | K271 | J70 | S |
| 3-0059 | —(CH₂)₂— | —C(=O)—NH— | K271 | J77 | S |
| 3-0060 | —(CH₂)₂— | —C(=O)—NH— | K273 | J3 | S |
| 3-0061 | —(CH₂)₂— | —C(=O)—NH— | K273 | J9 | S |
| 3-0062 | —(CH₂)₂— | —C(=O)—NH— | K273 | J78 | S |
| 3-0063 | —(CH₂)₂— | —C(=O)—NH— | K273 | J130 | S |
| 3-0064 | —(CH₂)₂— | —C(=O)—N(CH₃)— | K274 | J9 | S |

TABLE 105

| Compound No. | -A¹- | -A²- | -G¹-A³-A⁴-G² | -A⁵-R² | X |
|---|---|---|---|---|---|
| 3-0065 | —(CH₂)₂— | —C(=O)—NH— | K275 | J9 | S |
| 3-0066 | —(CH₂)₂— | —C(=O)—NH— | K279 | J10 | S |
| 3-0067 | —(CH₂)₂— | —C(=O)—NH— | K279 | J13 | S |
| 3-0068 | —(CH₂)₂— | —C(=O)—NH— | K279 | J19 | S |
| 3-0069 | —(CH₂)₂— | —C(=O)—NH— | K279 | J57 | S |

TABLE 105-continued

| Compound No. | -A¹- | -A²- | -G¹-A³-A⁴-G² | -A⁵-R² | X |
|---|---|---|---|---|---|
| 3-0070 | —(CH₂)₂— | —C(=O)—NH— | K279 | J126 | S |
| 3-0071 | —(CH₂)₂— | —C(=O)—NH— | K279 | J128 | S |
| 3-0072 | —(CH₂)₂— | —C(=O)—NH— | K279 | J140 | S |
| 3-0073 | —(CH₂)₂— | —C(=O)—NH— | K11 | J9 | S |
| 3-0074 | —(CH₂)₂— | —C(=O)—NH— | K11 | J78 | S |
| 3-0075 | —(CH₂)₂— | —C(=O)—NH— | K37 | J1 | S |
| 3-0076 | —(CH₂)₂— | —C(=O)—NH— | K37 | J6 | S |
| 3-0077 | —(CH₂)₂— | —C(=O)—NH— | K37 | J22 | S |
| 3-0078 | —(CH₂)₂— | —C(=O)—NH— | K37 | J30 | S |
| 3-0079 | —(CH₂)₂— | —C(=O)—NH— | K37 | J70 | S |
| 3-0080 | —(CH₂)₂— | —C(=O)—NH— | K37 | J77 | S |
| 3-0081 | —(CH₂)₂— | —C(=O)—NH— | K19 | J9 | S |
| 3-0082 | —(CH₂)₂— | —C(=O)—NH— | K283 | J9 | S |
| 3-0083 | —(CH₂)₂— | —C(=O)—NH— | K14 | J9 | S |
| 3-0084 | —(CH₂)₂— | —C(=O)—NH— | K284 | J9 | S |
| 3-0085 | —(CH₂)₂— | —C(=O)—NH— | K23 | J9 | S |
| 3-0086 | —(CH₂)₂— | —C(=O)—NH— | K45 | J9 | S |
| 3-0087 | —(CH₂)₂— | —C(=O)—NH— | K286 | J9 | S |
| 3-0088 | —(CH₂)₂— | —C(=O)—NH— | K286 | J10 | S |
| 3-0089 | —(CH₂)₂— | —C(=O)—NH— | K286 | J13 | S |
| 3-0090 | —(CH₂)₂— | —C(=O)—NH— | K32 | J9 | S |
| 3-0091 | —(CH₂)₂— | —C(=O)—NH— | K287 | J9 | S |
| 3-0092 | —(CH₂)₂— | —C(=O)—NH— | K287 | J42 | S |
| 3-0093 | —(CH₂)₂— | —C(=O)—NH— | K287 | J43 | S |
| 3-0094 | —(CH₂)₂— | —C(=O)—NH— | K287 | J49 | S |
| 3-0095 | —(CH₂)₂— | —C(=O)—NH— | K287 | J50 | S |
| 3-0096 | —(CH₂)₂— | —C(=O)—NH— | K287 | J58 | S |

TABLE 106

| Compound No. | -A¹- | -A²- | -G¹-A³-A⁴-G² | -A⁵-R² | X |
|---|---|---|---|---|---|
| 3-0097 | —(CH₂)₂— | —C(=O)—NH— | K287 | J59 | S |
| 3-0098 | —(CH₂)₂— | —C(=O)—NH— | K287 | J64 | S |
| 3-0099 | —(CH₂)₂— | —C(=O)—N(CH₃)— | K11 | J9 | S |
| 3-0100 | —(CH₂)₂— | —C(=O)—N(CH₃)— | K24 | J9 | S |
| 3-0101 | —(CH₂)₂— | —C(=O)—N(CH₃)— | K24 | J96 | S |
| 3-0102 | —(CH₂)₂— | —C(=O)—N(CH₃)— | K24 | J100 | S |
| 3-0103 | —(CH₂)₂— | —C(=O)—N(CH₃)— | K24 | J104 | S |
| 3-0104 | —(CH₂)₂— | —C(=O)—N(CH₃)— | K24 | J119 | S |
| 3-0105 | —(CH₂)₂— | —C(=O)—N(CH₃)— | K24 | J120 | S |
| 3-0106 | —(CH₂)₂— | —C(=O)—N(CH₃)— | K294 | J42 | S |
| 3-0107 | —(CH₂)₂— | —C(=O)—N(CH₃)— | K294 | J43 | S |
| 3-0108 | —(CH₂)₂— | —C(=O)—N(CH₃)— | K294 | J59 | S |
| 3-0109 | —(CH₂)₂— | —C(=O)—NH— | K70 | J9 | S |
| 3-0110 | —(CH₂)₂— | —C(=O)—NH— | K72 | J9 | S |
| 3-0111 | —(CH₂)₂— | —C(=O)—NH— | K72 | J137 | S |
| 3-0112 | —(CH₂)₂— | —C(=O)—NH— | K68 | J9 | S |
| 3-0113 | —(CH₂)₂— | —C(=O)—NH— | K68 | J20 | S |
| 3-0114 | —(CH₂)₂— | —C(=O)—NH— | K68 | J48 | S |
| 3-0115 | —(CH₂)₂— | —C(=O)—NH— | K302 | J9 | S |
| 3-0116 | —(CH₂)₂— | —C(=O)—NH— | K99 | J9 | S |
| 3-0117 | —(CH₂)₂— | —C(=O)—NH— | K99 | J78 | S |
| 3-0118 | —(CH₂)₂— | —C(=O)—NH— | K308 | J9 | S |
| 3-0119 | —(CH₂)₂— | —C(=O)—NH— | K309 | J9 | S |
| 3-0120 | —(CH₂)₂— | —C(=O)—NH— | K309 | J138 | S |
| 3-0121 | —(CH₂)₂— | —C(=O)—NH— | K309 | J147 | O |
| 3-0122 | —(CH₂)₂— | —C(=O)—NH— | K309 | J165 | O |
| 3-0123 | —(CH₂)₂— | —C(=O)—NH— | K309 | J178 | S |
| 3-0124 | —(CH₂)₂— | —C(=O)—NH— | K103 | J9 | S |
| 3-0125 | —(CH₂)₂— | —C(=O)—NH— | K105 | J9 | S |
| 3-0126 | —(CH₂)₂— | —C(=O)—NH— | K106 | J9 | S |
| 3-0127 | —(CH₂)₂— | —C(=O)—NH— | K106 | J73 | S |
| 3-0128 | —(CH₂)₂— | —C(=O)—NH— | K106 | J74 | O |

TABLE 107

| Compound No. | -A¹- | -A²- | -G¹-A³-A⁴-G² | -A⁵-R² | X |
|---|---|---|---|---|---|
| 3-0129 | —(CH$_2$)$_2$— | —C(=O)—NH— | K106 | J75 | S |
| 3-0130 | —(CH$_2$)$_2$— | —C(=O)—NH— | K106 | J81 | S |
| 3-0131 | —(CH$_2$)$_2$— | —C(=O)—NH— | K106 | J82 | O |
| 3-0132 | —(CH$_2$)$_2$— | —C(=O)—NH— | K106 | J83 | O |
| 3-0133 | —(CH$_2$)$_2$— | —C(=O)—NH— | K106 | J92 | S |
| 3-0134 | —(CH$_2$)$_2$— | —C(=O)—NH— | K109 | J9 | S |
| 3-0135 | —(CH$_2$)$_2$— | —C(=O)—NH— | K109 | J78 | S |
| 3-0136 | —(CH$_2$)$_2$— | —C(=O)—NH— | K110 | J9 | S |
| 3-0137 | —(CH$_2$)$_2$— | —C(=O)—NH— | K110 | J78 | S |
| 3-0138 | —(CH$_2$)$_2$— | —C(=O)—NH— | K120 | J9 | O |
| 3-0139 | —(CH$_2$)$_2$— | —C(=O)—NH— | K120 | J9 | S |
| 3-0140 | —(CH$_2$)$_2$— | —C(=O)—NH— | K120 | J78 | S |
| 3-0141 | —(CH$_2$)$_2$— | —C(=O)—N(CH$_3$)— | K99 | J1 | S |
| 3-0142 | —(CH$_2$)$_2$— | —C(=O)—N(CH$_3$)— | K99 | J6 | S |
| 3-0143 | —(CH$_2$)$_2$— | —C(=O)—N(CH$_3$)— | K99 | J9 | S |
| 3-0144 | —(CH$_2$)$_2$— | —C(=O)—N(CH$_3$)— | K99 | J22 | S |
| 3-0145 | —(CH$_2$)$_2$— | —C(=O)—N(CH$_3$)— | K99 | J30 | S |
| 3-0146 | —(CH$_2$)$_2$— | —C(=O)—N(CH$_3$)— | K99 | J70 | S |
| 3-0147 | —(CH$_2$)$_2$— | —C(=O)—N(CH$_3$)— | K99 | J77 | S |
| 3-0148 | —(CH$_2$)$_2$— | —C(=O)— | K314 | J9 | S |
| 3-0149 | —(CH$_2$)$_2$— | —C(=O)— | K314 | J10 | S |
| 3-0150 | —(CH$_2$)$_2$— | —C(=O)— | K314 | J13 | S |
| 3-0151 | —(CH$_2$)$_2$— | —C(=O)— | K315 | J3 | S |
| 3-0152 | —(CH$_2$)$_2$— | —C(=O)— | K315 | J9 | S |
| 3-0153 | —(CH$_2$)$_2$— | —C(=O)— | K315 | J42 | S |
| 3-0154 | —(CH$_2$)$_2$— | —C(=O)— | K315 | J43 | S |
| 3-0155 | —(CH$_2$)$_2$— | —C(=O)— | K315 | J59 | S |
| 3-0156 | —(CH$_2$)$_2$— | —C(=O)— | K315 | J78 | S |
| 3-0157 | —(CH$_2$)$_2$— | —C(=O)— | K315 | J130 | S |
| 3-0158 | —(CH$_2$)$_2$— | —C(=O)— | K316 | J132 | S |
| 3-0159 | —(CH$_2$)$_2$— | —C(=O)— | K316 | J133 | S |
| 3-0160 | —(CH$_2$)$_2$— | —C(=O)— | K317 | J9 | S |

TABLE 108

| Compound No. | -A¹- | -A²- | -G¹-A³-A⁴-G² | -A⁵-R² | X |
|---|---|---|---|---|---|
| 3-0161 | —(CH$_2$)$_2$— | —C(=O)— | K317 | J134 | S |
| 3-0162 | —(CH$_2$)$_2$— | —C(=O)— | K317 | J137 | S |
| 3-0163 | —(CH$_2$)$_2$— | —C(=O)— | K317 | J154 | S |
| 3-0164 | —(CH$_2$)$_2$— | —C(=O)— | K317 | J157 | S |
| 3-0165 | —(CH$_2$)$_2$— | —C(=O)— | K317 | J168 | S |
| 3-0166 | —(CH$_2$)$_2$— | —C(=O)— | K317 | J174 | O |
| 3-0167 | —(CH$_2$)$_2$— | —C(=O)— | K317 | J177 | O |
| 3-0168 | —(CH$_2$)$_2$— | —C(=O)— | K318 | J9 | S |
| 3-0169 | —(CH$_2$)$_2$— | —C(=O)— | K318 | J11 | S |
| 3-0170 | —(CH$_2$)$_2$— | —C(=O)— | K318 | J20 | S |
| 3-0171 | —(CH$_2$)$_2$— | —C(=O)— | K318 | J48 | O |
| 3-0172 | —(CH$_2$)$_2$— | —C(=O)— | K318 | J51 | S |
| 3-0173 | —(CH$_2$)$_2$— | —C(=O)— | K318 | J52 | S |
| 3-0174 | —(CH$_2$)$_2$— | —C(=O)— | K318 | J87 | O |
| 3-0175 | —(CH$_2$)$_2$— | —C(=O)— | K319 | J9 | S |
| 3-0176 | —(CH$_2$)$_2$— | —C(=O)— | K319 | J19 | S |
| 3-0177 | —(CH$_2$)$_2$— | —C(=O)— | K319 | J57 | S |
| 3-0178 | —(CH$_2$)$_2$— | —C(=O)— | K319 | J105 | O |
| 3-0179 | —(CH$_2$)$_2$— | —C(=O)— | K319 | J126 | S |
| 3-0180 | —(CH$_2$)$_2$— | —C(=O)— | K319 | J127 | S |
| 3-0181 | —(CH$_2$)$_2$— | —C(=O)— | K319 | J128 | S |
| 3-0182 | —(CH$_2$)$_2$— | —C(=O)— | K319 | J129 | S |
| 3-0183 | —(CH$_2$)$_2$— | —C(=O)— | K319 | J140 | S |
| 3-0184 | —(CH$_2$)$_2$— | —C(=O)— | K320 | J9 | S |
| 3-0185 | —(CH$_2$)$_2$— | —C(=O)— | K325 | J1 | S |
| 3-0186 | —(CH$_2$)$_2$— | —C(=O)— | K325 | J3 | S |
| 3-0187 | —(CH$_2$)$_2$— | —C(=O)— | K325 | J6 | S |
| 3-0188 | —(CH$_2$)$_2$— | —C(=O)— | K325 | J9 | S |
| 3-0189 | —(CH$_2$)$_2$— | —C(=O)— | K325 | J22 | S |
| 3-0190 | —(CH$_2$)$_2$— | —C(=O)— | K325 | J30 | S |
| 3-0191 | —(CH$_2$)$_2$— | —C(=O)— | K325 | J70 | S |
| 3-0192 | —(CH$_2$)$_2$— | —C(=O)— | K325 | J77 | S |

TABLE 109

| Compound No. | -A¹- | -A²- | -G¹-A³-A⁴-G² | -A⁵-R² | X |
|---|---|---|---|---|---|
| 3-0193 | —(CH$_2$)$_2$— | —C(=O)— | K325 | J78 | S |
| 3-0194 | —(CH$_2$)$_2$— | —C(=O)— | K325 | J130 | S |
| 3-0195 | —(CH$_2$)$_2$— | —C(=O)— | K329 | J10 | S |
| 3-0196 | —(CH$_2$)$_2$— | —C(=O)— | K329 | J13 | S |
| 3-0197 | —(CH$_2$)$_2$— | —C(=O)— | K330 | J9 | S |
| 3-0198 | —(CH$_2$)$_2$— | —C(=O)— | K331 | J9 | S |
| 3-0199 | —(CH$_2$)$_2$— | —C(=O)— | K331 | J42 | S |
| 3-0200 | —(CH$_2$)$_2$— | —C(=O)— | K331 | J43 | S |
| 3-0201 | —(CH$_2$)$_2$— | —C(=O)— | K331 | J49 | S |
| 3-0202 | —(CH$_2$)$_2$— | —C(=O)— | K331 | J50 | S |
| 3-0203 | —(CH$_2$)$_2$— | —C(=O)— | K331 | J58 | S |
| 3-0204 | —(CH$_2$)$_2$— | —C(=O)— | K331 | J59 | S |
| 3-0205 | —(CH$_2$)$_2$— | —C(=O)— | K331 | J64 | S |
| 3-0206 | —(CH$_2$)$_2$— | —C(=O)— | K332 | J9 | S |
| 3-0207 | —(CH$_2$)$_2$— | —C(=O)— | K332 | J78 | S |
| 3-0208 | —(CH$_2$)$_2$— | —C(=O)— | K332 | J96 | S |
| 3-0209 | —(CH$_2$)$_2$— | —C(=O)— | K332 | J100 | S |
| 3-0210 | —(CH$_2$)$_2$— | —C(=O)— | K332 | J104 | S |
| 3-0211 | —(CH$_2$)$_2$— | —C(=O)— | K332 | J119 | S |
| 3-0212 | —(CH$_2$)$_2$— | —C(=O)— | K332 | J120 | S |
| 3-0213 | —(CH$_2$)$_2$— | —C(=O)— | K332 | J132 | S |
| 3-0214 | —(CH$_2$)$_2$— | —C(=O)— | K332 | J133 | S |
| 3-0215 | —(CH$_2$)$_2$— | —C(=O)— | K334 | J134 | S |
| 3-0216 | —(CH$_2$)$_2$— | —C(=O)— | K334 | J137 | S |
| 3-0217 | —(CH$_2$)$_2$— | —C(=O)— | K335 | J9 | S |
| 3-0218 | —(CH$_2$)$_2$— | —C(=O)— | K335 | J20 | O |
| 3-0219 | —(CH$_2$)$_2$— | —C(=O)— | K335 | J48 | S |
| 3-0220 | —(CH$_2$)$_2$— | —C(=O)— | K336 | J9 | S |
| 3-0221 | —(CH$_2$)$_2$— | —C(=O)— | K336 | J19 | S |
| 3-0222 | —(CH$_2$)$_2$— | —C(=O)— | K336 | J57 | S |
| 3-0223 | —(CH$_2$)$_2$— | —C(=O)— | K336 | J126 | S |
| 3-0224 | —(CH$_2$)$_2$— | —C(=O)— | K336 | J128 | S |

TABLE 110

| Compound No. | -A¹- | -A²- | -G¹-A³-A⁴-G² | -A⁵-R² | X |
|---|---|---|---|---|---|
| 3-0225 | —(CH$_2$)$_2$— | —C(=O)— | K336 | J138 | S |
| 3-0226 | —(CH$_2$)$_2$— | —C(=O)— | K336 | J140 | S |
| 3-0227 | —(CH$_2$)$_2$— | —C(=O)— | K336 | J147 | S |
| 3-0228 | —(CH$_2$)$_2$— | —C(=O)— | K336 | J165 | O |
| 3-0229 | —(CH$_2$)$_2$— | —C(=O)— | K336 | J178 | S |
| 3-0230 | —(CH$_2$)$_2$— | —C(=O)— | K337 | J3 | S |
| 3-0231 | —(CH$_2$)$_2$— | —C(=O)— | K337 | J9 | S |
| 3-0232 | —(CH$_2$)$_2$— | —C(=O)— | K337 | J73 | S |
| 3-0233 | —(CH$_2$)$_2$— | —C(=O)— | K337 | J74 | O |
| 3-0234 | —(CH$_2$)$_2$— | —C(=O)— | K337 | J75 | O |
| 3-0235 | —(CH$_2$)$_2$— | —C(=O)— | K337 | J78 | S |
| 3-0236 | —(CH$_2$)$_2$— | —C(=O)— | K337 | J81 | S |
| 3-0237 | —(CH$_2$)$_2$— | —C(=O)— | K337 | J82 | S |
| 3-0238 | —(CH$_2$)$_2$— | —C(=O)— | K337 | J83 | O |
| 3-0239 | —(CH$_2$)$_2$— | —C(=O)— | K337 | J92 | S |
| 3-0240 | —(CH$_2$)$_2$— | —C(=O)— | K337 | J130 | S |
| 3-0241 | —(CH$_2$)$_2$— | —C(=O)— | K338 | J9 | S |
| 3-0242 | —(CH$_2$)$_2$— | —C(=O)— | K338 | J78 | S |
| 3-0243 | —(CH$_2$)$_2$— | —C(=O)— | K339 | J9 | S |
| 3-0244 | —(CH$_2$)$_2$— | —C(=O)— | K340 | J9 | S |
| 3-0245 | —(CH$_2$)$_2$— | —C(=O)— | K343 | J9 | S |
| 3-0246 | —(CH$_2$)$_2$— | —C(=O)— | K344 | J9 | O |
| 3-0247 | —(CH$_2$)$_2$— | —C(=O)— | K346 | J1 | S |
| 3-0248 | —(CH$_2$)$_2$— | —C(=O)— | K346 | J6 | S |
| 3-0249 | —(CH$_2$)$_2$— | —C(=O)— | K346 | J22 | S |
| 3-0250 | —(CH$_2$)$_2$— | —C(=O)— | K346 | J30 | S |
| 3-0251 | —(CH$_2$)$_2$— | —C(=O)— | K346 | J70 | S |
| 3-0252 | —(CH$_2$)$_2$— | —C(=O)— | K346 | J77 | S |
| 3-0253 | —(CH$_2$)$_2$— | —C(=O)— | K349 | J10 | S |
| 3-0254 | —(CH$_2$)$_2$— | —C(=O)— | K349 | J13 | S |
| 3-0255 | —(CH$_2$)$_2$— | —C(=O)— | K350 | J42 | S |
| 3-0256 | —(CH$_2$)$_2$— | —C(=O)— | K350 | J43 | S |

TABLE 111

| Compound No. | -A¹- | -A²- | -G¹-A³-A⁴-G² | -A⁵-R² | X |
|---|---|---|---|---|---|
| 3-0257 | —(CH₂)₂— | —C(=O)— | K350 | J59 | S |
| 3-0258 | —(CH₂)₂— | —C(=O)— | K352 | J137 | S |
| 3-0259 | —(CH₂)₂— | —C(=O)— | K352 | J154 | S |
| 3-0260 | —(CH₂)₂— | —C(=O)— | K352 | J157 | S |
| 3-0261 | —(CH₂)₂— | —C(=O)— | K352 | J168 | S |
| 3-0262 | —(CH₂)₂— | —C(=O)— | K352 | J174 | S |
| 3-0263 | —(CH₂)₂— | —C(=O)— | K352 | J177 | O |
| 3-0264 | —(CH₂)₂— | —C(=O)— | K353 | J11 | S |
| 3-0265 | —(CH₂)₂— | —C(=O)— | K353 | J20 | S |
| 3-0266 | —(CH₂)₂— | —C(=O)— | K353 | J48 | O |
| 3-0267 | —(CH₂)₂— | —C(=O)— | K353 | J51 | O |
| 3-0268 | —(CH₂)₂— | —C(=O)— | K353 | J52 | S |
| 3-0269 | —(CH₂)₂— | —C(=O)— | K353 | J87 | S |
| 3-0270 | —(CH₂)₂— | —C(=O)— | K354 | J19 | S |
| 3-0271 | —(CH₂)₂— | —C(=O)— | K354 | J57 | S |
| 3-0272 | —(CH₂)₂— | —C(=O)— | K354 | J105 | O |
| 3-0273 | —(CH₂)₂— | —C(=O)— | K354 | J126 | S |
| 3-0274 | —(CH₂)₂— | —C(=O)— | K354 | J127 | S |
| 3-0275 | —(CH₂)₂— | —C(=O)— | K354 | J128 | S |
| 3-0276 | —(CH₂)₂— | —C(=O)— | K354 | J129 | S |
| 3-0277 | —(CH₂)₂— | —C(=O)— | K354 | J138 | O |
| 3-0278 | —(CH₂)₂— | —C(=O)— | K354 | J140 | S |
| 3-0279 | —(CH₂)₂— | —C(=O)— | K354 | J147 | O |
| 3-0280 | —(CH₂)₂— | —C(=O)— | K354 | J165 | S |
| 3-0281 | —(CH₂)₂— | —C(=O)— | K354 | J178 | S |
| 3-0282 | —(CH₂)₂— | —C(=O)— | K355 | J3 | S |
| 3-0283 | —(CH₂)₂— | —C(=O)— | K355 | J9 | S |
| 3-0284 | —(CH₂)₂— | —C(=O)— | K355 | J73 | O |
| 3-0285 | —(CH₂)₂— | —C(=O)— | K355 | J74 | S |
| 3-0286 | —(CH₂)₂— | —C(=O)— | K355 | J75 | S |
| 3-0287 | —(CH₂)₂— | —C(=O)— | K355 | J78 | S |
| 3-0288 | —(CH₂)₂— | —C(=O)— | K355 | J81 | O |

TABLE 112

| Compound No. | -A¹- | -A²- | -G¹-A³-A⁴-G² | -A⁵-R² | X |
|---|---|---|---|---|---|
| 3-0289 | —(CH₂)₂— | —C(=O)— | K355 | J82 | O |
| 3-0290 | —(CH₂)₂— | —C(=O)— | K355 | J83 | S |
| 3-0291 | —(CH₂)₂— | —C(=O)— | K355 | J92 | S |
| 3-0292 | —(CH₂)₂— | —C(=O)— | K355 | J130 | S |
| 3-0293 | —(CH₂)₂— | —C(=O)— | K356 | J9 | O |
| 3-0294 | —(CH₂)₂— | —C(=O)— | K358 | J9 | S |
| 3-0295 | —(CH₂)₂— | —C(=O)— | K358 | J19 | S |
| 3-0296 | —(CH₂)₂— | —C(=O)— | K358 | J57 | S |
| 3-0297 | —(CH₂)₂— | —C(=O)— | K358 | J78 | S |
| 3-0298 | —(CH₂)₂— | —C(=O)— | K358 | J126 | S |
| 3-0299 | —(CH₂)₂— | —C(=O)— | K358 | J128 | S |
| 3-0300 | —(CH₂)₂— | —C(=O)— | K358 | J140 | S |
| 3-0301 | —(CH₂)₂— | —C(=O)— | K359 | J1 | S |
| 3-0302 | —(CH₂)₂— | —C(=O)— | K359 | J6 | S |
| 3-0303 | —(CH₂)₂— | —C(=O)— | K359 | J22 | S |
| 3-0304 | —(CH₂)₂— | —C(=O)— | K359 | J30 | S |
| 3-0305 | —(CH₂)₂— | —C(=O)— | K359 | J70 | S |
| 3-0306 | —(CH₂)₂— | —C(=O)— | K359 | J77 | S |
| 3-0307 | —(CH₂)₂— | —C(=O)— | K360 | J10 | S |
| 3-0308 | —(CH₂)₂— | —C(=O)— | K360 | J13 | S |
| 3-0309 | —(CH₂)₂— | —C(=O)— | K361 | J42 | S |
| 3-0310 | —(CH₂)₂— | —C(=O)— | K361 | J43 | S |
| 3-0311 | —(CH₂)₂— | —C(=O)— | K361 | J49 | S |
| 3-0312 | —(CH₂)₂— | —C(=O)— | K361 | J50 | S |
| 3-0313 | —(CH₂)₂— | —C(=O)— | K361 | J58 | S |
| 3-0314 | —(CH₂)₂— | —C(=O)— | K361 | J59 | S |
| 3-0315 | —(CH₂)₂— | —C(=O)— | K361 | J64 | S |
| 3-0316 | —(CH₂)₂— | —C(=O)— | K362 | J96 | S |
| 3-0317 | —(CH₂)₂— | —C(=O)— | K362 | J100 | S |
| 3-0318 | —(CH₂)₂— | —C(=O)— | K362 | J104 | S |
| 3-0319 | —(CH₂)₂— | —C(=O)— | K362 | J119 | S |
| 3-0320 | —(CH₂)₂— | —C(=O)— | K362 | J120 | S |

TABLE 113

| Compound No. | -A¹- | -A²- | -G¹-A³-A⁴-G² | -A⁵-R² | X |
|---|---|---|---|---|---|
| 3-0321 | —(CH₂)₂— | —C(=O)— | K362 | J132 | S |
| 3-0322 | —(CH₂)₂— | —C(=O)— | K362 | J133 | S |
| 3-0323 | —(CH₂)₂— | —C(=O)— | K363 | J134 | S |
| 3-0324 | —(CH₂)₂— | —C(=O)— | K363 | J137 | S |
| 3-0325 | —(CH₂)₂— | —C(=O)— | K364 | J9 | S |
| 3-0326 | —(CH₂)₂— | —C(=O)— | K364 | J20 | O |
| 3-0327 | —(CH₂)₂— | —C(=O)— | K364 | J48 | S |
| 3-0328 | —(CH₂)₂— | —C(=O)— | K364 | J51 | S |
| 3-0329 | —(CH₂)₂— | —C(=O)— | K364 | J52 | O |
| 3-0330 | —(CH₂)₂— | —C(=O)— | K364 | J87 | O |
| 3-0331 | —(CH₂)₂— | —C(=O)— | K365 | J9 | S |
| 3-0332 | —(CH₂)₂— | —C(=O)— | K365 | J105 | S |
| 3-0333 | —(CH₂)₂— | —C(=O)— | K365 | J127 | S |
| 3-0334 | —(CH₂)₂— | —C(=O)— | K365 | J129 | O |
| 3-0335 | —(CH₂)₂— | —C(=O)— | K365 | J138 | S |
| 3-0336 | —(CH₂)₂— | —C(=O)— | K365 | J147 | S |
| 3-0337 | —(CH₂)₂— | —C(=O)— | K365 | J165 | O |
| 3-0338 | —(CH₂)₂— | —C(=O)— | K365 | J178 | S |
| 3-0339 | —(CH₂)₂— | —C(=O)— | K367 | J9 | S |
| 3-0340 | —(CH₂)₂— | —C(=O)— | K368 | J9 | S |
| 3-0341 | —(CH₂)₂— | —C(=O)— | K368 | J73 | S |
| 3-0342 | —(CH₂)₂— | —C(=O)— | K368 | J74 | S |
| 3-0343 | —(CH₂)₂— | —C(=O)— | K368 | J75 | O |
| 3-0344 | —(CH₂)₂— | —C(=O)— | K368 | J81 | S |
| 3-0345 | —(CH₂)₂— | —C(=O)— | K368 | J82 | S |
| 3-0346 | —(CH₂)₂— | —C(=O)— | K368 | J83 | O |
| 3-0347 | —(CH₂)₂— | —C(=O)— | K368 | J92 | O |
| 3-0348 | —(CH₂)₂— | —C(=O)— | K369 | J9 | S |
| 3-0349 | —(CH₂)₂— | —C(=O)— | K371 | J9 | S |
| 3-0350 | —(CH₂)₂— | —C(=O)— | K372 | J9 | S |
| 3-0351 | —(CH₂)₂— | —C(=O)— | K373 | J9 | S |
| 3-0352 | —(CH₂)₂— | —C(=O)— | K374 | J9 | S |

TABLE 114

| Compound No. | -A¹- | -A²- | -G¹-A³-A⁴-G² | -A⁵-R² | X |
|---|---|---|---|---|---|
| 3-0353 | —(CH₂)₂— | —C(=O)— | K377 | J9 | S |
| 3-0354 | —(CH₂)₂— | —C(=O)— | K380 | J9 | S |
| 3-0355 | —(CH₂)₂— | —C(=O)— | K381 | J1 | S |
| 3-0356 | —(CH₂)₂— | —C(=O)— | K381 | J6 | S |
| 3-0357 | —(CH₂)₂— | —C(=O)— | K381 | J9 | S |
| 3-0358 | —(CH₂)₂— | —C(=O)— | K381 | J22 | S |
| 3-0359 | —(CH₂)₂— | —C(=O)— | K381 | J30 | S |
| 3-0360 | —(CH₂)₂— | —C(=O)— | K381 | J70 | S |
| 3-0361 | —(CH₂)₂— | —C(=O)— | K381 | J77 | S |
| 3-0362 | —(CH₂)₂— | —C(=O)— | K381 | J78 | S |
| 3-0363 | —(CH₂)₂— | —C(=O)— | K382 | J3 | S |
| 3-0364 | —(CH₂)₂— | —C(=O)— | K382 | J9 | S |
| 3-0365 | —(CH₂)₂— | —C(=O)— | K382 | J10 | S |
| 3-0366 | —(CH₂)₂— | —C(=O)— | K382 | J13 | S |
| 3-0367 | —(CH₂)₂— | —C(=O)— | K382 | J78 | S |
| 3-0368 | —(CH₂)₂— | —C(=O)— | K382 | J130 | S |
| 3-0369 | —(CH₂)₂— | —C(=O)— | K383 | J42 | S |
| 3-0370 | —(CH₂)₂— | —C(=O)— | K383 | J43 | S |
| 3-0371 | —(CH₂)₂— | —C(=O)— | K383 | J59 | S |
| 3-0372 | —(CH₂)₂— | —C(=O)— | K384 | J132 | S |
| 3-0373 | —(CH₂)₂— | —C(=O)— | K384 | J133 | S |
| 3-0374 | —(CH₂)₂— | —C(=O)— | K385 | J134 | S |
| 3-0375 | —(CH₂)₂— | —C(=O)— | K385 | J137 | S |
| 3-0376 | —(CH₂)₂— | —C(=O)— | K385 | J154 | S |
| 3-0377 | —(CH₂)₂— | —C(=O)— | K385 | J157 | S |
| 3-0378 | —(CH₂)₂— | —C(=O)— | K385 | J168 | S |
| 3-0379 | —(CH₂)₂— | —C(=O)— | K385 | J174 | S |
| 3-0380 | —(CH₂)₂— | —C(=O)— | K385 | J177 | O |
| 3-0381 | —(CH₂)₂— | —C(=O)— | K386 | J11 | S |
| 3-0382 | —(CH₂)₂— | —C(=O)— | K386 | J20 | S |
| 3-0383 | —(CH₂)₂— | —C(=O)— | K386 | J48 | S |
| 3-0384 | —(CH₂)₂— | —C(=O)— | K387 | J138 | S |

TABLE 115

| Compound No. | -A¹- | -A²- | -G¹-A³-A⁴-G² | -A⁵-R² | X |
|---|---|---|---|---|---|
| 3-0385 | —(CH$_2$)$_2$— | —C(=O)— | K387 | J147 | O |
| 3-0386 | —(CH$_2$)$_2$— | —C(=O)— | K387 | J165 | S |
| 3-0387 | —(CH$_2$)$_2$— | —C(=O)— | K387 | J178 | S |
| 3-0388 | —(CH$_2$)$_2$— | —C(=O)— | K388 | J73 | O |
| 3-0389 | —(CH$_2$)$_2$— | —C(=O)— | K388 | J74 | O |
| 3-0390 | —(CH$_2$)$_2$— | —C(=O)— | K388 | J75 | S |
| 3-0391 | —(CH$_2$)$_2$— | —C(=O)— | K388 | J81 | S |
| 3-0392 | —(CH$_2$)$_2$— | —C(=O)— | K388 | J82 | O |
| 3-0393 | —(CH$_2$)$_2$— | —C(=O)— | K388 | J83 | S |
| 3-0394 | —(CH$_2$)$_2$— | —C(=O)— | K388 | J92 | S |
| 3-0395 | —(CH$_2$)$_2$— | —C(=O)— | K389 | J9 | O |
| 3-0396 | —(CH$_2$)$_2$— | —C(=O)— | K391 | J9 | O |
| 3-0397 | —(CH$_2$)$_2$— | —C(=O)— | K391 | J9 | S |
| 3-0398 | —(CH$_2$)$_2$— | —C(=O)— | K392 | J9 | S |
| 3-0399 | —(CH$_2$)$_2$— | —C(=O)— | K393 | J9 | S |
| 3-0400 | —(CH$_2$)$_2$— | —C(=O)— | K394 | J1 | S |
| 3-0401 | —(CH$_2$)$_2$— | —C(=O)— | K394 | J6 | S |
| 3-0402 | —(CH$_2$)$_2$— | —C(=O)— | K394 | J19 | S |
| 3-0403 | —(CH$_2$)$_2$— | —C(=O)— | K394 | J22 | S |
| 3-0404 | —(CH$_2$)$_2$— | —C(=O)— | K394 | J30 | S |
| 3-0405 | —(CH$_2$)$_2$— | —C(=O)— | K394 | J57 | S |
| 3-0406 | —(CH$_2$)$_2$— | —C(=O)— | K394 | J70 | S |
| 3-0407 | —(CH$_2$)$_2$— | —C(=O)— | K394 | J77 | S |
| 3-0408 | —(CH$_2$)$_2$— | —C(=O)— | K394 | J126 | S |
| 3-0409 | —(CH$_2$)$_2$— | —C(=O)— | K394 | J128 | S |
| 3-0410 | —(CH$_2$)$_2$— | —C(=O)— | K394 | J140 | S |
| 3-0411 | —(CH$_2$)$_2$— | —C(=O)— | K395 | J10 | S |
| 3-0412 | —(CH$_2$)$_2$— | —C(=O)— | K395 | J13 | S |
| 3-0413 | —(CH$_2$)$_2$— | —C(=O)— | K396 | J42 | S |
| 3-0414 | —(CH$_2$)$_2$— | —C(=O)— | K396 | J43 | S |
| 3-0415 | —(CH$_2$)$_2$— | —C(=O)— | K396 | J49 | S |
| 3-0416 | —(CH$_2$)$_2$— | —C(=O)— | K396 | J50 | S |

TABLE 116

| Compound No. | -A¹- | -A²- | -G¹-A³-A⁴-G² | -A⁵-R² | X |
|---|---|---|---|---|---|
| 3-0417 | —(CH$_2$)$_2$— | —C(=O)— | K396 | J58 | S |
| 3-0418 | —(CH$_2$)$_2$— | —C(=O)— | K396 | J59 | S |
| 3-0419 | —(CH$_2$)$_2$— | —C(=O)— | K396 | J64 | S |
| 3-0420 | —(CH$_2$)$_2$— | —C(=O)— | K397 | J3 | S |
| 3-0421 | —(CH$_2$)$_2$— | —C(=O)— | K397 | J9 | S |
| 3-0422 | —(CH$_2$)$_2$— | —C(=O)— | K397 | J78 | S |
| 3-0423 | —(CH$_2$)$_2$— | —C(=O)— | K397 | J96 | S |
| 3-0424 | —(CH$_2$)$_2$— | —C(=O)— | K397 | J100 | S |
| 3-0425 | —(CH$_2$)$_2$— | —C(=O)— | K397 | J104 | S |
| 3-0426 | —(CH$_2$)$_2$— | —C(=O)— | K397 | J119 | S |
| 3-0427 | —(CH$_2$)$_2$— | —C(=O)— | K397 | J120 | S |
| 3-0428 | —(CH$_2$)$_2$— | —C(=O)— | K397 | J130 | S |
| 3-0429 | —(CH$_2$)$_2$— | —C(=O)— | K398 | J137 | S |
| 3-0430 | —(CH$_2$)$_2$— | —C(=O)—NH— | K399 | J9 | S |
| 3-0431 | —(CH$_2$)$_2$— | —C(=O)—NH— | K402 | J20 | O |
| 3-0432 | —(CH$_2$)$_2$— | —C(=O)—NH— | K402 | J48 | O |
| 3-0433 | —(CH$_2$)$_2$— | —C(=O)—NH— | K402 | J51 | S |
| 3-0434 | —(CH$_2$)$_2$— | —C(=O)—NH— | K402 | J52 | S |
| 3-0435 | —(CH$_2$)$_2$— | —C(=O)—NH— | K402 | J87 | O |
| 3-0436 | —(CH$_2$)$_2$— | —C(=O)—NH— | K167 | J105 | S |
| 3-0437 | —(CH$_2$)$_2$— | —C(=O)—NH— | K167 | J127 | S |
| 3-0438 | —(CH$_2$)$_2$— | —C(=O)—NH— | K167 | J129 | O |
| 3-0439 | —(CH$_2$)$_2$— | —C(=O)— | K412 | J1 | S |
| 3-0440 | —(CH$_2$)$_2$— | —C(=O)— | K412 | J6 | S |
| 3-0441 | —(CH$_2$)$_2$— | —C(=O)— | K412 | J22 | S |
| 3-0442 | —(CH$_2$)$_2$— | —C(=O)— | K412 | J30 | S |
| 3-0443 | —(CH$_2$)$_2$— | —C(=O)— | K412 | J70 | S |
| 3-0444 | —(CH$_2$)$_2$— | —C(=O)— | K412 | J77 | S |
| 3-0445 | —(CH$_2$)$_2$— | —C(=O)— | K413 | J10 | S |
| 3-0446 | —(CH$_2$)$_2$— | —C(=O)— | K413 | J13 | S |
| 3-0447 | —(CH$_2$)$_2$— | —C(=O)— | K414 | J42 | S |
| 3-0448 | —(CH$_2$)$_2$— | —C(=O)— | K414 | J43 | S |

TABLE 117

| Compound No. | -A¹- | -A²- | -G¹-A³-A⁴-G² | -A⁵-R² | X |
|---|---|---|---|---|---|
| 3-0449 | —(CH$_2$)$_2$— | —C(=O)— | K414 | J59 | S |
| 3-0450 | —(CH$_2$)$_2$— | —C(=O)— | K415 | J132 | S |
| 3-0451 | —(CH$_2$)$_2$— | —C(=O)— | K415 | J133 | S |
| 3-0452 | —(CH$_2$)$_2$— | —C(=O)— | K416 | J134 | S |
| 3-0453 | —(CH$_2$)$_2$— | —C(=O)— | K416 | J137 | S |
| 3-0454 | —(CH$_2$)$_2$— | —C(=O)— | K416 | J154 | S |
| 3-0455 | —(CH$_2$)$_2$— | —C(=O)— | K416 | J157 | S |
| 3-0456 | —(CH$_2$)$_2$— | —C(=O)— | K416 | J168 | O |
| 3-0457 | —(CH$_2$)$_2$— | —C(=O)— | K416 | J174 | S |
| 3-0458 | —(CH$_2$)$_2$— | —C(=O)— | K416 | J177 | S |
| 3-0459 | —(CH$_2$)$_2$— | —C(=O)— | K417 | J11 | O |
| 3-0460 | —(CH$_2$)$_2$— | —C(=O)— | K417 | J20 | S |
| 3-0461 | —(CH$_2$)$_2$— | —C(=O)— | K417 | J48 | S |
| 3-0462 | —(CH$_2$)$_2$— | —C(=O)— | K418 | J3 | S |
| 3-0463 | —(CH$_2$)$_2$— | —C(=O)— | K418 | J9 | S |
| 3-0464 | —(CH$_2$)$_2$— | —C(=O)— | K418 | J78 | S |
| 3-0465 | —(CH$_2$)$_2$— | —C(=O)— | K418 | J130 | S |
| 3-0466 | —(CH$_2$)$_2$— | —C(=O)— | K418 | J138 | S |
| 3-0467 | —(CH$_2$)$_2$— | —C(=O)— | K418 | J147 | O |
| 3-0468 | —(CH$_2$)$_2$— | —C(=O)— | K418 | J165 | O |
| 3-0469 | —(CH$_2$)$_2$— | —C(=O)— | K418 | J178 | S |
| 3-0470 | —(CH$_2$)$_2$— | —C(=O)— | K419 | J73 | S |
| 3-0471 | —(CH$_2$)$_2$— | —C(=O)— | K419 | J74 | O |
| 3-0472 | —(CH$_2$)$_2$— | —C(=O)— | K419 | J75 | S |
| 3-0473 | —(CH$_2$)$_2$— | —C(=O)— | K419 | J81 | S |
| 3-0474 | —(CH$_2$)$_2$— | —C(=O)— | K419 | J82 | O |
| 3-0475 | —(CH$_2$)$_2$— | —C(=O)— | K419 | J83 | O |
| 3-0476 | —(CH$_2$)$_2$— | —C(=O)— | K419 | J92 | S |
| 3-0477 | —(CH$_2$)$_2$— | —C(=O)— | K420 | J9 | S |
| 3-0478 | —(CH$_2$)$_2$— | —C(=O)— | K421 | J9 | O |
| 3-0479 | —(CH$_2$)$_2$— | —C(=O)—N(CH$_3$)— | K422 | J1 | S |
| 3-0480 | —(CH$_2$)$_2$— | —C(=O)—N(CH$_3$)— | K422 | J6 | S |

TABLE 118

| Compound No. | -A¹- | -A²- | -G¹-A³-A⁴-G² | -A⁵-R² | X |
|---|---|---|---|---|---|
| 3-0481 | —(CH$_2$)$_2$— | —C(=O)—N(CH$_3$)— | K422 | J19 | S |
| 3-0482 | —(CH$_2$)$_2$— | —C(=O)—N(CH$_3$)— | K422 | J22 | S |
| 3-0483 | —(CH$_2$)$_2$— | —C(=O)—N(CH$_3$)— | K422 | J30 | S |
| 3-0484 | —(CH$_2$)$_2$— | —C(=O)—N(CH$_3$)— | K422 | J57 | S |
| 3-0485 | —(CH$_2$)$_2$— | —C(=O)—N(CH$_3$)— | K422 | J70 | S |
| 3-0486 | —(CH$_2$)$_2$— | —C(=O)—N(CH$_3$)— | K422 | J77 | S |
| 3-0487 | —(CH$_2$)$_2$— | —C(=O)—N(CH$_3$)— | K422 | J126 | S |
| 3-0488 | —(CH$_2$)$_2$— | —C(=O)—N(CH$_3$)— | K422 | J128 | S |
| 3-0489 | —(CH$_2$)$_2$— | —C(=O)—N(CH$_3$)— | K422 | J140 | S |
| 3-0490 | —(CH$_2$)$_2$— | —C(=O)—NH— | K422 | J10 | S |
| 3-0491 | —(CH$_2$)$_2$— | —C(=O)—NH— | K422 | J13 | S |
| 3-0492 | —(CH$_2$)$_2$— | —C(=O)—N(CH$_3$)— | K186 | J42 | S |
| 3-0493 | —(CH$_2$)$_2$— | —C(=O)—N(CH$_3$)— | K186 | J43 | S |
| 3-0494 | —(CH$_2$)$_2$— | —C(=O)—N(CH$_3$)— | K186 | J49 | S |
| 3-0495 | —(CH$_2$)$_2$— | —C(=O)—N(CH$_3$)— | K186 | J50 | S |
| 3-0496 | —(CH$_2$)$_2$— | —C(=O)—N(CH$_3$)— | K186 | J58 | S |
| 3-0497 | —(CH$_2$)$_2$— | —C(=O)—N(CH$_3$)— | K186 | J59 | S |
| 3-0498 | —(CH$_2$)$_2$— | —C(=O)—N(CH$_3$)— | K186 | J64 | S |
| 3-0499 | —(CH$_2$)$_2$— | —C(=O)—NH— | K34 | J96 | S |
| 3-0500 | —(CH$_2$)$_2$— | —C(=O)—NH— | K34 | J100 | S |
| 3-0501 | —(CH$_2$)$_2$— | —C(=O)—NH— | K34 | J104 | S |
| 3-0502 | —(CH$_2$)$_2$— | —C(=O)—NH— | K34 | J119 | S |
| 3-0503 | —(CH$_2$)$_2$— | —C(=O)—NH— | K34 | J120 | S |
| 3-0504 | —(CH$_2$)$_2$— | —C(=O)—NH— | K34 | J132 | S |
| 3-0505 | —(CH$_2$)$_2$— | —C(=O)—NH— | K34 | J133 | S |
| 3-0506 | —(CH$_2$)$_2$— | —C(=O)—NH— | K423 | J134 | S |
| 3-0507 | —(CH$_2$)$_2$— | —C(=O)—NH— | K423 | J137 | S |
| 3-0508 | —(CH$_2$)$_2$— | —C(=O)—NH— | K424 | J20 | S |
| 3-0509 | —(CH$_2$)$_2$— | —C(=O)—NH— | K424 | J48 | O |
| 3-0510 | —(CH$_2$)$_2$— | —C(=O)—NH— | K424 | J51 | S |
| 3-0511 | —(CH$_2$)$_2$— | —C(=O)—NH— | K424 | J52 | S |
| 3-0512 | —(CH$_2$)$_2$— | —C(=O)—NH— | K424 | J87 | O |

TABLE 119

| Compound No. | -A¹- | -A²- | -G¹-A³-A⁴-G² | -A⁵-R² | X |
|---|---|---|---|---|---|
| 3-0513 | —(CH$_2$)$_2$— | —C(=O)—NH— | K425 | J105 | O |
| 3-0514 | —(CH$_2$)$_2$— | —C(=O)—NH— | K425 | J127 | S |
| 3-0515 | —(CH$_2$)$_2$— | —C(=O)—NH— | K425 | J129 | S |
| 3-0516 | —(CH$_2$)$_2$— | —C(=O)—NH— | K425 | J138 | O |
| 3-0517 | —(CH$_2$)$_2$— | —C(=O)—NH— | K425 | J147 | S |
| 3-0518 | —(CH$_2$)$_2$— | —C(=O)—NH— | K425 | J165 | S |
| 3-0519 | —(CH$_2$)$_2$— | —C(=O)—NH— | K425 | J178 | O |
| 3-0520 | —(CH$_2$)$_2$— | —C(=O)—NH— | K426 | J73 | O |
| 3-0521 | —(CH$_2$)$_2$— | —C(=O)—NH— | K426 | J74 | S |
| 3-0522 | —(CH$_2$)$_2$— | —C(=O)—NH— | K426 | J75 | S |
| 3-0523 | —(CH$_2$)$_2$— | —C(=O)—NH— | K426 | J81 | O |
| 3-0524 | —(CH$_2$)$_2$— | —C(=O)—NH— | K426 | J82 | S |
| 3-0525 | —(CH$_2$)$_2$— | —C(=O)—NH— | K426 | J83 | S |
| 3-0526 | —(CH$_2$)$_2$— | —C(=O)—NH— | K426 | J92 | O |
| 3-0527 | —(CH$_2$)$_2$— | —C(=O)—NH— | K427 | J9 | O |
| 3-0528 | —(CH$_2$)$_3$— | —C(=O)—NH— | K4 | J2 | S |
| 3-0529 | —(CH$_2$)$_3$— | —C(=O)—NH— | K4 | J4 | S |
| 3-0530 | —(CH$_2$)$_3$— | —C(=O)—NH— | K4 | J28 | S |
| 3-0531 | —(CH$_2$)$_3$— | —C(=O)—NH— | K4 | J31 | S |
| 3-0532 | —(CH$_2$)$_3$— | —C(=O)—NH— | K256 | J9 | S |
| 3-0533 | —(CH$_2$)$_3$— | —C(=O)—NH— | K256 | J50 | S |
| 3-0534 | —(CH$_2$)$_3$— | —C(=O)—NH— | K256 | J58 | S |
| 3-0535 | —(CH$_2$)$_3$— | —C(=O)—NH— | K256 | J64 | S |
| 3-0536 | —(CH$_2$)$_3$— | —C(=O)—NH— | K257 | J96 | S |
| 3-0537 | —(CH$_2$)$_3$— | —C(=O)—NH— | K257 | J100 | S |
| 3-0538 | —(CH$_2$)$_3$— | —C(=O)—NH— | K257 | J104 | S |
| 3-0539 | —(CH$_2$)$_3$— | —C(=O)—NH— | K257 | J119 | S |
| 3-0540 | —(CH$_2$)$_3$— | —C(=O)—NH— | K257 | J120 | S |
| 3-0541 | —(CH$_2$)$_3$— | —C(=O)—N(CH$_3$)— | K132 | J9 | S |
| 3-0542 | —(CH$_2$)$_3$— | —C(=O)—N(CH$_3$)— | K268 | J9 | S |
| 3-0543 | —(CH$_2$)$_3$— | —C(=O)—NH— | K7 | J9 | S |
| 3-0544 | —(CH$_2$)$_3$— | —C(=O)—N(CH$_3$)— | K274 | J9 | S |

TABLE 120

| Compound No. | -A¹- | -A²- | -G¹-A³-A⁴-G² | -A⁵-R² | X |
|---|---|---|---|---|---|
| 3-0545 | —(CH$_2$)$_3$— | —C(=O)—NH— | K275 | J9 | S |
| 3-0546 | —(CH$_2$)$_3$— | —C(=O)—NH— | K279 | J2 | S |
| 3-0547 | —(CH$_2$)$_3$— | —C(=O)—NH— | K279 | J4 | S |
| 3-0548 | —(CH$_2$)$_3$— | —C(=O)—NH— | K279 | J28 | S |
| 3-0549 | —(CH$_2$)$_3$— | —C(=O)—NH— | K279 | J31 | S |
| 3-0550 | —(CH$_2$)$_3$— | —C(=O)—NH— | K281 | J9 | S |
| 3-0551 | —(CH$_2$)$_3$— | —C(=O)—NH— | K11 | J9 | S |
| 3-0552 | —(CH$_2$)$_3$— | —C(=O)—NH— | K282 | J9 | S |
| 3-0553 | —(CH$_2$)$_3$— | —C(=O)—NH— | K35 | J9 | S |
| 3-0554 | —(CH$_2$)$_3$— | —C(=O)—NH— | K37 | J9 | S |
| 3-0555 | —(CH$_2$)$_3$— | —C(=O)—NH— | K15 | J9 | S |
| 3-0556 | —(CH$_2$)$_3$— | —C(=O)—NH— | K283 | J9 | S |
| 3-0557 | —(CH$_2$)$_3$— | —C(=O)—NH— | K13 | J9 | S |
| 3-0558 | —(CH$_2$)$_3$— | —C(=O)—NH— | K14 | J9 | S |
| 3-0559 | —(CH$_2$)$_3$— | —C(=O)—NH— | K284 | J9 | S |
| 3-0560 | —(CH$_2$)$_3$— | —C(=O)—NH— | K23 | J9 | S |
| 3-0561 | —(CH$_2$)$_3$— | —C(=O)—NH— | K30 | J9 | S |
| 3-0562 | —(CH$_2$)$_3$— | —C(=O)—NH— | K286 | J2 | S |
| 3-0563 | —(CH$_2$)$_3$— | —C(=O)—NH— | K286 | J4 | S |
| 3-0564 | —(CH$_2$)$_3$— | —C(=O)—NH— | K286 | J9 | S |
| 3-0565 | —(CH$_2$)$_3$— | —C(=O)—NH— | K286 | J28 | S |
| 3-0566 | —(CH$_2$)$_3$— | —C(=O)—NH— | K286 | J31 | S |
| 3-0567 | —(CH$_2$)$_3$— | —C(=O)—NH— | K32 | J9 | S |
| 3-0568 | —(CH$_2$)$_3$— | —C(=O)—NH— | K289 | J9 | S |
| 3-0569 | —(CH$_2$)$_3$— | —C(=O)—N(CH$_3$)— | K24 | J132 | S |
| 3-0570 | —(CH$_2$)$_3$— | —C(=O)—N(CH$_3$)— | K24 | J133 | S |
| 3-0571 | —(CH$_2$)$_3$— | —C(=O)—N(CH$_3$)— | K294 | J49 | S |
| 3-0572 | —(CH$_2$)$_3$— | —C(=O)—N(CH$_3$)— | K294 | J50 | S |
| 3-0573 | —(CH$_2$)$_3$— | —C(=O)—N(CH$_3$)— | K294 | J58 | S |
| 3-0574 | —(CH$_2$)$_3$— | —C(=O)—N(CH$_3$)— | K294 | J64 | S |
| 3-0575 | —(CH$_2$)$_3$— | —C(=O)—NH— | K70 | J9 | S |
| 3-0576 | —(CH$_2$)$_3$— | —C(=O)—NH— | K71 | J9 | S |

TABLE 121

| Compound No. | -A¹- | -A²- | -G¹-A³-A⁴-G² | -A⁵-R² | X |
|---|---|---|---|---|---|
| 3-0577 | —(CH$_2$)$_3$— | —C(=O)—NH— | K72 | J9 | S |
| 3-0578 | —(CH$_2$)$_3$— | —C(=O)—NH— | K72 | J134 | S |
| 3-0579 | —(CH$_2$)$_3$— | —C(=O)—NH— | K72 | J154 | S |
| 3-0580 | —(CH$_2$)$_3$— | —C(=O)—NH— | K72 | J157 | S |
| 3-0581 | —(CH$_2$)$_3$— | —C(=O)—NH— | K72 | J168 | O |
| 3-0582 | —(CH$_2$)$_3$— | —C(=O)—NH— | K72 | J174 | S |
| 3-0583 | —(CH$_2$)$_3$— | —C(=O)—NH— | K72 | J177 | S |
| 3-0584 | —(CH$_2$)$_3$— | —C(=O)—NH— | K68 | J9 | S |
| 3-0585 | —(CH$_2$)$_3$— | —C(=O)—NH— | K68 | J11 | O |
| 3-0586 | —(CH$_2$)$_3$— | —C(=O)—NH— | K68 | J51 | O |
| 3-0587 | —(CH$_2$)$_3$— | —C(=O)—NH— | K68 | J52 | O |
| 3-0588 | —(CH$_2$)$_3$— | —C(=O)—NH— | K68 | J87 | S |
| 3-0589 | —(CH$_2$)$_3$— | —C(=O)—NH— | K99 | J9 | S |
| 3-0590 | —(CH$_2$)$_3$— | —C(=O)—NH— | K100 | J9 | S |
| 3-0591 | —(CH$_2$)$_3$— | —C(=O)—NH— | K308 | J9 | S |
| 3-0592 | —(CH$_2$)$_3$— | —C(=O)—NH— | K309 | J9 | S |
| 3-0593 | —(CH$_2$)$_3$— | —C(=O)—NH— | K309 | J105 | S |
| 3-0594 | —(CH$_2$)$_3$— | —C(=O)—NH— | K309 | J127 | O |
| 3-0595 | —(CH$_2$)$_3$— | —C(=O)—NH— | K309 | J129 | S |
| 3-0596 | —(CH$_2$)$_3$— | —C(=O)—NH— | K103 | J9 | S |
| 3-0597 | —(CH$_2$)$_3$— | —C(=O)—NH— | K310 | J9 | S |
| 3-0598 | —(CH$_2$)$_3$— | —C(=O)—NH— | K105 | J9 | S |
| 3-0599 | —(CH$_2$)$_3$— | —C(=O)—NH— | K106 | J9 | S |
| 3-0600 | —(CH$_2$)$_3$— | —C(=O)—NH— | K109 | J9 | S |
| 3-0601 | —(CH$_2$)$_3$— | —C(=O)— | K314 | J2 | S |
| 3-0602 | —(CH$_2$)$_3$— | —C(=O)— | K314 | J4 | S |
| 3-0603 | —(CH$_2$)$_3$— | —C(=O)— | K314 | J28 | S |
| 3-0604 | —(CH$_2$)$_3$— | —C(=O)— | K314 | J31 | S |
| 3-0605 | —(CH$_2$)$_3$— | —C(=O)— | K315 | J9 | S |
| 3-0606 | —(CH$_2$)$_3$— | —C(=O)— | K315 | J49 | S |
| 3-0607 | —(CH$_2$)$_3$— | —C(=O)— | K315 | J50 | S |
| 3-0608 | —(CH$_2$)$_3$— | —C(=O)— | K315 | J58 | S |

TABLE 122

| Compound No. | -A¹- | -A²- | -G¹-A³-A⁴-G² | -A⁵-R² | X |
|---|---|---|---|---|---|
| 3-0609 | —(CH$_2$)$_3$— | —C(=O)— | K315 | J64 | S |
| 3-0610 | —(CH$_2$)$_3$— | —C(=O)— | K316 | J96 | S |
| 3-0611 | —(CH$_2$)$_3$— | —C(=O)— | K316 | J100 | S |
| 3-0612 | —(CH$_2$)$_3$— | —C(=O)— | K316 | J104 | S |
| 3-0613 | —(CH$_2$)$_3$— | —C(=O)— | K316 | J119 | S |
| 3-0614 | —(CH$_2$)$_3$— | —C(=O)— | K316 | J120 | S |
| 3-0615 | —(CH$_2$)$_3$— | —C(=O)— | K318 | J9 | S |
| 3-0616 | —(CH$_2$)$_3$— | —C(=O)— | K319 | J9 | S |
| 3-0617 | —(CH$_2$)$_3$— | —C(=O)— | K319 | J138 | O |
| 3-0618 | —(CH$_2$)$_3$— | —C(=O)— | K319 | J147 | S |
| 3-0619 | —(CH$_2$)$_3$— | —C(=O)— | K319 | J165 | S |
| 3-0620 | —(CH$_2$)$_3$— | —C(=O)— | K319 | J178 | O |
| 3-0621 | —(CH$_2$)$_3$— | —C(=O)— | K320 | J73 | O |
| 3-0622 | —(CH$_2$)$_3$— | —C(=O)— | K320 | J74 | S |
| 3-0623 | —(CH$_2$)$_3$— | —C(=O)— | K320 | J75 | S |
| 3-0624 | —(CH$_2$)$_3$— | —C(=O)— | K320 | J81 | O |
| 3-0625 | —(CH$_2$)$_3$— | —C(=O)— | K320 | J82 | S |
| 3-0626 | —(CH$_2$)$_3$— | —C(=O)— | K320 | J83 | S |
| 3-0627 | —(CH$_2$)$_3$— | —C(=O)— | K320 | J92 | O |
| 3-0628 | —(CH$_2$)$_3$— | —C(=O)— | K322 | J9 | S |
| 3-0629 | —(CH$_2$)$_3$— | —C(=O)— | K322 | J9 | S |
| 3-0630 | —(CH$_2$)$_3$— | —C(=O)— | K329 | J2 | S |
| 3-0631 | —(CH$_2$)$_3$— | —C(=O)— | K329 | J4 | S |
| 3-0632 | —(CH$_2$)$_3$— | —C(=O)— | K329 | J28 | S |
| 3-0633 | —(CH$_2$)$_3$— | —C(=O)— | K329 | J31 | S |
| 3-0634 | —(CH$_2$)$_3$— | —C(=O)— | K330 | J9 | S |
| 3-0635 | —(CH$_2$)$_3$— | —C(=O)— | K331 | J9 | S |
| 3-0636 | —(CH$_2$)$_3$— | —C(=O)— | K332 | J9 | S |
| 3-0637 | —(CH$_2$)$_3$— | —C(=O)— | K334 | J154 | S |
| 3-0638 | —(CH$_2$)$_3$— | —C(=O)— | K334 | J157 | S |
| 3-0639 | —(CH$_2$)$_3$— | —C(=O)— | K334 | J168 | O |
| 3-0640 | —(CH$_2$)$_3$— | —C(=O)— | K334 | J174 | S |

TABLE 123

| Compound No. | -A¹- | -A²- | -G¹-A³-A⁴-G² | -A⁵-R² | X |
|---|---|---|---|---|---|
| 3-0641 | —(CH₂)₃— | —C(=O)— | K334 | J177 | S |
| 3-0642 | —(CH₂)₃— | —C(=O)— | K335 | J9 | S |
| 3-0643 | —(CH₂)₃— | —C(=O)— | K335 | J11 | O |
| 3-0644 | —(CH₂)₃— | —C(=O)— | K335 | J51 | S |
| 3-0645 | —(CH₂)₃— | —C(=O)— | K335 | J52 | O |
| 3-0646 | —(CH₂)₃— | —C(=O)— | K335 | J87 | S |
| 3-0647 | —(CH₂)₃— | —C(=O)— | K336 | J9 | S |
| 3-0648 | —(CH₂)₃— | —C(=O)— | K336 | J105 | S |
| 3-0649 | —(CH₂)₃— | —C(=O)— | K336 | J127 | O |
| 3-0650 | —(CH₂)₃— | —C(=O)— | K336 | J129 | O |
| 3-0651 | —(CH₂)₃— | —C(=O)— | K339 | J9 | S |
| 3-0652 | —(CH₂)₃— | —C(=O)— | K340 | J9 | S |
| 3-0653 | —(CH₂)₃— | —C(=O)— | K341 | J9 | S |
| 3-0654 | —(CH₂)₃— | —C(=O)— | K342 | J9 | S |
| 3-0655 | —(CH₂)₃— | —C(=O)— | K349 | J2 | S |
| 3-0656 | —(CH₂)₃— | —C(=O)— | K349 | J4 | S |
| 3-0657 | —(CH₂)₃— | —C(=O)— | K349 | J28 | S |
| 3-0658 | —(CH₂)₃— | —C(=O)— | K349 | J31 | S |
| 3-0659 | —(CH₂)₃— | —C(=O)— | K350 | J49 | S |
| 3-0660 | —(CH₂)₃— | —C(=O)— | K350 | J50 | S |
| 3-0661 | —(CH₂)₃— | —C(=O)— | K350 | J58 | S |
| 3-0662 | —(CH₂)₃— | —C(=O)— | K350 | J64 | S |
| 3-0663 | —(CH₂)₃— | —C(=O)— | K351 | J96 | S |
| 3-0664 | —(CH₂)₃— | —C(=O)— | K351 | J100 | S |
| 3-0665 | —(CH₂)₃— | —C(=O)— | K351 | J104 | S |
| 3-0666 | —(CH₂)₃— | —C(=O)— | K351 | J119 | S |
| 3-0667 | —(CH₂)₃— | —C(=O)— | K351 | J120 | S |
| 3-0668 | —(CH₂)₃— | —C(=O)— | K351 | J132 | S |
| 3-0669 | —(CH₂)₃— | —C(=O)— | K351 | J133 | S |
| 3-0670 | —(CH₂)₃— | —C(=O)— | K352 | J134 | S |
| 3-0671 | —(CH₂)₃— | —C(=O)— | K360 | J2 | S |
| 3-0672 | —(CH₂)₃— | —C(=O)— | K360 | J4 | S |

TABLE 124

| Compound No. | -A¹- | -A²- | -G¹-A³-A⁴-G² | -A⁵-R² | X |
|---|---|---|---|---|---|
| 3-0673 | —(CH₂)₃— | —C(=O)— | K360 | J28 | S |
| 3-0674 | —(CH₂)₃— | —C(=O)— | K360 | J31 | S |
| 3-0675 | —(CH₂)₃— | —C(=O)— | K363 | J154 | S |
| 3-0676 | —(CH₂)₃— | —C(=O)— | K363 | J157 | S |
| 3-0677 | —(CH₂)₃— | —C(=O)— | K363 | J168 | O |
| 3-0678 | —(CH₂)₃— | —C(=O)— | K363 | J174 | O |
| 3-0679 | —(CH₂)₃— | —C(=O)— | K363 | J177 | S |
| 3-0680 | —(CH₂)₃— | —C(=O)— | K364 | J9 | S |
| 3-0681 | —(CH₂)₃— | —C(=O)— | K364 | J11 | S |
| 3-0682 | —(CH₂)₃— | —C(=O)— | K365 | J9 | S |
| 3-0683 | —(CH₂)₃— | —C(=O)— | K367 | J9 | S |
| 3-0684 | —(CH₂)₃— | —C(=O)— | K368 | J9 | S |
| 3-0685 | —(CH₂)₃— | —C(=O)— | K369 | J9 | S |
| 3-0686 | —(CH₂)₃— | —C(=O)— | K372 | J9 | S |
| 3-0687 | —(CH₂)₃— | —C(=O)— | K373 | J9 | S |
| 3-0988 | —(CH₂)₃— | —C(=O)— | K374 | J9 | S |
| 3-0689 | —(CH₂)₃— | —C(=O)— | K377 | J9 | S |
| 3-0690 | —(CH₂)₃— | —C(=O)— | K381 | J9 | S |
| 3-0691 | —(CH₂)₃— | —C(=O)— | K382 | J2 | S |
| 3-0692 | —(CH₂)₃— | —C(=O)— | K382 | J4 | S |
| 3-0693 | —(CH₂)₃— | —C(=O)— | K382 | J28 | S |
| 3-0694 | —(CH₂)₃— | —C(=O)— | K382 | J31 | S |
| 3-0695 | —(CH₂)₃— | —C(=O)— | K383 | J49 | S |
| 3-0696 | —(CH₂)₃— | —C(=O)— | K383 | J50 | S |
| 3-0697 | —(CH₂)₃— | —C(=O)— | K383 | J58 | S |
| 3-0698 | —(CH₂)₃— | —C(=O)— | K383 | J64 | S |
| 3-0699 | —(CH₂)₃— | —C(=O)— | K384 | J96 | S |
| 3-0700 | —(CH₂)₃— | —C(=O)— | K384 | J100 | S |
| 3-0701 | —(CH₂)₃— | —C(=O)— | K384 | J104 | S |
| 3-0702 | —(CH₂)₃— | —C(=O)— | K384 | J119 | S |
| 3-0703 | —(CH₂)₃— | —C(=O)— | K384 | J120 | S |
| 3-0704 | —(CH₂)₃— | —C(=O)— | K386 | J51 | O |

TABLE 125

| Compound No. | -A¹- | -A²- | -G¹-A³-A⁴-G² | -A⁵-R² | X |
|---|---|---|---|---|---|
| 3-0705 | —(CH₂)₃— | —C(=O)— | K386 | J52 | S |
| 3-0706 | —(CH₂)₃— | —C(=O)— | K386 | J87 | S |
| 3-0707 | —(CH₂)₃— | —C(=O)— | K387 | J105 | O |
| 3-0708 | —(CH₂)₃— | —C(=O)— | K387 | J127 | O |
| 3-0709 | —(CH₂)₃— | —C(=O)— | K387 | J129 | S |
| 3-0710 | —(CH₂)₃— | —C(=O)— | K391 | J9 | S |
| 3-0711 | —(CH₂)₃— | —C(=O)— | K393 | J9 | S |
| 3-0712 | —(CH₂)₃— | —C(=O)— | K395 | J2 | S |
| 3-0713 | —(CH₂)₃— | —C(=O)— | K395 | J4 | S |
| 3-0714 | —(CH₂)₃— | —C(=O)— | K395 | J28 | S |
| 3-0715 | —(CH₂)₃— | —C(=O)— | K395 | J31 | S |
| 3-0716 | —(CH₂)₃— | —C(=O)— | K397 | J132 | S |
| 3-0717 | —(CH₂)₃— | —C(=O)— | K397 | J133 | S |
| 3-0718 | —(CH₂)₃— | —C(=O)— | K398 | J134 | S |
| 3-0719 | —(CH₂)₃— | —C(=O)— | K398 | J154 | S |
| 3-0720 | —(CH₂)₃— | —C(=O)— | K398 | J157 | S |
| 3-0721 | —(CH₂)₃— | —C(=O)— | K398 | J168 | S |
| 3-0722 | —(CH₂)₃— | —C(=O)— | K398 | J174 | O |
| 3-0723 | —(CH₂)₃— | —C(=O)— | K398 | J177 | S |
| 3-0724 | —(CH₂)₃— | —C(=O)—NH— | K399 | J9 | S |
| 3-0725 | —(CH₂)₃— | —C(=O)—NH— | K400 | J9 | S |
| 3-0726 | —(CH₂)₃— | —C(=O)—NH— | K24 | J9 | S |
| 3-0727 | —(CH₂)₃— | —C(=O)—NH— | K401 | J9 | S |
| 3-0728 | —(CH₂)₃— | —C(=O)—NH— | K402 | J11 | S |
| 3-0729 | —(CH₂)₃— | —C(=O)—NH— | K167 | J138 | O |
| 3-0730 | —(CH₂)₃— | —C(=O)—NH— | K167 | J147 | S |
| 3-0731 | —(CH₂)₃— | —C(=O)—NH— | K167 | J165 | S |
| 3-0732 | —(CH₂)₃— | —C(=O)—NH— | K167 | J178 | O |
| 3-0733 | —(CH₂)₃— | —C(=O)— | K405 | J73 | S |
| 3-0734 | —(CH₂)₃— | —C(=O)— | K405 | J74 | S |
| 3-0735 | —(CH₂)₃— | —C(=O)— | K405 | J75 | O |
| 3-0736 | —(CH₂)₃— | —C(=O)— | K405 | J81 | O |

TABLE 126

| Compound No. | -A¹- | -A²- | -G¹-A³-A⁴-G² | -A⁵-R² | X |
|---|---|---|---|---|---|
| 3-0737 | —(CH₂)₃— | —C(=O)— | K405 | J82 | S |
| 3-0738 | —(CH₂)₃— | —C(=O)— | K405 | J83 | S |
| 3-0739 | —(CH₂)₃— | —C(=O)— | K405 | J92 | O |
| 3-0740 | —(CH₂)₃— | —C(=O)— | K406 | J9 | S |
| 3-0741 | —(CH₂)₃— | —C(=O)— | K411 | J9 | S |
| 3-0742 | —(CH₂)₃— | —C(=O)— | K413 | J2 | S |
| 3-0743 | —(CH₂)₃— | —C(=O)— | K413 | J4 | S |
| 3-0744 | —(CH₂)₃— | —C(=O)— | K413 | J28 | S |
| 3-0745 | —(CH₂)₃— | —C(=O)— | K413 | J31 | S |
| 3-0746 | —(CH₂)₃— | —C(=O)— | K414 | J49 | S |
| 3-0747 | —(CH₂)₃— | —C(=O)— | K414 | J50 | S |
| 3-0748 | —(CH₂)₃— | —C(=O)— | K414 | J58 | S |
| 3-0749 | —(CH₂)₃— | —C(=O)— | K414 | J64 | S |
| 3-0750 | —(CH₂)₃— | —C(=O)— | K415 | J96 | S |
| 3-0751 | —(CH₂)₃— | —C(=O)— | K415 | J100 | S |
| 3-0752 | —(CH₂)₃— | —C(=O)— | K415 | J104 | S |
| 3-0753 | —(CH₂)₃— | —C(=O)— | K415 | J119 | S |
| 3-0754 | —(CH₂)₃— | —C(=O)— | K415 | J120 | S |
| 3-0755 | —(CH₂)₃— | —C(=O)— | K417 | J51 | O |
| 3-0756 | —(CH₂)₃— | —C(=O)— | K417 | J52 | O |
| 3-0757 | —(CH₂)₃— | —C(=O)— | K417 | J87 | S |
| 3-0758 | —(CH₂)₃— | —C(=O)— | K418 | J105 | S |
| 3-0759 | —(CH₂)₃— | —C(=O)— | K418 | J127 | O |
| 3-0760 | —(CH₂)₃— | —C(=O)— | K418 | J129 | S |
| 3-0761 | —(CH₂)₃— | —C(=O)—NH— | K422 | J2 | S |
| 3-0762 | —(CH₂)₃— | —C(=O)—NH— | K422 | J4 | S |
| 3-0763 | —(CH₂)₃— | —C(=O)—NH— | K422 | J28 | S |
| 3-0764 | —(CH₂)₃— | —C(=O)—NH— | K422 | J31 | S |
| 3-0765 | —(CH₂)₃— | —C(=O)—NH— | K423 | J154 | S |
| 3-0766 | —(CH₂)₃— | —C(=O)—NH— | K423 | J157 | S |
| 3-0767 | —(CH₂)₃— | —C(=O)—NH— | K423 | J168 | S |
| 3-0768 | —(CH₂)₃— | —C(=O)—NH— | K423 | J174 | O |

TABLE 127

| Compound No. | -A¹- | -A²- | -G¹-A³-A⁴-G² | -A⁵-R² | X |
|---|---|---|---|---|---|
| 3-0769 | —(CH$_2$)$_3$— | —C(=O)—NH— | K423 | J177 | O |
| 3-0770 | —(CH$_2$)$_3$— | —C(=O)—NH— | K424 | J11 | S |
| 3-0771 | —(CH$_2$)$_2$— | —C(=O)— | K314 | J3 | S |
| 3-0772 | —(CH$_2$)$_2$— | —C(=O)— | K316 | J3 | S |
| 3-0773 | —(CH$_2$)$_2$— | —C(=O)— | K317 | J3 | S |
| 3-0774 | —(CH$_2$)$_2$— | —C(=O)— | K318 | J3 | S |
| 3-0775 | —(CH$_2$)$_2$— | —C(=O)— | K319 | J3 | S |
| 3-0776 | —(CH$_2$)$_2$— | —C(=O)— | K320 | J3 | S |
| 3-0777 | —(CH$_2$)$_2$— | —C(=O)— | K321 | J3 | S |
| 3-0778 | —(CH$_2$)$_2$— | —C(=O)— | K322 | J3 | S |
| 3-0779 | —(CH$_2$)$_2$— | —C(=O)— | K323 | J3 | S |
| 3-0780 | —(CH$_2$)$_2$— | —C(=O)— | K324 | J3 | S |
| 3-0781 | —(CH$_2$)$_2$— | —C(=O)— | K326 | J3 | S |
| 3-0782 | —(CH$_2$)$_2$— | —C(=O)— | K327 | J3 | S |
| 3-0783 | —(CH$_2$)$_2$— | —C(=O)— | K328 | J3 | S |
| 3-0784 | —(CH$_2$)$_2$— | —C(=O)— | K329 | J3 | S |
| 3-0785 | —(CH$_2$)$_2$— | —C(=O)— | K330 | J3 | S |
| 3-0786 | —(CH$_2$)$_2$— | —C(=O)— | K331 | J3 | S |
| 3-0787 | —(CH$_2$)$_2$— | —C(=O)— | K332 | J3 | S |
| 3-0788 | —(CH$_2$)$_2$— | —C(=O)— | K333 | J3 | S |
| 3-0789 | —(CH$_2$)$_2$— | —C(=O)— | K334 | J3 | S |
| 3-0790 | —(CH$_2$)$_2$— | —C(=O)— | K335 | J3 | S |
| 3-0791 | —(CH$_2$)$_2$— | —C(=O)— | K336 | J3 | S |
| 3-0792 | —(CH$_2$)$_2$— | —C(=O)— | K338 | J3 | S |
| 3-0793 | —(CH$_2$)$_2$— | —C(=O)— | K339 | J3 | S |
| 3-0794 | —(CH$_2$)$_2$— | —C(=O)— | K340 | J3 | S |
| 3-0795 | —(CH$_2$)$_2$— | —C(=O)— | K341 | J3 | S |
| 3-0796 | —(CH$_2$)$_2$— | —C(=O)— | K342 | J3 | S |
| 3-0797 | —(CH$_2$)$_2$— | —C(=O)— | K343 | J3 | S |
| 3-0798 | —(CH$_2$)$_2$— | —C(=O)— | K344 | J3 | S |
| 3-0799 | —(CH$_2$)$_2$— | —C(=O)— | K345 | J3 | S |
| 3-0800 | —(CH$_2$)$_2$— | —C(=O)— | K346 | J3 | S |

TABLE 128

| Compound No. | -A¹- | -A²- | -G¹-A³-A⁴-G² | -A⁵-R² | X |
|---|---|---|---|---|---|
| 3-0801 | —(CH$_2$)$_2$— | —C(=O)— | K347 | J3 | S |
| 3-0802 | —(CH$_2$)$_2$— | —C(=O)— | K348 | J3 | S |
| 3-0803 | —(CH$_2$)$_2$— | —C(=O)— | K349 | J3 | S |
| 3-0804 | —(CH$_2$)$_2$— | —C(=O)— | K350 | J3 | S |
| 3-0805 | —(CH$_2$)$_2$— | —C(=O)— | K351 | J3 | S |
| 3-0806 | —(CH$_2$)$_2$— | —C(=O)— | K352 | J3 | S |
| 3-0807 | —(CH$_2$)$_2$— | —C(=O)— | K353 | J3 | S |
| 3-0808 | —(CH$_2$)$_2$— | —C(=O)— | K354 | J3 | S |
| 3-0809 | —(CH$_2$)$_2$— | —C(=O)— | K356 | J3 | S |
| 3-0810 | —(CH$_2$)$_2$— | —C(=O)— | K357 | J3 | S |
| 3-0811 | —(CH$_2$)$_2$— | —C(=O)— | K358 | J3 | S |
| 3-0812 | —(CH$_2$)$_2$— | —C(=O)— | K359 | J3 | S |
| 3-0813 | —(CH$_2$)$_2$— | —C(=O)— | K360 | J3 | S |
| 3-0814 | —(CH$_2$)$_2$— | —C(=O)— | K361 | J3 | S |
| 3-0815 | —(CH$_2$)$_2$— | —C(=O)— | K362 | J3 | S |
| 3-0816 | —(CH$_2$)$_2$— | —C(=O)— | K363 | J3 | S |
| 3-0817 | —(CH$_2$)$_2$— | —C(=O)— | K364 | J3 | S |
| 3-0818 | —(CH$_2$)$_2$— | —C(=O)— | K365 | J3 | S |
| 3-0819 | —(CH$_2$)$_2$— | —C(=O)— | K366 | J3 | S |
| 3-0820 | —(CH$_2$)$_2$— | —C(=O)— | K367 | J3 | S |
| 3-0821 | —(CH$_2$)$_2$— | —C(=O)— | K368 | J3 | S |
| 3-0822 | —(CH$_2$)$_2$— | —C(=O)— | K369 | J3 | S |
| 3-0823 | —(CH$_2$)$_2$— | —C(=O)— | K370 | J3 | S |
| 3-0824 | —(CH$_2$)$_2$— | —C(=O)— | K371 | J3 | S |
| 3-0825 | —(CH$_2$)$_2$— | —C(=O)— | K372 | J3 | S |
| 3-0826 | —(CH$_2$)$_2$— | —C(=O)— | K373 | J3 | S |
| 3-0827 | —(CH$_2$)$_2$— | —C(=O)— | K374 | J3 | S |
| 3-0828 | —(CH$_2$)$_2$— | —C(=O)— | K375 | J3 | S |
| 3-0829 | —(CH$_2$)$_2$— | —C(=O)— | K376 | J3 | S |
| 3-0830 | —(CH$_2$)$_2$— | —C(=O)— | K377 | J3 | S |
| 3-0831 | —(CH$_2$)$_2$— | —C(=O)— | K378 | J3 | S |
| 3-0832 | —(CH$_2$)$_2$— | —C(=O)— | K379 | J3 | S |

TABLE 129

| Compound No. | -A¹- | -A²- | -G¹-A³-A⁴-G² | -A⁵-R² | X |
|---|---|---|---|---|---|
| 3-0833 | —(CH$_2$)$_2$— | —C(=O)— | K380 | J3 | S |
| 3-0834 | —(CH$_2$)$_2$— | —C(=O)— | K381 | J3 | S |
| 3-0835 | —(CH$_2$)$_2$— | —C(=O)— | K383 | J3 | S |
| 3-0836 | —(CH$_2$)$_2$— | —C(=O)— | K384 | J3 | S |
| 3-0837 | —(CH$_2$)$_2$— | —C(=O)— | K385 | J3 | S |
| 3-0838 | —(CH$_2$)$_2$— | —C(=O)— | K386 | J3 | S |
| 3-0839 | —(CH$_2$)$_2$— | —C(=O)— | K387 | J3 | S |
| 3-0840 | —(CH$_2$)$_2$— | —C(=O)— | K388 | J3 | S |
| 3-0841 | —(CH$_2$)$_2$— | —C(=O)— | K389 | J3 | S |
| 3-0842 | —(CH$_2$)$_2$— | —C(=O)— | K390 | J3 | S |
| 3-0843 | —(CH$_2$)$_2$— | —C(=O)— | K391 | J3 | S |
| 3-0844 | —(CH$_2$)$_2$— | —C(=O)— | K392 | J3 | S |
| 3-0845 | —(CH$_2$)$_2$— | —C(=O)— | K393 | J3 | S |
| 3-0846 | —(CH$_2$)$_2$— | —C(=O)— | K394 | J3 | S |
| 3-0847 | —(CH$_2$)$_2$— | —C(=O)— | K395 | J3 | S |
| 3-0848 | —(CH$_2$)$_2$— | —C(=O)— | K396 | J3 | S |
| 3-0849 | —(CH$_2$)$_2$— | —C(=O)— | K398 | J3 | S |
| 3-0850 | —(CH$_2$)$_2$— | —C(=O)— | K405 | J3 | S |
| 3-0851 | —(CH$_2$)$_2$— | —C(=O)— | K406 | J3 | S |
| 3-0852 | —(CH$_2$)$_2$— | —C(=O)— | K407 | J3 | S |
| 3-0853 | —(CH$_2$)$_2$— | —C(=O)— | K408 | J3 | S |
| 3-0854 | —(CH$_2$)$_2$— | —C(=O)— | K409 | J3 | S |
| 3-0855 | —(CH$_2$)$_2$— | —C(=O)— | K410 | J3 | S |
| 3-0856 | —(CH$_2$)$_2$— | —C(=O)— | K411 | J3 | S |
| 3-0857 | —(CH$_2$)$_2$— | —C(=O)— | K412 | J3 | S |
| 3-0858 | —(CH$_2$)$_2$— | —C(=O)— | K413 | J3 | S |
| 3-0859 | —(CH$_2$)$_2$— | —C(=O)— | K414 | J3 | S |
| 3-0860 | —(CH$_2$)$_2$— | —C(=O)— | K415 | J3 | S |
| 3-0861 | —(CH$_2$)$_2$— | —C(=O)— | K416 | J3 | S |
| 3-0862 | —(CH$_2$)$_2$— | —C(=O)— | K417 | J3 | S |
| 3-0863 | —(CH$_2$)$_2$— | —C(=O)— | K419 | J3 | S |
| 3-0864 | —(CH$_2$)$_2$— | —C(=O)— | K420 | J3 | S |

TABLE 130

| Compound No. | -A¹- | -A²- | -G¹-A³-A⁴-G² | -A⁵-R² | X |
|---|---|---|---|---|---|
| 3-0865 | —(CH$_2$)$_2$— | —C(=O)— | K421 | J3 | S |
| 3-0866 | —(CH$_2$)$_2$— | —C(=O)— | K726 | J3 | S |
| 3-0867 | —(CH$_2$)$_2$— | —C(=O)— | K727 | J3 | S |
| 3-0868 | —(CH$_2$)$_2$— | —C(=O)— | K728 | J3 | S |
| 3-0869 | —(CH$_2$)$_2$— | —C(=O)— | K729 | J3 | S |
| 3-0870 | —(CH$_2$)$_2$— | —C(=O)— | K730 | J3 | S |
| 3-0871 | —(CH$_2$)$_2$— | —C(=O)— | K731 | J3 | S |
| 3-0872 | —(CH$_2$)$_2$— | —C(=O)— | K732 | J3 | S |
| 3-0873 | —(CH$_2$)$_2$— | —C(=O)— | K733 | J3 | S |
| 3-0874 | —(CH$_2$)$_2$— | —C(=O)— | K734 | J3 | S |
| 3-0875 | —(CH$_2$)$_2$— | —C(=O)— | K735 | J3 | S |
| 3-0876 | —(CH$_2$)$_2$— | —C(=O)— | K736 | J3 | S |
| 3-0877 | —(CH$_2$)$_2$— | —C(=O)— | K737 | J3 | S |
| 3-0878 | —(CH$_2$)$_2$— | —C(=O)— | K738 | J3 | S |
| 3-0879 | —(CH$_2$)$_2$— | —C(=O)— | K739 | J3 | S |
| 3-0880 | —(CH$_2$)$_2$— | —C(=O)— | K740 | J3 | S |
| 3-0881 | —(CH$_2$)$_2$— | —C(=O)— | K741 | J3 | S |
| 3-0882 | —(CH$_2$)$_2$— | —C(=O)— | K742 | J3 | S |
| 3-0883 | —(CH$_2$)$_2$— | —C(=O)— | K743 | J3 | S |
| 3-0884 | —(CH$_2$)$_2$— | —C(=O)— | K744 | J3 | S |
| 3-0885 | —(CH$_2$)$_2$— | —C(=O)— | K745 | J3 | S |
| 3-0886 | —(CH$_2$)$_2$— | —C(=O)— | K746 | J3 | S |
| 3-0887 | —(CH$_2$)$_2$— | —C(=O)— | K747 | J3 | S |
| 3-0888 | —(CH$_2$)$_2$— | —C(=O)— | K748 | J3 | S |
| 3-0889 | —(CH$_2$)$_2$— | —C(=O)— | K749 | J3 | S |
| 3-0890 | —(CH$_2$)$_2$— | —C(=O)— | K750 | J3 | S |
| 3-0891 | —(CH$_2$)$_2$— | —C(=O)— | K751 | J3 | S |
| 3-0892 | —(CH$_2$)$_2$— | —C(=O)— | K752 | J3 | S |
| 3-0893 | —(CH$_2$)$_2$— | —C(=O)— | K753 | J3 | S |
| 3-0894 | —(CH$_2$)$_2$— | —C(=O)— | K754 | J3 | S |
| 3-0895 | —(CH$_2$)$_2$— | —C(=O)— | K755 | J3 | S |
| 3-0896 | —(CH$_2$)$_2$— | —C(=O)— | K756 | J3 | S |

TABLE 131

| Compound No. | -A¹- | -A²- | -G¹-A³-A⁴-G² | -A⁵-R² | X |
|---|---|---|---|---|---|
| 3-0897 | —(CH$_2$)$_2$— | —C(=O)— | K757 | J3 | S |
| 3-0898 | —(CH$_2$)$_2$— | —C(=O)— | K316 | J9 | S |
| 3-0899 | —(CH$_2$)$_2$— | —C(=O)— | K321 | J9 | S |
| 3-0900 | —(CH$_2$)$_2$— | —C(=O)— | K322 | J9 | S |
| 3-0901 | —(CH$_2$)$_2$— | —C(=O)— | K323 | J9 | S |
| 3-0902 | —(CH$_2$)$_2$— | —C(=O)— | K324 | J9 | S |
| 3-0903 | —(CH$_2$)$_2$— | —C(=O)— | K326 | J9 | S |
| 3-0904 | —(CH$_2$)$_2$— | —C(=O)— | K327 | J9 | S |
| 3-0905 | —(CH$_2$)$_2$— | —C(=O)— | K328 | J9 | S |
| 3-0906 | —(CH$_2$)$_2$— | —C(=O)— | K329 | J9 | S |
| 3-0907 | —(CH$_2$)$_2$— | —C(=O)— | K333 | J9 | S |
| 3-0908 | —(CH$_2$)$_2$— | —C(=O)— | K334 | J9 | S |
| 3-0909 | —(CH$_2$)$_2$— | —C(=O)— | K341 | J9 | S |
| 3-0910 | —(CH$_2$)$_2$— | —C(=O)— | K342 | J9 | S |
| 3-0911 | —(CH$_2$)$_2$— | —C(=O)— | K344 | J9 | S |
| 3-0912 | —(CH$_2$)$_2$— | —C(=O)— | K345 | J9 | S |
| 3-0913 | —(CH$_2$)$_2$— | —C(=O)— | K346 | J9 | S |
| 3-0914 | —(CH$_2$)$_2$— | —C(=O)— | K347 | J9 | S |
| 3-0915 | —(CH$_2$)$_2$— | —C(=O)— | K348 | J9 | S |
| 3-0916 | —(CH$_2$)$_2$— | —C(=O)— | K349 | J9 | S |
| 3-0917 | —(CH$_2$)$_2$— | —C(=O)— | K350 | J9 | S |
| 3-0918 | —(CH$_2$)$_2$— | —C(=O)— | K351 | J9 | S |
| 3-0919 | —(CH$_2$)$_2$— | —C(=O)— | K352 | J9 | S |
| 3-0920 | —(CH$_2$)$_2$— | —C(=O)— | K353 | J9 | S |
| 3-0921 | —(CH$_2$)$_2$— | —C(=O)— | K354 | J9 | S |
| 3-0922 | —(CH$_2$)$_2$— | —C(=O)— | K356 | J9 | S |
| 3-0923 | —(CH$_2$)$_2$— | —C(=O)— | K357 | J9 | S |
| 3-0924 | —(CH$_2$)$_2$— | —C(=O)— | K359 | J9 | S |
| 3-0925 | —(CH$_2$)$_2$— | —C(=O)— | K360 | J9 | S |
| 3-0926 | —(CH$_2$)$_2$— | —C(=O)— | K361 | J9 | S |
| 3-0927 | —(CH$_2$)$_2$— | —C(=O)— | K362 | J9 | S |
| 3-0928 | —(CH$_2$)$_2$— | —C(=O)— | K363 | J9 | S |

TABLE 132

| Compound No. | -A¹- | -A²- | -G¹-A³-A⁴-G² | -A⁵-R² | X |
|---|---|---|---|---|---|
| 3-0929 | —(CH$_2$)$_2$— | —C(=O)— | K366 | J9 | S |
| 3-0930 | —(CH$_2$)$_2$— | —C(=O)— | K370 | J9 | S |
| 3-0931 | —(CH$_2$)$_2$— | —C(=O)— | K375 | J9 | S |
| 3-0932 | —(CH$_2$)$_2$— | —C(=O)— | K376 | J9 | S |
| 3-0933 | —(CH$_2$)$_2$— | —C(=O)— | K378 | J9 | S |
| 3-0934 | —(CH$_2$)$_2$— | —C(=O)— | K379 | J9 | S |
| 3-0935 | —(CH$_2$)$_2$— | —C(=O)— | K383 | J9 | S |
| 3-0936 | —(CH$_2$)$_2$— | —C(=O)— | K384 | J9 | S |
| 3-0937 | —(CH$_2$)$_2$— | —C(=O)— | K385 | J9 | S |
| 3-0938 | —(CH$_2$)$_2$— | —C(=O)— | K386 | J9 | S |
| 3-0939 | —(CH$_2$)$_2$— | —C(=O)— | K387 | J9 | S |
| 3-0940 | —(CH$_2$)$_2$— | —C(=O)— | K388 | J9 | S |
| 3-0941 | —(CH$_2$)$_2$— | —C(=O)— | K389 | J9 | S |
| 3-0942 | —(CH$_2$)$_2$— | —C(=O)— | K390 | J9 | S |
| 3-0943 | —(CH$_2$)$_2$— | —C(=O)— | K394 | J9 | S |
| 3-0944 | —(CH$_2$)$_2$— | —C(=O)— | K395 | J9 | S |
| 3-0945 | —(CH$_2$)$_2$— | —C(=O)— | K396 | J9 | S |
| 3-0946 | —(CH$_2$)$_2$— | —C(=O)— | K398 | J9 | S |
| 3-0947 | —(CH$_2$)$_2$— | —C(=O)— | K405 | J9 | S |
| 3-0948 | —(CH$_2$)$_2$— | —C(=O)— | K406 | J9 | S |
| 3-0949 | —(CH$_2$)$_2$— | —C(=O)— | K407 | J9 | S |
| 3-0950 | —(CH$_2$)$_2$— | —C(=O)— | K408 | J9 | S |
| 3-0951 | —(CH$_2$)$_2$— | —C(=O)— | K409 | J9 | S |
| 3-0952 | —(CH$_2$)$_2$— | —C(=O)— | K410 | J9 | S |
| 3-0953 | —(CH$_2$)$_2$— | —C(=O)— | K411 | J9 | S |
| 3-0954 | —(CH$_2$)$_2$— | —C(=O)— | K412 | J9 | S |
| 3-0955 | —(CH$_2$)$_2$— | —C(=O)— | K413 | J9 | S |
| 3-0956 | —(CH$_2$)$_2$— | —C(=O)— | K414 | J9 | S |
| 3-0957 | —(CH$_2$)$_2$— | —C(=O)— | K415 | J9 | S |
| 3-0958 | —(CH$_2$)$_2$— | —C(=O)— | K416 | J9 | S |
| 3-0959 | —(CH$_2$)$_2$— | —C(=O)— | K417 | J9 | S |
| 3-0960 | —(CH$_2$)$_2$— | —C(=O)— | K419 | J9 | S |

TABLE 133

| Compound No. | -A¹- | -A²- | -G¹-A³-A⁴-G² | -A⁵-R² | X |
|---|---|---|---|---|---|
| 3-0961 | —(CH$_2$)$_2$— | —C(=O)— | K421 | J9 | S |
| 3-0962 | —(CH$_2$)$_2$— | —C(=O)— | K726 | J9 | S |
| 3-0963 | —(CH$_2$)$_2$— | —C(=O)— | K727 | J9 | S |
| 3-0964 | —(CH$_2$)$_2$— | —C(=O)— | K728 | J9 | S |
| 3-0965 | —(CH$_2$)$_2$— | —C(=O)— | K729 | J9 | S |
| 3-0966 | —(CH$_2$)$_2$— | —C(=O)— | K730 | J9 | S |
| 3-0967 | —(CH$_2$)$_2$— | —C(=O)— | K731 | J9 | S |
| 3-0968 | —(CH$_2$)$_2$— | —C(=O)— | K732 | J9 | S |
| 3-0969 | —(CH$_2$)$_2$— | —C(=O)— | K733 | J9 | S |
| 3-0970 | —(CH$_2$)$_2$— | —C(=O)— | K734 | J9 | S |
| 3-0971 | —(CH$_2$)$_2$— | —C(=O)— | K735 | J9 | S |
| 3-0972 | —(CH$_2$)$_2$— | —C(=O)— | K736 | J9 | S |
| 3-0973 | —(CH$_2$)$_2$— | —C(=O)— | K737 | J9 | S |
| 3-0974 | —(CH$_2$)$_2$— | —C(=O)— | K738 | J9 | S |
| 3-0975 | —(CH$_2$)$_2$— | —C(=O)— | K739 | J9 | S |
| 3-0976 | —(CH$_2$)$_2$— | —C(=O)— | K740 | J9 | S |
| 3-0977 | —(CH$_2$)$_2$— | —C(=O)— | K741 | J9 | S |
| 3-0978 | —(CH$_2$)$_2$— | —C(=O)— | K742 | J9 | S |
| 3-0979 | —(CH$_2$)$_2$— | —C(=O)— | K743 | J9 | S |
| 3-0980 | —(CH$_2$)$_2$— | —C(=O)— | K744 | J9 | S |
| 3-0981 | —(CH$_2$)$_2$— | —C(=O)— | K745 | J9 | S |
| 3-0982 | —(CH$_2$)$_2$— | —C(=O)— | K746 | J9 | S |
| 3-0983 | —(CH$_2$)$_2$— | —C(=O)— | K747 | J9 | S |
| 3-0984 | —(CH$_2$)$_2$— | —C(=O)— | K748 | J9 | S |
| 3-0985 | —(CH$_2$)$_2$— | —C(=O)— | K749 | J9 | S |
| 3-0986 | —(CH$_2$)$_2$— | —C(=O)— | K750 | J9 | S |
| 3-0987 | —(CH$_2$)$_2$— | —C(=O)— | K751 | J9 | S |
| 3-0988 | —(CH$_2$)$_2$— | —C(=O)— | K752 | J9 | S |
| 3-0989 | —(CH$_2$)$_2$— | —C(=O)— | K753 | J9 | S |
| 3-0990 | —(CH$_2$)$_2$— | —C(=O)— | K754 | J9 | S |
| 3-0991 | —(CH$_2$)$_2$— | —C(=O)— | K755 | J9 | S |
| 3-0992 | —(CH$_2$)$_2$— | —C(=O)— | K756 | J9 | S |

TABLE 134

| Compound No. | -A¹- | -A²- | -G¹-A³-A⁴-G² | -A⁵-R² | X |
|---|---|---|---|---|---|
| 3-0993 | —(CH$_2$)$_2$— | —C(=O)— | K757 | J9 | S |
| 3-0994 | —(CH$_2$)$_2$— | —C(=O)— | K314 | J126 | S |
| 3-0995 | —(CH$_2$)$_2$— | —C(=O)— | K315 | J126 | S |
| 3-0996 | —(CH$_2$)$_2$— | —C(=O)— | K316 | J126 | S |
| 3-0997 | —(CH$_2$)$_2$— | —C(=O)— | K317 | J126 | S |
| 3-0998 | —(CH$_2$)$_2$— | —C(=O)— | K318 | J126 | S |
| 3-0999 | —(CH$_2$)$_2$— | —C(=O)— | K320 | J126 | S |
| 3-1000 | —(CH$_2$)$_2$— | —C(=O)— | K321 | J126 | S |
| 3-1001 | —(CH$_2$)$_2$— | —C(=O)— | K322 | J126 | S |
| 3-1002 | —(CH$_2$)$_2$— | —C(=O)— | K323 | J126 | S |
| 3-1003 | —(CH$_2$)$_2$— | —C(=O)— | K324 | J126 | S |
| 3-1004 | —(CH$_2$)$_2$— | —C(=O)— | K325 | J126 | S |
| 3-1005 | —(CH$_2$)$_2$— | —C(=O)— | K326 | J126 | S |
| 3-1006 | —(CH$_2$)$_2$— | —C(=O)— | K327 | J126 | S |
| 3-1007 | —(CH$_2$)$_2$— | —C(=O)— | K328 | J126 | S |
| 3-1008 | —(CH$_2$)$_2$— | —C(=O)— | K329 | J126 | S |
| 3-1009 | —(CH$_2$)$_2$— | —C(=O)— | K330 | J126 | S |
| 3-1010 | —(CH$_2$)$_2$— | —C(=O)— | K331 | J126 | S |
| 3-1011 | —(CH$_2$)$_2$— | —C(=O)— | K332 | J126 | S |
| 3-1012 | —(CH$_2$)$_2$— | —C(=O)— | K333 | J126 | S |
| 3-1013 | —(CH$_2$)$_2$— | —C(=O)— | K334 | J126 | S |
| 3-1014 | —(CH$_2$)$_2$— | —C(=O)— | K335 | J126 | S |
| 3-1015 | —(CH$_2$)$_2$— | —C(=O)— | K337 | J126 | S |
| 3-1016 | —(CH$_2$)$_2$— | —C(=O)— | K338 | J126 | S |
| 3-1017 | —(CH$_2$)$_2$— | —C(=O)— | K339 | J126 | S |
| 3-1018 | —(CH$_2$)$_2$— | —C(=O)— | K340 | J126 | S |
| 3-1019 | —(CH$_2$)$_2$— | —C(=O)— | K341 | J126 | S |
| 3-1020 | —(CH$_2$)$_2$— | —C(=O)— | K342 | J126 | S |
| 3-1021 | —(CH$_2$)$_2$— | —C(=O)— | K343 | J126 | S |
| 3-1022 | —(CH$_2$)$_2$— | —C(=O)— | K344 | J126 | S |
| 3-1023 | —(CH$_2$)$_2$— | —C(=O)— | K345 | J126 | S |
| 3-1024 | —(CH$_2$)$_2$— | —C(=O)— | K346 | J126 | S |

TABLE 135

| Compound No. | -A¹- | -A²- | -G¹-A³-A⁴-G² | -A⁵-R² | X |
|---|---|---|---|---|---|
| 3-1025 | —(CH$_2$)$_2$— | —C(=O)— | K347 | J126 | S |
| 3-1026 | —(CH$_2$)$_2$— | —C(=O)— | K348 | J126 | S |
| 3-1027 | —(CH$_2$)$_2$— | —C(=O)— | K349 | J126 | S |
| 3-1028 | —(CH$_2$)$_2$— | —C(=O)— | K350 | J126 | S |
| 3-1029 | —(CH$_2$)$_2$— | —C(=O)— | K351 | J126 | S |
| 3-1030 | —(CH$_2$)$_2$— | —C(=O)— | K352 | J126 | S |
| 3-1031 | —(CH$_2$)$_2$— | —C(=O)— | K353 | J126 | S |
| 3-1032 | —(CH$_2$)$_2$— | —C(=O)— | K355 | J126 | S |
| 3-1033 | —(CH$_2$)$_2$— | —C(=O)— | K356 | J126 | S |
| 3-1034 | —(CH$_2$)$_2$— | —C(=O)— | K357 | J126 | S |
| 3-1035 | —(CH$_2$)$_2$— | —C(=O)— | K359 | J126 | S |
| 3-1036 | —(CH$_2$)$_2$— | —C(=O)— | K360 | J126 | S |
| 3-1037 | —(CH$_2$)$_2$— | —C(=O)— | K361 | J126 | S |
| 3-1038 | —(CH$_2$)$_2$— | —C(=O)— | K362 | J126 | S |
| 3-1039 | —(CH$_2$)$_2$— | —C(=O)— | K363 | J126 | S |
| 3-1040 | —(CH$_2$)$_2$— | —C(=O)— | K364 | J126 | S |
| 3-1041 | —(CH$_2$)$_2$— | —C(=O)— | K365 | J126 | S |
| 3-1042 | —(CH$_2$)$_2$— | —C(=O)— | K366 | J126 | S |
| 3-1043 | —(CH$_2$)$_2$— | —C(=O)— | K367 | J126 | S |
| 3-1044 | —(CH$_2$)$_2$— | —C(=O)— | K368 | J126 | S |
| 3-1045 | —(CH$_2$)$_2$— | —C(=O)— | K369 | J126 | S |
| 3-1046 | —(CH$_2$)$_2$— | —C(=O)— | K370 | J126 | S |
| 3-1047 | —(CH$_2$)$_2$— | —C(=O)— | K371 | J126 | S |
| 3-1048 | —(CH$_2$)$_2$— | —C(=O)— | K372 | J126 | S |
| 3-1049 | —(CH$_2$)$_2$— | —C(=O)— | K373 | J126 | S |
| 3-1050 | —(CH$_2$)$_2$— | —C(=O)— | K374 | J126 | S |
| 3-1051 | —(CH$_2$)$_2$— | —C(=O)— | K375 | J126 | S |
| 3-1052 | —(CH$_2$)$_2$— | —C(=O)— | K376 | J126 | S |
| 3-1053 | —(CH$_2$)$_2$— | —C(=O)— | K377 | J126 | S |
| 3-1054 | —(CH$_2$)$_2$— | —C(=O)— | K378 | J126 | S |
| 3-1055 | —(CH$_2$)$_2$— | —C(=O)— | K379 | J126 | S |
| 3-1056 | —(CH$_2$)$_2$— | —C(=O)— | K380 | J126 | S |

TABLE 136

| Compound No. | -A¹- | -A²- | -G¹-A³-A⁴-G² | -A⁵-R² | X |
|---|---|---|---|---|---|
| 3-1057 | —(CH$_2$)$_2$— | —C(=O)— | K383 | J78 | S |
| 3-1058 | —(CH$_2$)$_2$— | —C(=O)— | K384 | J78 | S |
| 3-1059 | —(CH$_2$)$_2$— | —C(=O)— | K385 | J78 | S |
| 3-1060 | —(CH$_2$)$_2$— | —C(=O)— | K386 | J78 | S |
| 3-1061 | —(CH$_2$)$_2$— | —C(=O)— | K387 | J78 | S |
| 3-1062 | —(CH$_2$)$_2$— | —C(=O)— | K388 | J78 | S |
| 3-1063 | —(CH$_2$)$_2$— | —C(=O)— | K389 | J78 | S |
| 3-1064 | —(CH$_2$)$_2$— | —C(=O)— | K390 | J78 | S |
| 3-1065 | —(CH$_2$)$_2$— | —C(=O)— | K391 | J78 | S |
| 3-1066 | —(CH$_2$)$_2$— | —C(=O)— | K392 | J78 | S |
| 3-1067 | —(CH$_2$)$_2$— | —C(=O)— | K393 | J78 | S |
| 3-1068 | —(CH$_2$)$_2$— | —C(=O)— | K394 | J78 | S |
| 3-1069 | —(CH$_2$)$_2$— | —C(=O)— | K395 | J78 | S |
| 3-1070 | —(CH$_2$)$_2$— | —C(=O)— | K396 | J78 | S |
| 3-1071 | —(CH$_2$)$_2$— | —C(=O)— | K398 | J78 | S |
| 3-1072 | —(CH$_2$)$_2$— | —C(=O)— | K405 | J78 | S |
| 3-1073 | —(CH$_2$)$_2$— | —C(=O)— | K406 | J78 | S |
| 3-1074 | —(CH$_2$)$_2$— | —C(=O)— | K407 | J78 | S |
| 3-1075 | —(CH$_2$)$_2$— | —C(=O)— | K408 | J78 | S |
| 3-1076 | —(CH$_2$)$_2$— | —C(=O)— | K409 | J78 | S |
| 3-1077 | —(CH$_2$)$_2$— | —C(=O)— | K410 | J78 | S |
| 3-1078 | —(CH$_2$)$_2$— | —C(=O)— | K411 | J78 | S |
| 3-1079 | —(CH$_2$)$_2$— | —C(=O)— | K412 | J78 | S |
| 3-1080 | —(CH$_2$)$_2$— | —C(=O)— | K413 | J78 | S |
| 3-1081 | —(CH$_2$)$_2$— | —C(=O)— | K414 | J78 | S |
| 3-1082 | —(CH$_2$)$_2$— | —C(=O)— | K415 | J78 | S |
| 3-1083 | —(CH$_2$)$_2$— | —C(=O)— | K416 | J78 | S |
| 3-1084 | —(CH$_2$)$_2$— | —C(=O)— | K417 | J78 | S |
| 3-1085 | —(CH$_2$)$_2$— | —C(=O)— | K419 | J78 | S |
| 3-1086 | —(CH$_2$)$_2$— | —C(=O)— | K420 | J78 | S |
| 3-1087 | —(CH$_2$)$_2$— | —C(=O)— | K421 | J78 | S |
| 3-1088 | —(CH$_2$)$_2$— | —C(=O)— | K726 | J78 | S |

TABLE 137

| Compound No. | -A¹- | -A²- | -G¹-A³-A⁴-G² | -A⁵-R² | X |
|---|---|---|---|---|---|
| 3-1089 | —(CH$_2$)$_2$— | —C(=O)— | K727 | J78 | S |
| 3-1090 | —(CH$_2$)$_2$— | —C(=O)— | K728 | J78 | S |
| 3-1091 | —(CH$_2$)$_2$— | —C(=O)— | K729 | J78 | S |
| 3-1092 | —(CH$_2$)$_2$— | —C(=O)— | K730 | J78 | S |
| 3-1093 | —(CH$_2$)$_2$— | —C(=O)— | K731 | J78 | S |
| 3-1094 | —(CH$_2$)$_2$— | —C(=O)— | K732 | J78 | S |
| 3-1095 | —(CH$_2$)$_2$— | —C(=O)— | K733 | J78 | S |
| 3-1096 | —(CH$_2$)$_2$— | —C(=O)— | K734 | J78 | S |
| 3-1097 | —(CH$_2$)$_2$— | —C(=O)— | K735 | J78 | S |
| 3-1098 | —(CH$_2$)$_2$— | —C(=O)— | K736 | J78 | S |
| 3-1099 | —(CH$_2$)$_2$— | —C(=O)— | K737 | J78 | S |
| 3-1100 | —(CH$_2$)$_2$— | —C(=O)— | K738 | J78 | S |
| 3-1101 | —(CH$_2$)$_2$— | —C(=O)— | K739 | J78 | S |
| 3-1102 | —(CH$_2$)$_2$— | —C(=O)— | K740 | J78 | S |
| 3-1103 | —(CH$_2$)$_2$— | —C(=O)— | K741 | J78 | S |
| 3-1104 | —(CH$_2$)$_2$— | —C(=O)— | K742 | J78 | S |
| 3-1105 | —(CH$_2$)$_2$— | —C(=O)— | K743 | J78 | S |
| 3-1106 | —(CH$_2$)$_2$— | —C(=O)— | K744 | J78 | S |
| 3-1107 | —(CH$_2$)$_2$— | —C(=O)— | K745 | J78 | S |
| 3-1108 | —(CH$_2$)$_2$— | —C(=O)— | K746 | J78 | S |
| 3-1109 | —(CH$_2$)$_2$— | —C(=O)— | K747 | J78 | S |
| 3-1110 | —(CH$_2$)$_2$— | —C(=O)— | K748 | J78 | S |
| 3-1111 | —(CH$_2$)$_2$— | —C(=O)— | K749 | J78 | S |
| 3-1112 | —(CH$_2$)$_2$— | —C(=O)— | K750 | J78 | S |
| 3-1113 | —(CH$_2$)$_2$— | —C(=O)— | K751 | J78 | S |
| 3-1114 | —(CH$_2$)$_2$— | —C(=O)— | K752 | J78 | S |
| 3-1115 | —(CH$_2$)$_2$— | —C(=O)— | K753 | J78 | S |
| 3-1116 | —(CH$_2$)$_2$— | —C(=O)— | K754 | J78 | S |
| 3-1117 | —(CH$_2$)$_2$— | —C(=O)— | K755 | J78 | S |
| 3-1118 | —(CH$_2$)$_2$— | —C(=O)— | K756 | J78 | S |
| 3-1119 | —(CH$_2$)$_2$— | —C(=O)— | K757 | J78 | S |
| 3-1120 | —(CH$_2$)$_2$— | —C(=O)— | K314 | J129 | S |

TABLE 138

| Compound No. | -A¹- | -A²- | -G¹-A³-A⁴-G² | -A⁵-R² | X |
|---|---|---|---|---|---|
| 3-1121 | —(CH$_2$)$_2$— | —C(=O)— | K315 | J129 | S |
| 3-1122 | —(CH$_2$)$_2$— | —C(=O)— | K316 | J129 | S |
| 3-1123 | —(CH$_2$)$_2$— | —C(=O)— | K317 | J129 | S |
| 3-1124 | —(CH$_2$)$_2$— | —C(=O)— | K318 | J129 | S |
| 3-1125 | —(CH$_2$)$_2$— | —C(=O)— | K320 | J129 | S |
| 3-1126 | —(CH$_2$)$_2$— | —C(=O)— | K321 | J129 | S |
| 3-1127 | —(CH$_2$)$_2$— | —C(=O)— | K322 | J129 | S |
| 3-1128 | —(CH$_2$)$_2$— | —C(=O)— | K323 | J129 | S |
| 3-1129 | —(CH$_2$)$_2$— | —C(=O)— | K324 | J129 | S |
| 3-1130 | —(CH$_2$)$_2$— | —C(=O)— | K325 | J129 | S |
| 3-1131 | —(CH$_2$)$_2$— | —C(=O)— | K326 | J129 | S |
| 3-1132 | —(CH$_2$)$_2$— | —C(=O)— | K327 | J129 | S |
| 3-1133 | —(CH$_2$)$_2$— | —C(=O)— | K328 | J129 | S |
| 3-1134 | —(CH$_2$)$_2$— | —C(=O)— | K329 | J129 | S |
| 3-1135 | —(CH$_2$)$_2$— | —C(=O)— | K330 | J129 | S |
| 3-1136 | —(CH$_2$)$_2$— | —C(=O)— | K331 | J129 | S |
| 3-1137 | —(CH$_2$)$_2$— | —C(=O)— | K332 | J129 | S |
| 3-1138 | —(CH$_2$)$_2$— | —C(=O)— | K333 | J129 | S |
| 3-1139 | —(CH$_2$)$_2$— | —C(=O)— | K334 | J129 | S |
| 3-1140 | —(CH$_2$)$_2$— | —C(=O)— | K335 | J129 | S |
| 3-1141 | —(CH$_2$)$_2$— | —C(=O)— | K336 | J129 | S |
| 3-1142 | —(CH$_2$)$_2$— | —C(=O)— | K337 | J129 | S |
| 3-1143 | —(CH$_2$)$_2$— | —C(=O)— | K338 | J129 | S |
| 3-1144 | —(CH$_2$)$_2$— | —C(=O)— | K339 | J129 | S |
| 3-1145 | —(CH$_2$)$_2$— | —C(=O)— | K340 | J129 | S |
| 3-1146 | —(CH$_2$)$_2$— | —C(=O)— | K341 | J129 | S |
| 3-1147 | —(CH$_2$)$_2$— | —C(=O)— | K342 | J129 | S |
| 3-1148 | —(CH$_2$)$_2$— | —C(=O)— | K343 | J129 | S |
| 3-1149 | —(CH$_2$)$_2$— | —C(=O)— | K344 | J129 | S |
| 3-1150 | —(CH$_2$)$_2$— | —C(=O)— | K345 | J129 | S |
| 3-1151 | —(CH$_2$)$_2$— | —C(=O)— | K346 | J129 | S |
| 3-1152 | —(CH$_2$)$_2$— | —C(=O)— | K347 | J129 | S |

TABLE 139

| Compound No. | -A$^1$- | -A$^2$- | -G$^1$-A$^3$-A$^4$-G$^2$ | -A$^5$-R$^2$ | X |
|---|---|---|---|---|---|
| 3-1153 | —(CH$_2$)$_2$— | —C(=O)— | K348 | J129 | S |
| 3-1154 | —(CH$_2$)$_2$— | —C(=O)— | K349 | J129 | S |
| 3-1155 | —(CH$_2$)$_2$— | —C(=O)— | K350 | J129 | S |
| 3-1156 | —(CH$_2$)$_2$— | —C(=O)— | K351 | J129 | S |
| 3-1157 | —(CH$_2$)$_2$— | —C(=O)— | K352 | J129 | S |
| 3-1158 | —(CH$_2$)$_2$— | —C(=O)— | K353 | J129 | S |
| 3-1159 | —(CH$_2$)$_2$— | —C(=O)— | K355 | J129 | S |
| 3-1160 | —(CH$_2$)$_2$— | —C(=O)— | K356 | J129 | S |
| 3-1161 | —(CH$_2$)$_2$— | —C(=O)— | K357 | J129 | S |
| 3-1162 | —(CH$_2$)$_2$— | —C(=O)— | K358 | J129 | S |
| 3-1163 | —(CH$_2$)$_2$— | —C(=O)— | K359 | J129 | S |
| 3-1164 | —(CH$_2$)$_2$— | —C(=O)— | K360 | J129 | S |
| 3-1165 | —(CH$_2$)$_2$— | —C(=O)— | K361 | J129 | S |
| 3-1166 | —(CH$_2$)$_2$— | —C(=O)— | K362 | J129 | S |
| 3-1167 | —(CH$_2$)$_2$— | —C(=O)— | K363 | J129 | S |
| 3-1168 | —(CH$_2$)$_2$— | —C(=O)— | K364 | J129 | S |
| 3-1169 | —(CH$_2$)$_2$— | —C(=O)— | K365 | J129 | S |
| 3-1170 | —(CH$_2$)$_2$— | —C(=O)— | K366 | J129 | S |
| 3-1171 | —(CH$_2$)$_2$— | —C(=O)— | K367 | J129 | S |
| 3-1172 | —(CH$_2$)$_2$— | —C(=O)— | K368 | J129 | S |
| 3-1173 | —(CH$_2$)$_2$— | —C(=O)— | K369 | J129 | S |
| 3-1174 | —(CH$_2$)$_2$— | —C(=O)— | K370 | J129 | S |
| 3-1175 | —(CH$_2$)$_2$— | —C(=O)— | K371 | J129 | S |
| 3-1176 | —(CH$_2$)$_2$— | —C(=O)— | K372 | J129 | S |
| 3-1177 | —(CH$_2$)$_2$— | —C(=O)— | K373 | J129 | S |
| 3-1178 | —(CH$_2$)$_2$— | —C(=O)— | K374 | J129 | S |
| 3-1179 | —(CH$_2$)$_2$— | —C(=O)— | K375 | J129 | S |
| 3-1180 | —(CH$_2$)$_2$— | —C(=O)— | K376 | J129 | S |
| 3-1181 | —(CH$_2$)$_2$— | —C(=O)— | K377 | J129 | S |
| 3-1182 | —(CH$_2$)$_2$— | —C(=O)— | K378 | J129 | S |
| 3-1183 | —(CH$_2$)$_2$— | —C(=O)— | K379 | J129 | S |
| 3-1184 | —(CH$_2$)$_2$— | —C(=O)— | K380 | J129 | S |

TABLE 140

| Compound No. | -A$^1$- | -A$^2$- | -G$^1$-A$^3$-A$^4$-G$^2$ | -A$^5$-R$^2$ | X |
|---|---|---|---|---|---|
| 3-1185 | —(CH$_2$)$_2$— | —C(=O)— | K381 | J130 | S |
| 3-1186 | —(CH$_2$)$_2$— | —C(=O)— | K383 | J130 | S |
| 3-1187 | —(CH$_2$)$_2$— | —C(=O)— | K384 | J130 | S |
| 3-1188 | —(CH$_2$)$_2$— | —C(=O)— | K385 | J130 | S |
| 3-1189 | —(CH$_2$)$_2$— | —C(=O)— | K386 | J130 | S |
| 3-1190 | —(CH$_2$)$_2$— | —C(=O)— | K387 | J130 | S |
| 3-1191 | —(CH$_2$)$_2$— | —C(=O)— | K388 | J130 | S |
| 3-1192 | —(CH$_2$)$_2$— | —C(=O)— | K389 | J130 | S |
| 3-1193 | —(CH$_2$)$_2$— | —C(=O)— | K390 | J130 | S |
| 3-1194 | —(CH$_2$)$_2$— | —C(=O)— | K391 | J130 | S |
| 3-1195 | —(CH$_2$)$_2$— | —C(=O)— | K392 | J130 | S |
| 3-1196 | —(CH$_2$)$_2$— | —C(=O)— | K393 | J130 | S |
| 3-1197 | —(CH$_2$)$_2$— | —C(=O)— | K394 | J130 | S |
| 3-1198 | —(CH$_2$)$_2$— | —C(=O)— | K395 | J130 | S |
| 3-1199 | —(CH$_2$)$_2$— | —C(=O)— | K396 | J130 | S |
| 3-1200 | —(CH$_2$)$_2$— | —C(=O)— | K398 | J130 | S |
| 3-1201 | —(CH$_2$)$_2$— | —C(=O)— | K405 | J130 | S |
| 3-1202 | —(CH$_2$)$_2$— | —C(=O)— | K406 | J130 | S |
| 3-1203 | —(CH$_2$)$_2$— | —C(=O)— | K407 | J130 | S |
| 3-1204 | —(CH$_2$)$_2$— | —C(=O)— | K408 | J130 | S |
| 3-1205 | —(CH$_2$)$_2$— | —C(=O)— | K409 | J130 | S |
| 3-1206 | —(CH$_2$)$_2$— | —C(=O)— | K410 | J130 | S |
| 3-1207 | —(CH$_2$)$_2$— | —C(=O)— | K411 | J130 | S |
| 3-1208 | —(CH$_2$)$_2$— | —C(=O)— | K412 | J130 | S |
| 3-1209 | —(CH$_2$)$_2$— | —C(=O)— | K413 | J130 | S |
| 3-1210 | —(CH$_2$)$_2$— | —C(=O)— | K414 | J130 | S |
| 3-1211 | —(CH$_2$)$_2$— | —C(=O)— | K415 | J130 | S |
| 3-1212 | —(CH$_2$)$_2$— | —C(=O)— | K416 | J130 | S |
| 3-1213 | —(CH$_2$)$_2$— | —C(=O)— | K417 | J130 | S |
| 3-1214 | —(CH$_2$)$_2$— | —C(=O)— | K419 | J130 | S |
| 3-1215 | —(CH$_2$)$_2$— | —C(=O)— | K420 | J130 | S |
| 3-1216 | —(CH$_2$)$_2$— | —C(=O)— | K421 | J130 | S |

TABLE 141

| Compound No. | -A$^1$- | -A$^2$- | -G$^1$-A$^3$-A$^4$-G$^2$ | -A$^5$-R$^2$ | X |
|---|---|---|---|---|---|
| 3-1217 | —(CH$_2$)$_2$— | —C(=O)— | K726 | J130 | S |
| 3-1218 | —(CH$_2$)$_2$— | —C(=O)— | K727 | J130 | S |
| 3-1219 | —(CH$_2$)$_2$— | —C(=O)— | K728 | J130 | S |
| 3-1220 | —(CH$_2$)$_2$— | —C(=O)— | K729 | J130 | S |
| 3-1221 | —(CH$_2$)$_2$— | —C(=O)— | K730 | J130 | S |
| 3-1222 | —(CH$_2$)$_2$— | —C(=O)— | K731 | J130 | S |
| 3-1223 | —(CH$_2$)$_2$— | —C(=O)— | K732 | J130 | S |
| 3-1224 | —(CH$_2$)$_2$— | —C(=O)— | K733 | J130 | S |
| 3-1225 | —(CH$_2$)$_2$— | —C(=O)— | K734 | J130 | S |
| 3-1226 | —(CH$_2$)$_2$— | —C(=O)— | K735 | J130 | S |
| 3-1227 | —(CH$_2$)$_2$— | —C(=O)— | K736 | J130 | S |
| 3-1228 | —(CH$_2$)$_2$— | —C(=O)— | K737 | J130 | S |
| 3-1229 | —(CH$_2$)$_2$— | —C(=O)— | K738 | J130 | S |
| 3-1230 | —(CH$_2$)$_2$— | —C(=O)— | K739 | J130 | S |
| 3-1231 | —(CH$_2$)$_2$— | —C(=O)— | K740 | J130 | S |
| 3-1232 | —(CH$_2$)$_2$— | —C(=O)— | K741 | J130 | S |
| 3-1233 | —(CH$_2$)$_2$— | —C(=O)— | K742 | J130 | S |
| 3-1234 | —(CH$_2$)$_2$— | —C(=O)— | K743 | J130 | S |
| 3-1235 | —(CH$_2$)$_2$— | —C(=O)— | K744 | J130 | S |
| 3-1236 | —(CH$_2$)$_2$— | —C(=O)— | K745 | J130 | S |
| 3-1237 | —(CH$_2$)$_2$— | —C(=O)— | K746 | J130 | S |
| 3-1238 | —(CH$_2$)$_2$— | —C(=O)— | K747 | J130 | S |
| 3-1239 | —(CH$_2$)$_2$— | —C(=O)— | K748 | J130 | S |
| 3-1240 | —(CH$_2$)$_2$— | —C(=O)— | K749 | J130 | S |
| 3-1241 | —(CH$_2$)$_2$— | —C(=O)— | K750 | J130 | S |
| 3-1242 | —(CH$_2$)$_2$— | —C(=O)— | K751 | J130 | S |
| 3-1243 | —(CH$_2$)$_2$— | —C(=O)— | K752 | J130 | S |
| 3-1244 | —(CH$_2$)$_2$— | —C(=O)— | K753 | J130 | S |
| 3-1245 | —(CH$_2$)$_2$— | —C(=O)— | K754 | J130 | S |
| 3-1246 | —(CH$_2$)$_2$— | —C(=O)— | K755 | J130 | S |
| 3-1247 | —(CH$_2$)$_2$— | —C(=O)— | K756 | J130 | S |
| 3-1248 | —(CH$_2$)$_2$— | —C(=O)— | K757 | J130 | S |

TABLE 142

| Compound No. | -A$^1$- | -A$^2$- | -G$^1$-A$^3$-A$^4$-G$^2$ | -A$^5$-R$^2$ | X |
|---|---|---|---|---|---|
| 3-1249 | —(CH$_2$)$_2$— | —C(=O)— | K314 | J130 | S |
| 3-1250 | —(CH$_2$)$_2$— | —C(=O)— | K316 | J130 | S |
| 3-1251 | —(CH$_2$)$_2$— | —C(=O)— | K317 | J130 | S |
| 3-1252 | —(CH$_2$)$_2$— | —C(=O)— | K318 | J130 | S |
| 3-1253 | —(CH$_2$)$_2$— | —C(=O)— | K319 | J130 | S |
| 3-1254 | —(CH$_2$)$_2$— | —C(=O)— | K320 | J130 | S |
| 3-1255 | —(CH$_2$)$_2$— | —C(=O)— | K321 | J130 | S |
| 3-1256 | —(CH$_2$)$_2$— | —C(=O)— | K322 | J130 | S |
| 3-1257 | —(CH$_2$)$_2$— | —C(=O)— | K323 | J130 | S |
| 3-1258 | —(CH$_2$)$_2$— | —C(=O)— | K324 | J130 | S |
| 3-1259 | —(CH$_2$)$_2$— | —C(=O)— | K326 | J130 | S |
| 3-1260 | —(CH$_2$)$_2$— | —C(=O)— | K327 | J130 | S |
| 3-1261 | —(CH$_2$)$_2$— | —C(=O)— | K328 | J130 | S |
| 3-1262 | —(CH$_2$)$_2$— | —C(=O)— | K329 | J130 | S |
| 3-1263 | —(CH$_2$)$_2$— | —C(=O)— | K330 | J130 | S |
| 3-1264 | —(CH$_2$)$_2$— | —C(=O)— | K331 | J130 | S |
| 3-1265 | —(CH$_2$)$_2$— | —C(=O)— | K332 | J130 | S |
| 3-1266 | —(CH$_2$)$_2$— | —C(=O)— | K333 | J130 | S |
| 3-1267 | —(CH$_2$)$_2$— | —C(=O)— | K334 | J130 | S |
| 3-1268 | —(CH$_2$)$_2$— | —C(=O)— | K335 | J130 | S |
| 3-1269 | —(CH$_2$)$_2$— | —C(=O)— | K336 | J130 | S |
| 3-1270 | —(CH$_2$)$_2$— | —C(=O)— | K338 | J130 | S |
| 3-1271 | —(CH$_2$)$_2$— | —C(=O)— | K339 | J130 | S |
| 3-1272 | —(CH$_2$)$_2$— | —C(=O)— | K340 | J130 | S |
| 3-1273 | —(CH$_2$)$_2$— | —C(=O)— | K341 | J130 | S |
| 3-1274 | —(CH$_2$)$_2$— | —C(=O)— | K342 | J130 | S |
| 3-1275 | —(CH$_2$)$_2$— | —C(=O)— | K343 | J130 | S |
| 3-1276 | —(CH$_2$)$_2$— | —C(=O)— | K344 | J130 | S |
| 3-1277 | —(CH$_2$)$_2$— | —C(=O)— | K345 | J130 | S |
| 3-1278 | —(CH$_2$)$_2$— | —C(=O)— | K346 | J130 | S |
| 3-1279 | —(CH$_2$)$_2$— | —C(=O)— | K347 | J130 | S |
| 3-1280 | —(CH$_2$)$_2$— | —C(=O)— | K348 | J130 | S |

TABLE 143

| Compound No. | -A¹- | -A²- | -G¹-A³-A⁴-G² | -A⁵-R² | X |
|---|---|---|---|---|---|
| 3-1281 | —(CH$_2$)$_2$— | —C(=O)— | K349 | J130 | S |
| 3-1282 | —(CH$_2$)$_2$— | —C(=O)— | K350 | J130 | S |
| 3-1283 | —(CH$_2$)$_2$— | —C(=O)— | K351 | J130 | S |
| 3-1284 | —(CH$_2$)$_2$— | —C(=O)— | K352 | J130 | S |
| 3-1285 | —(CH$_2$)$_2$— | —C(=O)— | K353 | J130 | S |
| 3-1286 | —(CH$_2$)$_2$— | —C(=O)— | K354 | J130 | S |
| 3-1287 | —(CH$_2$)$_2$— | —C(=O)— | K356 | J130 | S |
| 3-1288 | —(CH$_2$)$_2$— | —C(=O)— | K357 | J130 | S |
| 3-1289 | —(CH$_2$)$_2$— | —C(=O)— | K358 | J130 | S |
| 3-1290 | —(CH$_2$)$_2$— | —C(=O)— | K359 | J130 | S |
| 3-1291 | —(CH$_2$)$_2$— | —C(=O)— | K360 | J130 | S |
| 3-1292 | —(CH$_2$)$_2$— | —C(=O)— | K361 | J130 | S |
| 3-1293 | —(CH$_2$)$_2$— | —C(=O)— | K362 | J130 | S |
| 3-1294 | —(CH$_2$)$_2$— | —C(=O)— | K363 | J130 | S |
| 3-1295 | —(CH$_2$)$_2$— | —C(=O)— | K364 | J130 | S |
| 3-1296 | —(CH$_2$)$_2$— | —C(=O)— | K365 | J130 | S |
| 3-1297 | —(CH$_2$)$_2$— | —C(=O)— | K366 | J130 | S |
| 3-1298 | —(CH$_2$)$_2$— | —C(=O)— | K367 | J130 | S |
| 3-1299 | —(CH$_2$)$_2$— | —C(=O)— | K368 | J130 | S |
| 3-1300 | —(CH$_2$)$_2$— | —C(=O)— | K369 | J130 | S |
| 3-1301 | —(CH$_2$)$_2$— | —C(=O)— | K370 | J130 | S |
| 3-1302 | —(CH$_2$)$_2$— | —C(=O)— | K371 | J130 | S |
| 3-1303 | —(CH$_2$)$_2$— | —C(=O)— | K372 | J130 | S |
| 3-1304 | —(CH$_2$)$_2$— | —C(=O)— | K373 | J130 | S |
| 3-1305 | —(CH$_2$)$_2$— | —C(=O)— | K374 | J130 | S |
| 3-1306 | —(CH$_2$)$_2$— | —C(=O)— | K375 | J130 | S |
| 3-1307 | —(CH$_2$)$_2$— | —C(=O)— | K376 | J130 | S |
| 3-1308 | —(CH$_2$)$_2$— | —C(=O)— | K377 | J130 | S |
| 3-1309 | —(CH$_2$)$_2$— | —C(=O)— | K378 | J130 | S |
| 3-1310 | —(CH$_2$)$_2$— | —C(=O)— | K379 | J130 | S |
| 3-1311 | —(CH$_2$)$_2$— | —C(=O)— | K380 | J130 | S |
| 3-1312 | —(CH$_2$)$_2$— | —C(=O)— | K381 | J138 | S |

TABLE 144

| Compound No. | -A¹- | -A²- | -G¹-A³-A⁴-G² | -A⁵-R² | X |
|---|---|---|---|---|---|
| 3-1313 | —(CH$_2$)$_2$— | —C(=O)— | K382 | J138 | S |
| 3-1314 | —(CH$_2$)$_2$— | —C(=O)— | K383 | J138 | S |
| 3-1315 | —(CH$_2$)$_2$— | —C(=O)— | K384 | J138 | S |
| 3-1316 | —(CH$_2$)$_2$— | —C(=O)— | K385 | J138 | S |
| 3-1317 | —(CH$_2$)$_2$— | —C(=O)— | K386 | J138 | S |
| 3-1318 | —(CH$_2$)$_2$— | —C(=O)— | K388 | J138 | S |
| 3-1319 | —(CH$_2$)$_2$— | —C(=O)— | K389 | J138 | S |
| 3-1320 | —(CH$_2$)$_2$— | —C(=O)— | K390 | J138 | S |
| 3-1321 | —(CH$_2$)$_2$— | —C(=O)— | K391 | J138 | S |
| 3-1322 | —(CH$_2$)$_2$— | —C(=O)— | K392 | J138 | S |
| 3-1323 | —(CH$_2$)$_2$— | —C(=O)— | K393 | J138 | S |
| 3-1324 | —(CH$_2$)$_2$— | —C(=O)— | K394 | J138 | S |
| 3-1325 | —(CH$_2$)$_2$— | —C(=O)— | K395 | J138 | S |
| 3-1326 | —(CH$_2$)$_2$— | —C(=O)— | K396 | J138 | S |
| 3-1327 | —(CH$_2$)$_2$— | —C(=O)— | K397 | J138 | S |
| 3-1328 | —(CH$_2$)$_2$— | —C(=O)— | K398 | J138 | S |
| 3-1329 | —(CH$_2$)$_2$— | —C(=O)— | K405 | J138 | S |
| 3-1330 | —(CH$_2$)$_2$— | —C(=O)— | K406 | J138 | S |
| 3-1331 | —(CH$_2$)$_2$— | —C(=O)— | K407 | J138 | S |
| 3-1332 | —(CH$_2$)$_2$— | —C(=O)— | K408 | J138 | S |
| 3-1333 | —(CH$_2$)$_2$— | —C(=O)— | K409 | J138 | S |
| 3-1334 | —(CH$_2$)$_2$— | —C(=O)— | K410 | J138 | S |
| 3-1335 | —(CH$_2$)$_2$— | —C(=O)— | K411 | J138 | S |
| 3-1336 | —(CH$_2$)$_2$— | —C(=O)— | K412 | J138 | S |
| 3-1337 | —(CH$_2$)$_2$— | —C(=O)— | K413 | J138 | S |
| 3-1338 | —(CH$_2$)$_2$— | —C(=O)— | K414 | J138 | S |
| 3-1339 | —(CH$_2$)$_2$— | —C(=O)— | K415 | J138 | S |
| 3-1340 | —(CH$_2$)$_2$— | —C(=O)— | K416 | J138 | S |
| 3-1341 | —(CH$_2$)$_2$— | —C(=O)— | K417 | J138 | S |
| 3-1342 | —(CH$_2$)$_2$— | —C(=O)— | K419 | J138 | S |
| 3-1343 | —(CH$_2$)$_2$— | —C(=O)— | K420 | J138 | S |
| 3-1344 | —(CH$_2$)$_2$— | —C(=O)— | K421 | J138 | S |

TABLE 145

| Compound No. | -A¹- | -A²- | -G¹-A³-A⁴-G² | -A⁵-R² | X |
|---|---|---|---|---|---|
| 3-1345 | —(CH$_2$)$_2$— | —C(=O)— | K726 | J138 | S |
| 3-1346 | —(CH$_2$)$_2$— | —C(=O)— | K727 | J138 | S |
| 3-1347 | —(CH$_2$)$_2$— | —C(=O)— | K728 | J138 | S |
| 3-1348 | —(CH$_2$)$_2$— | —C(=O)— | K729 | J138 | S |
| 3-1349 | —(CH$_2$)$_2$— | —C(=O)— | K730 | J138 | S |
| 3-1350 | —(CH$_2$)$_2$— | —C(=O)— | K731 | J138 | S |
| 3-1351 | —(CH$_2$)$_2$— | —C(=O)— | K732 | J138 | S |
| 3-1352 | —(CH$_2$)$_2$— | —C(=O)— | K733 | J138 | S |
| 3-1353 | —(CH$_2$)$_2$— | —C(=O)— | K734 | J138 | S |
| 3-1354 | —(CH$_2$)$_2$— | —C(=O)— | K735 | J138 | S |
| 3-1355 | —(CH$_2$)$_2$— | —C(=O)— | K736 | J138 | S |
| 3-1356 | —(CH$_2$)$_2$— | —C(=O)— | K737 | J138 | S |
| 3-1357 | —(CH$_2$)$_2$— | —C(=O)— | K738 | J138 | S |
| 3-1358 | —(CH$_2$)$_2$— | —C(=O)— | K739 | J138 | S |
| 3-1359 | —(CH$_2$)$_2$— | —C(=O)— | K740 | J138 | S |
| 3-1360 | —(CH$_2$)$_2$— | —C(=O)— | K741 | J138 | S |
| 3-1361 | —(CH$_2$)$_2$— | —C(=O)— | K742 | J138 | S |
| 3-1362 | —(CH$_2$)$_2$— | —C(=O)— | K743 | J138 | S |
| 3-1363 | —(CH$_2$)$_2$— | —C(=O)— | K744 | J138 | S |
| 3-1364 | —(CH$_2$)$_2$— | —C(=O)— | K745 | J138 | S |
| 3-1365 | —(CH$_2$)$_2$— | —C(=O)— | K746 | J138 | S |
| 3-1366 | —(CH$_2$)$_2$— | —C(=O)— | K747 | J138 | S |
| 3-1367 | —(CH$_2$)$_2$— | —C(=O)— | K748 | J138 | S |
| 3-1368 | —(CH$_2$)$_2$— | —C(=O)— | K749 | J138 | S |
| 3-1369 | —(CH$_2$)$_2$— | —C(=O)— | K750 | J138 | S |
| 3-1370 | —(CH$_2$)$_2$— | —C(=O)— | K751 | J138 | S |
| 3-1371 | —(CH$_2$)$_2$— | —C(=O)— | K752 | J138 | S |
| 3-1372 | —(CH$_2$)$_2$— | —C(=O)— | K753 | J138 | S |
| 3-1373 | —(CH$_2$)$_2$— | —C(=O)— | K754 | J138 | S |
| 3-1374 | —(CH$_2$)$_2$— | —C(=O)— | K755 | J138 | S |
| 3-1375 | —(CH$_2$)$_2$— | —C(=O)— | K756 | J138 | S |
| 3-1376 | —(CH$_2$)$_2$— | —C(=O)— | K757 | J138 | S |

TABLE 146

| Compound No. | -A¹- | -A²- | -G¹-A³-A⁴-G² | -A⁵-R² | X |
|---|---|---|---|---|---|
| 3-1377 | —(CH$_2$)$_2$— | —C(=O)— | K314 | J1 | S |
| 3-1378 | —(CH$_2$)$_2$— | —C(=O)— | K315 | J1 | S |
| 3-1379 | —(CH$_2$)$_2$— | —C(=O)— | K316 | J2 | S |
| 3-1380 | —(CH$_2$)$_2$— | —C(=O)— | K317 | J2 | S |
| 3-1381 | —(CH$_2$)$_2$— | —C(=O)— | K318 | J4 | S |
| 3-1382 | —(CH$_2$)$_2$— | —C(=O)— | K319 | J4 | S |
| 3-1383 | —(CH$_2$)$_2$— | —C(=O)— | K320 | J10 | S |
| 3-1384 | —(CH$_2$)$_2$— | —C(=O)— | K321 | J10 | S |
| 3-1385 | —(CH$_2$)$_2$— | —C(=O)— | K322 | J19 | S |
| 3-1386 | —(CH$_2$)$_2$— | —C(=O)— | K323 | J19 | S |
| 3-1387 | —(CH$_2$)$_2$— | —C(=O)— | K324 | J14 | S |
| 3-1388 | —(CH$_2$)$_2$— | —C(=O)— | K325 | J14 | S |
| 3-1389 | —(CH$_2$)$_2$— | —C(=O)— | K326 | J22 | S |
| 3-1390 | —(CH$_2$)$_2$— | —C(=O)— | K327 | J22 | S |
| 3-1391 | —(CH$_2$)$_2$— | —C(=O)— | K328 | J72 | S |
| 3-1392 | —(CH$_2$)$_2$— | —C(=O)— | K329 | J72 | S |
| 3-1393 | —(CH$_2$)$_2$— | —C(=O)— | K330 | J74 | S |
| 3-1394 | —(CH$_2$)$_2$— | —C(=O)— | K331 | J74 | S |
| 3-1395 | —(CH$_2$)$_2$— | —C(=O)— | K332 | J75 | S |
| 3-1396 | —(CH$_2$)$_2$— | —C(=O)— | K333 | J75 | S |
| 3-1397 | —(CH$_2$)$_2$— | —C(=O)— | K334 | J77 | S |
| 3-1398 | —(CH$_2$)$_2$— | —C(=O)— | K335 | J77 | S |
| 3-1399 | —(CH$_2$)$_2$— | —C(=O)— | K336 | J96 | S |
| 3-1400 | —(CH$_2$)$_2$— | —C(=O)— | K337 | J96 | S |
| 3-1401 | —(CH$_2$)$_2$— | —C(=O)— | K338 | J174 | S |
| 3-1402 | —(CH$_2$)$_2$— | —C(=O)— | K339 | J174 | S |
| 3-1403 | —(CH$_2$)$_2$— | —C(=O)— | K340 | J176 | S |
| 3-1404 | —(CH$_2$)$_2$— | —C(=O)— | K341 | J176 | S |
| 3-1405 | —(CH$_2$)$_2$— | —C(=O)— | K342 | J177 | S |
| 3-1406 | —(CH$_2$)$_2$— | —C(=O)— | K343 | J177 | S |
| 3-1407 | —(CH$_2$)$_2$— | —C(=O)— | K344 | J189 | S |
| 3-1408 | —(CH$_2$)$_2$— | —C(=O)— | K345 | J189 | S |

TABLE 147

| Compound No. | -A¹- | -A²- | -G¹-A³-A⁴-G² | -A⁵-R² | X |
|---|---|---|---|---|---|
| 3-1409 | —(CH$_2$)$_2$— | —C(=O)— | K346 | J182 | S |
| 3-1410 | —(CH$_2$)$_2$— | —C(=O)— | K347 | J182 | S |
| 3-1411 | —(CH$_2$)$_2$— | —C(=O)— | K348 | J183 | S |
| 3-1412 | —(CH$_2$)$_2$— | —C(=O)— | K349 | J183 | S |
| 3-1413 | —(CH$_2$)$_2$— | —C(=O)— | K350 | J1 | S |
| 3-1414 | —(CH$_2$)$_2$— | —C(=O)— | K351 | J1 | S |
| 3-1415 | —(CH$_2$)$_2$— | —C(=O)— | K352 | J2 | S |
| 3-1416 | —(CH$_2$)$_2$— | —C(=O)— | K353 | J2 | S |
| 3-1417 | —(CH$_2$)$_2$— | —C(=O)— | K354 | J4 | S |
| 3-1418 | —(CH$_2$)$_2$— | —C(=O)— | K355 | J4 | S |
| 3-1419 | —(CH$_2$)$_2$— | —C(=O)— | K356 | J10 | S |
| 3-1420 | —(CH$_2$)$_2$— | —C(=O)— | K357 | J10 | S |
| 3-1421 | —(CH$_2$)$_2$— | —C(=O)— | K359 | J19 | S |
| 3-1422 | —(CH$_2$)$_2$— | —C(=O)— | K360 | J14 | S |
| 3-1423 | —(CH$_2$)$_2$— | —C(=O)— | K361 | J14 | S |
| 3-1424 | —(CH$_2$)$_2$— | —C(=O)— | K362 | J22 | S |
| 3-1425 | —(CH$_2$)$_2$— | —C(=O)— | K363 | J22 | S |
| 3-1426 | —(CH$_2$)$_2$— | —C(=O)— | K364 | J72 | S |
| 3-1427 | —(CH$_2$)$_2$— | —C(=O)— | K365 | J72 | S |
| 3-1428 | —(CH$_2$)$_2$— | —C(=O)— | K366 | J74 | S |
| 3-1429 | —(CH$_2$)$_2$— | —C(=O)— | K367 | J74 | S |
| 3-1430 | —(CH$_2$)$_2$— | —C(=O)— | K368 | J75 | S |
| 3-1431 | —(CH$_2$)$_2$— | —C(=O)— | K369 | J75 | S |
| 3-1432 | —(CH$_2$)$_2$— | —C(=O)— | K370 | J77 | S |
| 3-1433 | —(CH$_2$)$_2$— | —C(=O)— | K371 | J77 | S |
| 3-1434 | —(CH$_2$)$_2$— | —C(=O)— | K372 | J96 | S |
| 3-1435 | —(CH$_2$)$_2$— | —C(=O)— | K373 | J96 | S |
| 3-1436 | —(CH$_2$)$_2$— | —C(=O)— | K374 | J174 | S |
| 3-1437 | —(CH$_2$)$_2$— | —C(=O)— | K375 | J174 | S |
| 3-1438 | —(CH$_2$)$_2$— | —C(=O)— | K376 | J176 | S |
| 3-1439 | —(CH$_2$)$_2$— | —C(=O)— | K377 | J176 | S |
| 3-1440 | —(CH$_2$)$_2$— | —C(=O)— | K378 | J177 | S |

TABLE 148

| Compound No. | -A¹- | -A²- | -G¹-A³-A⁴-G² | -A⁵-R² | X |
|---|---|---|---|---|---|
| 3-1441 | —(CH$_2$)$_2$— | —C(=O)— | K379 | J177 | S |
| 3-1442 | —(CH$_2$)$_2$— | —C(=O)— | K380 | J189 | S |
| 3-1443 | —(CH$_2$)$_2$— | —C(=O)— | K381 | J189 | S |
| 3-1444 | —(CH$_2$)$_2$— | —C(=O)— | K382 | J182 | S |
| 3-1445 | —(CH$_2$)$_2$— | —C(=O)— | K383 | J182 | S |
| 3-1446 | —(CH$_2$)$_2$— | —C(=O)— | K384 | J183 | S |
| 3-1447 | —(CH$_2$)$_2$— | —C(=O)— | K385 | J183 | S |
| 3-1448 | —(CH$_2$)$_2$— | —C(=O)— | K386 | J191 | S |
| 3-1449 | —(CH$_2$)$_2$— | —C(=O)— | K387 | J191 | S |
| 3-1450 | —(CH$_2$)$_2$— | —C(=O)— | K388 | J192 | S |
| 3-1451 | —(CH$_2$)$_2$— | —C(=O)— | K389 | J192 | S |
| 3-1452 | —(CH$_2$)$_2$— | —C(=O)— | K390 | J193 | S |
| 3-1453 | —(CH$_2$)$_2$— | —C(=O)— | K391 | J193 | S |
| 3-1454 | —(CH$_2$)$_2$— | —C(=O)— | K392 | J194 | S |
| 3-1455 | —(CH$_2$)$_2$— | —C(=O)— | K393 | J194 | S |
| 3-1456 | —(CH$_2$)$_2$— | —C(=O)— | K394 | J197 | S |
| 3-1457 | —(CH$_2$)$_2$— | —C(=O)— | K395 | J197 | S |
| 3-1458 | —(CH$_2$)$_2$— | —C(=O)— | K396 | J140 | S |
| 3-1459 | —(CH$_2$)$_2$— | —C(=O)— | K397 | J140 | S |
| 3-1460 | —(CH$_2$)$_2$— | —C(=O)— | K398 | J140 | S |
| 3-1461 | —(CH$_2$)$_2$— | —C(=O)— | K405 | J140 | S |
| 3-1462 | —(CH$_2$)$_2$— | —C(=O)— | K406 | J140 | S |
| 3-1463 | —(CH$_2$)$_2$— | —C(=O)— | K407 | J140 | S |
| 3-1464 | —(CH$_2$)$_2$— | —C(=O)— | K408 | J140 | S |
| 3-1465 | —(CH$_2$)$_2$— | —C(=O)— | K409 | J140 | S |
| 3-1466 | —(CH$_2$)$_2$— | —C(=O)— | K410 | J140 | S |
| 3-1467 | —(CH$_2$)$_2$— | —C(=O)— | K411 | J140 | S |
| 3-1468 | —(CH$_2$)$_2$— | —C(=O)— | K412 | J140 | S |
| 3-1469 | —(CH$_2$)$_2$— | —C(=O)— | K413 | J140 | S |
| 3-1470 | —(CH$_2$)$_2$— | —C(=O)— | K414 | J140 | S |
| 3-1471 | —(CH$_2$)$_2$— | —C(=O)— | K415 | J140 | S |
| 3-1472 | —(CH$_2$)$_2$— | —C(=O)— | K416 | J140 | S |

TABLE 149

| Compound No. | -A¹- | -A²- | -G¹-A³-A⁴-G² | -A⁵-R² | X |
|---|---|---|---|---|---|
| 3-1473 | —(CH$_2$)$_2$— | —C(=O)— | K417 | J140 | S |
| 3-1474 | —(CH$_2$)$_2$— | —C(=O)— | K418 | J140 | S |
| 3-1475 | —(CH$_2$)$_2$— | —C(=O)— | K419 | J140 | S |
| 3-1476 | —(CH$_2$)$_2$— | —C(=O)— | K420 | J140 | S |
| 3-1477 | —(CH$_2$)$_2$— | —C(=O)— | K421 | J140 | S |
| 3-1478 | —(CH$_2$)$_2$— | —C(=O)— | K726 | J140 | S |
| 3-1479 | —(CH$_2$)$_2$— | —C(=O)— | K727 | J140 | S |
| 3-1480 | —(CH$_2$)$_2$— | —C(=O)— | K728 | J140 | S |
| 3-1481 | —(CH$_2$)$_2$— | —C(=O)— | K729 | J140 | S |
| 3-1482 | —(CH$_2$)$_2$— | —C(=O)— | K730 | J140 | S |
| 3-1483 | —(CH$_2$)$_2$— | —C(=O)— | K731 | J140 | S |
| 3-1484 | —(CH$_2$)$_2$— | —C(=O)— | K732 | J140 | S |
| 3-1485 | —(CH$_2$)$_2$— | —C(=O)— | K733 | J140 | S |
| 3-1486 | —(CH$_2$)$_2$— | —C(=O)— | K734 | J140 | S |
| 3-1487 | —(CH$_2$)$_2$— | —C(=O)— | K735 | J140 | S |
| 3-1488 | —(CH$_2$)$_2$— | —C(=O)— | K736 | J140 | S |
| 3-1489 | —(CH$_2$)$_2$— | —C(=O)— | K737 | J140 | S |
| 3-1490 | —(CH$_2$)$_2$— | —C(=O)— | K738 | J140 | S |
| 3-1491 | —(CH$_2$)$_2$— | —C(=O)— | K739 | J140 | S |
| 3-1492 | —(CH$_2$)$_2$— | —C(=O)— | K740 | J140 | S |
| 3-1493 | —(CH$_2$)$_2$— | —C(=O)— | K741 | J140 | S |
| 3-1494 | —(CH$_2$)$_2$— | —C(=O)— | K742 | J140 | S |
| 3-1495 | —(CH$_2$)$_2$— | —C(=O)— | K743 | J140 | S |
| 3-1496 | —(CH$_2$)$_2$— | —C(=O)— | K744 | J140 | S |
| 3-1497 | —(CH$_2$)$_2$— | —C(=O)— | K745 | J140 | S |
| 3-1498 | —(CH$_2$)$_2$— | —C(=O)— | K746 | J140 | S |
| 3-1499 | —(CH$_2$)$_2$— | —C(=O)— | K747 | J140 | S |
| 3-1500 | —(CH$_2$)$_2$— | —C(=O)— | K748 | J140 | S |
| 3-1501 | —(CH$_2$)$_2$— | —C(=O)— | K749 | J140 | S |
| 3-1502 | —(CH$_2$)$_2$— | —C(=O)— | K750 | J140 | S |
| 3-1503 | —(CH$_2$)$_2$— | —C(=O)— | K751 | J140 | S |
| 3-1504 | —(CH$_2$)$_2$— | —C(=O)— | K752 | J140 | S |

TABLE 150

| Compound No. | -A¹- | -A²- | -G¹-A³-A⁴-G² | -A⁵-R² | X |
|---|---|---|---|---|---|
| 3-1505 | —(CH$_2$)$_2$— | —C(=O)— | K753 | J140 | S |
| 3-1506 | —(CH$_2$)$_2$— | —C(=O)— | K754 | J140 | S |
| 3-1507 | —(CH$_2$)$_2$— | —C(=O)— | K755 | J140 | S |
| 3-1508 | —(CH$_2$)$_2$— | —C(=O)— | K756 | J140 | S |
| 3-1509 | —(CH$_2$)$_2$— | —C(=O)— | K757 | J140 | S |
| 3-1510 | —(CH$_2$)$_2$— | —C(=O)— | K314 | J3 | O |
| 3-1511 | —(CH$_2$)$_2$— | —C(=O)— | K315 | J3 | O |
| 3-1512 | —(CH$_2$)$_2$— | —C(=O)— | K316 | J3 | O |
| 3-1513 | —(CH$_2$)$_2$— | —C(=O)— | K317 | J3 | O |
| 3-1514 | —(CH$_2$)$_2$— | —C(=O)— | K318 | J3 | O |
| 3-1515 | —(CH$_2$)$_2$— | —C(=O)— | K319 | J3 | O |
| 3-1516 | —(CH$_2$)$_2$— | —C(=O)— | K320 | J3 | O |
| 3-1517 | —(CH$_2$)$_2$— | —C(=O)— | K321 | J3 | O |
| 3-1518 | —(CH$_2$)$_2$— | —C(=O)— | K322 | J3 | O |
| 3-1519 | —(CH$_2$)$_2$— | —C(=O)— | K323 | J3 | O |
| 3-1520 | —(CH$_2$)$_2$— | —C(=O)— | K324 | J3 | O |
| 3-1521 | —(CH$_2$)$_2$— | —C(=O)— | K325 | J3 | O |
| 3-1522 | —(CH$_2$)$_2$— | —C(=O)— | K326 | J3 | O |
| 3-1523 | —(CH$_2$)$_2$— | —C(=O)— | K327 | J3 | O |
| 3-1524 | —(CH$_2$)$_2$— | —C(=O)— | K328 | J3 | O |
| 3-1525 | —(CH$_2$)$_2$— | —C(=O)— | K329 | J3 | O |
| 3-1526 | —(CH$_2$)$_2$— | —C(=O)— | K330 | J3 | O |
| 3-1527 | —(CH$_2$)$_2$— | —C(=O)— | K331 | J3 | O |
| 3-1528 | —(CH$_2$)$_2$— | —C(=O)— | K332 | J3 | O |
| 3-1529 | —(CH$_2$)$_2$— | —C(=O)— | K333 | J3 | O |
| 3-1530 | —(CH$_2$)$_2$— | —C(=O)— | K334 | J9 | O |
| 3-1531 | —(CH$_2$)$_2$— | —C(=O)— | K335 | J9 | O |
| 3-1532 | —(CH$_2$)$_2$— | —C(=O)— | K336 | J9 | O |
| 3-1533 | —(CH$_2$)$_2$— | —C(=O)— | K337 | J9 | O |
| 3-1534 | —(CH$_2$)$_2$— | —C(=O)— | K338 | J9 | O |
| 3-1535 | —(CH$_2$)$_2$— | —C(=O)— | K339 | J9 | O |
| 3-1536 | —(CH$_2$)$_2$— | —C(=O)— | K340 | J9 | O |

TABLE 151

| Compound No. | -A¹- | -A²- | -G¹-A³-A⁴-G² | -A⁵-R² | X |
|---|---|---|---|---|---|
| 3-1537 | —(CH₂)₂— | —C(=O)— | K341 | J9 | O |
| 3-1538 | —(CH₂)₂— | —C(=O)— | K342 | J9 | O |
| 3-1539 | —(CH₂)₂— | —C(=O)— | K343 | J9 | O |
| 3-1540 | —(CH₂)₂— | —C(=O)— | K345 | J9 | O |
| 3-1541 | —(CH₂)₂— | —C(=O)— | K346 | J9 | O |
| 3-1542 | —(CH₂)₂— | —C(=O)— | K347 | J9 | O |
| 3-1543 | —(CH₂)₂— | —C(=O)— | K348 | J9 | O |
| 3-1544 | —(CH₂)₂— | —C(=O)— | K349 | J9 | O |
| 3-1545 | —(CH₂)₂— | —C(=O)— | K350 | J9 | O |
| 3-1546 | —(CH₂)₂— | —C(=O)— | K351 | J9 | O |
| 3-1547 | —(CH₂)₂— | —C(=O)— | K352 | J9 | O |
| 3-1548 | —(CH₂)₂— | —C(=O)— | K353 | J9 | O |
| 3-1549 | —(CH₂)₂— | —C(=O)— | K354 | J126 | O |
| 3-1550 | —(CH₂)₂— | —C(=O)— | K355 | J126 | O |
| 3-1551 | —(CH₂)₂— | —C(=O)— | K356 | J126 | O |
| 3-1552 | —(CH₂)₂— | —C(=O)— | K357 | J126 | O |
| 3-1553 | —(CH₂)₂— | —C(=O)— | K358 | J126 | O |
| 3-1554 | —(CH₂)₂— | —C(=O)— | K359 | J126 | O |
| 3-1555 | —(CH₂)₂— | —C(=O)— | K360 | J126 | O |
| 3-1556 | —(CH₂)₂— | —C(=O)— | K361 | J126 | O |
| 3-1557 | —(CH₂)₂— | —C(=O)— | K362 | J126 | O |
| 3-1558 | —(CH₂)₂— | —C(=O)— | K363 | J126 | O |
| 3-1559 | —(CH₂)₂— | —C(=O)— | K364 | J126 | O |
| 3-1560 | —(CH₂)₂— | —C(=O)— | K365 | J126 | O |
| 3-1561 | —(CH₂)₂— | —C(=O)— | K366 | J126 | O |
| 3-1562 | —(CH₂)₂— | —C(=O)— | K367 | J126 | O |
| 3-1563 | —(CH₂)₂— | —C(=O)— | K368 | J126 | O |
| 3-1564 | —(CH₂)₂— | —C(=O)— | K369 | J126 | O |
| 3-1565 | —(CH₂)₂— | —C(=O)— | K370 | J126 | O |
| 3-1566 | —(CH₂)₂— | —C(=O)— | K371 | J126 | O |
| 3-1567 | —(CH₂)₂— | —C(=O)— | K372 | J126 | O |
| 3-1568 | —(CH₂)₂— | —C(=O)— | K373 | J126 | O |

TABLE 152

| Compound No. | -A¹- | -A²- | -G¹-A³-A⁴-G² | -A⁵-R² | X |
|---|---|---|---|---|---|
| 3-1569 | —(CH₂)₂— | —C(=O)— | K374 | J129 | O |
| 3-1570 | —(CH₂)₂— | —C(=O)— | K375 | J129 | O |
| 3-1571 | —(CH₂)₂— | —C(=O)— | K376 | J129 | O |
| 3-1572 | —(CH₂)₂— | —C(=O)— | K377 | J129 | O |
| 3-1573 | —(CH₂)₂— | —C(=O)— | K378 | J129 | O |
| 3-1574 | —(CH₂)₂— | —C(=O)— | K379 | J129 | O |
| 3-1575 | —(CH₂)₂— | —C(=O)— | K380 | J129 | O |
| 3-1576 | —(CH₂)₂— | —C(=O)— | K381 | J129 | O |
| 3-1577 | —(CH₂)₂— | —C(=O)— | K382 | J129 | O |
| 3-1578 | —(CH₂)₂— | —C(=O)— | K383 | J129 | O |
| 3-1579 | —(CH₂)₂— | —C(=O)— | K384 | J129 | O |
| 3-1580 | —(CH₂)₂— | —C(=O)— | K385 | J129 | O |
| 3-1581 | —(CH₂)₂— | —C(=O)— | K386 | J129 | O |
| 3-1582 | —(CH₂)₂— | —C(=O)— | K387 | J129 | O |
| 3-1583 | —(CH₂)₂— | —C(=O)— | K388 | J129 | O |
| 3-1584 | —(CH₂)₂— | —C(=O)— | K389 | J129 | O |
| 3-1585 | —(CH₂)₂— | —C(=O)— | K390 | J129 | O |
| 3-1586 | —(CH₂)₂— | —C(=O)— | K391 | J129 | O |
| 3-1587 | —(CH₂)₂— | —C(=O)— | K392 | J129 | O |
| 3-1588 | —(CH₂)₂— | —C(=O)— | K393 | J129 | O |
| 3-1589 | —(CH₂)₂— | —C(=O)— | K394 | J130 | O |
| 3-1590 | —(CH₂)₂— | —C(=O)— | K395 | J130 | O |
| 3-1591 | —(CH₂)₂— | —C(=O)— | K396 | J130 | O |
| 3-1592 | —(CH₂)₂— | —C(=O)— | K397 | J130 | O |
| 3-1593 | —(CH₂)₂— | —C(=O)— | K398 | J130 | O |
| 3-1594 | —(CH₂)₂— | —C(=O)— | K405 | J130 | O |
| 3-1595 | —(CH₂)₂— | —C(=O)— | K406 | J130 | O |
| 3-1596 | —(CH₂)₂— | —C(=O)— | K407 | J130 | O |
| 3-1597 | —(CH₂)₂— | —C(=O)— | K408 | J130 | O |
| 3-1598 | —(CH₂)₂— | —C(=O)— | K409 | J130 | O |
| 3-1599 | —(CH₂)₂— | —C(=O)— | K410 | J130 | O |
| 3-1600 | —(CH₂)₂— | —C(=O)— | K411 | J130 | O |

TABLE 153

| Compound No. | -A¹- | -A²- | -G¹-A³-A⁴-G² | -A⁵-R² | X |
|---|---|---|---|---|---|
| 3-1601 | —(CH₂)₂— | —C(=O)— | K412 | J130 | O |
| 3-1602 | —(CH₂)₂— | —C(=O)— | K413 | J130 | O |
| 3-1603 | —(CH₂)₂— | —C(=O)— | K414 | J130 | O |
| 3-1604 | —(CH₂)₂— | —C(=O)— | K415 | J130 | O |
| 3-1605 | —(CH₂)₂— | —C(=O)— | K416 | J130 | O |
| 3-1606 | —(CH₂)₂— | —C(=O)— | K417 | J130 | O |
| 3-1607 | —(CH₂)₂— | —C(=O)— | K418 | J130 | O |
| 3-1608 | —(CH₂)₂— | —C(=O)— | K419 | J130 | O |
| 3-1609 | —(CH₂)₂— | —C(=O)— | K420 | J138 | O |
| 3-1610 | —(CH₂)₂— | —C(=O)— | K421 | J138 | O |
| 3-1611 | —(CH₂)₂— | —C(=O)— | K726 | J138 | O |
| 3-1612 | —(CH₂)₂— | —C(=O)— | K727 | J138 | O |
| 3-1613 | —(CH₂)₂— | —C(=O)— | K728 | J138 | O |
| 3-1614 | —(CH₂)₂— | —C(=O)— | K729 | J138 | O |
| 3-1615 | —(CH₂)₂— | —C(=O)— | K730 | J138 | O |
| 3-1616 | —(CH₂)₂— | —C(=O)— | K731 | J138 | O |
| 3-1617 | —(CH₂)₂— | —C(=O)— | K732 | J138 | O |
| 3-1618 | —(CH₂)₂— | —C(=O)— | K733 | J138 | O |
| 3-1619 | —(CH₂)₂— | —C(=O)— | K734 | J138 | O |
| 3-1620 | —(CH₂)₂— | —C(=O)— | K735 | J138 | O |
| 3-1621 | —(CH₂)₂— | —C(=O)— | K736 | J138 | O |
| 3-1622 | —(CH₂)₂— | —C(=O)— | K737 | J138 | O |
| 3-1623 | —(CH₂)₂— | —C(=O)— | K738 | J138 | O |
| 3-1624 | —(CH₂)₂— | —C(=O)— | K739 | J138 | O |
| 3-1625 | —(CH₂)₂— | —C(=O)— | K740 | J138 | O |
| 3-1626 | —(CH₂)₂— | —C(=O)— | K741 | J138 | O |
| 3-1627 | —(CH₂)₂— | —C(=O)— | K742 | J138 | O |
| 3-1628 | —(CH₂)₂— | —C(=O)— | K743 | J138 | O |
| 3-1629 | —(CH₂)₂— | —C(=O)— | K744 | J140 | O |
| 3-1630 | —(CH₂)₂— | —C(=O)— | K745 | J140 | O |
| 3-1631 | —(CH₂)₂— | —C(=O)— | K746 | J140 | O |
| 3-1632 | —(CH₂)₂— | —C(=O)— | K747 | J140 | O |

TABLE 154

| Compound No. | -A¹- | -A²- | -G¹-A³-A⁴-G² | -A⁵-R² | X |
|---|---|---|---|---|---|
| 3-1633 | —(CH₂)₂— | —C(=O)— | K748 | J140 | O |
| 3-1634 | —(CH₂)₂— | —C(=O)— | K749 | J140 | O |
| 3-1635 | —(CH₂)₂— | —C(=O)— | K750 | J140 | O |
| 3-1636 | —(CH₂)₂— | —C(=O)— | K751 | J140 | O |
| 3-1637 | —(CH₂)₂— | —C(=O)— | K752 | J140 | O |
| 3-1638 | —(CH₂)₂— | —C(=O)— | K753 | J140 | O |
| 3-1639 | —(CH₂)₂— | —C(=O)— | K754 | J140 | O |
| 3-1640 | —(CH₂)₂— | —C(=O)— | K755 | J140 | O |
| 3-1641 | —(CH₂)₂— | —C(=O)— | K756 | J140 | O |
| 3-1642 | —(CH₂)₂— | —C(=O)— | K757 | J140 | O |
| 3-1643 | —(CH₂)₃— | —C(=O)— | K314 | J1 | S |
| 3-1644 | —(CH₂)₃— | —C(=O)— | K315 | J1 | S |
| 3-1645 | —(CH₂)₃— | —C(=O)— | K316 | J2 | S |
| 3-1646 | —(CH₂)₃— | —C(=O)— | K317 | J2 | S |
| 3-1647 | —(CH₂)₃— | —C(=O)— | K318 | J4 | S |
| 3-1648 | —(CH₂)₃— | —C(=O)— | K319 | J4 | S |
| 3-1649 | —(CH₂)₃— | —C(=O)— | K320 | J10 | S |
| 3-1650 | —(CH₂)₃— | —C(=O)— | K321 | J10 | S |
| 3-1651 | —(CH₂)₃— | —C(=O)— | K322 | J19 | S |
| 3-1652 | —(CH₂)₃— | —C(=O)— | K323 | J19 | S |
| 3-1653 | —(CH₂)₃— | —C(=O)— | K324 | J14 | S |
| 3-1654 | —(CH₂)₃— | —C(=O)— | K325 | J14 | S |
| 3-1655 | —(CH₂)₃— | —C(=O)— | K326 | J22 | S |
| 3-1656 | —(CH₂)₃— | —C(=O)— | K327 | J22 | S |
| 3-1657 | —(CH₂)₃— | —C(=O)— | K328 | J72 | S |
| 3-1658 | —(CH₂)₃— | —C(=O)— | K329 | J72 | S |
| 3-1659 | —(CH₂)₃— | —C(=O)— | K330 | J74 | S |
| 3-1660 | —(CH₂)₃— | —C(=O)— | K331 | J74 | S |
| 3-1661 | —(CH₂)₃— | —C(=O)— | K332 | J75 | S |
| 3-1662 | —(CH₂)₃— | —C(=O)— | K333 | J75 | S |
| 3-1663 | —(CH₂)₃— | —C(=O)— | K334 | J77 | S |
| 3-1664 | —(CH₂)₃— | —C(=O)— | K335 | J77 | S |

TABLE 155

| Compound No. | -A$^1$- | -A$^2$- | -G$^1$-A$^3$-A$^4$-G$^2$ | -A$^5$-R$^2$ | X |
|---|---|---|---|---|---|
| 3-1665 | —(CH$_2$)$_3$— | —C(=O)— | K336 | J96 | S |
| 3-1666 | —(CH$_2$)$_3$— | —C(=O)— | K337 | J96 | S |
| 3-1667 | —(CH$_2$)$_3$— | —C(=O)— | K338 | J174 | S |
| 3-1668 | —(CH$_2$)$_3$— | —C(=O)— | K339 | J174 | S |
| 3-1669 | —(CH$_2$)$_3$— | —C(=O)— | K340 | J176 | S |
| 3-1670 | —(CH$_2$)$_3$— | —C(=O)— | K341 | J176 | S |
| 3-1671 | —(CH$_2$)$_3$— | —C(=O)— | K342 | J177 | S |
| 3-1672 | —(CH$_2$)$_3$— | —C(=O)— | K343 | J177 | S |
| 3-1673 | —(CH$_2$)$_3$— | —C(=O)— | K344 | J189 | S |
| 3-1674 | —(CH$_2$)$_3$— | —C(=O)— | K345 | J189 | S |
| 3-1675 | —(CH$_2$)$_3$— | —C(=O)— | K346 | J182 | S |
| 3-1676 | —(CH$_2$)$_3$— | —C(=O)— | K347 | J182 | S |
| 3-1677 | —(CH$_2$)$_3$— | —C(=O)— | K348 | J183 | S |
| 3-1678 | —(CH$_2$)$_3$— | —C(=O)— | K349 | J183 | S |
| 3-1679 | —(CH$_2$)$_3$— | —C(=O)— | K350 | J1 | S |
| 3-1680 | —(CH$_2$)$_3$— | —C(=O)— | K351 | J1 | S |
| 3-1681 | —(CH$_2$)$_3$— | —C(=O)— | K352 | J2 | S |
| 3-1682 | —(CH$_2$)$_3$— | —C(=O)— | K353 | J2 | S |
| 3-1683 | —(CH$_2$)$_3$— | —C(=O)— | K354 | J4 | S |
| 3-1684 | —(CH$_2$)$_3$— | —C(=O)— | K355 | J4 | S |
| 3-1685 | —(CH$_2$)$_3$— | —C(=O)— | K356 | J10 | S |
| 3-1686 | —(CH$_2$)$_3$— | —C(=O)— | K357 | J10 | S |
| 3-1687 | —(CH$_2$)$_3$— | —C(=O)— | K358 | J19 | S |
| 3-1688 | —(CH$_2$)$_3$— | —C(=O)— | K359 | J19 | S |
| 3-1689 | —(CH$_2$)$_3$— | —C(=O)— | K360 | J14 | S |
| 3-1690 | —(CH$_2$)$_3$— | —C(=O)— | K361 | J14 | S |
| 3-1691 | —(CH$_2$)$_3$— | —C(=O)— | K362 | J22 | S |
| 3-1692 | —(CH$_2$)$_3$— | —C(=O)— | K363 | J22 | S |
| 3-1693 | —(CH$_2$)$_3$— | —C(=O)— | K364 | J72 | S |
| 3-1694 | —(CH$_2$)$_3$— | —C(=O)— | K365 | J72 | S |
| 3-1695 | —(CH$_2$)$_3$— | —C(=O)— | K366 | J74 | S |
| 3-1696 | —(CH$_2$)$_3$— | —C(=O)— | K367 | J74 | S |

TABLE 156

| Compound No. | -A$^1$- | -A$^2$- | -G$^1$-A$^3$-A$^4$-G$^2$ | -A$^5$-R$^2$ | X |
|---|---|---|---|---|---|
| 3-1697 | —(CH$_2$)$_3$— | —C(=O)— | K368 | J75 | S |
| 3-1698 | —(CH$_2$)$_3$— | —C(=O)— | K369 | J75 | S |
| 3-1699 | —(CH$_2$)$_3$— | —C(=O)— | K370 | J77 | S |
| 3-1700 | —(CH$_2$)$_3$— | —C(=O)— | K371 | J77 | S |
| 3-1701 | —(CH$_2$)$_3$— | —C(=O)— | K372 | J96 | S |
| 3-1702 | —(CH$_2$)$_3$— | —C(=O)— | K373 | J96 | S |
| 3-1703 | —(CH$_2$)$_3$— | —C(=O)— | K374 | J174 | S |
| 3-1704 | —(CH$_2$)$_3$— | —C(=O)— | K375 | J174 | S |
| 3-1705 | —(CH$_2$)$_3$— | —C(=O)— | K376 | J176 | S |
| 3-1706 | —(CH$_2$)$_3$— | —C(=O)— | K377 | J176 | S |
| 3-1707 | —(CH$_2$)$_3$— | —C(=O)— | K378 | J177 | S |
| 3-1708 | —(CH$_2$)$_3$— | —C(=O)— | K379 | J177 | S |
| 3-1709 | —(CH$_2$)$_3$— | —C(=O)— | K380 | J189 | S |
| 3-1710 | —(CH$_2$)$_3$— | —C(=O)— | K381 | J189 | S |
| 3-1711 | —(CH$_2$)$_3$— | —C(=O)— | K382 | J182 | S |
| 3-1712 | —(CH$_2$)$_3$— | —C(=O)— | K383 | J182 | S |
| 3-1713 | —(CH$_2$)$_3$— | —C(=O)— | K384 | J183 | S |
| 3-1714 | —(CH$_2$)$_3$— | —C(=O)— | K385 | J183 | S |
| 3-1715 | —(CH$_2$)$_3$— | —C(=O)— | K386 | J191 | S |
| 3-1716 | —(CH$_2$)$_3$— | —C(=O)— | K387 | J191 | S |
| 3-1717 | —(CH$_2$)$_3$— | —C(=O)— | K388 | J192 | S |
| 3-1718 | —(CH$_2$)$_3$— | —C(=O)— | K389 | J192 | S |
| 3-1719 | —(CH$_2$)$_3$— | —C(=O)— | K390 | J193 | S |
| 3-1720 | —(CH$_2$)$_3$— | —C(=O)— | K391 | J193 | S |
| 3-1721 | —(CH$_2$)$_3$— | —C(=O)— | K392 | J194 | S |
| 3-1722 | —(CH$_2$)$_3$— | —C(=O)— | K393 | J194 | S |
| 3-1723 | —(CH$_2$)$_3$— | —C(=O)— | K394 | J197 | S |
| 3-1724 | —(CH$_2$)$_3$— | —C(=O)— | K395 | J197 | S |
| 3-1725 | —(CH$_2$)$_3$— | —C(=O)— | K396 | J126 | S |
| 3-1726 | —(CH$_2$)$_3$— | —C(=O)— | K397 | J126 | S |
| 3-1727 | —(CH$_2$)$_3$— | —C(=O)— | K398 | J126 | S |
| 3-1728 | —(CH$_2$)$_3$— | —C(=O)— | K405 | J126 | S |

TABLE 157

| Compound No. | -A$^1$- | -A$^2$- | -G$^1$-A$^3$-A$^4$-G$^2$ | -A$^5$-R$^2$ | X |
|---|---|---|---|---|---|
| 3-1729 | —(CH$_2$)$_3$— | —C(=O)— | K406 | J126 | S |
| 3-1730 | —(CH$_2$)$_3$— | —C(=O)— | K407 | J126 | S |
| 3-1731 | —(CH$_2$)$_3$— | —C(=O)— | K408 | J126 | S |
| 3-1732 | —(CH$_2$)$_3$— | —C(=O)— | K409 | J126 | S |
| 3-1733 | —(CH$_2$)$_3$— | —C(=O)— | K410 | J126 | S |
| 3-1734 | —(CH$_2$)$_3$— | —C(=O)— | K411 | J126 | S |
| 3-1735 | —(CH$_2$)$_3$— | —C(=O)— | K412 | J129 | S |
| 3-1736 | —(CH$_2$)$_3$— | —C(=O)— | K413 | J129 | S |
| 3-1737 | —(CH$_2$)$_3$— | —C(=O)— | K414 | J129 | S |
| 3-1738 | —(CH$_2$)$_3$— | —C(=O)— | K415 | J129 | S |
| 3-1739 | —(CH$_2$)$_3$— | —C(=O)— | K416 | J129 | S |
| 3-1740 | —(CH$_2$)$_3$— | —C(=O)— | K417 | J129 | S |
| 3-1741 | —(CH$_2$)$_3$— | —C(=O)— | K419 | J129 | S |
| 3-1742 | —(CH$_2$)$_3$— | —C(=O)— | K420 | J129 | S |
| 3-1743 | —(CH$_2$)$_3$— | —C(=O)— | K421 | J129 | S |
| 3-1744 | —(CH$_2$)$_3$— | —C(=O)— | K726 | J130 | S |
| 3-1745 | —(CH$_2$)$_3$— | —C(=O)— | K727 | J130 | S |
| 3-1746 | —(CH$_2$)$_3$— | —C(=O)— | K728 | J130 | S |
| 3-1747 | —(CH$_2$)$_3$— | —C(=O)— | K729 | J130 | S |
| 3-1748 | —(CH$_2$)$_3$— | —C(=O)— | K730 | J130 | S |
| 3-1749 | —(CH$_2$)$_3$— | —C(=O)— | K731 | J130 | S |
| 3-1750 | —(CH$_2$)$_3$— | —C(=O)— | K732 | J130 | S |
| 3-1751 | —(CH$_2$)$_3$— | —C(=O)— | K733 | J130 | S |
| 3-1752 | —(CH$_2$)$_3$— | —C(=O)— | K734 | J130 | S |
| 3-1753 | —(CH$_2$)$_3$— | —C(=O)— | K735 | J130 | S |
| 3-1754 | —(CH$_2$)$_3$— | —C(=O)— | K736 | J138 | S |
| 3-1755 | —(CH$_2$)$_3$— | —C(=O)— | K737 | J138 | S |
| 3-1756 | —(CH$_2$)$_3$— | —C(=O)— | K738 | J138 | S |
| 3-1757 | —(CH$_2$)$_3$— | —C(=O)— | K739 | J138 | S |
| 3-1758 | —(CH$_2$)$_3$— | —C(=O)— | K740 | J138 | S |
| 3-1759 | —(CH$_2$)$_3$— | —C(=O)— | K741 | J138 | S |
| 3-1760 | —(CH$_2$)$_3$— | —C(=O)— | K742 | J138 | S |

TABLE 158

| Compound No. | -A$^1$- | -A$^2$- | -G$^1$-A$^3$-A$^4$-G$^2$ | -A$^5$-R$^2$ | X |
|---|---|---|---|---|---|
| 3-1761 | —(CH$_2$)$_3$— | —C(=O)— | K743 | J138 | S |
| 3-1762 | —(CH$_2$)$_3$— | —C(=O)— | K744 | J138 | S |
| 3-1763 | —(CH$_2$)$_3$— | —C(=O)— | K745 | J138 | S |
| 3-1764 | —(CH$_2$)$_3$— | —C(=O)— | K746 | J138 | S |
| 3-1765 | —(CH$_2$)$_3$— | —C(=O)— | K747 | J138 | S |
| 3-1766 | —(CH$_2$)$_3$— | —C(=O)— | K748 | J140 | S |
| 3-1767 | —(CH$_2$)$_3$— | —C(=O)— | K749 | J140 | S |
| 3-1768 | —(CH$_2$)$_3$— | —C(=O)— | K750 | J140 | S |
| 3-1769 | —(CH$_2$)$_3$— | —C(=O)— | K751 | J140 | S |
| 3-1770 | —(CH$_2$)$_3$— | —C(=O)— | K752 | J140 | S |

TABLE 158-continued

| Compound No. | -A¹- | -A²- | -G¹-A³-A⁴-G² | -A⁵-R² | X |
|---|---|---|---|---|---|
| 3-1771 | —(CH₂)₃— | —C(=O)— | K753 | J140 | S |
| 3-1772 | —(CH₂)₃— | —C(=O)— | K754 | J140 | S |
| 3-1773 | —(CH₂)₃— | —C(=O)— | K755 | J140 | S |
| 3-1774 | —(CH₂)₃— | —C(=O)— | K756 | J140 | S |
| 3-1775 | —(CH₂)₃— | —C(=O)— | K757 | J140 | S |
| 3-1776 | —(CH₂)₂— | —C(=O)—NH— | K11 | J126 | S |
| 3-1777 | —(CH₂)₂— | —C(=O)—NH— | K110 | J126 | S |
| 3-1778 | —(CH₂)₂— | —C(=O)—NH— | K332 | J126 | S |
| 3-1779 | —(CH₂)₂— | —C(=O)—NH— | K315 | J126 | S |
| 3-1780 | —(CH₂)₂— | —C(=O)—NH— | K759 | J9 | S |
| 3-1781 | —(CH₂)₂— | —C(=O)—NH— | K760 | J9 | S |
| 3-1782 | —(CH₂)₂— | —C(=O)—NH— | K713 | J9 | S |
| 3-1783 | —(CH₂)₂— | —C(=O)—NH— | K87 | J9 | S |
| 3-1784 | —(CH₂)₂— | —C(=O)—NH— | K259 | J9 | S |
| 3-1785 | —(CH₂)₂— | —C(=O)—N(CH₂CH(CH₃)₂)— | K87 | J9 | S |
| 3-1786 | —(CH₂)₂— | —C(=O)—N(CH₂CH₃)— | K728 | J9 | S |
| 3-1787 | —(CH₂)₂— | —C(=O)—N(CH₃)— | K264 | J9 | S |
| 3-1788 | —(CH₂)₂— | —C(=O)—N(CH₂C₆H₅)— | K266 | J9 | S |
| 3-1789 | —(CH₂)₂— | —C(=O)—N(CH₂CH₃)— | K3 | J9 | S |
| 3-1790 | —(CH₂)₂— | —C(=O)—N(CH₂CH₂CH₂CH₃)— | K699 | J9 | S |
| 3-1791 | —(CH₂)₂— | —C(=O)—NH— | K1 | J9 | S |
| 3-1792 | —(CH₂)₂— | —C(=O)—NH— | K2 | J9 | S |

TABLE 159

| Compound No. | -A¹- | -A²- | -G¹-A³-A⁴-G² | -A⁵-R² | X |
|---|---|---|---|---|---|
| 3-1793 | —(CH₂)₂— | —C(=O)—NH— | K3 | J9 | S |
| 3-1794 | —(CH₂)₂— | —C(=O)—N(CH₃)— | K795 | J9 | S |
| 3-1795 | —(CH₂)₂— | —C(=O)—NH— | K723 | J9 | S |
| 3-1796 | —(CH₂)₂— | —C(=O)—NH— | K731 | J9 | S |
| 3-1797 | —(CH₂)₂— | —C(=O)—NH— | K281 | J9 | S |
| 3-1798 | —(CH₂)₂— | —C(=O)—NH— | K722 | J9 | S |
| 3-1799 | —(CH₂)₂— | —C(=O)—N(CH₃)— | K1 | J9 | S |
| 3-1800 | —(CH₂)₂— | —C(=O)—N(CH₂C₆H₅)— | K4 | J9 | S |
| 3-1801 | —(CH₂)₂— | —C(=O)—N(CH₃)— | K736 | J9 | S |
| 3-1802 | —(CH₂)₂— | —C(=O)—N(CH₃)— | K430 | J9 | S |
| 3-1803 | —(CH₂)₂— | —C(=O)—N(CH₃)— | K660 | J9 | S |
| 3-1804 | —(CH₂)₂— | —C(=O)—N(CH₂C₆H₅)— | K99 | J9 | S |
| 3-1805 | —(CH₂)₂— | —C(=O)—N(CH₃)— | K739 | J9 | S |
| 3-1806 | —(CH₂)₂— | —C(=O)—N(CH₃)— | K740 | J9 | S |
| 3-1807 | —(CH₂)₂— | —C(=O)—N(CH₃)— | K694 | J9 | S |
| 3-1808 | —(CH₂)₂— | —C(=O)—N(CH₂CH=CH₂)— | K7 | J9 | S |
| 3-1809 | —(CH₂)₂— | —C(=O)—N(CH(CH₃)₂)— | K4 | J9 | S |
| 3-1810 | —(CH₂)₂— | —C(=O)—N(CH₃)— | K2 | J9 | S |
| 3-1811 | —(CH₂)₂— | —C(=O)—N(CH₃)— | K8 | J9 | S |
| 3-1812 | —(CH₂)₂— | —C(=O)—N(CH₃)— | K699 | J9 | S |
| 3-1813 | —(CH₂)₂— | —C(=O)—N(CH₂CH₃)— | K3 | J9 | S |
| 3-1814 | —(CH₂)₂— | —C(=O)—N(CH₃)— | K259 | J9 | S |
| 3-1815 | —(CH₂)₂— | —C(=O)—N(CH₃)— | K4 | J9 | S |
| 3-1816 | —(CH₂)₂— | —C(=O)—NH— | K758 | J9 | S |
| 3-1817 | —(CH₂)₂— | —C(=O)—NH— | K49 | J9 | S |
| 3-1818 | —(CH₂)₂— | —C(=O)—NH— | K288 | J9 | S |
| 3-1819 | —(CH₂)₂— | —C(=O)—NH— | K553 | J9 | S |
| 3-1820 | —(CH₂)₂— | —C(=O)—NH— | K36 | J9 | S |
| 3-1821 | —(CH₂)₂— | —C(=O)—NH— | K305 | J9 | S |
| 3-1822 | —(CH₂)₂— | —C(=O)—NH— | K291 | J9 | S |
| 3-1823 | —(CH₂)₂— | —C(=O)—NH— | K590 | J9 | S |
| 3-1824 | —(CH₂)₂— | —C(=O)—NH— | K30 | J9 | S |

TABLE 160

| Compound No. | —A¹— | —A²— | —G¹—A³—A⁴—G² | —A⁵—R² | X |
|---|---|---|---|---|---|
| 3-1825 | —(CH₂)₂— | —C(=O)—NH— | K591 | J9 | S |
| 3-1826 | —(CH₂)₂— | —C(=O)—NH— | K11 | J3 | S |

TABLE 161

| Compound No. | -A¹- | -A²- | -G¹-A³-A⁴-G² | -A⁵-R² | X |
|---|---|---|---|---|---|
| 4-0001 | —(CH$_2$)$_2$— | —C(=O)—O— | K240 | J9 | S |
| 4-0002 | —(CH$_2$)$_2$— | —C(=O)—O— | K240 | J78 | S |
| 4-0003 | —(CH$_2$)$_2$— | —C(=O)—O— | K2 | J6 | S |
| 4-0004 | —(CH$_2$)$_2$— | —C(=O)—O— | K2 | J9 | O |
| 4-0005 | —(CH$_2$)$_2$— | —C(=O)—O— | K2 | J9 | S |
| 4-0006 | —(CH$_2$)$_3$— | —C(=O)—O— | K2 | J9 | S |
| 4-0007 | —(CH$_2$)$_2$— | —C(=O)—O— | K2 | J78 | S |
| 4-0008 | —(CH$_2$)$_2$— | —C(=O)—O— | K4 | J3 | S |
| 4-0009 | —(CH$_2$)$_2$— | —C(=O)—O— | K428 | J19 | S |
| 4-0010 | —(CH$_2$)$_2$— | —C(=O)—O— | K257 | J9 | S |
| 4-0011 | —(CH$_2$)$_2$— | —C(=O)—O— | K257 | J22 | S |
| 4-0012 | —(CH$_2$)$_2$— | —C(=O)—O— | K260 | J57 | S |
| 4-0013 | —(CH$_2$)$_2$— | —C(=O)—O— | K264 | J126 | S |
| 4-0014 | —(CH$_2$)$_2$— | —C(=O)—O— | K8 | J9 | S |
| 4-0015 | —(CH$_2$)$_2$— | —C(=O)—O— | K269 | J9 | S |
| 4-0016 | —(CH$_2$)$_2$— | —C(=O)—O— | K160 | J9 | S |
| 4-0017 | —(CH$_2$)$_2$— | —C(=O)—O— | K441 | J9 | S |
| 4-0018 | —(CH$_2$)$_2$— | —C(=O)—O— | K441 | J128 | S |
| 4-0019 | —(CH$_2$)$_2$— | —C(=O)—O— | K99 | J9 | S |
| 4-0020 | —(CH$_2$)$_2$— | —C(=O)—O— | K100 | J9 | S |
| 4-0021 | —(CH$_2$)$_2$— | —C(=O)—O— | K309 | J131 | S |
| 4-0022 | —(CH$_2$)$_2$— | —C(=O)—O— | K446 | J140 | S |
| 4-0023 | —(CH$_2$)$_2$— | —C(=O)—O— | K110 | J9 | O |
| 4-0024 | —(CH$_2$)$_2$— | —C(=O)—O— | K111 | J9 | S |
| 4-0025 | —(CH$_2$)$_2$— | —C(=O)—O— | K111 | J78 | O |
| 4-0026 | —(CH$_2$)$_2$— | —C(=O)—O— | K302 | J9 | S |
| 4-0027 | —(CH$_2$)$_2$— | —C(=O)—O— | K302 | J130 | O |
| 4-0028 | —(CH$_2$)$_2$— | —C(=O)—O— | K448 | J1 | S |
| 4-0029 | —(CH$_2$)$_3$— | —C(=O)—O— | K240 | J9 | S |
| 4-0030 | —(CH$_2$)$_3$— | —C(=O)—O— | K2 | J9 | O |
| 4-0031 | —(CH$_2$)$_3$— | —C(=O)—O— | K2 | J9 | S |
| 4-0032 | —(CH$_2$)$_3$— | —C(=O)—O— | K8 | J30 | S |

TABLE 162

| Compound No. | -A¹- | -A²- | -G¹-A³-A⁴-G² | -A⁵-R² | X |
|---|---|---|---|---|---|
| 4-0033 | —(CH$_2$)$_3$— | —C(=O)—O— | K269 | J70 | S |
| 4-0034 | —(CH$_2$)$_3$— | —C(=O)—O— | K160 | J77 | S |
| 4-0035 | —(CH$_2$)$_3$— | —C(=O)—O— | K441 | J3 | S |
| 4-0036 | —(CH$_2$)$_3$— | —C(=O)—O— | K281 | J9 | O |
| 4-0037 | —(CH$_2$)$_3$— | —C(=O)—O— | K99 | J78 | O |
| 4-0038 | —(CH$_2$)$_3$— | —C(=O)—O— | K100 | J130 | O |
| 4-0039 | —(CH$_2$)$_2$— | —C(=O)—O— | K1 | J1 | S |
| 4-0040 | —(CH$_2$)$_2$— | —C(=O)—O— | K1 | J3 | S |
| 4-0041 | —(CH$_2$)$_2$— | —C(=O)—O— | K1 | J6 | S |
| 4-0042 | —(CH$_2$)$_2$— | —C(=O)—O— | K1 | J9 | S |
| 4-0043 | —(CH$_2$)$_2$— | —C(=O)—O— | K1 | J10 | S |
| 4-0044 | —(CH$_2$)$_2$— | —C(=O)—O— | K1 | J14 | S |
| 4-0045 | —(CH$_2$)$_2$— | —C(=O)—O— | K1 | J19 | S |
| 4-0046 | —(CH$_2$)$_2$— | —C(=O)—O— | K1 | J22 | S |
| 4-0047 | —(CH$_2$)$_2$— | —C(=O)—O— | K1 | J25 | S |
| 4-0048 | —(CH$_2$)$_2$— | —C(=O)—O— | K1 | J29 | S |
| 4-0049 | —(CH$_2$)$_2$— | —C(=O)—O— | K1 | J57 | S |
| 4-0050 | —(CH$_2$)$_2$— | —C(=O)—O— | K1 | J59 | S |
| 4-0051 | —(CH$_2$)$_2$— | —C(=O)—O— | K1 | J70 | S |
| 4-0052 | —(CH$_2$)$_2$— | —C(=O)—O— | K1 | J72 | S |
| 4-0053 | —(CH$_2$)$_2$— | —C(=O)—O— | K1 | J74 | S |
| 4-0054 | —(CH$_2$)$_2$— | —C(=O)—O— | K1 | J75 | S |
| 4-0055 | —(CH$_2$)$_2$— | —C(=O)—O— | K1 | J77 | S |
| 4-0056 | —(CH$_2$)$_2$— | —C(=O)—O— | K1 | J78 | S |
| 4-0057 | —(CH$_2$)$_2$— | —C(=O)—O— | K1 | J126 | S |
| 4-0058 | —(CH$_2$)$_2$— | —C(=O)—O— | K1 | J129 | S |
| 4-0059 | —(CH$_2$)$_2$— | —C(=O)—O— | K1 | J130 | S |
| 4-0060 | —(CH$_2$)$_2$— | —C(=O)—O— | K1 | J138 | S |
| 4-0061 | —(CH$_2$)$_2$— | —C(=O)—O— | K1 | J140 | S |
| 4-0062 | —(CH$_2$)$_2$— | —C(=O)—O— | K1 | J151 | S |
| 4-0063 | —(CH$_2$)$_2$— | —C(=O)—O— | K1 | J165 | S |
| 4-0064 | —(CH$_2$)$_2$— | —C(=O)—O— | K1 | J168 | S |

TABLE 163

| Compound No. | -A¹- | -A²- | -G¹-A³-A⁴-G² | -A⁵-R² | X |
|---|---|---|---|---|---|
| 4-0065 | —(CH$_2$)$_2$— | —C(=O)—O— | K1 | J174 | S |
| 4-0066 | —(CH$_2$)$_2$— | —C(=O)—O— | K1 | J176 | S |
| 4-0067 | —(CH$_2$)$_2$— | —C(=O)—O— | K1 | J177 | S |
| 4-0068 | —(CH$_2$)$_2$— | —C(=O)—O— | K1 | J178 | S |
| 4-0069 | —(CH$_2$)$_2$— | —C(=O)—O— | K1 | J185 | S |
| 4-0070 | —(CH$_2$)$_2$— | —C(=O)—O— | K1 | J191 | S |
| 4-0071 | —(CH$_2$)$_2$— | —C(=O)—O— | K1 | J193 | S |
| 4-0072 | —(CH$_2$)$_2$— | —C(=O)—O— | K1 | J195 | S |
| 4-0073 | —(CH$_2$)$_2$— | —C(=O)—O— | K1 | J197 | S |
| 4-0074 | —(CH$_2$)$_2$— | —C(=O)—O— | K5 | J9 | S |
| 4-0075 | —(CH$_2$)$_2$— | —C(=O)—O— | K5 | J140 | S |
| 4-0076 | —(CH$_2$)$_2$— | —C(=O)—O— | K5 | J78 | S |
| 4-0077 | —(CH$_2$)$_2$— | —C(=O)—O— | K5 | J130 | S |
| 4-0078 | —(CH$_2$)$_2$— | —C(=O)—O— | K5 | J138 | S |
| 4-0079 | —(CH$_2$)$_2$— | —C(=O)—O— | K5 | J129 | S |
| 4-0080 | —(CH$_2$)$_2$— | —C(=O)—O— | K11 | J9 | S |
| 4-0081 | —(CH$_2$)$_2$— | —C(=O)—O— | K11 | J140 | S |
| 4-0082 | —(CH$_2$)$_2$— | —C(=O)—O— | K11 | J78 | S |
| 4-0083 | —(CH$_2$)$_2$— | —C(=O)—O— | K11 | J130 | S |
| 4-0084 | —(CH$_2$)$_2$— | —C(=O)—O— | K11 | J138 | S |
| 4-0085 | —(CH$_2$)$_2$— | —C(=O)—O— | K11 | J129 | S |
| 4-0086 | —(CH$_2$)$_2$— | —C(=O)—O— | K99 | J140 | S |
| 4-0087 | —(CH$_2$)$_2$— | —C(=O)—O— | K99 | J78 | S |
| 4-0088 | —(CH$_2$)$_2$— | —C(=O)—O— | K99 | J130 | S |
| 4-0089 | —(CH$_2$)$_2$— | —C(=O)—O— | K99 | J138 | S |
| 4-0090 | —(CH$_2$)$_2$— | —C(=O)—O— | K99 | J129 | S |
| 4-0091 | —(CH$_2$)$_2$— | —C(=O)—O— | K240 | J1 | S |
| 4-0092 | —(CH$_2$)$_2$— | —C(=O)—O— | K240 | J3 | S |
| 4-0093 | —(CH$_2$)$_2$— | —C(=O)—O— | K240 | J6 | S |
| 4-0094 | —(CH$_2$)$_2$— | —C(=O)—O— | K240 | J10 | S |
| 4-0095 | —(CH$_2$)$_2$— | —C(=O)—O— | K240 | J14 | S |
| 4-0096 | —(CH$_2$)$_2$— | —C(=O)—O— | K240 | J19 | S |

TABLE 164

| Compound No. | -A¹- | -A²- | -G¹-A³-A⁴-G² | -A⁵-R² | X |
|---|---|---|---|---|---|
| 4-0097 | —(CH$_2$)$_2$— | —C(=O)—O— | K240 | J22 | S |
| 4-0098 | —(CH$_2$)$_2$— | —C(=O)—O— | K240 | J25 | S |
| 4-0099 | —(CH$_2$)$_2$— | —C(=O)—O— | K240 | J57 | S |
| 4-0100 | —(CH$_2$)$_2$— | —C(=O)—O— | K240 | J57 | S |
| 4-0101 | —(CH$_2$)$_2$— | —C(=O)—O— | K240 | J59 | S |
| 4-0102 | —(CH$_2$)$_2$— | —C(=O)—O— | K240 | J70 | S |
| 4-0103 | —(CH$_2$)$_2$— | —C(=O)—O— | K240 | J72 | S |
| 4-0104 | —(CH$_2$)$_2$— | —C(=O)—O— | K240 | J74 | S |
| 4-0105 | —(CH$_2$)$_2$— | —C(=O)—O— | K240 | J75 | S |
| 4-0106 | —(CH$_2$)$_2$— | —C(=O)—O— | K240 | J77 | S |
| 4-0107 | —(CH$_2$)$_2$— | —C(=O)—O— | K240 | J126 | S |
| 4-0108 | —(CH$_2$)$_2$— | —C(=O)—O— | K240 | J129 | S |
| 4-0109 | —(CH$_2$)$_2$— | —C(=O)—O— | K240 | J130 | S |
| 4-0110 | —(CH$_2$)$_2$— | —C(=O)—O— | K240 | J138 | S |
| 4-0111 | —(CH$_2$)$_2$— | —C(=O)—O— | K240 | J140 | S |
| 4-0112 | —(CH$_2$)$_2$— | —C(=O)—O— | K240 | J151 | S |
| 4-0113 | —(CH$_2$)$_2$— | —C(=O)—O— | K240 | J165 | S |
| 4-0114 | —(CH$_2$)$_2$— | —C(=O)—O— | K240 | J168 | S |
| 4-0115 | —(CH$_2$)$_2$— | —C(=O)—O— | K240 | J174 | S |
| 4-0116 | —(CH$_2$)$_2$— | —C(=O)—O— | K240 | J176 | S |
| 4-0117 | —(CH$_2$)$_2$— | —C(=O)—O— | K240 | J177 | S |
| 4-0118 | —(CH$_2$)$_2$— | —C(=O)—O— | K240 | J178 | S |
| 4-0119 | —(CH$_2$)$_2$— | —C(=O)—O— | K240 | J185 | S |
| 4-0120 | —(CH$_2$)$_2$— | —C(=O)—O— | K240 | J191 | S |
| 4-0121 | —(CH$_2$)$_2$— | —C(=O)—O— | K240 | J193 | S |
| 4-0122 | —(CH$_2$)$_2$— | —C(=O)—O— | K240 | J195 | S |
| 4-0123 | —(CH$_2$)$_2$— | —C(=O)—O— | K240 | J197 | S |
| 4-0124 | —(CH$_2$)$_3$— | —C(=O)—O— | K1 | J9 | S |
| 4-0125 | —(CH$_2$)$_3$— | —C(=O)—O— | K1 | J140 | S |
| 4-0126 | —(CH$_2$)$_3$— | —C(=O)—O— | K1 | J78 | S |
| 4-0127 | —(CH$_2$)$_3$— | —C(=O)—O— | K1 | J130 | S |
| 4-0128 | —(CH$_2$)$_3$— | —C(=O)—O— | K1 | J138 | S |

TABLE 165

| Compound No. | -A¹- | -A²- | -G¹-A³-A⁴-G² | -A⁵-R² | X |
|---|---|---|---|---|---|
| 4-0129 | —(CH$_2$)$_3$— | —C(=O)—O— | K1 | J129 | S |
| 4-0130 | —(CH$_2$)$_3$— | —C(=O)—O— | K5 | J9 | S |
| 4-0131 | —(CH$_2$)$_3$— | —C(=O)—O— | K5 | J140 | S |
| 4-0132 | —(CH$_2$)$_3$— | —C(=O)—O— | K5 | J78 | S |
| 4-0133 | —(CH$_2$)$_3$— | —C(=O)—O— | K5 | J130 | S |
| 4-0134 | —(CH$_2$)$_3$— | —C(=O)—O— | K5 | J138 | S |
| 4-0135 | —(CH$_2$)$_3$— | —C(=O)—O— | K5 | J129 | S |
| 4-0136 | —(CH$_2$)$_3$— | —C(=O)—O— | K11 | J9 | S |
| 4-0137 | —(CH$_2$)$_3$— | —C(=O)—O— | K11 | J140 | S |
| 4-0138 | —(CH$_2$)$_3$— | —C(=O)—O— | K11 | J78 | S |
| 4-0139 | —(CH$_2$)$_3$— | —C(=O)—O— | K11 | J130 | S |
| 4-0140 | —(CH$_2$)$_3$— | —C(=O)—O— | K11 | J138 | S |
| 4-0141 | —(CH$_2$)$_3$— | —C(=O)—O— | K11 | J129 | S |
| 4-0142 | —(CH$_2$)$_3$— | —C(=O)—O— | K99 | J9 | S |
| 4-0143 | —(CH$_2$)$_3$— | —C(=O)—O— | K99 | J140 | S |
| 4-0144 | —(CH$_2$)$_3$— | —C(=O)—O— | K99 | J78 | S |
| 4-0145 | —(CH$_2$)$_3$— | —C(=O)—O— | K99 | J130 | S |
| 4-0146 | —(CH$_2$)$_3$— | —C(=O)—O— | K99 | J138 | S |
| 4-0147 | —(CH$_2$)$_3$— | —C(=O)—O— | K99 | J129 | S |
| 4-0148 | —(CH$_2$)$_3$— | —C(=O)—O— | K240 | J1 | S |
| 4-0149 | —(CH$_2$)$_3$— | —C(=O)—O— | K240 | J3 | S |
| 4-0150 | —(CH$_2$)$_3$— | —C(=O)—O— | K240 | J6 | S |
| 4-0151 | —(CH$_2$)$_3$— | —C(=O)—O— | K240 | J10 | S |
| 4-0152 | —(CH$_2$)$_3$— | —C(=O)—O— | K240 | J14 | S |
| 4-0153 | —(CH$_2$)$_3$— | —C(=O)—O— | K240 | J19 | S |
| 4-0154 | —(CH$_2$)$_3$— | —C(=O)—O— | K240 | J22 | S |
| 4-0155 | —(CH$_2$)$_3$— | —C(=O)—O— | K240 | J25 | S |
| 4-0156 | —(CH$_2$)$_3$— | —C(=O)—O— | K240 | J29 | S |
| 4-0157 | —(CH$_2$)$_3$— | —C(=O)—O— | K240 | J57 | S |
| 4-0158 | —(CH$_2$)$_3$— | —C(=O)—O— | K240 | J59 | S |
| 4-0159 | —(CH$_2$)$_3$— | —C(=O)—O— | K240 | J70 | S |
| 4-0160 | —(CH$_2$)$_3$— | —C(=O)—O— | K240 | J72 | S |

TABLE 166

| Compound No. | -A¹- | -A²- | -G¹-A³-A⁴-G² | -A⁵-R² | X |
|---|---|---|---|---|---|
| 4-0161 | —(CH$_2$)$_3$— | —C(=O)—O— | K240 | J74 | S |
| 4-0162 | —(CH$_2$)$_3$— | —C(=O)—O— | K240 | J75 | S |
| 4-0163 | —(CH$_2$)$_3$— | —C(=O)—O— | K240 | J77 | S |
| 4-0164 | —(CH$_2$)$_3$— | —C(=O)—O— | K240 | J78 | S |
| 4-0165 | —(CH$_2$)$_3$— | —C(=O)—O— | K240 | J126 | S |
| 4-0166 | —(CH$_2$)$_3$— | —C(=O)—O— | K240 | J129 | S |
| 4-0167 | —(CH$_2$)$_3$— | —C(=O)—O— | K240 | J130 | S |
| 4-0168 | —(CH$_2$)$_3$— | —C(=O)—O— | K240 | J138 | S |
| 4-0169 | —(CH$_2$)$_3$— | —C(=O)—O— | K240 | J140 | S |
| 4-0170 | —(CH$_2$)$_3$— | —C(=O)—O— | K240 | J151 | S |
| 4-0171 | —(CH$_2$)$_3$— | —C(=O)—O— | K240 | J165 | S |
| 4-0172 | —(CH$_2$)$_3$— | —C(=O)—O— | K240 | J168 | S |
| 4-0173 | —(CH$_2$)$_3$— | —C(=O)—O— | K240 | J174 | S |
| 4-0174 | —(CH$_2$)$_3$— | —C(=O)—O— | K240 | J176 | S |
| 4-0175 | —(CH$_2$)$_3$— | —C(=O)—O— | K240 | J177 | S |
| 4-0176 | —(CH$_2$)$_3$— | —C(=O)—O— | K240 | J178 | S |
| 4-0177 | —(CH$_2$)$_3$— | —C(=O)—O— | K240 | J185 | S |
| 4-0178 | —(CH$_2$)$_3$— | —C(=O)—O— | K240 | J191 | S |
| 4-0179 | —(CH$_2$)$_3$— | —C(=O)—O— | K240 | J193 | S |
| 4-0180 | —(CH$_2$)$_3$— | —C(=O)—O— | K240 | J195 | S |
| 4-0181 | —(CH$_2$)$_3$— | —C(=O)—O— | K240 | J197 | S |
| 4-0182 | —(CH$_2$)$_2$— | —C(=O)—O— | K1 | J1 | O |
| 4-0183 | —(CH$_2$)$_2$— | —C(=O)—O— | K1 | J3 | O |
| 4-0184 | —(CH$_2$)$_2$— | —C(=O)—O— | K1 | J6 | O |
| 4-0185 | —(CH$_2$)$_2$— | —C(=O)—O— | K1 | J9 | O |
| 4-0186 | —(CH$_2$)$_2$— | —C(=O)—O— | K1 | J10 | O |
| 4-0187 | —(CH$_2$)$_2$— | —C(=O)—O— | K1 | J14 | O |
| 4-0188 | —(CH$_2$)$_2$— | —C(=O)—O— | K1 | J19 | O |
| 4-0189 | —(CH$_2$)$_2$— | —C(=O)—O— | K1 | J22 | O |
| 4-0190 | —(CH$_2$)$_2$— | —C(=O)—O— | K1 | J25 | O |
| 4-0191 | —(CH$_2$)$_2$— | —C(=O)—O— | K1 | J29 | O |
| 4-0192 | —(CH$_2$)$_2$— | —C(=O)—O— | K1 | J57 | O |

TABLE 167

| Compound No. | -A¹- | -A²- | -G¹-A³-A⁴-G² | -A⁵-R² | X |
|---|---|---|---|---|---|
| 4-0193 | —(CH$_2$)$_2$— | —C(=O)—O— | K1 | J59 | O |
| 4-0194 | —(CH$_2$)$_2$— | —C(=O)—O— | K1 | J70 | O |
| 4-0195 | —(CH$_2$)$_2$— | —C(=O)—O— | K1 | J72 | O |
| 4-0196 | —(CH$_2$)$_2$— | —C(=O)—O— | K1 | J74 | O |
| 4-0197 | —(CH$_2$)$_2$— | —C(=O)—O— | K1 | J75 | O |
| 4-0198 | —(CH$_2$)$_2$— | —C(=O)—O— | K1 | J77 | O |
| 4-0199 | —(CH$_2$)$_2$— | —C(=O)—O— | K1 | J78 | O |
| 4-0200 | —(CH$_2$)$_2$— | —C(=O)—O— | K1 | J126 | O |
| 4-0201 | —(CH$_2$)$_2$— | —C(=O)—O— | K1 | J129 | O |
| 4-0202 | —(CH$_2$)$_2$— | —C(=O)—O— | K1 | J130 | O |
| 4-0203 | —(CH$_2$)$_2$— | —C(=O)—O— | K1 | J138 | O |
| 4-0204 | —(CH$_2$)$_2$— | —C(=O)—O— | K1 | J140 | O |
| 4-0205 | —(CH$_2$)$_2$— | —C(=O)—O— | K1 | J151 | O |
| 4-0206 | —(CH$_2$)$_2$— | —C(=O)—O— | K1 | J165 | O |
| 4-0207 | —(CH$_2$)$_2$— | —C(=O)—O— | K1 | J168 | O |
| 4-0208 | —(CH$_2$)$_2$— | —C(=O)—O— | K1 | J174 | O |
| 4-0209 | —(CH$_2$)$_2$— | —C(=O)—O— | K1 | J176 | O |
| 4-0210 | —(CH$_2$)$_2$— | —C(=O)—O— | K1 | J177 | O |
| 4-0211 | —(CH$_2$)$_2$— | —C(=O)—O— | K1 | J178 | O |
| 4-0212 | —(CH$_2$)$_2$— | —C(=O)—O— | K1 | J185 | O |
| 4-0213 | —(CH$_2$)$_2$— | —C(=O)—O— | K1 | J191 | O |
| 4-0214 | —(CH$_2$)$_2$— | —C(=O)—O— | K1 | J193 | O |
| 4-0215 | —(CH$_2$)$_2$— | —C(=O)—O— | K1 | J195 | O |
| 4-0216 | —(CH$_2$)$_2$— | —C(=O)—O— | K1 | J197 | O |
| 4-0217 | —(CH$_2$)$_2$— | —C(=O)—O— | K5 | J9 | O |
| 4-0218 | —(CH$_2$)$_2$— | —C(=O)—O— | K5 | J140 | O |
| 4-0219 | —(CH$_2$)$_2$— | —C(=O)—O— | K5 | J78 | O |
| 4-0220 | —(CH$_2$)$_2$— | —C(=O)—O— | K5 | J130 | O |
| 4-0221 | —(CH$_2$)$_2$— | —C(=O)—O— | K5 | J138 | O |
| 4-0222 | —(CH$_2$)$_2$— | —C(=O)—O— | K5 | J129 | O |
| 4-0223 | —(CH$_2$)$_2$— | —C(=O)—O— | K11 | J9 | O |
| 4-0224 | —(CH$_2$)$_2$— | —C(=O)—O— | K11 | J140 | O |

TABLE 168

| Compound No. | -A¹- | -A²- | -G¹-A³-A⁴-G² | -A⁵-R² | X |
|---|---|---|---|---|---|
| 4-0225 | —(CH$_2$)$_2$— | —C(=O)—O— | K11 | J78 | O |
| 4-0226 | —(CH$_2$)$_2$— | —C(=O)—O— | K11 | J130 | O |
| 4-0227 | —(CH$_2$)$_2$— | —C(=O)—O— | K11 | J138 | O |
| 4-0228 | —(CH$_2$)$_2$— | —C(=O)—O— | K11 | J129 | O |
| 4-0229 | —(CH$_2$)$_2$— | —C(=O)—O— | K99 | J9 | O |
| 4-0230 | —(CH$_2$)$_2$— | —C(=O)—O— | K99 | J140 | O |
| 4-0231 | —(CH$_2$)$_2$— | —C(=O)—O— | K99 | J78 | O |
| 4-0232 | —(CH$_2$)$_2$— | —C(=O)—O— | K99 | J130 | O |
| 4-0233 | —(CH$_2$)$_2$— | —C(=O)—O— | K99 | J138 | O |
| 4-0234 | —(CH$_2$)$_2$— | —C(=O)—O— | K99 | J129 | O |
| 4-0235 | —(CH$_2$)$_2$— | —C(=O)—O— | K240 | J1 | O |
| 4-0236 | —(CH$_2$)$_2$— | —C(=O)—O— | K240 | J3 | O |
| 4-0237 | —(CH$_2$)$_2$— | —C(=O)—O— | K240 | J6 | O |
| 4-0238 | —(CH$_2$)$_2$— | —C(=O)—O— | K240 | J9 | O |
| 4-0239 | —(CH$_2$)$_2$— | —C(=O)—O— | K240 | J10 | O |
| 4-0240 | —(CH$_2$)$_2$— | —C(=O)—O— | K240 | J14 | O |
| 4-0241 | —(CH$_2$)$_2$— | —C(=O)—O— | K240 | J19 | O |
| 4-0242 | —(CH$_2$)$_2$— | —C(=O)—O— | K240 | J22 | O |
| 4-0243 | —(CH$_2$)$_2$— | —C(=O)—O— | K240 | J25 | O |
| 4-0244 | —(CH$_2$)$_2$— | —C(=O)—O— | K240 | J29 | O |
| 4-0245 | —(CH$_2$)$_2$— | —C(=O)—O— | K240 | J57 | O |
| 4-0246 | —(CH$_2$)$_2$— | —C(=O)—O— | K240 | J59 | O |
| 4-0247 | —(CH$_2$)$_2$— | —C(=O)—O— | K240 | J70 | O |
| 4-0248 | —(CH$_2$)$_2$— | —C(=O)—O— | K240 | J72 | O |
| 4-0249 | —(CH$_2$)$_2$— | —C(=O)—O— | K240 | J74 | O |
| 4-0250 | —(CH$_2$)$_2$— | —C(=O)—O— | K240 | J75 | O |
| 4-0251 | —(CH$_2$)$_2$— | —C(=O)—O— | K240 | J77 | O |
| 4-0252 | —(CH$_2$)$_2$— | —C(=O)—O— | K240 | J78 | O |
| 4-0253 | —(CH$_2$)$_2$— | —C(=O)—O— | K240 | J126 | O |
| 4-0254 | —(CH$_2$)$_2$— | —C(=O)—O— | K240 | J129 | O |
| 4-0255 | —(CH$_2$)$_2$— | —C(=O)—O— | K240 | J130 | O |
| 4-0256 | —(CH$_2$)$_2$— | —C(=O)—O— | K240 | J138 | O |

TABLE 169

| Compound No. | -A¹- | -A²- | -G¹-A³-A⁴-G² | -A⁵-R² | X |
|---|---|---|---|---|---|
| 4-0257 | —(CH₂)₂— | —C(=O)—O— | K240 | J140 | O |
| 4-0258 | —(CH₂)₂— | —C(=O)—O— | K240 | J151 | O |
| 4-0259 | —(CH₂)₂— | —C(=O)—O— | K240 | J165 | O |
| 4-0260 | —(CH₂)₂— | —C(=O)—O— | K240 | J168 | O |
| 4-0261 | —(CH₂)₂— | —C(=O)—O— | K240 | J174 | O |
| 4-0262 | —(CH₂)₂— | —C(=O)—O— | K240 | J176 | O |
| 4-0263 | —(CH₂)₂— | —C(=O)—O— | K240 | J177 | O |
| 4-0264 | —(CH₂)₂— | —C(=O)—O— | K240 | J178 | O |
| 4-0265 | —(CH₂)₂— | —C(=O)—O— | K240 | J185 | O |
| 4-0266 | —(CH₂)₂— | —C(=O)—O— | K240 | J191 | O |
| 4-0267 | —(CH₂)₂— | —C(=O)—O— | K240 | J193 | O |
| 4-0268 | —(CH₂)₂— | —C(=O)—O— | K240 | J195 | O |
| 4-0269 | —(CH₂)₂— | —C(=O)—O— | K240 | J197 | O |
| 4-0270 | —(CH₂)₃— | —C(=O)—O— | K1 | J9 | O |
| 4-0271 | —(CH₂)₃— | —C(=O)—O— | K1 | J140 | O |
| 4-0272 | —(CH₂)₃— | —C(=O)—O— | K1 | J78 | O |
| 4-0273 | —(CH₂)₃— | —C(=O)—O— | K1 | J130 | O |
| 4-0274 | —(CH₂)₃— | —C(=O)—O— | K1 | J138 | O |
| 4-0275 | —(CH₂)₃— | —C(=O)—O— | K1 | J129 | O |
| 4-0276 | —(CH₂)₃— | —C(=O)—O— | K5 | J9 | O |
| 4-0277 | —(CH₂)₃— | —C(=O)—O— | K5 | J140 | O |
| 4-0278 | —(CH₂)₃— | —C(=O)—O— | K5 | J78 | O |
| 4-0279 | —(CH₂)₃— | —C(=O)—O— | K5 | J130 | O |
| 4-0280 | —(CH₂)₃— | —C(=O)—O— | K5 | J138 | O |
| 4-0281 | —(CH₂)₃— | —C(=O)—O— | K5 | J129 | O |
| 4-0282 | —(CH₂)₃— | —C(=O)—O— | K11 | J9 | O |
| 4-0283 | —(CH₂)₃— | —C(=O)—O— | K11 | J140 | O |
| 4-0284 | —(CH₂)₃— | —C(=O)—O— | K11 | J78 | O |
| 4-0285 | —(CH₂)₃— | —C(=O)—O— | K11 | J130 | O |
| 4-0286 | —(CH₂)₃— | —C(=O)—O— | K11 | J138 | O |
| 4-0287 | —(CH₂)₃— | —C(=O)—O— | K11 | J129 | O |
| 4-0288 | —(CH₂)₃— | —C(=O)—O— | K99 | J9 | O |

TABLE 170

| Compound No. | -A¹- | -A²- | -G¹-A³-A⁴-G² | -A⁵-R² | X |
|---|---|---|---|---|---|
| 4-0289 | —(CH₂)₃— | —C(=O)—O— | K99 | J140 | O |
| 4-0290 | —(CH₂)₃— | —C(=O)—O— | K99 | J130 | O |
| 4-0291 | —(CH₂)₃— | —C(=O)—O— | K99 | J138 | O |
| 4-0292 | —(CH₂)₃— | —C(=O)—O— | K99 | J129 | O |
| 4-0293 | —(CH₂)₃— | —C(=O)—O— | K240 | J1 | O |
| 4-0294 | —(CH₂)₃— | —C(=O)—O— | K240 | J3 | O |
| 4-0295 | —(CH₂)₃— | —C(=O)—O— | K240 | J6 | O |
| 4-0296 | —(CH₂)₃— | —C(=O)—O— | K240 | J9 | O |
| 4-0297 | —(CH₂)₃— | —C(=O)—O— | K240 | J10 | O |
| 4-0298 | —(CH₂)₃— | —C(=O)—O— | K240 | J14 | O |
| 4-0299 | —(CH₂)₃— | —C(=O)—O— | K240 | J19 | O |
| 4-0300 | —(CH₂)₃— | —C(=O)—O— | K240 | J22 | O |
| 4-0301 | —(CH₂)₃— | —C(=O)—O— | K240 | J25 | O |
| 4-0302 | —(CH₂)₃— | —C(=O)—O— | K240 | J29 | O |
| 4-0303 | —(CH₂)₃— | —C(=O)—O— | K240 | J57 | O |
| 4-0304 | —(CH₂)₃— | —C(=O)—O— | K240 | J59 | O |
| 4-0305 | —(CH₂)₃— | —C(=O)—O— | K240 | J70 | O |
| 4-0306 | —(CH₂)₃— | —C(=O)—O— | K240 | J72 | O |
| 4-0307 | —(CH₂)₃— | —C(=O)—O— | K240 | J74 | O |
| 4-0308 | —(CH₂)₃— | —C(=O)—O— | K240 | J75 | O |
| 4-0309 | —(CH₂)₃— | —C(=O)—O— | K240 | J77 | O |
| 4-0310 | —(CH₂)₃— | —C(=O)—O— | K240 | J78 | O |
| 4-0311 | —(CH₂)₃— | —C(=O)—O— | K240 | J126 | O |
| 4-0312 | —(CH₂)₃— | —C(=O)—O— | K240 | J129 | O |
| 4-0313 | —(CH₂)₃— | —C(=O)—O— | K240 | J130 | O |
| 4-0314 | —(CH₂)₃— | —C(=O)—O— | K240 | J138 | O |
| 4-0315 | —(CH₂)₃— | —C(=O)—O— | K240 | J140 | O |
| 4-0316 | —(CH₂)₃— | —C(=O)—O— | K240 | J151 | O |
| 4-0317 | —(CH₂)₃— | —C(=O)—O— | K240 | J165 | O |
| 4-0318 | —(CH₂)₃— | —C(=O)—O— | K240 | J168 | O |
| 4-0319 | —(CH₂)₃— | —C(=O)—O— | K240 | J174 | O |
| 4-0320 | —(CH₂)₃— | —C(=O)—O— | K240 | J176 | O |

TABLE 171

| Compound No. | -A¹- | -A²- | -G¹-A³-A⁴-G² | -A⁵-R² | X |
|---|---|---|---|---|---|
| 4-0321 | —(CH₂)₃— | —C(=O)—O— | K240 | J177 | O |
| 4-0322 | —(CH₂)₃— | —C(=O)—O— | K240 | J178 | O |
| 4-0323 | —(CH₂)₃— | —C(=O)—O— | K240 | J185 | O |
| 4-0324 | —(CH₂)₃— | —C(=O)—O— | K240 | J191 | O |
| 4-0325 | —(CH₂)₃— | —C(=O)—O— | K240 | J193 | O |
| 4-0326 | —(CH₂)₃— | —C(=O)—O— | K240 | J195 | O |
| 4-0327 | —(CH₂)₃— | —C(=O)—O— | K240 | J197 | O |
| 4-0328 | —(CH₂)₂— | —C(=O)—O— | K2 | J126 | O |
| 4-0329 | —(CH₂)₂— | —C(=O)—O— | K2 | J126 | S |

TABLE 172

| Compound No. | -A¹- | -A²- | -G¹-A³-A⁴-G² | -A⁵-R² | X |
|---|---|---|---|---|---|
| 5-0001 | —(CH₂)₂— | —C(=O)— | K1 | J9 | S |
| 5-0002 | —(CH₂)₂— | —C(=O)— | K1 | J10 | S |
| 5-0003 | —(CH₂)₂— | —C(=O)— | K1 | J51 | O |
| 5-0004 | —(CH₂)₂— | —C(=O)— | K1 | J78 | S |
| 5-0005 | —(CH₂)₂— | —C(=O)— | K8 | J9 | S |
| 5-0006 | —(CH₂)₂— | —C(=O)— | K11 | J9 | S |
| 5-0007 | —(CH₂)₂— | —C(=O)— | K24 | J70 | S |
| 5-0008 | —(CH₂)₂— | —C(=O)— | K34 | J78 | S |
| 5-0009 | —(CH₂)₂— | —C(=O)— | K34 | J131 | S |
| 5-0010 | —(CH₂)₂— | —C(=O)— | K36 | J128 | S |
| 5-0011 | —(CH₂)₂— | —C(=O)— | K36 | J149 | S |
| 5-0012 | —(CH₂)₂— | —C(=O)— | K48 | J126 | S |
| 5-0013 | —(CH₂)₂— | —C(=O)— | K48 | J140 | O |
| 5-0014 | —(CH₂)₂— | —C(=O)— | K74 | J19 | S |
| 5-0015 | —(CH₂)₂— | —C(=O)— | K74 | J70 | O |
| 5-0016 | —(CH₂)₂— | —C(=O)— | K99 | J9 | S |
| 5-0017 | —(CH₂)₂— | —C(=O)— | K101 | J30 | S |
| 5-0018 | —(CH₂)₂— | —C(=O)— | K107 | J19 | S |
| 5-0019 | —(CH₂)₂— | —C(=O)— | K110 | J51 | S |
| 5-0020 | —(CH₂)₂— | —C(=O)— | K110 | J78 | O |
| 5-0021 | —(CH₂)₂— | —C(=O)— | K110 | J131 | S |
| 5-0022 | —(CH₂)₂— | —C(=O)— | K160 | J126 | S |
| 5-0023 | —(CH₂)₂— | —C(=O)— | K167 | J70 | S |
| 5-0024 | —(CH₂)₂— | —C(=O)— | K175 | J10 | S |
| 5-0025 | —(CH₂)₂— | —C(=O)— | K175 | J131 | O |
| 5-0026 | —(CH₂)₂— | —C(=O)— | K176 | J128 | S |
| 5-0027 | —(CH₂)₂— | —C(=O)— | K176 | J149 | S |
| 5-0028 | —(CH₂)₂— | —C(=O)— | K180 | J126 | O |
| 5-0029 | —(CH₂)₂— | —C(=O)— | K180 | J140 | S |
| 5-0030 | —(CH₂)₂— | —C(=O)— | K183 | J19 | O |
| 5-0031 | —(CH₂)₂— | —C(=O)— | K185 | J30 | S |
| 5-0032 | —(CH₂)₂— | —C(=O)— | K189 | J3 | S |

TABLE 173

| Compound No. | -A¹- | -A²- | -G¹-A³-A⁴-G² | -A⁵-R² | X |
|---|---|---|---|---|---|
| 5-0033 | —(CH₂)₂— | —C(=O)— | K189 | J30 | S |
| 5-0034 | —(CH₂)₂— | —C(=O)— | K190 | J78 | S |
| 5-0035 | —(CH₂)₂— | —C(=O)— | K190 | J131 | S |
| 5-0036 | —(CH₂)₂— | —C(=O)— | K193 | J128 | O |
| 5-0037 | —(CH₂)₂— | —C(=O)— | K193 | J149 | S |
| 5-0038 | —(CH₂)₂— | —C(=O)— | K205 | J9 | S |
| 5-0039 | —(CH₂)₂— | —C(=O)— | K205 | J126 | S |
| 5-0040 | —(CH₂)₂— | —C(=O)— | K205 | J140 | O |
| 5-0041 | —(CH₂)₂— | —C(=O)— | K206 | J9 | S |
| 5-0042 | —(CH₂)₂— | —C(=O)— | K207 | J19 | S |
| 5-0043 | —(CH₂)₂— | —C(=O)— | K207 | J70 | S |
| 5-0044 | —(CH₂)₂— | —C(=O)— | K215 | J10 | S |
| 5-0045 | —(CH₂)₂— | —C(=O)— | K215 | J51 | S |
| 5-0046 | —(CH₂)₂— | —C(=O)— | K217 | J128 | S |
| 5-0047 | —(CH₂)₂— | —C(=O)— | K217 | J149 | O |
| 5-0048 | —(CH₂)₂— | —C(=O)— | K229 | J140 | S |
| 5-0049 | —(CH₂)₃— | —C(=O)— | K1 | J9 | S |
| 5-0050 | —(CH₂)₃— | —C(=O)— | K1 | J131 | O |

TABLE 173-continued

| Compound No. | -A¹- | -A²- | -G¹-A³-A⁴-G² | -A⁵-R² | X |
|---|---|---|---|---|---|
| 5-0051 | —(CH₂)₃— | —C(=O)— | K8 | J9 | S |
| 5-0052 | —(CH₂)₃— | —C(=O)— | K8 | J128 | O |
| 5-0053 | —(CH₂)₃— | —C(=O)— | K8 | J149 | S |
| 5-0054 | —(CH₂)₃— | —C(=O)— | K11 | J9 | S |
| 5-0055 | —(CH₂)₃— | —C(=O)— | K13 | J126 | S |
| 5-0056 | —(CH₂)₃— | —C(=O)— | K13 | J140 | S |
| 5-0057 | —(CH₂)₃— | —C(=O)— | K24 | J19 | O |
| 5-0058 | —(CH₂)₃— | —C(=O)— | K34 | J10 | S |
| 5-0059 | —(CH₂)₃— | —C(=O)— | K34 | J51 | S |
| 5-0060 | —(CH₂)₃— | —C(=O)— | K99 | J9 | S |
| 5-0061 | —(CH₂)₃— | —C(=O)— | K101 | J3 | S |
| 5-0062 | —(CH₂)₃— | —C(=O)— | K107 | J70 | O |
| 5-0063 | —(CH₂)₃— | —C(=O)— | K110 | J10 | O |
| 5-0064 | —(CH₂)₃— | —C(=O)— | K150 | J128 | S |

TABLE 174

| Compound No. | -A¹- | -A²- | -G¹-A³-A⁴-G² | -A⁵-R² | X |
|---|---|---|---|---|---|
| 5-0065 | —(CH₂)₃— | —C(=O)— | K150 | J149 | O |
| 5-0066 | —(CH₂)₃— | —C(=O)— | K160 | J140 | S |
| 5-0067 | —(CH₂)₃— | —C(=O)— | K167 | J19 | S |
| 5-0068 | —(CH₂)₃— | —C(=O)— | K175 | J51 | S |
| 5-0069 | —(CH₂)₃— | —C(=O)— | K175 | J78 | S |
| 5-0070 | —(CH₂)₃— | —C(=O)— | K183 | J70 | S |
| 5-0071 | —(CH₂)₃— | —C(=O)— | K185 | J3 | S |
| 5-0072 | —(CH₂)₃— | —C(=O)— | K190 | J10 | S |
| 5-0073 | —(CH₂)₃— | —C(=O)— | K190 | J51 | O |
| 5-0074 | —(CH₂)₃— | —C(=O)— | K205 | J9 | S |
| 5-0075 | —(CH₂)₃— | —C(=O)— | K215 | J78 | O |
| 5-0076 | —(CH₂)₃— | —C(=O)— | K215 | J131 | S |
| 5-0077 | —(CH₂)₃— | —C(=O)— | K229 | J126 | S |
| 5-0078 | —(CH₂)₂— | —C(=O)— | K1 | J126 | S |
| 5-0079 | —(CH₂)₂— | —C(=O)— | K1 | J129 | S |
| 5-0080 | —(CH₂)₂— | —C(=O)— | K1 | J130 | S |
| 5-0081 | —(CH₂)₂— | —C(=O)— | K1 | J138 | S |
| 5-0082 | —(CH₂)₂— | —C(=O)— | K1 | J140 | S |
| 5-0083 | —(CH₂)₂— | —C(=O)— | K2 | J9 | S |
| 5-0084 | —(CH₂)₂— | —C(=O)— | K2 | J126 | S |
| 5-0085 | —(CH₂)₂— | —C(=O)— | K2 | J129 | S |
| 5-0086 | —(CH₂)₂— | —C(=O)— | K2 | J130 | S |
| 5-0087 | —(CH₂)₂— | —C(=O)— | K2 | J138 | S |
| 5-0088 | —(CH₂)₂— | —C(=O)— | K2 | J140 | S |
| 5-0089 | —(CH₂)₂— | —C(=O)— | K3 | J9 | S |
| 5-0090 | —(CH₂)₂— | —C(=O)— | K3 | J126 | S |
| 5-0091 | —(CH₂)₂— | —C(=O)— | K3 | J129 | S |
| 5-0092 | —(CH₂)₂— | —C(=O)— | K3 | J130 | S |
| 5-0093 | —(CH₂)₂— | —C(=O)— | K3 | J138 | S |
| 5-0094 | —(CH₂)₂— | —C(=O)— | K3 | J140 | S |
| 5-0095 | —(CH₂)₂— | —C(=O)— | K4 | J9 | S |
| 5-0096 | —(CH₂)₂— | —C(=O)— | K4 | J126 | S |

TABLE 175

| Compound No. | -A¹- | -A²- | -G¹-A³-A⁴-G² | -A⁵-R² | X |
|---|---|---|---|---|---|
| 5-0097 | —(CH₂)₂— | —C(=O)— | K4 | J129 | S |
| 5-0098 | —(CH₂)₂— | —C(=O)— | K4 | J130 | S |
| 5-0099 | —(CH₂)₂— | —C(=O)— | K4 | J138 | S |
| 5-0100 | —(CH₂)₂— | —C(=O)— | K4 | J140 | S |
| 5-0101 | —(CH₂)₂— | —C(=O)— | K11 | J126 | S |
| 5-0102 | —(CH₂)₂— | —C(=O)— | K11 | J129 | S |
| 5-0103 | —(CH₂)₂— | —C(=O)— | K11 | J130 | S |
| 5-0104 | —(CH₂)₂— | —C(=O)— | K11 | J138 | S |
| 5-0105 | —(CH₂)₂— | —C(=O)— | K11 | J140 | S |
| 5-0106 | —(CH₂)₂— | —C(=O)— | K99 | J126 | S |
| 5-0107 | —(CH₂)₂— | —C(=O)— | K99 | J129 | S |
| 5-0108 | —(CH₂)₂— | —C(=O)— | K99 | J130 | S |
| 5-0109 | —(CH₂)₂— | —C(=O)— | K99 | J138 | S |

TABLE 175-continued

| Compound No. | -A¹- | -A²- | -G¹-A³-A⁴-G² | -A⁵-R² | X |
|---|---|---|---|---|---|
| 5-0110 | —(CH₂)₂— | —C(=O)— | K99 | J140 | S |
| 5-0111 | —(CH₂)₂— | —C(=O)— | K1 | J9 | O |
| 5-0112 | —(CH₂)₂— | —C(=O)— | K1 | J126 | O |
| 5-0113 | —(CH₂)₂— | —C(=O)— | K1 | J129 | O |
| 5-0114 | —(CH₂)₂— | —C(=O)— | K1 | J130 | O |
| 5-0115 | —(CH₂)₂— | —C(=O)— | K1 | J138 | O |
| 5-0116 | —(CH₂)₂— | —C(=O)— | K1 | J140 | O |
| 5-0117 | —(CH₂)₂— | —C(=O)— | K2 | J9 | O |
| 5-0118 | —(CH₂)₂— | —C(=O)— | K2 | J126 | O |
| 5-0119 | —(CH₂)₂— | —C(=O)— | K2 | J129 | O |
| 5-0120 | —(CH₂)₂— | —C(=O)— | K2 | J130 | O |
| 5-0121 | —(CH₂)₂— | —C(=O)— | K2 | J138 | O |
| 5-0122 | —(CH₂)₂— | —C(=O)— | K2 | J140 | O |
| 5-0123 | —(CH₂)₂— | —C(=O)— | K3 | J9 | O |
| 5-0124 | —(CH₂)₂— | —C(=O)— | K3 | J126 | O |
| 5-0125 | —(CH₂)₂— | —C(=O)— | K3 | J129 | O |
| 5-0126 | —(CH₂)₂— | —C(=O)— | K3 | J130 | O |
| 5-0127 | —(CH₂)₂— | —C(=O)— | K3 | J138 | O |
| 5-0128 | —(CH₂)₂— | —C(=O)— | K3 | J140 | O |

TABLE 176

| Compound No. | -A¹- | -A²- | -G¹-A³-A⁴-G² | -A⁵-R² | X |
|---|---|---|---|---|---|
| 5-0129 | —(CH₂)₂— | —C(=O)— | K4 | J9 | O |
| 5-0130 | —(CH₂)₂— | —C(=O)— | K4 | J126 | O |
| 5-0131 | —(CH₂)₂— | —C(=O)— | K4 | J129 | O |
| 5-0132 | —(CH₂)₂— | —C(=O)— | K4 | J130 | O |
| 5-0133 | —(CH₂)₂— | —C(=O)— | K4 | J138 | O |
| 5-0134 | —(CH₂)₂— | —C(=O)— | K4 | J140 | O |
| 5-0135 | —(CH₂)₂— | —C(=O)— | K11 | J9 | O |
| 5-0136 | —(CH₂)₂— | —C(=O)— | K11 | J126 | O |
| 5-0137 | —(CH₂)₂— | —C(=O)— | K11 | J129 | O |
| 5-0138 | —(CH₂)₂— | —C(=O)— | K11 | J130 | O |
| 5-0139 | —(CH₂)₂— | —C(=O)— | K11 | J138 | O |
| 5-0140 | —(CH₂)₂— | —C(=O)— | K11 | J140 | O |
| 5-0141 | —(CH₂)₂— | —C(=O)— | K99 | J9 | O |
| 5-0142 | —(CH₂)₂— | —C(=O)— | K99 | J126 | O |
| 5-0143 | —(CH₂)₂— | —C(=O)— | K99 | J129 | O |
| 5-0144 | —(CH₂)₂— | —C(=O)— | K99 | J130 | O |
| 5-0145 | —(CH₂)₂— | —C(=O)— | K99 | J138 | O |
| 5-0146 | —(CH₂)₂— | —C(=O)— | K99 | J140 | O |
| 5-0147 | —(CH₂)₃— | —C(=O)— | K1 | J9 | O |
| 5-0148 | —(CH₂)₃— | —C(=O)— | K1 | J126 | O |
| 5-0149 | —(CH₂)₃— | —C(=O)— | K1 | J129 | O |
| 5-0150 | —(CH₂)₃— | —C(=O)— | K1 | J130 | O |
| 5-0151 | —(CH₂)₃— | —C(=O)— | K1 | J138 | O |
| 5-0152 | —(CH₂)₃— | —C(=O)— | K1 | J140 | O |
| 5-0153 | —(CH₂)₃— | —C(=O)— | K2 | J9 | O |
| 5-0154 | —(CH₂)₃— | —C(=O)— | K2 | J126 | O |
| 5-0155 | —(CH₂)₃— | —C(=O)— | K2 | J129 | O |
| 5-0156 | —(CH₂)₃— | —C(=O)— | K2 | J130 | O |
| 5-0157 | —(CH₂)₃— | —C(=O)— | K2 | J138 | O |
| 5-0158 | —(CH₂)₃— | —C(=O)— | K2 | J140 | O |
| 5-0159 | —(CH₂)₃— | —C(=O)— | K3 | J9 | O |
| 5-0160 | —(CH₂)₃— | —C(=O)— | K3 | J126 | O |

TABLE 177

| Compound No. | -A¹- | -A²- | -G¹-A³-A⁴-G² | -A⁵-R² | X |
|---|---|---|---|---|---|
| 5-0161 | —(CH₂)₃— | —C(=O)— | K3 | J129 | O |
| 5-0162 | —(CH₂)₃— | —C(=O)— | K3 | J130 | O |
| 5-0163 | —(CH₂)₃— | —C(=O)— | K3 | J138 | O |
| 5-0164 | —(CH₂)₃— | —C(=O)— | K3 | J140 | O |
| 5-0165 | —(CH₂)₃— | —C(=O)— | K4 | J9 | S |
| 5-0166 | —(CH₂)₃— | —C(=O)— | K4 | J126 | S |
| 5-0167 | —(CH₂)₃— | —C(=O)— | K4 | J129 | S |
| 5-0168 | —(CH₂)₃— | —C(=O)— | K4 | J130 | S |

TABLE 177-continued

| Compound No. | -A¹- | -A²- | -G¹-A³-A⁴-G² | -A⁵-R² | X |
|---|---|---|---|---|---|
| 5-0169 | —(CH₂)₃— | —C(=O)— | K4 | J138 | S |
| 5-0170 | —(CH₂)₃— | —C(=O)— | K4 | J140 | S |
| 5-0171 | —(CH₂)₃— | —C(=O)— | K11 | J126 | S |
| 5-0172 | —(CH₂)₃— | —C(=O)— | K11 | J129 | S |
| 5-0173 | —(CH₂)₃— | —C(=O)— | K11 | J130 | S |
| 5-0174 | —(CH₂)₃— | —C(=O)— | K11 | J138 | S |
| 5-0175 | —(CH₂)₃— | —C(=O)— | K11 | J140 | S |
| 5-0176 | —(CH₂)₃— | —C(=O)— | K99 | J126 | S |
| 5-0177 | —(CH₂)₃— | —C(=O)— | K99 | J129 | S |
| 5-0178 | —(CH₂)₃— | —C(=O)— | K99 | J130 | S |
| 5-0179 | —(CH₂)₃— | —C(=O)— | K99 | J138 | S |
| 5-0180 | —(CH₂)₃— | —C(=O)— | K99 | J140 | S |
| 5-0181 | —(CH₂)₂— | —C(=O)— | K699 | J9 | S |

TABLE 178

| Compound No. | -A¹- | -A²- | -G¹-A³-A⁴-G² | -A⁵-R² | X |
|---|---|---|---|---|---|
| 6-0001 | single bond | single bond | K1 | N1 | O |
| 6-0002 | single bond | single bond | K1 | N1 | S |
| 6-0003 | single bond | single bond | K1 | N2 | O |
| 6-0004 | single bond | single bond | K1 | N2 | S |
| 6-0005 | single bond | single bond | K1 | N9 | S |
| 6-0006 | single bond | single bond | K1 | N12 | S |
| 6-0007 | single bond | single bond | K1 | N24 | S |
| 6-0008 | single bond | single bond | K1 | N40 | S |
| 6-0009 | single bond | single bond | K1 | N115 | S |
| 6-0010 | single bond | single bond | K1 | N128 | S |
| 6-0011 | single bond | single bond | K1 | N130 | S |
| 6-0012 | single bond | single bond | K1 | N140 | S |
| 6-0013 | single bond | single bond | K1 | N149 | S |
| 6-0014 | single bond | single bond | K1 | N150 | S |
| 6-0015 | single bond | single bond | K2 | N9 | S |
| 6-0016 | single bond | single bond | K2 | N24 | S |
| 6-0017 | single bond | single bond | K2 | N69 | S |
| 6-0018 | single bond | single bond | K2 | N115 | S |
| 6-0019 | single bond | single bond | K2 | N128 | S |
| 6-0020 | single bond | single bond | K2 | N140 | S |
| 6-0021 | single bond | single bond | K2 | N149 | S |
| 6-0022 | single bond | single bond | K2 | N150 | S |
| 6-0023 | single bond | single bond | K11 | N1 | S |
| 6-0024 | single bond | single bond | K11 | N2 | S |
| 6-0025 | single bond | single bond | K11 | N3 | S |
| 6-0026 | single bond | single bond | K11 | N4 | S |
| 6-0027 | single bond | single bond | K11 | N5 | S |
| 6-0028 | single bond | single bond | K11 | N24 | S |
| 6-0029 | single bond | single bond | K11 | N69 | S |
| 6-0030 | single bond | single bond | K11 | N115 | S |
| 6-0031 | single bond | single bond | K11 | N128 | S |
| 6-0032 | single bond | single bond | K11 | N140 | S |

TABLE 179

| Compound No. | -A¹- | -A²- | -G¹-A³-A⁴-G² | -A⁵-R² | X |
|---|---|---|---|---|---|
| 6-0033 | single bond | single bond | K11 | N149 | S |
| 6-0034 | single bond | single bond | K11 | N150 | S |
| 6-0035 | single bond | single bond | K99 | N2 | S |
| 6-0036 | single bond | single bond | K99 | N4 | S |
| 6-0037 | single bond | single bond | K99 | N9 | S |
| 6-0038 | single bond | single bond | K99 | N24 | S |
| 6-0039 | single bond | single bond | K99 | N69 | S |
| 6-0040 | single bond | single bond | K99 | N115 | S |
| 6-0041 | single bond | single bond | K99 | N130 | S |
| 6-0042 | single bond | single bond | K99 | N140 | S |
| 6-0043 | single bond | single bond | K99 | N149 | S |
| 6-0044 | single bond | single bond | K99 | N150 | S |
| 6-0045 | single bond | single bond | K103 | N4 | S |
| 6-0046 | single bond | single bond | K103 | N9 | S |

TABLE 179-continued

| Compound No. | -A¹- | -A²- | -G¹-A³-A⁴-G² | -A⁵-R² | X |
|---|---|---|---|---|---|
| 6-0047 | single bond | single bond | K103 | N128 | S |
| 6-0048 | single bond | single bond | K103 | N140 | S |
| 6-0049 | single bond | single bond | K103 | N149 | S |
| 6-0050 | single bond | single bond | K240 | N1 | S |
| 6-0051 | single bond | single bond | K240 | N2 | S |
| 6-0052 | single bond | single bond | K240 | N3 | S |
| 6-0053 | single bond | single bond | K240 | N4 | S |
| 6-0054 | single bond | single bond | K240 | N5 | S |
| 6-0055 | single bond | single bond | K240 | N69 | S |
| 6-0056 | single bond | single bond | K240 | N115 | S |
| 6-0057 | single bond | single bond | K240 | N128 | S |
| 6-0058 | single bond | single bond | K240 | N130 | S |
| 6-0059 | single bond | single bond | K240 | N140 | S |
| 6-0060 | single bond | single bond | K240 | N145 | S |
| 6-0061 | single bond | single bond | K240 | N149 | S |
| 6-0062 | single bond | single bond | K240 | N150 | S |
| 6-0063 | single bond | single bond | K240 | N151 | S |
| 6-0064 | single bond | single bond | K240 | N152 | S |

TABLE 180

| Compound No. | -A¹- | -A²- | -G¹-A³-A⁴-G² | -A⁵-R² | X |
|---|---|---|---|---|---|
| 6-0065 | single bond | single bond | K240 | N153 | S |
| 6-0066 | single bond | single bond | K240 | N154 | S |
| 6-0067 | single bond | single bond | K240 | N150 | O |
| 6-0068 | —(CH₂)₂— | —O— | K1 | N1 | O |
| 6-0069 | —(CH₂)₂— | —O— | K1 | N1 | S |
| 6-0070 | —(CH₂)₂— | —O— | K4 | N2 | S |
| 6-0071 | —(CH₂)₂— | —O— | K11 | N2 | S |
| 6-0072 | —(CH₂)₂— | —O— | K99 | N2 | S |
| 6-0073 | —(CH₂)₂— | —O— | K1 | N3 | O |
| 6-0074 | —(CH₂)₂— | —O— | K1 | N3 | S |
| 6-0075 | —(CH₂)₂— | —O— | K4 | N3 | S |
| 6-0076 | —(CH₂)₂— | —O— | K11 | N3 | S |
| 6-0077 | —(CH₂)₂— | —O— | K99 | N3 | S |
| 6-0078 | —(CH₂)₂— | —O— | K1 | N4 | O |
| 6-0079 | —(CH₂)₂— | —O— | K1 | N4 | S |
| 6-0080 | —(CH₂)₂— | —O— | K4 | N4 | S |
| 6-0081 | —(CH₂)₂— | —O— | K99 | N4 | S |
| 6-0082 | —(CH₂)₂— | —O— | K1 | N9 | O |
| 6-0083 | —(CH₂)₂— | —O— | K1 | N9 | S |
| 6-0084 | —(CH₂)₂— | —O— | K1 | N10 | S |
| 6-0085 | —(CH₂)₂— | —O— | K1 | N11 | S |
| 6-0086 | —(CH₂)₂— | —O— | K1 | N12 | S |
| 6-0087 | —(CH₂)₂— | —O— | K1 | N12 | O |
| 6-0088 | —(CH₂)₂— | —O— | K1 | N13 | S |
| 6-0089 | —(CH₂)₂— | —O— | K1 | N14 | S |
| 6-0090 | —(CH₂)₂— | —O— | K1 | N15 | S |
| 6-0091 | —(CH₂)₂— | —O— | K1 | N16 | S |
| 6-0092 | —(CH₂)₂— | —O— | K1 | N17 | S |
| 6-0093 | —(CH₂)₂— | —O— | K1 | N18 | S |
| 6-0094 | —(CH₂)₂— | —O— | K1 | N19 | S |
| 6-0095 | —(CH₂)₂— | —O— | K1 | N20 | S |
| 6-0096 | —(CH₂)₂— | —O— | K1 | N21 | S |

TABLE 181

| Compound No. | -A¹- | -A²- | -G¹-A³-A⁴-G² | -A⁵-R² | X |
|---|---|---|---|---|---|
| 6-0097 | —(CH₂)₂— | —O— | K1 | N22 | S |
| 6-0098 | —(CH₂)₂— | —O— | K1 | N23 | S |
| 6-0099 | —(CH₂)₂— | —O— | K1 | N24 | O |
| 6-0100 | —(CH₂)₂— | —O— | K1 | N24 | S |
| 6-0101 | —(CH₂)₂— | —O— | K2 | N24 | S |
| 6-0102 | —(CH₂)₂— | —O— | K4 | N24 | S |
| 6-0103 | —(CH₂)₂— | —O— | K11 | N24 | S |
| 6-0104 | —(CH₂)₂— | —O— | K99 | N24 | S |
| 6-0105 | —(CH₂)₂— | —O— | K1 | N25 | S |

TABLE 181-continued

| Compound No. | -A$^1$- | -A$^2$- | -G$^1$-A$^3$-A$^4$-G$^2$ | -A$^5$-R$^2$ | X |
|---|---|---|---|---|---|
| 6-0106 | —(CH$_2$)$_2$— | —O— | K1 | N26 | S |
| 6-0107 | —(CH$_2$)$_2$— | —O— | K1 | N27 | S |
| 6-0108 | —(CH$_2$)$_2$— | —O— | K1 | N28 | S |
| 6-0109 | —(CH$_2$)$_2$— | —O— | K1 | N29 | S |
| 6-0110 | —(CH$_2$)$_2$— | —O— | K1 | N30 | S |
| 6-0111 | —(CH$_2$)$_2$— | —O— | K1 | N31 | S |
| 6-0112 | —(CH$_2$)$_2$— | —O— | K1 | N32 | S |
| 6-0113 | —(CH$_2$)$_2$— | —O— | K1 | N33 | S |
| 6-0114 | —(CH$_2$)$_2$— | —O— | K1 | N34 | S |
| 6-0115 | —(CH$_2$)$_2$— | —O— | K1 | N35 | S |
| 6-0116 | —(CH$_2$)$_2$— | —O— | K1 | N36 | S |
| 6-0117 | —(CH$_2$)$_2$— | —O— | K1 | N37 | S |
| 6-0118 | —(CH$_2$)$_2$— | —O— | K1 | N38 | S |
| 6-0119 | —(CH$_2$)$_2$— | —O— | K1 | N39 | S |
| 6-0120 | —(CH$_2$)$_2$— | —O— | K1 | N40 | S |
| 6-0121 | —(CH$_2$)$_2$— | —O— | K1 | N41 | S |
| 6-0122 | —(CH$_2$)$_2$— | —O— | K1 | N42 | S |
| 6-0123 | —(CH$_2$)$_2$— | —O— | K1 | N43 | S |
| 6-0124 | —(CH$_2$)$_2$— | —O— | K1 | N44 | S |
| 6-0125 | —(CH$_2$)$_2$— | —O— | K1 | N45 | S |
| 6-0126 | —(CH$_2$)$_2$— | —O— | K1 | N46 | S |
| 6-0127 | —(CH$_2$)$_2$— | —O— | K1 | N47 | S |
| 6-0128 | —(CH$_2$)$_2$— | —O— | K1 | N48 | S |

TABLE 182

| Compound No. | -A$^1$- | -A$^2$- | -G$^1$-A$^3$-A$^4$-G$^2$ | -A$^5$-R$^2$ | X |
|---|---|---|---|---|---|
| 6-0129 | —(CH$_2$)$_2$— | —O— | K1 | N49 | S |
| 6-0130 | —(CH$_2$)$_2$— | —O— | K1 | N50 | S |
| 6-0131 | —(CH$_2$)$_2$— | —O— | K1 | N51 | S |
| 6-0132 | —(CH$_2$)$_2$— | —O— | K1 | N52 | S |
| 6-0133 | —(CH$_2$)$_2$— | —O— | K1 | N53 | S |
| 6-0134 | —(CH$_2$)$_2$— | —O— | K1 | N54 | S |
| 6-0135 | —(CH$_2$)$_2$— | —O— | K1 | N55 | S |
| 6-0136 | —(CH$_2$)$_2$— | —O— | K1 | N56 | S |
| 6-0137 | —(CH$_2$)$_2$— | —O— | K1 | N57 | S |
| 6-0138 | —(CH$_2$)$_2$— | —O— | K1 | N58 | S |
| 6-0139 | —(CH$_2$)$_2$— | —O— | K1 | N59 | S |
| 6-0140 | —(CH$_2$)$_2$— | —O— | K1 | N60 | S |
| 6-0141 | —(CH$_2$)$_2$— | —O— | K1 | N61 | S |
| 6-0142 | —(CH$_2$)$_2$— | —O— | K1 | N62 | O |
| 6-0143 | —(CH$_2$)$_2$— | —O— | K1 | N63 | S |
| 6-0144 | —(CH$_2$)$_2$— | —O— | K1 | N64 | S |
| 6-0145 | —(CH$_2$)$_2$— | —O— | K1 | N65 | S |
| 6-0146 | —(CH$_2$)$_2$— | —O— | K1 | N66 | S |
| 6-0147 | —(CH$_2$)$_2$— | —O— | K1 | N67 | S |
| 6-0148 | —(CH$_2$)$_2$— | —O— | K1 | N68 | S |
| 6-0149 | —(CH$_2$)$_2$— | —O— | K1 | N69 | S |
| 6-0150 | —(CH$_2$)$_2$— | —O— | K1 | N70 | S |
| 6-0151 | —(CH$_2$)$_2$— | —O— | K1 | N71 | S |
| 6-0152 | —(CH$_2$)$_2$— | —O— | K1 | N72 | S |
| 6-0153 | —(CH$_2$)$_2$— | —O— | K1 | N73 | S |
| 6-0154 | —(CH$_2$)$_2$— | —O— | K1 | N74 | S |
| 6-0155 | —(CH$_2$)$_2$— | —O— | K1 | N75 | S |
| 6-0156 | —(CH$_2$)$_2$— | —O— | K1 | N76 | S |
| 6-0157 | —(CH$_2$)$_2$— | —O— | K1 | N77 | S |
| 6-0158 | —(CH$_2$)$_2$— | —O— | K1 | N78 | S |
| 6-0159 | —(CH$_2$)$_2$— | —O— | K1 | N79 | S |
| 6-0160 | —(CH$_2$)$_2$— | —O— | K1 | N80 | S |

TABLE 183

| Compound No. | -A$^1$- | -A$^2$- | -G$^1$-A$^3$-A$^4$-G$^2$ | -A$^5$-R$^2$ | X |
|---|---|---|---|---|---|
| 6-0161 | —(CH$_2$)$_2$— | —O— | K1 | N81 | S |
| 6-0162 | —(CH$_2$)$_2$— | —O— | K1 | N82 | S |
| 6-0163 | —(CH$_2$)$_2$— | —O— | K1 | N83 | S |
| 6-0164 | —(CH$_2$)$_2$— | —O— | K1 | N84 | S |

TABLE 183-continued

| Compound No. | -A$^1$- | -A$^2$- | -G$^1$-A$^3$-A$^4$-G$^2$ | -A$^5$-R$^2$ | X |
|---|---|---|---|---|---|
| 6-0165 | —(CH$_2$)$_2$— | —O— | K1 | N85 | S |
| 6-0166 | —(CH$_2$)$_2$— | —O— | K1 | N86 | S |
| 6-0167 | —(CH$_2$)$_2$— | —O— | K1 | N87 | S |
| 6-0168 | —(CH$_2$)$_2$— | —O— | K1 | N88 | S |
| 6-0169 | —(CH$_2$)$_2$— | —O— | K1 | N89 | S |
| 6-0170 | —(CH$_2$)$_2$— | —O— | K1 | N90 | S |
| 6-0171 | —(CH$_2$)$_2$— | —O— | K1 | N91 | S |
| 6-0172 | —(CH$_2$)$_2$— | —O— | K1 | N92 | S |
| 6-0173 | —(CH$_2$)$_2$— | —O— | K1 | N93 | S |
| 6-0174 | —(CH$_2$)$_2$— | —O— | K1 | N94 | S |
| 6-0175 | —(CH$_2$)$_2$— | —O— | K1 | N95 | O |
| 6-0176 | —(CH$_2$)$_2$— | —O— | K1 | N96 | S |
| 6-0177 | —(CH$_2$)$_2$— | —O— | K1 | N97 | S |
| 6-0178 | —(CH$_2$)$_2$— | —O— | K1 | N98 | S |
| 6-0179 | —(CH$_2$)$_2$— | —O— | K1 | N99 | S |
| 6-0180 | —(CH$_2$)$_2$— | —O— | K1 | N100 | S |
| 6-0181 | —(CH$_2$)$_2$— | —O— | K1 | N101 | S |
| 6-0182 | —(CH$_2$)$_2$— | —O— | K1 | N102 | S |
| 6-0183 | —(CH$_2$)$_2$— | —O— | K1 | N103 | S |
| 6-0184 | —(CH$_2$)$_2$— | —O— | K1 | N104 | S |
| 6-0185 | —(CH$_2$)$_2$— | —O— | K1 | N105 | S |
| 6-0186 | —(CH$_2$)$_2$— | —O— | K1 | N106 | S |
| 6-0187 | —(CH$_2$)$_2$— | —O— | K1 | N107 | S |
| 6-0188 | —(CH$_2$)$_2$— | —O— | K1 | N108 | S |
| 6-0189 | —(CH$_2$)$_2$— | —O— | K1 | N109 | S |
| 6-0190 | —(CH$_2$)$_2$— | —O— | K1 | N110 | S |
| 6-0191 | —(CH$_2$)$_2$— | —O— | K1 | N111 | S |
| 6-0192 | —(CH$_2$)$_2$— | —O— | K1 | N112 | S |

TABLE 184

| Compound No. | -A$^1$- | -A$^2$- | -G$^1$-A$^3$-A$^4$-G$^2$ | -A$^5$-R$^2$ | X |
|---|---|---|---|---|---|
| 6-0193 | —(CH$_2$)$_2$— | —O— | K1 | N113 | S |
| 6-0194 | —(CH$_2$)$_3$— | —O— | K1 | N114 | S |
| 6-0195 | —(CH$_2$)$_3$— | —O— | K1 | N115 | S |
| 6-0196 | —(CH$_2$)$_3$— | —O— | K1 | N116 | S |
| 6-0197 | —(CH$_2$)$_3$— | —O— | K1 | N117 | S |
| 6-0198 | —(CH$_2$)$_3$— | —O— | K1 | N118 | S |
| 6-0199 | —(CH$_2$)$_3$— | —O— | K1 | N119 | S |
| 6-0200 | —(CH$_2$)$_2$— | —O— | K1 | N120 | S |
| 6-0201 | —(CH$_2$)$_2$— | —O— | K1 | N121 | S |
| 6-0202 | —(CH$_2$)$_2$— | —O— | K1 | N122 | S |
| 6-0203 | —(CH$_2$)$_2$— | —O— | K1 | N123 | S |
| 6-0204 | —(CH$_2$)$_2$— | —O— | K1 | N124 | S |
| 6-0205 | —(CH$_2$)$_2$— | —O— | K1 | N125 | S |
| 6-0206 | —(CH$_2$)$_2$— | —O— | K1 | N126 | S |
| 6-0207 | —(CH$_2$)$_2$— | —O— | K1 | N127 | S |
| 6-0208 | —(CH$_2$)$_2$— | —O— | K1 | N128 | O |
| 6-0209 | —(CH$_2$)$_2$— | —O— | K1 | N128 | S |
| 6-0210 | —(CH$_2$)$_2$— | —O— | K2 | N128 | S |
| 6-0211 | —(CH$_2$)$_2$— | —O— | K4 | N128 | S |
| 6-0212 | —(CH$_2$)$_2$— | —O— | K11 | N128 | S |
| 6-0213 | —(CH$_2$)$_2$— | —O— | K99 | N128 | S |
| 6-0214 | —(CH$_2$)$_2$— | —O— | K1 | N129 | S |
| 6-0215 | —(CH$_2$)$_2$— | —O— | K1 | N130 | S |
| 6-0216 | —(CH$_2$)$_2$— | —O— | K1 | N131 | S |
| 6-0217 | —(CH$_2$)$_2$— | —O— | K1 | N132 | S |
| 6-0218 | —(CH$_2$)$_2$— | —O— | K1 | N133 | S |
| 6-0219 | —(CH$_2$)$_2$— | —O— | K1 | N134 | S |
| 6-0220 | —(CH$_2$)$_2$— | —O— | K1 | N135 | S |
| 6-0221 | —(CH$_2$)$_2$— | —O— | K1 | N136 | S |
| 6-0222 | —(CH$_2$)$_2$— | —O— | K1 | N137 | S |
| 6-0223 | —(CH$_2$)$_2$— | —O— | K1 | N138 | S |
| 6-0224 | —(CH$_2$)$_2$— | —O— | K1 | N139 | S |

TABLE 185

| Compound No. | -A¹- | -A²- | -G¹-A³-A⁴-G² | -A⁵-R² | X |
|---|---|---|---|---|---|
| 6-0225 | —(CH$_2$)$_2$— | —O— | K1 | N140 | S |
| 6-0226 | —(CH$_2$)$_2$— | —O— | K1 | N141 | S |
| 6-0227 | —(CH$_2$)$_2$— | —O— | K1 | N142 | S |
| 6-0228 | —(CH$_2$)$_2$— | —O— | K1 | N143 | S |
| 6-0229 | —(CH$_2$)$_2$— | —O— | K1 | N144 | S |
| 6-0230 | —(CH$_2$)$_2$— | —O— | K1 | N145 | S |
| 6-0231 | —(CH$_2$)$_2$— | —O— | K1 | N146 | S |
| 6-0232 | —(CH$_2$)$_2$— | —O— | K1 | N147 | S |
| 6-0233 | —(CH$_2$)$_2$— | —O— | K1 | N132 | O |
| 6-0234 | —(CH$_2$)$_2$— | —O— | K1 | N133 | O |
| 6-0235 | —(CH$_2$)$_2$— | —O— | K1 | N134 | O |
| 6-0236 | —(CH$_2$)$_2$— | —O— | K1 | N135 | O |
| 6-0237 | —(CH$_2$)$_2$— | —O— | K1 | N136 | O |
| 6-0238 | —(CH$_2$)$_2$— | —O— | K1 | N137 | O |
| 6-0239 | —(CH$_2$)$_2$— | —O— | K1 | N138 | O |
| 6-0240 | —(CH$_2$)$_2$— | —O— | K1 | N139 | O |
| 6-0241 | —(CH$_2$)$_2$— | —O— | K1 | N140 | O |
| 6-0242 | —(CH$_2$)$_2$— | —O— | K1 | N141 | O |
| 6-0243 | —(CH$_2$)$_2$— | —O— | K1 | N142 | O |
| 6-0244 | —(CH$_2$)$_2$— | —O— | K1 | N143 | O |
| 6-0245 | —(CH$_2$)$_2$— | —O— | K1 | N144 | O |
| 6-0246 | —(CH$_2$)$_2$— | —O— | K1 | N145 | O |
| 6-0247 | —(CH$_2$)$_2$— | —O— | K1 | N146 | O |
| 6-0248 | —(CH$_2$)$_2$— | —O— | K1 | N147 | O |
| 6-0249 | —(CH$_2$)$_2$— | —O— | K1 | N148 | S |
| 6-0250 | —(CH$_2$)$_2$— | —O— | K1 | N149 | S |
| 6-0251 | —(CH$_2$)$_2$— | —O— | K99 | N149 | S |
| 6-0252 | —(CH$_2$)$_2$— | —O— | K1 | N150 | S |
| 6-0253 | —(CH$_2$)$_2$— | —O— | K99 | N150 | S |
| 6-0254 | —(CH$_2$)$_2$— | —O— | K1 | N151 | S |
| 6-0255 | —(CH$_2$)$_2$— | —O— | K1 | N152 | S |
| 6-0256 | —(CH$_2$)$_2$— | —O— | K99 | N152 | S |

TABLE 186

| Compound No. | -A¹- | -A²- | -G¹-A³-A⁴-G² | -A⁵-R² | X |
|---|---|---|---|---|---|
| 6-0257 | —(CH$_2$)$_2$— | —O— | K1 | N153 | O |
| 6-0258 | —(CH$_2$)$_2$— | —O— | K1 | N153 | S |
| 6-0259 | —(CH$_2$)$_2$— | —O— | K99 | N153 | S |
| 6-0260 | —(CH$_2$)$_2$— | —O— | K1 | N154 | O |
| 6-0261 | —(CH$_2$)$_2$— | —O— | K1 | N154 | S |
| 6-0262 | —(CH$_2$)$_2$— | —O— | K1 | N155 | S |
| 6-0263 | —(CH$_2$)$_2$— | —O— | K1 | N156 | S |
| 6-0264 | —(CH$_2$)$_2$— | —O— | K1 | N157 | S |
| 6-0265 | —(CH$_2$)$_2$— | —O— | K1 | N158 | S |
| 6-0266 | —(CH$_2$)$_3$— | —O— | K1 | N4 | O |
| 6-0267 | —(CH$_2$)$_3$— | —O— | K1 | N4 | S |
| 6-0268 | —(CH$_2$)$_3$— | —O— | K4 | N4 | S |
| 6-0269 | —(CH$_2$)$_3$— | —O— | K11 | N4 | S |
| 6-0270 | —(CH$_2$)$_3$— | —O— | K99 | N4 | S |
| 6-0271 | —(CH$_2$)$_3$— | —O— | K1 | N9 | O |
| 6-0272 | —(CH$_2$)$_3$— | —O— | K1 | N9 | S |
| 6-0273 | —(CH$_2$)$_3$— | —O— | K4 | N9 | S |
| 6-0274 | —(CH$_2$)$_3$— | —O— | K11 | N9 | S |
| 6-0275 | —(CH$_2$)$_3$— | —O— | K99 | N9 | S |
| 6-0276 | —(CH$_2$)$_3$— | —O— | K1 | N11 | O |
| 6-0277 | —(CH$_2$)$_3$— | —O— | K1 | N11 | S |
| 6-0278 | —(CH$_2$)$_3$— | —O— | K4 | N11 | S |
| 6-0279 | —(CH$_2$)$_3$— | —O— | K11 | N11 | S |
| 6-0280 | —(CH$_2$)$_3$— | —O— | K99 | N11 | S |
| 6-0281 | —(CH$_2$)$_3$— | —O— | K1 | N16 | O |
| 6-0282 | —(CH$_2$)$_3$— | —O— | K1 | N16 | S |
| 6-0283 | —(CH$_2$)$_3$— | —O— | K4 | N16 | S |
| 6-0284 | —(CH$_2$)$_3$— | —O— | K11 | N16 | S |
| 6-0285 | —(CH$_2$)$_3$— | —O— | K99 | N16 | S |
| 6-0286 | —(CH$_2$)$_3$— | —O— | K1 | N24 | O |
| 6-0287 | —(CH$_2$)$_3$— | —O— | K1 | N24 | S |
| 6-0288 | —(CH$_2$)$_3$— | —O— | K4 | N24 | S |

TABLE 187

| Compound No. | -A¹- | -A²- | -G¹-A³-A⁴-G² | -A⁵-R² | X |
|---|---|---|---|---|---|
| 6-0289 | —(CH$_2$)$_3$— | —O— | K11 | N24 | S |
| 6-0290 | —(CH$_2$)$_3$— | —O— | K99 | N24 | S |
| 6-0291 | —(CH$_2$)$_3$— | —O— | K1 | N53 | O |
| 6-0292 | —(CH$_2$)$_3$— | —O— | K1 | N53 | S |
| 6-0293 | —(CH$_2$)$_3$— | —O— | K4 | N53 | S |
| 6-0294 | —(CH$_2$)$_3$— | —O— | K11 | N53 | S |
| 6-0295 | —(CH$_2$)$_3$— | —O— | K99 | N53 | S |
| 6-0296 | —(CH$_2$)$_3$— | —O— | K1 | N65 | O |
| 6-0297 | —(CH$_2$)$_3$— | —O— | K1 | N65 | S |
| 6-0298 | —(CH$_2$)$_3$— | —O— | K4 | N65 | S |
| 6-0299 | —(CH$_2$)$_3$— | —O— | K1 | N69 | S |
| 6-0300 | —(CH$_2$)$_3$— | —O— | K4 | N69 | S |
| 6-0301 | —(CH$_2$)$_3$— | —O— | K11 | N69 | S |
| 6-0302 | —(CH$_2$)$_3$— | —O— | K99 | N69 | S |
| 6-0303 | —(CH$_2$)$_3$— | —O— | K1 | N70 | S |
| 6-0304 | —(CH$_2$)$_3$— | —O— | K4 | N70 | S |
| 6-0305 | —(CH$_2$)$_3$— | —O— | K11 | N70 | S |
| 6-0306 | —(CH$_2$)$_3$— | —O— | K99 | N70 | S |
| 6-0307 | —(CH$_2$)$_3$— | —O— | K1 | N76 | S |
| 6-0308 | —(CH$_2$)$_3$— | —O— | K4 | N76 | S |
| 6-0309 | —(CH$_2$)$_3$— | —O— | K11 | N76 | S |
| 6-0310 | —(CH$_2$)$_3$— | —O— | K99 | N76 | S |
| 6-0311 | —(CH$_2$)$_3$— | —O— | K1 | N77 | S |
| 6-0312 | —(CH$_2$)$_3$— | —O— | K4 | N77 | S |
| 6-0313 | —(CH$_2$)$_3$— | —O— | K11 | N77 | S |
| 6-0314 | —(CH$_2$)$_3$— | —O— | K99 | N77 | S |
| 6-0315 | —(CH$_2$)$_3$— | —O— | K1 | N100 | S |
| 6-0316 | —(CH$_2$)$_3$— | —O— | K4 | N100 | S |
| 6-0317 | —(CH$_2$)$_3$— | —O— | K11 | N100 | S |
| 6-0318 | —(CH$_2$)$_3$— | —O— | K99 | N100 | S |
| 6-0319 | —(CH$_2$)$_3$— | —O— | K1 | N115 | O |
| 6-0320 | —(CH$_2$)$_3$— | —O— | K4 | N115 | S |

TABLE 188

| Compound No. | -A¹- | -A²- | -G¹-A³-A⁴-G² | -A⁵-R² | X |
|---|---|---|---|---|---|
| 6-0321 | —(CH$_2$)$_3$— | —O— | K11 | N115 | S |
| 6-0322 | —(CH$_2$)$_3$— | —O— | K99 | N115 | S |
| 6-0323 | —(CH$_2$)$_3$— | —O— | K1 | N116 | O |
| 6-0324 | —(CH$_2$)$_3$— | —O— | K4 | N116 | S |
| 6-0325 | —(CH$_2$)$_3$— | —O— | K11 | N116 | S |
| 6-0326 | —(CH$_2$)$_3$— | —O— | K99 | N116 | S |
| 6-0327 | —(CH$_2$)$_3$— | —O— | K1 | N122 | S |
| 6-0328 | —(CH$_2$)$_3$— | —O— | K4 | N122 | S |
| 6-0329 | —(CH$_2$)$_3$— | —O— | K11 | N122 | S |
| 6-0330 | —(CH$_2$)$_3$— | —O— | K99 | N122 | S |
| 6-0331 | —(CH$_2$)$_3$— | —O— | K4 | N123 | S |
| 6-0332 | —(CH$_2$)$_3$— | —O— | K1 | N128 | S |
| 6-0333 | —(CH$_2$)$_3$— | —O— | K4 | N128 | S |
| 6-0334 | —(CH$_2$)$_3$— | —O— | K11 | N128 | S |
| 6-0335 | —(CH$_2$)$_3$— | —O— | K99 | N128 | S |
| 6-0336 | —(CH$_2$)$_3$— | —O— | K1 | N129 | S |
| 6-0337 | —(CH$_2$)$_3$— | —O— | K4 | N129 | S |
| 6-0338 | —(CH$_2$)$_3$— | —O— | K11 | N129 | S |
| 6-0339 | —(CH$_2$)$_3$— | —O— | K99 | N129 | S |
| 6-0340 | —(CH$_2$)$_3$— | —O— | K1 | N130 | S |
| 6-0341 | —(CH$_2$)$_3$— | —O— | K4 | N130 | S |
| 6-0342 | —(CH$_2$)$_3$— | —O— | K1 | N135 | S |
| 6-0343 | —(CH$_2$)$_3$— | —O— | K4 | N135 | S |
| 6-0344 | —(CH$_2$)$_3$— | —O— | K1 | N139 | S |
| 6-0345 | —(CH$_2$)$_3$— | —O— | K4 | N139 | S |
| 6-0346 | —(CH$_2$)$_3$— | —O— | K1 | N140 | S |
| 6-0347 | —(CH$_2$)$_3$— | —O— | K4 | N140 | S |
| 6-0348 | —(CH$_2$)$_3$— | —O— | K1 | N141 | S |
| 6-0349 | —(CH$_2$)$_3$— | —O— | K4 | N141 | S |
| 6-0350 | —(CH$_2$)$_3$— | —O— | K11 | N141 | S |
| 6-0351 | —(CH$_2$)$_3$— | —O— | K99 | N141 | S |
| 6-0352 | —(CH$_2$)$_3$— | —O— | K1 | N142 | S |

TABLE 189

| Compound No. | -A¹- | -A²- | -G¹-A³-A⁴-G² | -A⁵-R² | X |
|---|---|---|---|---|---|
| 6-0353 | —(CH₂)₃— | —O— | K4 | N142 | S |
| 6-0354 | —(CH₂)₃— | —O— | K11 | N142 | S |
| 6-0355 | —(CH₂)₃— | —O— | K99 | N142 | S |
| 6-0356 | —(CH₂)₃— | —O— | K1 | N143 | S |
| 6-0357 | —(CH₂)₃— | —O— | K4 | N143 | S |
| 6-0358 | —(CH₂)₃— | —O— | K11 | N143 | S |
| 6-0359 | —(CH₂)₃— | —O— | K99 | N143 | S |
| 6-0360 | —(CH₂)₃— | —O— | K1 | N144 | S |
| 6-0361 | —(CH₂)₃— | —O— | K4 | N144 | S |
| 6-0362 | —(CH₂)₃— | —O— | K11 | N144 | S |
| 6-0363 | —(CH₂)₃— | —O— | K99 | N144 | S |
| 6-0364 | —(CH₂)₃— | —O— | K1 | N145 | S |
| 6-0365 | —(CH₂)₃— | —O— | K1 | N146 | S |
| 6-0366 | —(CH₂)₃— | —O— | K4 | N146 | S |
| 6-0367 | —(CH₂)₃— | —O— | K11 | N146 | S |
| 6-0368 | —(CH₂)₃— | —O— | K99 | N146 | S |
| 6-0369 | —(CH₂)₃— | —O— | K1 | N147 | S |
| 6-0370 | —(CH₂)₃— | —O— | K4 | N147 | S |
| 6-0371 | —(CH₂)₃— | —O— | K11 | N147 | S |
| 6-0372 | —(CH₂)₃— | —O— | K99 | N147 | S |
| 6-0373 | —(CH₂)₃— | —O— | K1 | N148 | S |
| 6-0374 | —(CH₂)₃— | —O— | K4 | N148 | S |
| 6-0375 | —(CH₂)₃— | —O— | K11 | N148 | S |
| 6-0376 | —(CH₂)₃— | —O— | K99 | N148 | S |
| 6-0377 | —(CH₂)₃— | —O— | K1 | N149 | S |
| 6-0378 | —(CH₂)₃— | —O— | K4 | N149 | S |
| 6-0379 | —(CH₂)₃— | —O— | K11 | N149 | S |
| 6-0380 | —(CH₂)₃— | —O— | K99 | N149 | S |
| 6-0381 | —(CH₂)₃— | —O— | K1 | N150 | S |
| 6-0382 | —(CH₂)₃— | —O— | K4 | N150 | S |
| 6-0383 | —(CH₂)₃— | —O— | K11 | N150 | S |
| 6-0384 | —(CH₂)₃— | —O— | K99 | N150 | S |

TABLE 190

| Compound No. | -A¹- | -A²- | -G¹-A³-A⁴-G² | -A⁵-R² | X |
|---|---|---|---|---|---|
| 6-0385 | —(CH₂)₃— | —O— | K1 | N151 | S |
| 6-0386 | —(CH₂)₃— | —O— | K4 | N152 | S |
| 6-0387 | —(CH₂)₃— | —O— | K11 | N153 | S |
| 6-0388 | —(CH₂)₃— | —O— | K99 | N154 | S |
| 6-0389 | —(CH₂)₃— | —O— | K1 | N155 | S |
| 6-0390 | —(CH₂)₃— | —O— | K4 | N155 | S |
| 6-0391 | —(CH₂)₃— | —O— | K11 | N155 | S |
| 6-0392 | —(CH₂)₃— | —O— | K99 | N155 | S |
| 6-0393 | —(CH₂)₃— | —O— | K1 | N156 | S |
| 6-0394 | —(CH₂)₃— | —O— | K4 | N156 | S |
| 6-0395 | —(CH₂)₃— | —O— | K11 | N156 | S |
| 6-0396 | —(CH₂)₃— | —O— | K1 | N157 | S |
| 6-0397 | —(CH₂)₃— | —O— | K1 | N158 | S |
| 6-0398 | —(CH₂)₂— | —NH—C(=O)— | K1 | N3 | S |
| 6-0399 | —(CH₂)₂— | —NH—C(=O)— | K1 | N9 | S |
| 6-0400 | —(CH₂)₂— | —NH—C(=O)— | K1 | N69 | S |
| 6-0401 | —(CH₂)₂— | —NH—C(=O)— | K1 | N12 | S |
| 6-0402 | —(CH₂)₂— | —NH—C(=O)— | K1 | N115 | S |
| 6-0403 | —(CH₂)₂— | —NH—C(=O)— | K1 | N116 | S |
| 6-0404 | —(CH₂)₂— | —NH—C(=O)— | K1 | N128 | S |
| 6-0405 | —(CH₂)₂— | —NH—C(=O)— | K1 | N140 | S |
| 6-0406 | —(CH₂)₂— | —NH—C(=O)— | K1 | N150 | S |
| 6-0407 | —(CH₂)₂— | —NH—C(=O)— | K1 | N153 | S |
| 6-0408 | —(CH₂)₂— | —NH—C(=O)— | K8 | N3 | S |
| 6-0409 | —(CH₂)₂— | —NH—C(=O)— | K8 | N9 | S |
| 6-0410 | —(CH₂)₂— | —NH—C(=O)— | K8 | N69 | S |
| 6-0411 | —(CH₂)₂— | —NH—C(=O)— | K8 | N115 | S |
| 6-0412 | —(CH₂)₂— | —NH—C(=O)— | K11 | N3 | S |
| 6-0413 | —(CH₂)₂— | —NH—C(=O)— | K11 | N9 | S |
| 6-0414 | —(CH₂)₂— | —NH—C(=S)— | K11 | N9 | S |
| 6-0415 | —(CH₂)₂— | —NH—C(=O)— | K11 | N69 | S |
| 6-0416 | —(CH₂)₂— | —NH—C(=O)— | K11 | N115 | S |

TABLE 191

| Compound No. | -A¹- | -A²- | -G¹-A³-A⁴-G² | -A⁵-R² | X |
|---|---|---|---|---|---|
| 6-0417 | —(CH₂)₂— | —NH—C(=O)— | K11 | N116 | S |
| 6-0418 | —(CH₂)₂— | —NH—C(=O)— | K11 | N128 | S |
| 6-0419 | —(CH₂)₂— | —NH—C(=O)— | K11 | N140 | S |
| 6-0420 | —(CH₂)₂— | —NH—C(=O)— | K11 | N150 | S |
| 6-0421 | —(CH₂)₂— | —NH—C(=O)— | K11 | N153 | S |
| 6-0422 | —(CH₂)₂— | —NH—C(=O)— | K13 | N3 | S |
| 6-0423 | —(CH₂)₂— | —NH—C(=O)— | K13 | N9 | S |
| 6-0424 | —(CH₂)₂— | —NH—C(=O)— | K13 | N69 | S |
| 6-0425 | —(CH₂)₂— | —NH—C(=O)— | K13 | N115 | S |
| 6-0426 | —(CH₂)₂— | —NH—C(=O)— | K14 | N3 | S |
| 6-0427 | —(CH₂)₂— | —NH—C(=O)— | K14 | N9 | S |
| 6-0428 | —(CH₂)₂— | —NH—C(=O)— | K14 | N69 | S |
| 6-0429 | —(CH₂)₂— | —NH—C(=O)— | K14 | N115 | S |
| 6-0430 | —(CH₂)₂— | —NH—C(=O)— | K14 | N128 | S |
| 6-0431 | —(CH₂)₂— | —NH—C(=O)— | K15 | N3 | S |
| 6-0432 | —(CH₂)₂— | —NH—C(=O)— | K15 | N9 | S |
| 6-0433 | —(CH₂)₂— | —NH—C(=O)— | K15 | N115 | S |
| 6-0434 | —(CH₂)₂— | —NH—C(=O)— | K16 | N3 | S |
| 6-0435 | —(CH₂)₂— | —NH—C(=O)— | K16 | N9 | S |
| 6-0436 | —(CH₂)₂— | —NH—C(=O)— | K16 | N115 | S |
| 6-0437 | —(CH₂)₂— | —NH—C(=O)— | K19 | N3 | S |
| 6-0438 | —(CH₂)₂— | —NH—C(=O)— | K19 | N9 | S |
| 6-0439 | —(CH₂)₂— | —NH—C(=O)— | K19 | N115 | S |
| 6-0440 | —(CH₂)₂— | —NH—C(=O)— | K23 | N3 | S |
| 6-0441 | —(CH₂)₂— | —NH—C(=O)— | K23 | N9 | S |
| 6-0442 | —(CH₂)₂— | —NH—C(=O)— | K23 | N115 | S |
| 6-0443 | —(CH₂)₂— | —NH—C(=O)— | K24 | N3 | S |
| 6-0444 | —(CH₂)₂— | —NH—C(=O)— | K24 | N9 | S |
| 6-0445 | —(CH₂)₂— | —NH—C(=O)— | K24 | N115 | S |
| 6-0446 | —(CH₂)₂— | —NH—C(=O)— | K34 | N3 | S |
| 6-0447 | —(CH₂)₂— | —NH—C(=O)— | K34 | N9 | S |
| 6-0448 | —(CH₂)₂— | —NH—C(=O)— | K34 | N115 | S |

TABLE 192

| Compound No. | -A¹- | -A²- | -G¹-A³-A⁴-G² | -A⁵-R² | X |
|---|---|---|---|---|---|
| 6-0449 | —(CH₂)₂— | —NH—C(=O)— | K35 | N3 | S |
| 6-0450 | —(CH₂)₂— | —NH—C(=O)— | K35 | N9 | S |
| 6-0451 | —(CH₂)₂— | —NH—C(=O)— | K35 | N115 | S |
| 6-0452 | —(CH₂)₂— | —NH—C(=O)— | K37 | N3 | S |
| 6-0453 | —(CH₂)₂— | —NH—C(=O)— | K37 | N9 | S |
| 6-0454 | —(CH₂)₂— | —NH—C(=O)— | K37 | N115 | S |
| 6-0455 | —(CH₂)₂— | —NH—C(=O)— | K39 | N3 | S |
| 6-0456 | —(CH₂)₂— | —NH—C(=O)— | K39 | N9 | S |
| 6-0457 | —(CH₂)₂— | —NH—C(=O)— | K39 | N115 | S |
| 6-0458 | —(CH₂)₂— | —NH—C(=O)— | K46 | N3 | S |
| 6-0459 | —(CH₂)₂— | —NH—C(=O)— | K46 | N9 | S |
| 6-0460 | —(CH₂)₂— | —NH—C(=O)— | K46 | N115 | S |
| 6-0461 | —(CH₂)₂— | —NH—C(=O)— | K47 | N3 | S |
| 6-0462 | —(CH₂)₂— | —NH—C(=O)— | K47 | N9 | S |
| 6-0463 | —(CH₂)₂— | —NH—C(=O)— | K47 | N115 | S |
| 6-0464 | —(CH₂)₂— | —NH—C(=O)— | K50 | N3 | S |
| 6-0465 | —(CH₂)₂— | —NH—C(=O)— | K50 | N9 | S |
| 6-0466 | —(CH₂)₂— | —NH—C(=O)— | K50 | N115 | S |
| 6-0467 | —(CH₂)₂— | —NH—C(=O)— | K53 | N3 | S |
| 6-0468 | —(CH₂)₂— | —NH—C(=O)— | K53 | N9 | S |
| 6-0469 | —(CH₂)₂— | —NH—C(=O)— | K53 | N115 | S |
| 6-0470 | —(CH₂)₂— | —NH—C(=O)— | K54 | N3 | S |
| 6-0471 | —(CH₂)₂— | —NH—C(=O)— | K54 | N9 | S |
| 6-0472 | —(CH₂)₂— | —NH—C(=O)— | K54 | N115 | S |
| 6-0473 | —(CH₂)₂— | —NH—C(=O)— | K56 | N3 | S |
| 6-0474 | —(CH₂)₂— | —NH—C(=O)— | K56 | N9 | S |
| 6-0475 | —(CH₂)₂— | —NH—C(=O)— | K56 | N115 | S |
| 6-0476 | —(CH₂)₂— | —NH—C(=O)— | K50 | N3 | O |
| 6-0477 | —(CH₂)₂— | —NH—C(=O)— | K60 | N9 | S |
| 6-0478 | —(CH₂)₂— | —NH—C(=O)— | K60 | N115 | S |
| 6-0479 | —(CH₂)₂— | —NH—C(=O)— | K62 | N3 | S |
| 6-0480 | —(CH₂)₂— | —NH—C(=O)— | K62 | N9 | S |

TABLE 193

| Compound No. | -A¹- | -A²- | -G¹-A³-A⁴-G² | -A⁵-R² | X |
|---|---|---|---|---|---|
| 6-0481 | —(CH$_2$)$_2$— | —NH—C(=O)— | K62 | N115 | S |
| 6-0482 | —(CH$_2$)$_2$— | —NH—C(=O)— | K63 | N3 | S |
| 6-0483 | —(CH$_2$)$_2$— | —NH—C(=O)— | K63 | N9 | S |
| 6-0484 | —(CH$_2$)$_2$— | —NH—C(=O)— | K63 | N115 | S |
| 6-0485 | —(CH$_2$)$_2$— | —NH—C(=O)— | K64 | N3 | S |
| 6-0486 | —(CH$_2$)$_2$— | —NH—C(=O)— | K64 | N9 | S |
| 6-0487 | —(CH$_2$)$_2$— | —NH—C(=O)— | K64 | N115 | S |
| 6-0488 | —(CH$_2$)$_2$— | —NH—C(=O)— | K75 | N3 | S |
| 6-0489 | —(CH$_2$)$_2$— | —NH—C(=O)— | K75 | N9 | S |
| 6-0490 | —(CH$_2$)$_2$— | —NH—C(=O)— | K75 | N115 | S |
| 6-0491 | —(CH$_2$)$_2$— | —NH—C(=O)— | K77 | N3 | S |
| 6-0492 | —(CH$_2$)$_2$— | —NH—C(=O)— | K77 | N9 | S |
| 6-0493 | —(CH$_2$)$_2$— | —NH—C(=O)— | K77 | N115 | S |
| 6-0494 | —(CH$_2$)$_2$— | —NH—C(=O)— | K99 | N3 | S |
| 6-0495 | —(CH$_2$)$_2$— | —NH—C(=O)— | K99 | N9 | S |
| 6-0496 | —(CH$_2$)$_2$— | —NH—C(=O)— | K99 | N115 | S |
| 6-0497 | —(CH$_2$)$_2$— | —NH—C(=O)— | K100 | N3 | S |
| 6-0498 | —(CH$_2$)$_2$— | —NH—C(=O)— | K100 | N9 | S |
| 6-0499 | —(CH$_2$)$_2$— | —NH—C(=O)— | K100 | N115 | S |
| 6-0500 | —(CH$_2$)$_2$— | —NH—C(=O)— | K102 | N3 | S |
| 6-0501 | —(CH$_2$)$_2$— | —NH—C(=O)— | K102 | N9 | S |
| 6-0502 | —(CH$_2$)$_2$— | —NH—C(=O)— | K102 | N115 | S |
| 6-0503 | —(CH$_2$)$_2$— | —NH—C(=O)— | K241 | N3 | S |
| 6-0504 | —(CH$_2$)$_2$— | —NH—C(=O)— | K241 | N9 | S |
| 6-0505 | —(CH$_2$)$_2$— | —NH—C(=O)— | K241 | N115 | S |
| 6-0506 | —(CH$_2$)$_2$— | —NH—C(=O)— | K242 | N3 | S |
| 6-0507 | —(CH$_2$)$_2$— | —NH—C(=O)— | K242 | N9 | S |
| 6-0508 | —(CH$_2$)$_2$— | —NH—C(=O)— | K242 | N115 | S |
| 6-0509 | —(CH$_2$)$_2$— | —NH—C(=O)— | K243 | N3 | S |
| 6-0510 | —(CH$_2$)$_2$— | —NH—C(=O)— | K243 | N9 | S |
| 6-0511 | —(CH$_2$)$_2$— | —NH—C(=O)— | K243 | N115 | S |
| 6-0512 | —(CH$_2$)$_2$— | —NH—C(=O)— | K244 | N3 | S |

TABLE 194

| Compound No. | -A¹- | -A²- | -G¹-A³-A⁴-G² | -A⁵-R² | X |
|---|---|---|---|---|---|
| 6-0513 | —(CH$_2$)$_2$— | —NH—C(=O)— | K244 | N9 | S |
| 6-0514 | —(CH$_2$)$_2$— | —NH—C(=O)— | K244 | N115 | S |
| 6-0515 | —(CH$_2$)$_2$— | —NH—C(=O)— | K245 | N3 | S |
| 6-0516 | —(CH$_2$)$_2$— | —NH—C(=O)— | K245 | N9 | S |
| 6-0517 | —(CH$_2$)$_2$— | —NH—C(=O)— | K245 | N115 | S |
| 6-0518 | —(CH$_2$)$_2$— | —NH—C(=O)— | K246 | N3 | S |
| 6-0519 | —(CH$_2$)$_2$— | —NH—C(=O)— | K246 | N9 | S |
| 6-0520 | —(CH$_2$)$_2$— | —NH—C(=O)— | K246 | N115 | S |
| 6-0521 | —(CH$_2$)$_2$— | —NH—C(=O)— | K247 | N3 | S |
| 6-0522 | —(CH$_2$)$_2$— | —NH—C(=O)— | K247 | N9 | S |
| 6-0523 | —(CH$_2$)$_2$— | —NH—C(=O)— | K247 | N115 | S |
| 6-0524 | —(CH$_2$)$_2$— | —NH—C(=O)— | K248 | N3 | S |
| 6-0525 | —(CH$_2$)$_2$— | —NH—C(=O)— | K248 | N9 | S |
| 6-0526 | —(CH$_2$)$_2$— | —NH—C(=O)— | K248 | N115 | S |
| 6-0527 | —(CH$_2$)$_2$— | —NH—C(=O)— | K249 | N115 | S |
| 6-0528 | —(CH$_2$)$_2$— | —NH—C(=O)— | K253 | N115 | S |
| 6-0529 | —(CH$_2$)$_2$— | —NH—C(=O)— | K254 | N115 | S |
| 6-0530 | —(CH$_2$)$_3$— | —NH—C(=O)— | K1 | N1 | S |
| 6-0531 | —(CH$_2$)$_3$— | —NH—C(=O)— | K1 | N3 | S |
| 6-0532 | —(CH$_2$)$_3$— | —NH—C(=O)— | K1 | N9 | S |
| 6-0533 | —(CH$_2$)$_3$— | —NH—C(=O)— | K1 | N69 | S |
| 6-0534 | —(CH$_2$)$_3$— | —NH—C(=O)— | K1 | N12 | S |
| 6-0535 | —(CH$_2$)$_3$— | —NH—C(=O)— | K1 | N115 | S |
| 6-0536 | —(CH$_2$)$_3$— | —NH—C(=O)— | K1 | N116 | S |
| 6-0537 | —(CH$_2$)$_3$— | —NH—C(=O)— | K1 | N128 | S |
| 6-0538 | —(CH$_2$)$_3$— | —NH—C(=O)— | K1 | N140 | S |
| 6-0539 | —(CH$_2$)$_3$— | —NH—C(=O)— | K1 | N150 | S |
| 6-0540 | —(CH$_2$)$_3$— | —NH—C(=O)— | K1 | N153 | S |
| 6-0541 | —(CH$_2$)$_3$— | —NH—C(=O)— | K11 | N1 | S |
| 6-0542 | —(CH$_2$)$_3$— | —NH—C(=O)— | K11 | N3 | S |
| 6-0543 | —(CH$_2$)$_3$— | —NH—C(=O)— | K11 | N9 | S |
| 6-0544 | —(CH$_2$)$_3$— | —NH—C(=O)— | K11 | N69 | S |

TABLE 195

| Compound No. | -A¹- | -A²- | -G¹-A³-A⁴-G² | -A⁵-R² | X |
|---|---|---|---|---|---|
| 6-0545 | —(CH$_2$)$_3$— | —NH—C(=O)— | K11 | N12 | S |
| 6-0546 | —(CH$_2$)$_3$— | —NH—C(=O)— | K11 | N115 | S |
| 6-0547 | —(CH$_2$)$_3$— | —NH—C(=O)— | K11 | N116 | S |
| 6-0548 | —(CH$_2$)$_3$— | —NH—C(=O)— | K11 | N128 | S |
| 6-0549 | —(CH$_2$)$_3$— | —NH—C(=O)— | K11 | N140 | S |
| 6-0550 | —(CH$_2$)$_3$— | —NH—C(=O)— | K11 | N150 | S |
| 6-0551 | —(CH$_2$)$_3$— | —NH—C(=O)— | K11 | N153 | S |
| 6-0552 | —(CH$_2$)$_3$— | —NH—C(=O)— | K35 | N1 | S |
| 6-0553 | —(CH$_2$)$_3$— | —NH—C(=O)— | K35 | N3 | S |
| 6-0554 | —(CH$_2$)$_3$— | —NH—C(=O)— | K35 | N9 | S |
| 6-0555 | —(CH$_2$)$_3$— | —NH—C(=O)— | K35 | N69 | S |
| 6-0556 | —(CH$_2$)$_3$— | —NH—C(=O)— | K35 | N12 | S |
| 6-0557 | —(CH$_2$)$_3$— | —NH—C(=O)— | K35 | N115 | S |
| 6-0558 | —(CH$_2$)$_3$— | —NH—C(=O)— | K35 | N116 | S |
| 6-0559 | —(CH$_2$)$_3$— | —NH—C(=O)— | K35 | N128 | S |
| 6-0560 | —(CH$_2$)$_3$— | —NH—C(=O)— | K35 | N140 | S |
| 6-0561 | —(CH$_2$)$_3$— | —NH—C(=O)— | K35 | N150 | S |
| 6-0562 | —(CH$_2$)$_3$— | —NH—C(=O)— | K35 | N153 | S |
| 6-0563 | —(CH$_2$)$_3$— | —NH—C(=O)— | K37 | N1 | S |
| 6-0564 | —(CH$_2$)$_3$— | —NH—C(=O)— | K37 | N3 | S |
| 6-0565 | —(CH$_2$)$_3$— | —NH—C(=O)— | K37 | N9 | S |
| 6-0566 | —(CH$_2$)$_3$— | —NH—C(=O)— | K37 | N69 | S |
| 6-0567 | —(CH$_2$)$_3$— | —NH—C(=O)— | K37 | N12 | S |
| 6-0568 | —(CH$_2$)$_3$— | —NH—C(=O)— | K37 | N115 | S |
| 6-0569 | —(CH$_2$)$_3$— | —NH—C(=O)— | K37 | N116 | S |
| 6-0570 | —(CH$_2$)$_3$— | —NH—C(=O)— | K37 | N128 | S |
| 6-0571 | —(CH$_2$)$_3$— | —NH—C(=O)— | K37 | N140 | S |
| 6-0572 | —(CH$_2$)$_3$— | —NH—C(=O)— | K37 | N150 | S |
| 6-0573 | —(CH$_2$)$_3$— | —NH—C(=O)— | K37 | N153 | S |
| 6-0574 | —(CH$_2$)$_3$— | —NH—C(=O)— | K50 | N1 | S |
| 6-0575 | —(CH$_2$)$_3$— | —NH—C(=O)— | K50 | N3 | S |
| 6-0576 | —(CH$_2$)$_3$— | —NH—C(=O)— | K50 | N9 | S |

TABLE 196

| Compound No. | -A¹- | -A²- | -G¹-A³-A⁴-G² | -A⁵-R² | X |
|---|---|---|---|---|---|
| 6-0577 | —(CH$_2$)$_3$— | —NH—C(=O)— | K50 | N69 | S |
| 6-0578 | —(CH$_2$)$_3$— | —NH—C(=O)— | K50 | N12 | S |
| 6-0579 | —(CH$_2$)$_3$— | —NH—C(=O)— | K50 | N115 | S |
| 6-0580 | —(CH$_2$)$_3$— | —NH—C(=O)— | K50 | N116 | S |
| 6-0581 | —(CH$_2$)$_3$— | —NH—C(=O)— | K50 | N128 | S |
| 6-0582 | —(CH$_2$)$_3$— | —NH—C(=O)— | K50 | N140 | S |
| 6-0583 | —(CH$_2$)$_3$— | —NH—C(=O)— | K50 | N150 | S |
| 6-0584 | —(CH$_2$)$_3$— | —NH—C(=O)— | K50 | N153 | S |
| 6-0585 | —(CH$_2$)$_3$— | —NH—C(=O)— | K62 | N1 | S |
| 6-0586 | —(CH$_2$)$_3$— | —NH—C(=O)— | K62 | N3 | S |
| 6-0587 | —(CH$_2$)$_3$— | —NH—C(=O)— | K62 | N9 | S |
| 6-0588 | —(CH$_2$)$_3$— | —NH—C(=O)— | K62 | N69 | S |
| 6-0589 | —(CH$_2$)$_3$— | —NH—C(=O)— | K62 | N12 | S |
| 6-0590 | —(CH$_2$)$_3$— | —NH—C(=O)— | K62 | N115 | S |
| 6-0591 | —(CH$_2$)$_3$— | —NH—C(=O)— | K62 | N116 | S |
| 6-0592 | —(CH$_2$)$_3$— | —NH—C(=O)— | K62 | N128 | S |
| 6-0593 | —(CH$_2$)$_3$— | —NH—C(=O)— | K62 | N140 | S |
| 6-0594 | —(CH$_2$)$_3$— | —NH—C(=O)— | K62 | N150 | S |
| 6-0595 | —(CH$_2$)$_3$— | —NH—C(=O)— | K62 | N153 | S |
| 6-0596 | —(CH$_2$)$_3$— | —NH—C(=O)— | K72 | N1 | S |
| 6-0597 | —(CH$_2$)$_3$— | —NH—C(=O)— | K72 | N3 | S |
| 6-0598 | —(CH$_2$)$_3$— | —NH—C(=O)— | K72 | N9 | S |
| 6-0599 | —(CH$_2$)$_3$— | —NH—C(=O)— | K72 | N69 | S |
| 6-0600 | —(CH$_2$)$_3$— | —NH—C(=O)— | K72 | N12 | S |
| 6-0601 | —(CH$_2$)$_3$— | —NH—C(=O)— | K72 | N115 | S |
| 6-0602 | —(CH$_2$)$_3$— | —NH—C(=O)— | K72 | N116 | S |
| 6-0603 | —(CH$_2$)$_3$— | —NH—C(=O)— | K72 | N128 | S |
| 6-0604 | —(CH$_2$)$_3$— | —NH—C(=O)— | K72 | N140 | S |
| 6-0605 | —(CH$_2$)$_3$— | —NH—C(=O)— | K72 | N150 | S |
| 6-0606 | —(CH$_2$)$_3$— | —NH—C(=O)— | K72 | N153 | S |
| 6-0607 | —(CH$_2$)$_3$— | —NH—C(=O)— | K78 | N1 | S |
| 6-0608 | —(CH$_2$)$_3$— | —NH—C(=O)— | K78 | N3 | S |

TABLE 197

| Compound No. | -A$^1$- | -A$^2$- | -G$^1$-A$^3$-A$^4$-G$^2$ | -A$^5$-R$^2$ | X |
|---|---|---|---|---|---|
| 6-0609 | —(CH$_2$)$_3$— | —NH—C(=O)— | K78 | N9 | S |
| 6-0610 | —(CH$_2$)$_3$— | —NH—C(=O)— | K78 | N69 | S |
| 6-0611 | —(CH$_2$)$_3$— | —NH—C(=O)— | K78 | N12 | S |
| 6-0612 | —(CH$_2$)$_3$— | —NH—C(=O)— | K78 | N115 | S |
| 6-0613 | —(CH$_2$)$_3$— | —NH—C(=O)— | K78 | N116 | S |
| 6-0614 | —(CH$_2$)$_3$— | —NH—C(=O)— | K78 | N128 | S |
| 6-0615 | —(CH$_2$)$_3$— | —NH—C(=O)— | K78 | N140 | S |
| 6-0616 | —(CH$_2$)$_3$— | —NH—C(=O)— | K78 | N150 | S |
| 6-0617 | —(CH$_2$)$_3$— | —NH—C(=O)— | K78 | N153 | S |
| 6-0618 | —(CH$_2$)$_3$— | —NH—C(=O)— | K99 | N1 | S |
| 6-0619 | —(CH$_2$)$_3$— | —NH—C(=O)— | K99 | N3 | S |
| 6-0620 | —(CH$_2$)$_3$— | —NH—C(=O)— | K99 | N9 | S |
| 6-0621 | —(CH$_2$)$_3$— | —NH—C(=O)— | K99 | N69 | S |
| 6-0622 | —(CH$_2$)$_3$— | —NH—C(=O)— | K99 | N12 | S |
| 6-0623 | —(CH$_2$)$_3$— | —NH—C(=O)— | K99 | N115 | S |
| 6-0624 | —(CH$_2$)$_3$— | —NH—C(=O)— | K99 | N116 | S |
| 6-0625 | —(CH$_2$)$_3$— | —NH—C(=O)— | K99 | N128 | S |
| 6-0626 | —(CH$_2$)$_3$— | —NH—C(=O)— | K99 | N140 | S |
| 6-0627 | —(CH$_2$)$_3$— | —NH—C(=O)— | K99 | N150 | S |
| 6-0628 | —(CH$_2$)$_3$— | —NH—C(=O)— | K99 | N153 | S |
| 6-0629 | —(CH$_2$)$_3$— | —NH—C(=O)— | K241 | N1 | S |
| 6-0630 | —(CH$_2$)$_3$— | —NH—C(=O)— | K241 | N3 | S |
| 6-0631 | —(CH$_2$)$_3$— | —NH—C(=O)— | K241 | N9 | S |
| 6-0632 | —(CH$_2$)$_3$— | —NH—C(=O)— | K241 | N69 | S |
| 6-0633 | —(CH$_2$)$_3$— | —NH—C(=O)— | K241 | N12 | S |
| 6-0634 | —(CH$_2$)$_3$— | —NH—C(=O)— | K241 | N115 | S |
| 6-0635 | —(CH$_2$)$_3$— | —NH—C(=O)— | K241 | N116 | S |
| 6-0636 | —(CH$_2$)$_3$— | —NH—C(=O)— | K241 | N128 | S |
| 6-0637 | —(CH$_2$)$_3$— | —NH—C(=O)— | K241 | N140 | S |
| 6-0638 | —(CH$_2$)$_3$— | —NH—C(=O)— | K241 | N150 | S |
| 6-0639 | —(CH$_2$)$_3$— | —NH—C(=O)— | K241 | N153 | S |
| 6-0640 | —(CH$_2$)$_3$— | —NH—C(=O)— | K242 | N1 | S |

TABLE 198

| Compound No. | -A$^1$- | -A$^2$- | -G$^1$-A$^3$-A$^4$-G$^2$ | -A$^5$-R$^2$ | X |
|---|---|---|---|---|---|
| 6-0641 | —(CH$_2$)$_3$— | —NH—C(=O)— | K242 | N3 | S |
| 6-0642 | —(CH$_2$)$_3$— | —NH—C(=O)— | K242 | N9 | S |
| 6-0643 | —(CH$_2$)$_3$— | —NH—C(=O)— | K242 | N69 | S |
| 6-0644 | —(CH$_2$)$_3$— | —NH—C(=O)— | K242 | N12 | S |
| 6-0645 | —(CH$_2$)$_3$— | —NH—C(=O)— | K242 | N115 | S |
| 6-0646 | —(CH$_2$)$_3$— | —NH—C(=O)— | K242 | N116 | S |
| 6-0647 | —(CH$_2$)$_3$— | —NH—C(=O)— | K242 | N128 | S |
| 6-0648 | —(CH$_2$)$_3$— | —NH—C(=O)— | K242 | N140 | S |
| 6-0649 | —(CH$_2$)$_3$— | —NH—C(=O)— | K242 | N150 | S |
| 6-0650 | —(CH$_2$)$_3$— | —NH—C(=O)— | K242 | N153 | S |
| 6-0651 | —(CH$_2$)$_3$— | —NH—C(=O)— | K245 | N1 | S |
| 6-0652 | —(CH$_2$)$_3$— | —NH—C(=O)— | K245 | N3 | S |
| 6-0653 | —(CH$_2$)$_3$— | —NH—C(=O)— | K245 | N9 | S |
| 6-0654 | —(CH$_2$)$_3$— | —NH—C(=O)— | K245 | N69 | S |
| 6-0655 | —(CH$_2$)$_3$— | —NH—C(=O)— | K245 | N12 | S |
| 6-0656 | —(CH$_2$)$_3$— | —NH—C(=O)— | K245 | N115 | S |
| 6-0657 | —(CH$_2$)$_3$— | —NH—C(=O)— | K245 | N116 | S |
| 6-0658 | —(CH$_2$)$_3$— | —NH—C(=O)— | K245 | N128 | S |
| 6-0659 | —(CH$_2$)$_3$— | —NH—C(=O)— | K245 | N140 | S |
| 6-0660 | —(CH$_2$)$_3$— | —NH—C(=O)— | K245 | N150 | S |
| 6-0661 | —(CH$_2$)$_3$— | —NH—C(=O)— | K245 | N153 | S |
| 6-0662 | —(CH$_2$)$_3$— | —NH—C(=O)— | K246 | N1 | S |
| 6-0663 | —(CH$_2$)$_3$— | —NH—C(=O)— | K246 | N3 | S |
| 6-0664 | —(CH$_2$)$_3$— | —NH—C(=O)— | K246 | N9 | S |
| 6-0665 | —(CH$_2$)$_3$— | —NH—C(=O)— | K246 | N69 | S |
| 6-0666 | —(CH$_2$)$_3$— | —NH—C(=O)— | K246 | N12 | S |
| 6-0667 | —(CH$_2$)$_3$— | —NH—C(=O)— | K246 | N115 | S |
| 6-0668 | —(CH$_2$)$_3$— | —NH—C(=O)— | K246 | N116 | S |
| 6-0669 | —(CH$_2$)$_3$— | —NH—C(=O)— | K246 | N128 | S |
| 6-0670 | —(CH$_2$)$_3$— | —NH—C(=O)— | K246 | N140 | S |
| 6-0671 | —(CH$_2$)$_3$— | —NH—C(=O)— | K246 | N150 | S |
| 6-0672 | —(CH$_2$)$_3$— | —NH—C(=O)— | K246 | N153 | S |

TABLE 199

| Compound No. | -A$^1$- | -A$^2$- | -G$^1$-A$^3$-A$^4$-G$^2$ | -A$^5$-R$^2$ | X |
|---|---|---|---|---|---|
| 6-0673 | —(CH$_2$)$_3$— | —NH—C(=O)— | K248 | N1 | S |
| 6-0674 | —(CH$_2$)$_3$— | —NH—C(=O)— | K248 | N3 | S |
| 6-0675 | —(CH$_2$)$_3$— | —NH—C(=O)— | K248 | N9 | S |
| 6-0676 | —(CH$_2$)$_3$— | —NH—C(=O)— | K248 | N69 | S |
| 6-0677 | —(CH$_2$)$_3$— | —NH—C(=O)— | K248 | N12 | S |
| 6-0678 | —(CH$_2$)$_3$— | —NH—C(=O)— | K248 | N115 | S |
| 6-0679 | —(CH$_2$)$_3$— | —NH—C(=O)— | K248 | N116 | S |
| 6-0680 | —(CH$_2$)$_3$— | —NH—C(=O)— | K248 | N128 | S |
| 6-0681 | —(CH$_2$)$_3$— | —NH—C(=O)— | K248 | N140 | S |
| 6-0682 | —(CH$_2$)$_3$— | —NH—C(=O)— | K248 | N150 | S |
| 6-0683 | —(CH$_2$)$_3$— | —NH—C(=O)— | K248 | N153 | S |
| 6-0684 | —(CH$_2$)$_3$— | —NH—C(=O)— | K250 | N1 | S |
| 6-0685 | —(CH$_2$)$_3$— | —NH—C(=O)— | K250 | N3 | S |
| 6-0686 | —(CH$_2$)$_3$— | —NH—C(=O)— | K250 | N9 | S |
| 6-0687 | —(CH$_2$)$_3$— | —NH—C(=O)— | K250 | N69 | S |
| 6-0688 | —(CH$_2$)$_3$— | —NH—C(=O)— | K250 | N12 | S |
| 6-0689 | —(CH$_2$)$_3$— | —NH—C(=O)— | K250 | N115 | S |
| 6-0690 | —(CH$_2$)$_3$— | —NH—C(=O)— | K250 | N116 | S |
| 6-0691 | —(CH$_2$)$_3$— | —NH—C(=O)— | K250 | N128 | S |
| 6-0692 | —(CH$_2$)$_3$— | —NH—C(=O)— | K250 | N140 | S |
| 6-0693 | —(CH$_2$)$_3$— | —NH—C(=S)— | K250 | N150 | S |
| 6-0694 | —(CH$_2$)$_3$— | —NH—C(=S)— | K250 | N153 | S |
| 6-0695 | —(CH$_2$)$_2$— | —C(=O)—N(CH$_2$CH$_3$)— | K2 | N1 | S |
| 6-0696 | —(CH$_2$)$_2$— | —C(=O)—N(CH$_2$CH$_3$)— | K2 | N3 | S |
| 6-0697 | —(CH$_2$)$_2$— | —C(=O)—N(CH$_2$CH$_3$)— | K2 | N9 | S |
| 6-0698 | —(CH$_2$)$_2$— | —C(=O)—N(CH$_2$CH$_3$)— | K2 | N69 | S |
| 6-0699 | —(CH$_2$)$_2$— | —C(=O)—N(CH$_2$CH$_3$)— | K2 | N12 | S |
| 6-0700 | —(CH$_2$)$_2$— | —C(=O)—N(CH$_2$CH$_3$)— | K2 | N115 | S |
| 6-0701 | —(CH$_2$)$_2$— | —C(=O)—N(CH$_2$CH$_3$)— | K2 | N116 | S |
| 6-0702 | —(CH$_2$)$_2$— | —C(=O)—N(CH$_2$CH$_3$)— | K2 | N128 | S |
| 6-0703 | —(CH$_2$)$_2$— | —C(=O)—N(CH$_2$CH$_3$)— | K2 | N140 | S |
| 6-0704 | —(CH$_2$)$_2$— | —C(=O)—N(CH$_2$CH$_3$)— | K2 | N150 | S |

TABLE 200

| Compound No. | -A$^1$- | -A$^2$- | -G$^1$-A$^3$-A$^4$-G$^2$ | -A$^5$-R$^2$ | X |
|---|---|---|---|---|---|
| 6-0705 | —(CH$_2$)$_2$— | —C(=O)—N(CH$_2$CH$_3$)— | K2 | N153 | S |
| 6-0706 | —(CH$_2$)$_2$— | —C(=O)—N(CH$_3$)— | K1 | N1 | S |
| 6-0707 | —(CH$_2$)$_2$— | —C(=O)—N(CH$_3$)— | K1 | N3 | S |
| 6-0708 | —(CH$_2$)$_2$— | —C(=O)—N(CH$_3$)— | K1 | N9 | S |
| 6-0709 | —(CH$_2$)$_2$— | —C(=O)—N(CH$_3$)— | K1 | N69 | S |
| 6-0710 | —(CH$_2$)$_2$— | —C(=O)—N(CH$_3$)— | K1 | N12 | S |
| 6-0711 | —(CH$_2$)$_2$— | —C(=O)—N(CH$_3$)— | K1 | N115 | S |
| 6-0712 | —(CH$_2$)$_2$— | —C(=O)—N(CH$_3$)— | K1 | N116 | S |
| 6-0713 | —(CH$_2$)$_2$— | —C(=O)—N(CH$_3$)— | K1 | N128 | S |
| 6-0714 | —(CH$_2$)$_2$— | —C(=O)—N(CH$_3$)— | K1 | N140 | S |
| 6-0715 | —(CH$_2$)$_2$— | —C(=O)—N(CH$_3$)— | K1 | N150 | S |
| 6-0716 | —(CH$_2$)$_2$— | —C(=O)—N(CH$_3$)— | K1 | N153 | S |
| 6-0717 | —(CH$_2$)$_2$— | —C(=O)—N(CH$_3$)— | K132 | N1 | S |
| 6-0718 | —(CH$_2$)$_2$— | —C(=O)—NH— | K8 | N3 | S |
| 6-0719 | —(CH$_2$)$_2$— | —C(=O)—NH— | K8 | N9 | S |
| 6-0720 | —(CH$_2$)$_2$— | —C(=O)—NH— | K8 | N69 | S |
| 6-0721 | —(CH$_2$)$_2$— | —C(=O)—NH— | K8 | N12 | S |
| 6-0722 | —(CH$_2$)$_2$— | —C(=O)—NH— | K8 | N115 | S |
| 6-0723 | —(CH$_2$)$_2$— | —C(=O)—NH— | K8 | N116 | S |
| 6-0724 | —(CH$_2$)$_2$— | —C(=O)—NH— | K8 | N128 | S |
| 6-0725 | —(CH$_2$)$_2$— | —C(=O)—NH— | K8 | N140 | S |
| 6-0726 | —(CH$_2$)$_2$— | —C(=O)—NH— | K8 | N150 | S |
| 6-0727 | —(CH$_2$)$_2$— | —C(=O)—NH— | K8 | N153 | S |
| 6-0728 | —(CH$_2$)$_2$— | —NH—C(=O)—NH— | K11 | N1 | S |
| 6-0729 | —(CH$_2$)$_2$— | —NH—C(=O)—NH— | K11 | N3 | S |
| 6-0730 | —(CH$_2$)$_2$— | —NH—C(=O)—NH— | K11 | N9 | S |
| 6-0731 | —(CH$_2$)$_2$— | —NH—C(=O)—NH— | K11 | N69 | S |
| 6-0732 | —(CH$_2$)$_2$— | —NH—C(=O)—NH— | K11 | N12 | S |
| 6-0733 | —(CH$_2$)$_2$— | —NH—C(=O)—NH— | K11 | N115 | S |
| 6-0734 | —(CH$_2$)$_2$— | —NH—C(=O)—NH— | K11 | N116 | S |
| 6-0735 | —(CH$_2$)$_2$— | —NH—C(=O)—NH— | K11 | N128 | S |
| 6-0736 | —(CH$_2$)$_2$— | —NH—C(=O)—NH— | K11 | N140 | S |

TABLE 201

| Compound No. | -A¹- | -A²- | -G¹-A³-A⁴-G² | -A⁵-R² | X |
|---|---|---|---|---|---|
| 6-0737 | —(CH₂)₂— | —NH—C(=O)—NH— | K11 | N150 | S |
| 6-0738 | —(CH₂)₂— | —NH—C(=O)—NH— | K11 | N153 | S |
| 6-0739 | —(CH₂)₂— | —C(=O)—NH— | K62 | N1 | S |
| 6-0740 | —(CH₂)₂— | —C(=O)—NH— | K62 | N3 | S |
| 6-0741 | —(CH₂)₂— | —C(=O)—NH— | K62 | N9 | S |
| 6-0742 | —(CH₂)₂— | —C(=O)—NH— | K62 | N69 | S |
| 6-0743 | —(CH₂)₂— | —C(=O)—NH— | K62 | N12 | S |
| 6-0744 | —(CH₂)₂— | —C(=O)—NH— | K62 | N115 | S |
| 6-0745 | —(CH₂)₂— | —C(=O)—NH— | K62 | N116 | S |
| 6-0746 | —(CH₂)₂— | —C(=O)—NH— | K62 | N128 | S |
| 6-0747 | —(CH₂)₂— | —C(=O)—NH— | K62 | N140 | S |
| 6-0748 | —(CH₂)₂— | —C(=O)—NH— | K62 | N150 | S |
| 6-0749 | —(CH₂)₂— | —C(=O)—NH— | K62 | N153 | S |
| 6-0750 | —(CH₂)₂— | —C(=O)—N(CH₃)— | K99 | N1 | S |
| 6-0751 | —(CH₂)₂— | —C(=O)—N(CH₃)— | K99 | N3 | S |
| 6-0752 | —(CH₂)₂— | —C(=O)—N(CH₃)— | K99 | N9 | S |
| 6-0753 | —(CH₂)₂— | —C(=O)—N(CH₃)— | K99 | N69 | S |
| 6-0754 | —(CH₂)₂— | —C(=O)—N(CH₃)— | K99 | N12 | S |
| 6-0755 | —(CH₂)₂— | —C(=O)—N(CH₃)— | K99 | N115 | S |
| 6-0756 | —(CH₂)₂— | —C(=O)—N(CH₃)— | K99 | N116 | S |
| 6-0757 | —(CH₂)₂— | —C(=O)—N(CH₃)— | K99 | N128 | S |
| 6-0758 | —(CH₂)₂— | —C(=O)—N(CH₃)— | K99 | N140 | S |
| 6-0759 | —(CH₂)₂— | —C(=O)—N(CH₃)— | K99 | N150 | S |
| 6-0760 | —(CH₂)₂— | —C(=O)—N(CH₃)— | K99 | N153 | S |
| 6-0761 | —(CH₂)₂— | —C(=O)— | K315 | N1 | S |
| 6-0762 | —(CH₂)₂— | —C(=O)— | K315 | N3 | S |
| 6-0763 | —(CH₂)₂— | —C(=O)— | K315 | N9 | S |
| 6-0764 | —(CH₂)₂— | —C(=O)— | K315 | N69 | S |
| 6-0765 | —(CH₂)₂— | —C(=O)— | K315 | N12 | S |
| 6-0766 | —(CH₂)₂— | —C(=O)— | K315 | N115 | S |
| 6-0767 | —(CH₂)₂— | —C(=O)— | K315 | N116 | S |
| 6-0768 | —(CH₂)₂— | —C(=O)— | K315 | N128 | S |

TABLE 202

| Compound No. | -A¹- | -A²- | -G¹-A³-A⁴-G² | -A⁵-R² | X |
|---|---|---|---|---|---|
| 6-0769 | —(CH₂)₂— | —C(=O)— | K315 | N140 | S |
| 6-0770 | —(CH₂)₂— | —C(=O)— | K315 | N150 | S |
| 6-0771 | —(CH₂)₂— | —C(=O)— | K315 | N153 | S |
| 6-0772 | —(CH₂)₂— | —C(=O)— | K332 | N1 | S |
| 6-0773 | —(CH₂)₂— | —C(=O)— | K332 | N3 | S |
| 6-0774 | —(CH₂)₂— | —C(=O)— | K332 | N9 | S |
| 6-0775 | —(CH₂)₂— | —C(=O)— | K332 | N69 | S |
| 6-0776 | —(CH₂)₂— | —C(=O)— | K332 | N12 | S |
| 6-0777 | —(CH₂)₂— | —C(=O)— | K332 | N115 | S |
| 6-0778 | —(CH₂)₂— | —C(=O)— | K332 | N116 | S |
| 6-0779 | —(CH₂)₂— | —C(=O)— | K332 | N128 | S |
| 6-0780 | —(CH₂)₂— | —C(=O)— | K332 | N140 | S |
| 6-0781 | —(CH₂)₂— | —C(=O)— | K332 | N150 | S |
| 6-0782 | —(CH₂)₂— | —C(=O)— | K332 | N153 | S |
| 6-0783 | —(CH₂)₂— | —C(=O)— | K336 | N1 | S |
| 6-0784 | —(CH₂)₂— | —C(=O)— | K336 | N3 | S |
| 6-0785 | —(CH₂)₂— | —C(=O)— | K336 | N9 | S |
| 6-0786 | —(CH₂)₂— | —C(=O)— | K336 | N69 | S |
| 6-0787 | —(CH₂)₂— | —C(=O)— | K336 | N12 | S |
| 6-0788 | —(CH₂)₂— | —C(=O)— | K336 | N115 | S |
| 6-0789 | —(CH₂)₂— | —C(=O)— | K336 | N116 | S |
| 6-0790 | —(CH₂)₂— | —C(=O)— | K336 | N128 | S |
| 6-0791 | —(CH₂)₂— | —C(=O)— | K336 | N140 | S |
| 6-0792 | —(CH₂)₂— | —C(=O)— | K336 | N150 | S |
| 6-0793 | —(CH₂)₂— | —C(=O)— | K336 | N153 | S |
| 6-0794 | —(CH₂)₂— | —C(=O)— | K337 | N1 | S |
| 6-0795 | —(CH₂)₂— | —C(=O)— | K337 | N3 | S |
| 6-0796 | —(CH₂)₂— | —C(=O)— | K337 | N9 | S |
| 6-0797 | —(CH₂)₂— | —C(=O)— | K337 | N69 | S |
| 6-0798 | —(CH₂)₂— | —C(=O)— | K337 | N12 | S |
| 6-0799 | —(CH₂)₂— | —C(=O)— | K337 | N115 | S |
| 6-0800 | —(CH₂)₂— | —C(=O)— | K337 | N116 | S |

TABLE 203

| Compound No. | -A¹- | -A²- | -G¹-A³-A⁴-G² | -A⁵-R² | X |
|---|---|---|---|---|---|
| 6-0801 | —(CH₂)₂— | —C(=O)— | K337 | N128 | S |
| 6-0802 | —(CH₂)₂— | —C(=O)— | K337 | N140 | S |
| 6-0803 | —(CH₂)₂— | —C(=O)— | K337 | N150 | S |
| 6-0804 | —(CH₂)₂— | —C(=O)— | K337 | N153 | S |
| 6-0805 | —(CH₂)₂— | —C(=O)— | K338 | N1 | S |
| 6-0806 | —(CH₂)₂— | —C(=O)— | K338 | N3 | S |
| 6-0807 | —(CH₂)₂— | —C(=O)— | K338 | N9 | S |
| 6-0808 | —(CH₂)₂— | —C(=O)— | K338 | N69 | S |
| 6-0809 | —(CH₂)₂— | —C(=O)— | K338 | N12 | S |
| 6-0810 | —(CH₂)₂— | —C(=O)— | K338 | N115 | S |
| 6-0811 | —(CH₂)₂— | —C(=O)— | K338 | N116 | S |
| 6-0812 | —(CH₂)₂— | —C(=O)— | K338 | N128 | S |
| 6-0813 | —(CH₂)₂— | —C(=O)— | K338 | N140 | S |
| 6-0814 | —(CH₂)₂— | —C(=O)— | K338 | N150 | S |
| 6-0815 | —(CH₂)₂— | —C(=O)— | K338 | N153 | S |
| 6-0816 | —(CH₂)₂— | —C(=O)— | K377 | N1 | S |
| 6-0817 | —(CH₂)₂— | —C(=O)— | K377 | N3 | S |
| 6-0818 | —(CH₂)₂— | —C(=O)— | K377 | N9 | S |
| 6-0819 | —(CH₂)₂— | —C(=O)— | K377 | N69 | S |
| 6-0820 | —(CH₂)₂— | —C(=O)— | K377 | N12 | S |
| 6-0821 | —(CH₂)₂— | —C(=O)— | K377 | N115 | S |
| 6-0822 | —(CH₂)₂— | —C(=O)— | K377 | N116 | S |
| 6-0823 | —(CH₂)₂— | —C(=O)— | K377 | N128 | S |
| 6-0824 | —(CH₂)₂— | —C(=O)— | K377 | N140 | S |
| 6-0825 | —(CH₂)₂— | —C(=O)— | K377 | N150 | S |
| 6-0826 | —(CH₂)₂— | —C(=O)— | K377 | N153 | S |
| 6-0827 | —(CH₂)₂— | —C(=O)— | K378 | N1 | S |
| 6-0828 | —(CH₂)₂— | —C(=O)— | K378 | N3 | S |
| 6-0829 | —(CH₂)₂— | —C(=O)— | K378 | N9 | S |
| 6-0830 | —(CH₂)₂— | —C(=O)— | K378 | N69 | S |
| 6-0831 | —(CH₂)₂— | —C(=O)— | K378 | N12 | S |
| 6-0832 | —(CH₂)₂— | —C(=O)— | K378 | N115 | S |

TABLE 204

| Compound No. | -A¹- | -A²- | -G¹-A³-A⁴-G² | -A⁵-R² | X |
|---|---|---|---|---|---|
| 6-0833 | —(CH₂)₂— | —C(=O)— | K378 | N116 | S |
| 6-0834 | —(CH₂)₂— | —C(=O)— | K378 | N128 | S |
| 6-0835 | —(CH₂)₂— | —C(=O)— | K378 | N140 | S |
| 6-0836 | —(CH₂)₂— | —C(=O)— | K378 | N150 | S |
| 6-0837 | —(CH₂)₂— | —C(=O)— | K378 | N153 | S |
| 6-0838 | —(CH₂)₂— | —C(=O)— | K381 | N1 | S |
| 6-0839 | —(CH₂)₂— | —C(=O)— | K381 | N3 | S |
| 6-0840 | —(CH₂)₂— | —C(=O)— | K381 | N9 | S |
| 6-0841 | —(CH₂)₂— | —C(=O)— | K381 | N69 | S |
| 6-0842 | —(CH₂)₂— | —C(=O)— | K381 | N12 | S |
| 6-0843 | —(CH₂)₂— | —C(=O)— | K381 | N115 | S |
| 6-0844 | —(CH₂)₂— | —C(=O)— | K381 | N116 | S |
| 6-0845 | —(CH₂)₂— | —C(=O)— | K381 | N128 | S |
| 6-0846 | —(CH₂)₂— | —C(=O)— | K381 | N140 | S |
| 6-0847 | —(CH₂)₂— | —C(=O)— | K381 | N150 | S |
| 6-0848 | —(CH₂)₂— | —C(=O)— | K381 | N153 | S |
| 6-0849 | —(CH₂)₂— | —C(=O)— | K382 | N1 | S |
| 6-0850 | —(CH₂)₂— | —C(=O)— | K382 | N3 | S |
| 6-0851 | —(CH₂)₂— | —C(=O)— | K382 | N9 | S |
| 6-0852 | —(CH₂)₂— | —C(=O)— | K382 | N69 | S |
| 6-0853 | —(CH₂)₂— | —C(=O)— | K382 | N12 | S |
| 6-0854 | —(CH₂)₂— | —C(=O)— | K382 | N115 | S |
| 6-0855 | —(CH₂)₂— | —C(=O)— | K382 | N116 | S |
| 6-0856 | —(CH₂)₂— | —C(=O)— | K382 | N128 | S |
| 6-0857 | —(CH₂)₂— | —C(=O)— | K382 | N140 | S |
| 6-0858 | —(CH₂)₂— | —C(=O)— | K382 | N150 | S |
| 6-0859 | —(CH₂)₂— | —C(=O)— | K382 | N153 | S |
| 6-0860 | —(CH₂)₂— | —C(=O)— | K384 | N1 | S |
| 6-0861 | —(CH₂)₂— | —C(=O)— | K384 | N3 | S |
| 6-0862 | —(CH₂)₂— | —C(=O)— | K384 | N9 | S |
| 6-0863 | —(CH₂)₂— | —C(=O)— | K384 | N69 | S |
| 6-0864 | —(CH₂)₂— | —C(=O)— | K384 | N12 | S |

TABLE 205

| Compound No. | -A¹- | -A²- | -G¹-A³-A⁴-G² | -A⁵-R² | X |
|---|---|---|---|---|---|
| 6-0865 | —(CH₂)₂— | —C(=O)— | K384 | N115 | S |
| 6-0866 | —(CH₂)₂— | —C(=O)— | K384 | N116 | S |
| 6-0867 | —(CH₂)₂— | —C(=O)— | K384 | N128 | S |
| 6-0868 | —(CH₂)₂— | —C(=O)— | K384 | N140 | S |
| 6-0869 | —(CH₂)₂— | —C(=O)— | K384 | N150 | S |
| 6-0870 | —(CH₂)₂— | —C(=O)— | K384 | N153 | S |
| 6-0871 | —(CH₂)₂— | —C(=O)— | K396 | N1 | S |
| 6-0872 | —(CH₂)₂— | —C(=O)— | K396 | N3 | S |
| 6-0873 | —(CH₂)₂— | —C(=O)— | K396 | N9 | S |
| 6-0874 | —(CH₂)₂— | —C(=O)— | K396 | N69 | S |
| 6-0875 | —(CH₂)₂— | —C(=O)— | K396 | N12 | S |
| 6-0876 | —(CH₂)₂— | —C(=O)— | K396 | N115 | S |
| 6-0877 | —(CH₂)₂— | —C(=O)— | K396 | N116 | S |
| 6-0878 | —(CH₂)₂— | —C(=O)— | K396 | N128 | S |
| 6-0879 | —(CH₂)₂— | —C(=O)— | K396 | N140 | S |
| 6-0880 | —(CH₂)₂— | —C(=O)— | K396 | N150 | S |
| 6-0881 | —(CH₂)₂— | —C(=O)— | K396 | N153 | S |
| 6-0882 | —(CH₂)₂— | —C(=O)— | K419 | N1 | S |
| 6-0883 | —(CH₂)₂— | —C(=O)— | K419 | N3 | S |
| 6-0884 | —(CH₂)₂— | —C(=O)— | K419 | N9 | S |
| 6-0885 | —(CH₂)₂— | —C(=O)— | K419 | N69 | S |
| 6-0886 | —(CH₂)₂— | —C(=O)— | K419 | N12 | S |
| 6-0887 | —(CH₂)₂— | —C(=O)— | K419 | N115 | S |
| 6-0888 | —(CH₂)₂— | —C(=O)— | K419 | N116 | S |
| 6-0889 | —(CH₂)₂— | —C(=O)— | K419 | N128 | S |
| 6-0890 | —(CH₂)₂— | —C(=O)— | K419 | N140 | S |
| 6-0891 | —(CH₂)₂— | —C(=O)— | K419 | N150 | S |
| 6-0892 | —(CH₂)₂— | —C(=O)— | K419 | N153 | S |
| 6-0893 | —(CH₂)₃— | —C(=O)—N(CH₂CH₃)— | K2 | N3 | S |
| 6-0894 | —(CH₂)₃— | —C(=O)—N(CH₂CH₃)— | K2 | N9 | S |
| 6-0895 | —(CH₂)₃— | —C(=O)—N(CH₂CH₃)— | K2 | N115 | S |
| 6-0896 | —(CH₂)₃— | —C(=O)—N(CH₂CH₃)— | K2 | N128 | S |

TABLE 206

| Compound No. | -A¹- | -A²- | -G¹-A³-A⁴-G² | -A⁵-R² | X |
|---|---|---|---|---|---|
| 6-0897 | —(CH₂)₃— | —C(=O)—N(CH₂CH₃)— | K2 | N140 | S |
| 6-0898 | —(CH₂)₃— | —C(=O)—N(CH₂CH₃)— | K2 | N144 | S |
| 6-0899 | —(CH₂)₃— | —C(=O)—N(CH₃)— | K1 | N3 | S |
| 6-0900 | —(CH₂)₃— | —C(=O)—N(CH₃)— | K1 | N9 | S |
| 6-0901 | —(CH₂)₃— | —C(=O)—N(CH₃)— | K1 | N115 | S |
| 6-0902 | —(CH₂)₃— | —C(=O)—N(CH₃)— | K1 | N128 | S |
| 6-0903 | —(CH₂)₃— | —C(=O)—N(CH₃)— | K1 | N140 | S |
| 6-0904 | —(CH₂)₃— | —C(=O)—N(CH₃)— | K1 | N144 | S |
| 6-0905 | —(CH₂)₃— | —C(=O)—NH— | K8 | N3 | S |
| 6-0906 | —(CH₂)₃— | —C(=O)—NH— | K8 | N9 | S |
| 6-0907 | —(CH₂)₃— | —C(=O)—NH— | K8 | N115 | S |
| 6-0908 | —(CH₂)₃— | —C(=O)—NH— | K8 | N128 | S |
| 6-0909 | —(CH₂)₃— | —C(=O)—NH— | K8 | N140 | S |
| 6-0910 | —(CH₂)₃— | —C(=O)—NH— | K8 | N144 | S |
| 6-0911 | —(CH₂)₃— | —NH—C(=O)—NH— | K11 | N3 | S |
| 6-0912 | —(CH₂)₃— | —NH—C(=O)—NH— | K11 | N9 | S |
| 6-0913 | —(CH₂)₃— | —NH—C(=O)—NH— | K11 | N115 | S |
| 6-0914 | —(CH₂)₃— | —NH—C(=O)—NH— | K11 | N128 | S |
| 6-0915 | —(CH₂)₃— | —NH—C(=O)—NH— | K11 | N140 | S |
| 6-0916 | —(CH₂)₃— | —NH—C(=O)—NH— | K11 | N144 | S |
| 6-0917 | —(CH₂)₃— | —C(=O)—NH— | K62 | N3 | S |
| 6-0918 | —(CH₂)₃— | —C(=O)—NH— | K62 | N9 | S |
| 6-0919 | —(CH₂)₃— | —C(=O)—NH— | K62 | N115 | S |
| 6-0920 | —(CH₂)₃— | —C(=O)—NH— | K62 | N128 | S |
| 6-0921 | —(CH₂)₃— | —C(=O)—NH— | K62 | N140 | S |
| 6-0922 | —(CH₂)₃— | —C(=O)—NH— | K62 | N144 | S |
| 6-0923 | —(CH₂)₃— | —C(=O)—N(CH₃)— | K99 | N3 | S |
| 6-0924 | —(CH₂)₃— | —C(=O)—N(CH₃)— | K99 | N9 | S |
| 6-0925 | —(CH₂)₃— | —C(=O)—N(CH₃)— | K99 | N115 | S |
| 6-0926 | —(CH₂)₃— | —C(=O)— | K315 | N3 | S |
| 6-0927 | —(CH₂)₃— | —C(=O)— | K315 | N9 | S |
| 6-0928 | —(CH₂)₃— | —C(=O)— | K315 | N115 | S |

TABLE 207

| Compound No. | -A¹- | -A²- | -G¹-A³-A⁴-G² | -A⁵-R² | X |
|---|---|---|---|---|---|
| 6-0929 | —(CH₂)₃— | —C(=O)— | K315 | N128 | S |
| 6-0930 | —(CH₂)₃— | —C(=O)— | K315 | N140 | S |
| 6-0931 | —(CH₂)₃— | —C(=O)— | K315 | N144 | S |
| 6-0932 | —(CH₂)₃— | —C(=O)— | K316 | N3 | S |
| 6-0933 | —(CH₂)₃— | —C(=O)— | K316 | N9 | S |
| 6-0934 | —(CH₂)₃— | —C(=O)— | K316 | N115 | S |
| 6-0935 | —(CH₂)₃— | —C(=O)— | K316 | N128 | S |
| 6-0936 | —(CH₂)₃— | —C(=O)— | K316 | N140 | S |
| 6-0937 | —(CH₂)₃— | —C(=O)— | K316 | N144 | S |
| 6-0938 | —(CH₂)₃— | —C(=O)— | K318 | N3 | S |
| 6-0939 | —(CH₂)₃— | —C(=O)— | K318 | N9 | S |
| 6-0940 | —(CH₂)₃— | —C(=O)— | K318 | N115 | S |
| 6-0941 | —(CH₂)₃— | —C(=O)— | K318 | N128 | S |
| 6-0942 | —(CH₂)₃— | —C(=O)— | K319 | N3 | S |
| 6-0943 | —(CH₂)₃— | —C(=O)— | K319 | N9 | S |
| 6-0944 | —(CH₂)₃— | —C(=O)— | K319 | N115 | S |
| 6-0945 | —(CH₂)₃— | —C(=O)— | K319 | N128 | S |
| 6-0946 | —(CH₂)₃— | —C(=O)— | K332 | N3 | S |
| 6-0947 | —(CH₂)₃— | —C(=O)— | K332 | N9 | S |
| 6-0948 | —(CH₂)₃— | —C(=O)— | K332 | N115 | S |
| 6-0949 | —(CH₂)₃— | —C(=O)— | K332 | N128 | S |
| 6-0950 | —(CH₂)₃— | —C(=O)— | K336 | N3 | S |
| 6-0951 | —(CH₂)₃— | —C(=O)— | K336 | N9 | S |
| 6-0952 | —(CH₂)₃— | —C(=O)— | K336 | N115 | S |
| 6-0953 | —(CH₂)₃— | —C(=O)— | K336 | N128 | S |
| 6-0954 | —(CH₂)₃— | —C(=O)— | K337 | N1 | S |
| 6-0955 | —(CH₂)₃— | —C(=O)— | K337 | N3 | S |
| 6-0956 | —(CH₂)₃— | —C(=O)— | K337 | N9 | S |
| 6-0957 | —(CH₂)₃— | —C(=O)— | K337 | N115 | S |
| 6-0958 | —(CH₂)₃— | —C(=O)— | K337 | N128 | S |
| 6-0959 | —(CH₂)₂— | —C(=O)— | K1 | N128 | S |
| 6-0960 | —(CH₂)₂— | —C(=O)— | K2 | N128 | S |

TABLE 208

| Compound No. | -A¹- | -A²- | -G¹-A³-A⁴-G² | -A⁵-R² | X |
|---|---|---|---|---|---|
| 6-0961 | —(CH₂)₂— | —C(=O)— | K8 | N128 | S |
| 6-0962 | —(CH₂)₂— | —C(=O)— | K11 | N128 | S |
| 6-0963 | —(CH₂)₂— | —C(=O)— | K99 | N128 | S |
| 6-0964 | —(CH₂)₂— | —C(=O)— | K206 | N128 | S |
| 6-0965 | —(CH₂)₂— | —C(=O)—O— | K1 | N128 | S |
| 6-0966 | —(CH₂)₂— | —C(=O)—O— | K11 | N128 | S |
| 6-0967 | —(CH₂)₂— | —C(=O)—O— | K99 | N128 | S |
| 6-0968 | —(CH₂)₂— | —NH—C(=O)—O— | K99 | N115 | S |
| 6-0969 | —(CH₂)₂— | —NH—C(=O)—O— | K5 | N115 | O |
| 6-0970 | —(CH₂)₂— | —NH—C(=O)—O— | K5 | N115 | O |
| 6-0971 | —(CH₂)₂— | —NH—C(=O)—NH— | K1 | N115 | S |
| 6-0972 | —(CH₂)₂— | —NH—C(=O)—NH— | K4 | N115 | S |
| 6-0973 | —(CH₂)₂— | —NH—C(=O)—NH— | K8 | N115 | S |
| 6-0974 | —(CH₂)₂— | —NH—C(=O)—NH— | K11 | N115 | O |
| 6-0975 | —(CH₂)₂— | —NH—C(=O)—NH— | K14 | N115 | S |
| 6-0976 | —(CH₂)₂— | —NH—C(=O)—NH— | K32 | N115 | S |
| 6-0977 | —(CH₂)₂— | —NH—C(=O)—NH— | K4 | N115 | O |
| 6-0978 | —(CH₂)₂— | —NH—C(=S)—NH— | K11 | N115 | S |
| 6-0979 | —(CH₂)₂— | —NH—S(=O)₂— | K1 | N115 | S |
| 6-0980 | —(CH₂)₂— | —NH—S(=O)₂— | K11 | N115 | S |
| 6-0981 | —(CH₂)₂— | —NH—S(=O)₂— | K99 | N115 | S |
| 6-0982 | —(CH₂)₂— | —NH— | K1 | N115 | S |
| 6-0983 | —(CH₂)₂— | —NH— | K2 | N115 | S |
| 6-0984 | —(CH₂)₂— | —NH— | K3 | N115 | S |
| 6-0985 | —(CH₂)₂— | —NH— | K99 | N115 | S |
| 6-0986 | —(CH₂)₂— | —NH— | K100 | N115 | S |
| 6-0987 | —(CH₂)₂— | —NH— | K101 | N115 | S |
| 6-0988 | —(CH₂)₂— | —NH— | K102 | N115 | S |
| 6-0989 | —(CH₂)₂— | —NH— | K103 | N115 | S |
| 6-0990 | —(CH₂)₂— | —NH— | K105 | N115 | S |
| 6-0991 | —(CH₂)₂— | —NH— | K106 | N115 | S |
| 6-0992 | —(CH₂)₃— | —C(=O)— | K1 | N128 | S |

TABLE 209

| Compound No. | -A¹- | -A²- | -G¹-A³-A⁴-G² | -A⁵-R² | X |
|---|---|---|---|---|---|
| 6-0993 | —(CH₂)₃— | —C(=O)— | K2 | N128 | S |
| 6-0994 | —(CH₂)₃— | —C(=O)— | K8 | N128 | S |
| 6-0995 | —(CH₂)₃— | —C(=O)— | K11 | N128 | S |
| 6-0996 | —(CH₂)₃— | —C(=O)— | K99 | N128 | S |
| 6-0997 | —(CH₂)₃— | —C(=O)— | K206 | N128 | S |
| 6-0998 | —(CH₂)₃— | —C(=O)—O— | K1 | N128 | S |
| 6-0999 | —(CH₂)₃— | —C(=O)—O— | K11 | N128 | S |
| 6-1000 | —(CH₂)₃— | —C(=O)—O— | K99 | N128 | S |
| 6-1001 | —(CH₂)₃— | —NH—C(=O)—O— | K99 | N115 | S |
| 6-1002 | —(CH₂)₃— | —NH—C(=O)—O— | K5 | N115 | O |
| 6-1003 | —(CH₂)₃— | —NH—C(=O)—O— | K5 | N115 | S |
| 6-1004 | —(CH₂)₃— | —NH—C(=O)—NH— | K1 | N115 | S |
| 6-1005 | —(CH₂)₃— | —NH—C(=O)—NH— | K4 | N115 | S |
| 6-1006 | —(CH₂)₃— | —NH—C(=O)—NH— | K8 | N115 | S |
| 6-1007 | —(CH₂)₃— | —NH—C(=O)—NH— | K11 | N115 | O |
| 6-1008 | —(CH₂)₃— | —NH—C(=O)—NH— | K14 | N115 | S |
| 6-1009 | —(CH₂)₃— | —NH—C(=O)—NH— | K32 | N115 | S |
| 6-1010 | —(CH₂)₃— | —NH—C(=O)—NH— | K4 | N115 | O |
| 6-1011 | —(CH₂)₃— | —NH—C(=S)—NH— | K1 | N115 | S |
| 6-1012 | —(CH₂)₃— | —NH—S(=O)₂— | K1 | N115 | S |
| 6-1013 | —(CH₂)₃— | —NH—S(=O)₂— | K11 | N115 | S |
| 6-1014 | —(CH₂)₃— | —NH—S(=O)₂— | K99 | N115 | S |
| 6-1015 | —(CH₂)₃— | —NH— | K1 | N115 | S |
| 6-1016 | —(CH₂)₃— | —NH— | K2 | N115 | S |
| 6-1017 | —(CH₂)₃— | —NH— | K3 | N115 | S |
| 6-1018 | —(CH₂)₃— | —NH— | K99 | N115 | S |
| 6-1019 | —(CH₂)₃— | —NH— | K100 | N115 | S |
| 6-1020 | —(CH₂)₃— | —NH— | K101 | N115 | S |
| 6-1021 | —(CH₂)₃— | —NH— | K102 | N115 | S |
| 6-1022 | —(CH₂)₃— | —NH— | K103 | N115 | S |
| 6-1023 | —(CH₂)₃— | —NH— | K105 | N115 | S |
| 6-1024 | —(CH₂)₃— | —NH— | K106 | N115 | S |

TABLE 210

| Compound No. | -A¹- | -A²- | -G¹-A³-A⁴-G² | -A⁵-R² | X |
|---|---|---|---|---|---|
| 6-1025 | —(CH₂)₂— | —NH—C(=O)— | K283 | N4 | S |
| 6-1026 | —(CH₂)₂— | —NH—C(=O)— | K283 | N9 | S |
| 6-1027 | —(CH₂)₂— | —NH—C(=O)— | K283 | N10 | S |
| 6-1028 | —(CH₂)₂— | —NH—C(=O)— | K283 | N41 | S |
| 6-1029 | —(CH₂)₂— | —NH—C(=O)— | K283 | N69 | S |
| 6-1030 | —(CH₂)₂— | —NH—C(=O)— | K283 | N81 | S |
| 6-1031 | —(CH₂)₂— | —NH—C(=O)— | K283 | N115 | S |
| 6-1032 | —(CH₂)₂— | —NH—C(=O)— | K283 | N109 | S |
| 6-1033 | —(CH₂)₂— | —NH—C(=O)— | K283 | N116 | S |
| 6-1034 | —(CH₂)₂— | —NH—C(=O)— | K83 | N128 | S |
| 6-1035 | —(CH₂)₂— | —NH—C(=O)— | K283 | N144 | S |
| 6-1036 | —(CH₂)₂— | —NH—C(=O)— | K242 | N4 | S |
| 6-1037 | —(CH₂)₂— | —NH—C(=O)— | K243 | N9 | O |
| 6-1038 | —(CH₂)₂— | —NH—C(=O)— | K244 | N10 | S |
| 6-1039 | —(CH₂)₂— | —NH—C(=O)— | K245 | N41 | S |
| 6-1040 | —(CH₂)₂— | —NH—C(=O)— | K246 | N69 | S |
| 6-1041 | —(CH₂)₂— | —NH—C(=O)— | K247 | N81 | S |
| 6-1042 | —(CH₂)₂— | —NH—C(=O)— | K248 | N84 | S |
| 6-1043 | —(CH₂)₂— | —NH—C(=O)— | K249 | N109 | S |
| 6-1044 | —(CH₂)₂— | —NH—C(=O)— | K250 | N116 | S |
| 6-1045 | —(CH₂)₂— | —NH—C(=O)— | K251 | N128 | S |
| 6-1046 | —(CH₂)₂— | —NH—C(=O)— | K292 | N144 | S |
| 6-1047 | —(CH₂)₂— | —NH—C(=O)— | K295 | N4 | S |
| 6-1048 | —(CH₂)₂— | —NH—C(=O)— | K300 | N9 | S |
| 6-1049 | —(CH₂)₂— | —NH—C(=O)— | K301 | N10 | S |
| 6-1050 | —(CH₂)₂— | —NH—C(=O)— | K305 | N41 | S |
| 6-1051 | —(CH₂)₂— | —NH—C(=O)— | K306 | N69 | S |
| 6-1052 | —(CH₂)₂— | —NH—C(=O)— | K307 | N81 | S |
| 6-1053 | —(CH₂)₂— | —NH—C(=O)— | K423 | N84 | S |
| 6-1054 | —(CH₂)₂— | —NH—C(=O)— | K424 | N109 | S |
| 6-1055 | —(CH₂)₂— | —NH—C(=O)— | K425 | N116 | S |
| 6-1056 | —(CH₂)₂— | —NH—C(=O)— | K478 | N128 | S |

TABLE 211

| Compound No. | -A¹- | -A²- | -G¹-A³-A⁴-G² | -A⁵-R² | X |
|---|---|---|---|---|---|
| 6-1057 | —(CH₂)₂— | —NH—C(=O)— | K485 | N144 | S |
| 6-1058 | —(CH₂)₂— | —NH—C(=O)— | K499 | N4 | S |
| 6-1059 | —(CH₂)₂— | —NH—C(=O)— | K500 | N9 | S |
| 6-1060 | —(CH₂)₂— | —NH—C(=O)— | K501 | N10 | S |
| 6-1061 | —(CH₂)₂— | —NH—C(=O)— | K502 | N41 | S |
| 6-1062 | —(CH₂)₂— | —NH—C(=O)— | K503 | N69 | S |
| 6-1063 | —(CH₂)₂— | —NH—C(=O)— | K504 | N81 | S |
| 6-1064 | —(CH₂)₂— | —NH—C(=O)— | K505 | N84 | S |
| 6-1065 | —(CH₂)₂— | —NH—C(=O)— | K506 | N109 | S |
| 6-1066 | —(CH₂)₂— | —NH—C(=O)— | K507 | N116 | S |
| 6-1067 | —(CH₂)₂— | —NH—C(=O)— | K508 | N128 | S |
| 6-1068 | —(CH₂)₂— | —NH—C(=O)— | K509 | N144 | S |
| 6-1069 | —(CH₂)₂— | —NH—C(=O)— | K510 | N4 | S |
| 6-1070 | —(CH₂)₂— | —NH—C(=O)— | K511 | N9 | S |
| 6-1071 | —(CH₂)₂— | —NH—C(=O)— | K512 | N10 | S |
| 6-1072 | —(CH₂)₂— | —NH—C(=O)— | K513 | N41 | S |
| 6-1073 | —(CH₂)₂— | —NH—C(=O)— | K514 | N69 | S |
| 6-1074 | —(CH₂)₂— | —NH—C(=O)— | K516 | N81 | S |
| 6-1075 | —(CH₂)₂— | —NH—C(=O)— | K517 | N84 | S |
| 6-1076 | —(CH₂)₂— | —NH—C(=O)— | K518 | N109 | S |
| 6-1077 | —(CH₂)₂— | —NH—C(=O)— | K519 | N116 | S |
| 6-1078 | —(CH₂)₂— | —NH—C(=O)— | K523 | N128 | S |
| 6-1079 | —(CH₂)₂— | —NH—C(=O)— | K525 | N144 | S |
| 6-1080 | —(CH₂)₂— | —NH—C(=O)— | K526 | N4 | S |
| 6-1081 | —(CH₂)₂— | —NH—C(=O)— | K528 | N9 | S |
| 6-1082 | —(CH₂)₂— | —NH—C(=O)— | K542 | N10 | S |
| 6-1083 | —(CH₂)₂— | —NH—C(=O)— | K543 | N41 | S |
| 6-1084 | —(CH₂)₂— | —NH—C(=O)— | K545 | N69 | S |
| 6-1085 | —(CH₂)₂— | —NH—C(=O)— | K546 | N81 | S |
| 6-1086 | —(CH₂)₂— | —NH—C(=O)— | K547 | N84 | S |
| 6-1087 | —(CH₂)₂— | —NH—C(=O)— | K548 | N109 | S |
| 6-1088 | —(CH₂)₂— | —NH—C(=O)— | K549 | N116 | S |

TABLE 212

| Compound No. | -A¹- | -A²- | -G¹-A³-A⁴-G² | -A⁵-R² | X |
|---|---|---|---|---|---|
| 6-1089 | —(CH₂)₂— | —NH—C(=O)— | K554 | N128 | S |
| 6-1090 | —(CH₂)₂— | —NH—C(=O)— | K563 | N144 | S |
| 6-1091 | —(CH₂)₂— | —NH—C(=O)— | K564 | N4 | S |
| 6-1092 | —(CH₂)₂— | —NH—C(=O)— | K567 | N9 | S |
| 6-1093 | —(CH₂)₂— | —NH—C(=O)— | K568 | N10 | S |
| 6-1094 | —(CH₂)₂— | —NH—C(=O)— | K569 | N41 | S |
| 6-1095 | —(CH₂)₂— | —NH—C(=O)— | K570 | N69 | S |
| 6-1096 | —(CH₂)₂— | —NH—C(=O)— | K571 | N81 | S |
| 6-1097 | —(CH₂)₂— | —NH—C(=O)— | K572 | N84 | S |
| 6-1098 | —(CH₂)₂— | —NH—C(=O)— | K573 | N109 | S |
| 6-1099 | —(CH₂)₂— | —NH—C(=O)— | K574 | N116 | S |
| 6-1100 | —(CH₂)₂— | —NH—C(=O)— | K575 | N128 | S |
| 6-1101 | —(CH₂)₂— | —NH—C(=O)— | K576 | N144 | S |
| 6-1102 | —(CH₂)₂— | —NH—C(=O)— | K577 | N4 | S |
| 6-1103 | —(CH₂)₂— | —NH—C(=O)— | K578 | N9 | S |
| 6-1104 | —(CH₂)₂— | —NH—C(=O)— | K579 | N10 | S |
| 6-1105 | —(CH₂)₂— | —NH—C(=O)— | K580 | N41 | S |
| 6-1106 | —(CH₂)₂— | —NH—C(=O)— | K581 | N69 | S |
| 6-1107 | —(CH₂)₂— | —NH—C(=O)— | K582 | N81 | S |
| 6-1108 | —(CH₂)₂— | —NH—C(=O)— | K583 | N84 | S |
| 6-1109 | —(CH₂)₂— | —NH—C(=O)— | K584 | N109 | S |
| 6-1110 | —(CH₂)₂— | —NH—C(=O)— | K585 | N116 | S |
| 6-1111 | —(CH₂)₂— | —NH—C(=O)— | K590 | N128 | S |
| 6-1112 | —(CH₂)₂— | —NH—C(=O)— | K591 | N144 | S |
| 6-1113 | —(CH₂)₂— | —NH—C(=O)— | K592 | N4 | S |
| 6-1114 | —(CH₂)₂— | —NH—C(=O)— | K593 | N9 | S |
| 6-1115 | —(CH₂)₂— | —NH—C(=O)— | K594 | N10 | S |
| 6-1116 | —(CH₂)₂— | —NH—C(=O)— | K595 | N41 | S |
| 6-1117 | —(CH₂)₂— | —NH—C(=O)— | K596 | N69 | S |
| 6-1118 | —(CH₂)₂— | —NH—C(=O)— | K608 | N81 | S |
| 6-1119 | —(CH₂)₂— | —NH—C(=O)— | K611 | N84 | S |
| 6-1120 | —(CH₂)₂— | —NH—C(=O)— | K618 | N109 | S |

TABLE 213

| Compound No. | -A¹- | -A²- | -G¹-A³-A⁴-G² | -A⁵-R² | X |
|---|---|---|---|---|---|
| 6-1121 | —(CH$_2$)$_2$— | —NH—C(=O)— | K623 | N116 | S |
| 6-1122 | —(CH$_2$)$_2$— | —NH—C(=O)— | K634 | N128 | S |
| 6-1123 | —(CH$_2$)$_2$— | —NH—C(=O)— | K635 | N144 | S |
| 6-1124 | —(CH$_2$)$_2$— | —NH—C(=O)— | K636 | N4 | S |
| 6-1125 | —(CH$_2$)$_2$— | —NH—C(=O)— | K637 | N9 | S |
| 6-1126 | —(CH$_2$)$_2$— | —NH—C(=O)— | K638 | N10 | S |
| 6-1127 | —(CH$_2$)$_2$— | —NH—C(=O)— | K639 | N41 | S |
| 6-1128 | —(CH$_2$)$_2$— | —NH—C(=O)— | K655 | N69 | S |
| 6-1129 | —(CH$_2$)$_2$— | —NH—C(=O)— | K761 | N81 | S |
| 6-1130 | —(CH$_2$)$_2$— | —NH— | K70 | N84 | S |
| 6-1131 | —(CH$_2$)$_2$— | —NH— | K73 | N109 | S |
| 6-1132 | —(CH$_2$)$_2$— | —NH— | K74 | N116 | S |
| 6-1133 | —(CH$_2$)$_2$— | —NH— | K96 | N128 | S |
| 6-1134 | —(CH$_2$)$_2$— | —NH— | K498 | N144 | S |
| 6-1135 | —(CH$_2$)$_2$— | —NH— | K617 | N4 | S |
| 6-1136 | —(CH$_2$)$_2$— | —NH— | K642 | N9 | S |
| 6-1137 | —(CH$_2$)$_2$— | —NH— | K763 | N10 | S |
| 6-1138 | —(CH$_2$)$_2$— | —NH— | K764 | N41 | S |
| 6-1139 | —(CH$_2$)$_2$— | —NH— | K765 | N69 | S |
| 6-1140 | —(CH$_2$)$_2$— | —NH— | K766 | N81 | S |
| 6-1141 | —(CH$_2$)$_2$— | —NH— | K767 | N84 | S |
| 6-1142 | —(CH$_2$)$_2$— | —NH— | K768 | N109 | S |
| 6-1143 | —(CH$_2$)$_2$— | —NH— | K769 | N116 | S |
| 6-1144 | —(CH$_2$)$_2$— | —NH— | K770 | N128 | S |
| 6-1145 | —(CH$_2$)$_2$— | —NH— | K771 | N144 | S |
| 6-1146 | —(CH$_2$)$_2$— | —NH— | K772 | N4 | S |
| 6-1147 | —(CH$_2$)$_2$— | —NH— | K773 | N9 | S |
| 6-1148 | —(CH$_2$)$_2$— | —NH— | K774 | N10 | S |
| 6-1149 | —(CH$_2$)$_2$— | —NH— | K775 | N41 | S |
| 6-1150 | —(CH$_2$)$_2$— | —NH— | K776 | N69 | S |
| 6-1151 | —(CH$_2$)$_2$— | —NH— | K777 | N81 | S |
| 6-1152 | —(CH$_2$)$_2$— | —NH— | K778 | N84 | S |

TABLE 214

| Compound No. | -A¹- | -A²- | -G¹-A³-A⁴-G² | -A⁵-R² | X |
|---|---|---|---|---|---|
| 6-1153 | —(CH$_2$)$_2$— | —NH— | K779 | N109 | S |
| 6-1154 | —(CH$_2$)$_2$— | —NH— | K780 | N116 | S |
| 6-1155 | —(CH$_2$)$_2$— | —C(=O)— | K337 | N144 | S |
| 6-1156 | —(CH$_2$)$_2$— | —C(=O)— | K337 | N4 | S |
| 6-1157 | —(CH$_2$)$_2$— | —C(=O)— | K337 | N10 | S |
| 6-1158 | —(CH$_2$)$_2$— | —C(=O)— | K321 | N4 | S |
| 6-1159 | —(CH$_2$)$_2$— | —C(=O)— | K321 | N9 | S |
| 6-1160 | —(CH$_2$)$_2$— | —C(=O)— | K321 | N69 | S |
| 6-1161 | —(CH$_2$)$_2$— | —C(=O)— | K321 | N12 | S |
| 6-1162 | —(CH$_2$)$_2$— | —C(=O)— | K321 | N115 | S |
| 6-1163 | —(CH$_2$)$_2$— | —C(=O)— | K321 | N116 | S |
| 6-1164 | —(CH$_2$)$_2$— | —C(=O)— | K321 | N128 | S |
| 6-1165 | —(CH$_2$)$_2$— | —C(=O)— | K321 | N140 | S |
| 6-1166 | —(CH$_2$)$_2$— | —C(=O)— | K321 | N150 | S |
| 6-1167 | —(CH$_2$)$_2$— | —C(=O)— | K321 | N153 | S |
| 6-1168 | —(CH$_2$)$_2$— | —C(=O)— | K315 | N4 | S |
| 6-1169 | —(CH$_2$)$_2$— | —C(=O)— | K377 | N4 | S |
| 6-1170 | —(CH$_2$)$_2$— | —C(=O)— | K379 | N69 | S |
| 6-1171 | —(CH$_2$)$_2$— | —C(=O)— | K380 | N12 | S |
| 6-1172 | —(CH$_2$)$_2$— | —C(=O)— | K383 | N128 | S |
| 6-1173 | —(CH$_2$)$_2$— | —C(=O)— | K385 | N150 | S |
| 6-1174 | —(CH$_2$)$_2$— | —C(=O)— | K386 | N153 | S |
| 6-1175 | —(CH$_2$)$_2$— | —C(=O)— | K387 | N4 | S |
| 6-1176 | —(CH$_2$)$_2$— | —C(=O)— | K388 | N9 | S |
| 6-1177 | —(CH$_2$)$_2$— | —C(=O)— | K389 | N69 | S |
| 6-1178 | —(CH$_2$)$_2$— | —C(=O)— | K390 | N12 | S |
| 6-1179 | —(CH$_2$)$_2$— | —C(=O)— | K391 | N115 | S |
| 6-1180 | —(CH$_2$)$_2$— | —C(=O)— | K392 | N116 | S |
| 6-1181 | —(CH$_2$)$_2$— | —C(=O)— | K393 | N128 | S |
| 6-1182 | —(CH$_2$)$_2$— | —C(=O)— | K394 | N140 | S |
| 6-1183 | —(CH$_2$)$_2$— | —C(=O)— | K395 | N150 | S |
| 6-1184 | —(CH$_2$)$_2$— | —C(=O)— | K741 | N9 | S |

As preferred combinations of the groups mentioned as preferred examples of X, A¹, A², G¹, A³, A⁴ and G² in formula (I) according to the invention, there may be mentioned the following combinations 1) to 12).

1) In formula (I), when X is sulfur, A¹ is —(CH$_2$)$_2$—, A¹-A²-G¹ bonds in the form of A¹-NHC(=O)-G¹ and G¹ is a divalent benzene group, the divalent benzene group as G¹ is preferably substituted with one or more substituents selected from among those mentioned above as preferred examples of substituents for the substituted C$_{6-14}$ aromatic hydrocarbon groups for G¹.

2) In formula (I), when X is sulfur, A¹ is —(CH$_2$)$_2$—, A¹-A²-G¹ bonds in the form of A¹-NHC(=O)-G¹, G¹ is a divalent benzene group and the divalent benzene group as G¹ is not substituted, -A³-A⁴-G² collectively represent a group other than hydrogen.

3) In formula (I), when X is sulfur, A¹ is —(CH$_2$)$_2$— and A¹-A²-G¹ bonds in the form of A¹-NHC(=O)-G¹, G¹ is a divalent monocyclic or bicyclic C$_{3-9}$ aromatic heterocycle having in the ring 1 to 3 and preferably 1 or 2 atoms selected from the group consisting of oxygen, nitrogen and sulfur atoms.

4) In formula (I), when X is sulfur, A¹ is —(CH$_2$)$_2$— and A¹-A²-G¹ bonds in the form of A¹-NHC(=O)-G¹, G¹ is a divalent monocyclic or bicyclic C$_{2-9}$ aromatic heterocycle having in the ring 1 to 3 and preferably 1 or 2 atoms selected from the group consisting of oxygen, nitrogen and sulfur atoms, and the divalent aromatic heterocycle as G¹ is more preferably substituted with one or more substituents selected from among those mentioned as preferred examples of substituents for substituted heterocyclic groups having in the ring 1 to 4 atoms selected from the group consisting of oxygen, nitrogen and sulfur atoms for G¹.

5) In formula (I), when X is sulfur, A¹ is —(CH$_2$)$_2$— and A¹-A²-G¹ bonds in the form of A¹-NHC(=O)-G¹, G¹ is a divalent monocyclic or bicyclic C$_{2-9}$ aromatic heterocycle having in the ring 1 to 3 and preferably 1 or 2 atoms selected from the group consisting of oxygen, nitrogen and sulfur atoms, and more preferably, when the divalent aromatic heterocycle as G¹ is not substituted, -A³-A⁴-G² collectively represent a group other than hydrogen.

6) In formula (I), when X is sulfur, A¹ is —(CH$_2$)$_2$—, A¹-A²-G¹ bonds in the form of A¹-NH-G¹ and G¹ is a divalent benzene group, the divalent benzene group as G¹ is preferably substituted with one or more substituents selected from among those mentioned above as preferred examples of substituents for the substituted C$_{6-14}$ aromatic hydrocarbon groups for G¹.

7) In formula (I), when X is sulfur, A¹ is —(CH$_2$)$_2$—, A¹-A²-G¹ bonds in the form of A¹-NH-G¹, G¹ is a divalent benzene group and the divalent benzene group as G¹ is not substituted, -A³-A⁴-G² collectively represent a group other than hydrogen.

8) In formula (I), when X is sulfur, A¹ is —(CH$_2$)$_2$—, A¹-A²-G¹ bonds in the form of A¹-NH-G¹, and G¹ is a divalent monocyclic or bicyclic C$_{2-9}$ aromatic heterocycle having in the ring 1 to 3 atoms selected from the group consisting of oxygen, nitrogen and sulfur atoms, the aromatic heterocycle is preferably substituted with one or more substituents selected from among those mentioned as preferred examples of substituents for substituted heterocyclic groups having in the ring 1 to 4 atoms selected from the group consisting of oxygen, nitrogen and sulfur atoms for G¹.

9) In formula (I), when X is sulfur, A¹ is —(CH$_2$)$_2$—, A¹-A²-G¹ bonds in the form of A¹-NH-G¹, G¹ is a divalent monocyclic or bicyclic C$_{2-9}$ aromatic heterocycle having in the ring 1 to 3 atoms selected from the group consisting of oxygen, nitrogen and sulfur atoms, and the aromatic heterocycle is not substituted, $-A^3-A^4-G^2$ collectively represent a group other than hydrogen.

10) In formula (I), when X is sulfur, $A^1$ is —$(CH_2)_2$— and $A^1-A^2-G^1$ bonds in the form of $A^1-C(=O)-G^1$, $G^1$ is preferably a divalent monocyclic $C_{2-9}$ heterocycle having in the ring 1 or 2 atoms selected from the group consisting of oxygen, nitrogen and sulfur atoms, such as pyrrolidine, piperidine, morpholine, thiomorpholine, homopiperidine, homopiperazine, 1,2,3,6-tetrahydropyridine or piperazine, and $G^1$ is preferably bonded to $A^1-C(=O)$— at a nitrogen atom.

11) In formula (I), when X is sulfur, $A^1$ is —$(CH_2)_2$— and $A^1-A^2-G^1$ bonds in the form of $A^1-C(=O)-G^1$, $G^1$ is preferably a divalent monocyclic $C_{2-9}$ heterocycle having in the ring 1 or 2 atoms selected from the group consisting of oxygen, nitrogen and sulfur atoms, such as pyrrolidine, piperidine, morpholine, thiomorpholine, homopiperidine, homopiperazine, 1,2,3,6-tetrahydropyridine or piperazine, and $G^1$ is preferably bonded to $A^1-C(=O)$— at a nitrogen atom, where the divalent monocyclic $C_{2-9}$ heterocycle having in the ring 1 or 2 atoms selected from the group consisting of oxygen, nitrogen and sulfur atoms for $G^1$ is preferably substituted with one or more substituents selected from among those mentioned as preferred examples of substituents for substituted heterocyclic groups having in the ring 1 to 4 atoms selected from the group consisting of oxygen, nitrogen and sulfur atoms for $G^1$.

12) In formula (I), when X is sulfur, $A^1$ is —$(CH_2)_2$— and $A^1-A^2-G^1$ bonds in the form of $A^1-C(=O)-G^1$, $G^1$ is preferably a divalent monocyclic $C_{2-9}$ heterocycle having in the ring 1 or 2 atoms selected from the group consisting of oxygen, nitrogen and sulfur atoms, such as pyrrolidine, piperidine, morpholine, thiomorpholine, homopiperidine, homopiperazine, 1,2,3,6-tetrahydropyridine or piperazine, and $G^1$ is preferably bonded to $A^1-C(=O)$— at a nitrogen atom, and when the divalent monocyclic $C_{2-9}$ heterocycle having in the ring 1 or 2 atoms selected from the group consisting of oxygen, nitrogen and sulfur atoms for $G^1$ is not substituted, $-A^3-A^4-G^2$ collectively represent a group other than hydrogen.

The preferred combinations for X, $A^1$, $A^2$, $G^1$, $A^3$, $A^4$ and $G^2$ in formula (I) according to the invention, described by 1) to 12) above, are also preferably in combination with the preferred groups represented by $R^2-A^5$-, that is, $R^2-A^5$ groups wherein $A^1$ is a single bond and $R^2$ is a substituted or unsubstituted monocyclic $C_{3-5}$ aromatic heterocyclic group having in the ring 1 or 2 atoms selected from the group consisting of oxygen, nitrogen and sulfur atoms.

The pyrrolo[3,2-d]pyrimidine derivatives represented by formula (I) above exist as tautomers represented by the following formula (III):

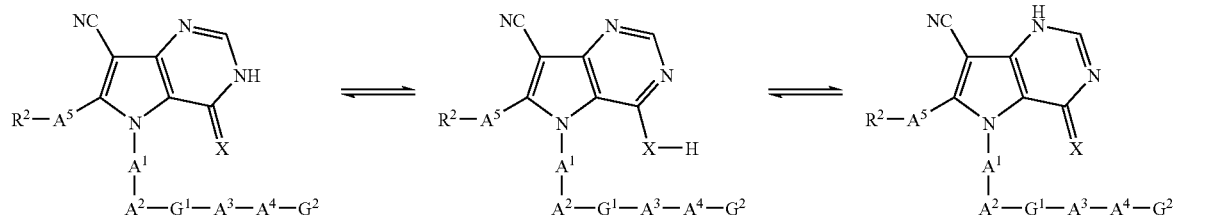

(III)

[wherein $A^1$, $A^2$, $A^3$, $A^4$, $A^5$, $G^1$, $G^2$, $R^2$ and X have the same definitions as $A^1$, $A^2$, $A^3$, $A^4$, $A^5$, $G^1$, $G^2$, $R^2$ and X in formula (I)], and their tautomers are also encompassed within the scope of the present invention.

When the atoms forming the molecules of the pyrrolo[3,2-d]pyrimidine derivatives represented by formula (I) are in an asymmetrical relationship, the optically active isomers and mixtures thereof in any proportion are also encompassed within the scope of the invention.

The pyrrolo[3,2-d]pyrimidine derivatives represented by formula (I) may contain basic groups in their molecules, in which case they may be converted to medically acceptable acid-addition salts if necessary. As acids there may be mentioned inorganic acids such as hydrochloric acid, hydrobromic acid, sulfuric acid, phosphoric acid and carbonic acid, or organic acids such as acetic acid, citric acid, malic acid, oxalic acid, tartaric acid, lactic acid, maleic acid, fumaric acid and methanesulfonic acid.

The pyrrolo[3,2-d]pyrimidine derivatives represented by formula (I) may also contain acidic groups in their molecules, in which case they may be converted to medically acceptable salts if necessary. As such salts there may be mentioned non-toxic cation salts, and specifically there may be mentioned salts with alkali metal ions such as Na+ and K+, alkaline earth metal ions such as $Mg^{2+}$ and $Ca^{2+}$, metal ions such as $Al^{3+}$ and $Zn^{2+}$, or organic bases such as ammonia, triethylamine, ethylenediamine, propanediamine, pyrrolidine, piperidine, piperazine, pyridine, lysine, choline, ethanolamine, N,N-dimethylethanolamine, 4-hydroxypiperidine, glucosamine and N-methylglucamine.

The definitions of $A^1$, $A^2$, $A^3$, $A^4$, $A^5$, $G^1$ $G^2$ and $R^2$ in formula (II) above are the same as the respective definitions of $A^1$, $A^2$, $A^3$, $A^4$, $A^5$, $G^1$, $G^2$ and $R^2$ in formula (I), and as examples there may be mentioned the same ones as mentioned above.

In formula (II), $X^1$ represents chlorine, bromine, iodine, $C_{2-10}$ acylthio, $C_{2-8}$ alkoxymethylthio or $C_{1-8}$ alkyl- or arylsulfonyloxy. As examples of $C_{2-10}$ acylthio groups when $X^1$ represents a $C_{2-10}$ acylthio group, there may be mentioned acetylthio, trifluoroacetylthio, propionylthio, butyrylthio, isobutyrylthio, valerylthio, isovalerylthio, pivaloylthio, hexanoylthio, benzoylthio, phenylacetylthio, phenylpropionylthio and cinnamoylthio. As examples of $C_{2-8}$ alkoxymethylthio groups when $X^1$ represents a $C_{2-8}$ alkoxymethylthio group, there may be mentioned methoxymethylthio, methoxyethoxymethylthio, t-butoxymethylthio, 2-(trimethylsilyl)ethoxymethylthio, benzyloxymethylthio, p-methoxybenzyloxymethylthio, p-nitrobenzyloxymethylthio, o-nitrobenzyloxymethylthio and 4-methoxyphenoxymethylthio. As examples of $C_{1-8}$ alkyl- or arylsulfonyloxy groups when $X^1$ represents a $C_{1-8}$ alkyl- or arylsulfonyloxy group, there may be mentioned sulfonyloxy groups comprising optionally substituted $C_{1-8}$ alkyl or aryl groups with sulfonyl groups, such as methylsulfonyloxy, trifluoromethylsulfonyloxy, ethylsulfonyloxy, propylsulfonyloxy, butylsulfonyloxy, t-butylsulfonyloxy, nonafluorobutylsulfonyloxy, phenylsulfonyloxy, p-bromophenylsulfonyloxy, p-toluylsulfonyloxy, benzylsulfonyloxy, α-phenethylsulfonyloxy and β-phenethylsulfonyloxy. As preferred examples of $X^1$ there may be mentioned chlorine, bromine, iodine and trifluoromethylsulfonyloxy, with chlorine and trifluoromethylsulfonyloxy being particularly preferred.

The definitions of $A^1$, $A^2$, $A^3$, $A^4$, $A^5$, $G^1$, $G^2$, $R^2$ and X in formula (Ic) above are the same as the respective definitions of $A^1$, $A^2$, $A^3$, $A^4$, $A^5$, $G^1$ $G^2$, $R^2$ and X in formula (I), and as examples there may be mentioned the same ones as mentioned above.

In formula (Ic), $R^3$ represents $C_{2-10}$ acyl, $C_{2-10}$ alkoxymethyl or substituted or unsubstituted benzyl. As examples of $C_{2-10}$ acyl groups when $R^3$ represents a $C_{2-10}$ acyl group, there may be mentioned acetyl, trifluoroacetyl, propionyl, butyryl, isobutyryl, valeryl, isovaleryl, pivaloyl, hexanoyl, benzoyl, phenylacetyl, phenylpropionyl and cinnamoyl. As examples of $C_{2-10}$ alkoxymethyl groups when $R^3$ represents a $C_{2-10}$ alkoxymethyl group, there may be mentioned methoxymethyl, methoxyethoxymethyl, t-butoxymethyl, 2-(trimethylsilyl)ethoxymethyl, benzyloxymethyl, p-methoxybenzyloxymethyl, p-nitrobenzyloxymethyl, o-nitrobenzyloxymethyl and 4-methoxyphenoxymethyl. As examples of substituted or unsubstituted benzyl groups when $R^3$ represents a substituted or unsubstituted benzyl group, there may be mentioned benzyl, p-methoxybenzyl, 3,4-dimethoxybenzyl, o-nitrobenzyl, p-nitrobenzyl and p-cyanobenzyl. As a preferred example for $R^3$ there may be mentioned 2-(trimethylsilyl)ethoxymethyl.

A pyrrolo[3,2-d]pyrimidine derivative represented by formula (Ia) above may be synthesized from a pyrrolo[3,2-d]pyrimidine derivative represented by formula (II), by the following Synthesis Scheme A.

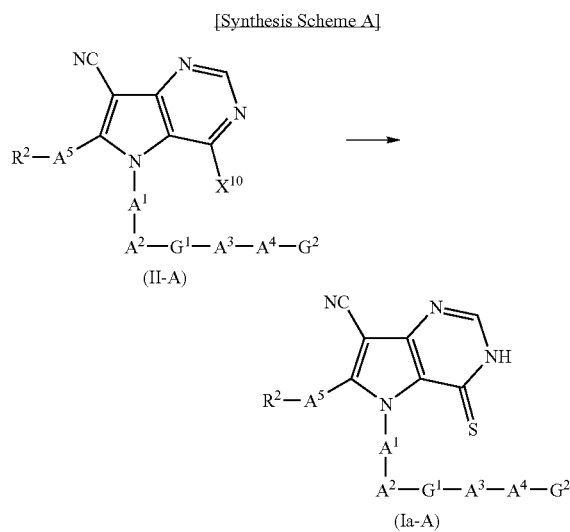

[wherein $A^1$, $A^2$, $A^3$, $A^4$, $A^5$, $G^1$, $G^2$ and $R^2$ have the same definitions as $A^1$, $A^2$, $A^3$, $A^4$, $A^5$, $G^1$, $G^2$ and $R^2$ in formula (I) above, and $X^{10}$ represents chlorine, bromine, iodine or $C_{1-8}$ alkyl- or arylsulfonyloxy].

Specifically, a pyrrolo[3,2-d]pyrimidine derivative (Ia-A) of the invention may be synthesized by reacting a pyrrolo[3,2-d]pyrimidine derivative (II-A) of the invention with thiourea. The thiooxo conversion with thiourea may be carried out, for example, by reaction in a solvent such as dioxane, ethanol or 2-propanol in a temperature range from 0-150° C.

Of the pyrrolo[3,2-d]pyrimidine derivatives represented by formula (II) above, a pyrrolo[3,2-d]pyrimidine derivative represented by the following formula (II-B) may be synthesized from a pyrrolo[3,2-d]pyrimidine derivative represented by formula (Ib), by the following Synthesis Scheme (B).

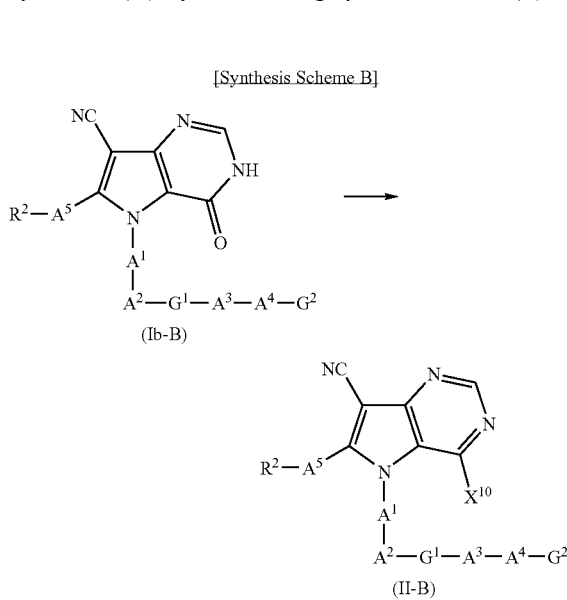

[wherein $A^1$, $A^2$, $A^3$, $A^4$, $A^5$, $G^1$, $G^2$ and $R^2$ have the same definitions as $A^1$, $A^2$, $A^3$, $A^4$, $A^5$, $G^1$, $G^2$ and $R^2$ in formula (I) above, and $X^{10}$ is as defined above].

Specifically, when $X^{10}$ is chlorine, for example, a pyrrolo[3,2-d]pyrimidine derivative (Ib-B) of the invention may be reacted with phosphorus oxychloride to synthesize a pyrrolo[3,2-d]pyrimidine derivative (II-B) of the invention. The chlorination reaction with phosphorus oxychloride may be conducted under ordinary chlorine reaction conditions, for example, in the presence or absence of triethylamine, 4-dimethylaminopyridine or dimethylaniline, in the presence or absence of a solvent such as acetonitrile, and in a temperature range from 0-150° C.

Or, for example, when $X^{10}$ is a trifluoromethanesulfonyloxy group, the pyrrolo[3,2-d]pyrimidine derivative (Ib-B) of the invention may be reacted with trifluoromethanesulfonic anhydride to synthesize a pyrrolo[3,2-d]pyrimidine derivative (II-B) of the invention. The trifluoromethanesulfonyloxy conversion with trifluoromethanesulfonic anhydride may be conducted together with an amine such as pyridine or triethylamine, in the presence or absence of a solvent such as dichloromethane, and in a temperature range from 0-100° C.

Of the pyrrolo[3,2-d]pyrimidine derivatives represented by formula (Ib) above, a pyrrolo[3,2-d]pyrimidine derivative represented by (Ib-C2) below may be synthesized from a pyrrolo[3,2-d]pyrimidine derivative represented by (Ib-C1) below by the following Synthesis Scheme (C).

[Synthesis Scheme (C)]

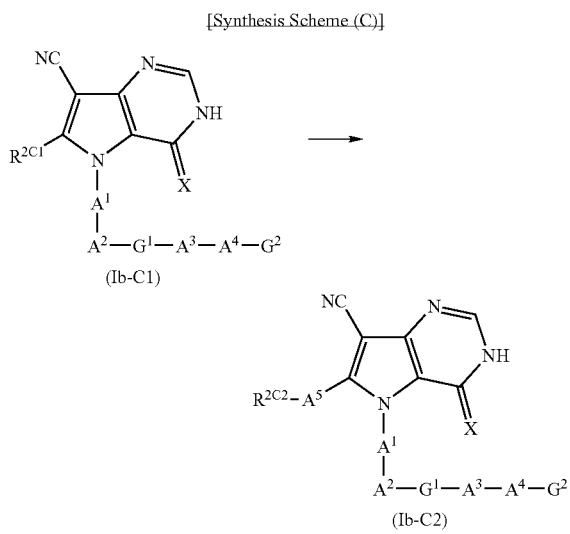

[wherein $A^1$, $A^2$, $A^3$, $A^4$, $A^5$, $G^1$, $G^2$ and X have the same definitions as $A^1$, $A^2$, $A^3$, $A^4$, $A^5$, $G^1$, $G^2$ and X in formula (I) above, $R^{2C1}$ represents chlorine or bromine, when $A^1$ is $-NR^{201}$-(where $R^{201}$ has the same definition as $R^{201}$ in formula (I)), $R^{2C2}$ represents a group as defined for $R^2$ of formula (I) except for fluorine, chlorine, bromine or iodine, and when $A^5$ is a single bond, $R^{2C2}$ represents a substituted or unsubstituted heterocyclic group having in the ring 1 to 4 atoms selected from the group consisting of oxygen, nitrogen and sulfur atoms, bonded to As at a nitrogen atom].

Specifically, a pyrrolo[3,2-d]pyrimidine derivative (Ib-C1) of the invention may be reacted with a primary or secondary amine to synthesize a pyrrolo[3,2-d]pyrimidine derivative (Ib-C2) of the invention. The aminating reaction with a primary or secondary amine may be carried out under solventless conditions or using a solvent such as dimethylsulfoxide, dimethylformamide, dioxane, tetrahydrofuran or toluene, in the presence or absence of a base such as pyridine, triethylamine, diisopropylethylamine, 4-dimethylaminopyridine or sodium carbonate, in the presence or absence of a transition metal complex catalyst produced by mixing a palladium salt such as palladium acetate with a phosphorus ligand such as triphenylphosphine, and in a temperature range of 0-150° C.

Of the pyrrolo[3,2-d]pyrimidine derivatives represented by formula (Ib), a pyrrolo[3,2-d]pyrimidine derivative represented by formula (Ib-D2) below may be synthesized from a pyrrolo[3,2-d]pyrimidine derivative represented by formula (Ib-D1) below by the following Synthesis Scheme (D).

[Synthesis Scheme (D)]

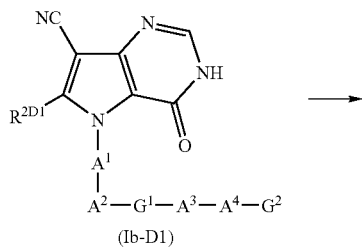

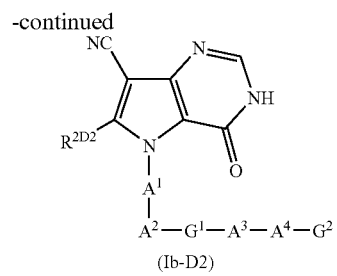

[wherein $A^1$, $A^2$, $A^3$, $A^4$, $G^1$ and $G^2$ have the same definitions as $A^1$, $A^2$, $A^3$, $A^4$, $G^1$ and $G^2$ in formula (I) above, $R^{2D1}$ represents chlorine or bromine, and $R^{2D2}$ represents a substituted or unsubstituted $C_{6-14}$ aromatic hydrocarbon group].

Specifically, a pyrrolo[3,2-d]pyrimidine derivative (Ib-D1) of the invention may be reacted with, for example, a boronic acid derivative [$R^{2D2}$—B(OH)$_2$, where $R^{2D2}$ has the same definition as in Synthesis Scheme (D) above], to synthesize a pyrrolo[3,2-d]pyrimidine derivative (Ib-D2) of the invention. The reaction with the boronic acid derivative may be conducted under conditions for an ordinary Suzuki reaction, for example, using a solvent such as 2-propanol and/or water, using palladium acetate or the like as a catalyst in the presence of an inorganic base such as sodium carbonate, with addition of triphenylphosphine or the like as a ligand, and in a temperature range of 0-150° C.

Of the pyrrolo[3,2-d]pyrimidine derivatives represented by formula (Ib), a pyrrolo[3,2-d]pyrimidine derivative represented by (Ib-E2) below may be synthesized from a pyrrolo [3,2-d]pyrimidine derivative represented by (Ib-E1) below, by the following Synthesis Scheme (E)).

[Synthesis Scheme (E)]

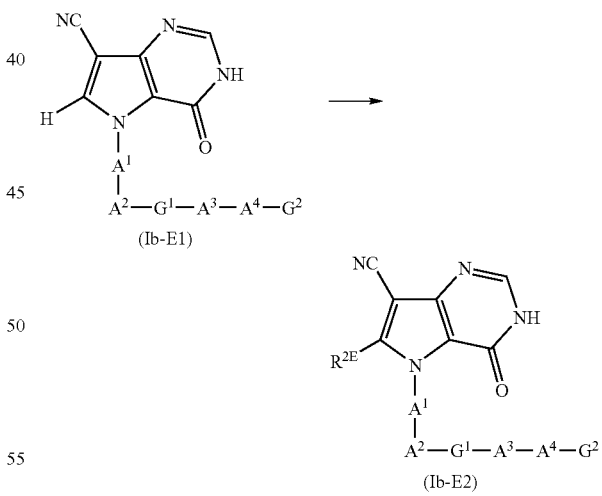

[wherein $A^1$, $A^2$, $A^3$, $A^4$, $G^1$ and $G^2$ have the same definitions as $A^1$, $A^2$, $A^3$, $A^4$, $G^1$ and $G^2$ in formula (I) above, and $R^{2E}$ represents chlorine, bromine or iodine].

Specifically, a pyrrolo[3,2-d]pyrimidine derivative (Ib-E1) of the invention may be subjected to halogenation reaction to obtain a pyrrolo[3,2-d]pyrimidine derivative (Ib-E2) of the invention. The halogenation reaction may be carried out, for example, using a halogenating reagent such as N-chlorosuccinimide, N-bromosuccinimide or the like, in the presence of a solvent such as dimethylformamide, dioxane or tetrahydrofuran, and in a temperature range of −20° C. to 150° C.

Of the pyrrolo[3,2-d]pyrimidine derivatives represented by formula (Ib), a pyrrolo[3,2-d]pyrimidine derivative represented by formula (Ib-F) below may be synthesized from a pyrrole derivative represented by formula (IV-F) below, by the following Synthesis Scheme (F).

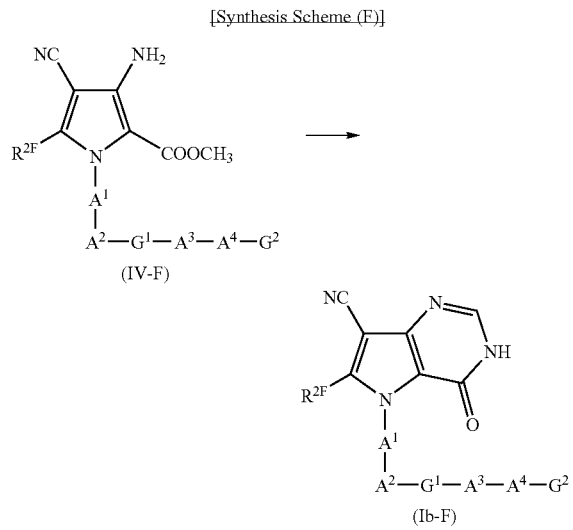

[Synthesis Scheme (F)]

(IV-F)

(Ib-F)

[wherein $A^1$, $A^2$, $A^3$, $A^4$, $G^1$ and $G^2$ have the same definitions as $A^1$, $A^2$, $A^3$, $A^4$, $G^1$ and $G^2$ in formula (I) above, and $R^{2F}$ represents a group as defined for $R^2$ of formula (I) except for fluorine, chlorine, bromine, iodine and substituted or unsubstituted heterocyclic groups having in the ring 1 to 4 atoms selected from the group consisting of oxygen, nitrogen and sulfur atoms, bonded at a nitrogen atom to the carbon of the pyrrole ring to which $R^{2F}$ is bonded].

Specifically, a pyrrole derivative represented by formula (IV-F) above may be subjected to cyclization reaction using formamidine or formamide, to synthesize a pyrrolo[3,2-d]pyrimidine derivative represented by formula (Ib-F) of the invention. A cyclization reaction using formamidine may be conducted, for example, using formamidine acetate, using a solvent such as 2-propanol, and in a temperature range of 0-150° C. A cyclization reaction using formamide may be smoothly carried out, for example, using a base such as formamide or sodium methoxide, in the presence or absence of dimethylsulfoxide or dimethoxyethane, and in a temperature range of 0-150° C.

Of the pyrrolo[3,2-d]pyrimidine derivatives represented by formula (II), a pyrrolo[3,2-d]pyrimidine derivative represented by formula (II-G) below may be synthesized from a pyrrolo[3,2-d]pyrimidine derivative represented by formula (Ib-G) below, by the following Synthesis Scheme (G).

[Synthesis Scheme (G)]

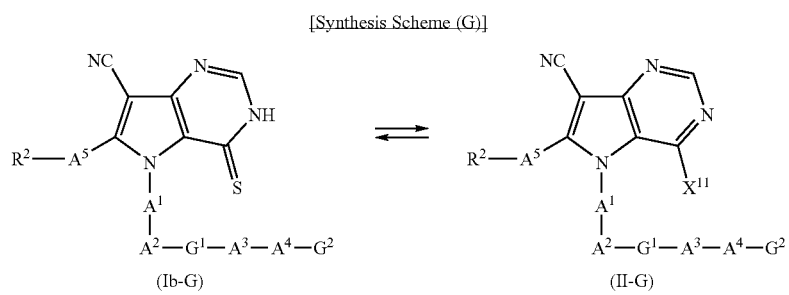

(Ib-G)     (II-G)

[wherein $A^1$, $A^2$, $A^3$, $A^4$, $A^5$, $G^1$, $G^2$ and $R^2$ have the same definitions as $A^1$, $A^2$, $A^3$, $A^4$, $A^5$, $G$-, $G^2$ and $R^2$ in formula (I) above, and $X^{11}$ represents a $C_{2-10}$ acylthio or $C_{2-8}$ alkoxymethylthio group].

Specifically, when $X^{11}$ is an acylthio group, for example, a pyrrolo[3,2-d]pyrimidine derivative (Ib-G) of the invention may be reacted with an acyl halide to synthesize a pyrrolo[3,2-d]pyrimidine derivative (II-G) of the invention. The acylation reaction with the acyl halide may be conducted under ordinary acylating conditions, for example, in the presence of triethylamine or pyridine and in a temperature range of 0-100° C.

Also, when $X^{11}$ is an alkoxymethylthio group, for example, a pyrrolo[3,2-d]pyrimidine derivative (Ib-G) of the invention may be reacted with an alkoxymethyl halide to synthesize a pyrrolo[3,2-d]pyrimidine derivative (II-G) of the invention. The alkoxymethylating reaction with the alkoxymethyl halide may be conducted under ordinary alkoxymethylating conditions, for example, in the presence of triethylamine or pyridine and in a temperature range of 0-100° C.

The groups $A^1$, $A^2$, $A^3$, $A^4$, $A^5$, $G^1$, $G^2$ and/or R in a pyrrolo[3,2-d]pyrimidine derivative (II-G) of the invention obtained in this manner may be subjected to conversion reactions which are well known to those skilled in the art. The pyrrolo[3,2-d]pyrimidine derivative (II-G) may be subjected to hydrolysis reaction under neutral or basic conditions when $X^{11}$ is acylthio or under acidic conditions with trifluoroacetic acid or the like when $X^{11}$ is alkoxymethylthio, for conversion to a pyrrolo[3,2-d]pyrimidine derivative (Ib-G) of the invention.

A pyrrolo[3,2-d]pyrimidine derivative represented by formula (Ic) may be synthesized from a pyrrolo[3,2-d]pyrimidine derivative represented by formula (I-H) below, by the following Synthesis Scheme (H).

[Synthesis Scheme (H)]

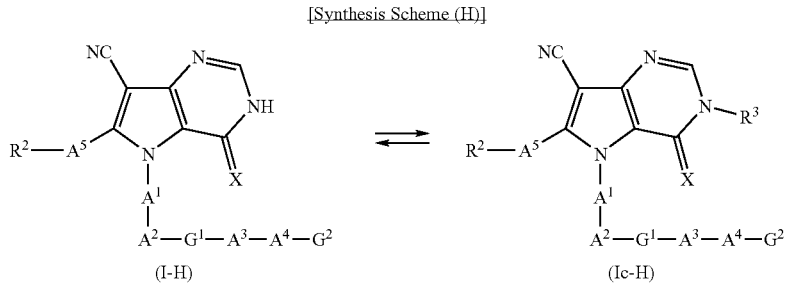

[wherein $A^1$, $A^2$, $A^3$, $A^4$, $A^5$, $G^1$, $G^2$ and $R^2$ have the same definitions as $A^1$, $A^2$, $A^3$, $A^4$, $A^5$, $G^1$, $G^2$ and $R^2$ in formula (I) above, and $R^3$ represents a $C_{2-10}$ acyl, $C_{2-10}$ alkoxymethyl or substituted or unsubstituted benzyl group].

Specifically, when $R^3$ is an acyl group, for example, a pyrrolo[3,2-d]pyrimidine derivative (I-H) of the invention may be reacted with an acyl halide to synthesize a pyrrolo[3,2-d]pyrimidine derivative (Ic-H) of the invention. The acylation reaction with the acyl halide may be conducted under ordinary acylating conditions, for example, in the presence of triethylamine or pyridine and in a temperature range of 0-100° C.

Also, when $R^3$ is an alkoxymethyl or benzyl group, for example, a pyrrolo[3,2-d]pyrimidine derivative (1-H) of the invention may be reacted with an alkoxymethyl halide or benzyl halide to synthesize a pyrrolo[3,2-d]pyrimidine derivative (Ic-H) of the invention. The reaction with the alkoxymethyl halide or benzyl halide may be conducted, for example, in the presence of sodium hydride, and in a temperature range of 0-100° C.

The groups $A^1$, $A^2$, $A^3$, $A^4$, $A^5$, $G^1$, $G^2$ and/or $R^2$ in a pyrrolo[3,2-d]pyrimidine derivative (Ic-H) of the invention obtained in this manner may be subjected to conversion reactions which are well known to those skilled in the art. The pyrrolo[3,2-d]pyrimidine derivative (Ic-H) may be subjected to hydrolysis reaction under neutral or basic conditions when $R^3$ is an acyl group, to hydrolysis reaction under acidic conditions with trifluoroacetic acid or the like when $R^3$ is an alkoxymethyl group, or to hydrogenation reaction when $R^3$ is a benzyl group, for conversion to a pyrrolo[3,2-d]pyrimidine derivative (1-H) of the invention.

When the pyrrolo[3,2-d]pyrimidine derivatives of the invention synthesized according to Synthesis Schemes (A), (B), (C), (D), (E), (F), (G) and (H) above have easily convertible substituents such as alkoxycarbonyl, acyloxy, aromatic nitro groups or the like, they may be converted to pyrrolo[3,2-d]pyrimidine derivatives of the invention having groups such as carboxyl, hydroxy, amino or the like by carrying out reactions well known to those skilled in the art.

When the pyrrolo[3,2-d]pyrimidine derivatives of the invention synthesized according to Synthesis Schemes (A), (B), (C), (D), (E), (F), (G) and (H) above have carboxyl groups, they may be converted to pyrrolo[3,2-d]pyrimidine derivatives of the invention having groups such as alkoxycarbonyl, carbamoyl or N-alkylcarbamoyl, by carrying out condensation reactions well known to those skilled in the art.

When the pyrrolo[3,2-d]pyrimidine derivatives of the invention synthesized according to Synthesis Schemes (A), (B), (C), (D), (E), (F), (G) and (H) above have amino groups, they may be converted to pyrrolo[3,2-d]pyrimidine derivatives of the invention having groups such as acylamino or alkylsulfonylamino, by carrying out condensation reactions well known to those skilled in the art.

Alternatively when the derivatives have amino groups, they may be converted to pyrrolo[3,2-d]pyrimidine derivatives of the invention having groups such as monoalkylamino or dialkylamino, by carrying out reductive alkylation reactions well known to those skilled in the art.

When the pyrrolo[3,2-d]pyrimidine derivatives of the invention synthesized according to Synthesis Schemes (A), (B), (C), (D), (E), (F), (G) and (H) above have hydroxy groups, they may be converted to pyrrolo[3,2-d]pyrimidine derivatives of the invention having groups such as acyloxy or the like, by carrying out condensation reactions well known to those skilled in the art.

When the pyrrolo[3,2-d]pyrimidine derivatives of the invention synthesized according to Synthesis Schemes (A), (B), (C), (D), (E), (F), (G) and (H) above have formyl groups, they may be converted to pyrrolo[3,2-d]pyrimidine derivatives of the invention having groups such as alkylaminomethyl or the like, by carrying out reductive alkylation reactions well known to those skilled in the art.

A pyrrole derivative represented by formula (IV-F) above used as the starting material in a synthesis scheme for a pyrrolo[3,2-d]pyrimidine derivative represented by formula (I) may be synthesized, for example, from an alkoxymethyl-enemalononitrile derivative represented by formula (VI-J) below, by the following Synthesis Scheme (J).

[Synthesis Scheme (J)]

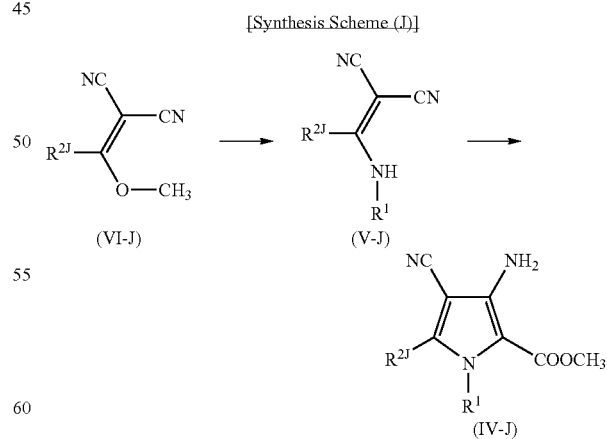

[wherein $R^1$ is a group that can be converted to $A^1$-$A^2$-$G^1$-$A^3$-$A^4$-$G^2$ in formula (I), and $R^{2J}$ represents a group as defined for $R^2$ of formula (I) except for fluorine, chlorine, bromine, iodine and substituted or unsubstituted heterocyclic groups having in the ring 1 to 4 atoms selected from the group consisting of oxygen, nitrogen and sulfur atoms, bonded at a nitrogen atom to the carbon of the pyrrole ring to which $R^{2\text{-}J}$ is bonded].

Specifically, an alkoxymethylenemalononitrile (VI-J) may be reacted with a primary amine ($R^1$—$NH_2$, where $R^1$ has the same definition as $R^1$ in Synthesis Scheme (J) above), to synthesize an aminomethylenemalononitrile derivative (V-J). This aminomethylenemalononitrile derivative (V-J) may be reacted with methyl bromoacetate in the presence of a base and then cyclized to synthesize a pyrrole derivative (IV-J).

The reaction between the alkoxymethylenemalononitrile derivative (VI-J) and the primary amine may be conducted, for example, using a solvent such as methanol or ethanol, and in a temperature range of 0-100° C.

The reaction between the aminomethylenemalononitrile derivative (V-J) and the methyl bromoacetate may be conducted, for example, using potassium carbonate or the like as a base, using a solvent such as acetonitrile, and in a temperature range of 0-150° C.

Pyrrolo[3,2-d]pyrimidine derivatives represented by formula (I) obtained in the manner described above have effects of inhibiting GSK-3 activity, and may therefore be used as clinically effective prophylactic and/or treatment agents for GSK-3 activity inhibition. As conditions that are treatable with GSK-3 activity inhibitors there may be mentioned diabetes, diabetes complications, atherosclerosis, hypertension, obesity, syndrome X, Alzheimer's disease, neurodegenerative diseases (AIDS encephalopathy, Huntington's disease, Parkinson's disease, cerebral ischemia), manic depression, traumatic encephalopathy, alopecia, inflammatory diseases, cancer, immune deficiency and the like.

The pyrrolo[3,2-d]pyrimidine derivatives represented by formula (I) and their medically acceptable salts may be prepared as pharmaceutical compositions using pharmaceutically acceptable carriers and/or diluents. The pharmaceutical compositions may be administered either orally or parenterally, in any of various dosage forms. As modes of parenteral administration there may be mentioned, for example, intravenous, subcutaneous, intramuscular, percutaneous and rectal administration.

As oral dosage forms there may be mentioned, for example, tablets, pills, granules, powders, liquids, suspensions, syrups, capsules and the like.

Tablets may be molded by ordinary methods using pharmaceutically acceptable carriers such as an excipients, binders, disintegrators and the like. Pills, granules and powders may also be molded by ordinary methods using excipients and the like, as for tablets.

The preparation method for a liquid, suspension or syrup may be an ordinary method using a glycerin ester, alcohol, water and/or vegetable oil. A preparation method for capsules may entail filling granules, powder or a liquid into capsules of gelatin or the like.

For a parenteral agent to be administered intravenously, subcutaneously or intramuscularly, the administered agent may be in the form of an injection.

Injections include, for example, those dissolved in water-soluble liquids such as physiological brine, and those dissolved in non-water-soluble liquids comprising organic esters such as propylene glycol, polyethylene glycol, vegetable oils, and the like.

The dosage form for percutaneous administration may be an ointment, cream or the like. An ointment may be prepared by admixture with a fat or oil, vaseline or the like, and a cream may be prepared by admixture with an emulsifier.

If necessary, pharmaceutically acceptable carriers such as isotonizing agents, preservatives, antiseptics, humidifiers, buffers, emulsifiers, dispersing agents, stabilizers and the like may be added to these various preparation forms.

The various preparation forms may also, if necessary, be sterilized by appropriate means such as filtration using a bacteria capturing filter or addition of antimicrobial agents.

The dosage of a pyrrolo[3,2-d]pyrimidine derivative represented by formula (I) or a medically acceptable salt thereof will differ depending on the type of condition, the route of administration and the symptoms, age, gender and body weight of the patient, but in most cases it may be about 1-500 mg/day/patient for oral administration.

In the case of parenteral administration such as intravenous, subcutaneous, intramuscular or percutaneous administration, it may be about 0.1-100 mg/day/patient.

EXAMPLES

The invention will now be explained in greater detail by the following examples, with the understanding that the scope of the invention is not in any sense restricted by these examples. The numbers assigned to each of the compounds in the examples correspond to the Compound Nos. of the compounds listed as preferred examples in Tables 1 to 214 above.

The "HPLC Retention time" data for the compounds synthesized in the examples are the retention times (minutes) for the compounds in HPLC analysis carried out under the following conditions.

HPLC (High Performance Liquid Chromatography) Conditions
System: Hewlett-Packard 1100 HPLC
Column: Cadenza CD-C18 (Imtakt) 100 mm×4.6 mmφ
Solvent:
  A: $H_2O$/acetonitrile=95/5
    (0.05% trifluoroacetic acid)
  B: $H_2O$/acetonitrile=5/95
    (0.05% trifluoroacetic acid)
Flow rate: 1.0 mL/min
Gradient:
0-1 min, solvent B: 10% solvent A: 90%
1-14 min, solvent B: 10%→100% solvent A: 90%→0%
14-16 min, solvent B: 100% solvent A: 0%
Calculation of purity: Area % of UV absorption (254 nm)

Reference Example 1

Synthesis of (1-hydroxy-2-phenylethylidene)methane-1,1-dicarbonitrile

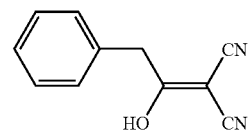

A suspension of sodium hydride (12.5 g) in tetrahydrofuran (188 mL) was cooled to 0° C. A solution of malononitrile (10.3 g) in tetrahydrofuran (65 mL) was added dropwise thereto over a period of 1 hour. After stirring the reaction mixture at room temperature for 1 hour, it was again cooled to 0° C., and then a solution of 2-phenylacetyl chloride (24.2 g) in tetrahydrofuran (52 mL) was added dropwise thereto over a period of 80 minutes. After stirring the reaction mixture at room temperature for 49 hours, water (26 mL) was added to the reaction solution. The solvent was distilled off under reduced pressure, diethyl ether (130 mL) and 1 mol/L hydrochloric acid (130 mL) were added to the residue and extraction was performed with diethyl ether. The organic layer was washed with saturated brine and dried over anhydrous sodium sulfate, and then the solvent was distilled off under reduced pressure to obtain the title compound as a crude product (31.2 g).

[Hydroxy(1-methylpyrrol-2-yl)methylene]methane-1,1-dicarbonitrile was synthesized in the same manner using malononitrile and 1-methylpyrrole-2-carbonylchloride. The ESI/MS data for this compound are shown below.

ESI/MS m/e: 174.2 (M$^+$+H, $C_9H_7N_3O$)

(2-Furylhydroxymethylene)methane-1,1-dicarbonitrile was obtained in the same manner using malononitrile and furan-2-carbonylchloride. The ESI/MS data for this compound are shown below.

ESI/MS m/e: (M$^+$+H, $C_8H_4N_2O_2$)

[Hydroxy(3-methyl(2-furyl))methylene]methane-1,1-dicarbonitrile was obtained in the same manner using malononitrile and 3-methylfuran-2-carbonylchloride. The NMR and ESI/MS data for this compound are shown below.

$^1$H-NMR (400 MHz, $CD_3OD$)δ(ppm): 2.29 (s, 3H), 6.34 (s, 1H), 7.41 (s, 1H). ESI/MS m/e: (M$^+$+H, $C_9H_6N_2O_2$)

[Hydroxy(3-methyl(2-thienyl))methylene]methane-1,1-dicarbonitrile was obtained in the same manner using malononitrile and 3-methylthiophene-2-carbonylchloride. The ESI/MS data for this compound are shown below.

ESI/MS m/e: (M$^+$+H, $C_9H_6N_2O$)

[(3-Chloro(2-thienyl))hydroxymethylene]methane-1,1-dicarbonitrile was obtained in the same manner using malononitrile and 3-chlorothiophene-2-carbonylchloride. The NMR and ESI/MS data for this compound are shown below.

$^1$H-NMR (400 MHz, $CD_3OD$) δ (ppm): 6.92 (d, J=5.1, 1H), 7.51 (d, J=5.4, 1H) ESI/MS m/e: (M$^+$+H, $COH_3ClN_2OS$)

Reference Example 2

Synthesis of (1-methoxy-2-phenylethylidenemethane-1,1-dicarbonitrile

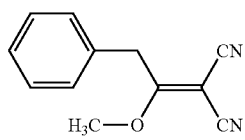

A suspension of sodium hydride (6.3 g) in tetrahydrofuran (100 mL) was cooled to 0° C. A solution of the crude (1-hydroxy-2-phenylethylidene)methane-1,1-dicarbonitrile (31.2 g) in tetrahydrofuran (130 mL) was added dropwise thereto over a period of 30 minutes. After stirring the reaction mixture at room temperature for 20 minutes, it was cooled to 0° C., and then a solution of dimethyl sulfate (19.7 g) in tetrahydrofuran (100 mL) was added dropwise thereto over a period of 1 hour. The mixture was heated to reflux for 21 hours and then cooled to room temperature, and the solvent was distilled off under reduced pressure. Ethyl acetate (100 mL) and aqueous saturated sodium bicarbonate (100 mL) were added to the residue and extraction was performed with ethyl acetate. The organic layer was washed with saturated brine, and then the solvent was distilled off under reduced pressure. The obtained crude product was purified by silica gel column chromatography (hexane/ethyl acetate=2/1) to obtain the title compound (4.6 g, 15%) as a brown solid. The NMR and ESI/MS data for this compound are shown below.

$^1$H-NMR (400 MHz, $CDCl_3$) δ (ppm): 4.02 (s, 2H), 4.03 (s, 3H), 7.24-7.42 (m, 5H). ESI/MS m/e: 199.2 (M$^+$+H, $C_{12}HON_2O$)

[Methoxy(1-methylpyrrol-2-yl)methylene]methane-1,1-dicarbonitrile was synthesized in the same manner using [hydroxy(1-methylpyrrol-2-yl)methylene]methane-1,1-dicarbonitrile. The ESI/MS data for this compound are shown below.

ESI/MS m/e: 188.1 (M$^+$+H, $CIoH_9N_3O$)

(2-Furylmethoxymethylene)methane-1,1-dicarbonitrile was synthesized in the same manner using (2-furylhydroxymethylene)methane-1,1-dicarbonitrile. The ESI/MS data for this compound are shown below.

ESI/MS m/e: (M$^+$+H, $C_9H_6N_2O_2$)

[Methoxy(3-methyl(2-furyl))methylene]methane-1,1-dicarbonitrile was synthesized in the same manner using [hydroxy(3-methyl(2-furyl))methylene]methane-1,1-dicarbonitrile. The ESI/MS data for this compound are shown below.

ESI/MS m/e: (M$^+$+H, $C_{10}H_8N_2O_2$)

[Methoxy(3-methyl(2-thienyl))methylene]methane-1,1-dicarbonitrile was obtained in the same manner using [hydroxy(3-methyl(2-thienyl))methylene]methane-1,1-dicarbonitrile. The ESI/MS data for this compound are shown below.

ESI/MS m/e: (M$^+$+H, $C_{10}H_8N_2OS$)

[(3-Chloro(2-thienyl))methoxymethylene]methane-1,1-dicarbonitrile was obtained in the same manner using [(3-chloro(2-thienyl))hydroxymethylene]methane-1,1-dicarbonitrile. The ESI/MS data for this compound are shown below.

ESI/MS m/e: (M$^+$+H, $C_9H_5ClN_2OS$)

(1-Methoxy-3-phenylpropylidene)methane-1,1-dicarbonitrile was synthesized using malononitrile and 3-phenylpropionyl chloride, in the same manner as Reference Example 1 and Reference Example 2. The NMR data for this compound are shown below.

$^1$H-NMR (400 MHz, $CDCl_3$) δ (ppm): 2.91-2.98 (m, 4H), 4.07 (s, 3H), 7.19-7.36 (m, 5H).

(1-Methoxy-3-methylbutylidene)methane-1,1-dicarbonitrile was synthesized in the same manner as Reference Example 1 and Reference Example 2 using malononitrile and isopentanoyl chloride. The NMR data for this compound are shown below.

$^1$H-NMR (400 MHz, $CDCl_3$) δ (ppm): 1.03-1.09 (m, 6H), 1.99-2.13 (m, 1H), 2.54 (d, J=7.6, 2H), 4.15 (s, 3H).

(Cyclopropylmethoxymethylene)methane-1,1-dicarbonitrile was synthesized in the same manner as Reference Example 1 and Reference Example 2 using malononitrile and cyclopropanecarbonyl chloride. The NMR data for this compound are shown below.

$^1$H-NMR (400 MHz, $CDCl_3$) δ (ppm): 1.10-1.22 (m, 4H), 2.10-2.22 (m, 1H), 4.27 (s, 3H).

[(2-Bromophenyl)methoxymethylene]methane-1,1-dicarbonitrile was synthesized in the same manner as Reference Examples 1 and 2 using 2-bromobenzoyl chloride. The ESI/MS data for this compound are shown below.

ESI/MS m/e: 263.0, 265.3 (M+H, $C_{11}H_7BrN_2O$)

Reference Example 3

Synthesis of methyl 3-amino-4-cyanopyrrole-2-carboxylate

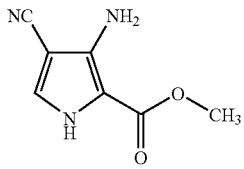

After dissolving dimethyl 2-aminomalonate (25.0 g) in methanol (300 mL), a solution of ethoxymethylene-malononitrile (16.6 g) and triethylamine (15.1 g) in methanol (50 mL) was added. The reaction mixture was stirred at room temperature for 18 hours and then cooled to 0° C., and a mixed solution of 28% sodium methoxide/methanol (31.5 g) and methanol (50 mL) was added dropwise thereto over a period of 10 minutes. The reaction mixture was stirred at room temperature for 49 hours and then cooled to 0° C., and acetic acid (10.3 g) was added. The solvent was distilled off under reduced pressure, ethyl acetate (200 mL) and water (200 mL) were added to the residue and extraction was performed with ethyl acetate. A saturated aqueous sodium bicarbonate solution was added to the organic layer until it exhibited a pH of 8, and extraction was performed with ethyl acetate. The organic layer was dried over anhydrous magnesium sulfate, and the solvent was distilled off under reduced pressure. The residue was purified by silica gel column chromatography (hexane/ethyl acetate=1/1) to obtain the title compound (13.7 g, 61%) as a brown solid. The NMR and ESI/MS data for this compound are shown below.

$^1$H-NMR (400 MHz, DMSO-$d_6$) δ (ppm): 3.77 (s, 3H), 5.52 (brs, 2H), 7.29 (s, 1H), 11.70 (brs, 1H). ESI/MS m/e: 199.2 ($M^++H$, $C_7H_7N_3O_2$)

Reference Example 4

Synthesis of N-{2-[(2,2-dicyanovinyl)amino]ethyl}(4-fluorophenyl)carboxamide

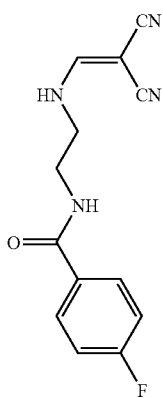

After adding acetonitrile (100 mL) and ethoxymethylen-emalononitrile (4.5 g) to N-(2-aminoethyl)(4-fluorophenyl) carboxamide hydrochloride (8.3 g), a solution of triethylamine (4.5 g) in acetonitrile (20 mL) was added thereto. After stirring at room temperature for 15 minutes, the solvent was distilled off under reduced pressure, water and ethyl acetate were added to the residue, and the mixture was stirred. The precipitated solid was filtered out to obtain the crude title compound (6.5 g) as a brown solid.

ESI/MS m/e: 259.2 ($M^++H$, $C_{13}H_{11}FN_4O$)

Reference Example 5

Synthesis of (methoxyphenylmethylene)methane-1,1-dicarbonitrile

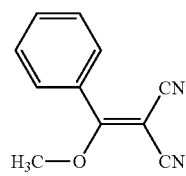

Trimethylorthobenzoic acid (5.01 g) and malononitrile (2.18 g) were added to acetic anhydride (50 mL) and the mixture was heated to reflux for 4 hours. After confirming complete consumption of the trimethylorthobenzoic acid by thin-layer chromatography (hexane/ethyl acetate=3/1), the mixture was cooled to room temperature and the solvent was distilled off under reduced pressure. The residue was purified by silica gel column chromatography (hexane/ethyl acetate=5/1→3/1) to obtain the title compound (3.44 g, yield: 68%) as a light yellow oil. The NMR and ESI/MS data for this compound are shown below.

$^1$H-NMR (400 MHz, CDCl$_3$) δ (ppm): 3.93 (s, 3H), 7.48-7.65 (m, 5H). ESI/MS m/e: 185.0 ($M^++H$, $C_{11}H_8N_2O$)

Reference Example 6

Synthesis of [(methylaminol phenylmethylene]methane-1,1-dicarbonitrile

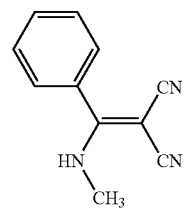

A 40% methanol solution (15 mL) containing methylamine was added to a solution of (methoxyphenylmethylene)methane-1,1-dicarbonitrile (3.44 g) in ethanol (50 mL), and the mixture was stirred for 10 minutes at room temperature and then for 1 hour while heating to reflux. After cooling to room temperature, the solvent was distilled off under reduced pressure. The residue was purified by silica gel column chromatography (hexane/ethyl acetate=3/1→1/1) to obtain the title compound (2.74 g, yield: 80%) as a white solid. The NMR and ESI/MS data for this compound are shown below.

H-NMR (400 MHz, CDCl$_3$) δ (ppm): 2.65 (d, J=4.9 Hz, 1.3H), 3.21 (d, J=5.1 Hz, 1.7H), 7.44-7.58 (m, 5H), 8.97-9.03 (m, 2H). ESI/MS m/e: 184.2 ($M^++H$, $C_{11}H_9N_3$)

[(Methylamino)methylene]methane-1,1-dicarbonitrile was synthesized in the same manner using (ethoxymethylene)methane-1,1-dicarbonitrile and methylamine. The NMR data for this compound are shown below.

$^1$H-NMR (400 MHz, CDCl$_3$) δ (ppm): 1.95 (s, 3H), 7.87 (s, 1H), 8.94 (brs, 1H).

[(Methylamino)ethylidene]methane-1,1-dicarbonitrile was synthesized in the same manner using (ethoxyethylidene)methane-1,1-dicarbonitrile and methylamine. The NMR data for this compound are shown below.

$^1$H-NMR (400 MHz, CDCl$_3$) δ (ppm): 1.08 (s, 0.8H), 2.15 (s, 2.2H), 2.89 (s, 2.1H), 3.07 (s, 0.9H), 8.69 (brs, 1H).

{[Benzylamino]methylene}methane-1,1-dicarbonitrile was synthesized in the same manner using (ethoxymethylene)methane-1,1-dicarbonitrile and benzylamine. The NMR data for this compound are shown below.

$^1$H-NMR (400 MHz, CDCl$_3$) δ (ppm): 1.44 (s, 2H), 7.28-7.39 (s, 5H), 8.09 (s, 1H), 9.60 (brs, 1H).

{[(4-Chlorophenyl)amino]methylene}methane-1,1-dicarbonitrile was synthesized in the same manner using (ethoxymethylene)methane-1,1-dicarbonitrile and 4-chloroaniline. The NMR data for this compound are shown below.

$^1$H-NMR (400 MHz, CDCl$_3$) δ (ppm): 7.44 (s, 4H), 8.50 (s, 1H), 11.15 (s, 1H).

N-(2-{[2,2-dicyano-1-(1-methylpyrrol-2-yl)vinyl]amino}ethyl)(tert-butoxy)carboxamide was synthesized in the same manner using [methoxy(1-methylpyrrol-2-yl)methylene]methane-1,1-dicarbonitrile and tert-butyl N-(2-aminoethyl)carbamate. The ESI/MS data for this compound are shown below.

ESI/MS m/e: 316.1 (M$^+$+H, C$_{16}$H$_{21}$N$_5$O$_2$)

N-{2-[(2,2-dicyano-1-(2-furyl)vinyl]amino]ethyl}(tert-butoxy)carboxamide was synthesized in the same manner using (2-furylmethoxymethylene)methane-1,1-dicarbonitrile and tert-butyl N-(2-aminoethyl)carbamate. The ESI/MS data for this compound are shown below.

ESI/MS m/e: 303.4 (M$^+$+H, C$_{15}$H$_{18}$N$_4$O$_3$)

N-(2-{[2,2-dicyano-1-(3-methyl(2-furyl))vinyl]amino}ethyl)(tert-butoxy)carboxamide was synthesized in the same manner using [methoxy(3-methyl(2-furyl))methylene]methane-1,1-dicarbonitrile and tert-butyl N-(2-aminoethyl)carbamate. The NMR and ESI/MS data for this compound are shown below.

$^1$H-NMR (400 MHz, CD$_3$OD) δ (ppm): 1.43(S, 9H), 2.23 (brs, 3H), 3.23-3.34 (brs, 4H), 3.75 (brs, 1H), 6.52 (s, 1H), 7.70 (brs, 1H). ESI/MS m/e: 317.4 (M$^+$+H, C$_{16}$H$_{20}$N$_4$O$_3$)

N-(2-{[2,2-dicyano-1-(3-methyl(2-thienyl))vinyl]amino}ethyl)(tert-butoxy)carboxamide was obtained in the same manner using [methoxy(3-methyl(2-thienyl))methylene]methane-1,1-dicarbonitrile and tert-butyl N-(2-aminoethyl)carbamate. The ESI/MS data for this compound are shown below.

ESI/MS m/e: (M$^+$+H, C$_{16}$H$_{20}$N$_4$O$_2$S)

(tert-Butoxy)-N-(2-{[1-(3-chloro(2-thienyl))-2,2-dicyanovinyl]aminolethyl}carboxamide was obtained in the same manner using [(3-chloro(2-thienyl))methoxymethylene]methane-1,1-dicarbonitrile and tert-butyl N-(2-aminoethyl)carbamate. The ESI/MS data for this compound are shown below.

ESI/MS m/e: 352.9 (M$^+$+H, C$_{15}$H$_{17}$ClN$_4$O$_2$S)

N-{3-[(2,2-dicyano-1-(2-furyl)vinyl)amino]propyl}(tert-butoxy)carboxamide was synthesized in the same manner using (2-furylmethoxymethylene)methane-1,1-dicarbonitrile and tert-butyl N-(2-aminopropyl)carbamate. The ESI/MS data for this compound are shown below.

ESI/MS m/e: 317.3 (M$^+$+H, C$_{16}$H$_{20}$N$_4$O$_3$)

Reference Example 7

Synthesis of methyl 3-amino-4-cyano-1-methyl-5-phenylpyrrole-2-carboxylate

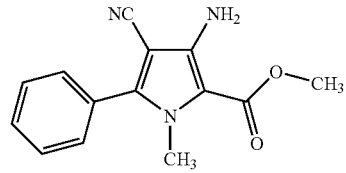

[(Methylamino)phenylmethylene]methane-1,1-dicarbonitrile (3.00 g) and anhydrous potassium carbonate (4.51 g) were added to acetonitrile (200 mL). A solution of methyl bromoacetate (3.09 mL) in acetonitrile (10 mL) was added thereto, and the mixture was heated to reflux for 3 hours. After cooling the mixture to room temperature, it was allowed to stand, the supernatant was separated by decantation, and the solvent was distilled off under reduced pressure. The concentrated residue was combined with the solid portion remaining after decantation, ethyl acetate and water were added, and extraction was performed 3 times with ethyl acetate. The organic layer was washed with water and saturated brine and then dried over anhydrous magnesium sulfate. After filtering off the magnesium sulfate, the solvent was distilled off under reduced pressure. The residue was recrystallized (hexane/ethyl acetate=1/1) to obtain the title compound (1.15 g) as a white solid. The recrystallized residue was purified by silica gel column chromatography (hexane/ethyl acetate=3/1→2/1) to obtain the title compound (1.21 g, (total of 2.36 g with the recrystallized portion), yield: 56%) as a white solid. The NMR and ESI/MS data for this compound are shown below.

$^1$H-NMR (400 MHz, CDCl$_3$) δ (ppm): 3.72 (s, 3H), 3.89 (s, 3H), 4.95 (brs, 2H), 7.42-7.51 (m, 5H). ESI/MS m/e: 256.2 (M$^+$+H, C$_{14}$H$_{13}$N$_3$O$_2$)

Methyl 3-amino-4-cyano-1-methylpyrrole-2-carboxylate was synthesized in the same manner using [(methylamino)methylene]methane-1,1-dicarbonitrile. The NMR data for this compound are shown below.

$^1$H-NMR (400 MHz, CDCl$_3$) δ (ppm): 2.80 (s, 3H), 3.86 (s, 3H), 4.86 (brs, 2H), 5.91 (s, 1H).

Methyl 3-amino-4-cyano-1,5-dimethylpyrrole-2-carboxylate was synthesized in the same manner using [(methylamino)ethylidene]methane-1,1-dicarbonitrile. The NMR data for this compound are shown below.

$^1$H-NMR (400 MHz, CDCl$_3$) δ (ppm): 2.30 (s, 3H), 3.71 (s, 3H), 3.84 (s, 3H), 4.84 (brs, 2H).

Methyl 3-amino-4-cyano-1-benzylpyrrole-2-carboxylate was synthesized in the same manner using {[benzylamino]methylene}methane-1,1-dicarbonitrile. The NMR data for this compound are shown below.

$^1$H-NMR (400 MHz, CDCl$_3$) δ (ppm): 3.79 (s, 3H), 4.91 (brs, 2H), 5.37 (s, 2H), 6.98 (s, 1H), 7.10-7.12 (m, 2H), 7.30-7.36 (m, 3H).

Methyl 3-amino-1-(4-chlorophenyl)-4-cyanopyrrole-2-carboxylate was synthesized in the same manner using {[(4-chlorophenyl)amino]methylene}methane-1,1-dicarbonitrile. The NMR data for this compound are shown below.

$^1$H-NMR (400 MHz, CDCl$_3$) δ (ppm): 3.68 (s, 3H), 5.03 (brs, 2H), 7.04 (s, 1H), 7.18-7.20 (m, 2H), 7.39-7.41 (m, 2H).

Methyl 3-amino-1-{2-[(tert-butoxy)carbonylamino]ethyl}-4-cyano-5-(1-methylpyrrol-2-yl)pyrrole-2-carboxylate was synthesized in the same manner using N-(2-{[2,2-dicyano-1-(1-methylpyrrol-2-yl)vinyl]amino}ethyl)(tert-butoxy)carboxamide. The ESI/MS data for this compound are shown below.

ESI/MS m/e: 388.3 (M$^+$+H, C$_{19}$H$_{25}$N$_5$O$_4$)

Methyl 3-amino-1-{2-[(tert-butoxy)carbonylamino]ethyl}-4-cyano-5-(2-furyl)pyrrole-2-carboxylate was synthesized in the same manner using N-{2-[(2,2-dicyano-1-(2-furyl)vinyl)amino]ethyl}(tert-butoxy)carboxamide. The ESI/MS data for this compound are shown below.

ESI/MS m/e: 375.3 (M$^+$+H, C$_{18}$H$_{22}$N$_4$O$_5$)

Methyl 3-amino-1-{2-[(tert-butoxy)carbonylamino]ethyl}-4-cyano-5-(3-methyl(2-furyl))pyrrole-2-carboxylate was synthesized in the same manner using N-(2-{[2,2-dicyano-1-(3-methyl(2-furyl))vinyl]amino}ethyl)(tert-butoxy)carboxamide. The NMR and ESI/MS data for this compound are shown below.

$^1$H-NMR (400 MHZ, CD$_3$OD) δ (ppm): 1.33 (s, 9H), 2.15 (s, 3H), 3.24-3.34 (m, 2H), 3.87 (s, 3H), 4.28 (m, 2H), 6.48 (s, 1H), 7.62 (s, 1H). ESI/MS m/e: 389.4 (M$^+$+H, C$_{19}$H$_{24}$N$_4$O$_5$)

Methyl 3-amino-1-{2-[(tert-butoxy)carbonylamino]ethyl}-4-cyano-5-(3-methyl(2-thienyl))pyrrole-2-carboxylate was synthesized in the same manner using N-(2-{[2,2-dicyano-1-(3-methyl(2-thienyl))vinyl]amino}ethyl)(tert-butoxy)carboxamide. The ESI/MS data for this compound are shown below.

ESI/MS m/e: (M$^+$+H, C$_{19}$H$_{24}$N$_4$O$_4$S)

Methyl 3-amino-1-{2-[(tert-butoxy)carbonylamino]ethyl}-5-(3-chloro(2-thienyl))-4-cyanopyrrole-2-carboxylate was synthesized in the same manner using (tert-butoxy)-N-(2-{[1-(3-chloro(2-thienyl))-2,2-dicyanovinyl]amino}ethyl)carboxamide. The ESIIMS data for this compound are shown below.

ESI/MS m/e: 425.2 (M$^+$+H, C$_{18}$H$_{21}$ClN$_4$O$_4$S)

Methyl 3-amino-4-cyano-1-{2-[(4-fluorophenyl)carbonylamino]ethyl}pyrrole-2-carboxylate was synthesized in the same manner using N-{2-[(2,2-dicyanovinyl)amino]ethyl}(4-fluorophenyl)carboxamide. The NMR and ESI/MS data for this compound are shown below.

$^1$H-NMR (400 MHz, DMSO-d$_6$) δ (ppm): 3.52 (m, 2H), 3.74 (s, 3H), 4.30 (m, 2H), 5.83 (brs, 2H), 7.29 (m, 2H), 7.45 (s, 1H), 7.84 (m, 2H), 8.52 (m, 1H). ESI/MS m/e: 331.2 (M$^+$+H, C$_{16}$H$_{15}$FN$_4$O$_3$)

Methyl 3-amino-1-{3-[(tert-butoxy)carbonylamino]propyl}-4-cyano-5-(2-furyl)pyrrole-2-carboxylate was synthesized in the same manner using N-{3-[(2,2-dicyano-1-(2-furyl)vinyl)amino]propyl}(tert-butoxy)carboxamide. The ESI/MS data for this compound are shown below.

ESI/MS m/e: 389.4 (M$^+$+H, C$_{19}$H$_{24}$N$_4$O$_5$)

Reference Example 8

Synthesis of methyl 3-amino-1-{2[(tert-butoxy)carbonylamino]ethyl}-4-cyano-5-phenylpyrrole-2-carboxylate

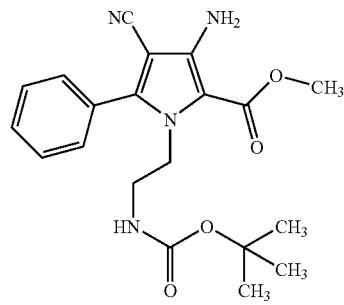

tert-Butyl N-(2-aminoethyl)carbamate (10.6 g) was added to a solution of (methoxyphenylmethylene)methane-1,1-dicarbonitrile (10.4 g) in acetonitrile (350 mL), and the mixture was stirred for 10 minutes. Anhydrous cesium carbonate (65.1 g) and methyl bromoacetate (13.5 mL) were added, and the mixture was heated to reflux for 1 hour. After cooling the mixture to room temperature, it was allowed to stand, the supernatant was separated by decantation, and the solvent was distilled off under reduced pressure. The concentrated residue was combined with the solid portion remaining after decantation, ethyl acetate and water were added, and extraction was performed 3 times with ethyl acetate. The organic layer was washed with water and saturated brine and then dried over anhydrous magnesium sulfate. After filtering off the magnesium sulfate, the solvent was distilled off under reduced pressure. The residue was purified by silica gel column chromatography (hexane/ethyl acetate 2/1) to obtain the title compound (20.6 g, yield: 95%) as a yellow transparent oil. The NMR and ESI/MS data for this compound-are shown below.

$^1$H-NMR (400 MHz, CDCl$_3$) δ (ppm): 1.35 (s, 9H), 3.30-3.31 (m, 2H), 3.90 (s, 3H), 4.30 (t, J=5.7, 2H), 4.40 (brs, 1H), 4.96 (brs, 2H), 7.41-7.52 (m, 5H). ESI/MS m/e: 385.3 (M$^+$+H, C$_{20}$H$_{24}$N$_4$O$_4$)

Reference Example 9

Synthesis of methyl 3-amino-1-{2-[(tert-butoxy]carbonylaminolethyl}-4-cyanopyrrole-2-carboxylate

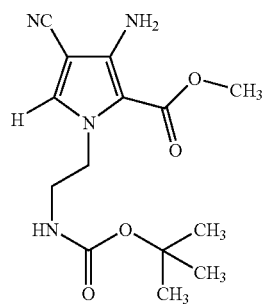

After dissolving ethoxymethylenemalononitrile (5.1 g) and tert-butyl N-(aminoethyl)carbamate (7.5 g) in acetonitrile (50 mL), a solution of triethylamine (830 mg) in acetonitrile (50 mL) was added and the mixture was stirred for 10 minutes at room temperature. After confirming complete consumption of the ethoxymethylene-malononitrile by thin-layer chromatography (hexane/ethyl acetate=1/1), the solvent was distilled off under reduced pressure. Acetonitrile (160 mL) and cesium carbonate (26.7 g) were added to the residue, and then a solution of methyl bromoacetate (12.9 g) in acetonitrile (12 mL) was added dropwise over a period of 30 minutes. The mixture was heated to reflux for 90 minutes and then cooled to room temperature, the supernatant was separated by decantation, and the solvent was distilled off under reduced pressure. The concentrated residue was combined with the solid portion remaining after decantation, ethyl acetate and water were added, and extraction was performed 3 times with ethyl acetate. The organic layer was washed with water and saturated brine in that order and then dried over magnesium sulfate. The solvent was distilled off under reduced pressure, and the resultant brown oil (17.9 g) was purified by silica gel column chromatography (hexane/ethyl acetate=3/2) to obtain the title compound (9.3 g, 74%).

Reference Example 10

Synthesis of ethyl 3-[4-amino-3-cyano-5-(methoxycarbonyl)-2-phenylpyrrolyl]propionate

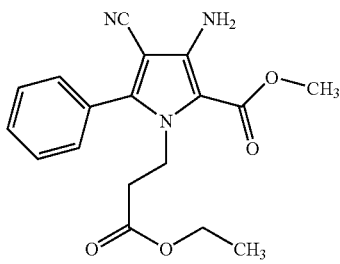

After dissolving (methoxyphenylmethylene)methane-1,1-dicarbonitrile (15.10 g) and β-alanine ethyl ester hydrochloride (15.11 g) in acetonitrile (300 mL), triethylamine (23.00 mL) was added and the mixture was stirred for 10 minutes at room temperature. After confirming complete consumption of the (methoxyphenyl-methylene)methane-1,1-dicarbonitrile by thin-layer chromatography (hexane/ethyl acetate=3/1), the solvent was distilled off under reduced pressure. Ethyl acetate and water were added to the residue, and extraction was performed 3 times with ethyl acetate. The organic layer was washed with water and saturated brine and then dried over anhydrous magnesium sulfate. After filtering off the magnesium sulfate, the solvent was distilled off under reduced pressure. Acetonitrile (700 mL) and anhydrous cesium carbonate (53.65 g) were added to the residue. Methyl bromoacetate (16.00 mL) was added thereto and the mixture was heated to reflux for 40 minutes. After cooling the mixture to room temperature, it was allowed to stand, the supernatant was separated by decantation, and the solvent was distilled off under reduced pressure. The residue was combined with the solid portion remaining after decantation, ethyl acetate and water were added, and extraction was performed 3 times with ethyl acetate. The organic layer was washed with water and saturated brine and then dried over anhydrous magnesium sulfate. After filtering off the magnesium sulfate, the solvent was distilled off under reduced pressure. The residue was passed through a chromatography column packed with a small amount of silica gel (elution with dichloromethane), for removal of the highly polar impurities, to obtain the title compound as a crude product (35.31 g).

Reference Example 11

Synthesis of (phenyl{[2-(1,1,2,2-tetramethyl-1-silapropoxy)ethyl]amino}methylene)methane-1,1-dicarbonitrile

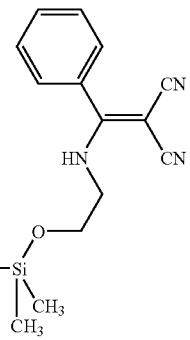

After dissolving (methoxyphenylmethylene)methane-1,1-dicarbonitrile (5.02 g) and aminoethanol (2.05 g) in methanol (50 mL), the solution was stirred for 10 minutes at room temperature. The solvent was distilled off under reduced pressure, a solution was prepared in tetrahydrofuran, and the solvent was distilled off under reduced pressure again to total distillation of the methanol. The residue was dissolved in tetrahydrofuran (60 mL), and then imidazole (3.87 g) and tert-butyldimethylsilyl chloride (7.39 g) were added thereto and the mixture was stirred for 8 hours at room temperature. After distilling off the solvent under reduced pressure, ethyl acetate and saturated aqueous ammonium chloride were added to the residue and extraction was performed 3 times with ethyl acetate. The organic layer was washed with water and saturated brine and then dried over anhydrous magnesium sulfate. After filtering off the magnesium sulfate, the solvent was distilled off under reduced pressure. The residue was purified by silica gel column chromatography (hexane/ethyl acetate=4/1) to obtain the title compound (6.47 g, yield: 73%) as a colorless transparent oil. The NMR and ESI/MS data for this compound are shown below.

$^1$H-NMR (400 MHz, CDCl$_3$) δ (ppm): 0.098 (s, 6H), 0.93 (s, 9H), 3.24 (m, 2H), 3.64 (t, J=4.88, 2H), 6.65 (brs, 1H), 7.37-7.39 (m, 2H), 7.52-7.54 (m, 3H). ESI/MS m/e: 328.2 (M$^+$+H, C$_{18}$H$_{25}$N$_3$OSi)

Reference Example 12

Synthesis of methyl 3-amino-4-cyano-5-phenyl-1-[2-(1,1,1,2-tetramethyl-1-silapropoxy)ethyl]pyrrole-2-carboxylate

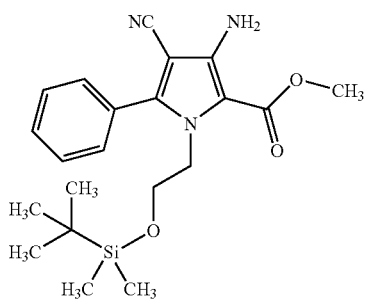

(Phenyl{[2-(1,1,2,2-tetramethyl-1-silapropoxy)ethyl]
amino}methylene)methane-1,1-dicarbonitrile (6.47 g) and
anhydrous cesium carbonate (12.9 g) were added to acetonitrile (150 mL). Methyl bromoacetate (3.8 mL) was added thereto, and the mixture was heated to reflux for 3 hours. After cooling the mixture to room temperature, it was allowed to stand, the supernatant was separated by decantation, and the solvent was distilled off under reduced pressure. The concentrated residue was combined with the solid portion remaining after decantation, ethyl acetate and water were added, and extraction was performed 3 times with ethyl acetate. The organic layer was washed with water and saturated brine and then dried over anhydrous magnesium sulfate. After filtering off the magnesium sulfate, the solvent was distilled off under reduced pressure. The residue was recrystallized (hexane/ethyl acetate=1/1) to obtain the title compound (5.13 g, yield: 65%) as a white solid. The NMR and ESI/MS data for this compound are shown below.

$^1$H-NMR (400 MHz, CDCl$_3$) δ (ppm): −0.11 (s, 6H), 0.78 (s, 9H), 3.73 (t, J=5.6, 2H), 3.88 (s, 3H), 4.33 (t, J=5.6, 2H), 4.96 (brs, 2H), 7.47-7.52 (m, 5H). ESI/MS m/e 400.3 (M$^+$+H, C$_{21}$H$_{29}$N$_3$O$_3$Si)

Methyl 3-amino-4-cyano-5-phenyl-1-[3-(1,1,2,2-tetramethyl-1-silapropoxy)propyl]pyrrole-2-carboxylate as synthesized in the same manner as Reference Example 11 and Reference Example 12 using (methoxyphenylmethylene)methane-1,1-dicarbonitrile and 3-amino-1-propanol. The NMR data for this compound are shown below.

$^1$H-NMR (400 MHz, CDCl$_3$) δ (ppm): −0.084 (s, 6H), 0.76 (s, 9H), 1.75-1.82 (m, 2H), 3.48 (t, J=6.0, 2H), 3.88 (s, 3H), 4.25 (t, J=7.6, 2H), 4.97 (brs, 2H), 7.40-7.43 (m, 2H), 7.47-7.49 (m, 3H).

Example 1

Synthesis of 5-methyl-4-oxo-6-phenyl-3-hydropyrrolo[3,2-d]pyrimidine-7-carbonitrile (Compound No: 1-0925)

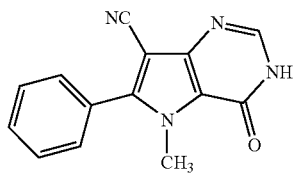

Methyl 3-amino-4-cyano-1-methyl-5-phenylpyrrole-2-carboxylate (1.74 g) and formamidine acetate (2.84 g) were added to 2-propanol (100 mL) and the mixture was heated to reflux for 72 hours. After cooling to room temperature, the produced precipitate was filtered out and washed with ethanol. This solid was recrystallized from ethanol to obtain the title compound (1.37 g, yield: 80%) as a white solid. The NMR and ESI/MS data for this compound are shown below.

$^1$H-NMR (400 MHz, DMSO-d$_6$) δ (ppm): 3.95 (s, 3H), 7.61-7.67 (m, 5H), 8.01 (s, 1H), 12.43 (brs, 1H). ESI/MS m/e: 251.1 (M$^+$+H, C$_{14}$H$_{10}$N$_4$O)

Example 2

Synthesis of 5-methyl-6-phenyl-4-thioxo-3-hydropyrrolo[3,2-d]pyrimidine-7-carbonitrile (Compound No: 1-0592)

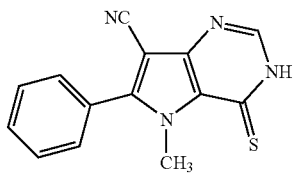

5-Methyl-4-oxo-6-phenyl-3-hydropyrrolo[3,2-d]pyrimidine-7-carbonitrile (101.8 mg) was added to phosphorus oxychloride (2 mL) and the mixture was heated to reflux at 100° C. for 1 hour. After cooling to room temperature, the excess phosphorus oxychloride was distilled off under reduced pressure. The residue was dissolved in 2-propanol (2 mL), thiourea (47 mg) was added and the mixture was heated to reflux at 100° C. for 1 hour. After cooling to room temperature, the solvent was distilled off under reduced pressure. The residue was recrystallized from ethanol to obtain the title compound (80.3 mg, yield: 74%) as a white solid. The NMR and ESI/MS data for this compound are shown below.

$^1$H-NMR (400 MHz, DMSO-d$_6$) δ (ppm): 4.22 (s, 3H), 7.63-7.70 (m, 5H), 8.16 (d, J=3.7, 1H), 13.7 (brs, 1H). ESI/MS m/e: 267.1 (M$^+$+H, C$_{14}$H$_{10}$N$_4$S)

Example 3

Synthesis of 5-(2-hydroxyethyl)-4-oxo-6-phenyl-3-hydropyrrolo[3,2-d]pyrimidine-7-carbonitrile (Compound No: 1-0181)

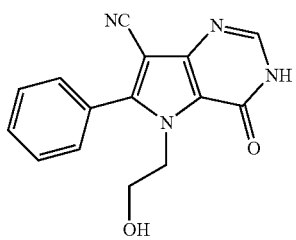

Formamide (20 mL) and a 28% solution of sodium methoxide in methanol (20 mL) were added to a solution of methyl 3-amino-4-cyano-5-phenyl-1-[2-(1,1,2,2-tetramethyl-1-silapropoxy)ethyl]pyrrole-2-carboxylate (5.00 g) in dimethylsulfoxide (20 mL), and the mixture was heated to reflux at 100° C. for 4 hours. After cooling to room temperature, water (100 mL) and 2 mol/L hydrochloric acid (100 mL) were added to acidify the solution. After stirring the mixture at room temperature for a while, the produced solid was filtered out. It was dissolved in ethanol (100 mL), and then a 4 mol/L hydrochloric acid/1,4-dioxane solution (10 mL) was added, and the mixture was stirred for 1 hour at room temperature. After distilling off the solvent under reduced pressure, the residue was recrystallized (ethanol/ethyl acetate/hexane=1/1/2) to obtain the title compound (2.77 g, yield: 77%) as a white solid. The NMR and ESI/MS data for this compound are shown below.

$^1$H-NMR (400 MHz, DMSO-$d_6$) δ (ppm): 3.61 (m, 2H), 4.36 (t, J=5.6, 2H), 4.85 (brs, 1H), 7.59-7.62 (m, 3H), 7.67-7.69 (m, 2H), 8.04 (s, 1H), 12.45 (brs, 1H). ESI/MS m/e: 281.2 (M$^+$+H, $C_{15}H_{12}N_4O_2$)

Example 4

Synthesis of 5-(3-hydroxyrropyl-4-oxo-6-phenyl-3-hydropyrrolo[3,2-d]pyrimidine-7-carbonitrile (Compound No: 1-0194)

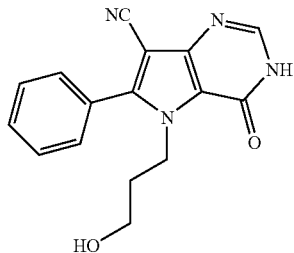

The title compound was synthesized in the same manner as Example 3 using methyl 3-amino-4-cyano-5-phenyl-1-[3-(1,1,2,2-tetramethyl-1-silapropoxy)propyl]pyrrole-2-carboxylate. The NMR and ESI/MS data for this compound are shown below.

$^1$H-NMR (400 MHz, DMSO-$d_6$) δ (ppm): 1.70-1.82 (m, 2H), 3.17-3.27 (m, 2H), 4.35-4.47 (m, 2H), 7.55-7.68 (m, 5H), 8.02 (d, J=1.0, 1H), 12.46 (brs, 1H). ESI/MS m/e: 295.2 (M$^+$+H, $C_{16}H_{14}N_4O_2$)

Example 5

Synthesis of 5-[3-(methylethoxy)propyl]-6-(4-nitrophenyl)-4-oxo-3-hydropyrrolo[3,2-d]pyrimidine-7-carbonitrile (Compound No: 1-1077)

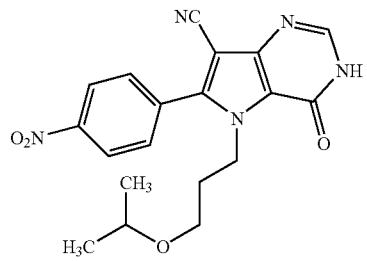

The title compound was synthesized in the same manner as Example 3 using methyl 3-amino-4-cyano-1-[3-(methylethoxy)propyl]-5-(4-nitrophenyl)pyrrole-2-carboxylate. The NMR and ESI/MS data for this compound are shown below.

$^1$H-NMR (400 MHz, DMSO-$d_6$) δ (ppm): 0.75-0.92 (m, 6H), 1.72-1.85 (m, 2H), 3.12 (t, J=5.1, 2H), 3.16-3.26 (m, 1H), 4.46 (t, J=6.8, 2H), 7.96 (dd, J=1.2, J=8.8, 2H), 8.06 (d, J=1.2, 1H), 8.45 (dd, J=1.2, J=8.8, 2H). ESI/MS m/e: 382.2 (M$^+$+H, $C_{19}H_{19}N_5O_4$)

Example 6

Synthesis of 2-(7-cyano-4-oxo-6-phenyl-3-hydropyrrolo[3,2-d]pyrimidin-5-yl)ethylbenzoate (Compound No: 2-05081

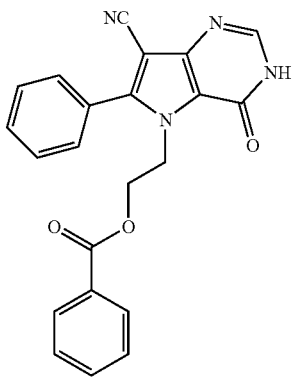

5-(2-Hydroxyethyl)-4-oxo-6-phenyl-3-hydropyrrolo[3,2-d]pyrimidine-7-carbonitrile (200 mg) was dissolved in pyridine (3 mL). Benzoyl chloride (250 µL) was added thereto, and the mixture was stirred for 1 hour at room temperature. Water (1 mL) was added to the reaction solution and the mixture was stirred for 1 hour at room temperature. After slowly adding thereto a 10% aqueous sodium carbonate solution (20 mL), the mixture was further stirred for 1 hour and the produced solid was filtered out. The solid was recrystallized from ethanol/ethyl acetate/hexane (ethanol/ethyl acetate/hexane=1/1/2) to obtain the title compound (209 mg, yield: 76%) as a white solid. The NMR and ESI/MS data for this compound are shown below.

$^1$H-NMR (400 MHz, DMSO-$d_6$) δ (ppm): 4.46 (t, J=4.8, 2H), 4.81 (t, J=4.8, 2H), 7.44-7.64 (m, 10H), 8.03 (s, 1H), 12.54 (brs, 1H). ESI/MS m/e: 385.2 (M$^+$+H, $C_{22}H_{16}N_4O_3$)

Example 7

Synthesis of (tert-butoxy)-N-[2-(7-cyano-4-oxo-6-phenyl(3-hydropyrrolo[3,2-d]pyrimidin-5-yl))ethyl] carboxamide (Compound No: 2-0199)

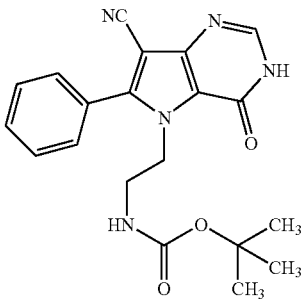

Methyl 3-amino-1-{2-[(tert-butoxy)carbonylamino]ethyl}-4-cyano-5-phenylpyrrole-2-carboxylate (19.7 g) and formamidine acetate (53.6 g) were added to 2-propanol (400 mL) and the mixture was heated to reflux for 30 hours. After cooling to room temperature, the solvent was distilled off under reduced pressure. Water was added to the residue, and the produced solid was filtered out and thoroughly washed with water. The solid was recrystallized (ethanol/ethyl acetate/hexane=1/2/1) to obtain the title compound (11.3 g, yield: 58.2%) as a white solid. The NMR and ESI/MS data for this compound are shown below.

$^1$H-NMR (400 MHz, DMSO-d$_6$) δ (ppm): 1.22 (s, 9H), 3.16-3.17 (m, 2H), 4.36 (t, J=5.0, 2H), 6.61 (brs, 1H), 7.59 (s, 5H), 8.03 (s, 1H), 12.44 (brs, 1H). ESI/MS m/e: 380.2 (M$^+$+H, $C_{20}H_{21}N_5O_3$)

Example 8

Synthesis of (tert-butoxy)-N-{2-[7-cyano-6-(1-methylpyrrol-2-yl)-4-oxo(3-hydropyrrolo[3,2-d]pyrimidin-5-yl)]ethyl}carboxamide (Compound No: 2-1958)

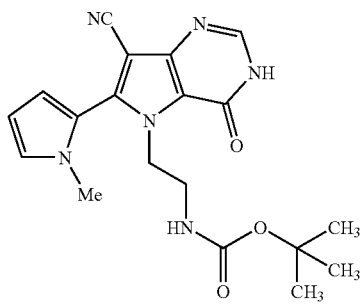

The title compound was synthesized in the same manner as Example 7 using 3-amino-1-{2-[(tert-butoxy)carbonylamino]ethyl}-4-cyano-5-(1-methylpyrrol-2-yl)pyrrole-2-carboxylate. The ESI/MS data for this compound are shown below.

ESI/MS m/e: 383.3 (M$^+$+H, $C_{19}H_{22}N_6O_3$)

Example 9

Synthesis of (tert-butoxy)-N-[2-(7-cyano-6-(2-furyl)-4-oxo(3-hydropyrrolo[3,2-d]pyrimidin-5-yl))ethyl]carboxamide (Compound No: 2-1959)

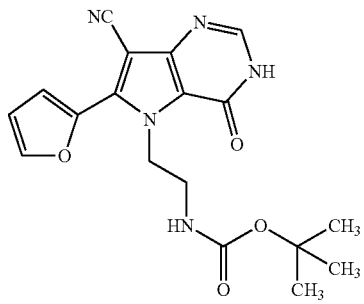

The title compound was obtained in the same manner as Example 7 using methyl 3-amino-1-{2-[(tert-butoxy)carbonylamino]ethyl}-4-cyano-5-(2-furyl)pyrrole-2-carboxylate. The NMR and ESI/MS data for this compound are shown below.

$^1$H-NMR (400 MHz, DMSO-d$_6$) δ (ppm): 1.21 (s, 9H), 3.31 (brs, 2H), 4.66 (m, 2H), 6.80 (m, 2H), 7.22 (m, 1H), 8.01 (m, 2H), 12.43 (brs, 1H). ESI/MS m/e: 370.3 (M$^+$+H, $C_{18}H_{19}N_5O_4$)

Example 10

Synthesis of (tert-butoxy)-N-{2-[7-cyano-6-(3-methyl(2-furyl))-4-oxo(3-hydropyrrolo[3,2-d]pyrimidin-5-yl)]ethyl}carboxamide (Compound No: 2-1960)

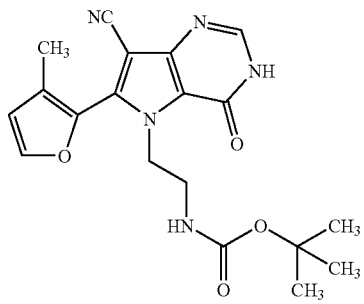

The title compound was obtained in the same manner as Example 7 using methyl 3-amino-1-{2-[(tert-butoxy)carbonylamino]ethyl}-4-cyano-5-(3-methyl(2-furyl))pyrrole-2-carboxylate. The NMR and ESI/MS data for this compound are shown below.

$^1$H-NMR (400 MHz, CD$_3$OD) δ (ppm): 1.28 (s, 9H), 2.24 (s, 3H), 3.40 (m, 2H), 4.55 (m, 2H), 6.57 (s, 1H), 7.73 (s, 1H), 7.95 (s, 1H). ESI/MS m/e: 384.4 (M$^+$+H, $C_{19}H_{21}N_5O_4$)

Example 11

Synthesis of (tert-butoxy)-N-{2-[7-cyano-6-(3-methyl(2-thienyl))-4-oxo(3-hydropyrrolo[3,2-d]pyrimidin-5-yl]ethyl}carboxamide (Compound No: 2-1961)

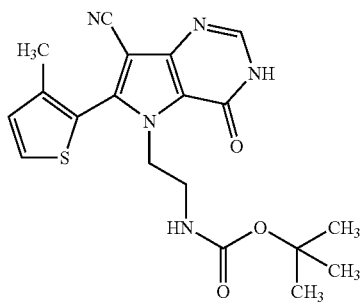

The title compound was synthesized in the same manner as Example 7 using methyl 3-amino-1-{2-[(tert-butoxy)carbonylamino]ethyl}-4-cyano-5-(3-methyl(2-thienyl))pyrrole-2-carboxylate. The NMR and ESI/MS data for this compound are shown below.

$^1$H-NMR (400 MHz, DMSO-d$_6$) δ (ppm): 1.22 (s, 9H), 2.17 (s, 3H), 3.23 (brs, 2H), 4.23-4.37 (brs, 2H), 6.60 (m, 1H), 7.13 (d, J=5.2, 1H), 7.83 (d, J=4.9, 1H), 8.03 (m, 1H), 12.47 (brs, 1H). ESI/MS m/e: 400.2 (M$^+$+H, C$_{19}$H$_{21}$N$_5$O$_3$S)

Example 12

Synthesis of (tert-butoxy)-N-{2-[6-(3-chloro(2-thienyl))-7-cyano-4-oxo(3-hydropyrrolo[3,2-d]pyrimidin-5-yl)]ethyl}carboxamide (Compound No: 2-1962)

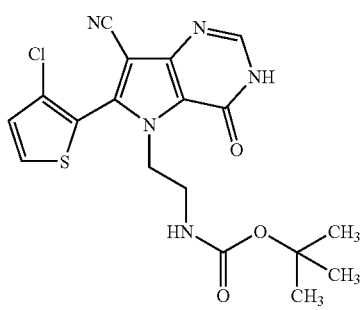

The title compound was obtained in the same manner as Example 7 using methyl 3-amino-1-{2-[(tert-butoxy)carbonylamino]ethyl}-5-(3-chloro(2-thienyl))-4-cyanopyrrole-2-carboxylate. The ESI/MS data for this compound are shown below.

ESI/MS m/e: 420.2 (M$^+$+H, C$_{18}$H$_{18}$ClN$_5$O$_3$S)

Example 13

Synthesis of (tert-butoxy)-N-[3-(7-cyano-6-(2-furyl)-4-oxo(3-hydropyrrolo[3,2-d]pyrimidin-5-yl))propyl]carboxamide (Compound No: 2-1963)

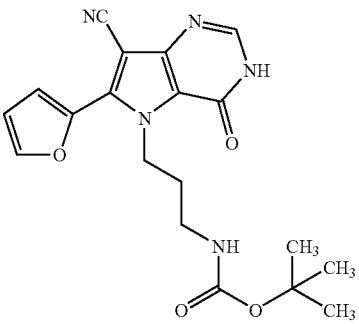

The title compound was synthesized in the same manner as Example 7 using methyl 3-amino-1-{3-[(tert-butoxy)carbonylamino]propyl}-4-cyano-5-(2-furyl)pyrrole-2-carboxylate. The NMR and ESI/MS data for this compound are shown below.

$^1$H-NMR (400 MHz, DMSO-d$_6$) δ (ppm): 1.35 (s, 9H), 1.84 (m, 2H), 2.92 (m, 2H), 4.64 (m, 2H), 6.82 (m, 2H), 7.18 (m, 1H), 7.98-8.08 (m, 2H), 12.45 (brs, 1H). ESI/MS m/e: 384.5 (M$^+$+H, C$_{19}$H$_{21}$N$_5$O$_4$)

Example 14

Synthesis of N-[2-(7-cyano-4-oxo(3-hydropyrrolo[3,2-d]pyrimidin-5-yl))ethyl](4-fluorophenyl)carboxamide (Compound No: 2-1952)

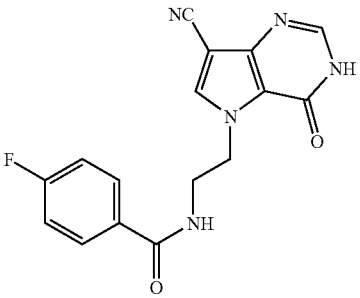

After adding a 28% solution of sodium methoxide in methanol (40 mL) to a suspension of methyl 3-amino-4-cyano-1-{2-[(4-fluorophenyl)carbonylamino]ethyl}pyrrole-2-carboxylate (7.9 g) in formamide (40 mL), the mixture was stirred for 80 minutes at 100° C. After cooling to 0° C., 2 mol/L hydrochloric acid (45 mL) was added and the precipitated solid was filtered out to obtain the title compound (5.8 g, 74%). The NMR and ESI/MS data for this compound are shown below.

$^1$H-NMR (400 MHz, DMSO-d$_6$) δ (ppm): 3.68 (m, 2H), 4.53 (m, 2H), 7.27 (m, 2H), 7.79 (m, 2H), 7.97 (s, 1H), 8.14 (s, 1H), 8.53 (m, 1H). ESI/MS m/e: 326.2 (M$^+$+H, C$_{16}$H$_{12}$FN$_5$O$_2$)

Example 15

Synthesis of (tert-butoxy)-N-[2-(7-cyano-4-oxo(3-hydropyrrolo[3,2-d]pyrimidin-5-yl))ethyl]carboxamide (Compound No: 2-1964)

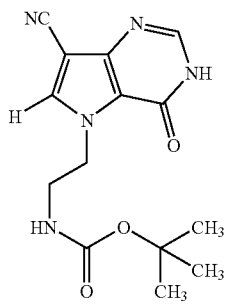

A methyl 3-amino-1-{2-[(tert-butoxy)carbonylamino]ethyl}-4-cyanopyrrole-2-carboxylate crude product (9.3 g), formamidine acetate (78.3 g) and 2-propanol (200 mL) were combined, and the mixture was heated to reflux for 14 hours. After cooling to room temperature, the supernatant was collected and concentrated under reduced pressure. This was mixed with the residue, and then ethyl acetate and water were added and extraction was performed 3 times with ethyl acetate. The organic layer was washed with water and saturated brine in that order and then dried over magnesium sulfate. The solvent was distilled off under reduced pressure to obtain the title compound as a crude product (1.69 g). The ESI/MS data for this compound are shown below.

ESI/MS m/e: 304.2 (M$^+$+H, $C_{14}H_{17}N_5O_3$)

Example 16

Synthesis of N-[2-(7-cyano-4-oxo(3-hydropyrrolo[3,2-d]pyrimidin-5-yl))ethyl]benzamide (Compound No: 2-1953)

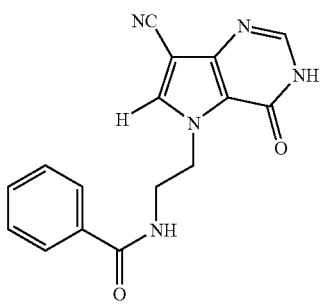

1,4-Dioxane (50 mL), a 4 mol/L hydrochloric acid/dioxane solution (5.6 mL) and methanol (10 mL) were added to a (tert-butoxy)-N-[2-(7-cyano-4-oxo(3-hydropyrrolo[3,2-d]pyrimidin-5-yl))ethyl]carboxamide crude product (1.69 g), the mixture was heated to 60° C., methanol (10 mL) was added and the mixture was stirred for 90 minutes. A 4 mol/L hydrochloric acid/dioxane solution (2 mL) and methanol (10 mL) were added, the mixture was stirred for 1 hour, and the solvent was distilled off under reduced pressure. N,N-dimethylformamide (100 mL) and triethylamine (1.7 g) were added to the residue, a solution of benzoyl chloride (1.6 g) in N,N-dimethylformamide (20 mL) was added thereto and the mixture was stirred for 1 hour. After cooling to 0° C., water and ethyl acetate were added and extraction was performed 3 times with ethyl acetate. The solvent was distilled off under reduced pressure, ethyl acetate and hexane were added to the residue, and the precipitated solid was filtered out to obtain the title compound (1.0 g, 59%). The ESI/MS data for this compound are shown below.

ESI/MS m/e: 308.1 (M$^+$+H, $C_{16}H_{13}N_5O_2$)

Example 17

Synthesis of N-[2-(6-chloro-7-cyano-4-oxo(3-hydroryrrolo[3,2-d]pyrimidin-5-yl))ethyl]benzamide (Compound No: 2-1954)

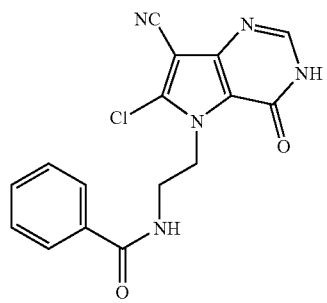

N,N-dimethylformamide (30 mL) and N-chlorosuccinimide (1.3 g) were added to N-[2-(7-cyano-4-oxo(3-hydropyrrolo[3,2-d]pyrimidin-5-yl))ethyl]benzamide (1.0 g), and the mixture was stirred for 13 hours at room temperature. After adding 30 mL of water, the mixture was cooled to 0° C. The precipitated solid was filtered out to obtain the title compound (980 mg, 87%). The NMR and ESI/MS data for this compound are shown below.

$^1$H-NMR (400 MHz, DMSO-d$_6$) δ (ppm): 3.64-3.73 (m, 2H), 4.60-4.67 (m, 2H), 7.37-7.56 (m, 3H), 7.64-7.74 (m, 2H), 8.02 (s, 1H), 8.54-8.60 (m, 1H), 12.6 (brs, 1H). ESI/MS m/e: 342.1 (M$^+$+H, $C_{16}H_{12}ClN_5O_2$)

Example 18

Synthesis of N-[2-(6-chloro-7-cyano-4-thioxo(3-hydropyrrolo[3,2-d]pyrimidin-5-yl))ethyl]benzamide (Compound No: 2-1896)

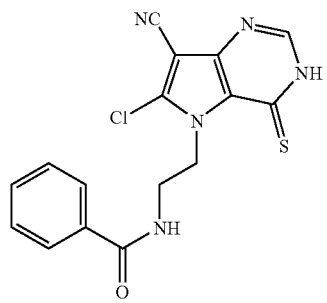

Phosphorus oxychloride (55 g) was added to N-[2-(6-chloro-7-cyano-4-oxo(3-hydropyrrolo[3,2-d]pyrimidin-5-yl))ethyl]benzamide (300 mg), and the mixture was heated to reflux for 30 minutes. After concentration under reduced pressure, toluene was added to the residue and the mixture was further concentrated under reduced pressure. 2-Propanol (20 mL) and thiourea (77 mg) were added to the residue and the mixture was heated to reflux for 30 minutes. The solvent was distilled off under reduced pressure, ethyl acetate and water were added to the residue, and extraction was performed 3 times with ethyl acetate. The organic layer was washed with water and saturated brine in that order and then dried over magnesium sulfate. The solvent was distilled off under reduced pressure to obtain the title compound as a crude product (411 mg). The ESI/MS data for this compound are shown below.

ESI/MS m/e: 358.1 (M$^+$+H, $C_{16}H_{12}ClN_5OS$)

Example 19

Synthesis of 5-[3-(methylethoxy)propyl]-4-oxo-3-hydropyrrolo[3,2-d]pyrimidine-7-carbonitrile (Compound No: 1-0845)

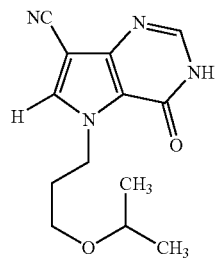

After dissolving ethoxymethylenemalononitrile (10.2 g) in acetonitrile (200 mL), 3-isopropoxypropylamine (9.8 g) was added thereto and the mixture was stirred for 10 minutes. Cesium carbonate (68 g) and methyl bromoacetate (32 g) were added and the mixture was heated to reflux for 30 minutes. After cooling to room temperature, the supernatant was separated by decantation, and the solvent was distilled off under reduced pressure. The concentrated residue was combined with the solid portion remaining after decantation, ethyl acetate and water were added, and extraction was performed 3 times with ethyl acetate. The organic layer was washed with saturated brine and then dried over magnesium sulfate, and the solvent was distilled off under reduced pressure. The residue was dissolved in ethyl acetate and passed through a silica gel, and then ethyl acetate (200 mL) was added for elution. The eluate was concentrated under reduced pressure to obtain a methyl 3-amino-4-cyano-1-[3-(methylethoxy)propyl]pyrrole-2-carboxylate crude product as a brown oil.

Dimethylsulfoxide (70 mL), formamide (70 mL) and a 28% solution of sodium methoxide in methanol (70 mL) were added thereto and the mixture was stirred at 100° C. for 10 hours. After cooling to room temperature, water (300 mL) and 2 mol/L hydrochloric acid (100 mL) were added to adjust the reaction solution to a pH of 4. After cooling the reaction solution to 0° C., the precipitated solid was filtered out. Ethanol (150 mL) was added to the solid, and the mixture was heated to dissolution and cooled to 0° C. The precipitated solid was filtered out to obtain the title compound (12.3 g, 57%) as light brownish crystals. The ESI/MS data for this compound are shown below.

ESI/MS m/e: 261.4 (M$^+$+H, $C_{13}H_{16}N_4O_2$)

Example 20

Synthesis of 6-chloro-5-[3-(methylethoxy) propyl]-4-oxo-3-hydropyrrolo[3,2-d]pyrimidine-7-carbonitrile (Compound No: 1-0861)

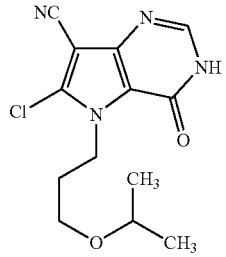

N,N-dimethylformamide (50 mL) and N-chlorosuccinimide (6.5 g) were added to 5-[3-(methylethoxy)propyl]-4-oxo-3-hydropyrrolo[3,2-d]pyrimidine-7-carbonitrile (4.3 g), and the mixture was stirred for 3 days at room temperature. After adding 200 mL of water, extraction was performed twice with ethyl acetate. The organic layer was washed with saturated brine and then dried over magnesium sulfate. The solvent was distilled off under reduced pressure to obtain the crude title compound as a brown solid. The ESI/MS data for this compound are shown below.

ESI/MS m/e: 295.3 (M$^+$+H, $C_{13}H_{15}ClN_4O_2$)

Example 21

Synthesis of 5-[3-(methylethoxy)propyl]-4-thioxo-3-hydropyrrolo[3,2-d]pyrimidine-7-carbonitrile (Compound No: 1-0527)

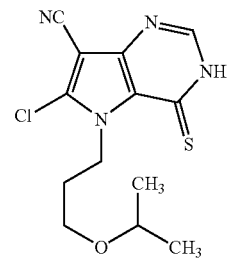

Phosphorus oxychloride (25 g) was added to the crude 6-chloro-5-[3-(methylethoxy)propyl]-4-oxo-3-hydropyrrolo[3,2-d]pyrimidine-7-carbonitrile, and the mixture was heated to reflux for 30 minutes. After concentration under reduced pressure, 2-propanol (100 mL) and thiourea (2.1 g) were added to the residue and the mixture was heated to reflux for 30 minutes. The solvent was distilled off under reduced pressure, water (200 mL) was added and extraction was performed twice with ethyl acetate. The organic layer was washed with saturated brine and then dried over magnesium sulfate. The solvent was distilled off under reduced pressure, and the obtained brown oil was purified by silica gel column chromatography (hexane/ethyl acetate=7/3) to obtain the title compound (2.1 g, 42%) as a light yellow solid. The ESI/MS data for this compound are shown below.

ESI/MS m/e: 311.2 (M$^+$+H, $C_{13}H_{15}ClN_4OS$)

Example 22

Synthesis of 5-(2-aminoethyl)-4-oxo-6-phenyl-3-hydropyrrolo[3,2-d]pyrimidine-7-carbonitrile hydrochloride (Compound No: 1-0151)

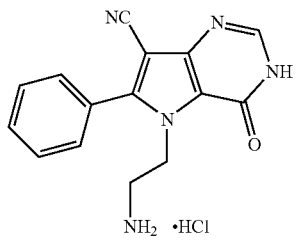

(tert-Butoxy)-N-[2-(7-cyano-4-oxo-6-phenyl(3-hydropyrrolo[3,2-d]pyrimidin-5-yl))ethyl]carboxamide (8.01 g) was dissolved in a mixed solution of ethanol (50 mL) and 1,4-dioxane (50 mL), and then a 4 mol/L hydrochloric acid/1,4-dioxane solution (50 mL) was added. After stirring for 1 hour at room temperature, the solvent was distilled off under reduced pressure and the residue was recrystallized (ethanol/ethyl acetate=1/2) to obtain the title compound (6.15 g, yield: 92%) as a white solid. The NMR and ESI/MS data for this compound are shown below.

$^1$H-NMR (400 MHz, DMSO-d$_6$) δ (ppm): 3.11-3.15 (m, 2H), 4.52 (t, J=6.8, 2H), 7.64 (s, 5H), 8.09 (brs, 3H), 12.7 (brs, 1H). ESI/MS m/e: 280.1 (M$^+$+H, C$_{15}$H$_{13}$N$_5$O)

Example 23

Synthesis of 5-(2-aminoethyl)-6-(2-furyl)-4-oxo-3-hydropyrrolo[3,2-d]pyrimidine-7-carbonitrile hydrochloride (Compound No: 1-0791)

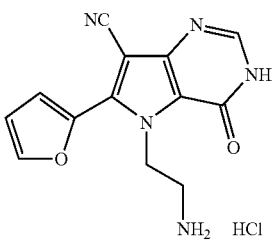

The title compound was obtained in the same manner as Example 22 using (tert-butoxy)-N-[2-(7-cyano-6-(2-furyl)-4-oxo(3-hydropyrrolo[3,2-d]pyrimidin-5-yl))ethyl]carboxamide. The ESI/MS data for this compound are shown below.

ESI/MS m/e: 270.1 (M$^+$+H, C$_{13}$H$_{11}$N$_5$O$_2$)

Example 24

Synthesis of 5-(2-aminoethyl)-6-(3-methyl(2-furyl))-4-oxo-3-hydropyrrolo[3,2-d]pyrimidine-7-carbonitrile hydrochloride (Compound No: 1-0792)

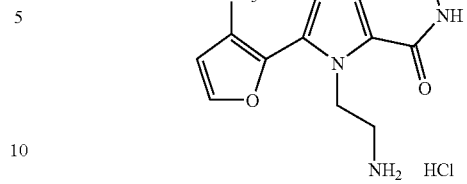

The title compound was obtained in the same manner as Example 22 using (tert-butoxy)-N-{2-[7-cyano-6-(3-methyl(2-furyl))-4-oxo(3-hydropyrrolo[3,2-d]pyrimidin-5-yl)]ethyl}carboxamide. The ESI/MS data for this compound are shown below.

ESI/MS m/e: 284.4 (M$^+$+H, C$_{14}$H$_{13}$N$_5$O$_2$)

Example 25

Synthesis of 5-(2-aminoethyl)-6-(3-methyl(2-thienyl))-4-oxo-3-hydropyrrolo[3,2-d]pyrimidine-7-carbonitrile hydrochloride (Compound No: 1-0793)

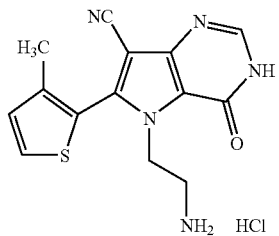

The title compound was obtained in the same manner as Example 22 using (tert-butoxy)-N-{2-[7-cyano-6-(3-methyl(2-thienyl))-4-oxo(3-hydropyrrolo[3,2-d]pyrimidin-5-yl)]ethyl}carboxamide. The ESI/MS data for this compound are shown below.

ESI/MS m/e: 300.2 (M$^+$+H, C$_{14}$H$_{13}$N$_5$OS)

Example 26

Synthesis of 5-(2-aminoethyl)-6-(3-chloro(2-thienyl))-4-oxo-3-hydropyrrolo[3,2-d]pyrimidine-7-carbonitrile hydrochloride (Compound No: 1-0794)

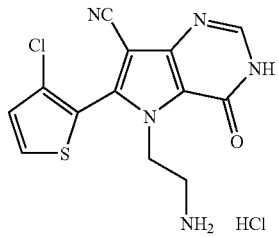

The title compound was obtained in the same manner as Example 22 using (tert-butoxy)-N-{2-[6-(3-chloro(2-thienyl))-7-cyano-4-oxo(3-hydropyrrolo[3,2-d]pyrimidin-5-yl)]ethyl}carboxamide. The ESI/MS data for this compound are shown below.

ESI/MS m/e: 320.0 (M$^+$+H, $C_{13}H_{10}ClN_5OS$)

Example 27

Synthesis of 5-(2-aminoethyl)-6-methyl-4-oxo-3-hydropyrrolo[3,2-d]pyrimidine-7-carbonitrile hydrochloride (Compound No: 1-0790)

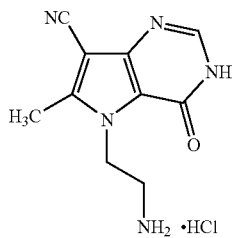

The title compound was synthesized in the same manner as Example 22 using (tert-butoxy)-N-[2-(7-cyano-6-methyl-4-oxo(3-hydropyrrolo[3,2-d]pyrimidin-5-yl))ethyl]carboxamide. The NMR and ESI/MS data for this compound are shown below.

$^1$H-NMR (400 MHz, DMSO-d$_6$) δ (ppm): 2.49 (s, 3H), 3.10-3.30 (m, 2H), 4.40-4.65 (m, 2H), 7.93 (s, 1H), 8.23 (brs, 1H), 12.48 (brs, 1H). ESI/MS m/e: 218.1 (M$^+$+H, $C_{10}H_{11}N_5O$)

Example 28

Synthesis of 5-(2-aminoethyl)-6-(2,6-difluorophenyl)-4-oxo-3-hydropyrrolo[3,2-d]pyrimidine-7-carbonitrile hydrochloride (Compound No: 1-0796)

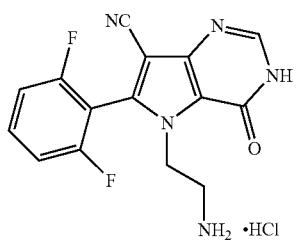

The title compound was synthesized in the same manner as Example 22 using N-{2-[6-(2,6-difluorophenyl)-7-cyano-4-oxo(3-hydropyrrolo[3,2-d]pyrimidin-5-yl)]ethyl}(tert-butoxy)carboxamide. The NMR and ESI/MS data for this compound are shown below.

$^1$H-NMR (400 MHz, DMSO-d$_6$) δ (ppm): 3.05-3.20 (m, 2H), 4.40-4.55 (m, 2H), 7.40-7.55 (m, 2H), 7.78-7.90 (m, 1H), 8.05-8.30 (m, 4H), 12.79 (brs, 1H).
ESI/MS m/e: 316.1 (M$^+$+H, $C_{15}H_{11}F_2N_5O$)

Example 29

Synthesis of 5-(2-aminoethyl)-6-(1-methylpyrrol-2-yl)-4-oxo-3-hydropyrrolo[3,2-d]pyrimidine-7-carbonitrile hydrochloride (Compound No: 1-0795)

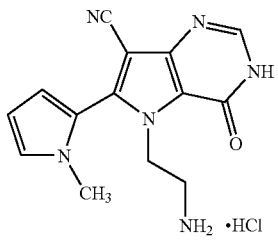

The title compound was synthesized in the same manner as Example 22 using (tert-butoxy)-N-{2-[7-cyano-6-(1-methylpyrrol-2-yl)-4-oxo(3-hydropyrrolo[3,2-d]pyrimidin-5-yl)]ethyl}carboxamide. The NMR and ESI/MS data for this compound are shown below.

$^1$H-NMR (400 MHz, DMSO-d$_6$) δ (ppm): 3.05-3.22 (m, 2H), 3.59 (s, 3H), 4.51 (brs, 2H), 6.20-6.35 (m, 1H), 6.48-6.60 (m, 1H), 7.10-7.23 (m, 1H), 7.90-8.18 (m, 4H), 12.67 (brs, 1H).
ESI/MS m/e: 283.1 (M$^+$+H, $C_{14}H_{14}N_6O$)

Example 30

Synthesis of 5-(3-aminopropyl)-6-(2-furyl)-4-oxo-3-hydropyrrolo[3,2-d]pyrimidine-7-carbonitrile hydrochloride (Compound No: 1-10811)

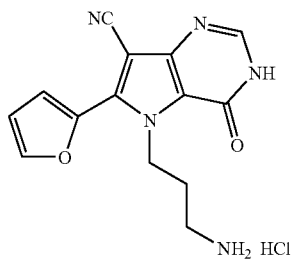

The title compound was synthesized in the same manner as Example 22 using (tert-butoxy)-N-[3-(7-cyano-6-(2-furyl)-4-oxo(3-hydropyrrolo[3,2-d]pyrimidin-5-yl))propyl]carboxamide. The ESI/MS data for this compound are shown below.

ESI/MS m/e: 284.5 (M$^+$+H, $C_{14}H_{13}N_5O_2$)

Example 31

Synthesis of N-[2-(7-cyano-4-oxo-6-phenyl(3-hydropyrrolo[3,2-d]pyrimidin-5-yl))ethyl]-2,2,2-trifluoroacetamide (Compound No: 2-1663)

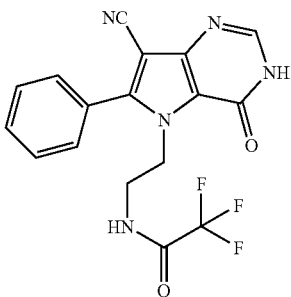

Trifluoroacetic anhydride (26.6 g) was added to a solution of 5-(2-aminoethyl)-4-oxo-6-phenyl-3-hydropyrrolo[3,2-d]pyrimidine-7-carbonitrile hydrochloride (4.00 g) in tetrahydrofuran (150 mL), the mixture was cooled to 0° C., and triethylamine (53 mL) was slowly added dropwise. The reaction mixture was stirred for 4 hours at room temperature, methanol was added dropwise to quench the reaction, and the solvent was distilled off under reduced pressure. Ethyl acetate and water were added to the residue and extraction was performed with ethyl acetate. The organic layer was washed with saturated brine and then dried over anhydrous magnesium sulfate and filtered. The solvent was distilled off under reduced pressure, and the produced solid was filtered out, washed with a small amount of methanol, and collected. The solvent of the filtrate was removed in vacuo again and the produced solid was collected and washed in the same manner and combined with the previously collected solid to obtain the title compound (3.69 g, yield: 78%) as a white solid. The NMR and ESI/MS data for this compound are shown below.

$^1$H-NMR (400 MHz, DMSO-$d_6$) δ (ppm): 3.34 (m, 2H), 4.53 (m, 2H), 7.54-7.62 (m, 5H), 8.06 (s, 1H), 9.30 (m, 1H), 12.56 (s, 1H). ESI/MS m/e: 376.1 (M$^+$+H, $C_{17}H_{12}F_3N_5O_2$)

Example 32

Synthesis of N-[2-(7-cyano-6-(2-furyl)-4-oxo(3-hydropyrrolo[3,2-d]pyrimidin-5-yl))ethyl]-2,2,2-trifluoroacetamide (Compound No: 2-1692)

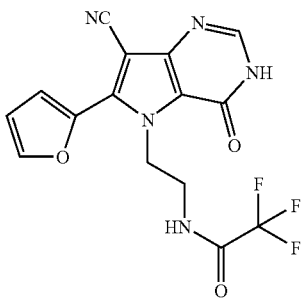

The title compound was obtained in the same manner as Example 31 using 5-(2-aminoethyl)-6-(2-furyl)-4-oxo-3-hydropyrrolo[3,2-d]pyrimidine-7-carbonitrile hydrochloride. The NMR and ESI/MS data for this compound are shown below.

$^1$H-NMR (400 MHz, DMSO-$d_6$) δ (ppm): 3.65 (m, 2H), 4.80 (m, 2H), 6.80 (m, 1H), 7.20 (d, J=3.4, 1H), 7.94-8.06 (m, 2H), 9.44 (m, 1H), 12.58 (s, 1H) ESI/MS m/e: 366.4 (M$^+$+H, $C_{15}H_{10}F_3N_5O_3$)

Example 33

Synthesis of N-{2-[7-cyano-6-(3-methyl(2-furyl))-4-oxo(3-hydropyrrolo[3,2-d]pyrimidin-5-yl)]ethyl}-2,2,2-trifluoroacetamide (Compound No: 2-1664)

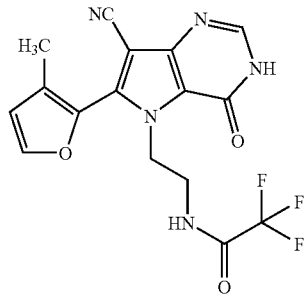

The title compound was obtained in the same manner as Example 31 using 5-(2-aminoethyl)-6-(3-methyl(2-furyl))-4-oxo-3-hydropyrrolo[3,2-d]pyrimidine-7-carbonitrile hydrochloride. The HPLC retention time and NMR and ESI/MS data for this compound are shown below.

HPLC retention time=7.852 (min) $^1$H-NMR (400 MHz, DMSO-$d_6$) δ (ppm): 2.11 (s, 3H), 3.53 (m, 2H), 4.52 (m, 2H), 6.64 (s, 1H), 7.86 (s, 1H), 8.04 (s, 1H), 9.35 (m, 1H), 12.53 (brs, 1H). ESI/MS m/e: 380.2 (M$^+$+H, $C_{16}H_{12}F_3N_5O_3$)

Example 34

Synthesis of N-{2-[7-cyano-6-(3-methyl(2-thienyl))-4-oxo(3-hydropyrrolo[3,2-d]pyrimidin-5-yl)]ethyl}-2,2,2-trifluoroacetamide (Compound No: 2-1665)

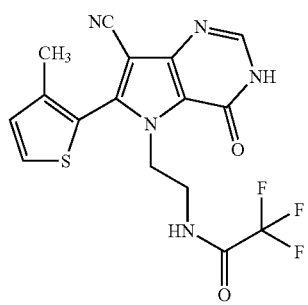

The title compound was obtained in the same manner as Example 31 using 5-(2-aminoethyl)-6-(3-methyl(2-thienyl))-4-oxo-3-hydropyrrolo[3,2-d]pyrimidine-7-carbonitrile hydrochloride. The ESI/MS data for this compound are shown below.

ESI/MS m/e: 396.1 (M$^+$+H, $C_{16}H_{12}F_3N_5O_2S$)

Example 35

Synthesis of N-{2-[6-(3-chloro(2-thienyl))-7-cyano-4-oxo(3-hydropyrrolo[3,2-d]pyrimidin-5-yl)]ethyl}-2,2,2-trifluoroacetamide (Compound No: 2-1666)

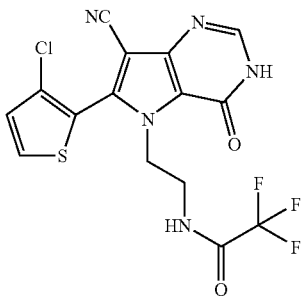

The title compound was obtained in the same manner as Example 31 using 5-(2-aminoethyl)-6-(3-chloro(2-thienyl))-4-oxo-3-hydropyrrolo[3,2-d]pyrimidine-7-carbonitrile hydrochloride. The ESI/MS data for this compound are shown below.

ESI/MS m/e: 416.1 (M$^+$+H, C$_{15}$H$_9$ClF$_3$N$_5$O$_2$S)

Example 36

Synthesis of N-{2-[6-(2,6-difluorophenyl)-7-cyano-4-oxo(3-hydropyrrolo[3,2-d]pyrimidin-5-yl)]ethyl}-2,2,2-trifluoroacetamide (Compound No: 2-1715)

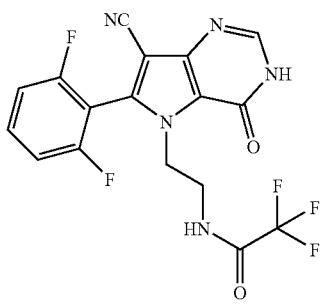

The title compound was synthesized in the same manner as Example 31 using 5-(2-aminoethyl)-6-(2,6-difluorophenyl)-4-oxo-3-hydropyrrolo[3,2-d]pyrimidine-7-carbonitrile hydrochloride. The NMR and ESI/MS data for this compound are shown below.

$^1$H-NMR (400 MHz, DMSO-d$_6$) δ (ppm): 3.48-3.58 (m, 2H), 4.30-4.40 (m, 2H), 7.41 (t, J=8.3, 2H), 7.73-7.85 (m, 1H), 8.09 (s, 1H), 12.65 (brs, 1H). ESI/MS m/e: 412.0 (M$^+$+H, C$_{17}$H$_{11}$F$_5$N$_5$O$_2$)

Example 37

Synthesis of N-{2-(7-cyano-6-methyl-4-oxo(3-hydropyrrolo[3,2-d]pyrimidin-5-yl))ethyl}-2,2,2-trifluoroacetamide (Compound No: 2-1691)

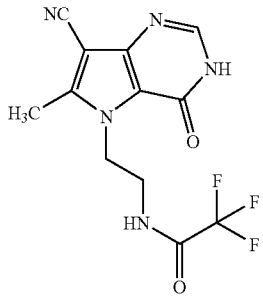

The title compound was synthesized in the same manner as Example 31 using 5-(2-aminoethyl)-6-methyl-4-oxo-3-hydropyrrolo[3,2-d]pyrimidine-7-carbonitrile hydrochloride. The NMR and ESI/MS data for this compound are shown below.

$^1$H-NMR (400 MHz, DMSO-d$_6$) δ (ppm): 3.35 (s, 3H), 3.58-3.70 (m, 2H), 4.48-4.60 (m, 2H), 7.99 (s, 1H), 9.56 (brs, 1H), 12.44 (brs, 1H). ESI/MS m/e: 314.1 (M$^+$+H, C$_{12}$H$_{10}$F$_3$N$_5$O$_2$)

Example 38

Synthesis of N-[2-(7-cyano-6-cyclopropyl-4-oxo(3-hydropyrrolo[3,2-d]pyrimidin-5-yl))ethyl]-2,2,2-trifluoroacetamide (Compound No: 2-1668)

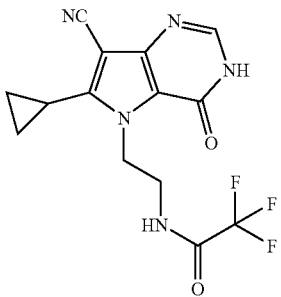

The title compound was synthesized in the same manner as Example 31 using 5-(2-aminoethyl)-6-cyclopropyl-4-oxo-3-hydropyrrolo[3,2-d]pyrimidine-7-carbonitrile hydrochloride. The NMR and ESI/MS data for this compound are shown below.

$^1$H-NMR (400 MHz, DMSO-d$_6$) δ (ppm): 0.98-1.25 (m, 4H), 2.15-2.27 (m, 1H), 3.18-3.33 (m, 2H), 4.65-4.80 (m, 2H), 7.98 (s, 1H), 8.29 (brs, 1H), 12.53 (brs, 1H). ESI/MS m/e: 340.2 (M$^+$+H, C$_{14}$H$_{12}$F$_3$N$_5$O$_2$)

Example 39

Synthesis of N-[2-(6-benzo[b]thiophen-2-yl-7-cyano-4-oxo(3-hydropyrrolo[3,2-d]pyrimidin-5-yl))ethyl]-2,2,2-trifluoroacetamide (Compound No: 2-1689)

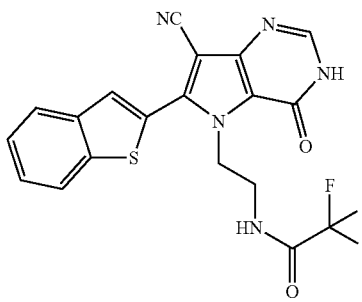

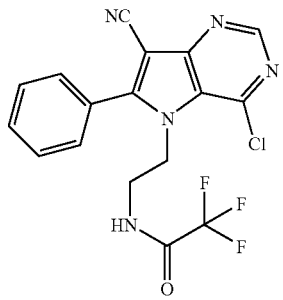

The title compound was synthesized in the same manner as Example 31 using 5-(2-aminoethyl)-6-benzo[b]thiophen-2-yl-4-oxo-3-hydropyrrolo[3,2-d]pyrimidine-7-carbonitrile hydrochloride. The NMR and ESI/MS data for this compound are shown below.

$^1$H-NMR (400 MHz, DMSO-$d_6$) δ (ppm): 3.15-3.33 (m, 2H), 4.65-4.83 (m, 2H), 7.45-7.70 (m, 2H), 7.80-8.28 (m, 5H), 12.74 (brs, 1H). ESI/MS m/e: 432.1 (M$^+$+H, $C_{19}H_{12}F_3N_5O_2S$)

Example 40

Synthesis of N-{2-[7-cyano-6-(1-methylpyrrol-2-yl)-4-oxo(3-hydropyrrolo[3,2-d]pyrimidin-5-yl)]ethyl}-2,2,2-trifluoroacetamide (Compound No: 2-1667)

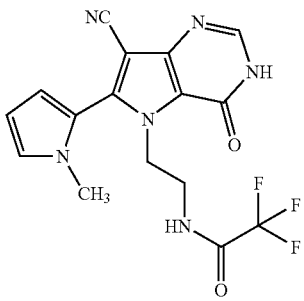

The title compound was synthesized in the same manner as Example 31 using 5-(2-aminoethyl)-6-(1-methylpyrrol-2-yl)-4-oxo-3-hydropyrrolo[3,2-d]pyrimidine-7-carbonitrile hydrochloride. The ESI/MS data for this compound are shown below.

ESI/MS m/e: 379.2 (M$^+$+H, $C_{16}H_{13}F_3N_6O_2$)

Example 41

Synthesis of N-[2-(4-chloro-7-cyano-6-phenylpyrrolo[3,2-d]pyrimidin-5-yl)ethyl]-2,2,2-trifluoroacetamide Phosphorus oxychloride (22.6 g) was added to a solution of N-[2-(7-cyano-4-oxo-6-phenyl(3-hydropyrrolo[3,2-d]pyrimidin-5-yl))ethyl]-2,2,2-trifluoroacetamide (3.69 g) in acetonitrile (50 mL) and the mixture was stirred at 110° C. overnight. The reaction mixture was cooled to room temperature, and the excess phosphorus oxychloride was distilled off under reduced pressure. The residue was dried under vacuum to obtain the title compound as a crude product. The product was used for the following reaction without purification. The ESI/MS data for this compound are shown below.

ESI/MS m/e: 394.1 (M$^+$+H, $C_{17}H_{11}ClF_3N_5O$)

Example 42

Synthesis of N-[2-(4-chloro-7-cyano-6-(2-furyl)pyrrolo[3,2-d]pyrimidin-5-yl)ethyl]-2,2,2-trifluoroacetamide

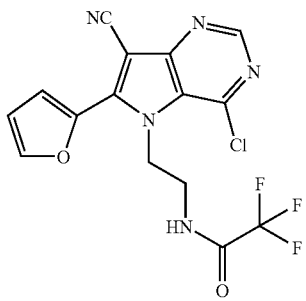

The title compound was obtained in the same manner as Example 41 using N-[2-(7-cyano-6-(2-furyl)-4-oxo(3-hydropyrrolo[3,2-d]pyrimidin-5-yl))ethyl]-2,2,2-trifluoroacetamide. The ESI/MS data for this compound are shown below.

ESI/MS m/e: 384.3 (M$^+$+H, $C_{15}H_9ClF_3N_5O_2$)

Example 43

Synthesis of N-{2-[4-chloro-7-cyano-6-(3-methyl(2-furyl))pyrrolo[3,2-d]pyrimidin-5-yl]ethyl}-2,2,2-trifluoroacetamide

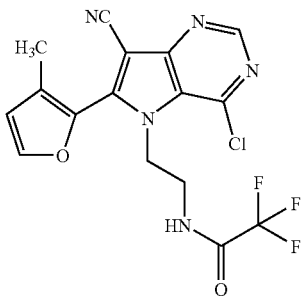

The title compound was obtained in the same manner as Example 41 using N-{2-[7-cyano-6-(3-methyl(2-furyl))-4-oxo(3-hydropyrrolo[3,2-d]pyrimidin-5-yl)]ethyl}-2,2,2-trifluoroacetamide. The ESI/MS data for this compound are shown below.

ESI/MS m/e: 398.4 (M$^+$+H, $C_{16}H_{11}ClF_3N_5O_2$)

Example 44

Synthesis of N-{2-[4-chloro-7-cyano-6-(3-methyl(2-thienyl))pyrrolo[3,2-d]pyrimidin-5-yl]ethyl}-2,2,2-trifluoroacetamide

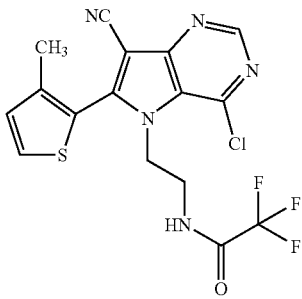

The title compound was obtained in the same manner as Example 41 using N-{2-[7-cyano-6-(3-methyl(2-thienyl))-4-oxo(3-hydropyrrolo[3,2-d]pyrimidin-5-yl)]ethyl}-2,2,2-trifluoroacetamide. The ESI/MS data for this compound are shown below.

ESI/MS m/e: 414.2 (M$^+$+H, $C_{16}H_{11}ClF_3N_{50}S$)

Example 45

Synthesis of N-{2-[4-chloro-6-(3-chloro(2-thienyl))-7-cyanopyrrolo[3,2-d]pyrimidin-5-yl]ethyl}-2,2,2-trifluoroacetamide

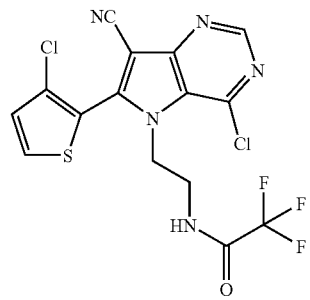

The title compound was obtained in the same manner as Example 41 using N-{2-[6-(3-chloro(2-thienyl))-7-cyano-4-oxo(3-hydropyrrolo[3,2-d]pyrimidin-5-yl)]ethyl}-2,2,2-trifluoroacetamide. The ESI/MS data for this compound are shown below.

ESI/MS m/e: 434.1 (M$^+$+H, $C_{15}H_8Cl_2F_3N_5OS$)

Example 46

Synthesis of N-{2-[4-chloro-7-cyano-6-(1-methylpyrrol-2-yl)pyrrolo[3,2-d]pyrimidin-5-yl]}ethyl}-2,2,2-trifluoroacetamide

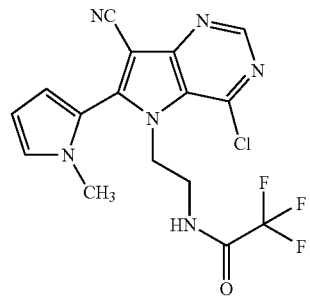

The title compound was synthesized in the same manner as Example 41 using N-{2-[7-cyano-6-(1-methylpyrrol-2-yl)-4-oxo(3-hydropyrrolo[3,2-d]pyrimidin-5-yl)]ethyl}-2,2,2-trifluoroacetamide. The ESI/MS data for this compound are shown below.

ESI/MS m/e: 397.3 (M$^+$+H, $C_{16}H_{12}ClF_3N_6O$)

Example 47

Synthesis of N-[2-(7-cyano-6-phenyl-4-thioxo(3-hydropyrrolo[3,2-d]pyrimidin-5-yl))ethyl]-2,2,2-trifluoroacetamide (Compound No: 2-0600)

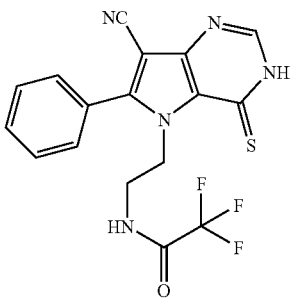

Thiourea (2.99 g) was added to a solution of crude N-[2-(4-chloro-7-cyano-6-phenylpyrrolo[3,2-d]pyrimidin-5-yl)]ethyl]-2,2,2-trifluoroacetamide in 1,4-dioxane (100 mL) and 2-propanol (20 mL), and the mixture was stirred at 80° C. for 4 hours. The reaction mixture was cooled to room temperature, and the solvent was distilled off under reduced pressure. Ethyl acetate and water were added to the residue and extraction was performed with ethyl acetate. The organic layer was washed with saturated brine and then dried over anhydrous magnesium sulfate and filtered. The solvent was distilled off under reduced pressure, and then a small and sufficient amount of hexane was added to the residue and the produced solid was filtered, washed with a small amount of methanol, and collected. The solvent of the filtrate was again distilled off under reduced pressure, and the produced solid was filtered and washed in the same manner and combined with the previously collected solid to obtain the title compound (4.24 g, quantitative yield) as a white solid. The HPLC retention time and NMR and ESI/MS data for this compound are shown below.

HPLC retention time=9.171 (min) $^1$H-NMR (400 MHz, DMSO-d$_6$) δ (ppm): 3.43 (m, 2H), 5.03 (brs, 2H), 7.61 (m, 5H), 8.24 (s, 1H), 9.21 (m, 1H), 13.88 (brs, 1H). ESI/MS m/e: 392.1 (M$^+$+H, C$_{11}$H$_{12}$F$_3$N$_5$OS)

Example 48

Synthesis of N-[2-(7-cyano-6-(2-furyl)-4-thioxo(3-hydropyrrolo[3,2-d]pyrimidin-5-yl))ethyl]-2,2,2-trifluoroacetamide (Compound No: 2-1804)

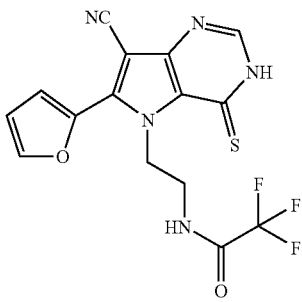

The title compound was synthesized in the same manner as Example 47 using N-[2-(4-chloro-7-cyano-6-(2-furyl)pyrrolo[3,2-d]pyrimidin-5-yl)ethyl]-2,2,2-trifluoroacetamide. The HPLC retention time and NMR and ESI/MS data for this compound are shown below.

HPLC retention time=8.592 (min) $^1$H-NMR (400 MHz, DMSO-d$_6$) δ (ppm): 3.60 (m, 2H), 5.35 (brs, 2H), 6.83 (m, 1H), 7.30 (m, 1H), 8.06 (s, 1H), 8.19 (m, 1H), 9.36 (m, 1H), 13.83 (brs, 1H) ESI/MS m/e: 382.3 (M$^+$+H, C$_{15}$H$_{10}$F$_3$N$_5$O$_2$S)

Example 49

Synthesis of N-{2-[7-cyano-6-(3-methyl(2-furyl))-4-thioxo(3-hydropyrrolo[3,2-d]pyrimidin-5-yl)]ethyl}-2,2,2-trifluoroacetamide (Compound No: 2-0601)

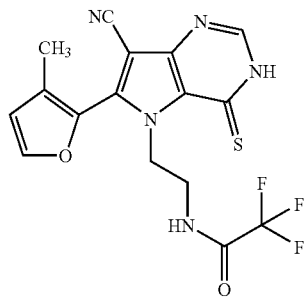

The title compound was synthesized in the same manner as Example 47 using N-{2-[4-chloro-7-cyano-6-(3-methyl(2-furyl))pyrrolo[3,2-d]pyrimidin-5-yl]ethyl}-2,2,2-trifluoroacetamide. The HPLC retention time and NMR and ESI/MS data for this compound are shown below.

HPLC retention time=9.215 (min) $^1$H-NMR (400 MHz, DMSO-d$_6$) δ (ppm): 2.12 (s, 3H), 3.55 (m, 2H), 5.03 (brs, 2H), 6.66 (s, 1H), 7.92 (s, 1H), 8.23 (s, 1H), 9.28 (m, 1H), 13.91 (s, 1H) ESI/MS m/e: 396.5 (M$^+$+H, C$_{16}$H$_{12}$F$_3$N$_5$O$_2$S)

Example 50

Synthesis of N-{2-[7-cyano-6-(3-methyl(2-thienyl))-4-thioxo(3-hydropyrrolo[3,2-d]pyrimidin-5-yl)]ethyl}-2,2,2-trifluoroacetamide (Compound No: 2-06021)

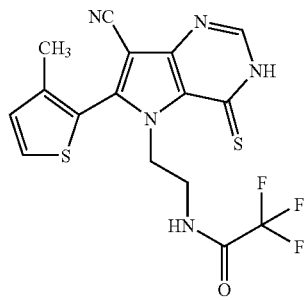

The title compound was synthesized in the same manner as Example 47 using N-{2-[4-chloro-7-cyano-6-(3-methyl(2-thienyl))pyrrolo[3,2-d]pyrimidin-5-yl]ethyl}-2,2,2-trifluoroacetamide. The NMR and ESI/MS data for this compound are shown below.

$^1$H-NMR (400 MHz, DMSO-d$_6$) δ (ppm): 2.18 (s, 3H), 3.50 (brs, 2H), 4.70 (brs, 1H), 5.21 (brs, 1H), 7.16 (d, J=5.1, 1H), 7.91 (d, J=5.1, 1H), 8.22 (s, 1H), 9.29 (m, 1H), 13.89 (s, 1H). ESI/MS m/e: 412.1 (M$^+$+H, $C_{16}H_{12}F_3N_5OS_2$)

Example 51

Synthesis of N-{2-[6-(3-chloro(2-thienyl))-7-cyano-4-thioxo(3-hydropyrrolo[3,2-d]pyrimidin-5-yl)]ethyl}-2,2,2-trifluoroacetamide (Compound No: 2-0603)

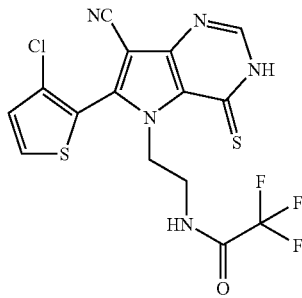

The title compound was synthesized in the same manner as Example 47 using N-{2-[4-chloro-6-(3-chloro(2-thienyl))-7-cyanopyrrolo[3,2-d]pyrimidin-5-yl]ethyl}-2,2,2-trifluoroacetamide. The NMR and ESI/MS data for this compound are shown below.

$^1$H-NMR (400 MHz, DMSO-d$_6$) δ (ppm): 3.54 (brs, 2H), 4.51 (brs, 1H), 5.41 (brs, 1H), 7.39 (m, 1H), 8.16 (m, 1H), 8.24 (s, 1H), 9.31 (m, 1H), 13.97 (brs, 1H). ESI/MS m/e: 432.1 (M$^+$+H, $C_{15}H_9ClF_3N_5OS_2$)

Example 52

Synthesis of N-{2-[7-cyano-6-(1-methylpyrrol-2-yl)-4-thioxo(3-hydropyrrolo[3,2-d]pyrimidin-5-yl)]ethyl}-2,2,2-trifluoroacetamide (Compound No: 2-0604)

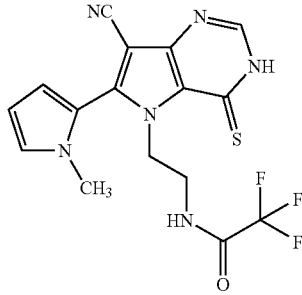

The title compound was synthesized in the same manner as Example 47 using N-{2-[4-chloro-7-cyano-6-(1-methylpyrrol-2-yl)pyrrolo[3,2-d]pyrimidin-5-yl]}ethyl}-2,2,2-trifluoroacetamide. The ESI/MS data for this compound are shown below.

ESI/MS m/e: 395.2 (M$^+$+H, $C_{16}H_{13}F_3N_6OS$)

Example 53

Synthesis of 5-(2-aminoethyl)-6-phenyl-4-thioxo-3-hydropyrrolo[3,2-d]pyrimidine-7-carbonitrile (Compound No: 1-0441)

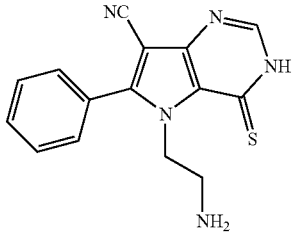

A 5 mol/L aqueous sodium hydroxide solution (4.34 mL) was added dropwise to a solution of N-[2-(7-cyano-6-phenyl-4-thioxo(3-hydropyrrolo[3,2-d]pyrimidin-5-yl))ethyl]-2,2,2-trifluoroacetamide (4.24 g) in dioxane (100 mL) and methanol (10 mL), and the mixture was stirred for 2 hours at room temperature. A 1 mol/L hydrochloric acid was added to the reaction mixture for neutralization. The solvent was distilled off under reduced pressure, a saturated aqueous sodium bicarbonate solution was added in excess to the residue, and the produced solid was filtered out. The filtered solid was washed with a sufficient amount of water to obtain the title compound (2.69 g, yield: 84%) as a white solid.

The HPLC retention time and NMR and ESI/MS data for this compound are shown below.

HPLC retention time=4.983 (min) $^1$H-NMR (400 MHz, DMSO-d$_6$) δ (ppm): 2.88 (m, 2H), 4.94 (m, 2H), 7.62 (m, 5H), 8.21 (s, 1H). ESI/MS m/e: 296.1 (M$^+$+H, $C_{15}H_{13}N_5S$)

Example 54

Synthesis of 5-(2-aminoethyl)-6-(2-furyl)-4-thioxo-3-hydropyrrolo[3,2-d]pyrimidine-7-carbonitrile (Compound No: 1-0455)

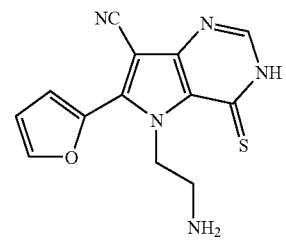

The title compound was synthesized in the same manner as Example 53 using N-[2-(7-cyano-6-(2-furyl)-4-thioxo(3-hydropyrrolo[3,2-d]pyrimidin-5-yl))ethyl]-2,2,2-trifluoroacetamide. The HPLC retention time and NMR and ESI/MS data for this compound are shown below.

HPLC retention time=4.405 (min) $^1$H-NMR (400 MHz, DMSO-d$_6$) δ (ppm): 3.30 (m, 2H), 5.30 (m, 2H), 6.86 (m, 1H), 7.42 (d, J=3.7, 1H), 8.12 (m, 1H), 8.20 (s, 1H), 9.36 (brs, 2H). ESI/MS m/e: 286.2 (M$^+$+H, $C_{13}H_{11}N_5OS$)

Example 55

Synthesis of 5-(2-aminoethyl)-6-(3-methyl(2-furyl))-4-thioxo-3-hydropyrrolo[3,2-d]pyrimidine-7-carbonitrile (Compound No: 1-0456)

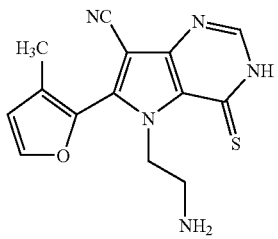

The title compound was synthesized in the same manner as Example 53 using N-{2-[7-cyano-6-(3-methyl(2-furyl))-4-thioxo(3-hydropyrrolo[3,2-d]pyrimidin-5-yl)]ethyl}-2,2,2-trifluoroacetamide. The HPLC retention time and NMR and ESI/MS data for this compound are shown below.

HPLC retention time=4.966 (min) $^1$H-NMR (400 MHz, DMSO-$d_6$) δ (ppm): 2.17 (s, 3H), 3.34 (m, 2H), 4.94 (m, 2H), 6.71 (s, 1H), 7.99 (s, 1H), 8.24 (m, 1H), 14.00 (brs, 1H). ESI/MS m/e: 300.3 (M$^+$+H, $C_{14}H_{13}N_5OS$)

Example 56

Synthesis of 5-(2-aminoethyl)-6-(3-methyl(2-thienyl))-4-thioxo-3-hydropyrrolo[3,2-d]pyrimidine-7-carbonitrile (Compound No: 1-0457)

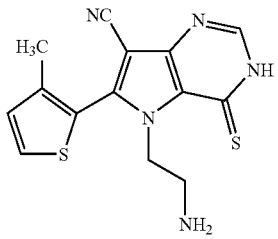

The title compound was synthesized in the same manner as Example 53 using N-{2-[7-cyano-6-(3-methyl(2-thienyl))-4-thioxo(3-hydropyrrolo[3,2-d]pyrimidin-5-yl)]ethyl}-2,2,2-trifluoroacetamide. The HPLC retention time and NMR and ESI/MS data for this compound are shown below.

HPLC retention time=5.197 (min) $^1$H-NMR (400 MHz, DMSO-$d_6$) δ (ppm): 2.18 (s, 3H), 2.92 (brs, 2H), 4.64 (brs, 1H), 5.17 (brs, 1H), 7.17 (d, J=5.1, 1H), 7.88 (d, J=4.9, 1H), 8.19 (s, 1H). ESI/MS m/e: 316.1 (M$^+$+H, $C_{14}H_{13}N_5S_2$)

Example 57

Synthesis of 5-(2-aminoethyl)-6-(3-chloro(2-thienyl))-4-thioxo-3-hydropyrrolo[3,2-d]pyrimidine-7-carbonitrile (Compound No: 1-0458)

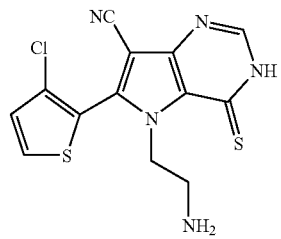

The title compound was synthesized in the same manner as Example 53 using N-{2-[6-(3-chloro(2-thienyl))-7-cyano-4-thioxo(3-hydropyrrolo[3,2-d]pyrimidin-5-yl)]ethyl}-2,2,2-trifluoroacetamide. The HPLC retention time and NMR and ESI/MS data for this compound are shown below.

HPLC retention time=5.357 (min) $^1$H-NMR (400 MHz, DMSO-$d_6$) δ (ppm): 3.31 (brs, 2H), 4.52 (brs, 1H), 5.35 (brs, 1H), 7.39 (d, J=5.4, 1H), 8.13 (d, J=5.4, 1H), 8.20 (s, 1H) ESI/MS m/e: 336.1 (M$^+$+H, $C_{13}H_{10}ClN_5S_2$)

Example 58

Synthesis of 5-(3-aminopropyl)-6-phenyl-4-thioxo-3-hydropyrrolo[3,2-d]pyrimidine-7-carbonitrile (Compound No: 1-05031)

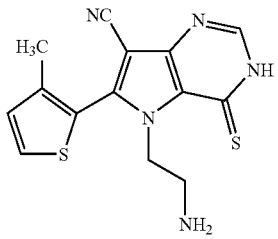

The title compound was synthesized in the same manner as Example 53 using N-[3-(7-cyano-6-phenyl-4-thioxo(3-hydropyrrolo[3,2-d]pyrimidin-5-yl))propyl]-2,2,2-trifluoroacetamide. The NMR and ESI/MS data for this compound are shown below.

$^1$H-NMR (400 MHz, DMSO-$d_6$) δ (ppm): 1.90-2.10 (m, 2H), 2.50-2.63 (m, 2H), 4.85 (t, J=7.0, 2H), 7.60-7.80 (m, 5H), 8.03 (brs, 3H), 8.22 (d, J=3.7, 1H), 13.96 (brs, 1H). ESI/MS m/e: 310.2 (M$^+$+H, $C_{16}H_{15}N_5S$)

Example 59

Synthesis of 5-(2-aminoethyl)-6-(2,6-difluorophenyl)-4-thioxo-3-hydropyrrolo[3,2-d]pyrimidine-7-carbonitrile (Compound No: 1-0460)

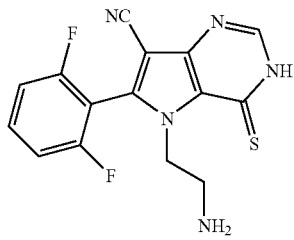

The title compound was synthesized in the same manner as Example 53 using N-{2-[6-(2,6-difluorophenyl)-7-cyano-4-thioxo(3-hydropyrrolo[3,2-d]pyrimidin-5-yl)]ethyl}-2,2,2-trifluoroacetamide. The NMR and ESI/MS data for this compound are shown below.

$^1$H-NMR (400 MHz, DMSO-d$_6$) δ (ppm): 3.06 (t, J=7.1, 2H), 3.20-3.50 (m, 3H), 4.89 (t, J=6.8, 2H), 7.49 (t, J=8.3, 2H), 7.76-7.93 (m, 1H), 8.27 (s, 1H). ESI/MS m/e: 332.0 (M$^+$+H, C$_{15}$H$_{11}$F$_2$N$_5$S)

Example 60

Synthesis of 5-(2-aminoethyl)-6-methyl-4-thioxo-3-hydropyrrolo[3,2-d]pyrimidine-7-carbonitrile (Compound No: 1-0454)

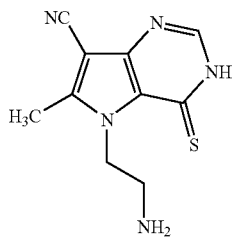

The title compound was synthesized in the same manner as Example 53 using N-[2-(7-cyano-6-methyl-4-thioxo(3-hydropyrrolo[3,2-d]pyrimidin-5-yl))ethyl]-2,2,2-trifluoroacetamide. The NMR and ESI/MS data for this compound are shown below.

$^1$H-NMR (400 MHz, DMSO-d$_6$) δ (ppm): 2.56 (s, 3H), 3.13-3.27 (m, 2H), 4.92-5.06 (m, 2H), 8.08 (s, 1H), 8.49 (brs, 3H), 13.79 (brs, 1H). ESI/MS m/e: 234.2 (M$^+$+H, C$_{10}$H$_{11}$N$_5$S)

Example 61

Synthesis of 5-(2-aminoethyl)-6-(1-methylpyrrol-2-yl)-4-thioxo-3-hydropyrrolo[3,2-d]pyrimidine-7-carbonitrile (Compound No: 1-0459)

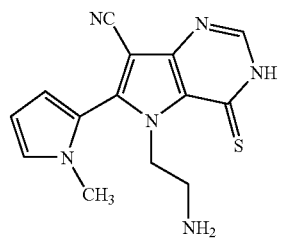

The title compound was synthesized in the same manner as Example 31, Example 41, Example 47 and Example 53 using 5-(2-aminoethyl)-6-(1-methylpyrrol-2-yl)-4-oxo-3-hydropyrrolo[3,2-d]pyrimidine-7-carbonitrile hydrochloride. The NMR and ESI/MS data for this compound are shown below.

$^1$H-NMR (400 MHz, DMSO-d$_6$) δ (ppm): 3.06-3.25 (m, 2H), 3.61 (s, 3H), 3.75-4.10 (m, 2H), 6.27-6.35 (m, 1H), 6.55-6.65 (m, 1H), 7.17-7.25 (m, 1H), 8.08-8.35 (m, 4H), 13.98 (brs, 1H). ESI/MS m/e: 299.1 (M$^+$+H, C$_{14}$H$_{14}$N$_6$S)

Example 62

Synthesis of 5-(2-aminoethyl)-6-cyclopropyl-4-thioxo-3-hydropyrrolo[3,2-d]pyrimidine-7-carbonitrile (Compound No: 1-0440)

The title compound was synthesized in the same manner as Example 41, Example 47 and Example 53 using N-[2-(7-cyano-6-cyclopropyl-4-oxo(3-hydropyrrolo[3,2-d]pyrimidin-5-yl))ethyl]-2,2,2-trifluoroacetamide. The NMR and ESI/MS data for this compound are shown below.

$^1$H-NMR (400 MHz, DMSO-d$_6$) δ (ppm): 1.05-1.35 (m, 4H), 2.25-2.37 (m, 1H), 3.25-3.47 (m, 5H), 5.15-5.28 (m, 2H), 8.19 (s, 1H). ESI/MS m/e: 260.2 (M$^+$+H, C$_{12}$H$_{13}$N$_5$S)

Example 63

Synthesis of 5-(2-aminoethyl)-6-benzo[b]thiophen-2-yl-4-thioxo-3-hydropyrrolo[3,2-d]pyrimidine-7-carbonitrile (Compound No: 1-0453)

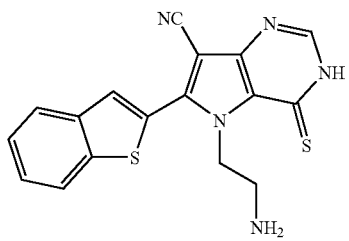

The title compound was synthesized in the same manner as Example 41, Example 47 and Example 53 using N-[2-(6-benzo[b]thiophen-2-yl-7-cyano-4-oxo(3-hydropyrrolo[3,2-d]pyrimidin-5-yl))ethyl]-2,2,2-trifluoroacetamide. The NMR and ESI/MS data for this compound are shown below.

$^1$H-NMR (400 MHz, DMSO-$d_6$) δ (ppm): 2.44-2.54 (m, 2H), 3.22-3.28 (m, 2H), 5.08-5.18 (m, 2H), 7.48-7.60 (m, 2H), 8.00 (s, 1H), 8.03-8.20 (m, 2H), 8.27 (s, 1H). ESI/MS m/e: 352.0 (M$^+$+H, $C_{17}H_{13}N_5S_2$)

Example 64

Synthesis of N-[3-(7-cyano-6-(2-furyl)-4-oxo(3-hydropyrrolo[3,2-d]pyrimidin-5-yl))propyl]-2,2,2-trifluoroacetamide (Compound No: 2-1955)

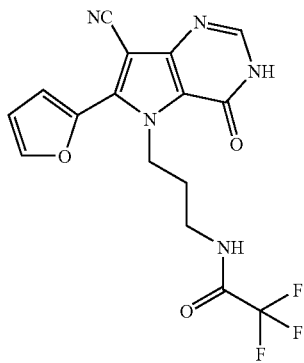

The title compound was synthesized in the same manner as Example 31 using 5-(3-aminopropyl)-6-(2-furyl)-4-oxo-3-hydropyrrolo[3,2-d]pyrimidine-7-carbonitrile. The ESI/MS data for this compound are shown below.

ESI/MS m/e: 380.4 (M$^+$+H, $C_{16}H_{12}F_3N_5O_3$)

Example 65

Synthesis of N-[3-(4-chloro-7-cyano-6-(2-furyl)pyrrolo[3,2-d]pyrimidin-5-yl)propyl]-2,2,2-trifluoroacetamide

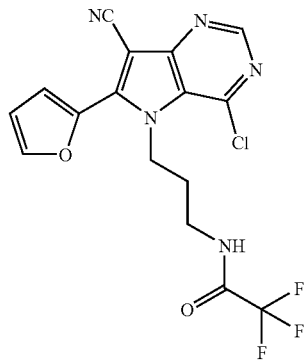

The title compound was synthesized in the same manner as Example 41 using N-[3-(7-cyano-6-(2-furyl)-4-oxo(3-hydropyrrolo[3,2-d]pyrimidin-5-yl))propyl]-2,2,2-trifluoroacetamide. The ESI/MS data for this compound are shown below.

ESI/MS m/e: 398.3 (M$^+$+H, $C_{16}H_{11}ClF_3N_5O_2$)

Example 66

Synthesis of N-[3-(7-cyano-6-(2-furyl)-4-thioxo(3-hydropyrrolo[3,2-d]pyrimidin-5-yl)propyl]-2,2,2-trifluoroacetamide (Compound No: 2-1805)

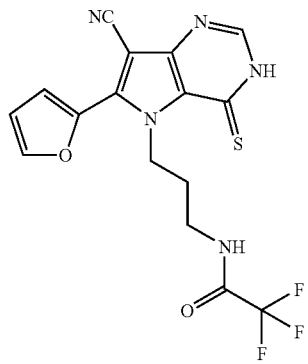

The title compound was synthesized in the same manner as Example 47 using N-[3-(4-chloro-7-cyano-6-(2-furyl)pyrrolo[3,2-d]pyrimidin-5-yl)propyl]-2,2,2-trifluoroacetamide. The HPLC retention time and NMR and ESI/MS data for this compound are shown below.

HPLC retention time=8.987 (min) $^1$H-NMR (400 MHz, DMSO-$d_6$) δ (ppm): 2.04 (m, 2H), 3.21 (m, 2H), 5.12 (m, 2H), 6.87 (m, 1H), 7.30 (d, J=3.7, 1H), 8.09 (s, 1H), 8.16 (s, 1H), 9.50 (m, 1H), 13.80 (s, 1H). ESI/MS m/e: 396.5 (M$^+$+H, $C_{16}H_{12}F_3N_5O_2S$)

Example 67

Synthesis of 5-(3-aminopropyl)-6-(2-furyl)-4-thioxo-3-hydropyrrolo[3,2-d]pyrimidine-7-carbonitrile (Compound No: 1-1082)

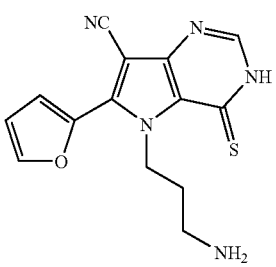

The title compound was synthesized in the same manner as Example 53 using N-[3-(7-cyano-6-(2-furyl)-4-thioxo(3-hydropyrrolo[3,2-d]pyrimidin-5-yl))propyl]-2,2,2-trifluoroacetamide. The HPLC retention time and NMR and ESI/MS data for this compound are shown below.

HPLC retention time=4.966 (min) $^1$H-NMR (400 MHz, DMSO-d$_6$) δ (ppm): 2.00 (m, 2H), 2.74 (m, 2H), 5.44 (brs, 2H), 6.82 (m, 1H), 7.24 (d, J=3.6, 1H), 8.03-8.15 (m, 2H). ESI/MS m/e: 300.2 (M$^+$+H, C$_{14}$H$_{13}$N$_5$OS)

Example 68

Synthesis of N-[2-(7-cyano-4-oxo-6-phenyl(3-hydropyrrolo[-3,2-d]pyrimidin-5-yl))ethyl]benzamide (Compound No: 2-0007)

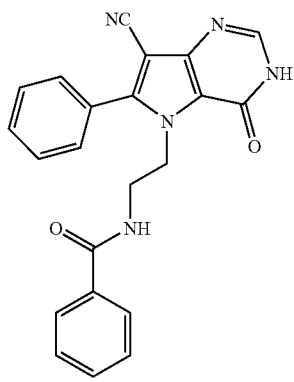

5-(2-Aminoethyl)-4-oxo-6-phenyl-3-hydropyrrolo[3,2-d]pyrimidine-7-carbonitrile (40 mg) and pyridine (1 mL) were added to N,N-dimethylformamide (1 mL). Benzoyl chloride (44 μL) was added thereto and the mixture was stirred for 1 hour at room temperature. Water (1 mL) was added to the reaction solution and the mixture was stirred for 1 hour at room temperature. A 10% aqueous sodium carbonate solution (10 mL) was slowly added thereto, the mixture was further stirred at room temperature for 1 hour, and the produced solid was filtered out. It was then recrystallized (ethanol/ethyl acetate/hexane=1/1/2) to obtain the title compound (34 mg, yield: 70%) as a white solid. The NMR and ESI/MS data for this compound are shown below.

$^1$H-NMR (400 MHz, DMSO-d$_6$) δ (ppm): 3.47-3.51 (m, 2H), 4.54 (t, J=5.3, 2H), 7.35-7.56 (m, 10H), 8.03 (s, 1H), 8.32 (t, J=6.0, 1H), 12.47 (brs, 1H). ESI/MS m/e: 384.2 (M$^+$+H, C$_{22}$H$_{17}$N$_5$O$_2$)

Example 69

Synthesis of N-[2-(7-cyano-6-phenyl-4-thioxo(3-hydropyrrolo[3,2-d]pyrimidin-5-yll)ethyl]benzamide (Compound No: 2-0558)

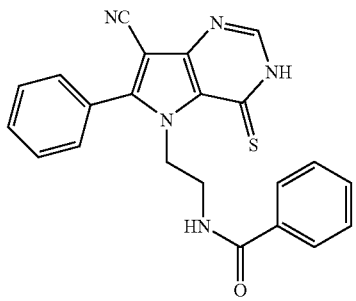

A solution of 5-(2-aminoethyl)-6-phenyl-4-thioxo-3-hydropyrrolo[3,2-d]pyrimidine-7-carbonitrile (30 mg) in N,N-dimethylformamide (2.5 mL) was added to benzoyl chloride (29 mg), and then triethylamine (0.3 mL) was added and the mixture was stirred for 3 hours at room temperature. Water (0.3 mL) was added to the reaction solution, the mixture was further stirred for 2 hours at room temperature, and the solvent was distilled off under reduced pressure. The residue was purified by preparative HPLC to obtain the title compound (8 mg, yield: 20%) as a white solid. The HPLC retention time and NMR and ESI/MS data for this compound are shown below.

HPLC retention time=8.944 (min) $^1$H-NMR (400 MHz, DMSO-d$_6$) δ (ppm): 3.51 (m, 2H), 5.06 (brs, 2H), 7.31-7.54 (m, 10H), 8.22 (m, 2H), 13.84 (brs, 1H). ESI/MS m/e: 400.5 (M$^+$H, C$_{22}$H$_{17}$N$_5$OS)

Example 70

Synthesis of 3-({N-[2-(7-cyano-6-phenyl-4-thioxo-3-hydropyrrolo[3,2-d]pyrimidin-5-yl)ethyl]carbamoyl}amino)benzoic acid (Compound No: 2-1777)

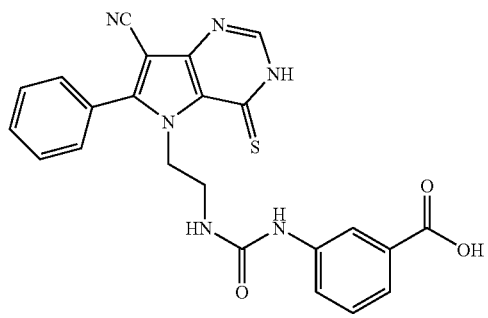

A solution of 5-(2-aminoethyl)-6-phenyl-4-thioxo-3-hydropyrrolo[3,2-d]pyrimidine-7-carbonitrile (40 mg) in N,N- dimethylformamide (0.5 mL) and tetrahydrofuran (1 mL) was added to methyl 3-isocyanatobenzoate (35 mg), and then triethylamine (0.5 mL) was added and the mixture was stirred for 2 hours at room temperature. The solvent was distilled off under reduced pressure, and the residue was purified by preparative HPLC to obtain the reaction product. Dioxane (3 mL) and a 1 mol/L aqueous sodium hydroxide solution (0.5 mL) were added thereto, the mixture was stirred overnight at room temperature, and acetic acid was added until the solution reached neutral to quench the reaction. The solvent was distilled off under reduced pressure and the residue was purified by preparative HPLC to obtain the title compound (9.8 mg, 2-steps yield: 16%) as a white solid. The HPLC retention time and NMR and ESI/MS data for this compound are shown below.

HPLC retention time=7.685 (min) $^1$H-NMR (400 MHz, DMSO-$d_6$) δ (ppm): 3.37 (m, 2H), 4.93 (brs, 2H), 5.92 (m, 1H), 7.27-7.47 (m, 8H), 7.56 (d, J=7.3, 1H), 7.79 (s, 1H), 8.22 (s, 1H), 8.46 (s, 1H), 13.84 (brs, 1H). ESI/MS m/e: 459.4 ($M^+$+H, $C_{23}H_{11}N_6O_3S$)

Example 71

Synthesis of (2-amino-5-methylphenyl)-N-[2-(7-cyano-6-phenyl-4-thioxo(3-hydropyrrolo[3,2-d]pyrimidin-5-yl))ethyl]carboxamide (Compound No: 2-0635)

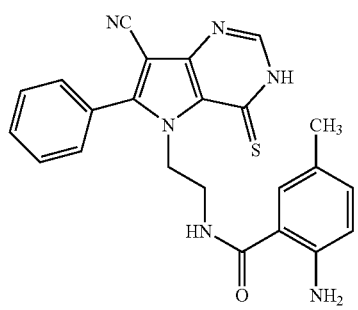

A solution of 5-(2-aminoethyl)-6-phenyl-4-thioxo-3-hydropyrrolo[3,2-d]pyrimidine-7-carbonitrile (20 mg) in N,N-dimethylformamide (2 mL) was added to 2-amino-5-methylbenzoic acid (10 mg), 1-ethyl-3-(3'-dimethylaminopropyl)carbodiimide hydrochloride (52 mg) and N-hydroxybenzotriazole (9 mg), and then triethylamine (0.3 mL) was added and the mixture was stirred for 5 hours at room temperature. Water (0.2 mL) was added to the reaction solution and stirring was continued overnight at room temperature. The solvent was distilled off under reduced pressure, and the residue was purified by preparative HPLC to obtain the title compound (8.9 mg, yield: 16%) as a white solid. The HPLC retention-time and NMR and ESI/MS data for this compound are shown below.

HPLC retention time=7.941 (min) $^1$H-NMR (400 MHz, DMSO-$d_6$) δ (ppm): 2.16 (s, 3H), 3.47 (m, 2H), 5.05 (brs, 2H), 6.67 (d, J=8.0, 1H), 7.02 (m, 2H), 7.41-7.55 (m, 5H), 8.01 (brs, 1H), 8.22 (s, 1H), 13.83 (brs, 1H). ESI/MS m/e: 429.3 ($M^+$+H, $C_{23}H_{20}N_6OS$)

Example 72

Synthesis of 5-[2-(2,4-dioxo(1,3-dihydroquinazolin-3-yl))ethyl]-6-phenyl-4-thioxo-3-hydropyrrolo[3,2-d]pyrimidine-7-carbonitrile (Compound No: 2-1849)

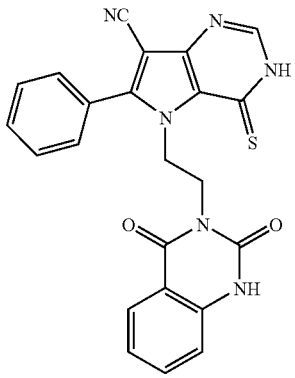

Triphosgene (57 mg) and triethylamine (0.5 mL) were added to a solution of (2-aminophenyl)-N-[2-(7-cyano-6-phenyl-4-thioxo(3-hydropyrrolo[3,2-d]pyrimidin-5-yl))ethyl]carboxamide (20 mg) in dichloromethane (2 mL), and the mixture was stirred for 2 hours at 50° C. The reaction mixture was cooled to room temperature, N,N-dimethylformamide (0.5 mL) and water (0.05 mL) were added, and the mixture was stirred for 30 minutes at room temperature. The solvent was distilled off under reduced pressure, and the residue was purified by preparative HPLC to obtain the title compound (5.3 mg, yield: 25%) as a white solid. The HPLC retention time and NMR and ESI/MS data for this compound are shown below.

HPLC retention time=8.402 (min) $^1$H-NMR (400 MHz, DMSO-$d_6$) δ (ppm): 4.19 (m, 2H), 5.37 (m, 2H), 7.08 (m, 4H), 7.28 (m, 1H), 7.48 (m, 1H), 7.62 (d, J=8.0, 1H), 7.70 (s, 1H), 7.82 (m, 2H), 8.26 (d, J=3.6, 1H), 13.90 (s, 1H). ESI/MS m/e: 441.2 ($M^+$+H, $C_{23}H_{16}N_6O_2S$)

Example 73

Synthesis of 6-(3-methyl(2-thienyl))-4-oxo-5-[2-(quinazolin-4-ylamino)ethyl]-3-hydropyrrolo[3,2-d]pyrimidine-7-carbonitrile (Compound No: 2-1951)

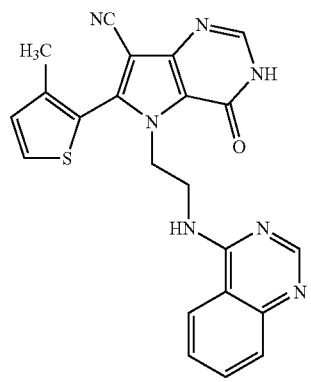

4-chloroquinazoline (206 mg) was added to a solution of 5-(2-aminoethyl)-6-(3-methyl(2-thienyl))-4-oxo-3-hydropyrrolo[3,2-d]pyrimidine-7-carbonitrile (200 mg) in acetonitrile (4 mL), and the mixture was stirred for 8 hours at 90° C. The reaction mixture was cooled to room temperature, and the solvent was distilled off under reduced pressure. The residue was purified by preparative HPLC to obtain the title compound (88 mg, yield: 49%) as a white solid. The HPLC retention time and NMR and ESI/MS data for this compound are shown below.

HPLC retention time=5.735 (min) $^1$H-NMR (400 MHz, DMSO-d$_6$) δ (ppm): 1.84 (s, 3H), 3.98 (brs, 2H), 4.62 (brs, 1H), 4.95 (brs, 1H), 6.80 (d, J=5.2, 1H), 7.61 (d, J=5.1, 1H), 7.74-7.84 (m, 2H), 8.05 (m, 2H), 8.13 (d, J=8.3, 1H), 8.65 (s, 1H), 9.94 (brs, 1H), 12.57 (brs, 1H). ESI/MS m/e: 428.2 (M$^+$+H, C$_{22}$H$_{17}$N$_7$OS)

Example 74

Synthesis of 5-[2-(1,3-dioxoisoindolin-2-yl)ethyl]-6-phenyl-4-thioxo-3-hydropyrrolo[3,2-d]pyrimidine-7-carbonitrile (Compound No: 1-0501)

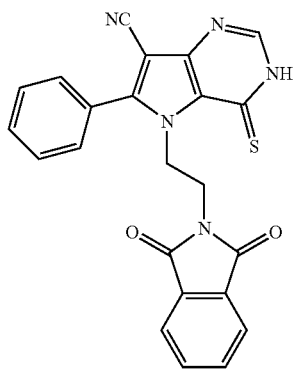

Phthalic anhydride (40 mg) was added to a solution of 5-(2-aminoethyl)-6-phenyl-4-thioxo-3-hydropyrrolo[3,2-d]pyrimidine-7-carbonitrile (20 mg) in acetic acid (2 mL), and the mixture was stirred for 3 hours at 100° C. The reaction solution was cooled to room temperature, water (0.3 mL) was added and the mixture was stirred for about 30 minutes at room temperature, after which the solvent was distilled off under reduced pressure. The residue was purified by preparative HPLC to obtain the title compound (18 mg, yield: 63%) as a white solid. The HPLC retention time and NMR and ESI/MS data for this compound are shown below.

HPLC retention time=9.542 (min) $^1$H-NMR (400 MHz, DMSO-d$_6$) δ (ppm): 3.82 (m, 2H), 5.26 (brs, 2H), 7.18 (d, J=7.6, 2H), 7.25 (t, J=7.8, 2H), 7.45 (m, 1H), 7.70 (m, 2H), 7.82 (m, 2H), 8.23 (s, 1H), 13.88 (brs, 1H). ESI/MS m/e: 426.2 (M$^+$+H, C$_{23}$H$_{15}$N$_5$O$_2$S)

Example 75

Synthesis of N-(2-{4-[(3,3-dimethyl-3-silabutoxy)methylthio]-7-cyano-6-phenylpyrrolo[3,2-d]pyrimidin-5-yl}ethyl)-2,2,2-trifluoroacetamide

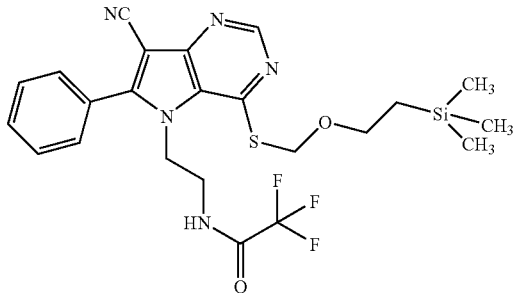

A solution of N-[2-(7-cyano-6-phenyl-4-thioxo(3-hydropyrrolo[3,2-d]pyrimidin-5-yl))ethyl]-2,2,2-trifluoroacetamide (2.50 g) in tetrahydrofuran (60 mL) solution was cooled to 0° C. under a nitrogen atmosphere, triethylamine (10 mL) was added thereto, and then 2-(chloromethoxy)ethyltrimethylsilane was added dropwise. The reaction system was returned to room temperature and stirred overnight, and methanol was added to quench the reaction. The solvent was distilled off under reduced pressure, and the residue was purified by silica gel column chromatography (hexane/ethyl acetate=3/1) to obtain the title compound (1.37 g, yield: 41%) as a oil. The ESI/MS data for this compound are shown below.

ESI/MS m/e: 522.3 (M$^+$+H, C$_{23}$H$_{26}$F$_3$N$_5$O$_2$SSi)

Example 76

Synthesis of 5-[2-(methylamino)ethyl]-6-phenyl-4-thioxo-3-hydropyrrolo[3,2-d]pyrimidine-7-carbonitrile (Compound No: 1-1083)

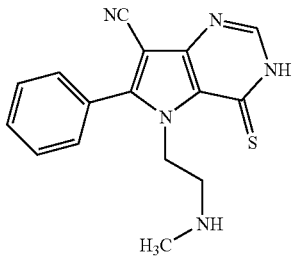

A solution of N-(2-{4-[(3,3-dimethyl-3-silabutoxy)methylthio]-7-cyano-6-phenylpyrrolo[3,2-d]pyrimidin-5-yl}ethyl)-2,2,2-trifluoroacetamide (520 mg) in N,N-dimethylformamide (15 mL) was cooled to 0° C. under a nitrogen atmosphere, and then sodium hydride (60 mg) was added. After stirring for 30 minutes at 0° C., methyl iodide (0.124 mL) was added dropwise. The mixture was further stirred for 1 hour at 0° C., and acetic acid was added until the solution reached neutral to quench the reaction. An excess of ethyl acetate and water were added to the reaction solution and extraction was performed with ethyl acetate. The organic layer was washed with saturated brine and then dried over anhydrous magnesium sulfate and filtered. The solvent was distilled off under reduced pressure, a mixed solvent of trifluoroacetic acid and dichloromethane (1:5) (20 mL) was added to the residue and the mixture was stirred for 2 hours at room temperature and then for 4 hours at 60° C. The reaction mixture was cooled to room temperature, ethyl acetate and saturated aqueous sodium bicarbonate were added and extraction was performed with ethyl acetate. The organic layer was dried over anhydrous magnesium sulfate and the solvent was distilled off under reduced pressure. The title compound (253 mg, 3-steps yield: 82%) was obtained as a white solid from the obtained residue by reaction in the same manner as Example 53. The NMR and ESI/MS data for this compound are shown below.

$^1$H-NMR (400 MHz, DMSO-d$_6$) δ (ppm): 1.99 (s, 3H), 2.77 (m, 2H), 4.95 (m, 2H), 7.66 (m, 6H), 8.22 (s, 1H). ESI/MS m/e: 310.2 (M$^+$+H, C$_{16}$H$_{15}$N$_5$S)

Example 77

Synthesis of 4-oxo-3-hydropyrrolo[3,2-d]pyrimidine-7-carbonitrile (Compound No: 1-0001)

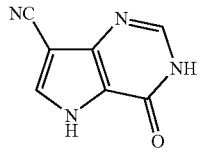

A 28% solution of sodium methoxide in methanol (50 mL) was added to a suspension of methyl 3-amino-4-cyanopyrrole-2-carboxylate (12.5 g) in formamide (100 mL). The reaction mixture was stirred for 23 hours at 100° C. and then cooled to 0° C., and then 2 mol/L hydrochloric acid (140 mL) was added. The precipitated solid was filtered out to obtain the title compound as a crude product (12.9 g). The NMR and ESI/MS data for this compound are shown below.

$^1$H-NMR (400 MHz, DMSO-d$_6$) δ (ppm): 7.97 (s, 1H), 8.18 (s, 1H). ESI/MS m/e: 161.1 (M$^+$+H, C$_7$H$_4$N$_4$O)

Example 78

Synthesis of 6-bromo-4-oxo-3-hydropyrrolo[3,2-d]pyrimidine-7-carbonitrile (Compound No: 1-0004)

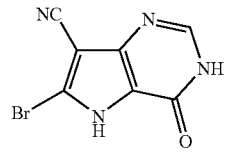

N-bromosuccinimide (36.6 g) was added to a suspension of the crude 4-oxo-3-hydropyrrolo[3,2-d]pyrimidine-7-carbonitrile (12.9 g) in N,N-dimethylformamide (500 mL). The reaction mixture was stirred for 20 hours, water (1 L) was added and the mixture was cooled to 0° C. The precipitated solid was filtered out to obtain the title compound (9.8 g, 54%) as a light brown solid. The NMR and ESI/MS data for this compound are shown below.

$^1$H-NMR (400 MHz, DMSO-d$_6$) δ (ppm): 7.99 (s, 1H), 12.44 (brs, 1H). ESI/MS m/e: 239.1 (M$^+$+H, C$_7$H$_3$BrN$_4$O)

Example 79

Synthesis of 6-(2-methoxyphenyl)-4-oxo-3-hydropyrrolo[3,2-d]pyrimidine-7-carbonitrile (Compound No: 1-0038)

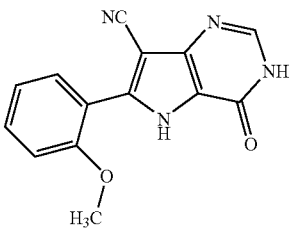

6-Bromo-4-oxo-3-hydropyrrolo[3,2-d]pyrimidine-7-carbonitrile (71.7 mg), 2-methoxyphenylboronic acid (137 mg), palladium acetate (3.4 mg), a 0.005 mol/L triphenylphosphine/2-propanol solution (3 mL) and a 0.2 mol/L aqueous sodium carbonate solution (3 mL) were added to a reactor filled with nitrogen gas, and then the reactor was refilled with nitrogen gas and sealed (the 2-propanol and water used were degassed). The reaction mixture was stirred for 10 hours at 100° C., the insoluble matter was filtered out while the reaction solution was still hot, and the filtrate was concentrated under reduced pressure. The obtained crude product was purified by preparative HPLC to obtain the title compound (25.8 mg, 32%) as a light yellow solid. The NMR and ESI/MS data for this compound are shown below.

$^1$H-NMR (400 MHz, DMSO-d$_6$) δ (ppm): 3.85 (s, 3H), 7.09-7.14 (m, 1H), 7.21-7.23 (m, 1H), 7.51-7.55 (m, 2H), 8.00 (s, 1H), 12.33 (brs, 1H), 13.15 (brs, 1H). ESI/MS m/e: 267.1 (M$^+$+H, C$_{14}$H$_{10}$N$_4$O$_2$)

Example 80

Synthesis of 6-(2-methoxyphenyl)-4-thioxo-3-hydropyrrolo[3,2-d]pyrimidine-7-carbonitrile (Compound No: 1-00039)

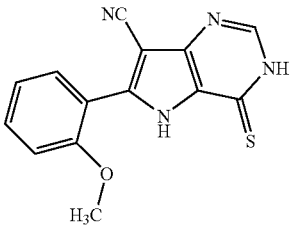

N,N-dimethylaniline (10.7 mg) and phosphorus oxychloride (338 mg) were added to a suspension of 6-(2-methoxyphenyl)-4-oxo-3-hydropyrrolo[3,2-d]pyrimidine-7-carbonitrile (19.6 mg) in acetonitrile (2 mL). The reaction mixture was stirred for 3 hours at 100° C. and then cooled to room temperature, and the solvent was distilled off under reduced pressure. 1,4-Dioxane (1 mL), 2-propanol (1 mL) and thiourea (14.0 mg) were added to the residue and the mixture was stirred for 1 hour at 100° C. After cooling to room temperature. the solvent was distilled off under reduced pressure. The obtained crude product was purified by preparative HPLC to obtain the title compound (6.1 mg, 29%) as a light yellow solid. The NMR and ESI/MS data for this compound are shown below.

$^1$H-NMR (400 MHz, DMSO-d$_6$) δ (ppm): 3.86 (s, 3H), 7.11-7.16 (m, 1H), 7.23-7.25 (m, 1H), 7.52-7.61 (m, 2H), 8.18 (s, 1H), 13.19 (brs, 1H), 13.77 (brs, 1H). ESI/MS m/e: 283.2 (M$^+$+H, C$_{14}$H$_{10}$N$_4$OS)

Example 81

Synthesis of 6-(3-hydroxyphenyl)-4-thioxo-3-hydropyrrolo[3,2-d]pyrimidine-7-carbonitrile (Compound No: 1-0698)

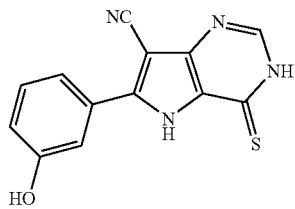

6-Bromo-4-oxo-3-hydropyrrolo-[3,2-d]pyrimidine-7-carbonitrile (23.9 mg), 3-(methoxymethoxy)phenylboronic acid (36.4 mg), palladium acetate (1.1 mg), a 0.005 mol/L triphenylphosphine/2-propanol solution (1 mL) and a 0.2 mol/L aqueous sodium carbonate solution (1 mL) were added to a reactor filled with nitrogen gas, and then the reactor was refilled with nitrogen gas and sealed (the 2-propanol and water used were degassed). The reaction mixture was stirred for 90 minutes at 100° C., the insoluble matter was filtered out while the reaction solution was still hot, and the filtrate was concentrated under reduced pressure. Phosphorus oxychloride (2 mL) and N,N-dimethylaniline (14.5 mg) were added to the concentrated residue, and the mixture was stirred for 1 hour at 100° C., cooled to room temperature and concentrated under reduced pressure. 1,4-Dioxane (1 mL), 2-propanol (1 mL) and thiourea (11.4 mg) were added to the concentrated residue, and the mixture was stirred for 1 hour at 100° C. The insoluble matter was filtered out while the reaction solution was still hot, and the filtrate was concentrated under reduced pressure. The obtained crude product was purified by preparative HPLC to obtain the title compound (0.5 mg, 2%) as a light yellow solid. The ESI/MS data for this compound are shown below.

ESI/MS m/e: 269.1 ($M^+$+H, $C_{13}H_8N_4OS$)

Example 82

Synthesis of 3-(7-cyano-4-thioxo-3-hydropyrrolo[4,5-d]pyrimidin-6-yl)benzoic acid (Compound No: 1-0687)

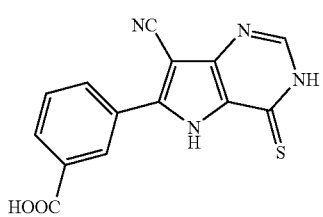

The title compound was synthesized in the same manner as Example 81 using 3-(methoxycarbonyl)phenylboronic acid. The HPLC retention time and ESI/MS data for this compound are shown below.

HPLC retention time: 6.13 (min) ESI/MS m/e: 297.5 ($M^+$+H, $C_{14}H_6N_4O_2S$)

Example 83

Synthesis of 4-(7-cyano-4-thioxo-3-hydropyrrolo[4,5-d]pyrimidin-6-yl)benzoic acid (Compound No: 1-0688)

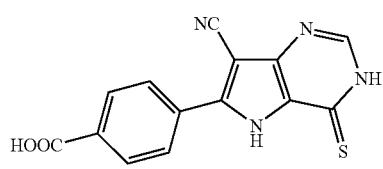

The title compound was synthesized in the same manner as Example 81 using 4-(methoxycarbonyl)phenylboronic acid. The HPLC retention time and ESI/MS data for this compound are shown below.

HPLC retention time: 5.95 (min) ESI/MS m/e: 297.4 ($M^+$+H, $C_{14}H_8N_4O_2S$)

Example 84

Synthesis of 6-(2-aminophenyl)-4-thioxo-3-hydropyrrolo[3,2-d]pyrimidine-7-carbonitrile (Compound No: 1-0753)

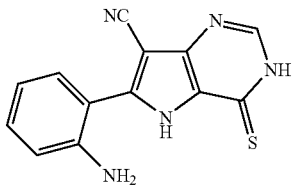

The title compound was synthesized in the same manner as Example 81 using 2-[(tert-butoxy)carbonylamino]phenylboronic acid. The HPLC retention time and ESI/MS data for this compound are shown below.

HPLC retention time: 4.72 (min) ESI/MS m/e: 268.5 ($M^+$+H, $C_{13}H_9N_5S$)

Example 85

Synthesis of 6-[3-(aminomethyl)phenyl]-4-thioxo-3-hydropyrrolo[3,2-d]pyrimidine-7-carbonitrile (Compound No: 1-0743)

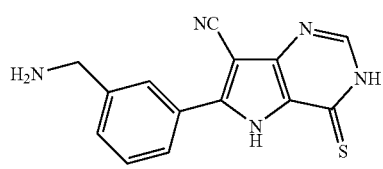

The title compound was synthesized in the same manner as Example 81 using 3-{[(tert-butoxy) carbonylamino]

methyl}phenyl]boronic acid. The HPLC retention time and ESI/MS data for this compound are shown below.

HPLC retention time: 3.87 (min) ESI/MS m/e: 282.5 (M$^+$+H, C$_{14}$H$_{11}$N$_5$S)

Example 86

Synthesis of N-{2-[7-cyano-6-(2-fluorophenyl)-4-thioxo(3-hydropyrrolo[3,2-d]pyrimidin-5-yl)]ethyl}benzamide (Compound No: 2-1956)

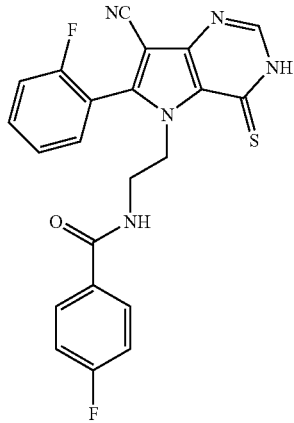

The title compound was synthesized in the same manner as Example 81 using N-[2-(6-chloro-7-cyano-4-oxo(3-hydropyrrolo[3,2-d]pyrimidin-5-yl))ethyl]benzamide and 2-fluorophenylboronic acid. The HPLC retention time and NMR and ESI/MS data for this compound are shown below.

HPLC retention time: 9.00 (min) $^1$H-NMR (400 MHz, DMSO-d$_6$) δ (ppm): 3.55 (m, 2H), 4.69 (m, 1H), 5.27 (m, 1H), 7.11 (m, 1H), 7.25 (m, 1H), 7.34 (m, 1H), 7.42 (m, 2H), 7.50-7.65 (m, 4H), 8.21-8.33 (m, 2H), 13.91 (brs, 1H). ESI/MS m/e: 418.2 (M$^+$+H, C$_{22}$H$_{16}$FN$_5$OS)

Example 87

Synthesis of N-{2-[7-cyano-6-(4-ethoxyphenyl)-4-thioxo(3-hydropyrrolo[3,2-d]pyrimidin-5-yl)]ethyl}benzamide (Compound No: 2-1957)

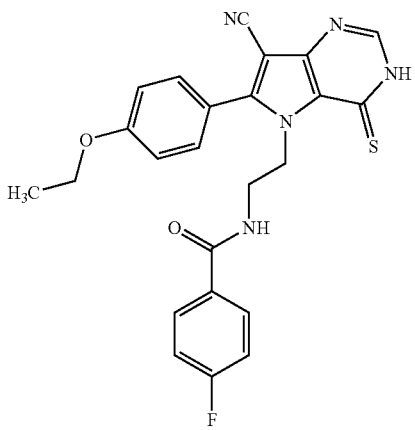

The title compound was synthesized in the same manner as Example 81 using N-[2-(6-chloro-7-cyano-4-oxo(3-hydropyrrolo[3,2-d]pyrimidin-5-yl))ethyl]benzamide and 4-ethoxyphenylboronic acid. The HPLC retention time and NMR and ESI/MS data for this compound are shown below.

HPLC retention time: 9.75 (min) $^1$H-NMR (400 MHz, DMSO-d$_6$) δ (ppm): 1.35 (t, J=7.1 Hz, 3H), 3.51 (m, 2H), 4.02 (q, J=7.1 Hz, 2H), 5.08 (brs, 2H), 6.84 (m, 2H), 7.30 (m, 2H), 7.41 (m, 2H), 7.49-7.60 (m, 3H), 8.20 (m, 2H), 13.78 (brs, 1H). ESI/MS m/e: 444.3 (M$^+$+H, C$_{24}$H$_{21}$N$_5$O$_2$S)

Example 88

Synthesis of 6-(2-bromophenyl)-4-oxo-3-hydropyrrolo[3,2-d]pyrimidine-7-carbonitrile (Compound No: 1-1040)

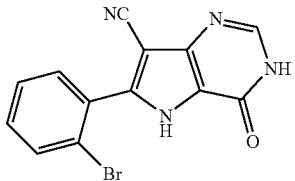

After dissolving crude [(2-bromophenyl)methoxymethylene]methane-1,1-dicarbonitrile (1.4 g) in methanol, glycine methyl ester hydrochloride (0.80 g) was added and the mixture was stirred at room temperature while slowly adding dropwise a 28% solution of sodium methoxide in methanol (4.0 g). The reaction mixture was heated to reflux for 1 hour and then cooled to room temperature, formamide (2.0 mL) was added and the mixture was further heated to reflux for 12 hours. After adding 50 mL of water and 50 mL of ethyl acetate to the reaction mixture, the product was extracted with ethyl acetate, the solvent was distilled off under reduced pressure, and the residue was purified by silica gel column chromatography (hexane/ethyl acetate=1/1) to obtain the title compound (55 mg, 3.3%) as a light yellow solid. The HPLC retention time and ESI/MS data for this compound are shown below.

HPLC retention time: 9.6 (min) ESI/MS m/e: 315.1, 317.1 (M$^+$+H, C$_{13}$H$_7$BrN$_4$O)

Example 89

Synthesis of 6-(2-bromophenyl)-4-thioxo-3-hydropyrrolo[3,2-d]pyrimidine-7-carbonitrile (Compound No: 1-0751)

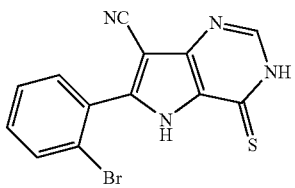

The title compound was synthesized in the same manner as Example 80 using 6-(2-bromophenyl)-4-oxo-3-hydropyrrolo[3,2-d]pyrimidine-7-carbonitrile. The HPLC retention time and ESI/MS data for this compound are shown below.

HPLC retention time: 8.2 (min) ESI/MS m/e: 331.1, 333.2 (M$^+$+H, C$_{13}$H$_7$BrN$_4$O)

Example 90

Synthesis of 6-methyl-4-oxo-5-benzyl-3-hydropyrrolo[3,2-d]pyrimidine-7-carbonitrile (Compound No: 1-0309)

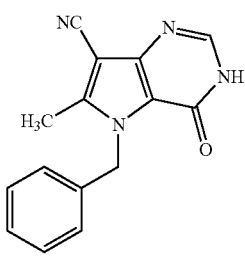

Formamide (1 mL) and a 28% solution of sodium methoxide in methanol (1 mL) were added to a solution of methyl 3-amino-4-cyano-1-benzyl-5-methylpyrrole-2-carboxylate (100 mg) in dimethylsulfoxide (2 mL), and the mixture was heated to reflux for 4 hours at 100° C. After cooling to room temperature, water (5 mL) and 2 mol/L hydrochloric acid (5 mL) were added to acidify the solution. After stirring the mixture for a while at room temperature, the produced solid was filtered out. It was then recrystallized (ethanol) to obtain the title compound (68.7 mg, yield: 70%) as a white solid. The NMR and ESI/MS data for this compound are shown below.

$^1$H-NMR (400 MHz, DMSO-$d_6$) δ (ppm): 2.39 (s, 3H), 5.74 (s, 2H), 7.10-7.12 (m, 2H), 7.25-7.35 (m, 3H), 7.98 (t, J=3.7, 1H), 12.4 (brs, 1H). ESI/MS m/e: 265.2 ($M^+$+H, $C_{15}H_{12}N_4O$)

Example 91

Synthesis of 6-(3,5-dihydroxyphenyl)-5-[3-(methylethoxy)propyl]-4-oxo-3-hydropyrrolo[3,2-d]pyrimidine-7-carbonitrile (Compound No: 1-0863)

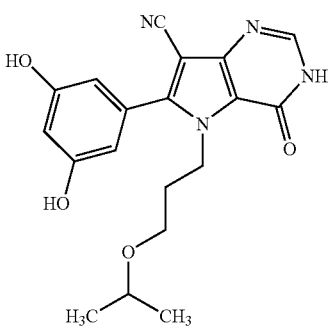

After dissolving 6-[3,5-bis(phenylmethoxy)phenyl]-5-[3-(methylethoxy)propyl]-4-oxo-3-hydropyrrolo[3,2-d]pyrimidine-7-carbonitrile (1.06 g) in ethanol (50 mL), palladium-active carbon (700 mg) was added and the mixture was stirred for 3 hours at 50° C. under a hydrogen atmosphere. After cooling to room temperature, the catalyst was filtered off with celite and the solvent was distilled off to obtain the crude title compound (710 mg, yield: 100%) as a light green liquid. The crude product was purified by preparative HPLC to obtain the title compound as a colorless solid. The ESI/MS data for this compound are shown below.

ESI/MS m/e: 369.3 ($M^+$+H, $C_{19}H_{20}N_4O_4$)

Example 92

Synthesis of 5-acetoxy-3-{7-cyano-5-[3-(methylethoxy)propyl]-4-[(trifluoromethyl)sulfonyloxy]pyrrolo[4,5-d]pyrimidin-6-yl}phenyl acetate

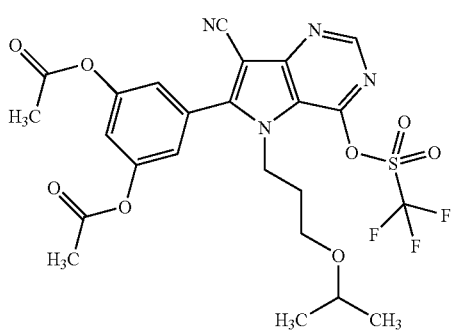

After dissolving 5-acetoxy-3-{7-cyano-5-[3-(methylethoxy)propyl]-4-oxo(3-hydropyrrolo[4,5-d]pyrimidin-6-yl)}phenylacetate (78.3 mg) in methylene dichloride (2.0 mL), pyridine (48.5 μL) was added dropwise thereto and the mixture was cooled to 0° C. Trifluoromethanesulfonic anhydride (50.5 μL) was added dropwise and the mixture was stirred for 3 hours at room temperature. Water was then added to the reaction solution. The solution was extracted 3 times with ethyl acetate, and the organic layer was washed with saturated brine and dried over sodium sulfate. After filtering off the sodium sulfate, the solvent was distilled off under reduced pressure. The title compound (116.9 mg, yield: 100%) was obtained as a colorless oil. The ESI/MS data for this compound are shown below.

ESI/MS m/e: 585.4 ($M^+$+H, $C_{24}H_{23}F_3N_4O_8S$)

Example 93

Synthesis of 5-acetoxy-3-{7-cyano-5-[3-(methylethoxy)propyl]-4-thioxo(3-hydropyrrolo[4,5-d]pyrimidin-6-yl)}phenylacetate (Compound No: 1-1078)

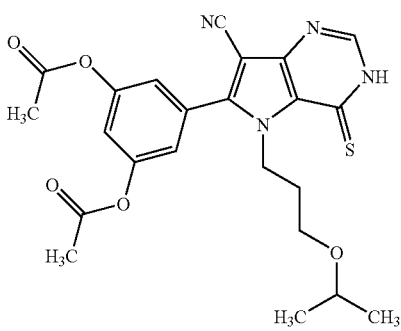

5-acetoxy-3-{7-cyano-5-[3-(methylethoxy)propyl]-4-[(trifluoromethyl)sulfonyloxy]pyrrolo[4,5-d]pyrimidin-6-yl}phenylacetate (116.9 mg) was dissolved in 2-propanol (2.0 mL), and then thiourea (22.8 mg) was added and the mixture was stirred for 2 hours at 100° C. The reaction solution was cooled and water was added thereto. The solution was extracted 3 times with ethyl acetate, and the organic layer was washed with saturated brine and then dried over sodium sulfate. After filtering off the sodium sulfate, the solvent was distilled off under reduced pressure. The residue was purified by silica gel column chromatography (hexane/ethyl acetate=2/1) to obtain the title compound (6.0 mg, yield: 6%) as a colorless oil.

ESI/MS m/e: 469.4 (M$^+$+H, $C_{23}H_{24}N_4O_5S$)

Example 94

Synthesis of 6-(3,5-dihydroxyphenyl)-5-[3-(methylethoxy)propyl]-4-thioxo-3-hydropyrrolo[3,2-d]pyrimidine-7-carbonitrile (Compound No: 1-0529)

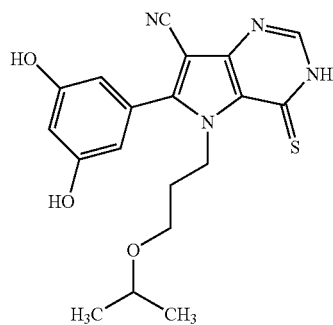

The title compound was obtained in the same manner as Example 53 using 5-acetoxy-3-{7-cyano-5-[3-(methylethoxy)propyl]-4-thioxo(3-hydropyrrolo[4,5-d]pyrimidin-6-yl)}phenylacetate. The NMR and ESI/MS data for this compound are shown below.

$^1$H-NMR (400 MHz, DMSO-d$_6$) δ (ppm): 0.88 (d, J=6.1, 6H), 1.79-1.90 (m, 2H), 3.18 (t, J=6.1, 2H), 3.20-3.31 (m, 1H), 4.86 (t, J=6.6, 2H), 6.35-6.47 (m, 3H), 8.17 (d, J=3.6, 1H), 9.77 (brs, 2H), 13.7 (brs, 1H). ESI/MS m/e: 385.3 (M$^+$+H, $C_{19}H_{20}N_4O_3S$)

Example 95

Synthesis of 6-(4-aminophenyl)-5-[3-(methylethoxy)propyl]-4-oxo-3-hydropyrrolo[3,2-d]pyrimidine-7-carbonitrile hydrochloride (Compound No: 1-0864)

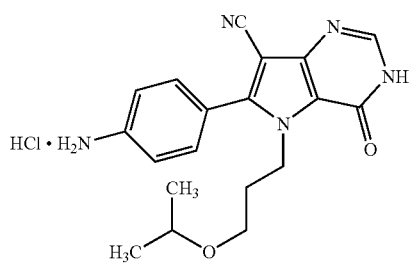

5-[3-(methylethoxy)propyl]-6-(4-nitrophenyl)-4-oxo-3-hydropyrrolo[3,2-d]pyrimidine-7-carbonitrile (0.381 g) was dissolved in ethanol (10 mL), palladium-active carbon (0.038 g) was added, and the mixture was stirred for 2 days at room temperature under a hydrogen atmosphere. The palladium-active carbon was filtered off with celite, and the solvent was distilled off under reduced pressure. After dissolving the residue in ethyl acetate (20 mL) and adding 1 mol/L hydrochloric acid (20 mL), the mixture was stirred and the aqueous layer was separated off. The organic layer was extracted twice with 1 mol/L hydrochloric acid (20 mL) and the aqueous layer was combined with the previous aqueous layer. The combined aqueous layers were washed with a 1:1 mixed solvent of ethyl acetate and hexane, and then the pH was adjusted to 8 with a 5 mol/L aqueous sodium hydroxide solution. The solution was extracted 3 times with ethyl acetate and then dried over sodium sulfate. After filtering off the sodium sulfate, the solvent was distilled off under reduced pressure. The title compound (0.292 g, yield: 83%) was obtained as a brown solid. The ESI/MS data for this compound are shown below.

ESI/MS m/e: 352.2 (M$^+$+H, $C_{19}H_{21}N_5O_2$ HCl)

Example 96

Synthesis of N-(4-{7-cyano-5-[3-(methylethoxy)propyl]-4-oxo(3-hydropyrrolo[4,5-d]pyrimidin-6-yl)}phenyl)-2,2,2-trifluoroacetamide (Compound No: 1-1079)

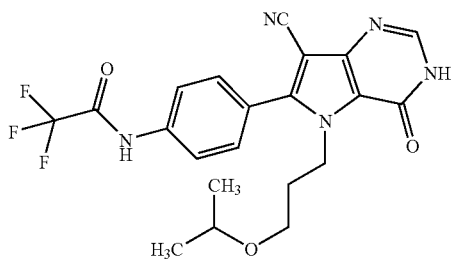

6-(4-aminophenyl)-5-[3-(methylethoxy)propyl]-4-oxo-3-hydropyrrolo[3,2-d]pyrimidine-7-carbonitrile hydrochloride (0.292 g) was suspended in tetrahydrofuran (1.0 mL), trifluoroacetic anhydride (0.344 mL) was added and the mixture was stirred at 0° C. Pyridine (0.403 mL) was added to the solution, and the mixture was stirred for 2 hours at room temperature. Methanol was added to quench the reaction, and the solvent was distilled off under reduced pressure. The residue was diluted with ethyl acetate and water, and then the solution was extracted 3 times with ethyl acetate. The organic layer was washed with saturated brine and then dried over magnesium sulfate. After filtering off the magnesium sulfate, the solvent was distilled off under reduced pressure. The title compound (0.338 g, yield: 91%) was obtained as a brown solid. The ESI/MS data for this compound are shown below.

ESI/MS m/e: 448.4 (M$^+$+H, $C_{21}H_{20}F_3N_5O_3$)

Example 97

Synthesis of N-(4-{4-chloro-7-cyano-5-[3-(methylethoxy)propyl]pyrrolo[4,5-d]pyrimidin-6-yl}phenyl)-2,2,2-trifluoroacetamide

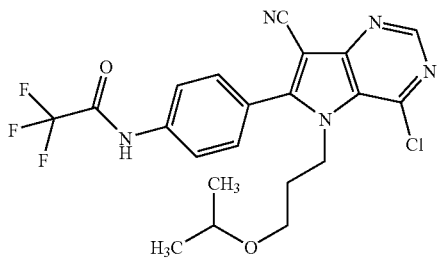

N-(4-{7-cyano-5-[3-(methylethoxy)propyl]-4-oxo(3-hydropyrrolo[4,5-d]pyrimidin-6-yl)}phenyl)-2,2,2-trifluoroacetamide (36.7 mg) was dissolved in acetonitrile (2.5 mL) and phosphorus oxychloride (5.0 mL), and the mixture was stirred for 2.5 hours at 100° C. The volatile matter was distilled off under reduced pressure to obtain the title compound (0.349 g, yield: 100%) as a brown solid. The ESI/MS data for this compound are shown below.

ESI/MS m/e: 466.2 (M$^+$+H, $C_{21}H_{19}ClF_3N_5O_2$)

Example 98

Synthesis of N-(4-{7-cyano-5-[3-(methylethoxy)propyl]-4-thioxo(3-hydropyrrolo[4,5-d]pyrimidin-6-yl)}phenyl)-2,2,2-trifluoroacetamide (Compound No: 1-10801)

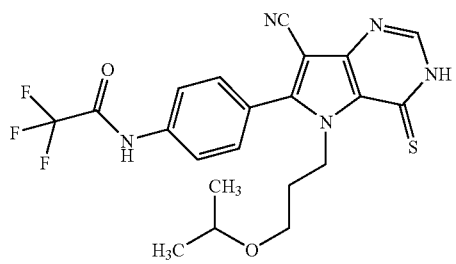

N-(4-{4-chloro-7-cyano-5-[3-(methylethoxy)propyl]pyrrolo[4,5-d]pyrimidin-6-yl}phenyl)-2,2,2-trifluoroacetamide (0.349 g) was dissolved in 2-propanol (7.5 mL), and then thiourea (0.086 g) was added and the mixture was stirred for 1.5 hours at 100° C. The reaction mixture was cooled and water was added thereto. After filtering out the solid, it was dried under reduced pressure to obtain the title compound (0.344 g, yield: 99%) as a brown solid. The ESI/MS data for this compound are shown below.

ESI/MS m/e: 464.3 (M$^+$+H, $C_{21}H_{20}F_3N_5O_2S$)

Example 99

Synthesis of 6-(4-aminophenyl)-5-[3-(methylethoxy)propyl]-4-thioxo-3-hydropyrrolo[3,2-d]pyrimidine-7-carbonitrile hydrochloride (Compound No: 1-0530)

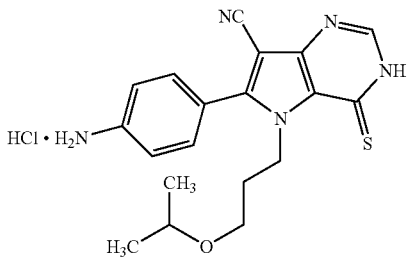

N-(4-{7-cyano-5-[3-(methylethoxy)propyl]-4-thioxo(3-hydropyrrolo[4,5-d]pyrimidin-6-yl)}phenyl)-2,2,2-trifluoroacetamide (0.344 g) was dissolved in methanol (5.0 mL), and then a 5 mol/L aqueous sodium hydroxide solution (2.5 mL) was added dropwise and the mixture was stirred for 1 hour at room temperature. After adding 1 mol/L hydrochloric acid to the reaction solution to adjust the pH to about 6, the solvent was distilled off under reduced pressure. The residue was dissolved in methanol, and the solid was filtered off. The filtrate was concentrated under reduced pressure, and the residue was dried under reduced pressure to obtain the title compound (0.299 g, yield: 100%) as a white solid. The NMR and ESI/MS data for this compound are shown below.

$^1$H-NMR (400 MHz, DMSO-d$_6$) δ (ppm): 0.42 (d, J=6.1, 6H), 1.25-1.42 (m, 2H), 2.62-2.75 (m, 2H), 2.75-2.85 (m, 1H), 3.15 (brs, 3H), 4.41 (t, J=6.6, 2H), 6.30 (d, J=8.3, 2H), 6.85 (d, J=8.6, 2H), 7.67 (d, J=3.7, 2H), 13.84 (brs, 1H). ESI/MS m/e: 368.4 (M$^+$+H, $C_{19}H_{21}N_{5}OS$ HCl)

Example 100

Synthesis of 5-[3-(methylethoxy)propyl]-6-{4-[benzylamino]phenyl}-4-thioxo-3-hydropyrrolo[3,2-d]pyrimidine-7-carbonitrile (Compound No: 1-0531)

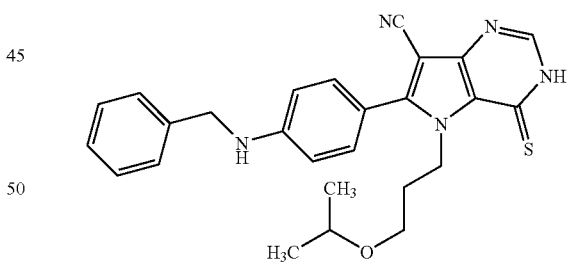

6-(4-aminophenyl)-5-[3-(methylethoxy)propyl]-4-thioxo-3-hydropyrrolo[3,2-d]pyrimidine-7-carbonitrile hydrochloride (40.4 mg) was dissolved in chloroform (0.9 mL) and acetic acid (0.1 mL), and then benzaldehyde (15.9 mg) was added dropwise and the mixture was stirred for 1 hour at room temperature. Sodium triacetoxyborohydride (42.4 mg) was added to the solution, and reaction was stirreded at room temperature for 5 hours. The reaction solution was concentrated under reduced pressure and the residue was purified by preparative HPLC to obtain the title compound (11.2 mg, yield: 20%) as a white solid. The ESI/MS data for this compound are shown below.

ESI/MS m/e: 458.3 (M⁺+H, $C_{26}H_{27}N_5OS$)

Example 101

Synthesis of N-(4-{7-cyano-5-[3-(methylethoxy)propyl]-4-thioxo(3-hydropyrrolo[4,5-d]pyrimidin-6-yl)}phenyl)-2-methoxyacetamide (Compound No: 1-0536)

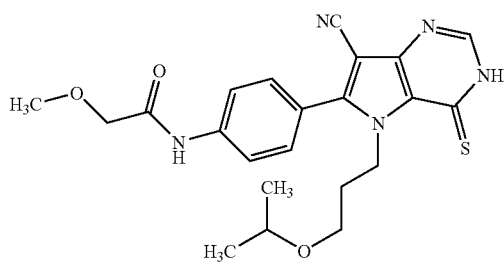

6-(4-Aminophenyl)-5-[3-(methylethoxy)propyl]-4-thioxo-3-hydropyrrolo[3,2-d]pyrimidine-7-carbonitrile hydrochloride (40.4 mg) was dissolved in N,N-dimethylformamide (1.0 mL), and then methoxyacetyl chloride (41.0 mg) and triethylamine (83.2 μL) were added and the mixture was stirred for 2 hours at room temperature. Water (1.0 mL) and 2 mol/L aqueous sodium hydroxide (100 μL) were added to the solution and the mixture was stirred for 1 hour at room temperature. After adding 1 mol/L hydrochloric acid to the reaction solution to adjust the pH to about 6, the solvent was distilled off under reduced pressure. The residue was purified by preparative HPLC to obtain the title compound (6.7 mg, yield: 14%) as a white solid. The ESI/MS data for this compound are shown below.

ESI/MS m/e: 440.3 (M⁺+H, $C_{22}H_{25}N_5O_3S$)

Example 102

Synthesis of 3-[(3,3-dimethyl-3-silabutoxy)methyl]-5-(3-hydroxypropyl)-4-oxo-6-phenyl-3-hydropyrrolo[3,2-d]pyrimidine-7-carbonitrile

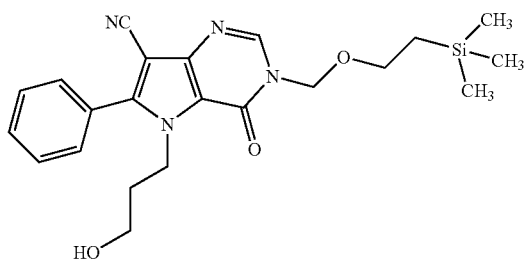

A suspension of sodium hydride (143 mg) in tetrahydrofuran (12 mL) was cooled to 0° C. A solution of 5-(3-hydroxypropyl)-4-oxo-6-phenyl-3-hydropyrrolo[3,2-d]pyrimidine-7-carbonitrile (1.00 g) in N,N-dimethylformamide (17 mL) was then added dropwise thereto. After stirring the reaction mixture at room temperature for 1 hour, it was again cooled to 0° C., and a solution of 2-(chloromethoxy)ethyl-trimethylsilane (0.68 mL) in tetrahydrofuran (5 mL) was added dropwise thereto. After stirring the reaction mixture at room temperature for 2 hours, saturated brine (100 mL) was added to the reaction solution. The solution was extracted 3 times with ethyl acetate and then dried over sodium sulfate. After filtering off the sodium sulfate, the solvent was distilled off under reduced pressure. The residue was purified by silica gel column chromatography (hexane/ethyl acetate=1/1) to obtain the title compound (1.28 g, yield: 89%) as a colorless viscous oil. The NMR and ESI/MS data for this compound are shown below.

¹H-NMR (400 MHz, DMSO-d₆) δ (ppm): 0.00 (s, 9H), 0.85-0.99 (m, 2H), 1.72-1.87 (m, 2H), 2.50-2.56 (m, 1H), 3.22-3.32 (m, 2H), 3.66 (t, J=8.0, 2H), 4.35-4.50 (m, 2H), 5.45 (s, 2H), 7.60-7.70 (m, 5H), 8.46 (s, 1H). ESI/MS m/e: 425.3 (M⁺+H, $C_{22}H_{28}N_4O_3Si$)

Example 103

Synthesis of 3-[(3,3-dimethyl-3-silabutoxy)methyl]-4-oxo-6-phenyl-5-(3-phenoxypropyl-3-hydropyrrolo[3,2-d]pyrimidine-7-carbonitrile

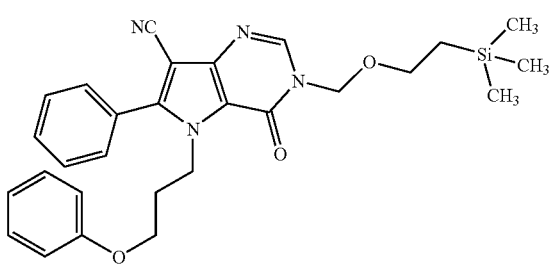

A solution of triphenylphosphine (191 mg) in tetrahydrofuran (3.0 mL) was cooled to 0° C. Diethyl azodicarboxylate (327 mg, 40% toluene solution) was added dropwise to the solution and the mixture was stirred for 5 minutes. After further adding dropwise a solution of 3-[(3,3-dimethyl-3-silabutoxy)methyl]-5-(3-hydroxypropyl)-4-oxo-6-phenyl-3-hydropyrrolo[3,2-d]pyrimidine-7-carbonitrile (212 mg) in tetrahydrofuran (1.0 mL), a solution of phenol (71 mg) in tetrahydrofuran (1.0 mL) was also added dropwise and the mixture was stirred for 4 hours at room temperature. Saturated brine was added to quench the reaction, and extraction was performed 3 times with ethyl acetate. The organic layer was washed with saturated brine and then dried over sodium sulfate. After filtering off the sodium sulfate, the solvent was distilled off under reduced pressure. The obtained crude product was purified by silica gel column chromatography (hexane/ethyl acetate=3:1) to obtain the title compound (248 mg, yield: 99%) as a white solid. The ESI/MS data for this compound are shown below.

ESI/MS m/e: 501.4 (M⁺+H, $C_{28}H_{32}N_4O_3Si$)

Example 104

Synthesis of 3-{3-[(3,3-dimethyl-3-silabutoxy)methyl]-7-cyano-4-oxo-6-phenyl-3-hydropyrrolo[3,2-d]pyrimidin-5-yl}propyl methylsulfonate

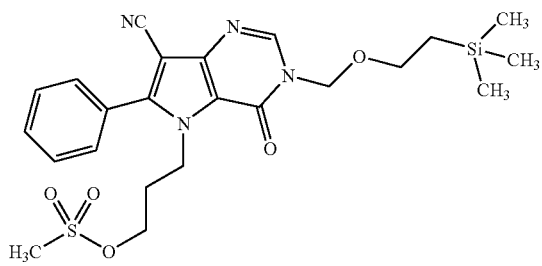

Tetrahydrofuran (10 mL) was cooled to 0° C., methanesulfonyl chloride (186 mg) and triethylamine (333 µL) were added dropwise and the mixture was stirred for 5 minutes at room temperature. The reaction mixture was again cooled to 0° C., a solution of 3-[(3,3-dimethyl-3-silabutoxy)methyl]-5-(3-hydroxypropyl)-4-oxo-6-phenyl-3-hydropyrrolo[3,2-d]pyrimidine-7-carbonitrile (849 mg) in tetrahydrofuran (10 mL) was added dropwise and the mixture was stirred for 4 hours at room temperature. Saturated brine was added to the reaction solution. Extraction was then performed 3 times with ethyl acetate, and the organic layer was washed with saturated brine and then dried over sodium sulfate. After filtering off the sodium sulfate, the solvent was distilled off under reduced pressure. The obtained crude product was purified by silica gel column chromatography (hexane/ethyl acetate=2:1) to obtain the title compound (891 mg, yield: 89%) as white oil. The ESI/MS data for this compound are shown below.

ESI/MS m/e: 503.4 (M$^+$+H, $C_{23}H_{30}N_4O_5SSi$)

Example 105

Synthesis of 3-[(3,3-dimethyl-3-silabutoxy)methyl]-5-{3-[2-(2-methoxyethyl)ethoxy]propyl}-4-oxo-6-phenyl-3-hydropyrrolo[3,2-d]pyrimidine-7-carbonitrile

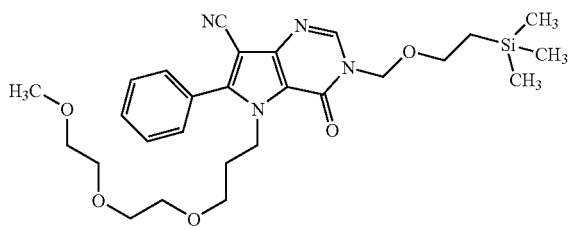

A suspension of sodium hydride (53 mg) in tetrahydrofuran (3.9 mL) was cooled to 0° C. A solution of 2-(2-methoxyethoxy)ethanol (159 mg) in tetrahydrofuran (2.0 mL) was then added dropwise thereto. After stirring the reaction mixture at 0° C. for 30 minutes, a solution of 3-{3-[(3,3-dimethyl-3-silabutoxy)methyl]-7-cyano-4-oxo-6-phenyl-3-hydropyrrolo[3,2-d]pyrimidin-5-yl}propyl methylsulfonate (445 mg) in tetrahydrofuran (3.0 mL) was added dropwise thereto. The reaction mixture was stirred at room temperature for 15 hours, and saturated brine was added thereto. The solution was extracted 3 times with ethyl acetate and then dried over sodium sulfate. After filtering off the sodium sulfate, the solvent was distilled off under reduced pressure. The residue was purified by silica gel column chromatography (hexane/ethyl acetate=1/1) to obtain the title compound (180 mg, yield: 89%) as a colorless rubber substance. The ESI/MS data for this compound are shown below.

ESI/MS m/e: 527.6 (M$^+$+H, $C_{27}H_{38}N_4O_5Si$)

Example 106

Synthesis of 3-[(3,3-dimethyl-3-silabutoxy) methyl]-4-oxo-6-phenyl-5-(3-phenoxypropyl)-3-hydropyrrolo [3,2-d]pyrimidine-7-carbonitrile (Compound No: 1-0537)

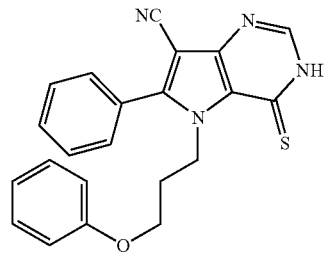

3-[(3,3-Dimethyl-3-silabutoxy)methyl]-4-oxo-6-phenyl-5-(3-phenoxypropyl)-3-hydropyrrolo[3,2-d]pyrimidine-7-carbonitrile (248 mg) was dissolved in a mixed solvent of methylene dichloride (4.0 mL) and trifluoroacetic acid (1.0 mL), and the mixture was stirred for 2 hours at room temperature. The solvent was distilled off under reduced pressure and the residue was purified by preparative HPLC. The purified compound was dissolved in phosphorus oxychloride (2.0 mL) and the mixture was stirred for 1 hour at 100° C. The solvent was distilled off under reduced pressure, the residue was dissolved in 2-propanol (5.0 mL), thiourea (57 mg) was added and the mixture was stirred for 1 hour at 100° C. After cooling the reaction solution, saturated brine was added. The solution was extracted 3 times with ethyl acetate and then washed with saturated brine and dried over sodium sulfate. After filtering off the sodium sulfate, the solvent was distilled off under reduced pressure. The residue was purified by preparative HPLC to obtain the title compound (3.2 mg, yield: 2%) as a white solid.

ESI/MS m/e: 387.3 (M$^+$+H, $C_{22}H_{18}N_4OS$)

Example 107

Synthesis of 6-phenyl-5-{2-[benzylamino]ethyl}-4-thioxo-3-hydropyrrolo[3,2-d]pyrimidine-7-carbonitrile (Compound No: 2-1775)

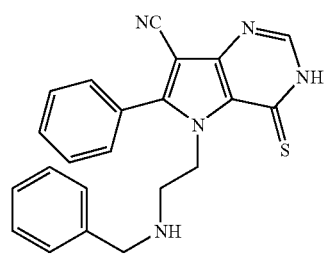

5-(3-Aminoethyl)-6-phenyl-4-thioxo-3-hydropyrrolo[3,2-d]pyrimidine-7-carbonitrile hydrochloride (14.8 mg) was dissolved in chloroform (0.45 mL) and acetic acid (0.05 mL), and then benzaldehyde (8.0 mg) was added dropwise, sodium triacetoxyborohydride (21.2 mg) was added, and reaction was stirred at room temperature for 2 hours. The reaction solution was concentrated under reduced pressure and the residue was purified by preparative HPLC to obtain the title compound (4.9 mg, yield: 20%) as a white solid. The ESI/MS data for this compound are shown below.

ESI/MS m/e: 386.3 (M$^+$+H, C$_{22}$H$_{19}$N$_5$S)

Example 108

Synthesis of 6-phenyl-5-[2-(3-phenyl(1,2,4-oxadiazol-5-yl))ethyl]-4-thioxo-3-hydropyrrolo[3,2-d]pyrimidine-7-carbonitrile (Compound No: 1-0495)

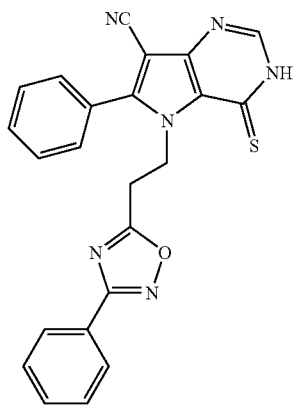

Benzamidoxime (27.2 mg) and 1-ethyl-3-(3'-diethylaminopropyl)carbodiimide hydrochloride (38.3 mg) were added to a solution of 3-(7-cyano-6-phenyl-4-thioxo-3-hydropyrrolo[3,2-d]pyrimidin-5-yl)propanoic acid (32.4 mg) in N,N-dimethylformamide (1.0 mL), and then triethylamine (27.7 µL) was added dropwise and reaction was stirred at room temperature for 2 hours. The reaction solution was then stirred for 2 hours at 100° C., and saturated brine was added thereto. The reaction solution was extracted 3 times with ethyl acetate and then the organic layer was washed with saturated brine and dried over sodium sulfate. After filtering off the sodium sulfate, the solvent was distilled off under reduced pressure and the residue was purified by preparative HPLC to obtain the title compound (6.1 mg, yield: 14%) as a white solid. The ESI/MS data for this compound are shown below.

ESI/MS m/e: 425.2 (M$^+$+H, C$_{23}$H$_{16}$N$_6$OS)

Example 109

Synthesis of 4-chloro-6-phenylpyrrolo[3,2-d]pyrimidine-7-carbonitrile

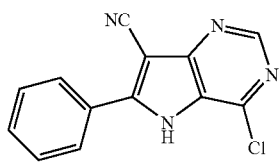

4-Oxo-6-phenyl-3-hydropyrrolo[3,2-d]pyrimidine-7-carbonitrile (2.36 g) was dissolved in acetonitrile (20 mL) and phosphorus oxychloride (20 mL) and the mixture was stirred for 7 hours at 100° C. The reaction mixture as cooled to room temperature, and the precipitated solid was filtered out. The solid was washed with acetonitrile to obtain the title compound (2.32 g, yield: 91%) as a white solid. The NMR and ESI/MS data for this compound are shown below.

$^1$H-NMR (400 MHz, DMSO-d$_6$) δ (ppm): 7.60-7.80 (m, 3H), 7.97-8.13 (m, 2H), 8.82 (s, 1H), 13.73 (brs, 1H). ESI/MS m/e: 255.2 (M$^+$+H, C$_{13}$H$_7$ClN$_4$)

Example 110

Synthesis of ethyl 3-(7-cyano-4-oxo-6-phenyl-3-hydropyrrolo[3,2-d]pyrimidin-5-yl)propanoate (Compound No: 4-0004)

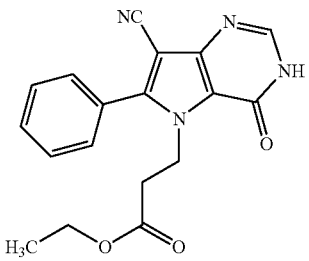

Crude ethyl 3-[4-amino-3-cyano-5-(methoxycarbonyl)-2-phenylpyrrolyl]propanoate (35.31 g) and formamidine acetate (215.2 g) were added to 2-propanol (1500 mL), and the mixture was heated to reflux for 40 hours. After cooling to room temperature, the solvent was distilled off under reduced pressure. Water was added to the residue and the insoluble matter was filtered out. The solid was recrystallized (ethyl acetate/hexane=1/5) to obtain the title compound (20.74 g, 3-steps yield from (methoxyphenylmethylene)methane-1,1-dicarbonitrile: 75%) as a white solid. The NMR and ESI/MS data for this compound are shown below.

$^1$H-NMR (400 MHz, DMSO-d$_6$) δ (ppm): 1.03 (t, J=7.1, 3H), 2.75 (t, J=7.3, 2H), 3.90 (dd, J=7.1, 2H), 4.54 (t, J=7.3, 2H), 7.61-7.63 (m, 5H), 8.05 (s, 1H), 12.52 (brs, 1H). ESI/MS m/e: 337.3 (M$^+$+H, C$_{19}$H$_{16}$N$_4$O$_3$)

Example 111

Synthesis of ethyl 3-[7-cyano-6-(3-methyl(2-furyl))-4-oxo-3-hydropyrrolo[3,2-d]pyrimidin-5-yl]propanoate (Compound No: 4-0328)

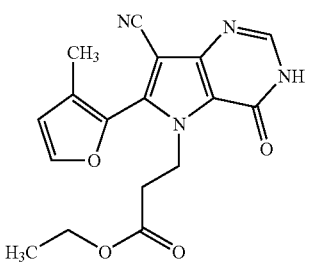

The title compound was synthesized in the same manner as Example 110 using ethyl 3-[4-amino-3-cyano-5-(methoxycarbonyl)-2-(3-methyl(2-furyl)pyrrolyl)propanoate. The NMR and ESI/MS data for this compound are shown below.

$^1$H-NMR (400 MHz, DMSO-d$_6$) δ (ppm): 1.07 (t, J=7.1, 3H), 2.12 (s, 3H), 2.74 (t, J=7.3, 2H), 3.94 (q, J=7.1, 2H), 4.58 (t, J=7.3, 2H), 6.68 (d, J=2.0, 1H), 7.95 (d, J=1.7, 1H), 8.04 (s, 1H). ESI/MS m/e: 341.2 (M$^+$+H, C$_{17}$H$_{16}$N$_4$O$_4$S)

Example 112

Synthesis of ethyl 3-(7-cyano-6-phenyl-4-thioxo-3-hydropyrrolo[3,2-d]pyrimidin-5-yl)propanoate (Compound No: 4-00051)

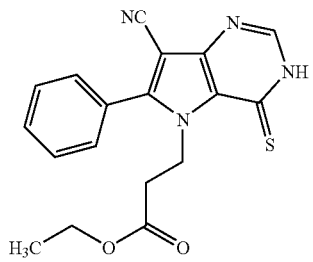

Phosphorus oxychloride (16.90 g) was added to ethyl 3-(7-cyano-4-oxo-6-phenyl-3-hydropyrrolo[3,2-d]pyrimidin-5-yl)propanoate (935.0 mg), and the mixture was stirred for 1 hour at 100° C. After cooling to room temperature, the phosphorus oxychloride was distilled off under reduced pressure. 2-Propanol (40 mL) and thiourea (262.3 mg) were added to the residue and the mixture was heated to reflux for 1 hour. After cooling to room temperature, the solvent was distilled off under reduced pressure. Ethyl acetate and water were added to the residue, and extraction was performed 3 times with ethyl acetate. The organic layer was washed with water and saturated brine and then dried over anhydrous magnesium sulfate. After filtering off the magnesium sulfate, the solvent was distilled off under reduced pressure. The residue was purified by silica gel column chromatography (hexane/ethyl acetate=3/1→2/1) to obtain the title compound (470.5 mg, yield: 48%) as a light yellow solid compound. The NMR and ESI/MS data for this compound are shown below.

$^1$H-NMR (400 MHz, DMSO-d$_6$) δ (ppm): 1.04 (t, J=7.1, 3H), 2.78 (t, J=7.6, 2H), 3.91 (dd, J=7.1, 2H), 4.95 (t, J=8.0, 2H), 7.60-7.70 (m, 5H), 8.22 (s, 1H), 13.9 (brs, 1H) ESI/MS m/e: 353.1 (M$^+$+H, C$_{18}$H$_{16}$N$_4$O$_2$S)

Example 113

Synthesis of ethyl 3-[7-cyano-6-(3-methyl(2-furyl))-4-thioxo-3-hydropyrrolo[3,2-d]pyrimidin-5-yl]propanoate (Compound No: 4-0329)

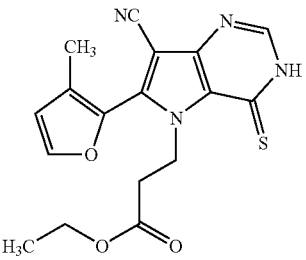

The title compound was synthesized in the same manner as Example 112 using ethyl 3-[7-cyano-6-(3-methyl(2-furyl))-4-oxo-3-hydropyrrolo[3,2-d]pyrimidin-5-yl]propanoate. The NMR and ESI/MS data for this compound are shown below.

$^1$H-NMR (400 MHz, DMSO-d$_6$) δ (ppm): 1.10 (t, J=6.6, 3H), 2.15 (s, 3H), 2.87 (t, J=7.6, 2H), 3.97 (q, J=7.1, 2H), 4.96 (t, J=7.3, 2H), 6.71 (s, 1H), 7.99 (s, 1H), 8.20 (d, J=3.6, 1H), 13.90 (brs, 1H). ESI/MS m/e: 357.2 (M$^+$+H, C$_{17}$H$_{16}$N$_4$O$_3$S)

Example 114

Synthesis of 3-(7-cyano-6-phenyl-4-thioxo-3-hydropyrrolo[3,2-d]-pyrimidin-5-yl)propanecarboxylic acid (Compound No: 4-0001)

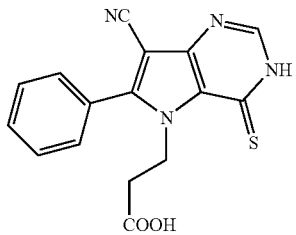

Ethyl 3-(7-cyano-6-phenyl-4-thioxo-3-hydropyrrolo[3,2-d]pyrimidin-5-yl)propanoate (151.4 mg) was dissolved in 1,4-dioxane (4.0 mL), and a 1N aqueous sodium hydroxide solution (4.0 mL) was added while cooling to 0° C. After stirring for 10 minutes at room temperature, 1N aqueous hydrochloric acid (5.0 mL) was added. The precipitated solid was filtered out and washed with water. The solid was dried under reduced pressure to obtain the title compound (134.7 mg, yield: 97%) as a light yellow solid. The NMR and ESI/MS data for this compound are shown below.

$^1$H-NMR (400 MHz, DMSO-d$_6$) δ (ppm): 2.72 (t, J=7.8, 2H), 4.87 (t, J=7.8, 2H), 7.52-7.60 (m, 5H), 8.22 (s, 1H), 12.38 (brs, 1H), 13.87 (brs, 1H). ESI/MS m/e: 325.1 (M$^+$+H, C$_{16}$H$_{12}$N$_4$O$_2$S)

Example 115

Synthesis of 3-[7-cyano-6-(3-methyl(2-furyl))-4-thioxo-3-hydropyrrolo[3,2-d]pyrimidin-5-yl]propanoic acid (Compound No: 4-0107)

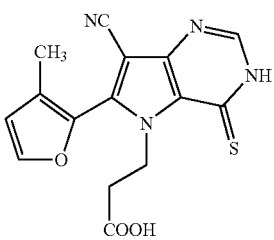

The title compound was synthesized in the same manner as Example 114 using ethyl 3-[7-cyano-6-(3-methyl(2-furyl))-4-thioxo-3-hydropyrrolo[3,2-d]pyrimidin-5-yl]propanoate. The NMR and ESI/MS data for this compound are shown below.

$^1$H-NMR (400 MHz, DMSO-$d_6$) δ (ppm): 2.14 (s, 3H), 2.78-2.90 (m, 2H), 4.82-4.97 (m, 2H), 6.70 (d, J=1.7, 1H), 8.00 (d, J=1.7, 1H), 8.19 (d, J=3.4, 1H), 12.45 (brs, 1H), 13.96 (brs, 1H). ESI/MS m/e: 329.2 (M$^+$+H, $C_{11}H_{12}N_4O_3S$)

Example 116

Synthesis of 3-(7-cyano-6-cyclopropyl-4-thioxo-3-hydropyrrolo[3,2-d]pyrimidin-5-yl)propanoic acid (Compound No: 4-0092)

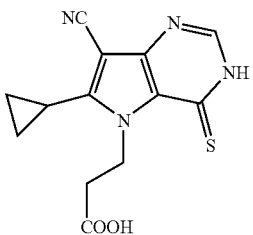

The title compound was synthesized in the same manner as Example 114 using ethyl 3-(7-cyano-6-cyclopropyl-4-thioxo-3-hydropyrrolo[3,2-d]pyrimidin-5-yl)propanoate. The NMR and ESI/MS data for this compound are shown below.

$^1$H-NMR (400 MHz, DMSO-$d_6$) δ (ppm): 1.05-1.25 (m, 4H), 2.26 (m, 1H), 2.85 (t, J=7.8, 2H), 5.13 (t, J=7.8, 2H), 8.11 (s, 1H), 12.49 (brs, 1H), 13.69 (brs, 1H). ESI/MS m/e: 289.2 (M$^+$+H, $C_{13}H_{12}N_4O_2S$)

Example 117

Synthesis of 3-(7-cyano-6-phenyl-4-thioxo-3-hydropyrrolo[3,2-d]pyrimidin-5-yl)-N-benzylpropanamide propanoate (Compound No: 3-0116)

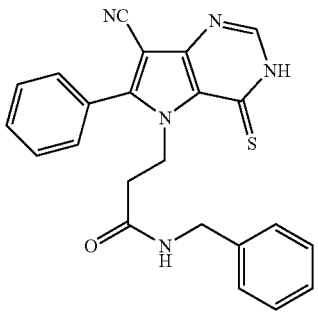

3-(7-Cyano-6-phenyl-4-thioxo-3-hydropyrrolo[3,2-d]pyrimidin-5-yl)propanecarboxylic acid (30.0 mg), 1-ethyl-3-(3-dimethylaminopropyl)carbodiimide hydrochloride (60.0 mg) and triethylamine (50 μL) were added to dichloromethane (4.0 mL), and the mixture was stirred for 10 minutes at room temperature. Benzylamine (50 μL) was added thereto and stirring was continued for 3 hours at room temperature. Saturated aqueous ammonium chloride solution (4.0 mL) was added to the reaction solution and extraction was performed 3 times with dichloromethane. The organic phase was washed with water and saturated brine and then dried over anhydrous magnesium sulfate. After filtering off the magnesium sulfate from the organic layer, the solvent was distilled off under reduced pressure. The obtained crude product was purified by preparative HPLC to obtain the title compound (20.7 mg, 54%) as a light yellow solid. The NMR and ESI/MS data for this compound are shown below.

$^1$H-NMR (400 MHz, DMSO-$d_6$) δ (ppm): 2.56 (t, J=7.1, 2H), 4.05 (d, J=5.8, 2H), 4.91 (t, J=7.1, 2H), 7.03 (d, J=6.8, 2H), 7.10-7.25 (m, 3H), 7.53-7.58 (m, 5H), 8.15 (s, 1H), 8.21 (t, J=5.9, 1H), 13.7 (brs, 1H). ESI/MS m/e: 414.3 (M$^+$+H, $C_{23}H_{19}N_5OS$)

Example 118

Synthesis of 1-[3-(7-cyano-6-phenyl-4-thioxo-3-hydropyrrolo[3,2-d]pyrimidin-5-yl)propanoyl]piperidine-4-carboxylic acid (Compound No: 3-0231)

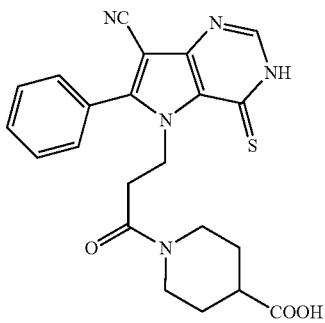

Ethyl 1-[3-(7-cyano-6-phenyl-4-thioxo-3-hydropyrrolo[3,2-d]pyrimidin-5-yl)propanoyl]piperidine-4-carboxylic acid (50.4 mg) was dissolved in 1,4-dioxane (4.0 mL), and a 1N aqueous sodium hydroxide solution (4.0 mL) was added while cooling to 0° C. After stirring for 30 minutes at room temperature, 1N hydrochloric acid (5.0 mL) was added. Ethyl acetate and water were added thereto, and extraction was performed 3 times with ethyl acetate. The organic layer was washed with water and saturated brine and then dried over anhydrous magnesium sulfate. After filtering off the magnesium sulfate, the solvent was distilled off under reduced pressure. The residue was purified by preparative HPLC to obtain the title compound (23.5 mg, 50%) as a light yellow solid. The NMR and ESI/MS data for this compound are shown below.

ESI/MS m/e: 436.2 (M$^+$+H, $C_{22}H_{21}N_5O_3S$)

Example 119

Synthesis of 3-[7-cyano-6-phenyl-4-thioxo(3-hydropyrrolo[3,2-d]pyrimidin-5-yl)]-N-methoxy-N-methylpropanamide (Compound No: 3-0037)

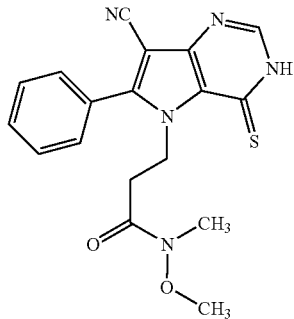

3-(7-cyano-6-phenyl-4-thioxo-3-hydropyrrolo[3,2-d]pyrimidin-5-yl)-N-methoxy-N-methylpropanoic acid (0.487 g) was dissolved in methylene chloride (15 mL), and then N,O-dimethylhydroxylamine hydrochloride (0.585 g) and 1-ethyl-3-(3'-dimethylaminopropyl)carbodiimide hydrochloride (1.150 g) were added and the mixture was stirred at 0° C. Triethylamine (0.83 mL) was then added and the mixture was stirred for 4 hours at room temperature. Aqueous saturated brine was added to quench the reaction, and the organic layer was separated off. The aqueous layer was extracted 3 times with ethyl acetate. The organic layer was washed with saturated brine and then dried over sodium sulfate. After filtering off the sodium sulfate, the solvent was distilled off under reduced pressure to obtain the title compound (0.551 g, yield: 100%) as a light yellow solid. The NMR and ESI/MS data for this compound are shown below.

$^1$H-NMR (400 MHz, DMSO-d$_6$) δ (ppm): 2.87 (brt, J=7.6, 2H), 2.96 (s, 3H), 3.50 (s, 3H), 4.90 (brt, J=7.1, 2H), 7.60-7.69 (m, 5H), 8.21 (s, 1H), 13.84 (brs, 1H). ESI/MS m/e: 368.4 (M$^+$+H, $C_{18}H_{17}N_5O_2S$)

Example 120

Synthesis of 5-(3-oxoheptyl)-6-phenyl-4-thioxo-3-hydropyrrolo[3,2-d]pyrimidine-7-carbonitrile (Compound No: 5-0181)

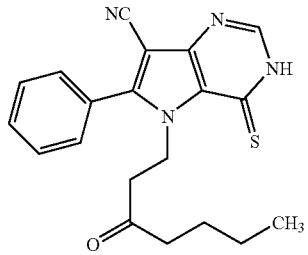

3-[7-cyano-6-phenyl-4-thioxo(3-hydropyrrolo[3,2-d]pyrimidin-5-yl)]-N-methoxy-N-methylpropanamide (36.7 mg) was dissolved in tetrahydrofuran (1.0 mL) and the solution was stirred at −78° C. n-Butyllithium (192 μL, 1.56 mol/L hexane solution) was added dropwise to the solution and the mixture was stirred for 1 hour at −78° C. Saturated aqueous brine was added to quench the reaction, and the pH was adjusted to 5 with 1 mol/L hydrochloric acid. The solution was extracted 3 times with ethyl acetate. The organic layer was washed with saturated brine and then dried over sodium sulfate. After filtering off the sodium sulfate, the solvent was distilled off under reduced pressure. The obtained crude product was purified by preparative HPLC to obtain the title compound (18.2 mg, yield: 50%) as a white solid. The NMR and ESI/MS data for this compound are shown below.

$^1$H-NMR (400 MHz, DMSO-d$_6$) δ (ppm): 0.78 (t, J=7.8, 3H), 1.14 (q, J=7.3, 2H), 1.33 (q, J=7.3, 2H), 2.27 (t, J=7.3, 2H), 2.94 (t, J=6.8, 2H), 4.85 (t, J=6.6, 2H), 7.57-7.71 (m, 5H), 8.21 (s, 1H), 13.82 (brs, 1H). ESI/MS m/e: 365.3 (M$^+$+H, $C_{20}H_{20}N_4OS$)

Example 121

Synthesis of 5-(3-oxo-3-phenylpropyl)-6-phenyl-4-thioxo-3-hydropyrrolo[3,2-d]pyrimidine-7-carbonitrile (Compound No: 5-0006)

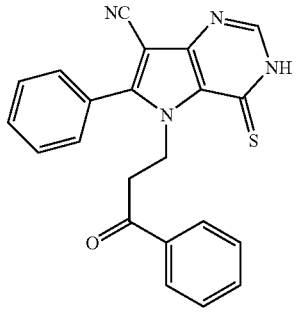

3-(7-cyano-6-phenyl-4-thioxo(3-hydropyrrolo[3,2-d]pyrimidin-5-yl)-N-methoxy-N-methylpropanamide (36.7 mg) was dissolved in tetrahydrofuran (1.0 mL), and the mixture was stirred at 0° C. Phenylmagnesium bromide (100 μL, 3.0 mol/L diethyl ether solution) was added dropwise to the solution and the mixture was stirred for 2 hours at 0° C. A saturated aqueous brine solution was added to quench the reaction, and the pH was adjusted to 5 with 1 mol/L hydrochloric acid. The solution was then extracted 3 times with ethyl acetate. The organic layer was washed with saturated brine and then dried over sodium sulfate. After filtering off the sodium sulfate, the solvent was distilled off under reduced pressure. The obtained crude product was purified by preparative HPLC to obtain the title compound (10.1 mg, yield: 26%) as a light yellow solid. The NMR and ESI/MS data for this compound are shown below.

¹H-NMR (400 MHz, DMSO-d₆) δ (ppm): 3.60 (t, J=6.8, 2H), 5.02 (t, J=6.6, 2H), 7.47 (t, J=7.6, 2H), 7.58-7.49 (m, 6H), 7.84 (d, J=8.0, 2H), 8.23 (s, 1H), 13.88 (brs, 1H). ESI/MS m/e: 385.1 (M⁺+H, $C_{22}H_{16}N_4OS$)

Example 122

Synthesis of 6-azaperhydroazepinyl-4-thioxo-3-hydropyrrolo[3,2-d]pyrimidine-7-carbonitrile (Compound No: 6-0061)

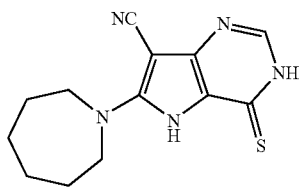

Hexamethyleneimine (236 mg) was added to 5-[3-(methylethoxy)propyl]-4-thioxo-3-hydropyrrolo[3,2-d]pyrimidine-7-carbonitrile (40 mg), and the mixture was stirred for 2 hours at 80° C. After cooling to room temperature, methanol (3 mL) was added to the reaction mixture. The mixture was passed through a cation-exchange resin column and the eluate was collected, after which methanol (3 mL) was passed through and the eluate was collected. The collected eluates were concentrated under reduced pressure to obtain the title compound (10.5 mg, 22%). The NMR and ESI/MS data for this compound are shown below.

¹H-NMR (400 MHz, CDCl₃) δ (ppm): 1.45-1.75 (m, 8H), 3.69 (t, J=6.1, 4H), 7.97 (s, 1H), 8.7 (brs, 1H), 13.9 (brs, 1H). ESI/MS m/e: 374.3 (M⁺+H, $C_{13}H_{15}N_5S$)

Example 123

Synthesis of 6-(cyclopropylamino)-5-[3-(methylethoxy)propyl]-4-thioxo-3-hydropyrrolo[3,2-d]pyrimidine-7-carbonitrile (Compound No: 6-0273)

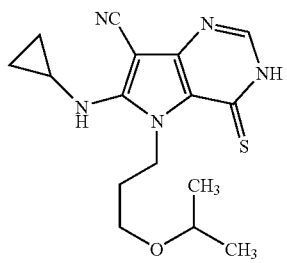

Cyclopropylamine (196 mg) was added to 5-[3-(methylethoxy)propyl]-4-thioxo-3-hydropyrrolo[3,2-d]pyrimidine-7-carbonitrile (40 mg), and the mixture was stirred for 4 hours at 80° C. After cooling to room temperature, methanol (3 mL) was added. The mixture was passed through a cation-exchange resin column and the eluate was collected, after which methanol (3 mL) was passed through and the eluate was collected. The collected eluates were concentrated under reduced pressure to obtain the title compound (6.3 mg, 15%). The NMR and ESI/MS data for this compound are shown below.

¹H-NMR (400 MHz, CDCl₃) δ (ppm): 0.68-0.75 (m, 2H), 0.93-0.99 (m, 2H), 1.20 (d, J=6.1, 6H), 2.12 (d, J=6.1, 2H), 2.93 (m, 1H), 3.40 (t, J=5.4, 2H) 3.66 (tt, J=6.1, 1H) 7.88 (s, 1H), 10.4 (brs, 1H). ESI/MS m/e: 332.3 (M⁺+H, $C_{16}H_{21}N_5OS$)

Example 124

Synthesis of N-{2-[7-cyano-6-(cyclopropylamino)-4-thioxo(3-hydropyrrolo[3,2-d]pyrimidin-5-yl)]ethyl}benzamide (Compound No: 6-0413)

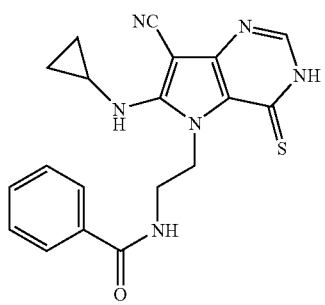

Acetonitrile (3 mL) and cyclopropylamine (3 mL) were added to crude N-[2-(6-chloro-7-cyano-4-thioxo(3-hydropyrrolo[3,2-d]pyrimidin-5-yl))ethyl]benzamide (136 mg), and the mixture was stirred for 4 hours at 80° C. The crude product obtained by concentration of the reaction mixture under reduced pressure was purified by preparative HPLC to obtain the title compound (10.3 mg, 8%) as a light yellow solid. The NMR and ESI/MS data for this compound are shown below.

¹H-NMR (400 MHz, DMSO-d₆) δ (ppm): 0.62 (m, 2H), 0.74-0.79 (m, 2H), 2.79 (m, 1H), 3.55-3.59 (m, 2H), 4.93 (brs, 2H), 7.43-7.55 (m, 3H), 7.76-7.79 (m, 2H), 8.00-8.05 (m, 2H), 8.63 (m, 1H) 13.2 (brs, 1H). ESI/MS m/e: 379.1 (M⁺+H, $C_{19}H_{18}N_6OS$)

Example 125

Synthesis of N-{2-[6-(dimethylamino)-7-cyano-4-thioxo(3-hydropyrrolo[3,2-d]pyrimidin-5-yl)]ethyl}(4-fluorophenyl)carboxamide (Compound No: 6-1029)

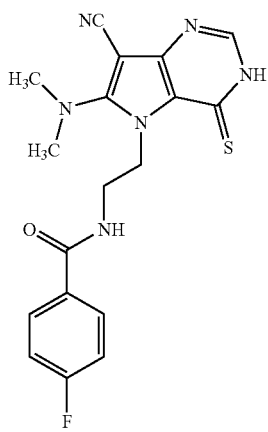

An aqueous dimethylamine solution (2 mL) was added to crude N-[2-(6-chloro-7-cyano-4-thioxo(3-hydropyrrolo[3,2-d]pyrimidin-5-yl))ethyl](4-fluorophenyl)carboxamide (80 mg), and the mixture was stirred for 2 hours at 50° C. After cooling to room temperature, the mixture was concentrated under reduced pressure, and the obtained crude product was purified by preparative HPLC to obtain the title compound (7.5 mg, 9%) as a light yellow solid. The NMR and ESI/MS data for this compound are shown below.

$^1$H-NMR (400 MHz, CDCl$_3$) δ (ppm): 2.90 (s, 6H), 3.46 (m, 2H), 4.96 (brs, 2H), 7.27 (m, 2H), 7.77 (m, 2H), 8.10 (s, 1H), 8.34 (m, 1H), 13.46 (brs, 1H). ESI/MS m/e: 385.3 (M$^+$+H, C$_{18}$H$_{17}$FN$_6$OS)

Example 126

Synthesis of N-[2-(7-cyano-6-pyrrolidinyl-4-thioxo(3-hydropyrrolo[3,2-d]pyrimidin-5-yl))ethyl](4-fluorophenyl)carboxamide (Compound No: 6-10311

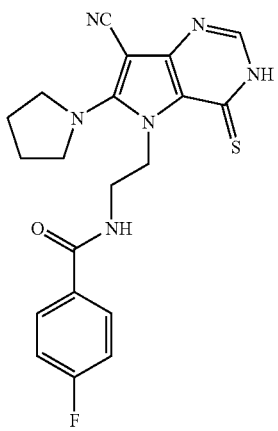

Pyrrolidine (2 mL) was added to crude N-[2-(6-chloro-7-cyano-4-thioxo(3-hydropyrrolo[3,2-d]pyrimidin-5-yl))ethyl](4-fluorophenyl)carboxamide (80 mg), and the mixture was stirred for 2 hours at 50° C. After cooling to room temperature, the mixture was concentrated under reduced pressure, and the obtained crude product was purified by prepara- tive HPLC to obtain the title compound (7.3 mg, 8%) as a light yellow solid. The NMR and ESI/MS data for this compound are shown below.

$^1$H-NMR (400 MHz, CDCl$_3$) δ (ppm): 1.79 (m, 4H), 3.36-3.70 (m, 6H), 5.19 (brs, 2H), 7.29 (m, 2H), 7.79 (m, 2H), 8.06 (m, 1H), 8.39 (m, 1H), 13.25 (brs, 1H). ESI/MS m/e: 411.3 (M$^+$+H, C$_{20}$H$_{19}$FN$_6$OS)

Example 127

Synthesis of N-{2-[7-cyano-6-(cyclobutylamino)-4-thioxo(3-hydropyrrolo[3,2-d]pyrimidin-5-yl)]ethyl}(4-fluorophenyl)carboxamide (Compound No: 6-1027)

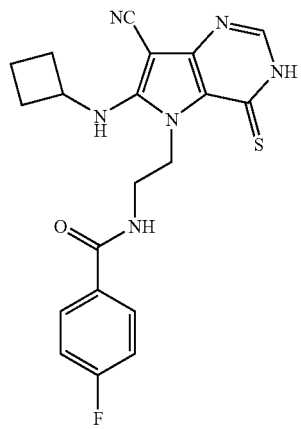

Cyclobutylamine (2 mL) was added to crude N-[2-(6-chloro-7-cyano-4-thioxo(3-hydropyrrolo[3,2-d]pyrimidin-5-yl))ethyl](4-fluorophenyl)carboxamide (70 mg), and the mixture was stirred for 6 hours at 80° C. After cooling to room temperature, the mixture was concentrated under reduced pressure and methanol (3 mL) was added thereto. The mixture was passed through a cation-exchange resin column and the eluate was collected, after which methanol (3 mL) was passed through and the eluate was collected. The collected eluates were concentrated under reduced pressure and the obtained crude product was purified by preparative HPLC to obtain the title compound (4.9 mg, 6%) as a light yellow solid. The NMR and ESI/MS data for this compound are shown below.

$^1$H-NMR (400 MHz, DMSO-d$_6$) δ (ppm): 1.68 (m, 2H), 2.09 (m, 2H), 2.29 (m, 2H), 3.57 (m, 2H), 4.27 (m, 1H), 4.98 (brs, 2H), 7.32 (m, 2H), 7.89 (m, 3H), 8.01 (m, 1H), 8.84 (m, 1H) 23 (brs, 1H). ESI/MS m/e: 411.3 (M$^+$+H, C$_{20}$H$_{19}$FN$_6$OS)

Examples 128-1174

The compounds of the invention listed below were synthesized according to the respective methods in Examples 1 to 128 using the corresponding starting materials and reactants. The ESI/MS data from HPLC/mass spectrum analysis of each compound, the retention time and purity of the compound in HPLC under the following conditions and the compound numbers corresponding to the synthesis method carried out are summarized in Tables 215 to 245.

HPLC (High Performance Liquid Chromatography) Conditions

System: Hewlett-Packard 1100 HPLC
Column: Cadenza CD-C18 (Imtakt) 100 mm×4.6 mm φ
Solvent:
  A: H$_2$O/acetonitrile=95/5
    0.05% TFA (trifluoroacetic acid)
  B: H$_2$O/acetonitrile=5/95
    0.05% TFA (trifluoroacetic acid)
Flow rate: 1.0 mL/min
Gradient:
0-1 min, solvent B: 10% solvent A: 90% 1-14 min, solvent B: 10%→100% solvent A: 90%→0% 14-16 min, solvent B: 100% solvent A: 0%
Calculation of purity: Area % of UV absorption (254 nm)

The compound numbers in the following tables represent the compound numbers in Tables 1 to 214 listed as the preferred examples.

TABLE 215

| Example | Compound No. | Compositional formula | ESI/MS m/e | HPLC (min) | Purity (%) | Synthesis method |
|---|---|---|---|---|---|---|
| 128 | 1-0005 | C13H14N4O | 243.3 | 8.4 | 97 | Example 79 |
| 129 | 1-0006 | C15H10N4O | 263.3 | 7.8 | 96 | Example 79 |
| 130 | 1-0007 | C13H8N4O | 237.2 | 6.4 | 88 | Example 1 |
| 131 | 1-0008 | C13H8N4S | 253.3 | 7.5 | 96 | Example 80 |
| 132 | 1-0009 | C14H10N4O | 251.2 | 6.7 | 100 | Example 79 |
| 133 | 1-0012 | C14H10N4O | 251.2 | 7.2 | 99 | Example 79 |
| 134 | 1-0013 | C14H10N4O | 251.2 | 7.2 | 97 | Example 79 |
| 135 | 1-0014 | C15H12N4O | 265.3 | 7.1 | 95 | Example 79 |
| 136 | 1-0015 | C15H12N4O | 265.3 | 7.3 | 99 | Example 79 |
| 137 | 1-0016 | C15H12N4S | 281.1 | 8.5 | 100 | Example 80 |
| 138 | 1-0017 | C15H12N4O | 265.3 | 8.0 | 100 | Example 79 |
| 139 | 1-0018 | C15H12N4O | 265.3 | 7.5 | 98 | Example 79 |
| 140 | 1-0020 | C17H16N4O | 293.4 | 9.4 | 97 | Example 79 |
| 141 | 1-0021 | C19H18N4O | 319.4 | 10.7 | 94 | Example 79 |
| 142 | 1-0022 | C13H7FN4O | 255.2 | 6.2 | 96 | Example 79 |
| 143 | 1-0023 | C13H7FN4O | 255.2 | 6.8 | 92 | Example 79 |
| 144 | 1-0024 | C13H7FN4O | 255.1 | 6.8 | 100 | Example 79 |
| 145 | 1-0025 | C13H7ClN4O | 271.3 | 6.5 | 100 | Example 79 |
| 146 | 1-0026 | C13H7ClN4S | 287.0 | 7.7 | 92 | Example 80 |
| 147 | 1-0028 | C13H7ClN4O | 271.1 | 7.5 | 98 | Example 79 |
| 148 | 1-0029 | C13H7ClN4O | 271.1 | 7.6 | 94 | Example 79 |
| 149 | 1-0031 | C13H6Cl2N4O | 305.2 | 8.6 | 95 | Example 79 |
| 150 | 1-0033 | C13H6Cl2N4O | 305.2 | 7.5 | 100 | Example 79 |
| 151 | 1-0035 | C13H6Cl2N4O | 305.2 | 8.6 | 90 | Example 79 |
| 152 | 1-0036 | C13H6Cl2N4O | 305.0 | 7.8 | 94 | Example 79 |
| 153 | 1-0037 | C13H6Cl2N4S | 321.0 | 9.0 | 94 | Example 79 |
| 154 | 1-0040 | C14H10N4O2 | 267.0 | 6.8 | 96 | Example 79 |
| 155 | 1-0041 | C14H10N4O2 | 267.2 | 6.7 | 96 | Example 79 |
| 156 | 1-0042 | C15H12N4O3 | 297.3 | 6.3 | 91 | Example 79 |
| 157 | 1-0043 | C15H12N4O3 | 297.3 | 6.8 | 98 | Example 79 |
| 158 | 1-0044 | C15H12N4O3 | 297.1 | 6.9 | 99 | Example 79 |
| 159 | 1-0045 | C15H12N4O2S | 313.2 | 8.2 | 96 | Example 80 |
| 160 | 1-0046 | C15H12N4O3 | 297.2 | 6.2 | 95 | Example 79 |
| 161 | 1-0047 | C15H12N4O2S | 313.1 | 7.3 | 100 | Example 79 |
| 162 | 1-0048 | C16H14N4O4 | 327.4 | 6.6 | 95 | Example 79 |
| 163 | 1-0049 | C16H14N4O4 | 327.1 | 6.7 | 100 | Example 1 |
| 164 | 1-0050 | C16H14N4O3S | 343.1 | 7.8 | 100 | Example 80 |
| 165 | 1-0051 | C14H8N4O2 | 265.3 | 6.0 | 80 | Example 79 |

TABLE 216

| Example | Compound No. | Compositional formula | ESI/MS m/e | HPLC (min) | Purity (%) | Synthesis method |
|---|---|---|---|---|---|---|
| 166 | 1-0052 | C14H8N4O2 | 265.3 | 5.8 | 88 | Example 79 |
| 167 | 1-0053 | C14H8N4O2 | 265.3 | 5.8 | 75 | Example 79 |
| 168 | 1-0054 | C14H8N4O3 | 281.2 | 5.3 | 61 | Example 79 |
| 169 | 1-0055 | C14H8N4O3 | 281.3 | 5.0 | 97 | Example 79 |
| 170 | 1-0056 | C14H7F3N4O | 305.3 | 7.0 | 100 | Example 79 |
| 171 | 1-0058 | C14H7F3N4O | 305.3 | 8.2 | 97 | Example 79 |
| 172 | 1-0059 | C14H7F3N4O | 305.3 | 8.4 | 99 | Example 79 |
| 173 | 1-0060 | C15H6F6N4O | 373.4 | 9.7 | 97 | Example 79 |
| 174 | 1-0061 | C15H10N4O2 | 279.3 | 6.1 | 95 | Example 79 |
| 175 | 1-0062 | C15H10N4O2 | 279.3 | 6.1 | 79 | Example 79 |
| 176 | 1-0063 | C15H10N4O2 | 279.1 | 6.1 | 96 | Example 79 |
| 177 | 1-0064 | C14H7F3N4O2 | 321.3 | 8.5 | 95 | Example 79 |
| 178 | 1-0065 | C14H7F3N4O2 | 321.3 | 8.6 | 98 | Example 79 |
| 179 | 1-0066 | C14H7N5O | 262.2 | 6.2 | 86 | Example 79 |
| 180 | 1-0067 | C14H7N5O | 262.0 | 6.3 | 100 | Example 79 |
| 181 | 1-0068 | C13H9N5O | 252.2 | 2.5 | 93 | Example 79 |
| 182 | 1-0069 | C15H13N5O | 280.2 | 6.2 | 96 | Example 79 |
| 183 | 1-0070 | C13H7N5O3 | 282.2 | 6.7 | 98 | Example 1 |
| 184 | 1-0071 | C13H7N5O2S | 298.1 | 7.8 | 86 | Example 80 |
| 185 | 1-0072 | C13H8N4O2 | 253.2 | 5.2 | 97 | Example 79 |
| 186 | 1-0073 | C14H10N4O2 | 267.3 | 4.9 | 97 | Example 79 |
| 187 | 1-0074 | C14H10N4O2 | 267.3 | 4.6 | 95 | Example 79 |
| 188 | 1-0075 | C16H13N5O3 | 324.4 | 2.4 | 96 | Example 79 |
| 189 | 1-0076 | C14H10N4OS | 283.3 | 7.6 | 94 | Example 79 |
| 190 | 1-0077 | C15H12N4O3S | 328.9 | 5.9 | 100 | Example 79 |
| 191 | 1-0078 | C19H12N4O2 | 329.1 | 9.2 | 99 | Example 1 |
| 192 | 1-0079 | C19H12N4OS | 345.1 | 10.4 | 84 | Example 80 |
| 193 | 1-0080 | C14H8N4O3 | 281.3 | 6.4 | 98 | Example 79 |
| 194 | 1-0081 | C19H12N4O | 313.3 | 9.1 | 98 | Example 79 |
| 195 | 1-0082 | C19H10N4O2 | 327.4 | 8.8 | 96 | Example 79 |
| 196 | 1-0083 | C17H10N4O | 287.4 | 8.2 | 97 | Example 79 |
| 197 | 1-0084 | C17H10N4O | 287.4 | 7.4 | 92 | Example 79 |
| 198 | 1-0085 | C21H12N4O | 337.4 | 8.8 | 84 | Example 79 |
| 199 | 1-0086 | C11H6N4OS | 243.2 | 6.0 | 96 | Example 79 |
| 200 | 1-0087 | C11H6N4S2 | 259.1 | 7.1 | 100 | Example 80 |
| 201 | 1-0088 | C11H6N4OS | 243.2 | 6.2 | 95 | Example 79 |
| 202 | 1-0089 | C12H8N4OS | 257.2 | 6.9 | 94 | Example 79 |
| 203 | 1-0090 | C13H8N4O2S | 285.3 | 6.0 | 94 | Example 79 |

TABLE 217

| Example | Compound No. | Compositional formula | ESI/MS m/e | HPLC (min) | Purity (%) | Synthesis method |
|---|---|---|---|---|---|---|
| 204 | 1-0091 | C15H8N4O2 | 277.1 | 7.7 | 97 | Example 79 |
| 205 | 1-0092 | C15H8N4OS | 293.2 | 8.1 | 98 | Example 79 |
| 206 | 1-0093 | C15H8N4OS | 293.3 | 7.5 | 73 | Example 79 |
| 207 | 1-0098 | C15H12N4O | 265.3 | 7.4 | 100 | Example 90 |
| 208 | 1-0099 | C15H12N4S | 281.3 | 9.2 | 99 | Example 90 |
| 209 | 1-0102 | C9H8N4O | 189.1 | 3.7 | 100 | Example 1 |
| 210 | 1-0103 | C16H14N4O | 279.2 | 8.5 | 100 | Example 1 |
| 211 | 1-0104 | C11H12N4O | 217.1 | 6.0 | 95 | Example 90 |
| 212 | 1-0105 | C11H12N4S | 233.3 | 8.2 | 100 | Example 2 |
| 213 | 1-0106 | C17H16N4O | 293.1 | 9.2 | 100 | Example 1 |
| 214 | 1-0107 | C12H14N4O | 231.3 | 6.9 | 100 | Example 90 |
| 215 | 1-0108 | C12H14N4S | 247.2 | 9.1 | 97 | Example 2 |
| 216 | 1-0113 | C18H18N4O | 307.2 | 10.0 | 100 | Example 90 |
| 217 | 1-0114 | C18H18N4S | 323.1 | 11.9 | 100 | Example 2 |
| 218 | 1-0121 | C13H16N4O | 245.1 | 8.1 | 100 | Example 90 |
| 219 | 1-0122 | C13H16N4S | 261.1 | 10.2 | 97 | Example 2 |
| 220 | 1-0125 | C18H18N4O | 307.2 | 9.9 | 97 | Example 1 |
| 221 | 1-0126 | C18H18N4S | 323.1 | 11.7 | 97 | Example 2 |
| 222 | 1-0127 | C13H16N4O | 245.1 | 7.8 | 95 | Example 90 |
| 223 | 1-0128 | C18H18N4O | 307.2 | 9.8 | 100 | Example 1 |
| 224 | 1-0129 | C18H18N4S | 323.1 | 11.6 | 100 | Example 2 |
| 225 | 1-0130 | C16H22N4O | 287.4 | 9.6 | 97 | Example 90 |
| 226 | 1-0131 | C19H20N4O | 321.2 | 10.4 | 81 | Example |

TABLE 217-continued

| Example | Compound No. | Compositional formula | ESI/MS m/e | HPLC (min) | Purity (%) | Synthesis method |
|---|---|---|---|---|---|---|
| 227 | 1-0132 | C18H18N4O | 307.2 | 10.1 | 100 | Example 90 |
| 228 | 1-0133 | C18H18N4S | 323.1 | 12.1 | 100 | Example 2 |
| 229 | 1-0134 | C13H16N4O | 245.1 | 8.1 | 98 | Example 90 |
| 230 | 1-0135 | C13H16N4S | 261.1 | 10.3 | 99 | Example 2 |
| 231 | 1-0136 | C19H20N4O | 321.2 | 10.7 | 99 | Example 90 |
| 232 | 1-0137 | C19H20N4S | 337.3 | 12.5 | 100 | Example 2 |
| 233 | 1-0144 | C16H12N4O | 277.1 | 7.7 | 100 | Example 1 |
| 234 | 1-0145 | C11H10N4O | 215.1 | 5.1 | 100 | Example 90 |
| 235 | 1-0146 | C13H7Cl1N4O | 271.1 | 7.5 | 100 | Example 1 |
| 236 | 1-0164 | C16H15N5O.ClH | 294.2 | 4.9 | 100 | Example 22 |
| 237 | 1-0194 | C16H14N4O2 | 295.1 | 6.2 | 100 | Example 3 |
| 238 | 1-0207 | C16H14N4O2 | 295.2 | 7.4 | 100 | Example 90 |
| 239 | 1-0208 | C16H14N4OS | 311.1 | 9.3 | 100 | Example 2 |
| 240 | 1-0209 | C11H12N4O2 | 233.2 | 5.0 | 100 | Example 90 |
| 241 | 1-0214 | C17H16N4O2 | 309.2 | 8.2 | 100 | Example 90 |

TABLE 218

| Example | Compound No. | Compositional formula | ESI/MS m/e | HPLC (min) | Purity (%) | Synthesis method |
|---|---|---|---|---|---|---|
| 242 | 1-0215 | C17H16N4OS | 325.1 | 10.1 | 100 | Example 2 |
| 243 | 1-0222 | C12H14N4O2 | 247.1 | 6.0 | 100 | Example 90 |
| 244 | 1-0225 | C15H20N4O2 | 289.4 | 8.0 | 100 | Example 90 |
| 245 | 1-0226 | C18H18N4O2 | 323.2 | 8.2 | 97 | Example 90 |
| 246 | 1-0227 | C17H16N4O2 | 309.2 | 7.7 | 100 | Example 1 |
| 247 | 1-0228 | C17H16N4OS | 325.1 | 9.5 | 100 | Example 2 |
| 248 | 1-0229 | C12H14N4O2 | 247.1 | 5.3 | 100 | Example 90 |
| 249 | 1-0230 | C12H14N4OS | 263.1 | 7.2 | 100 | Example 2 |
| 250 | 1-0231 | C16H22N4O2 | 303.4 | 8.8 | 100 | Example 90 |
| 251 | 1-0232 | C19H20N4O2 | 337.4 | 9.0 | 91 | Example 90 |
| 252 | 1-0233 | C19H20N4OS | 353.2 | 10.9 | 100 | Example 2 |
| 253 | 1-0234 | C18H18N4O2 | 323.1 | 8.5 | 100 | Example 1 |
| 254 | 1-0235 | C18H18N4OS | 339.3 | 10.3 | 100 | Example 2 |
| 255 | 1-0236 | C13H16N4O | 261.1 | 6.2 | 96 | Example 90 |
| 256 | 1-0237 | C13H16N4OS | 277.1 | 8.2 | 100 | Example 2 |
| 257 | 1-0238 | C17H24N4O2 | 317.4 | 10.4 | 99 | Example 90 |
| 258 | 1-0239 | C17H24N4OS | 333.2 | 11.7 | 100 | Example 2 |
| 259 | 1-0240 | C16H20N4O | 301.2 | 8.1 | 100 | Example 90 |
| 260 | 1-0241 | C16H20N4OS | 317.2 | 10.1 | 88 | Example 2 |
| 261 | 1-0243 | C20H22N4O2 | 351.2 | 9.7 | 95 | Example 90 |
| 262 | 1-0244 | C20H22N4OS | 367.2 | 11.6 | 100 | Example 2 |
| 263 | 1-0245 | C21H24N4O2 | 365.2 | 10.2 | 80 | Example 90 |
| 264 | 1-0246 | C21H24N4OS | 381.2 | 12.1 | 91 | Example 2 |
| 265 | 1-0247 | C19H20N4O2 | 337.3 | 9.2 | 100 | Example 90 |
| 266 | 1-0248 | C19H20N4OS | 353.0 | 11.0 | 95 | Example 2 |
| 267 | 1-0253 | C14H18N4OS | 275.1 | 7.1 | 100 | Example 90 |
| 268 | 1-0254 | C14H18N4OS | 291.3 | 9.2 | 83 | Example 2 |
| 269 | 1-0263 | C17H16N4OS | 325.1 | 8.8 | 100 | Example 90 |
| 270 | 1-0264 | C17H16N4S2 | 341.2 | 10.6 | 100 | Example 2 |
| 271 | 1-0265 | C12H14N4OS | 263.1 | 6.7 | 100 | Example 90 |
| 272 | 1-0272 | C16H11N5O | 290.1 | 6.9 | 99 | Example 1 |
| 273 | 1-0273 | C16H11N5S | 306.0 | 8.4 | 99 | Example 2 |
| 274 | 1-0274 | C17H14N4O | 291.2 | 8.7 | 100 | Example 90 |
| 275 | 1-0275 | C17H14N4S | 307.2 | 10.6 | 100 | Example 2 |
| 276 | 1-0280 | C20H20N4O | 333.3 | 10.8 | 100 | Example 1 |
| 277 | 1-0281 | C20H20N4S | 349.1 | 12.6 | 99 | Example 2 |
| 278 | 1-0288 | C15H18N4O | 271.1 | 8.9 | 100 | Example 90 |
| 279 | 1-0289 | C15H18N4S | 287.1 | 10.9 | 100 | Example 2 |

TABLE 219

| Example | Compound No. | Compositional formula | ESI/MS m/e | HPLC (min) | Purity (%) | Synthesis method |
|---|---|---|---|---|---|---|
| 280 | 1-0292 | C21H20N4O | 345.2 | 11.0 | 99 | Example 90 |
| 281 | 1-0293 | C21H20N4S | 361.2 | 12.9 | 76 | Example 2 |
| 282 | 1-0294 | C16H18N4O | 283.2 | 9.2 | 100 | Example 90 |
| 283 | 1-0295 | C16H18N4S | 299.2 | 11.4 | 57 | Example 2 |
| 284 | 1-0296 | C18H16N4O2 | 321.1 | 7.9 | 100 | Example 90 |
| 285 | 1-0297 | C18H16N4OS | 337.3 | 9.7 | 100 | Example 2 |
| 286 | 1-0298 | C13H14N4O2 | 259.2 | 5.6 | 100 | Example 90 |
| 287 | 1-0299 | C18H16N4O3 | 337.3 | 7.6 | 98 | Example 2 |
| 288 | 1-0300 | C14H10N4O | 251.2 | 7.0 | 100 | Example 1 |
| 289 | 1-0301 | C14H10N4S | 267.1 | 8.8 | 100 | Example 2 |
| 290 | 1-0302 | C18H18N4O | 307.0 | 9.6 | 89 | Example 90 |
| 291 | 1-0303 | C17H14N4O | 291.2 | 8.4 | 98 | Example 90 |
| 292 | 1-0304 | C17H14N4S | 307.2 | 10.0 | 90 | Example 2 |
| 293 | 1-0305 | C21H16N4O | 341.4 | 9.7 | 94 | Example 90 |
| 294 | 1-0306 | C22H18N4O | 355.2 | 10.2 | 87 | Example 90 |
| 295 | 1-0307 | C20H14N4O | 327.1 | 9.4 | 100 | Example 1 |
| 296 | 1-0308 | C20H14N4S | 343.1 | 10.9 | 93 | Example 2 |
| 297 | 1-0310 | C15H12N4S | 281.2 | 9.3 | 100 | Example 2 |
| 298 | 1-0311 | C21H16N4O | 341.2 | 9.8 | 100 | Example 1 |
| 299 | 1-0312 | C21H16N4S | 357.1 | 11.6 | 100 | Example 2 |
| 300 | 1-0313 | C16H14N4O | 279.1 | 8.0 | 79 | Example 90 |
| 301 | 1-0314 | C16H14N4S | 295.0 | 9.9 | 100 | Example 2 |
| 302 | 1-0315 | C20H22N4O | 335.4 | 10.7 | 86 | Example 90 |
| 303 | 1-0316 | C20H22N4S | 351.0 | 12.5 | 95 | Example 2 |
| 304 | 1-0317 | C19H18N4S | 335.2 | 11.4 | 90 | Example 2 |
| 305 | 1-0318 | C23H20N4O | 369.4 | 10.7 | 89 | Example 90 |
| 306 | 1-0319 | C24H22N4S | 399.2 | 12.7 | 91 | Example 2 |
| 307 | 1-0320 | C22H18N4O | 355.1 | 10.4 | 100 | Example 1 |
| 308 | 1-0321 | C22H18N4S | 371.1 | 12.1 | 97 | Example 2 |
| 309 | 1-0322 | C17H16N4O | 293.1 | 8.7 | 97 | Example 90 |
| 310 | 1-0323 | C17H16N4S | 309.3 | 10.5 | 100 | Example 2 |
| 311 | 1-0324 | C19H18N4O | 319.2 | 9.6 | 64 | Example 90 |
| 312 | 1-0325 | C24H22N4O | 383.2 | 11.2 | 60 | Example 90 |
| 313 | 1-0326 | C23H20N4O | 369.3 | 11.1 | 97 | Example 90 |
| 314 | 1-0327 | C27H20N4O | 417.2 | 11.3 | 99 | Example 90 |
| 315 | 1-0328 | C27H20N4S | 433.1 | 12.5 | 100 | Example 2 |
| 316 | 1-0329 | C14H8BrClN4O | 365.3 | 9.5 | 95 | Example 1 |
| 317 | 1-0334 | C20H13FN4O | 345.2 | 9.6 | 98 | Example 90 |

TABLE 220

| Example | Compound No. | Compositional formula | ESI/MS m/e | HPLC (min) | Purity (%) | Synthesis method |
|---|---|---|---|---|---|---|
| 318 | 1-0345 | C21H16N4O2 | 357.2 | 9.4 | 96 | Example 90 |
| 319 | 1-0346 | C21H15FN4O | 359.1 | 9.9 | 89 | Example 90 |
| 320 | 1-0349 | C21H15ClN4O | 375.1 | 10.6 | 90 | Example 90 |
| 321 | 1-0362 | C22H18N4O2 | 371.2 | 9.6 | 91 | Example 90 |
| 322 | 1-0369 | C19H20N4O2 | 337.4 | 10.1 | 62 | Example 90 |
| 323 | 1-0370 | C22H18N4O2 | 371.4 | 10.2 | 91 | Example 90 |
| 324 | 1-0371 | C21H16N4O2 | 357.1 | 9.7 | 98 | Example 90 |
| 325 | 1-0372 | C21H16N4OS | 373.1 | 11.3 | 100 | Example 2 |
| 326 | 1-0393 | C18H12N4O2 | 317.1 | 8.6 | 100 | Example 1 |
| 327 | 1-0394 | C18H12N4OS | 333.1 | 10.2 | 100 | Example 2 |
| 328 | 1-0395 | C13H10N4O2 | 255.1 | 6.6 | 100 | Example 90 |
| 329 | 1-0396 | C13H10N4OS | 271.1 | 8.4 | 100 | Example 2 |
| 330 | 1-0397 | C18H12N4O2 | 333.2 | 9.1 | 91 | Example 1 |
| 331 | 1-0398 | C13H10N4OS | 271.1 | 7.1 | 97 | Example 90 |
| 332 | 1-0399 | C19H14N4O2 | 331.2 | 9.3 | 99 | Example 1 |
| 333 | 1-0400 | C14H12N4O2 | 269.1 | 7.5 | 83 | Example 90 |
| 334 | 1-0415 | C19H14N4OS | 347.1 | 9.5 | 98 | Example 1 |
| 335 | 1-0416 | C19H14N4S2 | 363.1 | 11.2 | 96 | Example 2 |
| 336 | 1-0417 | C14H12N4OS | 285.2 | 7.6 | 96 | Example 90 |
| 337 | 1-0438 | C16H10N4O | 275.1 | 7.7 | 100 | Example 1 |
| 338 | 1-0010 | C14H10N4S | 267.1 | 7.9 | 100 | Example 80 |
| 339 | 1-0011 | C14H10N4S | 267.2 | 8.5 | 100 | Example 80 |
| 340 | 1-0019 | C15H12N4S | 281.1 | 8.7 | 100 | Example 80 |
| 341 | 1-0027 | C13H7ClN4S | 286.9 | 8.8 | 100 | Example 80 |
| 342 | 1-0030 | C13H7ClN4S | 287.1 | 8.9 | 98 | Example 80 |
| 343 | 1-0032 | C13H6Cl2N4S | 320.8 | 8.8 | 98 | Example 80 |
| 344 | 1-0034 | C13H6Cl2N4S | 320.9 | 8.8 | 95 | Example 80 |

TABLE 220-continued

| Example | Compound No. | Compositional formula | ESI/MS m/e | HPLC (min) | Purity (%) | Synthesis method |
|---|---|---|---|---|---|---|
| 345 | 1-0165 | C17H17N5O | 308.3 | 5.3 | 95 | Example 22 |
| 346 | 1-0250 | C19H19ClN4OS | 387.2 | 11.5 | 95 | Example 2 |
| 347 | 1-0460 | C15H11F2N5S | 332.2 | 5.2 | 97 | Example 69 |
| 348 | 1-0473 | C17H15FN4OS | 343.3 | 10.1 | 95 | Example 2 |
| 349 | 1-0476 | C16H16N4O2S | 329.3 | 9.9 | 90 | Example 2 |
| 350 | 1-0477 | C16H16N4OS2 | 345.2 | 10.3 | 90 | Example 2 |
| 351 | 1-0493 | C24H18N6OS | 439.2 | 12.4 | 99 | Example 108 |
| 352 | 1-0497 | C23H15FN6OS | 443.3 | 11.9 | 99 | Example 108 |
| 353 | 1-0499 | C19H15N5O2S | 378.2 | 7.5 | 98 | Example 74 |
| 354 | 1-0509 | C17H15ClN4OS | 359.1 | 10.0 | 95 | Example 2 |
| 355 | 1-0510 | C17H15ClN4OS | 359.2 | 10.6 | 95 | Example 2 |

TABLE 221

| Example | Compound No. | Compositional formula | ESI/MS m/e | HPLC (min) | Purity (%) | Synthesis method |
|---|---|---|---|---|---|---|
| 356 | 1-0511 | C13H16N4OS | 277.4 | 8.6 | 93 | Example 2 |
| 357 | 1-0512 | C20H22N4OS | 367.3 | 11.5 | 80 | Example 2 |
| 358 | 1-0514 | C19H19FN4OS | 371.3 | 11.0 | 87 | Example 2 |
| 359 | 1-0515 | C19H20N4O2S | 369.2 | 9.5 | 98 | Example 94 |
| 360 | 1-0516 | C17H18N4OS2 | 359.2 | 11.3 | 100 | Example 2 |
| 361 | 1-0517 | C17H18N4OS2 | 359.2 | 11.3 | 96 | Example 2 |
| 362 | 1-0518 | C17H18N4OS | 343.3 | 11.2 | 99 | Example 2 |
| 363 | 1-0519 | C18H20N4O2S | 357.2 | 11.0 | 95 | Example 2 |
| 364 | 1-0521 | C18H20N4OS2 | 373.2 | 11.3 | 90 | Example 2 |
| 365 | 1-0524 | C17H18N4O2S | 343.3 | 11.1 | 97 | Example 2 |
| 366 | 1-0526 | C19H18F2N4OS | 389.3 | 11.1 | 99 | Example 2 |
| 367 | 1-0532 | C23H25N5O4S | 468.3 | 9.2 | 100 | Example 101 |
| 368 | 1-0533 | C23H25N5O4S | 468.3 | 9.2 | 100 | Example 101 |
| 369 | 1-0534 | C24H29N5O4S | 484.3 | 9.6 | 98 | Example 101 |
| 370 | 1-0535 | C23H28N6O2S | 453.3 | 6.4 | 100 | Example 101 |
| 371 | 1-0543 | C23H18N4O3S | 431.2 | 9.7 | 91 | Example 106 |
| 372 | 1-0549 | C24H20N4O3S | 445.4 | 11.7 | 100 | Example 106 |
| 373 | 1-0555 | C24H22N4OS | 415.3 | 12.6 | 92 | Example 106 |
| 374 | 1-0567 | C22H25N5O2S | 424.4 | 6.5 | 94 | Example 106 |
| 375 | 1-0573 | C21H24N4O3S | 413.5 | 9.3 | 97 | Example 106 |
| 376 | 1-0585 | C25H20N6OS | 453.3 | 12.7 | 96 | Example 108 |
| 377 | 1-0586 | C24H18N6OS | 439.3 | 12.0 | 92 | Example 108 |
| 378 | 1-0587 | C24H17FN6OS | 457.2 | 12.2 | 91 | Example 108 |
| 379 | 1-0588 | C22H22N6O3S2 | 483.3 | 9.9 | 91 | Example 108 |
| 380 | 1-0593 | C15H12N4S | 281.3 | 9.6 | 95 | Example 2 |
| 381 | 1-0595 | C14H9FN4S | 285.3 | 9.0 | 95 | Example 2 |
| 382 | 1-0596 | C14H9ClN4S | 301.1 | 9.6 | 95 | Example 2 |
| 383 | 1-0601 | C12H8N4S2 | 273.1 | 9.2 | 100 | Example 2 |
| 384 | 1-0602 | C12H8N4S2 | 273.2 | 9.1 | 99 | Example 2 |
| 385 | 1-0607 | C12H8N4OS | 257.4 | 8.6 | 74 | Example 2 |
| 386 | 1-0608 | C14H16N4S | 273.2 | 10.1 | 95 | Example 2 |
| 387 | 1-0609 | C13H10N4OS | 271.1 | 9.0 | 90 | Example 2 |
| 388 | 1-0610 | C13H10N4S2 | 287.2 | 9.4 | 90 | Example 2 |
| 389 | 1-0612 | C12H8N4OS | 257.2 | 8.5 | 99 | Example 2 |
| 390 | 1-0667 | C20H13ClN4S | 377.1 | 11.2 | 95 | Example 2 |
| 391 | 1-0668 | C21H15ClN4S | 391.2 | 12.1 | 95 | Example 2 |
| 392 | 1-0671 | C14H10N4S | 267.1 | 8.5 | 99 | Example 80 |
| 393 | 1-0672 | C15H12N4S | 281.3 | 8.3 | 94 | Example 80 |

TABLE 222

| Example | Compound No. | Compositional formula | ESI/MS m/e | HPLC (min) | Purity (%) | Synthesis method |
|---|---|---|---|---|---|---|
| 394 | 1-0673 | C15H12N4S | 281.4 | 9.4 | 73 | Example 80 |
| 395 | 1-0674 | C17H16N4S | 309.4 | 9.3 | 100 | Example 2 |
| 396 | 1-0675 | C19H18N4S | 335.1 | 12.0 | 98 | Example 80 |
| 397 | 1-0676 | C13H7FN4S | 271.0 | 7.4 | 99 | Example 80 |
| 398 | 1-0678 | C13H7FN4S | 271.0 | 8.0 | 100 | Example 80 |
| 399 | 1-0679 | C13H7FN4S | 271.2 | 7.9 | 100 | Example 80 |
| 400 | 1-0680 | C13H6Cl2N4S | 323.0 | 10.6 | 96 | Example 80 |
| 401 | 1-0681 | C14H10N4OS | 283.1 | 8.0 | 100 | Example 80 |
| 402 | 1-0682 | C14H10N4OS | 283.1 | 7.8 | 100 | Example 80 |
| 403 | 1-0683 | C15H12N4O2S | 313.1 | 7.5 | 98 | Example 80 |
| 404 | 1-0684 | C15H12N4O2S | 313.1 | 8.3 | 99 | Example 80 |
| 405 | 1-0685 | C16H14N4O3S | 343.4 | 9.0 | 100 | Example 2 |
| 406 | 1-0686 | C14H8N4OS | 281.2 | 6.8 | 96 | Example 2 |
| 407 | 1-0689 | C14H7F3N4S | 321.1 | 9.4 | 100 | Example 80 |
| 408 | 1-0690 | C14H7F3N4S | 321.2 | 9.5 | 100 | Example 80 |
| 409 | 1-0691 | C15H6F6N4S | 389.2 | 9.6 | 100 | Example 2 |
| 410 | 1-0692 | C15H10N4OS | 295.2 | 7.1 | 100 | Example 2 |
| 411 | 1-0693 | C15H10N4OS | 295.3 | 7.1 | 99 | Example 80 |
| 412 | 1-0694 | C14H7F3N4OS | 337.4 | 8.6 | 98 | Example 2 |
| 413 | 1-0695 | C14H7F3N4OS | 337.4 | 8.6 | 99 | Example 2 |
| 414 | 1-0696 | C14H7N5S | 278.2 | 7.3 | 100 | Example 80 |
| 415 | 1-0697 | C15H13N5S | 296.2 | 8.0 | 100 | Example 80 |
| 416 | 1-0699 | C14H10N4OS | 283.4 | 5.6 | 99 | Example 2 |
| 417 | 1-0700 | C14H10N4OS | 283.4 | 5.4 | 100 | Example 2 |
| 418 | 1-0701 | C14H10N4S2 | 299.2 | 8.8 | 100 | Example 80 |
| 419 | 1-0702 | C15H12N4O2S2 | 345.2 | 6.8 | 86 | Example 2 |
| 420 | 1-0703 | C14H8N4O2S | 297.1 | 7.6 | 96 | Example 80 |
| 421 | 1-0704 | C19H10N4OS | 343.3 | 10.4 | 97 | Example 80 |
| 422 | 1-0705 | C17H10N4S | 303.0 | 9.4 | 96 | Example 80 |
| 423 | 1-0706 | C17H10N4S | 303.4 | 7.8 | 100 | Example 2 |
| 424 | 1-0707 | C21H12N4S | 353.2 | 10.0 | 98 | Example 80 |
| 425 | 1-0708 | C11H6N4S2 | 259.1 | 7.4 | 98 | Example 80 |
| 426 | 1-0709 | C12H8N4S2 | 273.0 | 8.1 | 99 | Example 80 |
| 427 | 1-0710 | C15H8N4OS | 293.3 | 9.0 | 98 | Example 2 |
| 428 | 1-0715 | C16H12N4O2S | 325.5 | 8.8 | 95 | Example 81 |
| 429 | 1-0721 | C14H9FN4S | 285.5 | 8.9 | 89 | Example 81 |
| 430 | 1-0722 | C13H6F2N4S | 289.5 | 8.5 | 100 | Example 81 |
| 431 | 1-0723 | C13H6F2N4S | 289.5 | 8.5 | 96 | Example 81 |

TABLE 223

| Example | Compound No. | Compositional formula | ESI/MS m/e | HPLC (min) | Purity (%) | Synthesis method |
|---|---|---|---|---|---|---|
| 432 | 1-0724 | C13H6F2N4S | 289.5 | 7.8 | 100 | Example 81 |
| 433 | 1-0725 | C13H6F2N4S | 289.5 | 7.8 | 100 | Example 81 |
| 434 | 1-0726 | C16H13N5OS | 324.5 | 6.1 | 100 | Example 81 |
| 435 | 1-0727 | C15H13N5S | 296.5 | 6.6 | 95 | Example 81 |
| 436 | 1-0728 | C15H12N4OS | 297.5 | 8.8 | 100 | Example 81 |
| 437 | 1-0729 | C15H12N4OS | 297.5 | 8.6 | 100 | Example 81 |
| 438 | 1-0730 | C15H12N4OS | 297.5 | 9.1 | 36 | Example 81 |
| 439 | 1-0731 | C15H12N4OS | 297.5 | 9.0 | 65 | Example 81 |
| 440 | 1-0732 | C15H12N4OS | 297.5 | 8.8 | 100 | Example 81 |
| 441 | 1-0733 | C14H10N4S2 | 299.5 | 8.9 | 88 | Example 81 |
| 442 | 1-0734 | C14H9FN4OS | 301.5 | 7.5 | 90 | Example 81 |
| 443 | 1-0735 | C14H9ClN4S | 301.5 | 8.9 | 100 | Example 81 |
| 444 | 1-0736 | C14H9ClN4OS | 317.5 | 8.9 | 97 | Example 81 |
| 445 | 1-0738 | C14H9FN4S | 285.4 | 8.2 | 99 | Example 80 |
| 446 | 1-0739 | C14H9FN4S | 285.3 | 8.3 | 99 | Example 80 |
| 447 | 1-0740 | C14H9FN4S | 285.1 | 8.2 | 100 | Example 80 |
| 448 | 1-0741 | C15H12N4OS | 297.4 | 8.0 | 100 | Example 80 |
| 449 | 1-0742 | C13H6Cl2N4S | 321.4 | 10.1 | 95 | Example 81 |
| 450 | 1-0748 | C15H12N4OS | 281.4 | 8.5 | 100 | Example 80 |
| 451 | 1-0749 | C12H8N4S2 | 273.3 | 8.2 | 98 | Example 80 |
| 452 | 1-0750 | C12H7N5S | 254.4 | 4.0 | 99 | Example 80 |
| 453 | 1-0752 | C15H12N4OS | 297.5 | 8.1 | 100 | Example 81 |
| 454 | 1-0759 | C20H21N5OS | 380.1 | 6.0 | 89 | Example 106 |
| 455 | 1-0760 | C13H12N4S | 257.5 | 7.2 | 85 | Example 2 |
| 456 | 1-0860 | C19H18F2N4O2 | 373.2 | 9.0 | 100 | Example 1 |
| 457 | 1-0926 | C15H12N4O | 265.2 | 7.6 | 95 | Example 3 |
| 458 | 1-0941 | C14H16N4O | 257.4 | 8.1 | 95 | Example 3 |
| 459 | 1-1065 | C23H20N4O2 | 385.3 | 10.4 | 97 | Example 1 |
| 460 | 1-1066 | C17H15ClN4O2 | 343.3 | 8.2 | 95 | Example 3 |
| 461 | 1-1067 | C14H9ClN4O | 285.2 | 7.6 | 95 | Example 3 |
| 462 | 1-1068 | C19H19ClN4O2 | 371.3 | 9.6 | 95 | Example 3 |
| 463 | 1-1069 | C17H15ClN4O2 | 343.3 | 8.7 | 95 | Example 3 |
| 464 | 1-1070 | C21H15ClN4O | 375.1 | 10.3 | 95 | Example 3 |
| 465 | 1-1071 | C20H13ClN4O | 361.3 | 9.7 | 95 | Example 3 |

TABLE 223-continued

| Example | Compound No. | Compositional formula | ESI/MS m/e | HPLC (min) | Purity (%) | Synthesis method |
|---|---|---|---|---|---|---|
| 466 | 1-1072 | C13H15BrN4O2 | 339.4 | 8.2 | 98 | Example 20 |
| 467 | 1-1073 | C33H32N4O4 | 549.5 | 13.4 | 99 | Example 1 |
| 468 | 1-1074 | C18H18N4O2 | 323.3 | 8.2 | 95 | Example 3 |
| 469 | 1-1075 | C23H20N4OS | 401.3 | 12.3 | 100 | Example 106 |

TABLE 224

| Example | Compound No. | Compositional formula | ESI/MS m/e | HPLC (min) | Purity (%) | Synthesis method |
|---|---|---|---|---|---|---|
| 470 | 1-1076 | C18H18N4OS | 339.4 | 10.0 | 95 | Example 2 |

TABLE 225

| Example | Compound No. | Compositional formula | ESI/MS m/e | HPLC (min) | Purity (%) | Synthesis method |
|---|---|---|---|---|---|---|
| 471 | 2-0010 | C22H16ClN5O2 | 418.2 | 8.6 | 100 | Example 68 |
| 472 | 2-0015 | C22H16ClN5O2 | 418.3 | 8.7 | 100 | Example 68 |
| 473 | 2-0016 | C23H16N6O2 | 409.3 | 7.6 | 95 | Example 68 |
| 474 | 2-0017 | C22H16N6O4 | 429.2 | 8.0 | 100 | Example 68 |
| 475 | 2-0018 | C22H16N6O4 | 429.2 | 8.1 | 99 | Example 68 |
| 476 | 2-0019 | C23H19N5O3 | 414.3 | 7.7 | 95 | Example 68 |
| 477 | 2-0026 | C24H19N5O4 | 442.3 | 7.9 | 95 | Example 68 |
| 478 | 2-0031 | C20H15N5O3 | 374.1 | 6.6 | 100 | Example 68 |
| 479 | 2-0032 | C20H15N5O2S | 390.2 | 7.4 | 98 | Example 68 |
| 480 | 2-0033 | C21H16N6O2 | 385.2 | 5.2 | 100 | Example 68 |
| 481 | 2-0034 | C21H16N6O2 | 385.2 | 5.2 | 100 | Example 68 |
| 482 | 2-0035 | C20H14N6O5 | 419.2 | 7.4 | 100 | Example 68 |
| 483 | 2-0036 | C21H18N6O3 | 403.3 | 7.1 | 99 | Example 68 |
| 484 | 2-0037 | C27H20ClN5O4S2 | 578.2 | 9.8 | 99 | Example 68 |
| 485 | 2-0058 | C25H22ClN5O3 | 476.2 | 10.0 | 85 | Example 68 |
| 486 | 2-0059 | C22H23N5O2 | 390.3 | 8.0 | 96 | Example 68 |
| 487 | 2-0060 | C23H19N5O2 | 398.2 | 8.0 | 100 | Example 68 |
| 488 | 2-0061 | C23H18ClN5O2 | 432.2 | 8.3 | 99 | Example 68 |
| 489 | 2-0062 | C23H18ClN5O2 | 432.2 | 9.0 | 100 | Example 68 |
| 490 | 2-0063 | C23H18ClN5O2 | 432.2 | 9.0 | 100 | Example 68 |
| 491 | 2-0072 | C24H18N6O2 | 423.3 | 8.0 | 100 | Example 68 |
| 492 | 2-0073 | C23H18N6O4 | 443.3 | 7.8 | 93 | Example 68 |
| 493 | 2-0074 | C23H18N6O4 | 443.3 | 8.4 | 100 | Example 68 |
| 494 | 2-0075 | C23H18N6O4 | 443.3 | 8.5 | 98 | Example 68 |
| 495 | 2-0092 | C25H21N5O4 | 456.2 | 8.2 | 98 | Example 68 |
| 496 | 2-0093 | C22H18N6O2 | 399.3 | 5.5 | 100 | Example 68 |
| 497 | 2-0096 | C22H18N6O2 | 399.2 | 5.5 | 100 | Example 68 |
| 498 | 2-0117 | C22H20N6O3 | 417.3 | 7.4 | 100 | Example 68 |
| 499 | 2-0146 | C24H20FN5O2 | 430.2 | 8.4 | 80 | Example 68 |
| 500 | 2-0147 | C22H19N5O2S | 418.3 | 7.9 | 79 | Example 68 |
| 501 | 2-0156 | C26H24ClN5O3 | 490.3 | 10.5 | 100 | Example 68 |
| 502 | 2-0208 | C21H23N5O3 | 394.3 | 9.1 | 97 | Example 7 |
| 503 | 2-0507 | C17H14N4O3 | 323.1 | 7.4 | 100 | Example 6 |
| 504 | 2-0509 | C22H15ClN4O3 | 419.2 | 10.3 | 99 | Example 6 |
| 505 | 2-0514 | C24H18N4O5 | 443.2 | 9.5 | 89 | Example 6 |
| 506 | 2-0519 | C18H16N4O3 | 337.3 | 7.6 | 100 | Example 1 |
| 507 | 2-0520 | C22H22N4O3 | 391.2 | 10.1 | 95 | Example 6 |
| 508 | 2-0521 | C23H18N4O3 | 399.3 | 9.6 | 100 | Example 6 |

TABLE 226

| Example | Compound No. | Compositional formula | ESI/MS m/e | HPLC (min) | Purity (%) | Synthesis method |
|---|---|---|---|---|---|---|
| 509 | 2-0522 | C23H17ClN4O3 | 433.2 | 9.9 | 100 | Example 6 |
| 510 | 2-0523 | C23H17ClN4O3 | 433.2 | 10.6 | 100 | Example 6 |
| 511 | 2-0524 | C23H17ClN4O3 | 433.1 | 10.7 | 92 | Example 6 |
| 512 | 2-0525 | C24H17N5O3 | 424.2 | 9.3 | 100 | Example 6 |
| 513 | 2-0526 | C23H17N5O5 | 444.2 | 9.6 | 100 | Example 6 |
| 514 | 2-0527 | C23H17N5O5 | 444.3 | 9.8 | 100 | Example 6 |
| 515 | 2-0528 | C24H20N4O4 | 429.2 | 9.6 | 98 | Example 6 |
| 516 | 2-0529 | C25H20N4O5 | 457.2 | 9.7 | 99 | Example 6 |
| 517 | 2-0530 | C21H16N4O4 | 389.1 | 8.3 | 100 | Example 6 |
| 518 | 2-0531 | C21H16N4O3S | 405.1 | 9.2 | 100 | Example 6 |
| 519 | 2-0536 | C22H17N5O3 | 400.2 | 6.6 | 89 | Example 6 |
| 520 | 2-0537 | C22H17N5O3 | 400.3 | 6.5 | 100 | Example 6 |
| 521 | 2-0538 | C21H15N5O6 | 434.2 | 8.9 | 100 | Example 6 |
| 522 | 2-0539 | C22H19N5O4 | 418.2 | 8.8 | 100 | Example 6 |
| 523 | 2-0552 | C17H15N5OS | 338.3 | 6.6 | 97 | Example 69 |

TABLE 226-continued

| Example | Compound No. | Compositional formula | ESI/MS m/e | HPLC (min) | Purity (%) | Synthesis method |
|---|---|---|---|---|---|---|
| 524 | 2-0557 | C24H21N5OS | 428.5 | 9.7 | 100 | Example 69 |
| 525 | 2-0559 | C21H17N5O2S | 404.5 | 8.9 | 96 | Example 69 |
| 526 | 2-0560 | C21H17N5OS2 | 420.3 | 9.1 | 100 | Example 71 |
| 527 | 2-0561 | C20H14ClN5OS2 | 440.1 | 9.1 | 95 | Example 71 |
| 528 | 2-0562 | C21H18N6OS | 403.2 | 8.6 | 93 | Example 69 |
| 529 | 2-0563 | C22H16ClN5OS | 434.3 | 9.2 | 95 | Example 69 |
| 530 | 2-0568 | C22H16ClN5OS | 434.3 | 9.9 | 94 | Example 69 |
| 531 | 2-0573 | C22H16ClN5OS | 434.4 | 9.9 | 94 | Example 69 |
| 532 | 2-0578 | C22H16FN5OS | 418.4 | 9.3 | 98 | Example 69 |
| 533 | 2-0586 | C23H19N5OS | 414.5 | 9.3 | 98 | Example 69 |
| 534 | 2-0590 | C23H19N5O2S | 430.2 | 9.1 | 91 | Example 69 |
| 535 | 2-0595 | C23H19N5O2S | 430.4 | 8.9 | 95 | Example 69 |
| 536 | 2-0596 | C22H19N5O3S | 434.3 | 8.9 | 95 | Example 69 |
| 537 | 2-0597 | C22H19N5O2S2 | 450.2 | 9.1 | 97 | Example 71 |
| 538 | 2-0598 | C21H16ClN5O2S2 | 470.1 | 9.2 | 99 | Example 71 |
| 539 | 2-0599 | C22H20N6O2S | 433.2 | 8.6 | 95 | Example 69 |
| 540 | 2-0607 | C27H22N6O3S2 | 543.5 | 10.5 | 95 | Example 71 |
| 541 | 2-0614 | C22H18N6OS | 415.2 | 8.3 | 96 | Example 71 |
| 542 | 2-0616 | C21H18N6OS2 | 435.3 | 8.5 | 93 | Example 71 |
| 543 | 2-0617 | C20H15ClN6OS2 | 455.0 | 8.6 | 98 | Example 71 |
| 544 | 2-0618 | C21H19N7OS | 418.2 | 7.9 | 99 | Example 69 |
| 545 | 2-0621 | C23H20N6OS | 429.2 | 9.1 | 99 | Example 71 |
| 546 | 2-0623 | C22H20N6OS2 | 449.1 | 9.2 | 99 | Example 71 |

TABLE 227

| Example | Compound No. | Compositional formula | ESI/MS m/e | HPLC (min) | Purity (%) | Synthesis method |
|---|---|---|---|---|---|---|
| 547 | 2-0624 | C21H17ClN6OS2 | 469.2 | 9.3 | 95 | Example 71 |
| 548 | 2-0625 | C22H21N7OS | 432.2 | 8.7 | 96 | Example 69 |
| 549 | 2-0642 | C22H17FN6OS | 433.2 | 9.4 | 100 | Example 71 |
| 550 | 2-0643 | C21H17FN6O2S | 437.1 | 9.3 | 96 | Example 71 |
| 551 | 2-0644 | C21H17FN6OS2 | 453.2 | 9.5 | 92 | Example 71 |
| 552 | 2-0645 | C20H14ClFN6OS2 | 473.1 | 9.6 | 92 | Example 71 |
| 553 | 2-0646 | C21H18FN7OS | 436.3 | 9.1 | 93 | Example 69 |
| 554 | 2-0656 | C23H19N5O2S | 430.5 | 11.1 | 100 | Example 71 |
| 555 | 2-0671 | C23H19N5O2S | 430.4 | 10.5 | 100 | Example 71 |
| 556 | 2-0682 | C23H16N6OS | 425.4 | 8.8 | 98 | Example 69 |
| 557 | 2-0687 | C23H16N6OS | 425.4 | 8.9 | 98 | Example 69 |
| 558 | 2-0688 | C22H17N5O2S | 416.5 | 9.8 | 94 | Example 71 |
| 559 | 2-0694 | C21H16FN5O2S | 422.4 | 9.3 | 97 | Example 69 |
| 560 | 2-0695 | C21H16FN5O2S | 438.2 | 9.4 | 96 | Example 71 |
| 561 | 2-0696 | C20H13ClFN5O2S | 458.0 | 9.5 | 96 | Example 71 |
| 562 | 2-0697 | C21H17FN6OS | 421.2 | 9.0 | 93 | Example 69 |
| 563 | 2-0698 | C23H19N5O2S | 430.0 | 9.2 | 97 | Example 69 |
| 564 | 2-0703 | C22H16N6O4S | 461.0 | 8.8 | 98 | Example 71 |
| 565 | 2-0706 | C23H16F3N5O2S | 484.2 | 10.7 | 97 | Example 69 |
| 566 | 2-0708 | C22H16N6O3S | 445.6 | 8.8 | 98 | Example 69 |
| 567 | 2-0710 | C24H21N5O3S | 460.4 | 9.3 | 99 | Example 69 |
| 568 | 2-0731 | C22H16N6O3S | 445.6 | 9.3 | 98 | Example 69 |
| 569 | 2-0740 | C23H17N5O3S | 444.3 | 8.8 | 98 | Example 69 |
| 570 | 2-0743 | C21H14ClN5O3S2 | 484.0 | 9.1 | 96 | Example 71 |
| 571 | 2-0761 | C22H16N6O3S | 445.6 | 9.4 | 97 | Example 69 |
| 572 | 2-0772 | C23H17N5O3S | 444.4 | 7.7 | 97 | Example 69 |
| 573 | 2-0773 | C22H17N5O4S | 448.4 | 7.7 | 90 | Example 69 |
| 574 | 2-0777 | C22H17N5O2S | 416.3 | 7.7 | 79 | Example 71 |
| 575 | 2-0782 | C22H18N6O3S2 | 479.1 | 7.4 | 87 | Example 71 |
| 576 | 2-0787 | C22H17N5O2S | 416.5 | 7.5 | 98 | Example 71 |
| 577 | 2-0790 | C20H14ClN5O2S2 | 456.1 | 7.9 | 91 | Example 71 |
| 578 | 2-0815 | C23H16F3N5OS | 468.3 | 10.5 | 95 | Example 69 |
| 579 | 2-0817 | C23H19N5OS | 414.4 | 9.5 | 96 | Example 69 |
| 580 | 2-0823 | C21H17N5OS2 | 420.2 | 9.3 | 90 | Example 71 |
| 581 | 2-0834 | C22H15F2N5OS | 436.4 | 9.6 | 98 | Example 69 |
| 582 | 2-0867 | C23H16F3N5O2S | 484.1 | 10.7 | 98 | Example 69 |
| 583 | 2-0869 | C22H16BrN5OS | 480.4 | 9.4 | 100 | Example 69 |
| 584 | 2-0882 | C22H16BrN5OS | 480.4 | 10.2 | 99 | Example 69 |

TABLE 228

| Example | Compound No. | Compositional formula | ESI/MS m/e | HPLC (min) | Purity (%) | Synthesis method |
|---|---|---|---|---|---|---|
| 585 | 2-0884 | C24H19N5O3S | 458.3 | 9.1 | 95 | Example 69 |
| 586 | 2-0886 | C23H19N5O3S2 | 478.2 | 9.3 | 97 | Example 71 |
| 587 | 2-0887 | C22H16ClN5O3S2 | 498.1 | 9.4 | 97 | Example 71 |
| 588 | 2-0888 | C23H20N6O3S | 461.1 | 8.9 | 95 | Example 69 |
| 589 | 2-0893 | C22H15Cl2N5OS | 468.1 | 11.1 | 97 | Example 69 |
| 590 | 2-1021 | C21H17N5O2S | 404.2 | 8.9 | 96 | Example 71 |
| 591 | 2-1052 | C22H15N7O5S | 490.4 | 10.0 | 96 | Example 69 |
| 592 | 2-1053 | C22H15Cl2N5OS | 468.2 | 10.9 | 98 | Example 69 |
| 593 | 2-1054 | C24H21N5O3S | 460.4 | 8.4 | 97 | Example 69 |
| 594 | 2-1057 | C22H18ClN5O3S2 | 500.2 | 8.7 | 99 | Example 71 |
| 595 | 2-1059 | C24H21N5O3S | 460.3 | 8.4 | 97 | Example 69 |
| 596 | 2-1060 | C22H16FN5OS | 418.4 | 9.1 | 97 | Example 69 |
| 597 | 2-1065 | C23H16F3N5OS | 468.2 | 9.8 | 95 | Example 69 |
| 598 | 2-1066 | C23H16F3N5OS | 468.4 | 10.4 | 93 | Example 69 |
| 599 | 2-1067 | C24H21N5O3S | 460.3 | 9.2 | 97 | Example 69 |
| 600 | 2-1068 | C23H18N6O3S | 459.2 | 9.3 | 98 | Example 71 |
| 601 | 2-1074 | C27H26N6O3S | 515.4 | 12.1 | 86 | Example 71 |
| 602 | 2-1075 | C23H16F3N5O2S | 484.1 | 10.1 | 96 | Example 69 |
| 603 | 2-1076 | C24H20N6O2S | 457.1 | 7.4 | 98 | Example 71 |
| 604 | 2-1079 | C22H17ClN6O2S2 | 497.1 | 7.8 | 93 | Example 71 |
| 605 | 2-1083 | C22H17N5O3S | 432.3 | 8.4 | 96 | Example 71 |
| 606 | 2-1086 | C22H17N5O3S | 432.4 | 8.5 | 88 | Example 71 |
| 607 | 2-1087 | C23H20N6OS | 429.2 | 9.3 | 99 | Example 71 |
| 608 | 2-1094 | C24H22N6OS | 443.4 | 6.6 | 97 | Example 71 |
| 609 | 2-1101 | C24H20N6O2S | 457.1 | 8.8 | 90 | Example 71 |
| 610 | 2-1108 | C24H21N7O2S | 472.2 | 6.7 | 99 | Example 71 |
| 611 | 2-1115 | C23H20N6OS | 429.2 | 7.8 | 99 | Example 71 |
| 612 | 2-1123 | C23H18N6O3S | 459.2 | 9.1 | 86 | Example 71 |
| 613 | 2-1128 | C24H19N5O3S | 458.1 | 9.7 | 98 | Example 71 |
| 614 | 2-1133 | C22H15ClN6O3S | 479.1 | 9.7 | 98 | Example 71 |
| 615 | 2-1134 | C23H19N5OS2 | 446.2 | 9.7 | 99 | Example 71 |
| 616 | 2-1135 | C24H20N6O2S | 457.1 | 7.5 | 96 | Example 71 |
| 617 | 2-1142 | C22H16BrN5OS | 480.4 | 10.2 | 100 | Example 69 |
| 618 | 2-1143 | C22H15F2N5OS | 436.4 | 9.6 | 100 | Example 69 |
| 619 | 2-1144 | C22H14F3N5OS | 454.4 | 10.1 | 100 | Example 69 |
| 620 | 2-1145 | C24H15F6N5OS | 536.4 | 11.1 | 100 | Example 69 |
| 621 | 2-1146 | C23H15F4N5OS | 486.4 | 10.7 | 100 | Example 69 |
| 622 | 2-1148 | C23H15F4N5OS | 486.4 | 9.9 | 100 | Example 69 |

TABLE 229

| Example | Compound No. | Compositional formula | ESI/MS m/e | HPLC (min) | Purity (%) | Synthesis method |
|---|---|---|---|---|---|---|
| 623 | 2-1149 | C23H15F4N5OS | 486.4 | 10.5 | 100 | Example 69 |
| 624 | 2-1150 | C23H15F4N5OS | 486.5 | 10.8 | 100 | Example 69 |
| 625 | 2-1151 | C24H21N5O2S | 444.5 | 9.7 | 100 | Example 69 |
| 626 | 2-1154 | C23H19N5O3S | 446.5 | 7.7 | 87 | Example 71 |
| 627 | 2-1161 | C22H16FN5O2S | 434.5 | 10.7 | 100 | Example 71 |
| 628 | 2-1162 | C22H13F4N5O2S | 488.4 | 8.8 | 84 | Example 71 |
| 629 | 2-1163 | C26H21N7O2S | 496.5 | 7.9 | 78 | Example 71 |
| 630 | 2-1170 | C25H19N7OS | 466.5 | 6.3 | 95 | Example 71 |
| 631 | 2-1177 | C27H26N6O3S | 515.5 | 10.3 | 97 | Example 71 |
| 632 | 2-1188 | C23H19N5O2S | 430.1 | 7.3 | 96 | Example 71 |
| 633 | 2-1195 | C23H20N6O2S | 445.3 | 8.9 | 99 | Example 71 |
| 634 | 2-1202 | C23H17F3N6OS | 483.2 | 10.8 | 98 | Example 71 |
| 635 | 2-1209 | C22H17ClN6OS | 449.2 | 10.3 | 98 | Example 71 |
| 636 | 2-1216 | C22H18N6O2S | 431.2 | 7.0 | 96 | Example 71 |
| 637 | 2-1223 | C23H20N6O2S | 445.4 | 6.9 | 92 | Example 71 |
| 638 | 2-1226 | C22H17FN6OS | 433.2 | 8.6 | 99 | Example 71 |
| 639 | 2-1229 | C22H17ClN6OS | 449.2 | 9.7 | 99 | Example 71 |
| 640 | 2-1232 | C22H17N7O3S | 460.1 | 9.2 | 93 | Example 71 |
| 641 | 2-1240 | C23H20N6OS | 429.3 | 8.2 | 96 | Example 71 |
| 642 | 2-1247 | C22H18N6O2S | 431.1 | 6.0 | 92 | Example 71 |
| 643 | 2-1254 | C22H17ClN6OS | 449.2 | 9.0 | 93 | Example 71 |
| 644 | 2-1261 | C22H17FN6OS | 433.0 | 9.2 | 97 | Example 71 |
| 645 | 2-1268 | C23H20N6O2S | 445.3 | 8.4 | 94 | Example 71 |
| 646 | 2-1282 | C29H21N5O2S | 504.2 | 10.4 | 71 | Example 71 |
| 647 | 2-1283 | C29H21N5O2S | 504.2 | 10.3 | 91 | Example 71 |
| 648 | 2-1284 | C28H25N5O2S | 496.2 | 11.1 | 93 | Example 71 |
| 649 | 2-1345 | C20H19N5O2S | 394.4 | 9.7 | 100 | Example 71 |
| 650 | 2-1346 | C19H17N5O3S | 396.4 | 8.0 | 100 | Example 69 |
| 651 | 2-1347 | C19H17N5OS | 364.1 | 7.7 | 92 | Example 71 |

TABLE 229-continued

| Example | Compound No. | Compositional formula | ESI/MS m/e | HPLC (min) | Purity (%) | Synthesis method |
|---|---|---|---|---|---|---|
| 652 | 2-1348 | C20H15N5O2S | 390.4 | 7.9 | 93 | Example 69 |
| 653 | 2-1350 | C19H15N5O2S2 | 410.1 | 8.2 | 98 | Example 71 |
| 654 | 2-1351 | C18H12ClN5O2S2 | 430.0 | 8.3 | 95 | Example 71 |
| 655 | 2-1352 | C19H16N6O2S | 393.2 | 7.7 | 92 | Example 69 |
| 656 | 2-1353 | C25H18N6OS | 467.5 | 9.4 | 100 | Example 69 |
| 657 | 2-1354 | C23H17N5O2S | 428.5 | 9.9 | 100 | Example 71 |
| 658 | 2-1355 | C24H19N5O2S | 442.5 | 10.4 | 100 | Example 71 |
| 659 | 2-1358 | C20H15N5OS2 | 406.2 | 8.5 | 97 | Example 71 |
| 660 | 2-1365 | C20H16N8OS | 417.2 | 8.1 | 99 | Example 71 |

TABLE 230

| Example | Compound No. | Compositional formula | ESI/MS m/e | HPLC (min) | Purity (%) | Synthesis method |
|---|---|---|---|---|---|---|
| 661 | 2-1377 | C20H15N5OS2 | 406.4 | 8.7 | 94 | Example 69 |
| 662 | 2-1378 | C19H15N5O2S2 | 410.4 | 8.7 | 96 | Example 69 |
| 663 | 2-1379 | C19H15N5OS3 | 426.2 | 8.9 | 97 | Example 71 |
| 664 | 2-1380 | C18H12ClN5OS3 | 446.3 | 9.0 | 96 | Example 71 |
| 665 | 2-1381 | C19H16N6OS2 | 409.2 | 8.4 | 93 | Example 69 |
| 666 | 2-1382 | C20H17N7O2S | 420.2 | 6.9 | 94 | Example 71 |
| 667 | 2-1387 | C21H15N5O3S | 418.1 | 7.7 | 93 | Example 71 |
| 668 | 2-1388 | C21H15N5O3S | 418.2 | 6.7 | 92 | Example 71 |
| 669 | 2-1389 | C22H21N7OS | 432.2 | 8.6 | 96 | Example 71 |
| 670 | 2-1392 | C20H18ClN7OS2 | 472.2 | 8.9 | 95 | Example 71 |
| 671 | 2-1396 | C20H14N6O4S | 435.5 | 8.7 | 94 | Example 69 |
| 672 | 2-1401 | C21H15ClN6OS | 435.3 | 7.9 | 93 | Example 69 |
| 673 | 2-1406 | C22H19N5O2S | 418.5 | 9.5 | 87 | Example 69 |
| 674 | 2-1411 | C22H18N6OS | 447.5 | 8.6 | 96 | Example 69 |
| 675 | 2-1416 | C20H14N6O3S2 | 451.2 | 9.2 | 97 | Example 71 |
| 676 | 2-1417 | C18H13N7OS2 | 408.3 | 7.9 | 83 | Example 69 |
| 677 | 2-1418 | C20H16N6OS | 389.3 | 7.1 | 94 | Example 71 |
| 678 | 2-1423 | C26H19N5OS | 450.2 | 12.5 | 99 | Example 69 |
| 679 | 2-1424 | C21H18N6OS | 403.3 | 9.0 | 98 | Example 69 |
| 680 | 2-1425 | C22H17N5O2S2 | 448.2 | 8.5 | 99 | Example 71 |
| 681 | 2-1426 | C22H19N5O2S2 | 450.3 | 9.4 | 94 | Example 71 |
| 682 | 2-1431 | C20H16N6O2S | 405.4 | 8.6 | 92 | Example 71 |
| 683 | 2-1438 | C20H16N6O2S | 405.3 | 8.2 | 92 | Example 71 |
| 684 | 2-1441 | C18H13ClN6O2S2 | 445.2 | 8.5 | 99 | Example 71 |
| 685 | 2-1445 | C21H17N5OS2 | 420.1 | 9.3 | 95 | Example 71 |
| 686 | 2-1452 | C20H14ClN5OS2 | 440.2 | 9.5 | 97 | Example 71 |
| 687 | 2-1455 | C20H14ClN5OS2 | 440.2 | 10.1 | 99 | Example 71 |
| 688 | 2-1458 | C19H14N8O3S | 435.1 | 7.9 | 97 | Example 71 |
| 689 | 2-1461 | C20H16N6OS | 389.4 | 8.0 | 98 | Example 71 |
| 690 | 2-1463 | C19H16N6OS2 | 409.2 | 8.3 | 95 | Example 71 |
| 691 | 2-1464 | C18H13ClN6OS2 | 429.1 | 8.3 | 97 | Example 71 |
| 692 | 2-1465 | C19H17N7OS | 392.3 | 7.8 | 84 | Example 69 |
| 693 | 2-1466 | C26H18ClFN6O2S | 533.5 | 10.5 | 100 | Example 69 |
| 694 | 2-1467 | C24H17N5OS2 | 456.4 | 10.3 | 100 | Example 69 |
| 695 | 2-1468 | C24H17N7OS | 452.5 | 9.3 | 100 | Example 69 |
| 696 | 2-1469 | C23H20ClN5O3S3 | 546.4 | 9.5 | 97 | Example 69 |
| 697 | 2-1470 | C26H17ClF3N7OS | 568.4 | 11.4 | 98 | Example 69 |
| 698 | 2-1471 | C27H17ClF3N5O2S | 568.4 | 12.8 | 94 | Example 69 |

TABLE 231

| Example | Compound No. | Compositional formula | ESI/MS m/e | HPLC (min) | Purity (%) | Synthesis method |
|---|---|---|---|---|---|---|
| 699 | 2-1472 | C26H19N5OS | 450.5 | 10.3 | 100 | Example 69 |
| 700 | 2-1473 | C24H18N6OS | 439.5 | 8.5 | 100 | Example 71 |
| 701 | 2-1474 | C23H17N7OS | 440.5 | 6.1 | 88 | Example 71 |
| 702 | 2-1479 | C24H18N6OS | 439.5 | 9.7 | 100 | Example 71 |
| 703 | 2-1485 | C24H18N6OS | 439.5 | 8.7 | 100 | Example 71 |
| 704 | 2-1486 | C25H17N5O3S | 468.4 | 9.7 | 91 | Example 71 |
| 705 | 2-1487 | C23H16N6O2S | 441.5 | 9.7 | 100 | Example 71 |
| 706 | 2-1488 | C19H14N8O3S | 435.2 | 7.5 | 98 | Example 71 |
| 707 | 2-1489 | C21H17N5OS3 | 452.2 | 9.8 | 96 | Example 71 |
| 708 | 2-1490 | C20H16N6O2S | 405.1 | 9.6 | 97 | Example 71 |
| 709 | 2-1497 | C24H22N6O2S | 459.1 | 8.0 | 98 | Example 71 |
| 710 | 2-1498 | C20H15N7O3S | 434.1 | 8.2 | 72 | Example 71 |
| 711 | 2-1499 | C21H17N7OS | 416.3 | 6.1 | 45 | Example 71 |
| 712 | 2-1516 | C19H15N7OS | 390.2 | 5.5 | 91 | Example 71 |
| 713 | 2-1521 | C21H16N6OS | 401.5 | 8.4 | 92 | Example 69 |
| 714 | 2-1526 | C21H16N6OS | 401.4 | 6.2 | 97 | Example 69 |
| 715 | 2-1531 | C21H16N6OS | 401.4 | 6.1 | 97 | Example 69 |
| 716 | 2-1532 | C20H16N6O2S | 405.5 | 6.2 | 94 | Example 69 |
| 717 | 2-1534 | C19H13ClN6OS2 | 441.2 | 6.5 | 97 | Example 71 |
| 718 | 2-1589 | C22H23N5OS | 406.3 | 9.5 | 96 | Example 69 |

TABLE 231-continued

| Example | Compound No. | Compositional formula | ESI/MS m/e | HPLC (min) | Purity (%) | Synthesis method |
|---|---|---|---|---|---|---|
| 719 | 2-1601 | C21H18N6O2S | 419.4 | 8.4 | 88 | Example 69 |
| 720 | 2-1662 | C23H19N5OS | 414.3 | 9.0 | 91 | Example 69 |
| 721 | 2-1768 | C23H19N5OS | 414.3 | 9.1 | 95 | Example 2 |
| 722 | 2-1769 | C25H21N5O3S | 472.3 | 9.3 | 95 | Example 2 |
| 723 | 2-1770 | C24H19N5O3S | 458.2 | 7.8 | 95 | Example 114 |
| 724 | 2-1771 | C25H23N5O2S | 458.2 | 7.4 | 88 | Example 107 |
| 725 | 2-1772 | C23H20N6O2S | 445.4 | 7.5 | 84 | Example 107 |
| 726 | 2-1773 | C24H23N5OS | 430.3 | 7.5 | 86 | Example 107 |
| 727 | 2-1774 | C24H23N5O2S2 | 478.2 | 6.8 | 64 | Example 107 |
| 728 | 2-1776 | C22H18N6OS | 415.4 | 9.1 | 94 | Example 70 |
| 729 | 2-1778 | C23H20N6OS | 429.5 | 9.4 | 98 | Example 70 |
| 730 | 2-1779 | C24H20N6O3S | 473.5 | 7.9 | 96 | Example 70 |
| 731 | 2-1780 | C23H29N7S2 | 468.3 | 6.7 | 90 | Example 70 |
| 732 | 2-1781 | C23H27N7S2 | 466.4 | 6.9 | 91 | Example 70 |
| 733 | 2-1782 | C22H25N7O2S2 | 468.5 | 6.4 | 95 | Example 70 |
| 734 | 2-1783 | C23H27N7O2S | 482.5 | 6.3 | 89 | Example 70 |
| 735 | 2-1784 | C24H31N7S2 | 482.4 | 6.8 | 92 | Example 70 |
| 736 | 2-1785 | C24H29N7S2 | 480.4 | 7.1 | 96 | Example 70 |

TABLE 232

| Example | Compound No. | Compositional formula | ESI/MS m/e | HPLC (min) | Purity (%) | Synthesis method |
|---|---|---|---|---|---|---|
| 737 | 2-1786 | C23H27N7OS2 | 482.3 | 6.6 | 98 | Example 70 |
| 738 | 2-1787 | C24H29N7OS2 | 496.4 | 6.5 | 92 | Example 70 |
| 739 | 2-1788 | C19H18N6O3S | 411.3 | 6.3 | 92 | Example 70 |
| 740 | 2-1789 | C19H18N6O3S | 411.4 | 6.5 | 95 | Example 70 |
| 741 | 2-1790 | C20H20N6O3S | 425.4 | 6.5 | 98 | Example 70 |
| 742 | 2-1791 | C21H22N6O3S | 439.4 | 6.7 | 97 | Example 70 |
| 743 | 2-1792 | C23H18N6O2S2 | 475.2 | 8.4 | 93 | Example 70 |
| 744 | 2-1793 | C22H17FN6OS | 433.3 | 9.5 | 92 | Example 70 |
| 745 | 2-1794 | C22H17FN6OS | 433.5 | 9.3 | 89 | Example 70 |
| 746 | 2-1795 | C23H20N6OS | 429.3 | 9.6 | 90 | Example 70 |
| 747 | 2-1796 | C23H20N6OS | 429.4 | 9.2 | 89 | Example 70 |
| 748 | 2-1797 | C23H20N6O2S | 445.6 | 9.4 | 81 | Example 70 |
| 749 | 2-1798 | C26H20N6OS | 465.3 | 9.7 | 87 | Example 70 |
| 750 | 2-1799 | C23H17F3N6OS | 483.4 | 10.7 | 95 | Example 70 |
| 751 | 2-1800 | C23H17F3N6OS | 483.4 | 10.6 | 86 | Example 70 |
| 752 | 2-1801 | C22H17FN6OS | 433.3 | 9.4 | 81 | Example 70 |
| 753 | 2-1802 | C26H20N6OS | 495.5 | 10.3 | 86 | Example 70 |
| 754 | 2-1803 | C18H17N5OS | 352.3 | 6.9 | 89 | Example 69 |
| 755 | 2-1806 | C21H21N5OS | 392.4 | 9.0 | 77 | Example 69 |
| 756 | 2-1807 | C20H15N5O2S | 390.2 | 8.4 | 96 | Example 69 |
| 757 | 2-1808 | C21H17N5O2S | 404.4 | 8.5 | 96 | Example 69 |
| 758 | 2-1809 | C21H17N5O3S | 420.4 | 8.5 | 96 | Example 69 |
| 759 | 2-1810 | C18H13N5O2S2 | 396.4 | 8.2 | 97 | Example 69 |
| 760 | 2-1811 | C19H14N6O2S | 391.3 | 5.7 | 94 | Example 69 |
| 761 | 2-1812 | C20H16N6O2S | 405.4 | 8.6 | 97 | Example 70 |
| 762 | 2-1813 | C22H18N6O3S | 447.5 | 8.3 | 97 | Example 70 |
| 763 | 2-1814 | C21H17N5O2S | 404.3 | 8.8 | 92 | Example 69 |
| 764 | 2-1815 | C22H19N5O2S | 418.3 | 8.9 | 96 | Example 69 |
| 765 | 2-1816 | C22H19N5O3S | 434.4 | 8.8 | 97 | Example 69 |
| 766 | 2-1817 | C19H15N5O2S2 | 410.4 | 8.6 | 96 | Example 69 |
| 767 | 2-1818 | C20H16N6O2S | 405.5 | 6.0 | 93 | Example 69 |
| 768 | 2-1819 | C20H19N5OS | 378.3 | 8.3 | 98 | Example 69 |
| 769 | 2-1820 | C21H17N5OS2 | 420.5 | 8.7 | 74 | Example 69 |
| 770 | 2-1821 | C23H24N6O2S | 449.5 | 6.7 | 90 | Example 69 |
| 771 | 2-1822 | C22H16FN5OS | 418.5 | 9.2 | 95 | Example 69 |
| 772 | 2-1823 | C20H21N5OS | 380.4 | 8.8 | 98 | Example 69 |
| 773 | 2-1824 | C21H16N6O4S | 449.4 | 8.9 | 96 | Example 69 |
| 774 | 2-1825 | C22H16N6O2S | 429.3 | 8.9 | 98 | Example 69 |

TABLE 233

| Example | Compound No. | Compositional formula | ESI/MS m/e | HPLC (min) | Purity (%) | Synthesis method |
|---|---|---|---|---|---|---|
| 775 | 2-1826 | C22H19N5O2S | 418.6 | 9.0 | 97 | Example 69 |
| 776 | 2-1827 | C24H21N5O2S | 444.5 | 8.9 | 96 | Example 69 |
| 777 | 2-1828 | C23H19N5OS | 414.4 | 9.5 | 89 | Example 69 |
| 778 | 2-1829 | C22H17N5O2S | 416.4 | 8.0 | 92 | Example 94 |
| 779 | 2-1830 | C20H19N5O2S | 394.4 | 7.6 | 95 | Example 71 |
| 780 | 2-1831 | C20H17N5O3S | 408.5 | 7.1 | 91 | Example 71 |
| 781 | 2-1832 | C20H19N5O2S | 394.3 | 7.0 | 94 | Example 71 |
| 782 | 2-1833 | C20H18N6O2S | 407.4 | 6.2 | 91 | Example 71 |
| 783 | 2-1834 | C22H21N5O3S | 436.1 | 7.9 | 94 | Example 71 |
| 784 | 2-1835 | C20H14FN5O2S | 408.2 | 8.9 | 97 | Example 69 |

TABLE 233-continued

| Example | Compound No. | Compositional formula | ESI/MS m/e | HPLC (min) | Purity (%) | Synthesis method |
|---|---|---|---|---|---|---|
| 785 | 2-1836 | C22H17N5OS2 | 432.2 | 9.3 | 97 | Example 94 |
| 786 | 2-1837 | C23H25N5O2S | 436.3 | 8.1 | 90 | Example 71 |
| 787 | 2-1838 | C20H19N5O3S | 410.4 | 7.5 | 86 | Example 69 |
| 788 | 2-1839 | C21H21N5O3S | 424.2 | 8.2 | 87 | Example 69 |
| 789 | 2-1840 | C19H20N6OS | 381.1 | 5.7 | 87 | Example 69 |
| 790 | 2-1841 | C24H27N5O3S | 446.2 | 9.3 | 97 | Example 69 |
| 791 | 2-1842 | C24H18N6OS | 439.1 | 8.1 | 95 | Example 72 |
| 792 | 2-1843 | C20H15N7O3S | 434.3 | 6.2 | 93 | Example 71 |
| 793 | 2-1844 | C24H21N5O2S | 444.3 | 9.4 | 95 | Example 71 |
| 794 | 2-1845 | C19H18N6OS2 | 411.2 | 6.1 | 98 | Example 71 |
| 795 | 2-1846 | C19H17N5O2S | 380.1 | 6.9 | 90 | Example 71 |
| 796 | 2-1847 | C20H16N6OS | 389.2 | 8.2 | 87 | Example 71 |
| 797 | 2-1848 | C23H16N6OS | 425.1 | 8.6 | 88 | Example 72 |
| 798 | 2-1850 | C20H20N6OS2 | 425.1 | 6.1 | 93 | Example 71 |
| 799 | 2-1851 | C25H24N6OS | 457.2 | 6.9 | 95 | Example 71 |
| 800 | 2-1852 | C20H19N5O2S | 394.2 | 7.1 | 91 | Example 71 |
| 801 | 2-1853 | C21H18N6OS | 403.2 | 8.5 | 96 | Example 71 |
| 802 | 2-1854 | C25H20N6OS | 453.2 | 8.3 | 96 | Example 72 |
| 803 | 2-1855 | C18H14F3N5OS | 406.2 | 9.8 | 99 | Example 69 |
| 804 | 2-1856 | C23H19N5OS | 414.3 | 8.5 | 98 | Example 69 |
| 805 | 2-1857 | C23H20N6OS | 429.2 | 8.0 | 99 | Example 71 |
| 806 | 2-1858 | C24H22N6OS | 443.3 | 8.9 | 98 | Example 71 |
| 807 | 2-1859 | C24H21N5O2S | 444.3 | 8.4 | 97 | Example 71 |
| 808 | 2-1860 | C25H22C1N5O2S | 492.5 | 11.3 | 100 | Example 69 |
| 809 | 2-1861 | C29H23N5OS | 490.5 | 10.9 | 100 | Example 69 |
| 810 | 2-1862 | C19H17N5OS | 364.3 | 7.9 | 97 | Example 69 |
| 811 | 2-1863 | C21H21N5O3S | 424.4 | 8.5 | 100 | Example 69 |
| 812 | 2-1864 | C24H19N5OS | 426.4 | 9.6 | 94 | Example 69 |

TABLE 234

| Example | Compound No. | Compositional formula | ESI/MS m/e | HPLC (min) | Purity (%) | Synthesis method |
|---|---|---|---|---|---|---|
| 813 | 2-1865 | C24H21N5O2S | 444.5 | 9.9 | 100 | Example 69 |
| 814 | 2-1866 | C18H17N5O2S | 368.4 | 7.3 | 100 | Example 69 |
| 815 | 2-1867 | C23H19N5O2S | 430.4 | 9.4 | 100 | Example 69 |
| 816 | 2-1868 | C24H21N5O3S | 444.5 | 9.6 | 100 | Example 69 |
| 817 | 2-1869 | C20H19N5O3S | 410.4 | 8.0 | 96 | Example 69 |
| 818 | 2-1870 | C23H18N5OS | 432.4 | 9.3 | 98 | Example 69 |
| 819 | 2-1871 | C22H23N5OS | 406.4 | 9.7 | 100 | Example 69 |
| 820 | 2-1872 | C21H21N5O3S | 424.4 | 7.8 | 100 | Example 69 |
| 821 | 2-1873 | C24H21N5O2S | 444.5 | 9.1 | 100 | Example 69 |
| 822 | 2-1874 | C30H25N5O2S | 520.5 | 11.1 | 100 | Example 69 |
| 823 | 2-1875 | C22H15 F2N5OS | 436.4 | 9.9 | 100 | Example 69 |
| 824 | 2-1876 | C25H23N5OS | 442.5 | 10.3 | 93 | Example 69 |
| 825 | 2-1877 | C23H19N5OS2 | 446.5 | 9.7 | 100 | Example 69 |
| 826 | 2-1878 | C20H21N5O3S | 412.4 | 7.4 | 100 | Example 69 |
| 827 | 2-1879 | C19H19N5OS | 366.4 | 8.1 | 100 | Example 69 |
| 828 | 2-1880 | C20H21N5OS | 380.4 | 8.8 | 100 | Example 69 |
| 829 | 2-1881 | C27H23ClN6O2S | 531.4 | 9.3 | 100 | Example 71 |
| 830 | 2-1882 | C29H30N6O3S | 543.6 | 11.0 | 100 | Example 71 |
| 831 | 2-1883 | C26H24N6O3S | 501.5 | 9.6 | 97 | Example 71 |
| 832 | 2-1884 | C25H22N6O3S | 487.5 | 9.1 | 100 | Example 71 |
| 833 | 2-1885 | C20H20N6O2S | 409.4 | 6.6 | 100 | Example 71 |
| 834 | 2-1886 | C23H26N6O2S | 451.4 | 8.2 | 100 | Example 71 |
| 835 | 2-1887 | C26H24N6O3S | 501.5 | 9.5 | 100 | Example 71 |
| 836 | 2-1888 | C21H17N7OS2 | 448.4 | 7.8 | 88 | Example 71 |
| 837 | 2-1889 | C22H18N6O3S | 447.5 | 7.3 | 92 | Example 71 |
| 838 | 2-1890 | C23H19N7O2S | 458.5 | 6.0 | 100 | Example 71 |
| 839 | 2-1891 | C21H22N6O2S | 423.5 | 6.8 | 100 | Example 71 |
| 840 | 2-1892 | C20H17N5OS | 376.2 | 7.9 | 93 | Example 71 |
| 841 | 2-1893 | C24H20N6O2S | 457.5 | 8.1 | 100 | Example 71 |
| 842 | 2-1894 | C23H22N8O2S | 475.5 | 5.7 | 100 | Example 71 |
| 843 | 2-1895 | C16H13N5OS | 324.1 | 6.8 | 74 | Example 18 |
| 844 | 2-1897 | C22H16ClN5OS | 434.0 | 9.5 | 85 | Example 81 |
| 845 | 2-1898 | C23H18N6O3S | 459.0 | 9.0 | 96 | Example 71 |
| 846 | 2-1899 | C19H19N5O2S | 382.2 | 7.1 | 97 | Example 71 |
| 847 | 2-1900 | C20H19N5OS | 378.1 | 8.4 | 90 | Example 71 |
| 848 | 2-1901 | C26H24N6O3S | 501.5 | 9.3 | 95 | Example 71 |
| 849 | 2-1902 | C20H19N5OS | 378.1 | 8.4 | 85 | Example 71 |
| 850 | 2-1903 | C19H17N5O3S | 396.1 | 6.5 | 97 | Example 71 |

TABLE 235

| Example | Compound No. | Compositional formula | ESI/MS m/e | HPLC (min) | Purity (%) | Synthesis method |
|---|---|---|---|---|---|---|
| 851 | 2-1904 | C22H24N6O2S2 | 469.3 | 7.5 | 95 | Example 71 |
| 852 | 2-1905 | C21H17N5O2S2 | 436.2 | 9.1 | 99 | Example 69 |
| 853 | 2-1906 | C22H16FN5OS | 418.2 | 9.0 | 96 | Example 81 |
| 854 | 2-1907 | C22H16FN5S | 434.1 | 10.6 | 96 | Example 81 |
| 855 | 2-1908 | C24H21N5O2S | 444.3 | 9.8 | 98 | Example 81 |
| 856 | 2-1909 | C22H15F2N5OS | 436.1 | 9.1 | 98 | Example 69 |
| 857 | 2-1910 | C22H14F3N5OS | 454.1 | 9.4 | 93 | Example 69 |
| 858 | 2-1911 | C24H17F2N5O3S | 494.3 | 9.3 | 97 | Example 69 |
| 859 | 2-1912 | C23H17F2N5O2S | 466.1 | 9.1 | 98 | Example 69 |
| 860 | 2-1913 | C22H16F2N6OS | 451.3 | 8.4 | 97 | Example 69 |
| 861 | 2-1914 | C22H15F3N6OS | 469.2 | 9.5 | 96 | Example 69 |
| 862 | 2-1915 | C23H18F2N6OS | 465.2 | 9.2 | 98 | Example 69 |
| 863 | 2-1916 | C20H13F2N5O2S | 426.2 | 8.1 | 99 | Example 69 |
| 864 | 2-1917 | C20H13F2N5OS2 | 442.3 | 8.9 | 96 | Example 69 |
| 865 | 2-1918 | C20H14F2N6OS | 425.1 | 8.1 | 98 | Example 69 |
| 866 | 2-1919 | C25H19N5O2S | 454.1 | 10.8 | 98 | Example 18 |
| 867 | 2-1920 | C25H19N5OS2 | 470.2 | 12.5 | 89 | Example 18 |
| 868 | 2-1921 | C22H17N5O3S | 432.2 | 6.5 | 67 | Example 53 |
| 869 | 2-1922 | C24H19N5O2S | 442.3 | 8.4 | 96 | Example 81 |
| 870 | 2-1923 | C24H22N6OS | 443.3 | 8.3 | 96 | Example 81 |
| 871 | 2-1924 | C25H23N5O4S | 490.2 | 8.6 | 90 | Example 81 |
| 872 | 2-1925 | C23H18FN5OS | 432.1 | 9.7 | 98 | Example 81 |
| 873 | 2-1926 | C24H21N5O2S | 444.3 | 9.4 | 94 | Example 81 |
| 874 | 2-1927 | C19H14ClN7OS2 | 456.1 | 6.4 | 93 | Example 71 |
| 875 | 2-1928 | C20H14ClN5O3S2 | 472.2 | 8.8 | 97 | Example 71 |
| 876 | 2-1929 | C20H14ClN5O2S3 | 487.9 | 8.9 | 91 | Example 71 |
| 877 | 2-1930 | C28H28N6O3S | 529.3 | 6.4 | 100 | Example 71 |
| 878 | 2-1931 | C24H21N5O2S | 444.4 | 7.1 | 73 | Example 107 |
| 879 | 2-1932 | C22H18N6O2S | 431.2 | 7.3 | 85 | Example 107 |
| 880 | 2-1933 | C23H21N5OS | 416.4 | 7.2 | 84 | Example 107 |
| 881 | 2-1934 | C23H21N5O2S2 | 464.1 | 6.4 | 80 | Example 107 |
| 882 | 2-1935 | C23H18N6S | 411.4 | 6.9 | 64 | Example 107 |
| 883 | 2-1936 | C22H18N6O2S | 431.3 | 7.2 | 100 | Example 107 |
| 884 | 2-1937 | C23H21N5OS | 416.4 | 7.5 | 94 | Example 107 |
| 885 | 2-1938 | C18H16N6O3S | 397.2 | 6.2 | 97 | Example 70 |
| 886 | 2-1939 | C20H20N6O3S | 425.5 | 6.4 | 97 | Example 70 |
| 887 | 2-1940 | C23H18N6O3S | 459.4 | 7.6 | 96 | Example 70 |
| 888 | 2-1941 | C23H20N6OS | 429.4 | 9.6 | 84 | Example 70 |

TABLE 236

| Example | Compound No. | Compositional formula | ESI/MS m/e | HPLC (min) | Purity (%) | Synthesis method |
|---|---|---|---|---|---|---|
| 889 | 2-1942 | C24H20N6O2S | 457.3 | 9.8 | 97 | Example 70 |
| 890 | 2-1943 | C24H20N6O2S | 457.3 | 8.6 | 99 | Example 70 |
| 891 | 2-1944 | C23H20N6OS | 429.2 | 8.1 | 99 | Example 71 |
| 892 | 2-1945 | C18H14F3N5OS | 406.2 | 9.4 | 98 | Example 71 |
| 893 | 2-1946 | C22H17N7S2 | 444.3 | 6.6 | 99 | Example 73 |
| 894 | 2-1947 | C18H14F3N5O2 | 390.3 | 8.2 | 95 | Example 31 |
| 895 | 2-1948 | C22H16FN5O2 | 402.1 | 8.0 | 99 | Example 69 |
| 896 | 2-1949 | C21H16FN5O3 | 406.2 | 7.9 | 99 | Example 69 |
| 897 | 2-1950 | C21H16FN5O2S | 422.2 | 8.2 | 98 | Example 68 |
| 898 | 2-2158 | C21H15N5O3S | 418.4 | 8.9 | 100 | Example 71 |
| 899 | 2-2159 | C21H15ClN6OS | 435.4 | 8.7 | 93 | Example 69 |

TABLE 237

| Example | Compound No. | Compositional formula | ESI/MS m/e | HPLC (min) | Purity (%) | Synthesis method |
|---|---|---|---|---|---|---|
| 900 | 3-0001 | C16H13N5OS | 324.1 | 6.4 | 95 | Example 117 |
| 901 | 3-0004 | C20H21N5OS | 380.2 | 9.0 | 98 | Example 117 |
| 902 | 3-0009 | C19H19N5OS | 366.3 | 8.2 | 95 | Example 117 |
| 903 | 3-0012 | C21H23N5OS | 394.3 | 9.5 | 98 | Example 117 |
| 904 | 3-0016 | C21H23N5OS | 394.3 | 9.6 | 95 | Example 117 |
| 905 | 3-0019 | C18H14F3N5OS | 406.2 | 8.9 | 95 | Example 117 |
| 906 | 3-0020 | C21H23N5O2S | 410.3 | 8.2 | 90 | Example 117 |
| 907 | 3-0021 | C19H18N6O2S | 395.3 | 6.2 | 95 | Example 117 |
| 908 | 3-0029 | C17H15N5O4S2 | 418.2 | 5.0 | 90 | Example 117 |
| 909 | 3-0036 | C22H26N6OS | 423.3 | 6.0 | 85 | Example 117 |

TABLE 237-continued

| Example | Compound No. | Compositional formula | ESI/MS m/e | HPLC (min) | Purity (%) | Synthesis method |
|---|---|---|---|---|---|---|
| 910 | 3-0038 | C21H21N5OS | 392.3 | 9.1 | 95 | Example 117 |
| 911 | 3-0053 | C23H25N5OS | 420.4 | 10.3 | 95 | Example 117 |
| 912 | 3-0064 | C23H26N6OS | 435.3 | 5.8 | 90 | Example 117 |
| 913 | 3-0065 | C20H19N5OS | 378.2 | 8.5 | 85 | Example 117 |
| 914 | 3-0073 | C22H17N5OS | 400.2 | 9.8 | 95 | Example 117 |
| 915 | 3-0074 | C20H15N5O2S | 390.3 | 9.4 | 100 | Example 117 |
| 916 | 3-0081 | C23H19N5OS | 414.3 | 9.8 | 95 | Example 117 |
| 917 | 3-0082 | C22H16FN5OS | 418.4 | 10.0 | 95 | Example 117 |
| 918 | 3-0083 | C22H16ClN5OS | 434.2 | 10.8 | 95 | Example 117 |
| 919 | 3-0084 | C23H19N5O2S | 430.2 | 10.1 | 95 | Example 117 |
| 920 | 3-0085 | C23H19N5O2S | 430.3 | 9.8 | 95 | Example 117 |
| 921 | 3-0086 | C23H19N5OS2 | 446.4 | 10.5 | 95 | Example 117 |
| 922 | 3-0087 | C24H18N6OS | 439.3 | 9.1 | 90 | Example 117 |
| 923 | 3-0090 | C24H19N5O2S | 442.3 | 9.2 | 95 | Example 117 |
| 924 | 3-0091 | C24H19N5O2S | 442.3 | 9.2 | 95 | Example 117 |
| 925 | 3-0099 | C23H19N5OS | 414.2 | 9.5 | 98 | Example 117 |
| 926 | 3-0100 | C24H21N5O2S | 444.4 | 9.6 | 95 | Example 117 |
| 927 | 3-0109 | C21H16N6OS | 401.3 | 6.8 | 95 | Example 117 |
| 928 | 3-0110 | C21H16N6OS | 401.3 | 6.3 | 95 | Example 117 |
| 929 | 3-0112 | C19H14N6OS2 | 407.3 | 8.4 | 90 | Example 117 |
| 930 | 3-0115 | C25H21N5OS | 440.3 | 9.9 | 95 | Example 117 |
| 931 | 3-0117 | C21H17N5O2S | 404.4 | 8.9 | 100 | Example 117 |
| 932 | 3-0118 | C23H18ClN5OS | 448.3 | 10.2 | 90 | Example 117 |
| 933 | 3-0119 | C24H21N5O2S | 444.3 | 9.2 | 95 | Example 117 |
| 934 | 3-0124 | C24H21N5OS | 428.3 | 9.7 | 95 | Example 117 |
| 935 | 3-0125 | C21H17N5O2S | 404.2 | 8.6 | 90 | Example 117 |
| 936 | 3-0126 | C21H17N5OS2 | 420.3 | 9.1 | 95 | Example 117 |
| 937 | 3-0134 | C22H18N6OS | 415.2 | 5.9 | 80 | Example 117 |

TABLE 238

| Example | Compound No. | Compositional formula | ESI/MS m/e | HPLC (min) | Purity (%) | Synthesis method |
|---|---|---|---|---|---|---|
| 938 | 3-0135 | C20H16N6O2S | 405.4 | 5.4 | 100 | Example 117 |
| 939 | 3-0136 | C22H18N6OS | 415.2 | 5.8 | 85 | Example 117 |
| 940 | 3-0137 | C20H16N6O2S | 405.4 | 5.3 | 100 | Example 117 |
| 941 | 3-0139 | C22H18N6OS | 415.3 | 5.8 | 85 | Example 117 |
| 942 | 3-0140 | C20H16N6O2S | 405.4 | 5.3 | 99 | Example 117 |
| 943 | 3-0143 | C24H21N5OS | 428.2 | 10.0 | 98 | Example 117 |
| 944 | 3-0148 | C20H19N5OS | 378.3 | 8.1 | 98 | Example 117 |
| 945 | 3-0152 | C21H21N5OS | 392.3 | 9.3 | 98 | Example 117 |
| 946 | 3-0156 | C19H19N5O2S | 382.1 | 8.8 | 98 | Example 117 |
| 947 | 3-0160 | C22H23N5OS | 406.3 | 9.8 | 98 | Example 117 |
| 948 | 3-0168 | C22H23N5OS | 406.4 | 10.0 | 98 | Example 117 |
| 949 | 3-0175 | C22H23N5OS | 406.4 | 10.0 | 98 | Example 117 |
| 950 | 3-0184 | C23H25N5OS | 420.4 | 10.8 | 98 | Example 117 |
| 951 | 3-0197 | C24H25N5O3S | 464.3 | 10.2 | 98 | Example 117 |
| 952 | 3-0198 | C24H25N5O3S | 464.3 | 9.6 | 95 | Example 117 |
| 953 | 3-0206 | C24H25N5O3S | 464.3 | 9.3 | 85 | Example 117 |
| 954 | 3-0207 | C22H23N5O4S | 454.5 | 9.0 | 99 | Example 117 |
| 955 | 3-0217 | C22H22N6O2S | 435.3 | 6.7 | 95 | Example 117 |
| 956 | 3-0220 | C22H22N6O2S | 435.2 | 6.4 | 95 | Example 117 |
| 957 | 3-0235 | C20H19N5O4S | 426.3 | 6.8 | 96 | Example 117 |
| 958 | 3-0241 | C28H25N5O2S | 496.4 | 10.1 | 98 | Example 117 |
| 959 | 3-0242 | C26H23N5O3S | 486.1 | 9.9 | 95 | Example 117 |
| 960 | 3-0243 | C26H30N6O2S | 491.3 | 8.7 | 98 | Example 117 |
| 961 | 3-0244 | C23H23N5O3S | 450.3 | 8.3 | 90 | Example 117 |
| 962 | 3-0294 | C20H19N5O2S | 394.3 | 7.6 | 95 | Example 117 |
| 963 | 3-0297 | C18H17N5O3S | 384.2 | 7.0 | 100 | Example 117 |
| 964 | 3-0325 | C20H18N6O2S | 407.3 | 6.2 | 80 | Example 117 |
| 965 | 3-0331 | C21H22N6OS | 407.3 | 5.7 | 98 | Example 117 |
| 966 | 3-0339 | C26H24N6OS | 469.2 | 9.6 | 98 | Example 117 |
| 967 | 3-0340 | C25H23N7OS | 470.3 | 6.1 | 98 | Example 117 |
| 968 | 3-0348 | C28H26N6O2S | 511.4 | 9.2 | 98 | Example 117 |
| 969 | 3-0349 | C24H26N6O3S | 479.4 | 6.4 | 95 | Example 117 |
| 970 | 3-0350 | C27H26N6OS | 483.2 | 6.9 | 98 | Example 117 |
| 971 | 3-0351 | C26H31N7OS | 490.3 | 5.5 | 98 | Example 117 |
| 972 | 3-0352 | C28H26N6O3S | 527.4 | 7.0 | 98 | Example 117 |
| 973 | 3-0353 | C22H22N6O2S | 435.3 | 6.9 | 98 | Example 117 |
| 974 | 3-0357 | C25H22N6O3S | 487.3 | 7.9 | 98 | Example 117 |
| 975 | 3-0362 | C23H20N6O4S | 477.2 | 7.6 | 97 | Example 117 |

TABLE 239

| Example | Compound No. | Compositional formula | ESI/MS m/e | HPLC (min) | Purity (%) | Synthesis method |
|---|---|---|---|---|---|---|
| 976 | 3-0397 | C23H24N6O3S | 465.2 | 8.7 | 98 | Example 117 |
| 977 | 3-0398 | C25H28N6O3S | 493.3 | 10.1 | 95 | Example 117 |
| 978 | 3-0399 | C28H26N6O3S | 527.4 | 10.1 | 98 | Example 117 |
| 979 | 3-0430 | C23H24N6O2S | 449.3 | 6.9 | 75 | Example 117 |
| 980 | 3-0532 | C21H23N5OS | 394.3 | 9.3 | 95 | Example 117 |
| 981 | 3-0541 | C22H25N5OS | 408.3 | 10.2 | 96 | Example 117 |
| 982 | 3-0542 | C19H19N5O2S | 382.4 | 8.6 | 99 | Example 117 |
| 983 | 3-0543 | C22H23N5OS | 406.3 | 9.3 | 95 | Example 117 |
| 984 | 3-0544 | C24H28N6OS | 449.4 | 6.1 | 95 | Example 117 |
| 985 | 3-0545 | C21H21N5OS | 392.3 | 8.7 | 95 | Example 117 |
| 986 | 3-0550 | C24H28N6O2S | 465.3 | 5.9 | 95 | Example 117 |
| 987 | 3-0551 | C23H19N5OS | 414.3 | 10.0 | 98 | Example 117 |
| 988 | 3-0552 | C23H19N5O2S | 430.2 | 9.4 | 98 | Example 117 |
| 989 | 3-0553 | C23H19N5O2S | 430.3 | 8.0 | 90 | Example 117 |
| 990 | 3-0554 | C23H19N5O2S | 430.3 | 8.0 | 98 | Example 117 |
| 991 | 3-0555 | C23H18FN5OS | 432.3 | 10.3 | 98 | Example 117 |
| 992 | 3-0556 | C23H18FN5OS | 432.2 | 10.1 | 95 | Example 117 |
| 993 | 3-0557 | C23H18ClN5OS | 448.3 | 10.9 | 98 | Example 117 |
| 994 | 3-0558 | C23H18ClN5OS | 448.3 | 10.9 | 98 | Example 117 |
| 995 | 3-0559 | C24H21N5O2S | 444.4 | 10.2 | 95 | Example 117 |
| 996 | 3-0560 | C24H21N5O2S | 444.3 | 9.9 | 95 | Example 117 |
| 997 | 3-0561 | C23H18N6O3S | 459.1 | 10.3 | 98 | Example 117 |
| 998 | 3-0564 | C25H20N6OS | 453.3 | 9.2 | 95 | Example 117 |
| 999 | 3-0567 | C25H21N5O2S | 456.2 | 9.4 | 98 | Example 117 |
| 1000 | 3-0568 | C25H19N5OS | 438.2 | 10.5 | 98 | Example 117 |
| 1001 | 3-0575 | C22H18N6OS | 415.3 | 6.9 | 98 | Example 117 |
| 1002 | 3-0577 | C22H18N6OS | 415.3 | 6.6 | 98 | Example 117 |
| 1003 | 3-0584 | C20H16N6OS2 | 421.2 | 8.6 | 94 | Example 117 |
| 1004 | 3-0589 | C24H21N5OS | 428.2 | 9.6 | 95 | Example 117 |
| 1005 | 3-0590 | C24H20FN5OS | 446.4 | 9.6 | 98 | Example 117 |
| 1006 | 3-0591 | C24H20ClN5OS | 462.1 | 10.5 | 98 | Example 117 |
| 1007 | 3-0592 | C25H23N5O2S | 458.2 | 9.4 | 90 | Example 117 |
| 1008 | 3-0596 | C25H23N5OS | 442.4 | 9.8 | 95 | Example 117 |
| 1009 | 3-0597 | C25H22FN5OS | 460.2 | 9.9 | 98 | Example 117 |
| 1010 | 3-0598 | C22H19N5O2S | 418.3 | 8.8 | 90 | Example 117 |
| 1011 | 3-0599 | C22H19N5OS2 | 434.3 | 9.3 | 95 | Example 117 |
| 1012 | 3-0600 | C23H20N6OS | 429.2 | 6.0 | 95 | Example 117 |
| 1013 | 3-0605 | C22H23N5OS | 406.3 | 9.4 | 95 | Example 117 |

TABLE 240

| Example | Compound No. | Compositional formula | ESI/MS m/e | HPLC (min) | Purity (%) | Synthesis method |
|---|---|---|---|---|---|---|
| 1014 | 3-0615 | C23H25N5OS | 420.3 | 10.3 | 95 | Example 117 |
| 1015 | 3-0616 | C23H25N5OS | 420.3 | 10.3 | 95 | Example 117 |
| 1016 | 3-0634 | C25H27N5O3S | 478.2 | 10.5 | 98 | Example 117 |
| 1017 | 3-0635 | C25H27N5O3S | 478.3 | 9.8 | 95 | Example 117 |
| 1018 | 3-0636 | C25H27N5O3S | 478.3 | 9.6 | 90 | Example 117 |
| 1019 | 3-0642 | C23H24N6O2S | 449.3 | 7.1 | 98 | Example 117 |
| 1020 | 3-0647 | C23H24N6O2S | 449.3 | 6.8 | 95 | Example 117 |
| 1021 | 3-0651 | C27H32N6O2S | 505.3 | 8.9 | 98 | Example 117 |
| 1022 | 3-0652 | C24H25N5O3S | 464.1 | 8.6 | 90 | Example 117 |
| 1023 | 3-0653 | C26H30N6OS | 475.3 | 6.4 | 98 | Example 117 |
| 1024 | 3-0654 | C24H23N5O4S | 478.2 | 9.6 | 80 | Example 117 |
| 1025 | 3-0680 | C21H20N6O2S | 421.3 | 6.6 | 95 | Example 117 |
| 1026 | 3-0682 | C22H24N6OS | 421.3 | 6.0 | 97 | Example 117 |
| 1027 | 3-0683 | C27H26N6OS | 483.3 | 9.8 | 90 | Example 117 |
| 1028 | 3-0684 | C26H25N7OS | 484.2 | 6.5 | 98 | Example 117 |
| 1029 | 3-0685 | C29H28N6O2S | 525.2 | 9.5 | 90 | Example 117 |
| 1030 | 3-0686 | C28H28N6OS | 497.3 | 7.2 | 98 | Example 117 |
| 1031 | 3-0687 | C27H33N7OS | 504.4 | 5.8 | 98 | Example 117 |
| 1032 | 3-0688 | C29H28N6O3S | 541.3 | 7.3 | 98 | Example 117 |
| 1033 | 3-0689 | C23H24N6O2S | 449.3 | 7.1 | 98 | Example 117 |
| 1034 | 3-0690 | C26H24N6O3S | 501.3 | 8.3 | 95 | Example 117 |
| 1035 | 3-0710 | C24H26N6O3S | 479.3 | 8.9 | 98 | Example 117 |
| 1036 | 3-0711 | C29H28N6O3S | 541.2 | 10.4 | 98 | Example 117 |
| 1037 | 3-0724 | C24H26N6O2S | 463.3 | 7.1 | 95 | Example 117 |
| 1038 | 3-0725 | C25H22FN5OS | 460.2 | 9.9 | 98 | Example 117 |
| 1039 | 3-0726 | C24H21N5O2S | 444.3 | 9.7 | 90 | Example 117 |
| 1040 | 3-0727 | C24H21N5OS2 | 460.2 | 10.5 | 90 | Example 117 |
| 1041 | 3-0898 | C22H23N5OS | 406.7 | 9.8 | 90 | Example 117 |
| 1042 | 3-0909 | C25H28N6OS | 461.7 | 6.2 | 85 | Example 117 |

TABLE 240-continued

| Example | Compound No. | Compositional formula | ESI/MS m/e | HPLC (min) | Purity (%) | Synthesis method |
|---|---|---|---|---|---|---|
| 1043 | 3-0924 | C20H19N5OS2 | 410.6 | 9.1 | 70 | Example 117 |
| 1044 | 3-0947 | C21H20BrN5OS | 470.6 | 10.0 | 83 | Example 117 |
| 1045 | 3-0949 | C22H24N6O2S | 437.7 | 5.9 | 94 | Example 117 |
| 1046 | 3-0950 | C25H27N5OS | 446.6 | 11.6 | 81 | Example 117 |
| 1047 | 3-0962 | C23H25N5OS | 420.6 | 10.4 | 68 | Example 117 |
| 1048 | 3-0963 | C23H25N5OS | 420.6 | 10.6 | 90 | Example 117 |
| 1049 | 3-0965 | C29H27N5O2S | 510.7 | 10.5 | 84 | Example 117 |
| 1050 | 3-0966 | C26H30N6OS | 475.8 | 6.5 | 86 | Example 117 |
| 1051 | 3-0968 | C25H28N6O3S | 493.6 | 9.2 | 47 | Example 117 |

TABLE 241

| Example | Compound No. | Compositional formula | ESI/MS m/e | HPLC (min) | Purity (%) | Synthesis method |
|---|---|---|---|---|---|---|
| 1052 | 3-0969 | C28H25N5O3S | 512.7 | 10.8 | 88 | Example 117 |
| 1053 | 3-0970 | C22H21N5O3S | 436.7 | 8.6 | 80 | Example 117 |
| 1054 | 3-0970 (S) | C22H21N5O3S | 436.6 | 8.6 | 79 | Example 117 |
| 1055 | 3-0971 | C25H27N5O3S | 478.7 | 10.5 | 93 | Example 117 |
| 1056 | 3-0973 | C22H23N5O2S | 422.7 | 8.8 | 73 | Example 117 |
| 1057 | 3-0974 | C21H19N5OS | 390.6 | 9.1 | 64 | Example 117 |
| 1058 | 3-0977 | C21H21N5O2S | 408.6 | 7.2 | 81 | Example 117 |
| 1059 | 3-0978 | C23H25N5OS | 420.7 | 10.6 | 83 | Example 117 |
| 1060 | 3-0979 | C23H25N5O2S | 436.7 | 8.3 | 43 | Example 117 |
| 1061 | 3-0980 | C22H23N5O2S | 422.7 | 7.5 | 53 | Example 117 |
| 1062 | 3-0981 | C25H23N7OS | 470.7 | 6.4 | 92 | Example 117 |
| 1063 | 3-0982 | C21H21N5O2S | 408.6 | 6.8 | 72 | Example 117 |
| 1064 | 3-0983 | C24H22N8OS | 471.7 | 8.1 | 71 | Example 117 |
| 1065 | 3-0984 | C26H23ClN6OS | 503.7 | 11.4 | 75 | Example 117 |
| 1066 | 3-0985 | C28H27N5OS | 482.7 | 11.9 | 79 | Example 117 |
| 1067 | 3-0986 | C25H27N5OS | 446.7 | 11.8 | 86 | Example 117 |
| 1068 | 3-0987 | C25H27N5OS | 446.7 | 11.6 | 81 | Example 117 |
| 1069 | 3-0988 | C27H25ClN6OS | 517.7 | 7.8 | 94 | Example 117 |
| 1070 | 3-0989 | C27H32N6O3S | 521.7 | 10.2 | 79 | Example 117 |
| 1071 | 3-0990 | C28H34N6O3S | 535.7 | 10.4 | 78 | Example 117 |
| 1072 | 3-0991 | C26H30N6O3S | 507.7 | 9.8 | 80 | Example 117 |
| 1073 | 3-0992 | C28H25N7O2S | 524.7 | 8.6 | 76 | Example 117 |
| 1074 | 3-0993 | C22H23N5O2S | 422.6 | 7.1 | 40 | Example 117 |
| 1075 | 3-1776 | C21H17N5O2S | 404.2 | 9.7 | 98 | Example 117 |
| 1076 | 3-1777 | C21H18N6O2S | 419.3 | 5.6 | 98 | Example 117 |
| 1077 | 3-1778 | C23H25N5O4S | 468.2 | 9.4 | 99 | Example 117 |
| 1078 | 3-1779 | C20H21N5O2S | 396.2 | 9.2 | 94 | Example 117 |
| 1079 | 3-1780 | C26H32N6O3S | 509.3 | 9.6 | 92 | Example 117 |
| 1080 | 3-1781 | C23H26N6O3S | 467.1 | 8.8 | 86 | Example 117 |
| 1081 | 3-1782 | C26H24N6O3S | 501.2 | 9.1 | 97 | Example 117 |
| 1082 | 3-1783 | C20H21N5OS | 380.5 | 9.1 | 70 | Example 117 |
| 1083 | 3-1784 | C19H19N5O2S | 382.5 | 7.3 | 76 | Example 117 |
| 1084 | 3-1785 | C24H29N5OS | 436.7 | 11.9 | 84 | Example 117 |
| 1085 | 3-1786 | C22H26N6OS | 423.7 | 6.4 | 75 | Example 117 |
| 1086 | 3-1787 | C23H28N6OS | 437.7 | 6.6 | 50 | Example 117 |
| 1087 | 3-1788 | C27H25N5O3S | 500.7 | 10.9 | 86 | Example 117 |
| 1088 | 3-1789 | C22H25N5OS | 408.6 | 10.7 | 98 | Example 117 |
| 1089 | 3-1790 | C24H29N5OS | 436.7 | 12.2 | 95 | Example 117 |

TABLE 242

| Example | Compound No. | Compositional formula | ESI/MS m/e | HPLC (min) | Purity (%) | Synthesis method |
|---|---|---|---|---|---|---|
| 1090 | 3-1791 | C17H15N5OS | 338.6 | 7.0 | 36 | Example 117 |
| 1091 | 3-1792 | C18H17N5OS | 352.6 | 7.6 | 93 | Example 117 |
| 1092 | 3-1793 | C19H19N5OS | 366.6 | 8.4 | 70 | Example 117 |
| 1093 | 3-1794 | C21H24N6OS | 451.8 | 6.9 | 96 | Example 117 |
| 1094 | 3-1795 | C22H24N6O2S | 437.7 | 6.0 | 92 | Example 117 |
| 1095 | 3-1796 | C25H30N6OS | 463.8 | 6.6 | 93 | Example 117 |
| 1096 | 3-1797 | C23H26N6O2S | 451.7 | 6.0 | 98 | Example 117 |
| 1097 | 3-1798 | C23H26N6OS | 435.7 | 6.3 | 92 | Example 117 |
| 1098 | 3-1799 | C18H17N5OS | 352.6 | 7.8 | 87 | Example 117 |
| 1099 | 3-1800 | C26H25N5OS | 456.7 | 11.3 | 74 | Example 117 |
| 1100 | 3-1801 | C23H25N5O3S | 452.7 | 10.2 | 94 | Example 117 |
| 1101 | 3-1802 | C20H17N5OS | 376.6 | 8.8 | 80 | Example 117 |

TABLE 242-continued

| Example | Compound No. | Compositional formula | ESI/MS m/e | HPLC (min) | Purity (%) | Synthesis method |
|---|---|---|---|---|---|---|
| 1102 | 3-1803 | C20H19N5OS | 378.6 | 9.0 | 79 | Example 117 |
| 1103 | 3-1804 | C30H25N5OS | 504.7 | 12.2 | 94 | Example 117 |
| 1104 | 3-1805 | C22H24N6OS | 421.7 | 6.2 | 85 | Example 117 |
| 1105 | 3-1806 | C21H21N5O3S | 424.6 | 8.2 | 67 | Example 117 |
| 1106 | 3-1807 | C21H21N5O3S | 424.6 | 9.0 | 69 | Example 117 |
| 1107 | 3-1808 | C24H25N5OS | 432.6 | 11.2 | 48 | Example 117 |
| 1108 | 3-1809 | C22H25N5OS | 408.6 | 10.8 | 81 | Example 117 |
| 1109 | 3-1810 | C19H19N5OS | 366.6 | 8.5 | 88 | Example 117 |
| 1110 | 3-1811 | C23H25N5OS | 420.6 | 10.7 | 96 | Example 117 |
| 1111 | 3-1812 | C21H23N5OS | 394.6 | 10.0 | 79 | Example 117 |
| 1112 | 3-1813 | C21H23N5OS | 394.6 | 10.0 | 77 | Example 117 |
| 1113 | 3-1814 | C20H21N5O2S | 396.6 | 8.2 | 88 | Example 117 |
| 1114 | 3-1815 | C20H21N5OS | 380.5 | 9.1 | 66 | Example 117 |
| 1115 | 3-1816 | C20H20N6O2S | 409.6 | 6.3 | 76 | Example 117 |
| 1116 | 3-1817 | C24H19N5O3S | 458.6 | 10.1 | 46 | Example 117 |
| 1117 | 3-1818 | C23H16F3N5O2S | 484.6 | 11.6 | 94 | Example 117 |
| 1118 | 3-1819 | C23H19N5OS2 | 446.6 | 10.7 | 87 | Example 117 |
| 1119 | 3-1820 | C22H18N6O3S2 | 479.6 | 8.4 | 37 | Example 117 |
| 1120 | 3-1821 | C23H17N5O3S | 444.6 | 9.7 | 66 | Example 117 |
| 1121 | 3-1822 | C24H21N5O3S | 460.7 | 10.1 | 70 | Example 117 |
| 1122 | 3-1823 | C25H21N5O3S | 472.7 | 10.8 | 78 | Example 117 |
| 1123 | 3-1824 | C22H16N6O3S | 445.6 | 10.4 | 58 | Example 117 |
| 1124 | 3-1825 | C23H18N6O2S | 443.6 | 7.5 | 76 | Example 117 |
| 1125 | 3-1826 | C19H17N5OS | 364.3 | 9.4 | 99 | Example 117 |

TABLE 243

| Example | Compound No. | Compositional formula | ESI/MS m/e | HPLC (min) | Purity (%) | Synthesis method |
|---|---|---|---|---|---|---|
| 1126 | 4-0002 | C14H10N4O3S | 315.3 | 6.8 | 100 | Example 114 |
| 1127 | 4-0007 | C16H14N4O3S | 343.3 | 9.4 | 91 | Example 112 |
| 1128 | 4-0029 | C17H14N4O2S | 339.3 | 7.7 | 95 | Example 114 |
| 1129 | 4-0030 | C19H18N4O3 | 351.3 | 8.5 | 80 | Example 110 |
| 1130 | 4-0031 | C19H18N4O2S | 367.3 | 10.1 | 84 | Example 112 |
| 1131 | 4-0040 | C19H18N4O3 | 317.3 | 8.8 | 89 | Example 112 |

TABLE 244

| Example | Compound No. | Compositional formula | ESI/MS m/e | HPLC (min) | Purity (%) | Synthesis method |
|---|---|---|---|---|---|---|
| 1132 | 5-0001 | C17H14N4OS | 323.2 | 8.7 | 100 | Example 120 |
| 1133 | 5-0005 | C22H22N4OS | 319.2 | 11.9 | 98 | Example 121 |
| 1134 | 5-0016 | C23H18N4OS | 399.3 | 10.8 | 90 | Example 121 |
| 1135 | 5-0041 | C18H14N4OS | 335.4 | 9.3 | 99 | Example 121 |
| 1136 | 5-0049 | C18H16N4OS | 337.3 | 9.0 | 100 | Example 120 |
| 1137 | 5-0051 | C23H24N4OS | 405.3 | 12.3 | 99 | Example 121 |
| 1138 | 5-0054 | C23H18N4OS | 399.3 | 11.1 | 98 | Example 121 |
| 1139 | 5-0060 | C24H20N4OS | 413.2 | 11.2 | 95 | Example 121 |
| 1140 | 5-0074 | C21H22N4OS | 379.2 | 11.5 | 98 | Example 120 |

TABLE 245

| Example | Compound No. | Compositional formula | ESI/MS m/e | HPLC (min) | Purity (%) | Synthesis method |
|---|---|---|---|---|---|---|
| 1141 | 6-0055 | C9H9N5S | 220.2 | 4.2 | 99 | Example 122 |
| 1142 | 6-0056 | C11H11N5S | 246.1 | 5.6 | 91 | Example 122 |
| 1143 | 6-0057 | C12H13N5S | 260.4 | 6.6 | 88 | Example 122 |
| 1144 | 6-0058 | C12H13N5OS | 276.1 | 4.1 | 92 | Example 122 |
| 1145 | 6-0268 | C16H23N5OS | 334.5 | 9.8 | 100 | Example 123 |
| 1146 | 6-0278 | C18H25N5OS | 360.4 | 11.0 | 76 | Example 123 |
| 1147 | 6-0283 | C19H28N6OS | 389.4 | 5.9 | 78 | Example 123 |
| 1148 | 6-0298 | C15H21N5O2S | 336.4 | 6.7 | 97 | Example 123 |
| 1149 | 6-0300 | C15H21N5OS | 320.4 | 8.8 | 97 | Example 123 |
| 1150 | 6-0304 | C16H23N5OS | 334.4 | 9.9 | 94 | Example 123 |
| 1151 | 6-0308 | C17H23N5OS | 346.3 | 10.5 | 91 | Example 123 |
| 1152 | 6-0312 | C17H21N5OS | 344.4 | 9.7 | 70 | Example 123 |

TABLE 245-continued

| Example | Compound No. | Compositional formula | ESI/MS m/e | HPLC (min) | Purity (%) | Synthesis method |
|---|---|---|---|---|---|---|
| 1153 | 6-0316 | C16H23N5O2S | 350.3 | 7.3 | 94 | Example 123 |
| 1154 | 6-0320 | C17H23N5OS | 346.3 | 10.1 | 92 | Example 123 |
| 1155 | 6-0324 | C17H23N5O2S | 362.4 | 6.9 | 95 | Example 123 |
| 1156 | 6-0328 (R) | C17H24N6OS | 361.3 | 5.1 | 90 | Example 123 |
| 1157 | 6-0328 (S) | C17H24N6OS | 361.4 | 5.1 | 86 | Example 123 |
| 1158 | 6-0333 | C18H25N5OS | 360.2 | 10.8 | 96 | Example 123 |
| 1159 | 6-0337 | C20H29N5OS | 388.4 | 13.0 | 97 | Example 123 |
| 1160 | 6-0341 | C18H25N5O2S | 376.3 | 8.1 | 96 | Example 123 |
| 1161 | 6-0343 | C19H28N6OS | 389.4 | 5.7 | 99 | Example 123 |
| 1162 | 6-0345 | C22H27N7OS | 438.3 | 6.3 | 96 | Example 123 |
| 1163 | 6-0347 | C17H23N5O2S | 362.4 | 8.8 | 99 | Example 123 |
| 1164 | 6-0349 | C17H24N6OS | 361.3 | 5.2 | 97 | Example 123 |
| 1165 | 6-0353 | C18H26N6OS | 375.3 | 5.4 | 91 | Example 123 |
| 1166 | 6-0366 | C23H35N7OS | 458.4 | 5.4 | 93 | Example 123 |
| 1167 | 6-0370 | C19H28N6O2S | 405.4 | 5.3 | 99 | Example 123 |
| 1168 | 6-0374 | C17H22N6O2S | 375.3 | 6.3 | 86 | Example 123 |
| 1169 | 6-0378 | C19H27N5OS | 374.3 | 11.8 | 96 | Example 123 |
| 1170 | 6-0382 | C18H26N6OS | 375.3 | 5.7 | 97 | Example 123 |
| 1171 | 6-0390 | C16H18N6OS | 343.2 | 6.8 | 88 | Example 123 |
| 1172 | 6-0394 | C17H20N6OS | 357.4 | 10.0 | 49 | Example 123 |
| 1173 | 6-0414 | C19H18N6S2 | 395.2 | 9.5 | 88 | Example 124 |
| 1174 | 6-1033 | C20H19FN6O2S | 427.3 | 6.1 | 96 | Example 122 |

Example 1175

The $^1$H-NMR spectra (400 MHz, DMSO-$d_6$ or CDCl$_3$) of the compounds of the invention were measured. The data for the chemical shifts (δ: ppm) and coupling constants (J: Hz) are shown in Tables 246 to 262 below. The compound numbers in the tables represent the compound numbers in Tables 1 to 214 listed as the preferred examples, and the examples in the tables represent the examples for synthesis of the corresponding compounds.

TABLE 246

| Compound No. | Example | NMR δ(ppm) | Solvent |
|---|---|---|---|
| 1-005 | 128 | 0.86-0.96(m, 3H), 1.32-1.48(m, 4H), 2.26-2.31(m, 2H), 6.44(d, J=16.1, 1H), 6.88-6.95(m, 1H), 7.95(s, 1H), 12.29(brs, 1H), 13.06(brs, 1H). | DMSO-d6 |
| 1-006 | 129 | 7.16(d, J=16.5, 1H), 7.37-7.47(m, 3H), 7.49(d, J=7.3, 2H), 7.76(d, J=16.5, 1H), 7.99(d, J=3.4, 1H), 12.38(brs, 1H), 13.31(brs, 1H). | DMSO-d6 |
| 1-009 | 132 | 2.32(s, 3H), 7.34-7.48(m, 4H), 8.02(s, 1H), 12.39(brs, 1H), 13.27(brs, 1H). | DMSO-d6 |
| 1-015 | 136 | 2.16(s, 3H), 2.32(s, 1H), 7.24-7.251(m, 2H), 7.34-7.36(m, 1H), 8.01(s, 1H), 12.36(brs, 1H), 13.23(brs, 1H). | DMSO-d6 |
| 1-016 | 137 | 2.18(s, 3H), 2.34(s, 1H), 7.24-7.31(m, 2H), 7.37-7.38(m, 1H), 8.20(s, 1H), 13.36(brs, 1H), 13.80(brs, 1H). | DMSO-d6 |
| 1-018 | 139 | 2.27(s, 3H), 2.34(s, 3H), 7.23-7.31(m, 3H), 8.02(d, J=3.4, 1H), 12.39(brs, 1H), 13.23(brs, 1H). | DMSO-d6 |
| 1-025 | 145 | 7.51-7.70(m, 4H), 8.02(s, 1H), 12.41(brs, 1H), 13.49(brs, 1H). | DMSO-d6 |
| 1-026 | 146 | 7.51-7.71(m, 4H), 8.22(s, 1H), 13.59(brs, 1H), 13.88(brs, 1H). | DMSO-d6 |
| 1-029 | 148 | 7.66-7.68(m, 2H), 7.96-8.02(m, 3H), 12.35(brs, 1H), 13.53(brs, 1H). | DMSO-d6 |
| 1-031 | 149 | 7.55-7.66(m, 2H), 7.87-7.89(m, 1H), 8.04-8.06(m, 1H), 12.48(brs, 1H), 13.60(brs, 1H). | DMSO-d6 |
| 1-033 | 150 | 7.67-7.75(m, 2H), 7.81-7.82(m, 1H), 8.05-8.06(m, 1H), 12.47(brs, 1H), 13.60(brs, 1H). | DMSO-d6 |
| 1-036 | 152 | 7.64-7.70(m, 2H), 7.91(d, J=2.0, 1H), 8.05(br, 1H), 12.46(brs, 1H), 13.58(brs, 1H). | DMSO-d6 |
| 1-037 | 153 | 7.65-7.74(m, 2H), 7.92(d, J=2.0, 1H), 8.23(d, J=3.4, 1H), 13.64(brs, 1H), 13.93(brs, 1H). | DMSO-d6 |
| 1-044 | 158 | 3.83(s, 3H), 3.84(s, 3H), 6.67-6.74(m, | DMSO-d6 |

TABLE 246-continued

| Compound No. | Example | NMR δ(ppm) | Solvent |
|---|---|---|---|
| | | 2H), 7.44(d, J=8.5, 1H), 7.96(d, J=3.6, 1H), 12.28(brs, 1H), 12.98(brs, 1H). | |
| 1-045 | 159 | 3.86(s, 3H), 3.87(s, 3H), 6.70-6.76(m, 2H), 7.52(d, J=8.6, 1H), 8.15(s, 1H) | DMSO-d6 |

TABLE 247

| Compound No. | Example | NMR δ(ppm) | Solvent |
|---|---|---|---|
| 1-086 | 199 | 7.26-7.28(m, 1H), 7.84-7.86(m, 1H), 7.95-7.97(m, 1H), 8.01(d, 1H), 12.40(brs, 1H), 13.54(brs, 1H). | DMSO-d6 |
| 1-087 | 200 | 7.29-7.31(m, 1H), 7.92-7.93(d, J=4.9, 1H), 8.17-8.18(m, 2H), 13.49(brs, 1H), 13.80(brs, 1H). | DMSO-d6 |
| 1-102 | 209 | 2.53(s, 3H), 3.99(s, 3H), 7.95(s, 1H), 12.32(brs, 1H). | DMSO-d6 |
| 1-106 | 213 | 0.56(d, J=6.8, 6H), 1.71-1.79(m, 1H), 4.30(d, J=7.6, 2H), 7.62(s, 5H), 8.03(s, 1H), 12.46(brs, 1H). | DMSO-d6 |
| 1-107 | 214 | 0.83(d, J=6.6, 6H), 2.05-2.13(m, 1H), 2.49(s, 3H), 4.21(d, J=7.6, 2H), 7.93(d, J=3.6, 1H), 12.29(brs, 1H). | DMSO-d6 |
| 1-122 | 219 | 0.94(d, J=6.6, 6H), 1.58-1.59(m, 2H), 1.69-1.76(m, 1H), 2.57(s, 3H), 4.87(t, J=8.3, 2H), 8.09(s, 1H), 13.63(brs, 1H). | DMSO-d6 |
| 1-125 | 220 | 0.50(d, J=6.6, 3H), 0.58(t, J=7.3, 3H), 0.78-0.89(m, 1H), 0.97-1.08(m, 1H), 1.48-1.57(m, 1H), 4.30(dd, J=13.4, 8.1, 1H), 4.40(dd, J=13.4, 6.7, 1H), 7.62(s, 5H), 8.03(s, 1H), 12.43(brs, 1H). | DMSO-d6 |
| 1-126 | 221 | 0.48(d, J=6.8, 3H), 0.56(t, J=7.3, 3H), 0.74-0.86(m, 1H), 0.99-1.09(m, 1H), 1.66-1.75(m, 1H), 4.79-4.80(m, 2H), 7.62-7.67(m, 5H), 8.20(s, 1H), 13.80(brs, 1H). | DMSO-d6 |
| 1-127 | 222 | 0.76(d, J=6.8, 3H), 0.85(t, J=7.4, 3H), 1.13-1.29(m, 2H), 1.84-1.92(m, 1H), 2.49(s, 3H), 4.18-4.31(m, 2H), 7.93(d, J=3.7, 1H), 12.28(brs, 1H). | DMSO-d6 |
| 1-129 | 224 | 0.59(s, 9H), 4.19(d, J=14.2, 1H), 6.28(d, J=14.2, 1H), 7.61-7.64(m, 3H), 7.74-7.76(m, 2H), 8.21(s, 1H), 13.79(brs, 1H). | DMSO-d6 |
| 1-134 | 229 | 0.84(t, J=6.9, 3H), 1.23-1.31(m, 4H), 1.66-1.71(m, 2H), 2.49(s, 3H), 4.36(t, J=7.6, 2H), 7.92(d, J=3.6, 1H), 12.28(brs, 1H). | DMSO-d6 |
| 1-135 | 230 | 0.86(t, J=6.8, 3H), 1.30-1.32(m, 4H), 1.70-1.72(m, 2H), 2.56(s, 3H), 4.83(t, J=7.8, 2H), 8.09(s, 1H), 13.63(brs, 1H). | DMSO-d6 |

TABLE 248

| Compound No. | Example | NMR δ(ppm) | Solvent |
|---|---|---|---|
| 1-144 | 233 | 0.53-0.55(m, 2H), 0.84-0.88(m, 2H), 3.77-3.80(m, 1H), 7.58-7.60(m, 3H), 7.72-7.74(m, 2H), 7.99(s, 1H), 12.33(brs, 1H). | DMSO-d6 |
| 1-145 | 234 | 0.98-1.08(m, 4H), 2.44(s, 3H), 3.30-3.34(m, 1H), 7.84(s, 1H), 12.14(brs, 1H). | DMSO-d6 |
| 1-146 | 235 | 7.59(s, 4H), 8.07(s, 1H), 8.50(s, 1H), 12.52(brs, 1H). | DMSO-d6 |
| 1-164 | 236 | 1.89-1.92(m, 2H), 2.52-2.60(m, 2H), 4.40(t, J=6.9, 2H), 7.64(s, 5H), 7.79(brs, 3H), 8.07(d, J=3.7, 1H), 12.60(brs, 1H). | DMSO-d6 |
| 1-194 | 237 | 1.71-1.78(m, 2H), 3.20-3.25(m, 2H), 4.37-4.41(m, 3H), 7.62(s, 5H), 8.03(s, 1H), 12.46(brs, 1H). | DMSO-d6 |
| 1-208 | 239 | 2.92(s, 3H), 3.54(t, J=5.6, 2H), 4.98(t, J=5.6, 2H), 7.62-7.65(m, 5H), 8.21(s, 1H), 13.84(s, 1H). | DMSO-d6 |
| 1-209 | 240 | 2.49(s, 3H), 3.19(s, 3H), 3.63(t, J=5.2, | DMSO-d6 |

TABLE 248-continued

| Compound No. | Example | NMR δ(ppm) | Solvent |
|---|---|---|---|
| 1-215 | 242 | 2H), 4.53(t, J=5.2, 2H), 7.94(d, J=3.6, 1H), 12.33(brs, 1H). 0.87(t, J=7.0, 3H), 3.09(q, J=7.0, 2H), 3.58(t, J=5.4, 2H), 4.96(t, J=5.4, 2H), 7.61-7.66(m, 5H), 8.21(s, 1H), 13.83(s, 1H). | DMSO-d6 |
| 1-222 | 243 | 0.99(t, J=7.0, 3H), 2.49(s, 3H), 3.34(q, J=7.0, 2H), 3.65(t, J=5.2, 2H), 4.50(t, J=5.2, 2H), 7.93(d, J=3.6, 1H), 12.32(brs, 1H). | DMSO-d6 |
| 1-229 | 248 | 1.94-1.98(m, 2H), 2.50(s, 3H), 3.17(s, 3H), 3.24-3.31(m, 2H), 4.39(t, J=7.0, 2H), 7.93(s, 1H), 12.31(brs, 1H). | DMSO-d6 |
| 1-233 | 252 | 1.10-1.30(m, 3H), 1.82-1.86(m, 2H), 3.29-3.47(m, 4H), 4.33-4.64(m, 4H), 7.20-7.36(m, 5H), 8.11(d, J=2.5, 1H), 13.68(brs, 1H). | DMSO-d6 |
| 1-241 | 260 | 0.99-1.07(m, 4H), 1.13-1.37(m, 6H), 1.85-2.14(m, 4H), 4.34-4.35(m, 4H), 8.15(d, J=2.5, 1H), 13.68(brs, 1H). | DMSO-d6 |
| 1-265 | 271 | 1.93-1.99(m, 2H), 2.02(s, 3H), 2.44-2.48(m, 2H), 2.47(s, 3H), 4.40(t, J=7.3, 2H), 7.91(d, J=3.4, 1H), 12.29(brs, 1H). | DMSO-d6 |

TABLE 249

| Compound No. | Example | NMR δ(ppm) | Solvent |
|---|---|---|---|
| 1-272 | 272 | 2.98(t, J=6.4, 2H), 4.56(t, J=6.4, 2H), 7.64(s, 5H), 8.09(d, J=3.4, 1H), 12.62(brs, 1H). | DMSO-d6 |
| 1-275 | 275 | −0.031(d, J=4.9, 2H), 0.24(d, J=6.6, 2H), 0.94-0.95(m, 1H), 4.92(d, J=7.1, 2H), 7.64-7.67(m, 5H), 8.22(s, 1H), 13.84(s, 1H). | DMSO-d6 |
| 1-280 | 276 | 0.58-0.60(m, 2H), 0.93(brs, 3H), 1.21-1.24(m, 2H), 1.44-1.46(m, 4H), 4.31(d, J=7.3, 2H), 7.62(s, 5H), 8.03(d, J=3.7, 1H), 12.43(brs, 1H). | DMSO-d6 |
| 1-294 | 282 | 1.44-1.47(m, 2H), 1.53-1.55(m, 2H), 1.84(brs, 2H), 1.94(brs, 2H), 2.28(t, J=7.0, 2H), 2.50(s, 3H), 4.44(t, J=7.0, 2H), 5.20(brs, 1H), 7.93(d, J=3.6, 1H), 12.30(brs, 1H). | DMSO-d6 |
| 1-298 | 286 | 1.55-1.63(m, 1H), 1.77-1.84(m, 2H), 1.90-1.99(m, 1H), 2.49(s, 3H), 3.58(dd, J=14.4, 7.6, 1H), 3.73(dd, J=14.4, 7.0, 1H), 4.31(dd, J=14.0, 8.4, 1H), 4.52(dd, J=14.0, 3.3, 1H), 7.92(s, 1H), 12.30(brs, 1H). | DMSO-d6 |
| 1-300 | 288 | 5.62(s, 2H), 7.28-7.33(m, 5H), 7.98(s, 1H), 8.40(s, 1H), 12.42(brs, 1H). | DMSO-d6 |
| 1-301 | 289 | 6.20(s, 2H), 7.19-7.32(m, 5H), 8.17(s, 1H), 8.63(s, 1H), 13.82(brs, 1H). | DMSO-d6 |
| 1-302 | 290 | 0.85(d, J=1.6, 6H), 1.75-1.85(m, 1H), 2.66(d, J=1.9, 2H), 5.77(s, 2H), 7.05(d, J=1.7, 2H), 7.22-7.34(m, 3H), 7.99(s, 1H), 12.38(brs, 1H). | DMSO-d6 |
| 1-303 | 291 | 0.95-1.09 (m, 4H), 1.87-1.94(m, 1H), 5.84(s, 2H), 7.13(d, J=1.7, 2H), 7.25-7.35(m, 3H), 7.97(s, 1H), 12.35(brs, 1H). | DMSO-d6 |
| 1-306 | 294 | 2.69 (t, J=1.8, 2H), 3.07 (t, J=1.8, 2H), 5.74(s, 2H), 7.05-7.37 (m, 10H), 8.00(s, 1H), 12.42(brs, 1H). | DMSO-d6 |
| 1-307 | 295 | 5.70(s, 2H), 6.78-6.80(m, 2H), 7.18-7.21(m, 3H), 7.50-7.57(m, 5H), 8.06(s, 1H), 12.46(brs, 1H). | DMSO-d6 |
| 1-311 | 298 | 2.89(t, J=7.1, 2H), 4.54(t, J=7.1, 2H), 6.78-6.79(m, 2H), 7.14-7.16(m, 3H), 7.31-7.33(m, 2H), 7.51-7.57(m, 3H), 8.05(d, J=3.7, 1H), 12.49(brs, 1H). | DMSO-d6 |

TABLE 250

| Compound No. | Example | NMR δ(ppm) | Solvent |
|---|---|---|---|
| 1-312 | 299 | 2.92(t, J=7.4, 2H), 4.97(t, J=7.4, 2H), 6.77-6.79(m, 2H), 7.15-7.16(m, 3H), 7.41-7.43(m, 2H), 7.55-7.61(m, 3H), 8.23(s, 1H), 13.88(s, 1H). | DMSO-d6 |
| 1-313 | 300 | 2.13(s, 3H), 3.01(t, J=7.1, 2H), 4.55(t, J=7.1, 2H), 7.07-7.09(m, 2H), 7.22-7.28(m, 3H), 7.95(d, J=3.9, 1H), 12.34(brs, 1H). | DMSO-d6 |
| 1-316 | 303 | 0.82-0.90(m, 6H), 1.87-1.95(m, 1H), 2.01-2.05(t, J=1.8, 2H), 2.60-2.72(m, 2H), 4.31-4.46(m, 4H), 7.15-7.30(m, 5H), 8.27(d, J=3.3, 1H). | DMSO-d6 |
| 1-318 | 305 | 1.75(t, J=1.7, 2H), 2.48-2.54(m, 2H), 4.20-4.34(m, 4H), 7.02-7.38(m, 10H), 7.98(t, J=1.7, 1H), 12.36(brs, 1H). | DMSO-d6 |
| 1-319 | 306 | 1.75(t, J=1.7, 2H), 2.64(t, J=1.9, 2H), 2.92 (t, J=1.8, 2H), 3.11 (t, J=1.8, 2H), 4.34-4.48(m, 2H), 7.06-7.27(m, 10H), 8.09(d, J=3.2, 1H), 13.63(brs, 1H). | DMSO-d6 |
| 1-320 | 307 | 1.87-1.94(m, 2H), 2.38(t, J=7.5, 2H), 4.37(t, J=7.5, 2H), 6.98(d, J=6.8, 2H), 7.10-7.18(m, 3H), 7.58(s, 5H), 8.03(s, 1H), 12.45(brs, 1H). | DMSO-d6 |
| 1-398 | 331 | 2.53(s, 3H), 5.88(s, 2H), 6.97(dd, J=5.1, 3.5, 1H), 7.12(d, J=3.5, 1H), 7.47(dd, J=5.1, 1.5, 1H), 7.98(d, J=3.6, 1H), 12.44(brs, 1H). | DMSO-d6 |
| 1-400 | 333 | 2.12(s, 3H), 2.43(s, 3H), 5.59(s, 2H), 5.93(s, 1H), 6.19(s, 1H), 7.89(d, J=3.4, 1H), 12.30(brs, 1H). | DMSO-d6 |
| 1-417 | 336 | 2.17(s, 3H), 3.26(t, J=6.9, 2H), 4.55(t, J=6.9 2H), 6.73-6.74(m, 1H), 6.92-6.95(m, 1H), 7.35-7.36(m, 1H), 7.96(d, J=3.7, 1H), 12.36(brs, 1H). | DMSO-d6 |
| 2-015 | 472 | 3.44-3.49(m, 2H), 4.54(t, J=5.1, 2H), 7.38-7.41(m, 4H), 7.47-7.50(m, 3H), 7.55-7.57(m, 2H), 8.03(s, 1H), 8.40(t, J=5.6, 1H), 12.48(brs, 1H). | DMSO-d6 |
| 2-026 | 477 | 3.48-3.50(m, 2H), 3.87(s, 3H), 4.56(t, J=5.0, 2H), 7.34-7.49(m, 5H), 7.66(d, J=8.5, 2H), 7.98(d, J=8.5, 2H), 8.04(s, 1H), 8.52(t, J=5.6, 1H), 12.48(brs, 1H). | DMSO-d6 |

TABLE 251

| Compound No. | Example | NMR δ(ppm) | Solvent |
|---|---|---|---|
| 2-031 | 478 | 3.39-3.47(m, 2H), 4.49(t, J=5.0, 2H), 6.58(dd, J=3.4, 1.7, 1H), 6.86(d, J=3.4, 1H), 7.36-7.37(m, 4H), 7.44-7.49(m, 1H), 7.78(d, J=1.7, 1H), 8.04(s, 1H), 8.17(t, J=5.9, 1H), 12.48(brs, 1H). | DMSO-d6 |
| 2-033 | 480 | 3.47-3.51(m, 2H), 4.58(t, J=5.1, 2H), 7.37-7.47(m, 6H), 7.86-7.89(m, 1H), 8.04(s, 1H), 8.53(t, J=6.0, 1H), 8.66-8.71(m, 2H), 12.50(brs, 1H). | DMSO-d6 |
| 2-034 | 481 | 3.47-3.51(m, 2H), 4.57(t, J=5.0, 2H), 7.35-7.49(m, 7H), 8.04(s, 1H), 8.63-8.67(m, 3H), 12.50(brs, 1H). | DMSO-d6 |
| 2-035 | 482 | 3.45-3.46(m, 2H), 4.55(t, J=4.5, 2H), 7.13(d, J=3.9, 1H), 7.37-7.46(m, 5H), 7.70(d, J=3.9, 1H), 8.06(s, 1H), 8.66(t, J=5.6, 1H), 12.50(brs, 1H). | DMSO-d6 |
| 2-062 | 489 | 1.85-1.90(m, 2H), 3.05-3.10(m, 2H), 4.41(t, J=7.2, 2H), 7.45-7.70(m, 9H), 8.03(s, 1H), 8.43(t, J=5.2, 1H), 12.48(brs, 1H). | DMSO-d6 |
| 2-063 | 490 | 1.82-1.89(m, 2H), 3.04-3.09(m, 2H), 4.41(t, J=7.4, 2H), 7.49-7.60(m, 7H), 7.70(d, J=8.6, 2H), 8.03(s, 1H), 8.39(t, J=5.4, 1H), 12.48(brs, 1H). | DMSO-d6 |
| 2-092 | 495 | 1.85-1.89(m, 2H), 3.06-3.11(m, 2H), 3.87(s, 3H), 4.42(t, J=7.2, 2H), 7.48-7.53(m, 3H), 7.58-7.60(m, 2H), 7.79-7.81(m, 2H), 7.98-8.03(m, 3H), 8.51(t, J=5.5, 1H)., 12.48(brs, 1H). | DMSO-d6 |
| 2-093 | 496 | 1.85-1.90(m, 2H), 3.07-3.11(m, 2H), 4.43(t, J=7.3, 2H), 7.45-7.60(m, 6H), 8.01-8.03(m, 2H), 8.51(t, J=5.5, 1H), 8.67-8.68(m, 1H), 8.84-8.85(m, 1H), 12.49(brs, 1H). | DMSO-d6 |
| 2-096 | 497 | 1.85-1.88(m, 2H), 3.06-3.10(m, 2H), 4.42(t, J=7.4, 2H), 7.49-7.61(m, 7H), 8.03(s, 1H), 8.60(t, J=5.4, 1H), 8.66-8.71(m, 2H), 12.49(brs, 1H). | DMSO-d6 |

TABLE 252

| Compound No. | Example | NMR δ(ppm) | Solvent |
|---|---|---|---|
| 2-147 | 500 | 1.72-1.75(m, 2H), 2.83-2.88(m, 2H), 3.46(s, 2H), 4.36(t, J=7.2, 2H), 6.81(d, J=3.4, 1H), 6.90-6.92(m, 1H), 7.30-7.32(m, 1H), 7.60(s, 5H), 7.93(t, J=5.5, 1H), 8.03(d, J=3.9, 1H), 12.47(brs, 1H). | DMSO-d6 |
| 2-208 | 502 | 1.30(s, 9H), 1.68-1.76(m, 2H), 2.71-2.74(m, 2H), 4.34(t, J=7.3, 2H), 6.64(t, J=5.7, 1H), 7.61(s, 5H), 8.03(d, J=3.7, 1H), 12.47(brs, 1H). | DMSO-d6 |
| 2-507 | 503 | 1.76(s, 3H), 4.20(t, J=4.9, 2H), 4.60(t, J=4.9, 2H), 7.63(s, 5H), 8.06(s, 1H), 12.54(brs, 1H). | DMSO-d6 |
| 2-509 | 504 | 4.45(t, J=4.6, 2H), 4.82(t, J=4.6, 2H), 7.49-7.61(m, 8H), 7.70-7.73(m, 1H), 8.04(s, 1H), 12.54(brs, 1H). | DMSO-d6 |
| 2-519 | 506 | 1.72(s, 3H), 1.86-1.92(m, 2H), 3.74(t, J=5.7, 2H), 4.46(t, J=7.0, 2H), 7.62(s, 5H), 8.04(s, 1H), 12.49(brs, 1H). | DMSO-d6 |
| 2-521 | 508 | 2.04-2.07(m, 2H), 4.05(t, J=5.5, 2H), 4.56(t, J=7.1, 2H), 7.44-7.64(m, 10H), 8.02(s, 1H), 12.49(brs, 1H). | DMSO-d6 |
| 2-523 | 510 | 2.05-2.08(m, 2H), 4.05(t, J=5.4, 2H), 4.57(t, J=6.7, 2H), 7.43-7.59(m, 8H), 7.70-7.73(m, 1H), 8.01(s, 1H), 12.48(brs, 1H). | DMSO-d6 |
| 2-530 | 517 | 2.00-2.04(m, 2H), 4.00(t, J=5.6, 2H), 4.53(t, J=6.8, 2H), 6.64(dd, J=3.7, 1.7, 1H), 6.96(dd, J=3.7, 0.85, 1H), 7.49-7.59(m, 5H), 7.90(dd, J=1.7, 0.85, 1H), 8.02(s, 1H), 12.49(brs, 1H). | DMSO-d6 |
| 2-147 | 500 | 1.72-1.75(m, 2H), 2.83-2.88(m, 2H), 3.46(s, 2H), 4.36(t, J=7.2, 2H), 6.81(d, J=3.4, 1H), 6.90-6.92(m, 1H), 7.30-7.32(m, 1H), 7.60(s, 5H), 7.93(t, J=5.5, 1H), 8.03(d, J=3.9, 1H), 12.47(brs, 1H). | DMSO-d6 |
| 2-208 | 502 | 1.30(s, 9H), 1.68-1.76(m, 2H), 2.71-2.74(m, 2H), 4.34(t, J=7.3, 2H), 6.64(t, J=5.7, 1H), 7.61(s, 5H), 8.03(d, J=3.7, 1H), 12.47(brs, 1H). | DMSO-d6 |
| 2-507 | 503 | 1.76(s, 3H), 4.20(t, J=4.9, 2H), 4.60(t, J=4.9, 2H), 7.63(s, 5H), 8.06(s, 1H), 12.54(brs, 1H). | DMSO-d6 |
| 2-509 | 504 | 4.45(t, J=4.6, 2H), 4.82(t, J=4.6, 2H), 7.49-7.61(m, 8H), 7.70-7.73(m, 1H), 8.04(s, 1H), 12.54(brs, 1H). | DMSO-d6 |

TABLE 253

| Compound No. | Example | NMR δ(ppm) | Solvent |
|---|---|---|---|
| 2-519 | 506 | 1.72(s, 3H), 1.86-1.92(m, 2H), 3.74(t, J=5.7, 2H), 4.46(t, J=7.0, 2H), 7.62(s, 5H), 8.04(s, 1H), 12.49(brs, 1H). | DMSO-d6 |
| 2-521 | 508 | 2.04-2.07(m, 2H), 4.05(t, J=5.5, 2H), 4.56(t, J=7.1, 2H), 7.44-7.64(m, 10H), 8.02(s, 1H), 12.49(brs, 1H). | DMSO-d6 |
| 2-523 | 510 | 2.05-2.08(m, 2H), 4.05(t, J=5.4, 2H), 4.57(t, J=6.7, 2H), 7.43-7.59(m, 8H), 7.70-7.73(m, 1H), 8.01(s, 1H), 12.48(brs, 1H). | DMSO-d6 |
| 2-530 | 517 | 2.00-2.04(m, 2H), 4.00(t, J=5.6, 2H), 4.53(t, J=6.8, 2H), 6.64(dd, J=3.7, 1.7, 1H), 6.96(dd, J=3.7, 0.85, 1H), 7.49-7.59(m, 5H), 7.90(dd, J=1.7, 0.85, 1H), 8.02(s, 1H), 12.49(brs, 1H). | DMSO-d6 |
| 2-147 | 500 | 1.72-1.75(m, 2H), 2.83-2.88(m, 2H), 3.46(s, 2H), 4.36(t, J=7.2, 2H), 6.81(d, J=3.4, 1H), 6.90-6.92(m, 1H), 7.30-7.32(m, 1H), 7.60(s, 5H), 7.93(t, J=5.5, 1H), 8.03(d, J=3.9, 1H), 12.47(brs, 1H). | DMSO-d6 |
| 2-208 | 502 | 1.30(s, 9H), 1.68-1.76(m, 2H), 2.71-2.74(m, 2H), 4.34(t, J=7.3, 2H), 6.64(t, J=5.7, 1H), 7.61(s, 5H), 8.03(d, J=3.7, 1H), 12.47(brs, 1H). | DMSO-d6 |

TABLE 253-continued

| Compound No. | Example | NMR δ(ppm) | Solvent |
| --- | --- | --- | --- |
| 2-519 | 506 | 1.72(s, 3H), 1.86-1.92(m, 2H), 3.74(t, J=5.7, 2H), 4.46(t, J=7.0, 2H), 7.62(s, 5H), 8.04(s, 1H), 12.49(brs, 1H). | DMSO-d6 |
| 2-521 | 508 | 2.04-2.07(m, 2H), 4.05(t, J=5.5, 2H), 4.56(t, J=7.1, 2H), 7.44-7.64(m, 10H), 8.02(s, 1H), 12.49(brs, 1H). | DMSO-d6 |
| 2-523 | 510 | 2.05-2.08(m, 2H), 4.05(t, J=5.4, 2H), 4.57(t, J=6.7, 2H), 7.43-7.59(m, 8H), 7.70-7.73(m, 1H), 8.01(s, 1H), 12.48(brs, 1H). | DMSO-d6 |
| 2-530 | 517 | 2.00-2.04(m, 2H), 4.00(t, J=5.6, 2H), 4.53(t, J=6.8, 2H), 6.64(dd, J=3.7, 1.7, 1H), 6.96(dd, J=3.7, 0.85, 1H), 7.49-7.59(m, 5H), 7.90(dd, J=1.7, 0.85, 1H), 8.02(s, 1H), 12.49(brs, 1H). | DMSO-d6 |
| 2-147 | 500 | 1.72-1.75(m, 2H), 2.83-2.88(m, 2H), 3.46(s, 2H), 4.36(t, J=7.2, 2H), 6.81(d, J=3.4, 1H), 6.90-6.92(m, 1H), 7.30-7.32(m, 1H), 7.60(s, 5H), 7.93(t, J=5.5, 1H), 8.03(d, J=3.9, 1H), 12.47(brs, 1H). | DMSO-d6 |

TABLE 254

| Compound No. | Example | NMR δ(ppm) | Solvent |
| --- | --- | --- | --- |
| 2-208 | 502 | 1.30(s, 9H), 1.68-1.76(m, 2H), 2.71-2.74(m, 2H), 4.34(t, J=7.3, 2H), 6.64(t, J=5.7, 1H), 7.61(s, 5H), 8.03(d, J=3.7, 1H), 12.47(brs, 1H). | DMSO-d6 |
| 2-507 | 503 | 1.76(s, 3H), 4.20(t, J=4.9, 2H), 4.60(t, J=4.9, 2H), 7.63(s, 5H) 8.06(s, 1H), 12.54(brs, 1H). | DMSO-d6 |
| 2-509 | 504 | 4.45(t, J=4.6, 2H), 4.82(t, J=4.6, 2H), 7.49-7.61(m, 8H), 7.70-7.73(m, 1H), 8.04(s, 1H), 12.54(brs, 1H). | DMSO-d6 |
| 2-519 | 506 | 1.72(s, 3H), 1.86-1.92(m, 2H), 3.74(t, J=5.7, 2H), 4.46(t, J=7.0, 2H), 7.62(s, 5H), 8.04(s, 1H), 12.49(brs, 1H). | DMSO-d6 |
| 2-521 | 508 | 2.04-2.07(m, 2H), 4.05(t, J=5.5, 2H), 4.56(t, J=7.1, 2H), 7.44-7.64(m, 10H), 8.02(s, 1H), 12.49(brs, 1H). | DMSO-d6 |
| 2-523 | 510 | 2.05-2.08(m, 2H), 4.05(t, J=5.4, 2H), 4.57(t, J=6.7, 2H), 7.43-7.59(m, 8H), 7.70-7.73(m, 1H), 8.01(s, 1H),12.48(brs, 1H). | DMSO-d6 |
| 2-530 | 517 | 2.00-2.04(m, 2H), 4.00(t, J=5.6, 2H), 4.53(t, J=6.8, 2H), 6.64(dd, J=3.7, 1.7, 1H), 6.96(dd, J=3.7, 0.85, 1H), 7.49-7.59(m, 5H), 7.90(dd, J=1.7, 0.85, 1H), 8.02(s, 1H), 12.49(brs, 1H). | DMSO-d6 |
| 3-012 | 903 | 0.68(t, J=7.6, 6H), 1.10-1.23(m, 2H), 1.26-1.36(m, 2H), 2.53(brq, J=5.7, 2H), 3.32-3.42(m, 1H), 4.92(t, J=7.6, 2H), 7.43(d, J=8.6, 1H), 7.55-7.69(m, 5H), 8.20(s, 1H), 13.81(brs, 1H) | DMSO-d6 |
| 3-073 | 914 | 2.77(t, J=7.3, 2H), 5.04(t, J=7.3, 2H), 7.01(t, J=7.4, 1H), 7.25(t, J=7.9, 2H), 7.41(d, J=7.8, 2H), 7.53-7.62(m, 5H), 8.23(s, 1H), 9.81(s, 1H), 13.83(brs, 1H) | DMSO-d6 |
| 3-099 | 925 | 2.51(br, 2H), 3.02(brs, 3H), 4.85(brt, J=7.1, 2H), 7.05(brd, J=7.1, 2H), 7.24-7.38(m, 3H), 7.55-7.68(m, 5H), 8.15(d, J=3.4, 1H), 13.71(brs, 1H) | DMSO-d6 |

TABLE 255

| Compound No. | Example | NMR δ(ppm) | Solvent |
| --- | --- | --- | --- |
| 3-148 | 944 | 1.62-1.79(m, 4H), 2.71(brt, J=7.8, 2H), 3.15(q, J=6.6, 4H), 4.92(brt, J=7.6, 2H), 7.62-7.68(m, 5H), 8.21(d, J=3.7, 1H), 13.83(brs, 1H) | DMSO-d6 |
| 3-152 | 945 | 1.28-1.36(m, 4H), 1.45-1.53(m, 2H), | DMSO-d6 |

TABLE 255-continued

| Compound No. | Example | NMR δ(ppm) | Solvent |
|---|---|---|---|
| | | 2.77(t, J=7.8, 2H), 3.14-3.18(m, 2H), 3.26-3.30(m, 2H), 4.88(t, J=7.6, 2H), 7.62-7.66(m, 5H), 8.21(s, 1H), 13.8(brs, 1H) | |
| 3-156 | 946 | 1.41-1.43(m, 4H), 1.54-1.56(m, 2H), 2.95(t, J=7.8, 6H), 3.31-3.42(m, 4H), 5.20-5.23(m, 2H), 6.87-6.88(m, 1H), 7.34(d, J=3.7, 1H), 8.14(s, 1H), 8.17(s, 1H), 13.79(s, 1H) | DMSO-d6 |
| 3-206 | 953 | 1.16(t, J=7.1, 3H), 1.20-1.39(m, 2H), 1.73(brt, J=9.5, 2H), 2.61(brt, J=10.5, 1H), 2.72-2.93(m, 3H), 3.57(brd, J=13.7, 1H), 4.00-4.10(m, 3H), 4.83-4.92(m, 2H), 7.60-7.68(m, 5H), 8.21(s, 1H), 13.82(brs, 1H) | DMSO-d6 |
| 3-148 | 944 | 1.62-1.79(m, 4H), 2.71(brt, J=7.8, 2H), 3.15(q, J=6.6, 4H), 4.92(brt, J=7.6, 2H), 7.62-7.68(m, 5H), 8.21(d, J=3.7, 1H), 13.83(brs, 1H) | DMSO-d6 |
| 3-152 | 945 | 1.28-1.36(m, 4H), 1.45-1.53(m, 2H), 2.77(t, J=7.8, 2H), 3.14-3.18(m, 2H), 3.26-3.30(m, 2H), 4.88(t, J=7.6, 2H), 7.62-7.66(m, 5H), 8.21(s, 1H), 13.8(brs, 1H) | DMSO-d6 |
| 3-156 | 946 | 1.41-1.43(m, 4H), 1.54-1.56(m, 2H), 2.95(t, J=7.8, 6H), 3.31-3.42(m, 4H), 5.20-5.23(m, 2H), 6.87-6.88(m, 1H), 7.34(d, J=3.7, 1H), 8.14(s, 1H), 8.17(s, 1H), 13.79(s, 1H) | DMSO-d6 |

TABLE 256

| Compound No. | Example | NMR δ(ppm) | Solvent |
|---|---|---|---|
| 3-206 | 953 | 1.16(t, J=7.1, 3H), 1.20-1.39(m, 2H), 1.73(brt, J=9.5, 2H), 2.61(brt, J=10.5, 1H), 2.72-2.93(m, 3H), 3.57(brd, J=13.7, 1H), 4.00-4.10(m, 3H), 4.83-4.92(m, 2H), 7.60-7.68(m, 5H), 8.21(s, 1H), 13.82(brs, 1H) | DMSO-d6 |
| 3-220 | 956 | 1.17-1.35(m, 2H), 1.61(brt, J=10.2, 2H), 2.24(tt, J=11.2, J=3.9, 1H), 2.40-2.50(m, 1H), 2.72-2.87(m, 3H), 3.63(brd, J=13.4, 1H), 4.18(brd, J=13.0, 1H), 4.88(t, J=7.0, 2H), 6.76(brs, 1H), 7.23(brs, 1H), 7.62-7.68(m, 5H), 8.21(d, J=3.7, 1H), 13.84(brs, 1H) | DMSO-d6 |
| 3-241 | 958 | 1.20-1.43(m, 2H), 1.72(brt, J=14.4, 2H), 2.67(brt, J=11.7, 1H), 2.74-2.80(m, 2H), 3.01(brt, J=11.5, 1H), 3.60-3.74(m, 2H), 4.24(brd, J=13.4, 1H), 4.82-4.97(m, 2H), 7.53(t, J=7.6, 2H), 7.61-7.68(m, 6H), 7.97(d, J=8.0, 2H), 8.21(s, 1H), 13.84(brs, 1H) | DMSO-d6 |
| 3-294 | 962 | 2.78(brt, J=7.6, 2H), 3.21(brt, J=4.9, 2H), 3.25-3.35(m, 2H), 3.38-3.48(m, 4H), 4.91(brt, J=7.1, 2H), 7.62-7.68(m, 5H), 8.21(s, 1H), 13.75(brs, 1H) | DMSO-d6 |
| 3-353 | 973 | 1.97(s, 3H), 2.81-2.83(m, 2H), 3.19-3.30(m, 8H), 4.89-4.93(m, 2H), 7.64-7.66(m, 5H), 8.22(d, J=3.9, 1H), 13.84(brs, 1H) | DMSO-d6 |
| 3-560 | 996 | 1.90(m, 2H), 2.11(t, J=7.6, 2H), 3.69(s, 3H), 4.87(t, J=6.6, 2H), 6.57(d, J=7.8, 1H), 6.96(d, J=8.2, 1H), 7.10-7.20(m, 2H), 7.55-7.59(m, 3H), 7.65-7.67(m, 2H), 8.19(s, 1H), 9.70(s, 1H), 13.8(brs, 1H) | DMSO-d6 |

TABLE 257

| Compound No. | Example | NMR δ(ppm) | Solvent |
|---|---|---|---|
| 3-577 | 1002 | 1.90-1.97(m, 2H), 2.30(t, J=7.0, 2H), 4.92(t, J=7.1, 2H), 7.56-7.57(m, 3H), 7.67-7.69(m, 2H), 7.85(d, J=5.6, 2H), 8.20(d, J=3.4, 1H), 8.64(d, J=6.6, 2H), 11.05(s, 1H), 13.83(s, 1H) | DMSO-d6 |
| 3-600 | 1012 | 1.85(tt, J=7.1, 2H), 2.00(t, J=7.3, 2H), 4.26(d, J=5.6, 2H), 4.84(t, J=7.6, 2H), 7.32(d, J=8.0, 1H), 7.40(m, 1H), 7.60-7.68(m, 5H), 7.90-7.95(m, 1H), 8.20(d, 3.64, 1H), 8.36(t, J=5.8, 1H), 8.54(d, J=5.1, 1H)13.8(brs, 1H) | DMSO-d6 |
| 3-616 | 1015 | 0.70-0.97(m, 5H), 1.51(brt, J=14.4, 3H), 1.73-1.85(m, 2H), 2.00-2.20(m, 2H), 2.32(td, J=10.7, J=1.5, 1H), 2.79(t, J=13.2, 1H), 3.50-3.62(m, 1H), 4.14(d, J=12.7, 1H), 4.84(t, J=8.1, 2H), 7.52-7.59(m, 5H), 8.20(d, J=3.6, 1H), 13.81(brs, 1H) | DMSO-d6 |
| 4-029 | 1128 | 1.78-1.85(m, 2H), 2.04(t, J=7.2, 2H), 4.83(t, J=7.3, 2H), 7.63-7.65(m, 5H), 8.20(s, 1H), 12.03(brs, 1H), 13.81(brs, 1H) | DMSO-d6 |
| 4-030 | 1129 | 1.05(t, J=7.1, 3H), 1.77-1.87(m, 2H), 2.09(t, J=7.1, 2H), 3.82(q, J=7.3, 2H), 4.42(t, J=6.8, 2H), 7.55-7.69(m, 5H), 8.04(s, 1H), 12.48(brs, 1H) | DMSO-d6 |
| 4-031 | 1130 | 1.05(t, J=7.1, 3H), 1.79-1.89(m, 2H), 2.12(t, J=7.3, 2H), 3.84(q, J=7.1, 2H), 4.85(t, J=7.1, 2H), 7.57-7.71(m, 5H), 8.20(s, 1H), 13.83(brs, 1H) | DMSO-d6 |

TABLE 258

| Compound No. | Example | NMR δ(ppm) | Solvent |
|---|---|---|---|
| 1-0460 | 347 | 3.06(t, J=7.1, 2H), 3.20-3.50(m, 3H), 4.89(t, J=6.8, 2H), 7.49(t, J=8.3, 2H), 7.76-7.93(m, 1H), 8.27(s, 1H) | DMSO-d6 |
| 1-0499 | 353 | 2.27(s, 4H), 3.55(m, 2H), 5.08(brs, 2H), 7.56(m, 5H), 8.17(d, J=3.2, 1H), 13.83(brs, 1H) | DMSO-d6 |
| 1-0511 | 356 | 1.10-1.40(m, 6H), 1.85-2.15(m, 4H), 3.87(s, 3H), 4.30-4.40(m, 4H), 8.10(d, J=2.5, 1H), 13.60(brs, 1H). | DMSO-d6 |
| 1-0526 | 366 | 0.92-0.93(m, 6H), 1.93(m, 1H), 3.27-3.35(m, 4H), 4.80(t, J=7.1, 2H), 7.13(t, J=8.0, 2H), 7.57-7.61(m, 1H), 8.15(s, 1H), 11.60(brs, 1H). | CDC13 |
| 1-0674 | 395 | 0.90-1.10(m, 9H), 7.30-7.40(m, 4H), 7.50-7.60(m, 4H), 8.10(d, J=2.5, 1H), 13.20(brs, 1H), 13.60(brs, 1H). | DMSO-d6 |
| 1-0685 | 405 | 3.50-3.80(m, 9H), 6.50(d, J=1.7, 1H), 7.00(d, J=1.7, 1H), 7.50-7.60(m, 4H), 8.10(d, J=2.5, 1H), 13.40(brs, 1H), 13.60(brs, 1H). | DMSO-d6 |
| 1-0686 | 406 | 7.50-7.80(m, 7H), 8.00(s, 1H), 8.15(d, J=2.5, 1H), 9.50-9.70(m, 1H), 13.40(brs, 1H), 13.60(brs, 1H). | DMSO-d6 |
| 1-0691 | 409 | 3.10-3.40(m, 4H), 7.00-7.20(m, 3H), 8.00(s, 1H), 13.40(brs, 1H), 13.60(brs, 1H). | DMSO-d6 |
| 1-0692 | 410 | 2.52-2.65(m, 3H), 7.50-7.70(m, 6H), 8.00(t, J=1.8, 2H), 8.15(d, J=2.5, 1H), 13.40(brs, 1H), 13.60(brs, 1H). | DMSO-d6 |
| 1-0694 | 412 | 6.90-7.35(m, 4H), 8.10(d, J=2.5, 1H), 13.40(brs, 1H), 13.60(brs, 1H). | DMSO-d6 |
| 1-0695 | 413 | 6.80-6.90(m, 2H), 7.35-7.40(m, 2H), 8.15(d, J=2.5, 1H), 13.40(brs, 1H), 13.60(brs, 1H). | DMSO-d6 |
| 1-0699 | 416 | 4.60-4.75(m, 2H), 7.10-7.35(m, 4H), 8.15(d, J=2.5, 1H), 13.40(brs, 1H), 13.60(brs, 1H). | DMSO-d6 |
| 1-0700 | 417 | 4.50-4.70(m, 2H), 7.20-7.40(m, 4H), 8.10(d, J=2.5, 1H), 13.30(brs, 1H), | DMSO-d6 |

TABLE 258-continued

| Compound No. | Example | NMR δ(ppm) | Solvent |
|---|---|---|---|
| 1-0702 | 419 | 13.50(brs, 1H). 1.10-1.30(m, 3H), 3.30-3.40(m, 2H), 7.50-7.60(m, 4H), 7.70-7.80(m, 2H), 7.95-8.05(m, 2H), 8.15(d, J=2.2, 1H), 13.40(brs, 1H), 13.60(brs, 1H). | DMSO-d6 |
| 1-0706 | 423 | 7.30(d, J=5.0, 2H), 7.40-7.60(m, 9H), 8.15(d, J=2.5, 1H), 13.20(brs, 1H), 13.50(brs, 1H) | DMSO-d6 |

TABLE 259

| Compound No. | Example | NMR δ(ppm) | Solvent |
|---|---|---|---|
| 1-0738 | 445 | 2.33(s, 3H), 7.22(m, 1H), 7.31(m, 1H), 7.54(m, 1H), 8.21(s, 1H), 13.39(brs, 1H), 13.87(brs, 1H). | DMSO-d6 |
| 1-0739 | 446 | 2.22(m, 3H), 7.31-7.46(m, 3H), 8.22(s, 1H), 13.47(brs, 1H), 13.88(brs, 1H). | DMSO-d6 |
| 1-0740 | 447 | 2.29(s, 3H), 7.31-7.40(m, 2H), 7.46(m, 1H), 8.22(s, 1H), 13.45(brs, 1H), 13.88(brs, 1H). | DMSO-d6 |
| 1-0741 | 448 | 2.32(s, 3H), 3.83(s, 3H), 6.91-7.01(m, 2H), 7.40(m, 1H), 8.17(s, 1H). | DMSO-d6 |
| 1-0749 | 451 | 2.29(s, 3H), 7.48(s, 1H), 8.00(s, 1H), 8.14(s, 1H), 13.30-13.80(brs, 2H). | DMSO-d6 |
| 1-0860 | 456 | 0.89-0.97(m, 6H), 1.90-1.96(m, 1H), 3.24(t, J=6.0, 2H), 3.29-3.35(m, 2H), 4.41(t, J=7.1, 2H), 7.12(t, J=7.6, 2H), 7.50-7.59(m, 1H), 7.98(s, 1H), 10.1(brs, 1H). | CDC13 |
| 1-1072 | 466 | 1.04-1.12(m, 6H), 2.04-2.10(m, 1H), 3.44-3.53(m, 4H), 4.63(t, J=7.1, 2H), 7.97(brs, 1H). | CDC13 |
| 2-0559 | 525 | 1.63(s, 3H), 3.57(m, 2H), 5.14(brs, 2H), 6.41(s, 1H), 7.39(m, 2H), 7.49(m, 1H), 7.58(m, 2H), 7.82(m, 1H), 8.22(m, 1H), 8.28(m, 1H), 13.85(brs, 1H) | DMSO-d6 |
| 2-0560 | 526 | 1.93(s, 3H), 3.57(brs, 2H), 4.89(brs, 1H), 5.17(brs, 1H), 6.99(d, J=5.1, 1H), 7.34-7.62(m, 5H), 7.78(d, J=5.2, 1H), 8.20(s, 1H), 8.30(m, 1H), 13.84(brs, 1H) | DMSO-d6 |
| 2-0568 | 530 | 3.50(m, 2H), 5.09(brs, 2H), 7.33-7.40(m, 4H), 7.45-7.52(m, 4H), 7.58(m, 1H), 8.23(s, 1H), 8.36(m, 1H), 13.86(brs, 1H) | DMSO-d6 |
| 2-0596 | 536 | 1.61(s, 3H), 3.49(brs, 2H), 3.73(s, 3H), 5.07(brs, 2H), 6.37(s, 1H), 6.87(m, 2H), 7.49(m, 2H), 7.75(s, 1H), 8.07(m, 1H), 8.16(m, 1H), | DMSO-d6 |
| 2-0597 | 537 | 1.94(s, 3H), 3.55(brs, 2H), 3.79(s, 3H), 4.86(brs, 1H), 5.15(brs, 1H), 6.92(d, J=8.6, 2H), 6.99(d, J=5.1, 1H), 7.56(d, J=8.5, 2H), 7.78(d, J=4.8, 1H), 8.14(m, 1H), 8.20(s, 1H), 13.84(brs, 1H) | DMSO-d6 |

TABLE 260

| Compound No. | Example | NMR δ(ppm) | Solvent |
|---|---|---|---|
| 2-0623 | 546 | 1.98(s, 3H), 2.01(s, 3H), 3.52(brs, 2H), 3.80(brs, 2H), 4.86(brs, 1H), 5.14(brs, 1H), 6.40(t, J=7.6, 1H), 7.01-7.17(m, 3H), 7.79(d, J=5.1, 1H), 8.03(m, 1H), 8.20(d, J=3.7, 1H), 13.83(brs, 1H) | DMSO-d6 |
| 2-0645 | 552 | 3.53(brs, 2H), 4.49(brs, 1H), 5.41(brs, 1H), 6.23(m, 1H), 6.38(m, 1H), 6.53(brs, 2H), 7.28(m, 2H), 8.01(m, 2H), 8.22(m, 1H), 13.91(brs, 1H) | DMSO-d6 |
| 2-0694 | 559 | 1.62(s, 3H), 3.51(m, 2H), 5.09(brs, 2H), 6.38(s, 1H), 7.18(m, 2H), 7.59(m, 2H), 7.76(m, 1H), 8.16(m, 1H), 8.26(m, 1H) | DMSO-d6 |
| 2-0696 | 561 | 3.59(m, 2H), 4.59(brs, 1H), 5.41(brs, 1H), 7.17-7.30(m, 3H), 7.67(m, 2H), 7.99(m, 1H), 8.22(s, 1H), 8.36(m, 1H), 13.92(brs, 1H) | DMSO-d6 |

TABLE 260-continued

| Compound No. | Example | NMR δ(ppm) | Solvent |
|---|---|---|---|
| 2-0731 | 568 | 3.53(m, 2H), 5.13(brs, 2H), 7.29-7.45(m, 5H), 7.74(m, 1H), 7.95(m, 1H), 8.23(s, 1H), 8.35(m, 2H), 8.63(m, 1H), 13.86(brs, 1H) | DMSO-d6 |
| 2-0761 | 571 | 3.52(m, 2H), 5.10(brs, 2H), 7.32-7.47(m, 5H), 7.74(m, 2H), 8.26(m, 3H), 8.57(m, 1H), 13.84(brs, 1H) | DMSO-d6 |
| 2-0772 | 572 | 3.51(m, 2H), 5.08(brs, 1H), 7.32-7.49(m, 5H), 7.62(m, 2H), 7.96(m, 2H), 8.22(s, 1H), 8.40(m, 1H), 13.20(brs, 1H), 13.85(brs, 1H) | DMSO-d6 |
| 2-0773 | 573 | 1.60(s, 3H), 3.53(m, 2H), 5.09(brs, 2H), 6.40(s, 1H), 7.62(m, 2H), 7.77(s, 1H), 7.90(m, 2H), 8.17(m, 1H), 8.41(m, 1H) | DMSO-d6 |
| 2-0886 | 586 | 1.95(s, 3H), 3.58(brs, 2H), 3.87(s, 3H), 4.87(brs, 1H), 5.20(brs, 1H), 7.00(d, J=5.1, 1H), 7.72(d, J=8.3, 2H), 7.79(d, J=5.1, 1H), 7.98(d, J=8.3, 2H), 8.20(s, 1H), 8.51(m, 1H), 13.84(brs, 1H) | DMSO-d6 |
| 2-0887 | 587 | 3.61(m, 2H), 3.87(s, 3H), 4.60(brs, 1H), 5.42(brs, 1H), 7.26(m, 1H), 7.72(m, 2H), 7.93-8.05(m, 3H), 8.22(m, 1H), 8.54(m, 1H), 13.92(m, 1H) | DMSO-d6 |
| 2-1087 | 607 | 2.72(s, 3H), 3.46(m, 2H), 5.04(brs, 2H), 6.49(t, J=7.4, 1H), 6.58(d, J=8.6, 1H), 7.20-7.38(m, 6H), 7.49(m, 1H), 7.97(m, 1H), 8.22(d, J=3.4, 1H), 13.82(brs, 1H) | DMSO-d6 |

TABLE 261

| Compound No. | Example | NMR δ(ppm) | Solvent |
|---|---|---|---|
| 2-1351 | 654 | 3.55(m, 2H), 4.54(brs, 1H), 5.35(brs, 1H), 6.56(m, 1H), 6.89(m, 1H), 7.27(m, 1H), 7.76(m, 1H), 8.00(m, 1H), 8.18-8.26(m, 2H), 13.91(brs, 1H) | DMSO-d6 |
| 2-1378 | 662 | 1.71(s, 3H), 3.54(m, 2H), 5.11(brs, 2H), 6.43(s, 1H), 7.07(m, 1H), 7.45(m, 1H), 7.70(m, 1H), 7.81(s, 1H), 8.22(m, 1H), 8.28(m, 1H), 8.28(m, 1H), 13.87(brs, 1H) | DMSO-d6 |
| 2-1406 | 673 | 2.21(s, 6H), 3.40(m, 2H), 4.99(brs, 2H), 6.12(s, 1H), 7.38(m, 4H), 7.52(m, 2H), 8.22(s, 1H), 13.83(brs, 1H) | DMSO-d6 |
| 2-1461 | 689 | 3.47(m, 2H), 4.97(brs, 2H), 6.05(m, 1H), 6.52(m, 1H), 6.79(m, 1H), 7.35(m, 4H), 7.49(m, 1H), 7.73(m, 1H), 8.22(s, 1H), 11.21(brs, 1H), 13.84(brs, 1H) | DMSO-d6 |
| 2-1779 | 730 | 1.82(m, 2H), 2.91(m, 2H), 4.83(m, 2H), 6.23(m, 1H), 7.31(m, 1H), 7.45-7.65(m, 7H), 7.97(s, 1H), 8.19(s, 1H), 8.55(s, 1H) | DMSO-d6 |
| 2-1792 | 743 | 3.80(brs, 2H), 5.09(brs, 2H), 7.42-7.64(m, 8H), 7.83(m, 2H), 8.23(m, 1H), 9.67(s, 1H), 12.74(brs, 1H), 13.85(brs, 1H) | DMSO-d6 |
| 2-1803 | 754 | 1.61(s, 3H), 2.82(m, 2H), 4.78(m, 2H), 7.63(m, 6H), 8.19(s, 1H) | DMSO-d6 |
| 2-1807 | 756 | 3.66(m, 2H), 5.38(brs, 2H), 6.53(m, 1H), 7.25(m, 1H), 7.36(m, 2H), 7.47(m, 1H), 7.57(m, 2H), 7.95(s, 1H), 8.17(m, 1H), 8.42(m, 1H), 13.78(brs, 1H) | DMSO-d6 |
| 2-1809 | 758 | 3.64(m, 2H), 3.78(s, 3H), 5.35(brs, 2H), 6.70(m, 1H), 6.91(m, 2H), 7.26(m, 1H), 7.56(m, 2H), 7.94(m, 1H), 8.18(m, 1H), 8.28(m, 1H), 13.79(brs, 1H) | DMSO-d6 |
| 2-1812 | 761 | 3.52(m, 2H), 5.22(brs, 2H), 6.22(m, 1H), 6.76(m, 1H), 6.88(m, 1H), 7.19(m, 2H), 7.26(m, 2H), 7.47(m, 2H), 8.03(m, 1H), 8.17(m, 1H), 8.33(s, 1H), 13.78(brs, 1H) | DMSO-d6 |
| 2-1822 | 771 | 3.44(m, 2H), 5.01(brs, 2H), 7.17-7.43(m, 7H), 7.54(m, 2H), 8.17(m, 2H), 13.78(brs, 1H) | DMSO-d6 |

TABLE 262

| Compound No. | Example | NMR δ(ppm) | Solvent |
|---|---|---|---|
| 2-1835 | 784 | 3.59(m, 2H), 5.33(brs, 2H), 6.64(m, 1H), 7.13-7.19(m, 3H), 7.58(m, 2H), 7.88(m, 1H), 8.12(s, 1H), 8.39(m, 1H), 13.71(brs, 1H) | DMSO-d6 |
| 2-1842 | 791 | 1.98(s, 3H), 4.32(brs, 2H), 5.44(brs, 2H), 7.11-7.18(m, 4H), 7.33(t, J=7.3, 1H), 7.41(t, J=7.6, 1H), 7.50(d, J=8.0, 1H), 7.75(m, 2H), 8.21(d, J=3.4, 1H), 13.90(brs, 1H) | DMSO-d6 |
| 2-1855 | 803 | 2.70(s, 3H), 3.63(m, 2H), 5.20(m, 2H), 7.65(m, 5H), 8.22(m, 1H), 13.88(brs, 1H) | DMSO-d6 |
| 2-1903 | 850 | 2.02-2.23(m, 4H), 3.27(m, 2H), 4.89(brs, 2H), 7.60(m, 6H), 8.22(m, 1H), 13.82(brs, 1H) | DMSO-d6 |
| 2-1906 | 853 | 3.55(m, 2H), 4.69(m, 1H), 5.27(m, 1H), 7.11(m, 1H), 7.25(m, 1H), 7.34(m, 1H), 7.42(m, 2H), 7.50-7.65(m, 4H), 8.21-8.33(m, 2H), 13.91(brs, 1H). | DMSO-d6 |
| 2-1908 | 855 | 1.35(t, J=7.1, 3H), 3.51(m, 2H), 4.02(q, J=7.1, 2H), 5.08(brs, 2H), 6.84(m, 2H), 7.30(m, 2H), 7.41(m, 2H), 7.49-7.60(m, 3H), 8.20(m, 2H), 13.78(brs, 1H). | DMSO-d6 |
| 2-1930 | 877 | 3.21-3.97(m, 12H), 4.41(brs, 2H), 5.03(brs, 2H), 7.03(m, 2H), 7.31-7.59(m, 6H), 8.09(m, 1H), 8.23(m, 1H), 10.10(brs, 1H), 13.84(brs, 1H) | DMSO-d6 |
| 2-1940 | 887 | 3.34(m, 2H), 4.94(brs, 2H), 6.02(m, 1H), 7.28(m, 2H), 7.40(m, 3H), 7.56(m, 2H), 7.77(m, 2H), 8.23(s, 1H), 8.64(m, 1H) | DMSO-d6 |
| 2-1946 | 893 | 1.86(s, 3H), 4.02(m, 2H), 5.11(brs, 1H), 5.49(brs, 1H), 6.78(m, 1H), 7.62(m, 1H), 7.77(m, 2H), 8.06-8.23(m, 3H), 8.64(m, 1H), 9.91(brs, 1H), 13.94(brs, 1H) | DMSO-d6 |
| 2-1948 | 895 | 3.47(m, 2H), 4.54(m, 2H), 7.15-7.70(m, 9H), 8.03(s, 1H), 8.34(t, J=5.6, 1H), 12.49(brs, 1H) | DMSO-d6 |
| 2-1949 | 896 | 1.72(s, 3H), 3.54(m, 2H), 4.61(brs, 2H), 6.43(s, 1H), 7.23(m, 2H), 7.65(m, 2H), 7.76(s, 1H), 8.03(m, 1H), 8.38(m, 1H), 12.53(brs, 1H) | DMSO-d6 |

Example 1176

Measurement of GSK-3 Enzyme Activity Inhibition

After adding 25 µL of phospho-glycogen synthase peptide-2 substrate solution [6 µM phospho-glycogen synthase peptide-2, 20 µM ATP, 16 mM MOPS buffer (pH 7.0), 0.2 mM EDTA, 20 mM magnesium acetate, 0.1 µCi [γ-$^{32}$P]ATP (specific activity: approximately 110 TBq/mmol)] to 5 µL of the test compound using 5% dimethylsulfoxide as the solvent, reaction was initiated by further addition of 20 µL of a GSK-3β enzyme solution [10 mU recombinant human GSK-3β, 20 mM MOPS buffer (pH 7.0), 1 mM EDTA, 0.1% polyoxyethylene lauryl ether (23 Lauryl Ether; Brij 35), 5% glycerol, 0.1% β-mercaptoethanol]. After conducting the reaction for 20 minutes at room temperature, an equivalent volume of a 200 mM phosphoric acid solution was added to quench the reaction, and 90 µL of the reaction product was adsorbed onto a MultiScreen PH plate (Millipore) and rinsed with a 100 mM phosphoric acid solution. After drying the plate, 30 µL of Micro Scint-O (Packard BioScience) was added, and the cpm was measured with a scintillation counter to determine the inhibiting activity. Phospho GS Peptide2 is Tyr-Arg-Arg-Ala-Ala-Val-Pro-Pro-Ser-Pro-Ser-Leu-Ser-Arg-His-Ser-Ser-Pro-His-Gln-Ser(P)-Glu-Asp-Glu-Glu-Glu (SEQ ID NO:1).

As a result of measuring the GSK-3 enzyme inhibiting activity ($IC_{50}$) of the compounds of the invention in this manner, inhibiting activity of $IC_{50}$<10 nM was found for Compound Nos. 2-0559, 2-0560, 2-0561, 2-0562, 2-0596, 2-0597, 2-0598, 2-0599, 2-0616, 2-0617, 2-0618, 2-0623, 2-0624, 2-0625, 2-0643, 2-0644, 2-0645, 2-0646, 2-0694, 2-0695, 2-0696, 2-0697, 2-0743, 2-0773, 2-0790, 2-0886, 2-0887, 2-0888, 2-1057, 2-1079, 2-1350, 2-1351, 2-1378, 2-1379, 2-1380, 2-1392, 2-1441, 2-1463, 2-1464, 2-1532, 2-1534, 2-1824, 2-1825, 2-1927, 2-1928, 2-1929, 2-1946, 3-0137, 3-0152, 3-0156, 3-0207, 3-0231, 3-0235, 3-1777, 3-1778 and 3-1779.

Inhibiting activity of 10 nM≦$IC_{50}$<30 nM was found for Compound Nos. 1-0026, 1-0529, 1-0595, 1-0610, 1-0698, 2-0595, 2-0601, 2-0607, 2-0614, 2-0621, 2-0642, 2-1076, 2-1108, 2-1170, 2-1352, 2-1381, 2-1499, 2-1807, 2-1809, 2-1810, 2-1811, 2-1826, 2-1829, 2-1835, 2-1836, 2-1906, 2-1907, 2-1909, 2-1910, 2-1911, 2-1912, 2-1913, 2-1914, 2-1915, 2-1917, 2-1919, 3-0004, 3-0074, 3-0160, 3-0168, 3-0175, 3-0206, 3-0220, 3-0242, 3-0297, 3-0362, 3-0898, 3-0974, 3-0978, 3-0982, 3-1776, 3-1810, 4-0092 and 6-0413.

Inhibiting activity of 30 nM≦$IC_{50}$<100 nM was found for Compound Nos. 1-0010, 1-0016, 1-0037, 1-0047, 1-0241, 1-0514, 1-0515, 1-0516, 1-0518, 1-0519, 1-0521, 1-0596, 1-0601, 1-0602, 1-0609, 1-0676, 1-0678, 1-0686, 1-0699, 1-0700, 1-0708, 1-0724, 1-0725, 1-0728, 1-0738, 1-0739, 1-0740, 1-0741, 1-0749, 1-0751, 2-0558, 2-0573, 2-0578, 2-0604, 2-0635, 2-0671, 2-0682, 2-0687, 2-0688, 2-0708, 2-0740, 2-0761, 2-0772, 2-0787, 2-0817, 2-0823, 2-0834, 2-0869, 2-0882, 2-0884, 2-1021, 2-1054, 2-1060, 2-1065, 2-1068, 2-1075, 2-1083, 2-1087, 2-1101, 2-1115, 2-1133, 2-1135, 2-1143, 2-1151, 2-1188, 2-1195, 2-1202, 2-1209, 2-1216, 2-1223, 2-1226, 2-1229, 2-1247, 2-1261, 2-1348, 2-1358, 2-1365, 2-1377, 2-1389, 2-1406, 2-1411, 2-1416, 2-1418, 2-1425, 2-1438, 2-1445, 2-1452, 2-1455, 2-1461, 2-1465, 2-1467, 2-1473, 2-1474, 2-1497, 2-1498, 2-1531, 2-1601, 2-1777, 2-1788, 2-1804, 2-1808, 2-1812, 2-1822, 2-1828, 2-1855, 2-1867, 2-1871, 2-1877, 2-1916, 2-1918, 2-1920, 2-1921, 2-1925, 2-1926, 2-1930, 2-1940, 2-1942, 3-0016, 3-0029, 3-0038, 3-0065, 3-0090, 3-0110, 3-0117, 3-0135, 3-0136, 3-0140, 3-0148, 3-0217, 3-0241, 3-0294, 3-0351, 3-0353, 3-0357, 3-0397, 3-0924, 3-0947, 3-0962, 3-0977, 3-0981, 3-0983, 3-0986, 3-0989, 3-0990, 3-0991, 3-1783, 3-1792, 3-1793, 3-1799, 3-1803, 3-1812, 3-1815, 3-1820, 4-0002, 6-0414, 6-1029, 6-1031 and 6-1033.

Inhibiting activity of 100 nM$\leq$IC$_{50}$<1 $\mu$M was found for Compound Nos. 1-0008, 1-0011, 1-0019, 1-0027, 1-0030, 1-0032, 1-0034, 1-0039, 1-0045, 1-0046, 1-0049, 1-0050, 1-0071, 1-0072, 1-0087, 1-0101, 1-0108, 1-0122, 1-0135, 1-0228, 1-0230, 1-0235, 1-0240, 1-0248, 1-0250, 1-0264, 1-0273, 1-0314, 1-0473, 1-0476, 1-0477, 1-0509, 1-0510, 1-0511, 1-0512, 1-0517, 1-0524, 1-0526, 1-0527, 1-0530, 1-0531, 1-0532, 1-0533, 1-0534, 1-0535, 1-0536, 1-0543, 1-0549, 1-0567, 1-0573, 1-0588, 1-0593, 1-0607, 1-0608, 1-0612, 1-0671, 1-0674, 1-0679, 1-0681, 1-0682, 1-0684, 1-0685, 1-0688, 1-0689, 1-0690, 1-0692, 1-0693, 1-0696, 1-0697, 1-0701, 1-0702, 1-0703, 1-0705, 1-0706, 1-0709, 1-0710, 1-0721, 1-0722, 1-0723, 1-0726, 1-0727, 1-0729, 1-0731, 1-0732, 1-0733, 1-0734, 1-0735, 1-0736, 1-0743, 1-0748, 1-0750, 1-0752, 1-0860, 1-0863, 1-1068, 1-1076, 2-0552, 2-0557, 2-0563, 2-0568, 2-0586, 2-0590, 2-0600, 2-0656, 2-0698, 2-0703, 2-0706, 2-0710, 2-0731, 2-0777, 2-0782, 2-0815, 2-0867, 2-1052, 2-1053, 2-1066, 2-1067, 2-1086, 2-1094, 2-1123, 2-1134, 2-1142, 2-1144, 2-1146, 2-1148, 2-1149, 2-1150, 2-1154, 2-1161, 2-1162, 2-1163, 2-1177, 2-1232, 2-1240, 2-1254, 2-1268, 2-1282, 2-1283, 2-1284, 2-1346, 2-1347, 2-1354, 2-1382, 2-1387, 2-1388, 2-1396, 2-1401, 2-1417, 2-1423, 2-1424, 2-1431, 2-1458, 2-1466, 2-1468, 2-1469, 2-1470, 2-1472, 2-1479, 2-1485, 2-1487, 2-1488, 2-1489, 2-1490, 2-1516, 2-1521, 2-1526, 2-1589, 2-1662, 2-1768, 2-1770, 2-1776, 2-1779, 2-1780, 2-1782, 2-1783, 2-1785, 2-1786, 2-1787, 2-1789, 2-1790, 2-1791, 2-1792, 2-1793, 2-1794, 2-1795, 2-1796, 2-1797, 2-1801, 2-1803, 2-1805, 2-1806, 2-1813, 2-1814, 2-1815, 2-1816, 2-1817, 2-1818, 2-1819, 2-1820, 2-1821, 2-1823, 2-1827, 2-1830, 2-1831, 2-1832, 2-1833, 2-1834, 2-1837, 2-1838, 2-1839, 2-1841, 2-1842, 2-1845, 2-1846, 2-1847, 2-1848, 2-1850, 2-1852, 2-1856, 2-1862, 2-1863, 2-1864, 2-1865, 2-1866, 2-1868, 2-1869, 2-1870, 2-1872, 2-1873, 2-1874, 2-1875, 2-1878, 2-1879, 2-1880, 2-1881, 2-1883, 2-1884, 2-1885, 2-1887, 2-1888, 2-1889, 2-1890, 2-1891, 2-1892, 2-1893, 2-1895, 2-1896, 2-1897, 2-1898, 2-1899, 2-1900, 2-1901, 2-1902, 2-1903, 2-1905, 2-1908, 2-1922, 2-1923, 2-1938, 2-1939, 2-1941, 2-1943, 2-1944, 2-1945, 2-1949, 2-1950, 2-1951, 2-2158, 2-2159, 3-0001, 3-0009, 3-0012, 3-0019, 3-0020, 3-0037, 3-0053, 3-0064, 3-0073, 3-0082, 3-0083, 3-0085, 3-0086, 3-0087, 3-0091, 3-0109, 3-0112, 3-0115, 3-0116, 3-0118, 3-0119, 3-0124, 3-0125, 3-0126, 3-0134, 3-0139, 3-0143, 3-0184, 3-0197, 3-0198, 3-0243, 3-0244, 3-0325, 3-0331, 3-0339, 3-0340, 3-0348, 3-0349, 3-0350, 3-0352, 3-0398, 3-0399, 3-0430, 3-0532, 3-0541, 3-0542, 3-0543, 3-0545, 3-0551, 3-0552, 3-0553, 3-0554, 3-0555, 3-0556, 3-0559, 3-0560, 3-0564, 3-0567, 3-0575, 3-0577, 3-0584, 3-0589, 3-0596, 3-0597, 3-0598, 3-0599, 3-0600, 3-0605, 3-0615, 3-0616, 3-0635, 3-0636, 3-0642, 3-0647, 3-0651, 3-0652, 3-0653, 3-0654, 3-0680, 3-0683, 3-0684, 3-0685, 3-0686, 3-0689, 3-0690, 3-0710, 3-0711, 3-0724, 3-0725, 3-0726, 3-0909, 3-0949, 3-0950, 3-0963, 3-0966, 3-0968, 3-0970, 3-0973, 3-0979, 3-0980, 3-0985, 3-0987, 3-0992, 3-0993, 3-1780, 3-1781, 3-1782, 3-1784, 3-1791, 3-1795, 3-1797, 3-1801, 3-1802, 3-1806, 3-1807, 3-1809, 3-1811, 3-1813, 3-1814, 3-1816, 3-1817, 3-1819, 3-1821, 3-1824, 3-1825, 3-1826, 4-0001, 4-0007, 4-0029, 4-0031, 5-0001, 5-0006, 5-0041, 5-0049, 5-0060, 5-0074, 6-0055, 6-0056, 6-0057, 6-0058, 6-0061, 6-0268, 6-0273, 6-0278, 6-0283, 6-0298, 6-0300, 6-0304, 6-0308, 6-0312, 6-0316, 6-0320, 6-0324, 6-0333, 6-0341, 6-0347, 6-0374, 6-0378 and 6-1027.

Inhibiting activity of 1 $\mu$M$\leq$IC$_{50}$<10 $\mu$M was found for Compound Nos. 1-0006, 1-0007, 1-0009, 1-0012, 1-0015, 1-0018, 1-0020, 1-0022, 1-0023, 1-0024, 1-0025, 1-0033, 1-0036, 1-0038, 1-0040, 1-0041, 1-0043, 1-0044, 1-0048, 1-0052, 1-0054, 1-0055, 1-0056, 1-0061, 1-0062, 1-0063, 1-0068, 1-0069, 1-0070, 1-0073, 1-0074, 1-0076, 1-0077, 1-0079, 1-0082, 1-0084, 1-0086, 1-0088, 1-0090, 1-0091, 1-0093, 1-0099, 1-0100, 1-0105, 1-0113, 1-0114, 1-0129, 1-0132, 1-0133, 1-0136, 1-0137, 1-0194, 1-0208, 1-0215, 1-0225, 1-0226, 1-0227, 1-0231, 1-0232, 1-0233, 1-0234, 1-0236, 1-0237, 1-0238, 1-0239, 1-0243, 1-0244, 1-0245, 1-0246, 1-0247, 1-0253, 1-0254, 1-0263, 1-0274, 1-0275, 1-0292, 1-0293, 1-0294, 1-0295, 1-0297, 1-0299, 1-0301, 1-0303, 1-0304, 1-0308, 1-0312, 1-0315, 1-0316, 1-0317, 1-0319, 1-0320, 1-0321, 1-0323, 1-0324, 1-0325, 1-0326, 1-0328, 1-0349, 1-0362, 1-0372, 1-0394, 1-0396, 1-0416, 1-0459, 1-0460, 1-0493, 1-0495, 1-0497, 1-0499, 1-0501, 1-0537, 1-0555, 1-0585, 1-0586, 1-0587, 1-0667, 1-0672, 1-0673, 1-0675, 1-0683, 1-0687, 1-0694, 1-0695, 1-0707, 1-0715, 1-0730, 1-0753, 1-0759, 1-0760, 1-0926, 1-0941, 1-1040, 1-1065, 1-1066, 1-1067, 1-1072, 1-1074, 1-1075, 2-0016, 2-0018, 2-0032, 2-0034, 2-0036, 2-0037, 2-0060, 2-0072, 2-0092, 2-0093, 2-0096, 2-0117, 2-0147, 2-0208, 2-0519, 2-0521, 2-0523, 2-0529, 2-0530, 2-0531, 2-0536, 2-0537, 2-0539, 2-0893, 2-1059, 2-1074, 2-1128, 2-1345, 2-1353, 2-1355, 2-1471, 2-1486, 2-1664, 2-1769, 2-1771, 2-1772, 2-1773, 2-1774, 2-1775, 2-1778, 2-1781, 2-1784, 2-1799, 2-1800, 2-1802, 2-1840, 2-1843, 2-1844, 2-1849, 2-1851, 2-1853, 2-1854, 2-1857, 2-1858, 2-1859, 2-1860, 2-1861, 2-1876, 2-1882, 2-1886, 2-1894, 2-1904, 2-1924, 2-1931, 2-1932, 2-1933, 2-1934, 2-1935, 2-1936, 2-1947, 2-1948, 3-0021, 3-0036, 3-0081, 3-0099, 3-0100, 3-0544, 3-0550, 3-0561, 3-0568, 3-0591, 3-0634, 3-0682, 3-0687, 3-0688, 3-0727, 3-0965, 3-0969, 3-0970(S), 3-0971, 3-0984, 3-0988, 3-1785, 3-1786, 3-1787, 3-1788, 3-1794, 3-1796, 3-1798, 3-1800, 3-1805, 3-1808, 3-1818, 3-1822, 3-1823, 4-0005, 4-0030, 5-0005, 5-0016, 5-0038, 5-0051, 5-0054, 6-0328(R), 6-0328(S), 6-0337, 6-0343, 6-0345, 6-0349, 6-0353, 6-0370, 6-0382, 6-0390 and 6-0394. The compound numbers represent the compound numbers in Tables 1 to 214 listed as the preferred examples.

The pyrrolopyrimidine derivatives of the invention thus exhibit powerful GSK-3 inhibiting activity. It was therefore demonstrated that they may be clinically useful as GSK-3 activity inhibitors to be used for prevention and/or treatment of various diseases associated with GSK-3.

Example 1177

Preparation of Tablets

Tablets were prepared each having the following composition.

| | |
|---|---|
| Compound(Example 1) | 50 mg |
| Lactose | 230 mg |
| Potato starch | 80 mg |
| Polyvinylpyrrolidone | 11 mg |
| Magnesium stearate | 5 mg |

The compound of the invention (compound of Example 1), lactose and potato starch were combined, and the mixture was evenly moistened with a 20% ethanol solution containing the polyvinylpyrrolidone and passed through a 20 nm mesh screen, dried at 45° C. and passed through a 15 nm mesh screen. The granules obtained in this manner were mixed with the magnesium stearate and compressed into tablets.

INDUSTRIAL APPLICABILITY

The pyrrolo[3,2-d]pyrimidine derivatives represented by formula (I) and their medically acceptable salts exhibit GSK-3 inhibiting activity. Drugs comprising the compounds as effective ingredients are therefore expected to be useful as therapeutic or prophylactic agents for conditions in which GSK-3 is implicated, such as diabetes, diabetes complications, Alzheimer's disease, neurodegenerative diseases, manic depression, traumatic encephalopathy, alopecia, inflammatory diseases, cancer and immune deficiency.

The invention claimed is:

1. A pyrrolo[3,2-d]pyrimidine represented by formula (I), or a medically acceptable salt thereof

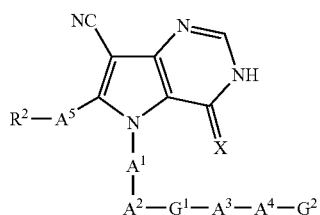

wherein X represents sulfur atom;

$A^1$ represents a group that links the nitrogen atom to which $A^1$ is bonded and $A^2$ in the form of $N-(CH_2)_2-A^2$;

$A^2$ represents a group binding $A^1$ and $G^1$ in the form of $A^1-C(=O)-G^1$, $A^1-NH-G^1$ or $A^1-NHC(=O)-G^1$;

$G^1$ represents one group selected from among the following 1) to 4):

1) a single bond
2) a substituted or unsubstituted $C_{3-8}$ alicyclic hydrocarbon group (as substituents there may be mentioned one or more selected from the group consisting of fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, oxo, $C_{1-6}$ alkylsulfonyloxy, optionally substituted $C_{2-7}$ acyl (the acyl is selected from acetyl, propionyl, butyryl, isobutyryl, valeryl, isovaleryl, pivaloyl, and hexanoyl), carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-8}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbons and optionally substituted $C_{1-6}$ aliphatic hydrocarbons)

3) a substituted or unsubstituted $C_{6-14}$ aromatic hydrocarbon group (as substituents there may be mentioned one or more selected from the group consisting of fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, $C_{1-6}$ alkylsulfonyloxy, optionally substituted $C_{2-7}$ acyl (the acyl is selected from acetyl, propionyl, butyryl, isobutyryl, valeryl, isovaleryl, pivaloyl, and hexanoyl), carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-8}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbons and optionally substituted $C_{1-6}$ aliphatic hydrocarbons)

4) a substituted or unsubstituted divalent heterocyclic group selected from the group consisting of furan, thiophene, pyrrole, pyrroline, pyrrolidine, oxazole, oxazolidine, isooxazole, isooxazolidine, thiazole, thiazolidine, isothiazole, isothiazolidine, furazan, imidazole, imidazoline, imidazolidine, pyrazole, pyrazoline, pyrazolidine, triazole, thiadiazole, oxadiazole, tetrazole, pyran, tetrahydropyran, thiopyran, tetrahydrothiopyran, tetrahydrofuran, 1,3-dioxolane, 1,4-dioxane, pyridine, pyrazine, pyrimidine, pyridazine, benzofuran, dibenzofuran, 1,4-dioxacycloheptane, benzothiophene, indole, 1,2-methylenedioxybenzene, benzimidazole, benzothiazole, benzoxazole, chromane, isochromane, quinoline, decahydroquinoline, isoquinoline, phthalazine, cinnoline, 1,8-naphthylidine, 1,2,3,4-tetrahydroisoquinoline, quinazoline, quinoxaline, purine, pteridine, azetidine, morpholine, thiomorpholine, piperidine, homopiperidine, piperazine, homopiperazine, indoline, isoindoline, phenoxazine, phenazine, phenothiazine, pyrrolopyrimidine, pyrazolopyrimidine and quinuclidine, wherein the heterocyclic group is bonded to $A^2$ via a carbon or nitrogen atom (as substituents there may be mentioned one or more selected from the group consisting of fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, oxo, $C_{1-6}$ alkylsulfonyloxy, optionally substituted $C_{2-7}$ acyl (the acyl is selected from acetyl, propionyl, butyryl, isobutyryl, valeryl, isovaleryl, pivaloyl, and hexanoyl), carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-8}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbons and optionally substituted $C_{1-6}$ aliphatic hydrocarbons);

$A^3$ represents a single bond, or a $C_{1-6}$ aliphatic hydrocarbon group having $G^1$ and $A^4$ bonded on the same or different carbon atoms;

$A^4$ represents a single bond or a group binding $A^3$ and $G^2$ in the form of $A^3$-C(=O)-$G^2$, $A^3$-C(=O)O-$G^2$, $A^3$-C(=O)NR$^{121}$-$G^2$, $A^3$-C(=S)NR$^{122}$-$G^2$, $A^3$-C(=NR$^{123}$)-$G^2$, $A^3$-O-$G^2$, $A^3$-OC(=O)-$G^2$, $A^3$-NR$^{124}$-$G^2$, $A^3$-NR$^{125}$C(=O)-$G^2$, $A^3$-NR$^{126}$S(=O)$_2$-$G^2$, $A^3$-NR$^{127}$C(=O)O-$G^2$, $A^3$-NR$^{128}$C(=O)NR$^{129}$-$G^2$, $A^3$-NR$^{130}$C(=S)-$G^2$, $A^3$-NR$^{131}$C(=S)NR$^{132}$-$G^2$, $A^3$-S-$G^2$, $A^3$-S(=O)-$G^2$, $A^3$-S(=O)$_2$-$G^2$, $A^3$-S(=O)$_2$NR$^{133}$-$G^2$ or $A^3$-S(=O)$_2$O-$G^2$ (where R$^{121}$, R$^{122}$, R$^{123}$, R$^{124}$, R$^{125}$, R$^{126}$, R$^{127}$, R$^{128}$, R$^{129}$, R$^{130}$, R$^{131}$, R$^{132}$, and R$^{133}$ each independently represent hydrogen or a $C_{1-4}$ aliphatic hydrocarbon group); and $G^2$ represents one group selected from among the following 1) to 5):

1) hydrogen;
2) a substituted or unsubstituted $C_{1-10}$ aliphatic hydrocarbon group (as substituents there may be mentioned one or more selected from the group consisting of fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, oxo, $C_{1-6}$ alkylsulfonyloxy, optionally substituted $C_{2-7}$ acyl (the acyl is selected from acetyl, propionyl, butyryl, isobutyryl, valeryl, isovaleryl, pivaloyl, and hexanoyl), carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-8}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbons, optionally substituted $C_{1-6}$ aliphatic hydrocarbons, optionally substituted $C_{6-14}$ aromatic hydrocarbons and optionally substituted heterocyclic groups (having in the ring 1 to 4 atoms selected from the group consisting of oxygen, nitrogen and sulfur))
3) a substituted or unsubstituted $C_{3-8}$ alicyclic hydrocarbon group (as substituents there may be mentioned one or more selected from the group consisting of fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, oxo, $C_{1-6}$ alkylsulfonyloxy, optionally substituted $C_{2-7}$ acyl (the acyl is selected from acetyl, propionyl, butyryl, isobutyryl, valeryl, isovaleryl, pivaloyl, and hexanoyl), carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-8}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbons, optionally substituted $C_{1-6}$ aliphatic hydrocarbons, optionally substituted $C_{6-14}$ aromatic hydrocarbons and optionally substituted heterocyclic groups (having in the ring 1 to 4 atoms selected from the group consisting of oxygen, nitrogen and sulfur))
4) a substituted or unsubstituted $C_{6-14}$ aromatic hydrocarbon group (as substituents there may be mentioned one or more selected from the group consisting of fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, $C_{1-6}$ alkylsulfonyloxy, optionally substituted $C_{2-7}$ acyl (the acyl is selected from acetyl, propionyl, butyryl, isobutyryl, valeryl, isovaleryl, pivaloyl, and hexanoyl), carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-8}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbons, optionally substituted $C_{1-6}$ aliphatic hydrocarbons, optionally substituted $C_{6-14}$ aromatic hydrocarbons and optionally substituted heterocyclic groups (having in the ring 1 to 4 atoms selected from the group consisting of oxygen, nitrogen and sulfur))
5) a substituted or unsubstituted monovalent heterocyclic group selected from the group consisting of furan, thiophene, pyrrole, pyrroline, pyrrolidine, oxazole, oxazolidine, isooxazole, isooxazolidine, thiazole, thiazolidine, isothiazole, isothiazolidine, imidazole, imidazoline, imidazolidine, pyrazole, pyrazoline, pyrazolidine, triazole, thiadiazole, oxadiazole, tetrazole, pyran, tetrahydropyran, thiopyran, tetrahydrothiopyran, pyridine, pyrazine, pyrimidine, pyridazine, benzofuran, dibenzofuran, benzothiophene, indole, 1,2-methylenedioxybenzene, benzimidazole, benzothiazole, benzoxazole, chromane, isochromane, quinoline, decahydroquinoline, isoquinoline, quinazoline, quinoxaline, purine, pteridine, azetidine, morpholine, thiomorpholine, piperidine, homopiperidine, piperazine, homopiperazine, indoline, isoindoline, phenoxazine, phenazine, phenothiazine and quinuclidine, wherein the heterocyclic group is bonded to $A^4$ via a carbon or nitrogen atom (as substituents there may be mentioned one or more selected from the group consisting of fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, oxo, $C_{1-6}$ alkylsulfonyloxy, optionally substituted $C_{2-7}$ acyl (the acyl is selected from acetyl, propionyl, butyryl, isobutyryl, valeryl, isovaleryl, pivaloyl, and hexanoyl), carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-8}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbons, optionally substituted $C_{1-6}$ aliphatic hydrocarbons, optionally substituted $C_{6-14}$ aromatic hydrocarbons and optionally substituted heterocyclic groups (having in the ring 1 to 4 atoms selected from the group consisting of oxygen, nitrogen and sulfur))

(the above being with the following provisos:
a) when $G^1$ and $A^3$ are both single bonds, then $A^1$, $A^2$, $A^4$ and $G^2$ together are $A^1$-C(=O)—C(=O)-$G^2$, and
b) when $A^3$ represents a $C_{1-6}$ aliphatic hydrocarbon group having $G^1$ and $A^4$ bonded on the same or different carbon atoms and $G^2$ represents a substituted or unsubstituted $C_{1-10}$ aliphatic hydrocarbon group, then $A^4$ is not a single bond)

$A^5$ represents a single bond, or a group binding the carbon atom of the pyrrole ring to which $A^5$ is bonded and $R^2$ in the form of $R^2$—$NR^{201}$-pyrrole ring carbon (where $R^{201}$ represents hydrogen or a $C_{1-4}$ aliphatic hydrocarbon group)

$R^2$ represents one group selected from among the following 1) to 6):
1) hydrogen
2) fluorine, chlorine, bromine or iodine
3) a substituted or unsubstituted $C_{1-10}$ aliphatic hydrocarbon group (as substituents there may be mentioned one or more selected from the group consisting of fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, oxo, $C_{1-6}$ alkylsulfonyloxy, optionally substituted $C_{2-7}$ acyl (the acyl is selected from acetyl, propionyl, butyryl, isobutyryl, valeryl, isovaleryl, pivaloyl, and hexanoyl), carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-8}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbons, optionally substituted $C_{1-6}$ aliphatic hydrocarbons, optionally substituted $C_{6-14}$ aromatic hydrocarbons and optionally substituted heterocyclic groups (having in the ring 1 to 4 atoms selected from the group consisting of oxygen, nitrogen and sulfur))
4) a substituted or unsubstituted $C_{3-8}$ alicyclic hydrocarbon group (as substituents there may be mentioned one or more selected from the group consisting of fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, oxo, $C_{1-6}$ alkylsulfonyloxy, optionally substituted $C_{2-7}$ acyl (the acyl is selected from acetyl, propionyl, butyryl, isobutyryl, valeryl, isovaleryl, pivaloyl, and hexanoyl), carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-8}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbons, optionally substituted $C_{1-6}$ aliphatic hydrocarbons, optionally substituted $C_{6-14}$ aromatic hydrocarbons and optionally substituted heterocyclic groups (having in the ring 1 to 4 atoms selected from the group consisting of oxygen, nitrogen and sulfur))
5) a substituted or unsubstituted $C_{6-14}$ aromatic hydrocarbon group (as substituents there may be mentioned one or more selected from the group consisting of fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, oxo, $C_{1-6}$ alkylsulfonyloxy, optionally substituted $C_{2-7}$ acyl (the acyl is selected from acetyl, propionyl, butyryl, isobutyryl, valeryl, isovaleryl, pivaloyl, and hexanoyl), carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-8}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbons, optionally substituted $C_{1-6}$ aliphatic hydrocarbons, optionally substituted $C_{6-14}$ aromatic hydrocarbons and optionally substituted heterocyclic groups (having in the ring 1 to 4 atoms selected from the group consisting of oxygen, nitrogen and sulfur))
6) a substituted or unsubstituted monovalent heterocyclic group selected from the group consisting of furan, thiophene, pyrrole, pyrroline, pyrrolidine, oxazole, oxazolidine, isooxazole, isooxazolidine, thiazole, thiazolidine, isothiazole, isothiazolidine, imidazole, imidazoline, imidazolidine, pyrazole, pyrazoline, pyrazolidine, triazole, thiadiazole, oxadiazole, tetrazole, pyran, tetrahydropyran, thiopyran, tetrahydrothiopyran, pyridine, pyrazine, pyrimidine, pyridazine, benzofuran, dibenzofuran, benzothiophene, indole, 1,2-methylenedioxybenzene, benzimidazole, benzothiazole, benzoxazole, chromane, isochromane, quinoline, decahydroquinoline, isoquinoline, quinazoline, quinoxaline, purine, pteridine, azetidine, morpholine, thiomorpholine, piperidine, homopiperidine, piperazine, homopiperazine, indoline, isoindoline, phenoxazine, phenazine, phenothiazine and quinuclidine, wherein the heterocyclic group is bonded to $A^5$ via a carbon or nitrogen atom (as substituents there may be mentioned one or more selected from the group consisting of fluorine, chlorine, bromine, iodine, hydroxyl, optionally substituted $C_{1-7}$ alkoxy, $C_{6-10}$ aryloxy, $C_{7-9}$ aralkoxy, $C_{2-7}$ acyloxy, oxo, $C^{1-6}$ alkylsulfonyloxy, optionally substituted $C_{2-7}$ acyl (the acyl is selected from acetyl, propionyl, butyryl, isobutyryl, valeryl, isovaleryl, pivaloyl, and hexanoyl), carboxyl, $C_{2-7}$ alkoxycarbonyl, carbamoyl, optionally substituted $C_{2-7}$ alkylcarbamoyl, amino, optionally substituted $C_{1-6}$ alkylamino, optionally substituted $C_{2-7}$ acylamino, $C_{2-8}$ alkoxycarbonylamino, $C_{1-6}$ alkylsulfonylamino, cyano, nitro, $C_{1-6}$ alkylthio, $C_{1-6}$ alkylsulfinyl, $C_{1-6}$ alkylsulfonyl, sulfamoyl, $C_{1-6}$ alkylaminosulfonyl, sulfo, optionally substituted $C_{3-6}$ alicyclic hydrocarbons, optionally substituted $C_{1-6}$ aliphatic hydrocarbons, optionally substituted $C_{6-14}$ aromatic hydrocarbons and optionally substituted heterocyclic groups (having in the ring 1 to 4 atoms selected from the group consisting of oxygen, nitrogen and sulfur))

the above being with the proviso that when $R^2$ is fluorine, chlorine, bromine or iodine, $A^5$ is a single bond wherein the heterocyclic groups as substituents for the $C_{1-10}$ aliphatic hydrocarbon groups, the $C_{3-8}$ alicyclic hydrocarbon groups, the $C_{6-14}$ aromatic hydrocarbon groups, and the heterocyclic groups represented by $G^2$ and $R^2$ are monovalent heterocyclic groups independently selected from the group consisting of furan, thiophene, pyrrole, pyrroline, pyrrolidine, oxazole, oxazolidine, isooxazole, isooxazolidine, thiazole, thiazolidine, isothiazole, isothiazolidine, imidazole, imidazoline, imidazolidine, pyrazole, pyrazoline, pyrazolidine, triazole, thiadiazole, oxadiazole, tetrazole, pyran, tetrahydropyran, thiopyran, tetrahydrothiopyran, pyridine, pyrazine, pyrimidine, pyridazine, benzofuran, dibenzofuran, benzothiophene, indole, benzimidazole, benzothiazole, benzoxazole, chromane, isochromane, quinoline, decahydroquinoline, isoquinoline, quinazoline, quinoxaline, purine, pteridine, azetidine, morpholine, thiomorpholine, piperidine, homopiperidine, piperazine, homopiperazine, indoline, isoindoline, phenoxazine, phenazine, phenothiazine and quinuclidine, and which are bonded to the $C_{1-10}$ aliphatic hydrocarbon groups, the $C_{3-8}$ alicyclic hydrocarbon groups, the $C_{6-14}$ aromatic hydrocarbon groups, and the heterocyclic groups represented by $G^2$ and $R^2$ via a carbon atom or a nitrogen atom.

2. A pyrrolo[3,2-d]pyrimidine or a medically acceptable salt thereof according to claim 1, wherein $A^1$-$A^2$-$G^1$ bond in the form of $A^1$-C(=O)-$G^1$.

3. A pyrrolo[3,2-d]pyrimidine or a medically acceptable salt thereof according to claim 1, wherein $A^1$-$A^2$-$G^1$ bond in the form of $A^1$-NH-$G^1$.

4. A pyrrolo[3,2-d]pyrimidine or a medically acceptable salt thereof according to claim 1, wherein $A^1$-$A^2$-$G^1$ bond in the form of $A^1$-NHC(=O)-$G^1$.

5. A pyrrolo[3,2-d]pyrimidine or a medically acceptable salt thereof according to claim 1, wherein $G^1$ is a single bond.

6. A pyrrolo[3,2-d]pyrimidine or a medically acceptable salt thereof according to claim 1 wherein $G^1$ is a substituted or unsubstituted $C_{6-14}$ aromatic hydrocarbon group.

7. A pyrrolo[3,2-d]pyrimidine or a medically acceptable salt thereof according to claim 1 wherein $G^1$ is a substituted or unsubstituted $C_{3-8}$ alicyclic hydrocarbon group.

8. A pyrrolo[3,2-d]pyrimidine or a medically acceptable salt thereof according to claim 1, wherein $G^1$ is a substituted or unsubstituted divalent heterocyclic group selected from the group consisting of furan, thiophene, pyrrole, pyrroline, pyrrolidine, oxazole, oxazolidine, isooxazole, isooxazolidine, thiazole, thiazolidine, isothiazole, isothiazolidine, furazan, imidazole, imidazoline, imidazolidine, pyrazole, pyrazoline, pyrazolidine, triazole, thiadiazole, oxadiazole, tetrazole, pyran, tetrahydropyran, thiopyran, tetrahydrothiopyran, tetrahydrofuran, 1,3-dioxolane, 1,4-dioxane, pyridine, pyrazine, pyrimidine, pyridazine, benzofuran, dibenzofuran, 1,4-dioxacycloheptane, benzothiophene, indole, 1,2-methylenedioxybenzene, benzimidazole, benzothiazole, benzoxazole, chromane, isochromane, quinoline, decahydroquinoline, isoquinoline, phthalazine, cinnoline, 1,8-naphthylidine, 1,2,3,4-tetrahydroisoquinoline, quinazoline, quinoxaline, purine, pteridine, azetidine, morpholine, thiomorpholine, piperidine, homopiperidine, piperazine, homopiperazine, indoline, isoindoline, phenoxazine, phenazine, phenothiazine, pyrrolopyrimidine, pyrazolopyrimidine and quinuclidine, wherein the heterocyclic group is bonded to $A^2$ via a carbon atom or a nitrogen atom.

9. A pyrrolo[3,2-d]pyrimidine or a medically acceptable salt thereof according to claim 1, wherein $G^1$ is an unsubstituted $C^{6-14}$ aromatic hydrocarbon group.

10. A pyrrolo[3,2-d]pyrimidine or a medically acceptable salt thereof according to claim 1, wherein $G^1$ is an unsubstituted $C^{3-8}$ alicyclic hydrocarbon group.

11. A pyrrolo[3,2-d]pyrimidine or a medically acceptable salt thereof according to claim 1, wherein $G^1$ is an unsubstituted divalent heterocyclic group selected from the group consisting of furan, thiophene, pyrrole, pyrroline, pyrrolidine, oxazole, oxazolidine, isooxazole, isooxazolidine, thiazole, thiazolidine, isothiazole, isothiazolidine, furazan, imidazole, imidazoline, imidazolidine, pyrazole, pyrazoline, pyrazolidine, triazole, thiadiazole, oxadiazole, tetrazole, pyran, tetrahydropyran, thiopyran, tetrahydrothiopyran, tetrahydrofliran, 1,3-dioxolane, 1,4-dioxane, pyridine, pyrazine, pyrimidine, pyridazine, benzofiiran, dibenzofuran, 1,4-dioxacycloheptane, benzothiophene, indole, 1,2-methylenedioxybenzene, benzimidazole, benzothiazole, benzoxazole, chromane, isochromane, quinoline, decahydroquinoline, isoquinoline, phthalazine, cinnoline, 1,8-naphthylidine, 1,2,3,4-tetrahydroisoquinoline, quinazoline, quinoxaline, purine, pteridine, azetidine, morpholine, thiomorpholine, piperidine, homopiperidine, piperazine, homopiperazine, indoline, isoindoline, phenoxazine, phenazine, phenothiazine, pyrrolopyrimidine, pyrazolopyrimidine and quinuclidine, wherein the heterocyclic group is bonded to $A^2$ via a carbon atom or a nitrogen atom.

12. A pyrrolo[3,2-d]pyrimidine or a medically acceptable salt thereof according to claim 1, wherein $G^1$ is a substituted $C_{6-14}$ aromatic hydrocarbon group.

13. A pyrrolo [3,2-d]pyrimidine or a medically acceptable salt thereof according to claim 1, wherein $G^1$ is a substituted $C_{3-8}$ alicyclic hydrocarbon group.

14. A pyrrolo[3,2-d]pyrimidine or a medically acceptable salt thereof according to claim 1, wherein $G^1$ is a substituted divalent heterocyclic group selected from the group consisting of substituted furan, substituted thiophene, substituted pyrrole, substituted pyrroline, substituted pyrrolidine, substituted oxazole, substituted oxazolidine, substituted isooxazole, substituted isooxazolidine, substituted thiazole, substituted thiazolidine, substituted isothiazole, substituted isothiazolidine, substituted furazan, substituted imidazole, substituted imidazoline, substituted imidazolidine, substituted pyrazole, substituted pyrazoline, substituted pyrazolidine, substituted triazole, substituted thiadiazole, substituted oxadiazole, substituted tetrazole, substituted pyran, substituted tetrahydropyran, substituted thiopyran, substituted tetrahydrothiopyran, substituted tetrahydrofuran, substituted 1,3-dioxolane, substituted 1,4-dioxane, substituted pyridine, substituted pyrazine, substituted pyrimidine, substituted pyridazine, substituted benzofuran, substituted dibenzofuran, substituted 1,4-dioxacycloheptane, substituted benzothiophene, substituted indole, 1,2-methylenedioxybenzene, substituted benzimidazole, substituted benzothiazole, substituted benzoxazole, substituted chromane, substituted isochromane, substituted quinoline, substituted decahydroquinoline, substituted isoquinoline, substituted phthalazine, substituted cinnoline, substituted 1,8-naphthylidine, substituted 1,2,3,4-tetrahydroisoquinoline, substituted quinazoline, substituted quinoxaline, substituted purine, substituted pteridine, substituted azetidine, substituted morpholine, substituted thiomorpholine, substituted piperidine, substituted homopiperidine, substituted piperazine, substituted homopiperazine, substituted indoline, substituted isoindoline, substituted phenoxazine, substituted phenazine, substituted phenothiazine, substituted pyrrolopyrimidine, substituted pyrazolopyrimidine and substituted quinuclidine, wherein the heterocyclic group is bonded to $A^2$ via a carbon atom or a nitrogen atom.

15. A pyrrolo[3,2-d]pyrimidine or a medically acceptable salt thereof according to claim 1, wherein $G^1$ is an unsubstituted aromatic divalent heterocyclic group selected from the group consisting of furan, pyrrole, thiophene, oxazole, thiazole, isooxazole, isothiazole, pyrazole, imidazole, pyridine, pyrimidine, pyrazine, pyridazine, benzothiophene, benzofuran, 1,2-methylenedioxybenzene, benzimidazole, indole, quinoline, isoquinoline and quinazoline, wherein the heterocyclic group is bonded to $A^2$ via a carbon atom.

16. A pyrrolo[3,2-d]pyrimidine or a medically acceptable salt thereof according to claim 1, wherein $G^1$ is a substituted aromatic heterocyclic group selected from the group consisting of furan, pyrrole, thiophene, oxazole, thiazole, isooxazole, isothiazole, pyrazole, imidazole, pyridine, pyrimidine, pyrazine, pyridazine, benzothiophene, benzofuran, 1,2-methylenedioxybenzene, benzimidazole, indole, quinoline, isoquinoline and quinazoline, wherein the heterocyclic group is bonded to $A^2$ via a carbon atom.

17. A pyrrolo[3,2-d]pyrimidine or a medically acceptable salt thereof according to claim 1, wherein $G^1$ is divalent unsubstituted furan, unsubstituted pyrrole, unsubstituted pyrrolidine, unsubstituted thiophene, unsubstituted oxazole, unsubstituted thiazole, unsubstituted isooxazole, unsubstituted isothiazole, unsubstituted pyrazole, unsubstituted imidazole, unsubstituted pyridine, unsubstituted pyrimidine, unsubstituted pyrazine, unsubstituted benzothiophene, unsubstituted benzofuran, unsubstituted benzimidazole, unsubstituted indole, unsubstituted quinoline, unsubstituted isoquinoline, unsubstituted quinazoline, unsubstituted purine, unsubstituted plithalazine, unsubstituted cinnoline, unsubstituted 1,8-naphthylidine or unsubstituted pteridine.

18. A pyrrolo[3,2-d]pyrimidine or a medically acceptable salt thereof according to claim 1, wherein $G^1$ is divalent substituted furan, substituted pyrrole, substituted pyrrolidine, substituted thiophene, substituted oxazole, substituted thiazole, substituted isooxazole, substituted isothiazole, substituted pyrazole, substituted imidazole, substituted pyridine, substituted pyrimidine, substituted pyrazine, substituted benzothiophene, substituted benzofuran, substituted benzimidazole, substituted indole, substituted quinoline, substituted isoquinoline, substituted quinazoline, substituted purine, substituted phthalazine, substituted cinnoline, substituted 1,8-naphthylidine or substituted pteridine.

19. A pyrrolo[3,2-d]pyrimidine or a medically acceptable salt thereof according to claim 1, wherein $G^1$ is divalent substituted benzene.

20. A pyrrolo[3,2-d]pyrimidine or a medically acceptable salt thereof according to claim 1, wherein $G^1$ is divalent unsubstituted benzene.

21. A pyrrolo[3,2-d]pyrimidine or a medically acceptable salt thereof according to claim 1, wherein $G^1$ is divalent substituted thiophene.

22. A pyrrolo[3,2-d]pyrimidine or a medically acceptable salt thereof according to claim 1, wherein $G^1$ is divalent unsubstituted thiophene.

23. A pyrrolo[3,2-d]pyrimidine or a medically acceptable salt thereof according to claim 1, wherein $G^1$ is divalent substituted pyridine.

24. A pyrrolo[3,2-d]pyrimidine or a medically acceptable salt thereof according to claim 1, wherein $G^1$ is divalent unsubstituted pyridine.

25. A pyrrolo[3,2-d]pyrimidine or a medically acceptable salt thereof according to claim 1, wherein $G^1$ is divalent substituted furan.

26. A pyrrolo[3,2-d]pyrimidine or a medically acceptable salt thereof according to claim 1, wherein $G^1$ is divalent unsubstituted furan.

27. A pyrrolo[3,2-d]pyrimidine or a medically acceptable salt thereof according to claim 1, wherein $G^1$ is divalent substituted pyrrole.

28. A pyrrolo[3,2-d]pyrimidine or a medically acceptable salt thereof according to claim 1, wherein $G^1$ is divalent unsubstituted pyrrole.

29. A pyrrolo[3,2-d]pyrimidine or a medically acceptable salt thereof according to claim 1, wherein $G^1$ is divalent substituted thiazole.

30. A pyrrolo[3,2-d]pyrimidine or a medically acceptable salt thereof according to claim 1, wherein $G^1$ is divalent unsubstituted thiazole.

31. A pyrrolo[3,2-d]pyrimidine or a medically acceptable salt thereof according to claim 1, wherein $G^1$ is divalent substituted isooxazole.

32. A pyrrolo[3,2-d]pyrimidine or a medically acceptable salt thereof according to claim 1, wherein $G^1$ is divalent unsubstituted isooxazole.

33. A pyrrolo[3,2-d]pyrimidine or a medically acceptable salt thereof according to claim 1, wherein $G^1$ is divalent substituted pyrazole.

34. A pyrrolo[3,2-d]pyrimidine or a medically acceptable salt thereof according to claim 1, wherein $G^1$ is divalent unsubstituted pyrazole.

35. A pyrrolo[3,2-d]pyrimidine or a medically acceptable salt thereof according to claim 1, wherein $G^1$ is divalent substituted pyrimidine.

36. A pyrrolo[3,2-d]pyrimidine or a medically acceptable salt thereof according to claim 1, wherein $G^1$ is divalent unsubstituted pyrimidine.

37. A pyrrolo[3,2-d]pyrimidine or a medically acceptable salt thereof according to claim 1, wherein $G^1$ is divalent substituted quinazoline.

38. A pyrrolo[3,2-d]pyrimidine or a medically acceptable salt thereof according to claim 1, wherein $G^1$ is divalent unsubstituted quinazoline.

39. A pyrrolo[3,2-d]pyrimidine or a medically acceptable salt thereof according to claim 1, wherein $A^1$-$A^2$-$G^1$ bond in the form of $A^1$-$C(=O)G^1$, and $G^1$ is divalent unsubstituted pyrrolidine, unsubstituted piperidine, unsubstituted morpholine, unsubstituted thiomorpholine, unsubstituted homopiperidine, unsubstituted homopiperazine, or unsubstituted piperazine, bonded to $A^1$-$C(=O)$ through the nitrogen atom.

40. A pyrrolo[3,2-d]pyrimidine or a medically acceptable salt thereof according to claim 1, wherein $A^1$-$A^2$-$G^1$ bond in the form of $A^1$-$C(=O)$-$G^1$, and $G^1$ is divalent substituted pyrrolidine, substituted piperidine, substituted morpholine, substituted thiomorpholine, substituted homopiperidine, substituted homopiperazine, or substituted piperazine, bonded to $A^1$-$C(=O)$ through the nitrogen atom.

41. A pyrrolo[3,2-d]pyrimidine or a medically acceptable salt thereof according to claim 1, wherein $A^1$-$A^2$-$G^1$ bond in the form of $A^1$-$C(=O)$-$G^1$, and $G^1$ is divalent substituted piperidine, bonded to $A^1$-$C(=O)$ through the nitrogen atom.

42. A pyrrolo[3,2-d]pyrimidine or a medically acceptable salt thereof according to claim 1, wherein $A^1$-$A^2$-$G^1$ bond in the form of $A^1$-$C(=O)G^1$, and $G^1$ is divalent unsubstituted piperidine, bonded to $A^1$-$C(=O)$ through the nitrogen atom.

43. A pyrrolo[3,2-d]pyrimidine or a medically acceptable salt thereof according to claim 1, wherein $A^1$-$A^2$-$G^1$ bond in the form of $A^1$-$C(=O)$-$G^1$, and $G^1$ is divalent substituted piperazine, bonded to $A^1$-$C(=O)$ through the nitrogen atom.

44. A pyrrolo[3,2-d]pyrimidine or a medically acceptable salt thereof according to claim 1, wherein $A^1$-$A^2$-$G^1$ bond in the form of $A^1$-$C(=O)$-$G^1$, and $G^1$ is divalent unsubstituted piperazine, bonded to $A^1$-$C(=O)$ through the nitrogen atom.

45. A pyrrolo[3,2-d]pyrimidine or a medically acceptable salt thereof according to claim 5, wherein $A^3$ is a single bond.

46. A pyrrolo[3,2-d]pyrimidine or a medically acceptable salt thereof according to claim 5, wherein $A^3$ is —$CH_2$—.

47. A pyrrolo[3,2-d]pyrimidine or a medically acceptable salt thereof according to claim 5, wherein $A^3$ is —$(CH_2)_2$—.

48. A pyrrolo[3,2-d]pyrimidine or a medically acceptable salt thereof according to claim 5, wherein $A^3$ is —$(CH_2)_3$—.

49. A pyrrolo[3,2-d]pyrimidine or a medically acceptable salt thereof according to claim 5, wherein $A^3$ is a single bond.

50. A pyrrolo[3,2-d]pyrimidine or a medically acceptable salt thereof according to claim 5, wherein $A^3$-$A^4$-$G^2$ bond in the form of $A^3$-C(=O)O-$G^2$.

51. A pyrrolo[3,2-d]pyrimidine or a medically acceptable salt thereof according to claim 5, wherein $A^3$-$A^4$-$G^2$ bond in the form of $A^3$C(=O)-$G^2$.

52. A pyrrolo[3,2-d]pyrimidine or a medically acceptable salt thereof according to claim 5, wherein $A^3$-$A^4$-$G^2$ bond in the form of $A^3$-C(=O)$NR^{121}$-$G^2$.

53. A pyrrolo[3,2-d]pyrimidine or a medically acceptable salt thereof according to claim 5, wherein $A^3$-$A^4$-$G^2$ bond in the form of $A^3$-O-$G^2$.

54. A pyrrolo[3,2-d]pyrimidine or a medically acceptable salt thereof according to claim 5, wherein $A^3$-$A^4$-$G^2$ bond in the form of $A^3$-$NR^{124}$-$G^2$.

55. A pyrrolo[3,2-d]pyrimidine or a medically acceptable salt thereof according to claim 5, wherein $A^3$-$A^4$-$G^2$ bond in the form of $A^3$-$NR^{125}$C(=O)-$G^2$.

56. A pyrrolo[3,2-d]pyrimidine or a medically acceptable salt thereof according to claim 5, wherein $A^3$-$A^4$-$G^2$ bond in the form of $A^3$-$NR^{126}$S(=O)$_2$-$G^2$.

57. A pyrrolo[3,2-d]pyrimidine or a medically acceptable salt thereof according to claim 5, wherein $A^3$-$A^4$-$G^2$ bond in the form of $A^3$-$NR^{127}$C(=O)O-$G^2$.

58. A pyrrolo[3,2-d]pyrimidine or a medically acceptable salt thereof according to claim 5, wherein $A^3$-$A^4$-$G^2$ bond in the form of $A^3$-$NR^{128}$C(=O)$NR^{129}$-$G^2$.

59. A pyrrolo[3,2-d]pyrimidine or a medically acceptable salt thereof according to claim 49, wherein $G^2$ is a hydrogen atom.

60. A pyrrolo[3,2-d]pyrimidine or a medically acceptable salt thereof according to claim 49, wherein $G^2$ is a substituted or unsubstituted $C_{1-10}$ aliphatic hydrocarbon group.

61. A pyrrolo[3,2-d]pyrimidine or a medically acceptable salt thereof according to claim 49, wherein $G^2$ is a substituted or unsubstituted $C_{3-8}$ alicyclic hydrocarbon group.

62. A pyrrolo[3,2-d]pyrimidine or a medically acceptable salt thereof according to claim 49, wherein $G^2$ is a substituted or unsubstituted $C_{6-14}$ aromatic hydrocarbon group.

63. A pyrrolo[3,2-d]pyrimidine or a medically acceptable salt thereof according to claim 49, wherein $G^2$ is a substituted or unsubstituted monovalent heterocyclic group selected from the group consisting of furan, thiophene, pyrrole, pyrroline, pyrrolidine, oxazole, oxazolidine, isooxazole, isooxazolidine, thiazole, thiazolidine, isothiazole, isothiazolidine, and quinuclidine, wherein the heterocyclic group is bonded to $A^4$ via a carbon atom or a nitrogen atom.

64. A pyrrolo[3,2-d]pyrimidine or a medically acceptable salt thereof according to claim 6, wherein $A^3$-$A^4$-$G^2$ collectively represent hydrogen.

65. A pyrrolo[3,2-d]pyrimidine or a medically acceptable salt thereof according to claim 6, wherein $A^3$-$A^4$-$G^2$ collectively represent a group other than hydrogen.

66. A pyrrolo[3,2-d]pyrimidine or a medically acceptable salt thereof according to claim 1, wherein X is sulfur, $A^1$ is —$(CH_2)^2$—, $A^1$-$A^2$-$G^1$ bond in the form of $A^1$-NHC(=O)-$G^1$, and $G^1$ is substituted divalent benzene.

67. A pyrrolo[3,2-d]pyrimidine or a medically acceptable salt thereof according to claim 1, wherein X is sulfur, $A^1$ is —$(CH_2)_2$—, $A^1$-$A^2$-$G^1$ bond in the form of $A^1$-NHC(=O)-$G^1$, $G^1$ is unsubstituted divalent benzene, and $A^3$-$A^4$-$G^2$ are collectively a group other than hydrogen.

68. A pyrrolo[3,2-d]pyrimidine or a medically acceptable salt thereof according to claim 1, wherein X is sulfur, $A^1$ is —$(CH_2)_2$—, $A^1$-$A^2$-$G^2$ bond in the form of $A^1$-NHC(=O)-$G^1$, and $G^1$ is a substituted or unsubstituted divalent monocyclic or bicyclic aromatic heterocyclic group selected from the group consisting of furan, pyrrole, thiophene, oxazole, thiazole, isooxazole, isothiazole, pyrazole, imidazole, pyridine, pyrimidine, pyrazine, pyridazine, benzothiophene, benzofuran, 1,2-methylenedioxybenzene, benzimidazole, indole, quinoline, isoquinoline, quinazoline, phthalazine, cinnoline, and 1,8-naphthylidine.

69. A pyrrolo[3,2-d]pyrimidine or a medically acceptable salt thereof according to claim 1, wherein X is sulfur, $A^1$ is —$(CH_2)_2$—, $A^1$-$A^2$-$G^1$ bond in the form of $A^1$-NHC(=O)-$G^1$, and $G^1$ is a substituted divalent monocyclic or bicyclic aromatic heterocyclic group selected from the group consisting of substituted furan, substituted pyrrole, substituted thiophene, substituted oxazole, substituted thiazole, substituted isooxazole, substituted isothiazole, substituted pyrazole, substituted imidazole, substituted pyridine, substituted pyrimidine, substituted pyrazine, substituted pyridazine, substituted benzothiophene, substituted benzofuran, substituted 1,2-methylenedioxybenzene, substituted benzimidazole, substituted indole, substituted quinoline, substituted isoquinoline, substituted quinazoline, substituted phthalazine, substituted cinnoline, and substituted 1,8-naphthylidine.

70. A pyrrolo[3,2-d]pyrimidine or a medically acceptable salt thereof according to claim 1, wherein X is sulfur, $A^1$ is —$(CH_2)_2$—, $A^1$-$A^2$-$G^1$ bond in the form of $A^1$-NHC(=O)-$G^1$, and $G^1$ is an unsubstituted divalent monocyclic or bicyclic aromatic heterocyclic group selected from the group consisting of unsubstituted furan, unsubstituted pyrrole, unsubstituted thiophene, unsubstituted oxazole, unsubstituted thiazole, unsubstituted isooxazole, unsubstituted isothiazole, unsubstituted pyrazole, unsubstituted imidazole, unsubstituted pyridine, unsubstituted pyrimidine, unsubstituted pyrazine, unsubstituted pyridazine, unsubstituted benzothiophene, unsubstituted benzofuran, unsubstituted 1,2-methylenedioxybenzene, unsubstituted benzimidazole, unsubstituted indole, unsubstituted quinoline, unsubstituted isoquinoline, unsubstituted quinazoline, unsubstituted phthalazine, unsubstituted cinnoline, and unsubstituted 1,8-naphthylidine, and $A^3$-$A^4$-$G^2$ are collectively a group other than hydrogen.

71. A pyrrolo[3,2-d]pyrimidine or a medically acceptable salt thereof according to claim 1, wherein X is sulfur, $A^1$ is —$(CH_2)_2$—, $A^1$-$A^2$-$G^1$ bond in the form of $A^1$-NH-$G^1$, and $G^1$ is substituted divalent benzene.

72. A pyrrolo[3,2-d]pyrimidine or a medically acceptable salt thereof according to claim 1, wherein X is sulfur, $A^1$ is —$(CH_2)_2$—, $A^1$-$A^2$-$G^1$ bond in the form of $A^1$-NH-$G^1$, $G^1$ is unsubstituted divalent benzene, and $A^3$-$A^4$-$G^2$ are collectively a group other than hydrogen.

73. A pyrrolo[3,2-d]pyrimidine or a medically acceptable salt thereof according to claim 1, wherein X is sulfur, $A^1$ is —$(CH_2)_2$—, $A^1$-$A^2$-$G^1$ bond in the form of $A^1$-NH-$G^1$, and $G^1$ is a substituted divalent monocyclic or bicyclic aromatic heterocyclic group selected from the group consisting of substituted furan, substituted pyrrole, substituted thiophene, substituted pyrazole, substituted oxazole, substituted thiazole, substituted isooxazole, substituted isothiazole, substituted imidazole, substituted pyridine, substituted pyrimidine, substituted pyrazine, substituted pyridazine, substituted benzothiophene, substituted benzofuran, substituted 1,2-methylenedioxybenzene, substituted benzimidazole, substituted indole, substituted quinoline, substituted isoquinoline, substituted quinazoline, substituted phthalazine, substituted cinnoline, and substituted 1,8-naphthylidine.

74. A pyrrolo[3,2-d]pyrimidine or a medically acceptable salt thereof according to claim 1, wherein X is sulfur, $A^1$ is —$(CH_2)_2$—, $A^1$-$A^2$-$G^1$ bond in the form of $A^1$-NH-$G^1$, and $G^1$ is an unsubstituted divalent monocyclic or bicyclic aromatic heterocyclic groupselected from the group consisting of unsubstituted furan, unsubstituted pyrrole, unsubstituted thiophene, unsubstituted oxazole, unsubstituted thiazole, unsubstituted isooxazole, unsubstituted isothiazole, unsubstituted pyrazole, unsubstituted imidazole, unsubstituted pyridine, unsubstituted pyrimidine, unsubstituted pyrazine, unsubstituted pyridazine, unsubstituted benzothiophene, unsubstituted benzofuran, unsubstituted 1,2-methylenedioxybenzene, unsubstituted benzimidazole, unsubstituted indole, unsubstituted quinoline, unsubstituted isoquinoline, unsubstituted quinazoline, unsubstituted phthalazine, unsubstituted cinnoline, and unsubstituted 1,8-naphthylidine, and $A^3$-$A^4$-$G^2$ are collectively a group other than hydrogen.

75. A pyrrolo[3,2-d]pyrimidine or a medically acceptable salt thereof according to claim 1, wherein X is sulfur, $A^1$ is —$(CH_2)_2$—, $A^1$-$A^2$-$G^1$ bond in the form of $A^1$-C(=O)-$G^1$, $G^1$ is a substituted or unsubstituted divalent monocyclic heterocyclic group selected from the group consisting of pyrrolidine, piperidine, morpholine, thiomorpholine, homopiperidine, homopiperazine, and piperazine, and $G^1$ is bonded to $A^1$-C(=O)— through a nitrogen atom.

76. A pyrrolo[3,2-d]pyrimidine or a medically acceptable salt thereof according to claim 1, wherein X is sulfur, $A^1$ is —$(CH_2)_2$—, $A^1$-$A^2$-$G^1$ bond in the form of $A^1$-C(=O)-$G^1$, $G^1$ is a substituted divalent monocyclic heterocyclic group selected from the group consisting of pyrrolidine, piperidine, morpholine, thiomorpholine, homopiperidine, homopiperazine, and piperazine, and $G^1$ is bonded to $A^1$-C(=O)— through a nitrogen atom.

77. A pyrrolo[3,2-d]pyrimidine or a medically acceptable salt thereof according to claim 1, wherein X is sulfur, $A^1$ is —$(CH_2)_2$—, $A^1$-$A^2$-$G^1$ bond in the form of $A^1$-C(=O)-$G^1$, $G^1$ is an unsubstituted divalent monocyclic heterocyclic group selected from the group consisting of unsubstituted pyrrolidine, unsubstituted piperidine, unsubstituted morpholine, unsubstituted thiomorpholine, unsubstituted homopiperidine, unsubstituted homopiperazine, and unsubstituted piperazine, $G^1$ is bonded to $A^1$-C(=O)— through a nitrogen atom, and $A^3$-$A^4$-$G^2$ are collectively a group other than hydrogen.

78. A pyrrolo[3,2-d]pyrimidine or a medically acceptable salt thereof according to claim 1, wherein $A^5$ is a single bond.

79. A pyrrolo[3,2-d]pyrimidine or a medically acceptable salt thereof according to claim 1, wherein $A^5$ is a group binding the carbon atom of the pyrrole ring to which $A^5$ is bonded and $R^2$ in the form of $R^2$—$NR^{201}$-pyrrole ring carbon.

80. A pyrrolo[3,2-d]pyrimidine or a medically acceptable salt thereof according to claim 79, wherein $R^2$ is a hydrogen atom.

81. A pyrrolo[3,2-d]pyrimidine or a medically acceptable salt thereof according to claim 78, wherein $R^2$ is fluorine, chlorine, bromine or iodine.

82. A pyrrolo[3,2-d]pyrimidine or a medically acceptable salt thereof according to claim 78 or 79, wherein $R^2$ is a substituted or unsubstituted $C_{1-10}$ aliphatic hydrocarbon group.

83. A pyrrolo[3,2-d]pyrimidine or a medically acceptable salt thereof according to claim 78 or 79, wherein $R^2$ is a substituted or unsubstituted $C_{3-8}$ aliphatic hydrocarbon group.

84. A pyrrolo[3,2-d]pyrimidine or a medically acceptable salt thereof according to claim 78 or 79, wherein $R^2$ is a substituted or unsubstituted $C_{6-14}$ aromatic hydrocarbon group.

85. A pyrrolo[3,2-d]pyrimidine or a medically acceptable salt thereof according to claim 78 or 79, wherein $R^2$ is a substituted or unsubstituted monovalent heterocyclic groupselected from the group consisting of furan, thiophene, pyrrole, pyrroline, pyrrolidine, oxazole, oxazolidine, isooxazole, isooxazolidine, thiazole, thiazolidine, isothiazole, isothiazolidine, imidazole, imidazoline, imidazolidine, pyrazole, pyrazoline, pyrazolidine, triazole, thiadiazole, oxadiazole, tetrazole, pyran, tetrahydropyran, thiopyran, tetrahydrothiopyran, pyridine, pyrazine, pyrimidine, pyridazine, benzofuran, dibenzofuran, benzothiophene, indole, 1,2-methylenedioxybenzene, benzimidazole, benzothiazole, benzoxazole, chromane, isochromane, quinoline, decahydroquinoline, isoquinoline, quinazoline, quinoxaline, purine, pteridine, azetidine, morpholine, thiomorpholine, piperidine, homopiperidine, piperazine, homopiperazine, indoline, isoindoline, phenoxazine, phenazine, phenothiazine and quinuclidine, wherein the heterocyclic group is bonded to $A^5$ via a carbon atom or a nitrogen atom.

86. A pyrrolo[3,2-d]pyrimidine or a medically acceptable salt thereof according to any one of claims 66 to 77, wherein $R^2$-$A^5$- is substituted or unsubstituted isopropylamino, substituted or unsubstituted cyclopropylamino, substituted or unsubstituted cyclopentylamino, substituted or unsubstituted dimethylamino, substituted or unsubstituted N-methyl-ethylamino, substituted or unsubstituted N-methyl-2-propenylamino, substituted or unsubstituted N-methyl-2-propynylamino, substituted or unsubstituted 1-pyrrolidinyl, substituted or unsubstituted 1-piperazinyl, substituted or unsubstituted 1-piperidino, substituted or unsubstituted 1-morpholino or substituted or unsubstituted 1-homopiperidinyl.

87. A pyrrolo[3,2-d]pyrimidine or a medically acceptable salt thereof according to any one of claims 66 to 77, wherein $R^2$-$A^5$- is substituted or unsubstituted cyclopropyl, substituted or unsubstituted phenyl, substituted or unsubstituted furyl, substituted or unsubstituted thienyl, substituted or unsubstituted pyrrolyl, substituted or unsubstituted pyrazolyl, substituted or unsubstituted oxazolyl, substituted or unsubstituted isooxazolyl, substituted or unsubstituted thiazolyl, substituted or unsubstituted isothiazolyl, substituted or unsubstituted imidazolyl, substituted or unsubstituted pyridyl, substituted or unsubstituted pyrazinyl, substituted or unsubstituted pyrimidinyl, substituted or unsubstituted pyridazinyl, substituted or unsubstituted benzofuranyl or substituted or unsubstituted benzothiophenyl.

88. A pyrrolo[3,2-d]pyrimidine or a medically acceptable salt thereof according to any one of claims 66 to 77, wherein $R^2$-$A^5$- is substituted or unsubstituted 2-furyl, substituted or unsubstituted 2-thienyl, substituted or unsubstituted 2-pyrrolyl, substituted or unsubstituted 2-imidazolyl, substituted or unsubstituted 5-imidazolyl, substituted or unsubstituted 2-oxazolyl, substituted or unsubstituted 5-oxazolyl, substituted or unsubstituted 5-isooxazolyl, substituted or unsubstituted 2-thiazolyl, substituted or unsubstituted 5-thiazolyl, substituted or unsubstituted 5-isothiazolyl, substituted or unsubstituted 3-isothiazolyl, substituted or unsubstituted 2-pyridyl, substituted or unsubstituted 2-pyrimidinyl, substituted or unsubstituted 2-benzofuranyl or substituted or unsubstituted 2-benzothiophenyl.

89. A pyrrolo[3,2-d]pyrimidine or a medically acceptable salt thereof according to any one of claims 66 to 77, wherein $R^2$-$A^5$- is substituted or unsubstituted 2-furyl, substituted or unsubstituted 2-thienyl or substituted or unsubstituted 2-pyrrolyl.

90. A pyrrolo[3,2-d]pyrimidine or a medically acceptable salt thereof according to any one of claims 66 to 77, wherein $R^2$-$A^5$- is 3-methyl(2-furyl), 3-chloro(2-furyl), 3-methyl(2-thienyl), 3-chloro(2-thienyl) or 1-methylpyrrol-2-yl.

91. A pyrrolo[3,2-d]pyrimidine or a medically acceptable salt thereof according to any one of claims 66 to 77, wherein $A^5$ is a group binding the carbon atom of the pyrrole ring to which $A^5$ is bonded and $R^2$ in the form of $R^2$—$NR^{201}$-pyrrole ring carbon, and $R^2$ is a substituted or unsubstituted heterocyclic group selected from the group consisting of furan, thiophene, pyrrole, pyrroline, pyrrolidine, oxazole, oxazolidine, isooxazole, isooxazolidine, thiazole, thiazolidine, isothiazole, isothiazolidine, and quinuclidine, wherein the heterocyclic group is bonded to $A^5$ via a carbon atom or a nitrogen atom.

92. A pharmaceutical composition comprising a pyrrolo[3,2-d]pyrimidine or a medically acceptable salt thereof according to any one of claims 1 and 66 to 77, and a pharmaceutically acceptable carrier.

\* \* \* \* \*

```
                        SEQUENCE LISTING

<160> NUMBER OF SEQ ID NOS: 1

<210> SEQ ID NO 1
<211> LENGTH: 26
<212> TYPE: PRT
<213> ORGANISM: Artificial Sequence
<220> FEATURE:
<223> OTHER INFORMATION: phospho-glycogen synthase peptide-2

<400> SEQUENCE: 1

Tyr Arg Arg Ala Ala Val Pro Pro Ser Pro Ser Leu Ser Arg His Ser
1               5                   10                  15

Ser Pro His Gln Ser Glu Asp Glu Glu Glu
            20                  25
```